(12) United States Patent
Aftab et al.

(10) Patent No.: US 9,011,863 B2
(45) Date of Patent: Apr. 21, 2015

(54) COMBINATIONS OF KINASE INHIBITORS FOR THE TREATMENT OF CANCER

(75) Inventors: Dana T. Aftab, San Rafael, CA (US); Carlos L. Arteaga, Nashville, TN (US); Veronique Blanc, Paris (FR); Anindita Chakrabarty, Nashville, TN (US); Marielle Chiron-Blonde, Paris (FR); Celine Nicolazzi, Choisy le Roi (FR); Ariella Hanker, Nashville, TN (US); Loic Vincent, Evry (FR)

(73) Assignee: Exelixis, Inc., South San Francisco, CA (US)

( * ) Notice: Subject to any disclaimer, the term of this patent is extended or adjusted under 35 U.S.C. 154(b) by 115 days.

(21) Appl. No.: 13/809,002

(22) PCT Filed: Jul. 8, 2011

(86) PCT No.: PCT/US2011/043401
§ 371 (c)(1),
(2), (4) Date: Aug. 26, 2013

(87) PCT Pub. No.: WO2012/006552
PCT Pub. Date: Jan. 12, 2012

(65) Prior Publication Data
US 2014/0271665 A1    Sep. 18, 2014

Related U.S. Application Data

(60) Provisional application No. 61/363,074, filed on Jul. 9, 2010, provisional application No. 61/421,929, filed on Dec. 10, 2010.

(51) Int. Cl.
| | | |
|---|---|---|
| *A61K 39/395* | (2006.01) | |
| *A61K 31/498* | (2006.01) | |
| *A01N 43/58* | (2006.01) | |
| *A01N 43/60* | (2006.01) | |
| *A61K 31/50* | (2006.01) | |
| *A61K 31/495* | (2006.01) | |
| *A61K 31/517* | (2006.01) | |
| *A61K 31/63* | (2006.01) | |
| *A61K 31/7088* | (2006.01) | |
| *A61K 45/06* | (2006.01) | |
| *C07K 16/32* | (2006.01) | |
| *A61K 39/00* | (2006.01) | |

(52) U.S. Cl.
CPC ........... *A61K 39/3955* (2013.01); *A61K 31/498* (2013.01); *A61K 31/517* (2013.01); *A61K 31/63* (2013.01); *A61K 31/7088* (2013.01); *A61K 39/39558* (2013.01); *A61K 45/06* (2013.01); *C07K 16/32* (2013.01); *C07K 2317/24* (2013.01); *C07K 2317/73* (2013.01); *C07K 2317/76* (2013.01); *C07K 2317/34* (2013.01); *A61K 2039/505* (2013.01)

(58) Field of Classification Search
CPC ............... C07K 16/2863; C07K 16/30; C07K 16/3015; C07K 16/3023; C07K 16/303; C07K 16/3046; C07K 16/3053; C07K 16/3061; C07K 16/3069
See application file for complete search history.

(56) References Cited

U.S. PATENT DOCUMENTS 7,846,440 B2 * 12/2010 Schoeberl et al. ......... 424/141.1

FOREIGN PATENT DOCUMENTS

WO   WO 2007/044729   *   4/2007
WO   2008/127594       10/2008

OTHER PUBLICATIONS

A. Chakrabarty, et al. "H1047R Phosphatidylinositol 3-kinase mutant enhances HER2-mediated transformation by heregulin production and activation of HER3", Oncongene, vol. 29, No. 37, Jun. 28, 2010, pp. 5193-5203.
Jang Ji-Young, et al. "Degradation of HER2/neu by ANT2 shRNA suppresses migration and invasiveness of breast cancer cells", BMC Cancer, Biomed Central, London, GB, vol. 10, No. 1, Jul. 23, 2010, p. 391.
International Search Report for PCT/US2011/043401, mailed Oct. 5, 2011.

* cited by examiner

*Primary Examiner* — Robert Landsman
(74) *Attorney, Agent, or Firm* — Honigman Miller Schwartz & Cohn LLP; Heidi M. Berven; Jonathan P. O'Brien

(57) ABSTRACT

The present invention provides methods of treating cancer by administering a compound of formula I, optionally as a pharmaceutically acceptable salt, solvate and/or hydrate thereof, in combination with an inhibitor that targets HER2 and/or HER3.

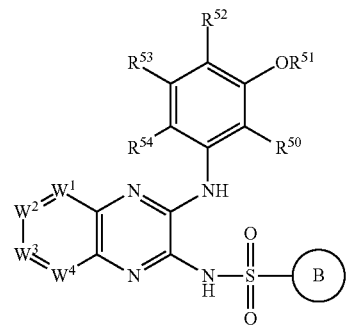

9 Claims, 24 Drawing Sheets

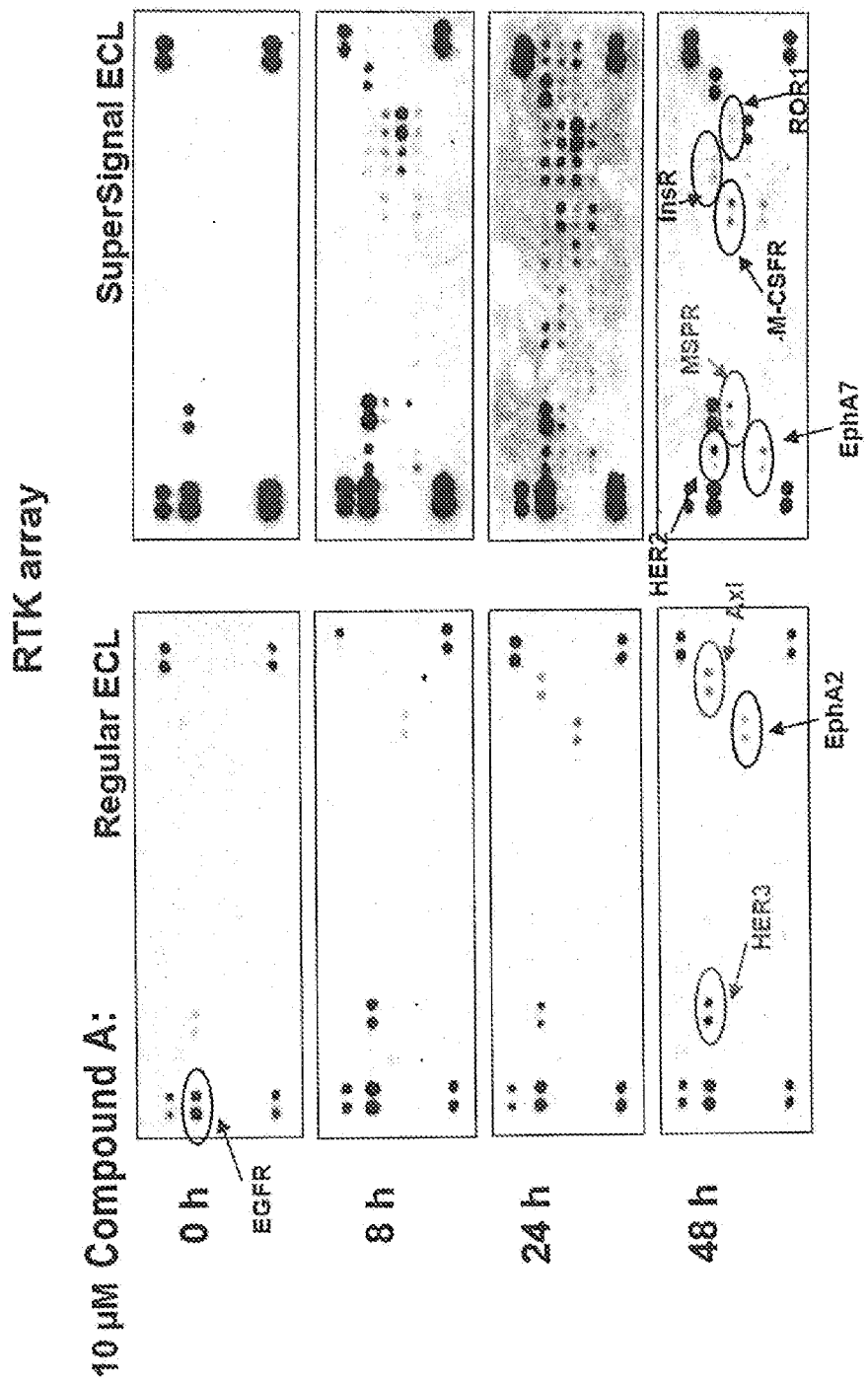

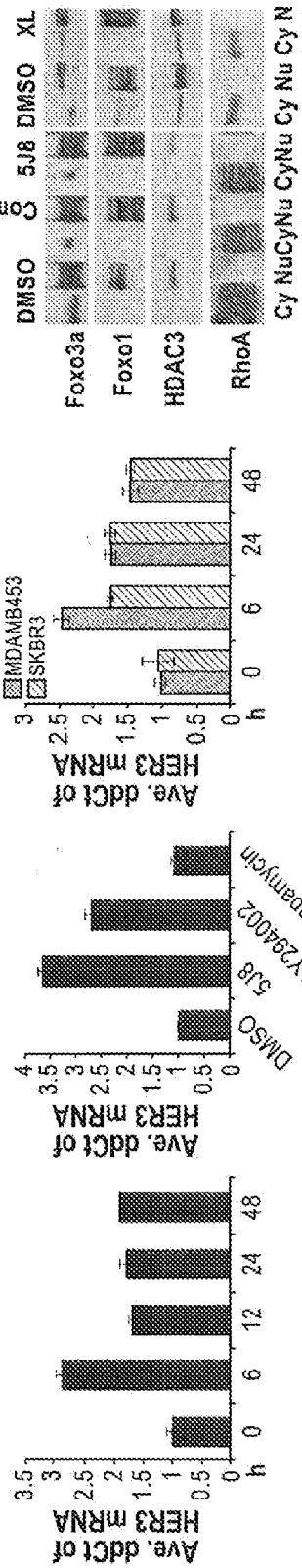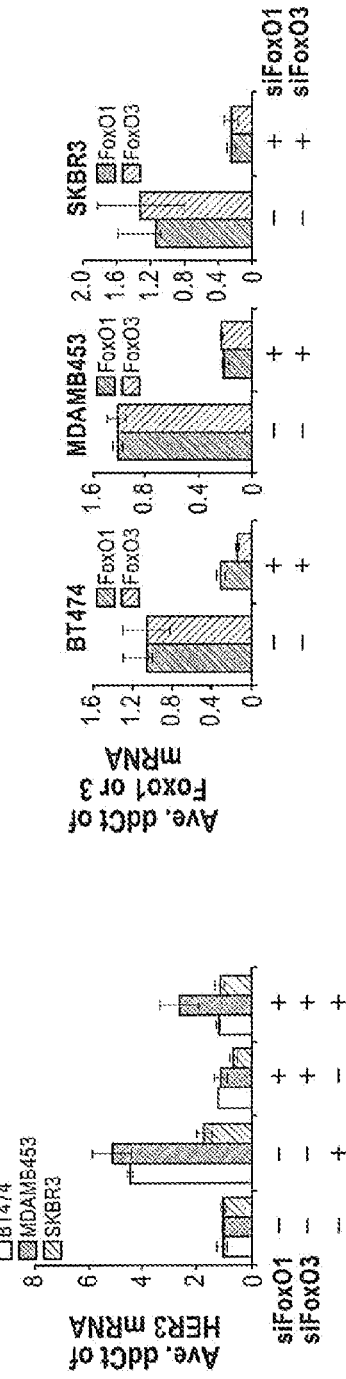
FIG. 12A, FIG. 12B, FIG. 12C, FIG. 12D, FIG. 12E, FIG. 12F

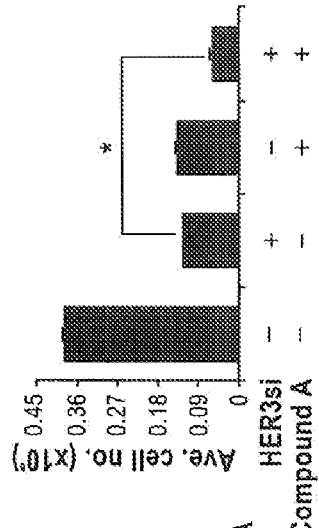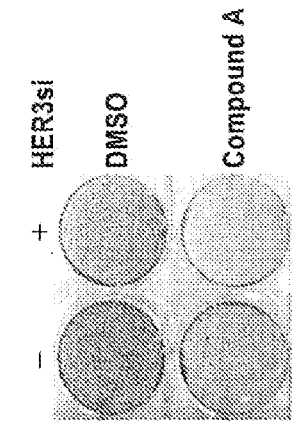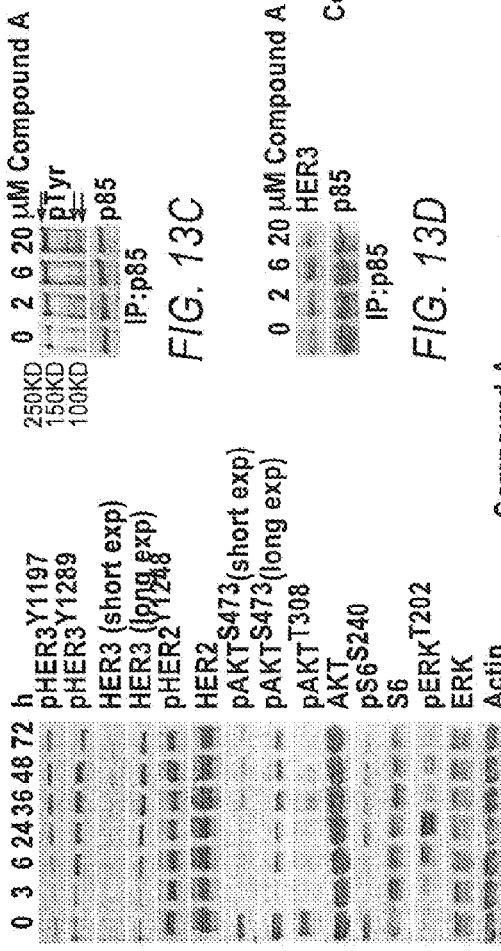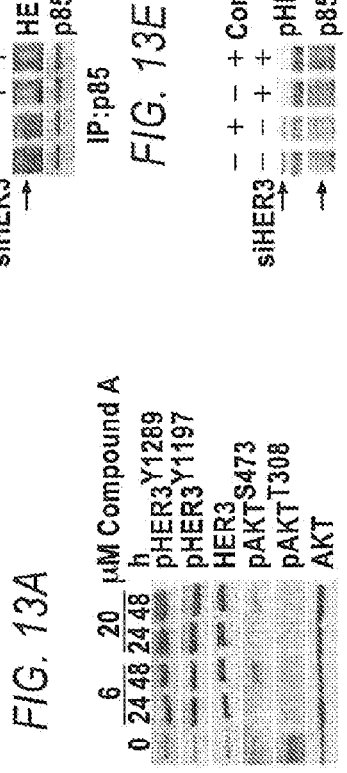
FIG. 13A
FIG. 13B
FIG. 13C
FIG. 13D
FIG. 13E
FIG. 13F
FIG. 13G
FIG. 13H

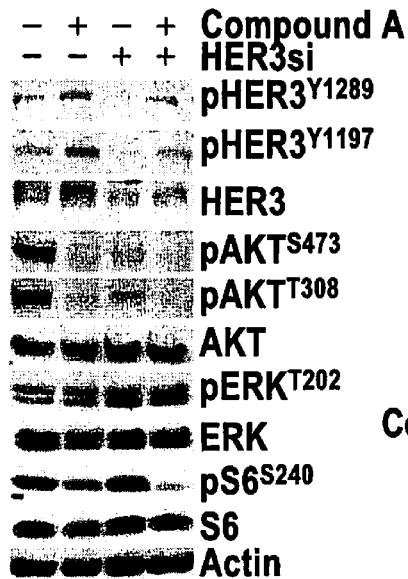
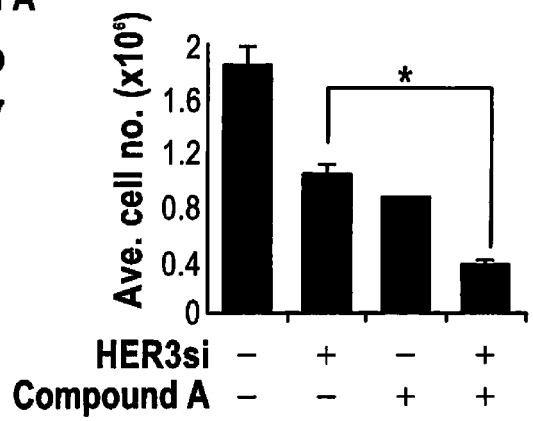
MDA453
FIG. 15A          FIG. 15B
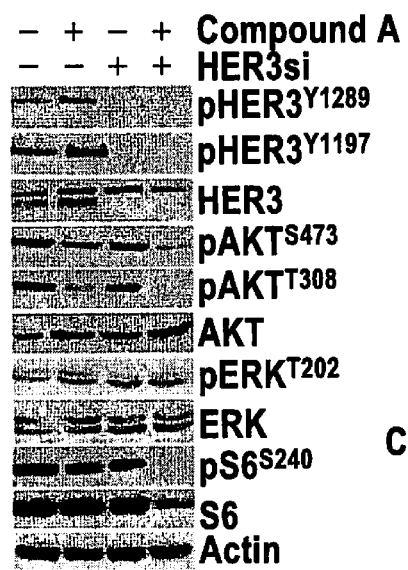
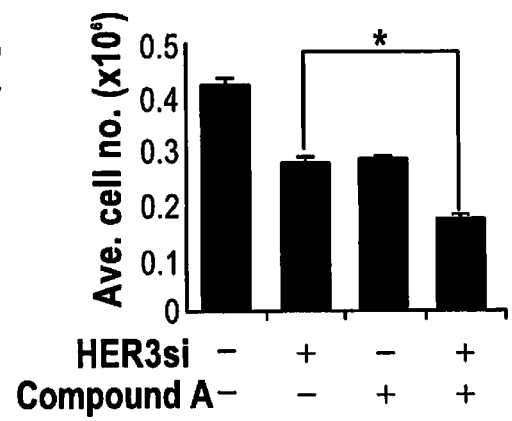
SKBR3
FIG. 15C          FIG. 15D

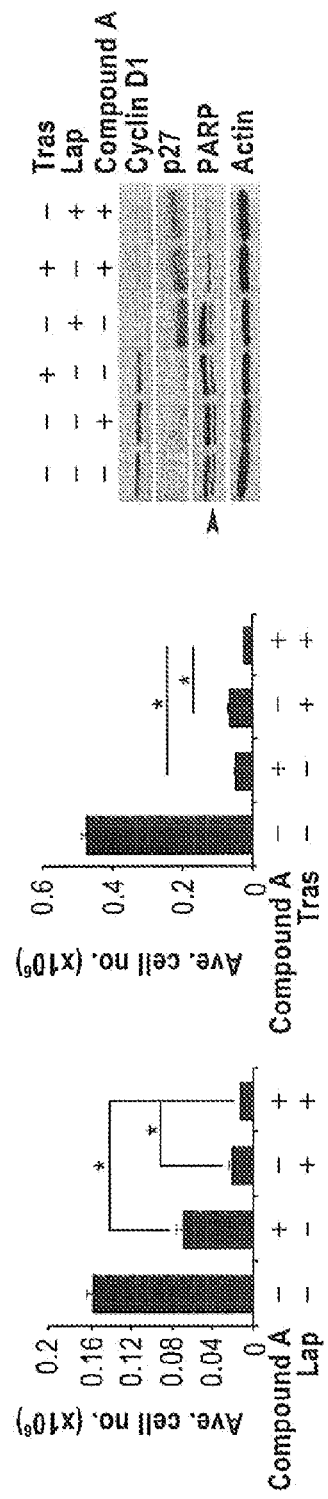

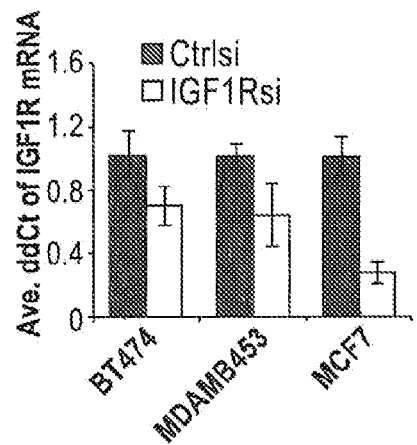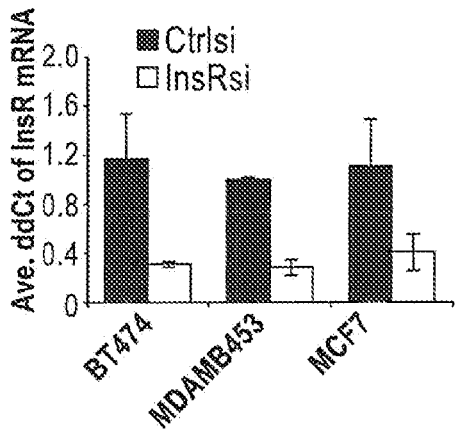
*FIG. 20A*  *FIG. 20B*
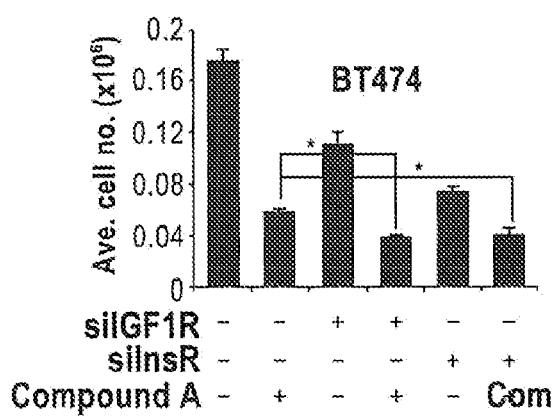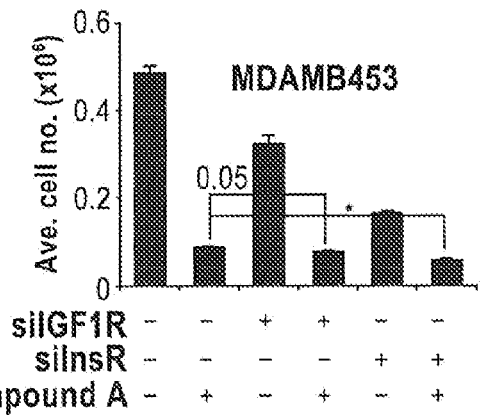
*FIG. 20C*  *FIG. 20D*
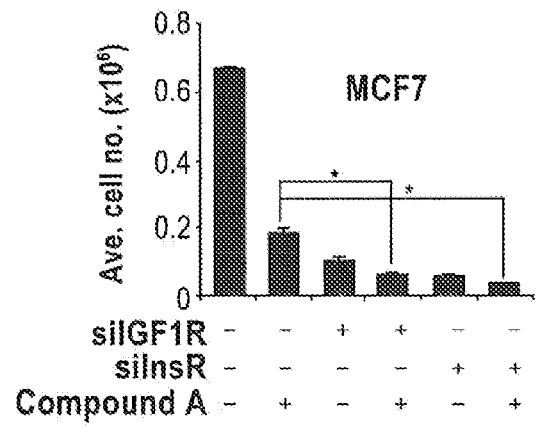
*FIG. 20E*

SEQUENCE LISTING

<160> NUMBER OF SEQ ID NOS: 22

<210> SEQ ID NO 1
<211> LENGTH: 4624
<212> TYPE: DNA
<213> ORGANISM: Homo sapiens

<400> SEQUENCE: 1

```
ggaggaggtg gaggaggagg gctgcttgag gaagtataag aatgaagttg tgaagctgag      60
attcccctcc attgggaccg gagaaaccag gggagccccc cgggcagccg cgcgcccctt     120
cccacggggc cctttactgc gccgcgcgcc cggccccac ccctcgcagc accccgcgcc     180
ccgcgccctc ccagccgggt ccagccggag ccatggggcc ggagccgcag tgagcaccat     240
ggagctggcg gccttgtgcc gctgggggct cctcctcgcc ctcttgcccc ccggagccgc     300
gagcacccaa gtgtgcaccg gcacagacat gaagctgcgg ctccctgcca gtcccgagac     360
ccacctggac atgctccgcc acctctacca gggctgccag gtggtgcagg gaaacctgga     420
actcacctac ctgcccacca atgccagcct gtccttcctg caggatatcc aggaggtgca     480
gggctacgtg ctcatcgctc acaaccaagt gaggcaggtc ccactgcaga ggctgcggat     540
tgtgcgaggc acccagctct ttgaggacaa ctatgccctg gccgtgctag acaatggaga     600
cccgctgaac aataccaccc ctgtcacagg ggcctcccca ggaggcctgc gggagctgca     660
gcttcgaagc ctcacagaga tcttgaaagg aggggtcttg atccagcgga accccagct     720 ctgctaccag gacacgattt tgtggaagga catcttccac aagaacaacc agctggctct     780
cacactgata gacaccaacc gctctcgggc ctgccacccc tgttctccga tgtgtaaggg     840
ctcccgctgc tgggagaga gttctgagga ttgtcagagc ctgacgcgca ctgtctgtgc     900
cggtggctgt gcccgctgca aggggccact gcccactgac tgctgccatg agcagtgtgc     960
tgccggctgc acgggcccca agcactctga ctgcctggcc tgcctccact caaccacag    1020 tggcatctgt gagctgcact gcccagccct ggtcacctac aacacagaca cgtttgagtc    1080
catgcccaat cccgagggcc ggtatacatt cggcgccagc tgtgtgactg cctgtcccta    1140
caactacctt tctacgacg tgggatcctg caccctcgtc tgcccctgc acaaccaaga    1200 ggtgacagca gaggatggaa cacagcggtg tgagaagtgc agcaagccct gtgcccgagt    1260
gtgctatggt ctgggcatgg agcacttgcg agaggtgagg gcagttacca gtgccaatat    1320
ccaggagttt gctggctgca agaagatctt tgggagcctg gcatttctgc cggagagctt    1380 tgatgggac ccagcctcca acactgcccc gctccagcca gagcagctcc aagtgtttga    1440
gactctggaa gagatcacag gttacctata catctcagca tggccggaca gcctgcctga    1500
cctcagcgtc ttccagaacc tgcaagtaat ccggggacga attctgcaca atggcgccta    1560
ctcgctgacc ctgcaagggc tgggcatcag ctggctgggg ctgcgctcac tgagggaact    1620
gggcagtgga ctggccctca tccaccataa cacccacctc tgcttcgtgc acacggtgcc    1680
ctgggaccag ctctttcgga acccgcacca agctctgctc cacactgcca accggccaga    1740
ggacgagtgt gtgggcgagg gcctggcctg ccaccagctg tgcgcccgag ggcactgctg    1800
gggtccaggg cccacccagt gtgtcaactg cagccagttc cttcggggcc aggagtgcgt    1860
```

-continued

```
ggaggaatgc cgagtactgc aggggctccc cagggagtat gtgaatgcca ggcactgttt    1920
gccgtgccac cctgagtgtc agccccagaa tggctcagtg acctgttttg gaccggaggc    1980
tgaccagtgt gtggcctgtg cccactataa ggaccctccc ttctgcgtgg cccgctgccc    2040
cagcggtgtg aaacctgacc tctcctacat gcccatctgg aagtttccag atgaggaggg    2100
cgcatgccag ccttgcccca tcaactgcac ccactcctgt gtggacctgg atgacaaggg    2160
ctgccccgcc gagcagagag ccagccctct gacgtccatc atctctgcgg tggttggcat    2220
tctgctggtc gtggtcttgg ggtggtcttt gggatcctc atcaagcgac ggcagcagaa    2280
gatccggaag tacacgatgc ggagactgct gcaggaaacg gagctggtgg agccgctgac    2340
acctagcgga gcgatgccca accaggcgca gatgcggatc ctgaaagaga cggagctgag    2400
gaaggtgaag gtgcttggat ctggcgcttt tggcacagtc tacaagggca tctggatccc    2460
tgatggggag aatgtgaaaa ttccagtggc catcaaagtg ttgagggaaa acacatcccc    2520
caaagccaac aaagaaatct tagacgaagc atacgtgatg ctggtgtgg gctcccccata    2580
tgtctcccgc cttctgggca tctgcctgac atccacggtg cagctggtga cacagcttat    2640
gccctatggc tgcctcttag accatgtccg ggaaaaccgc ggacgcctgg ctcccagga    2700
cctgctgaac tggtgtatgc agattgccaa ggggatgagc tacctggagg atgtgcggct    2760
cgtacacagg gacttggccg ctcggaacgt gctggtcaag agtcccaacc atgtcaaaat    2820
tacagacttc gggctggctc ggctgctgga cattgacgag acagagtacc atgcagatgg    2880
gggcaaggtg cccatcaagt ggatggcgct ggagtccatt ctccgccggc ggttcaccca    2940
ccagagtgat gtgtggagtt atggtgtgac tgtgtgggag ctgatgactt ttggggccaa    3000
accttacgat gggatcccag cccgggagat ccctgacctg ctggaaaagg gggagcggct    3060
gccccagccc cccatctgca ccattgatgt ctacatgatc atggtcaaat gttggatgat    3120
tgactctgaa tgtcggccaa gattccggga gttggtgtct gaattctccc gcatggccag    3180
ggaccccag cgctttgtgg tcatccagaa tgaggacttg gcccagcca gtcccttgga    3240
cagcaccttc taccgctcac tgctggagga cgatgacatg ggggacctgg tggatgctga    3300
ggagtatctg gtaccccagc agggcttctt ctgtccagac cctgccccgg cgctggggg    3360
catggtccac acaggcacc gcagctcatc taccaggagt ggcggtgggg acctgacact    3420
agggctggag ccctctgaag aggaggcccc caggtctcca ctggcaccct ccgaaggggc    3480
tggctccgat gtatttgatg gtgacctggg aatgggggca gccaaggggc tgcaaagcct    3540
ccccacacat gaccccagcc ctctacagcg gtacagtgag gacccccag tacccctgcc    3600
ctctgagact gatggctacg ttgccccct gacctgcagc cccagcctg aatatgtgaa    3660
ccagccagat gttcggcccc agccccttc gccccgagag ggccctctgc ctgctgcccg    3720
acctgctggt gccactctgg aaaggcccaa gactctctcc caggggaaga tgggggtcgt    3780
caaagacgtt tttgccttg ggggtgccgt ggagaacccc gagtacttga caccccaggg    3840
aggagctgcc cctcagcccc acctcctcc tgccttcagc ccagccttcg acaacctcta    3900
ttactgggac caggacccac cagagcgggg ggctccaccc agcaccttca agggacacc    3960
tacggcagag aacccagagt acctgggtct ggacgtgcca gtgtgaacca gaaggccaag    4020
tccgcagaag ccctgatgtg tcctcaggga gcagggaagg cctgacttct gctggcatca    4080
agaggtggga gggccctccg accacttcca ggggaacctg ccatgccagg aacctgtcct    4140
aaggaaccctt ccttcctgct tgagttccca gatggctgga aggggtccag cctcgttgga    4200
agaggaacag cactggggag tctttgtgga ttctgaggcc ctgcccaatg agactctagg    4260
```

-continued

```
gtccagtgga tgccacagcc cagcttggcc ctttccttcc agatcctggg tactgaaagc    4320
cttagggaag ctggcctgag aggggaagcg gccctaaggg agtgtctaag aacaaaagcg    4380
acccattcag agactgtccc tgaaacctag tactgccccc catgaggaag gaacagcaat    4440
ggtgtcagta tccaggcttt gtacagagta cttttctgtt tagttttac tttttttgtt     4500 ttgttttttt aaagatgaaa taaagaccca ggggagaat gggtgttgta tggggaggca      4560
agtgtggggg gtccttctcc acacccactt tgtccatttg caaatatatt ttggaaaaca    4620
gcta                                                                  4624
```

<210> SEQ ID NO 2
<211> LENGTH: 1254
<212> TYPE: PRT
<213> ORGANISM: Homo sapiens

<400> SEQUENCE: 2

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Gly Thr Gln Leu Phe Glu Asp Asn Tyr Ala
            100                 105                 110

Leu Ala Val Leu Asp Asn Gly Asp Pro Leu Asn Asn Thr Thr Pro Val
        115                 120                 125

Thr Gly Ala Ser Pro Gly Gly Leu Arg Glu Leu Gln Leu Arg Ser Leu
    130                 135                 140

Thr Glu Ile Leu Lys Gly Gly Val Leu Ile Gln Arg Asn Pro Gln Leu
145                 150                 155                 160

Cys Tyr Gln Asp Thr Ile Leu Trp Lys Asp Ile Phe His Lys Asn Asn
                165                 170                 175

Gln Leu Ala Leu Thr Leu Ile Asp Thr Asn Arg Ser Arg Ala Cys His
            180                 185                 190

Pro Cys Ser Pro Met Cys Lys Gly Ser Arg Cys Trp Gly Glu Ser Ser
        195                 200                 205

Glu Asp Cys Gln Ser Leu Thr Arg Thr Val Cys Ala Gly Gly Cys Ala
    210                 215                 220

Arg Cys Lys Gly Pro Leu Pro Thr Asp Cys Cys His Glu Gln Cys Ala
225                 230                 235                 240

Ala Gly Cys Thr Gly Pro Lys His Ser Asp Cys Leu Ala Cys Leu His
                245                 250                 255

Phe Asn His Ser Gly Ile Cys Glu Leu His Cys Pro Ala Leu Val Thr
            260                 265                 270

Tyr Asn Thr Asp Thr Phe Glu Ser Met Pro Asn Pro Glu Gly Arg Tyr
        275                 280                 285

Thr Phe Gly Ala Ser Cys Val Thr Ala Cys Pro Tyr Asn Tyr Leu Ser
    290                 295                 300
```

```
Thr Asp Val Gly Ser Cys Thr Leu Val Cys Pro Leu His Asn Gln Glu
305                 310                 315                 320

Val Thr Ala Glu Asp Gly Thr Gln Arg Cys Glu Lys Cys Ser Lys Pro
                325                 330                 335

Cys Ala Arg Val Cys Tyr Gly Leu Gly Met Glu His Leu Arg Glu Val
            340                 345                 350

Arg Ala Val Thr Ser Ala Asn Ile Gln Glu Phe Ala Gly Cys Lys Lys
        355                 360                 365

Ile Phe Gly Ser Leu Ala Phe Leu Pro Glu Ser Phe Asp Gly Asp Pro
370                 375                 380

Ala Ser Asn Thr Ala Pro Leu Gln Pro Glu Gln Leu Gln Val Phe Glu
385                 390                 395                 400

Thr Leu Glu Glu Ile Thr Gly Tyr Leu Tyr Ile Ser Ala Trp Pro Asp
                405                 410                 415

Ser Leu Pro Asp Leu Ser Val Phe Gln Asn Leu Gln Val Ile Arg Gly
            420                 425                 430

Arg Ile Leu His Asn Gly Ala Tyr Ser Leu Thr Leu Gln Gly Leu Gly
        435                 440                 445

Ile Ser Trp Leu Gly Leu Arg Ser Leu Arg Glu Leu Gly Ser Gly Leu
450                 455                 460

Ala Leu Ile His His Asn Thr His Leu Cys Phe Val His Thr Val Pro
465                 470                 475                 480

Trp Asp Gln Leu Phe Arg Asn Pro His Gln Ala Leu Leu His Thr Ala
                485                 490                 495

Asn Arg Pro Glu Asp Glu Cys Val Gly Glu Gly Leu Ala Cys His Gln
            500                 505                 510

Leu Cys Ala Arg Gly His Cys Trp Gly Pro Gly Pro Thr Gln Cys Val
        515                 520                 525

Asn Cys Ser Gln Phe Leu Arg Gly Gln Glu Cys Val Glu Glu Cys Arg
530                 535                 540

Val Leu Gln Gly Leu Pro Arg Glu Tyr Val Asn Ala Arg His Cys Leu
545                 550                 555                 560

Pro Cys His Pro Glu Cys Gln Pro Gln Asn Gly Ser Val Thr Cys Phe
                565                 570                 575

Gly Pro Glu Ala Asp Gln Cys Val Ala Cys Ala His Tyr Lys Asp Pro
            580                 585                 590

Pro Phe Cys Val Ala Arg Cys Pro Ser Gly Val Lys Pro Asp Leu Ser
        595                 600                 605

Tyr Met Pro Ile Trp Lys Phe Pro Asp Glu Glu Gly Ala Cys Gln Pro
610                 615                 620

Cys Pro Ile Asn Cys Thr His Ser Cys Val Asp Leu Asp Asp Lys Gly
625                 630                 635                 640

Cys Pro Ala Glu Gln Arg Ala Ser Pro Leu Thr Ser Ile Ile Ser Ala
                645                 650                 655

Val Val Gly Ile Leu Leu Val Val Leu Gly Val Val Phe Gly Ile
            660                 665                 670

Leu Ile Lys Arg Arg Gln Gln Lys Ile Arg Lys Tyr Thr Met Arg Arg
        675                 680                 685

Leu Leu Gln Glu Thr Glu Leu Val Glu Pro Leu Thr Pro Ser Gly Ala
690                 695                 700

Met Pro Asn Gln Ala Gln Met Arg Ile Leu Lys Glu Thr Glu Leu Arg
705                 710                 715                 720
```

-continued

```
Lys Val Lys Val Leu Gly Ser Gly Ala Phe Gly Thr Val Tyr Lys Gly
                725                 730                 735

Ile Trp Ile Pro Asp Gly Glu Asn Val Lys Ile Pro Val Ala Ile Lys
            740                 745                 750

Val Leu Arg Glu Asn Thr Ser Pro Lys Ala Asn Lys Glu Ile Leu Asp
        755                 760                 765

Glu Ala Tyr Val Met Ala Gly Val Gly Ser Pro Tyr Val Ser Arg Leu
    770                 775                 780

Leu Gly Ile Cys Leu Thr Ser Thr Val Gln Leu Val Thr Gln Leu Met
785                 790                 795                 800

Pro Tyr Gly Cys Leu Leu Asp His Val Arg Glu Asn Arg Gly Arg Leu
                805                 810                 815

Gly Ser Gln Asp Leu Leu Asn Trp Cys Met Gln Ile Ala Lys Gly Met
            820                 825                 830

Ser Tyr Leu Glu Asp Val Arg Leu Val His Arg Asp Leu Ala Ala Arg
        835                 840                 845

Asn Val Leu Val Lys Ser Pro Asn His Val Lys Ile Thr Asp Phe Gly
    850                 855                 860

Leu Ala Arg Leu Leu Asp Ile Asp Glu Thr Glu Tyr His Ala Asp Gly
865                 870                 875                 880

Gly Lys Val Pro Ile Lys Trp Met Ala Leu Glu Ser Ile Leu Arg Arg
                885                 890                 895

Arg Phe Thr His Gln Ser Asp Val Trp Ser Tyr Gly Val Thr Val Trp
            900                 905                 910

Glu Leu Met Thr Phe Gly Ala Lys Pro Tyr Asp Gly Ile Pro Ala Arg
        915                 920                 925

Glu Ile Pro Asp Leu Leu Glu Lys Gly Glu Arg Leu Pro Gln Pro Pro
    930                 935                 940

Ile Cys Thr Ile Asp Val Tyr Met Ile Met Val Lys Cys Trp Met Ile
945                 950                 955                 960

Asp Ser Glu Cys Arg Pro Arg Phe Arg Glu Leu Val Ser Glu Phe Ser
                965                 970                 975

Arg Met Ala Arg Asp Pro Gln Arg Phe Val Val Ile Gln Asn Glu Asp
            980                 985                 990

Leu Gly Pro Ala Ser Pro Leu Asp Ser Thr Phe Tyr Arg Ser Leu Leu
        995                1000                1005

Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala
    1025                1030                1035

Gly Gly Met Val His His Arg His Arg Ser Ser Ser Thr Arg Ser
    1040                1045                1050

Gly Gly Gly Asp Leu Thr Leu Gly Leu Glu Pro Ser Glu Glu Glu
    1055                1060                1065

Ala Pro Arg Ser Pro Leu Ala Pro Ser Glu Gly Ala Gly Ser Asp
    1070                1075                1080

Val Phe Asp Gly Asp Leu Gly Met Gly Ala Ala Lys Gly Leu Gln
    1085                1090                1095

Ser Leu Pro Thr His Asp Pro Ser Pro Leu Gln Arg Tyr Ser Glu
    1100                1105                1110

Asp Pro Thr Val Pro Leu Pro Ser Glu Thr Asp Gly Tyr Val Ala
    1115                1120                1125

Pro Leu Thr Cys Ser Pro Gln Pro Glu Tyr Val Asn Gln Pro Asp
```

-continued

```
            1130                1135                1140
Val  Arg  Pro  Gln  Pro  Pro  Ser  Pro  Arg  Glu  Gly  Pro  Leu  Pro  Ala
          1145                1150                1155

Ala  Arg  Pro  Ala  Gly  Ala  Thr  Leu  Glu  Arg  Pro  Lys  Thr  Leu  Ser
     1160                1165                1170

Pro  Gly  Lys  Asn  Gly  Val  Val  Lys  Asp  Val  Phe  Ala  Phe  Gly  Gly
1175                1180                1185

Ala  Val  Glu  Asn  Pro  Glu  Tyr  Leu  Thr  Pro  Gln  Gly  Gly  Ala  Ala
     1190                1195                1200

Pro  Gln  Pro  His  Pro  Pro  Pro  Ala  Phe  Ser  Pro  Ala  Phe  Asp  Asn
1205                1210                1215

Leu  Tyr  Tyr  Trp  Asp  Gln  Asp  Pro  Pro  Glu  Arg  Gly  Ala  Pro  Pro
     1220                1225                1230

Ser  Thr  Phe  Lys  Gly  Thr  Pro  Thr  Ala  Glu  Asn  Pro  Glu  Tyr  Leu
     1235                1240                1245

Gly  Leu  Asp  Val  Pro  Val
          1250

<210> SEQ ID NO 3
<211> LENGTH: 23
<212> TYPE: DNA
<213> ORGANISM: Artificial Sequence
<220> FEATURE:
<223> OTHER INFORMATION: HER2 siRNA inhibitor forward sequence

<400> SEQUENCE: 3
ccuggaacuc accuaccugd tdt                                              23

<210> SEQ ID NO 4
<211> LENGTH: 23
<212> TYPE: DNA
<213> ORGANISM: Artificial Sequence
<220> FEATURE:
<223> OTHER INFORMATION: HER2 siRNA inhibitor reverse sequence

<400> SEQUENCE: 4
cagguaggug aguuccaggd tdt                                              23

<210> SEQ ID NO 5
<211> LENGTH: 23
<212> TYPE: DNA
<213> ORGANISM: Artificial Sequence
<220> FEATURE:
<223> OTHER INFORMATION: HER2 siRNA inhibitor forward sequence

<400> SEQUENCE: 5
cuaccuuucu acggacgugd tdt                                              23

<210> SEQ ID NO 6
<211> LENGTH: 23
<212> TYPE: DNA
<213> ORGANISM: Artificial Sequence
<220> FEATURE:
<223> OTHER INFORMATION: HER2 siRNA inhibitor reverse sequence

<400> SEQUENCE: 6
cacguccgua gaaagguagd tdt                                              23

<210> SEQ ID NO 7
<211> LENGTH: 23
<212> TYPE: DNA
<213> ORGANISM: Artificial Sequence
```

-continued

```
<220> FEATURE:
<223> OTHER INFORMATION: HER2 siRNA inhibitor forward sequence

<400> SEQUENCE: 7
gauccggaag uacacgaugd tdt                                              23

<210> SEQ ID NO 8
<211> LENGTH: 23
<212> TYPE: DNA
<213> ORGANISM: Artificial Sequence
<220> FEATURE:
<223> OTHER INFORMATION: HER2 siRNA inhibitor reverse sequence

<400> SEQUENCE: 8
caucguguac uuccggaucd tdt                                              23

<210> SEQ ID NO 9
<211> LENGTH: 5
<212> TYPE: PRT
<213> ORGANISM: Artificial Sequence
<220> FEATURE:
<223> OTHER INFORMATION: anti-ErbB3 antibody VH CDR1

<400> SEQUENCE: 9

His Tyr Val Met Ala
1               5

<210> SEQ ID NO 10
<211> LENGTH: 17
<212> TYPE: PRT
<213> ORGANISM: Artificial Sequence
<220> FEATURE:
<223> OTHER INFORMATION: anti-ErbB3 antibody VH CDR2

<400> SEQUENCE: 10

Ser Ile Ser Ser Ser Gly Gly Trp Thr Leu Tyr Ala Asp Ser Val Lys
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: anti-ErbB3 antibody VH CDR3

<400> SEQUENCE: 11

Gly Leu Lys Met Ala Thr Ile Phe Asp Tyr
1               5                   10

<210> SEQ ID NO 12
<211> LENGTH: 14
<212> TYPE: PRT
<213> ORGANISM: Artificial Sequence
<220> FEATURE:
<223> OTHER INFORMATION: anti-ErbB3 antibody VL CDR1

<400> SEQUENCE: 12

Thr Gly Thr Ser Ser Asp Val Gly Ser Tyr Asn Val Val Ser
1               5                   10

<210> SEQ ID NO 13
<211> LENGTH: 7
<212> TYPE: PRT
<213> ORGANISM: Artificial Sequence
<220> FEATURE:
```

<223> OTHER INFORMATION: anti-ErbB3 antibody VL CDR2

<400> SEQUENCE: 13

Glu Val Ser Gln Arg Pro Ser
1               5

<210> SEQ ID NO 14
<211> LENGTH: 11
<212> TYPE: PRT
<213> ORGANISM: Artificial Sequence
<220> FEATURE:
<223> OTHER INFORMATION: anti-ErbB3 antibody VL CDR3

<400> SEQUENCE: 14

Cys Ser Tyr Ala Gly Ser Ser Ile Phe Val Ile
1               5                   10

<210> SEQ ID NO 15
<211> LENGTH: 118
<212> TYPE: PRT
<213> ORGANISM: Artificial Sequence
<220> FEATURE:
<223> OTHER INFORMATION: VH anti-ErbB3 antibody

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Arg Trp Val Arg Gln Ala Pro Gly Lys Gly Leu Glu Trp Val
        35                  40                  45

Ser Val Ile Tyr Pro Ser Gly Gly Ala Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Tyr Gly Met Asp Val Trp Gly Gln Gly Thr
            100                 105                 110

Leu Val Thr Val Ser Ser
        115

<210> SEQ ID NO 16
<211> LENGTH: 110
<212> TYPE: PRT
<213> ORGANISM: Artificial Sequence
<220> FEATURE:
<223> OTHER INFORMATION: VL anti-ErbB3 antibody of SEQ ID No: 15

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Gly Ser Asp Ser Asn Ile Gly Arg Asn
            20                  25                  30

Tyr Ile Tyr Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Ile Ser
    50                  55                  60

Gly Ser Lys Ser Gly Thr Ser Ala Ser Leu Ala Ile Ser Gly Leu Arg
65                  70                  75                  80

```
Ser Glu Asp Glu Ala Glu Tyr His Cys Gly Thr Trp Asp Asp Ser Leu
            85                  90                  95

Ser Gly Pro Val Phe Gly Gly Thr Lys Leu Thr Val Leu
        100                 105                 110

<210> SEQ ID NO 17
<211> LENGTH: 445
<212> TYPE: PRT
<213> ORGANISM: Artificial Sequence
<220> FEATURE:
<223> OTHER INFORMATION: MM-121 antibody - heavy chain

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335
```

```
Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 18
<211> LENGTH: 217
<212> TYPE: PRT
<213> ORGANISM: Artificial Sequence
<220> FEATURE:
<223> OTHER INFORMATION: MM-121 antibody - light chain

<400> SEQUENCE: 18

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Val Val Ser Trp Tyr Gln Gln His Pro Gly Lys Ala Pro Lys Leu
        35                  40                  45

Ile Ile Tyr Glu Val Ser Gln Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95

Ser Ile Phe Val Ile Phe Gly Gly Gly Thr Lys Val Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215

<210> SEQ ID NO 19
<211> LENGTH: 21
<212> TYPE: DNA
<213> ORGANISM: Artificial Sequence
<220> FEATURE:
```

```
<223> OTHER INFORMATION: FoxO1 sense strand

<400> SEQUENCE: 19
ccauggacaa caacaguaat t                                              21

<210> SEQ ID NO 20
<211> LENGTH: 21
<212> TYPE: DNA
<213> ORGANISM: Artificial Sequence
<220> FEATURE:
<223> OTHER INFORMATION: FoxO3a sense strand

<400> SEQUENCE: 20
gccuugucga auucugucat t                                              21

<210> SEQ ID NO 21
<211> LENGTH: 21
<212> TYPE: DNA
<213> ORGANISM: Artificial Sequence
<220> FEATURE:
<223> OTHER INFORMATION: IGF-IR sense strand

<400> SEQUENCE: 21
ggagaauaau ccaguccuat t                                              21

<210> SEQ ID NO 22
<211> LENGTH: 21
<212> TYPE: DNA
<213> ORGANISM: Artificial Sequence
<220> FEATURE:
<223> OTHER INFORMATION: InsR sense strand

<400> SEQUENCE: 22
gaacgauguu ggacucauat t                                              21
```

COMBINATIONS OF KINASE INHIBITORS FOR THE TREATMENT OF CANCER

CROSS-REFERENCE TO RELATED APPLICATIONS

This application is a United States National Phase filing of PCT/US2011/043401, filed Jul. 8, 2011, which claims priority to U.S. Provisional Application No. 61/363,074, filed Jul. 9, 2010, and to U.S. Provisional Application No. 61/421,929, filed Dec. 10, 2010, both of which are incorporated herein by reference.

SEQUENCE LISTING

This application incorporates by reference in its entirety the Sequence Listing entitled "SequenceListing.txt" (28.2 KB) which was created Jul. 8, 2011 and filed herewith on Jul. 8, 2011.

FIELD

This invention relates to methods of treating cancer with a quinaxoline PI3K inhibitor in combination with one or more additional kinase inhibitors.

BACKGROUND

Improvements in the specificity of agents used to treat various disease states such as cancer, metabolic, and inflammatory diseases is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Phosphatidylinositol 3-kinase (PI3K) is composed of a 110 kDa catalytic subunit (encoded by the PIK3CA gene) and an 85 kDa regulatory subunit. The catalytic subunit uses ATP to phosphorylate PtdIns, PtdIns4P, and PtdIns(4,5)P2 to create the second messengers PtdIns3P, PtdIns(3,4)P2, and PtdIns (3,4,5)P3 (PIP3). PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation, and differentiation processes. Increased copy number and expression of PIK3CA or activating mutations in PIK3CA are associated with a number of malignancies such as ovarian cancer (Campbell et al., *Cancer Res* 2004, 64, 7678-7681; Levine et al., *Clin Cancer Res* 2005, 11, 2875-2878; Wang et al., *Hum Mutat* 2005, 25, 322; Lee et al., *Gynecol Oncol* 2005, 97, 26-34), cervical cancer, breast cancer (Bachman, et al. *Cancer Biol Ther* 2004, 3, 772-775; Levine, et al., supra; Li et al., *Breast Cancer Res Treat* 2006, 96, 91-95; Saal et al., *Cancer Res* 2005, 65, 2554-2559; Samuels and Velculescu, *Cell Cycle* 2004, 3, 1221-1224), colorectal cancer (Samuels, et al. *Science* 2004, 304, 554; Velho et al. *Eur J Cancer* 2005, 41, 1649-1654), endometrial cancer (Oda et al. *Cancer Res*. 2005, 65, 10669-10673), gastric carcinomas (Byun et al., *Int J Cancer* 2003, 104, 318-327; Li et al., supra; Velho et al., supra; Lee et al., *Oncogene* 2005, 24, 1477-1480), hepatocellular carcinoma (Lee et al., id.), small and non-small cell lung cancer (Tang et al., *Lung Cancer* 2006, 51, 181-191; Massion et al., *Am J Respir Crit. Care Med* 2004, 170, 1088-1094), thyroid carcinoma (Wu et al., *J Clin Endocrinol Metab* 2005, 90, 4688-4693), acute myelogenous leukemia (AML) (Sujobert et al., *Blood* 1997, 106, 1063-1066), chronic myelogenous leukemia (CML) (Hickey and Cotter *J Biol Chem* 2006, 281, 2441-2450), and glioblastomas (Hartmann et al. *Acta Neuropathol (Berl)* 2005, 109, 639-642; Samuels et al., supra). In view of the important role of PI3K-α in biological processes and disease states, inhibitors and/or modulators of this lipid kinase are desirable.

In addition, combining treatments with different mechanisms of action may lead to enhanced anti-tumor activity as compared to single treatments administered alone. For example, activation of the PI3K pathway may contribute to the resistance of human tumor cells to certain chemotherapeutic agents, such as microtubule stabilizing agents like taxol (Brognard, J., et. al. *Cancer Res* 2001, 61, 3986-3997; Clark, A. S., et. al. *Mol Cancer Ther* 2002, 1, 707-717; Kraus, A. C., et. al. *Oncogene* 2002, 21, 8683-8695; Krystal, G. W., et. al. *Mol Cancer Ther* 2002, 1, 913-922; and Yuan, Z. Q., et. al. *J Biol Chem* 2003, 278, 23432-23440).

Accordingly, treatments that combine an inhibitor of PI3K-α with other agents are desirable and needed.

SUMMARY

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The compositions of the invention are used to treat diseases associated with abnormal and or unregulated cellular activities. Disease states which can be treated by the methods and compositions provided herein include cancer. The invention is directed to methods of treating these diseases by administering a compound of formula I or I(a) in combination with one or more treatments.

One aspect of the invention is directed to a method of treating cancer which method comprises administering to a patient a therapeutically effective amount of a compound of formula I:

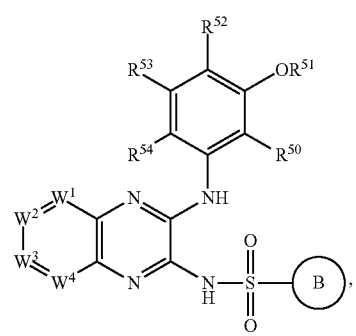

or a single isomer thereof, where the compound is optionally as a pharmaceutically acceptable salt, additionally optionally as a hydrate, and additionally optionally as a solvate thereof; or administering a pharmaceutical composition comprising a therapeutically effective amount of a compound of formula I and a pharmaceutically acceptable carrier, excipient, or diluent in combination with one or more inhibitors of HER3, HER2, MSPR, Axl, MAP3K (ERK, JNK, and p38 MAPK), MEKK kinases/kinase receptors, INSR, IGF-IR, and FGFR2, where the compound of formula I is that wherein:

$W^1$, $W^2$, $W^3$, and $W^4$ are —C($R^1$)═; or one or two of $W^1$, $W^2$, $W^3$, and $W^4$ are independently —N═ and the remaining are —C($R^1$)═; and where each $R^1$ is independently hydrogen, alkyl, haloalkyl, nitro, alkoxy, haloalkoxy, halo, hydroxy, cyano, amino, alkylamino, or dialkylamino;

$R^{51}$ is hydrogen or alkyl;

$R^{52}$ is hydrogen or halo;

$R^{50}$, $R^{53}$, and $R^{54}$ are independently hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$N$R^{55}$$R^{55a}$, or alkylcarbonylamino, and $R^{55}$ and $R^{55b}$ are independently hydrogen, alkyl, or alkenyl, and $R^{55a}$ is hydrogen, alkyl, alkenyl, hydroxy, or alkoxy; or $R^{53}$ and $R^{54}$ together with the carbons to which they are attached form a 5- or 6-membered heteroaryl or 5- or 6-membered heterocycloalkyl;

B is phenyl substituted with $R^{3a}$ and optionally further substituted with one, two, or three $R^3$; or B is heteroaryl optionally substituted with one, two, or three $R^3$;

$R^{3a}$ is cyano, hydroxyamino, carboxy, alkoxycarbonyl, alkylamino, dialkylamino, alkylcarbonyl, haloalkoxy, alkylsulfonyl, aminoalkyloxy, alkylaminoalkyloxy, or dialkylaminoalkyloxy; or a) —N($R^7$)C(O)—$C_1$-$C_6$-alkylene-N($R^{7a}$)($R^{7b}$), where $R^7$ is hydrogen, alkyl, or alkenyl, and $R^{7a}$ and $R^{7b}$ are independently hydrogen, alkyl, alkenyl, hydroxyalkyl, haloalkyl, alkoxy, alkoxyalkyl, aminoalkyl, alkylaminoalkyl, dialkylaminoalkyl, cycloalkyl, cycloalkylalkyl, heterocycloalkyl, heterocycloalkylalkyl, heteroaryl, heteroarylalkyl, aryl, arylalkyl, or arylalkyloxy, and where the aryl, cycloalkyl, heterocycloalkyl and heteroaryl rings in $R^{7a}$ and $R^{7b}$ (either alone or as part of arylalkyl, cycloalkylalkyl, heterocycloalkylalkyl, and heteroarylalkyl) are independently optionally substituted with 1, 2, or 3 groups independently selected from alkyl, amino, alkylamino, dialkylamino, hydroxy, halo, alkoxy, alkylthio, and oxo;

b) —C(O)N$R^8$$R^{8a}$, where $R^8$ is hydrogen, hydroxy, alkoxy, alkyl, alkenyl, haloalkyl, or haloalkoxy, and $R^{8a}$ is hydrogen, alkyl, alkenyl, hydroxyalkyl, cyanoalkyl, alkoxyalkyl, alkylthioalkyl, heterocycloalkyl, heterocycloalkylalkyl, cycloalkyl, cycloalkylalkyl, heteroaryl, heteroarylalkyl, aryl, or arylalkyl, and where the aryl, cycloalkyl, heteroaryl, and heterocycloalkyl rings in $R^{8a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, halo, haloalkyl, haloalkoxy, hydroxy, hydroxyalkyl, oxo, amino, alkylamino, dialkylamino, alkylcarbonyl, aminoalkyl, alkylaminoalkyl, dialkylaminoalkyl, alkoxycarbonyl, and —C(O)H;

c) —N$R^9$C(O)$R^{9a}$, where $R^9$ is hydrogen, hydroxy, alkoxy, alkyl, alkenyl, haloalkyl, or haloalkoxy, and $R^{9a}$ is hydrogen, $C_2$-$C_6$-alkyl, alkenyl, hydroxyalkyl, alkoxyalkyl, cycloalkyl, cycloalkylalkyl, heterocycloalkyl, heterocycloalkylalkyl, heteroaryl, heteroarylalkyl, aryl, or arylalkyl, and where the aryl, cycloalkyl, heteroaryl, and heterocycloalkyl rings in $R^{9a}$ (either alone or as part of arylalkyl, cycloalkylalkyl, heterocycloalkylalkyl, and heteroarylalkyl) are independently optionally substituted with 1, 2, or 3 groups independently selected from alkyl, alkenyl, alkoxy, hydroxy, hydroxyalkyl, halo, haloalkyl, haloalkoxy, oxo, amino, alkylamino, dialkylamino, alkylcarbonyl, alkoxycarbonyl, —C(O)H, aryl (optionally substituted with one or two halo), arylalkyl, heteroaryl, heteroarylalkyl, heterocycloalkyl, heterocycloalkylalkyl, cyloalkyl, cyloalkylalkyl, and cycloalkylcarbonyl;

d) —C(O)N($R^{10}$)—$C_1$-$C_6$-alkylene-N($R^{10a}$)$R^{10b}$, where $R^{10a}$ is hydrogen, hydroxy, alkoxy, alkyl, alkenyl, haloalkyl, aminoalkyl, alkylaminoalkyl, dialkylaminoalkyl, or hydroxyalkyl, and $R^{10}$ and $R^{10b}$ are independently hydrogen, alkyl, alkenyl, haloalkyl, aminoalkyl, alkylaminoalkyl, dialkylaminoalkyl, or hydroxyalkyl;

e) —N$R^{11}$C(O)N$R^{11a}$$R^{11b}$, where $R^{11a}$ is hydrogen, alkyl, alkenyl, hydroxy, or alkoxy, and $R^{11}$ and $R^{11b}$ are independently hydrogen, alkyl, alkenyl, aminoalkyl, alkylaminoalkyl, or dialkylaminoalkyl;

f) —C(O)$R^{12}$, where $R^{12}$ is heterocycloalkyl optionally substituted with 1, 2, or 3 groups selected from alkyl, oxo, amino, alkylamino, and heterocycloalkylalkyl;

g) —N$R^{13}$C(O)O$R^{13a}$, where $R^{13}$ is hydrogen, alkyl, or alkenyl, and $R^{13a}$ is aminoalkyl, alkylaminoalkyl, dialkylaminoalkyl, aryl, or arylalkyl;

h) —C(O)N($R^{14}$)N($R^{14a}$)($R^{14b}$), where $R^{14}$, $R^{14a}$, and $R^{14b}$ are independently hydrogen, alkyl, or alkenyl;

i) —S(O)$_2$N($R^{15}$)—$C_1$-$C_6$-alkylene-N($R^{15a}$)$R^{15b}$, where $R^{15}$, $R^{15a}$, and $R^{15b}$ are independently hydrogen, alkyl, or alkenyl;

j) —C(O)N($R^{16}$)—$C_1$-$C_6$-alkylene-C(O)O$R^{16a}$, where $R^{16}$ is hydrogen, alkyl, or alkenyl, and $R^{16a}$ is alkyl or alkenyl;

k) heteroaryl optionally substituted with one or two aminoalkyl, alkylaminoalkyl, or dialkylaminoalkyl;

l) —N($R^{17}$)—C(═N($R^{17b}$)($R^{17a}$))(N$R^{17c}$$R^{17d}$) where $R^{17}$, $R^{17a}$, $R^{17b}$, $R^{17c}$, and $R^{17d}$ are independently hydrogen, alkyl, or alkenyl;

m) —N($R^{18}$)C(O)—$C_1$-$C_6$-alkylene-N($R^{18b}$)C(O)$R^{18a}$, where $R^{18a}$ is hydrogen, alkyl, alkenyl, or alkoxy, and $R^{18}$ and $R^{18b}$ are independently hydrogen, alkyl, or alkenyl;

n) —C(O)N($R^{19}$)—$C_1$-$C_6$-alkylene-C(O)$R^{19a}$, where $R^{19}$ is hydrogen, alkyl, or alkenyl, and $R^{19a}$ is amino, alkylamino, dialkylamino, or heterocycloalkyl;

o) —N($R^{20}$)C(O)—$C_1$-$C_6$-alkylene-C(O)$R^{20a}$, where $R^{20}$ is hydrogen, alkyl, or alkenyl, and $R^{20a}$ is cycloalkyl or heterocycloalkyl;

p) —N$R^2$S(O)$_2$—$C_1$-$C_6$-alkylene-N($R^{21b}$)$R^{21a}$, where $R^{21}$ is hydrogen, alkyl, or alkenyl, and $R^{21a}$ and $R^{21b}$ are independently hydrogen, alkyl, or alkenyl;

q) —N($R^{22}$)C(O)—$C_1$-$C_6$-alkylene-N($R^{22b}$)—N($R^{22c}$)($R^{22a}$), where $R^{22}$, $R^{22a}$ and $R^{22b}$ are independently hydrogen, alkyl, or alkenyl;

r) —$C_0$-$C_6$-alkylene-N($R^{23}$)—$C_1$-$C_6$-alkylene-N($R^{23b}$)$R^{23a}$, where $R^{23}$, $R^{23a}$ and $R^{23b}$ are independently hydrogen, alkyl, or alkenyl; or s) —N$R^{24}$C(O)—$C_1$-$C_6$-alkylene-O$R^{24a}$, where $R^{24}$ is hydrogen, alkyl, or alkenyl, and $R^{24a}$ is alkoxyalkyl or aryl optionally substituted with one or two halo or alkyl; and wherein each of the alkylene in $R^{3a}$ is independently optionally further substituted with 1, 2, 3, 4, or 5 groups selected from halo, hydroxy, amino, alkylamino, and dialkylamino; and each $R^3$ (when $R^3$ is present) is independently alkyl, alkenyl, alkynyl, halo, hydroxy, oxo, alkoxy, cyano, hydroxyamino, carboxy, alkoxycarbonyl, amino, alkylamino, dialkylamino, alkylcarbonyl, haloalkoxy, alkylsulfonyl, aminoalkyloxy, alkylaminoalkyloxy, or dialkylaminoalkyloxy; or a) —N($R^7$)C(O)—$C_1$-$C_6$-alkylene-N($R^{7a}$)($R^{7b}$), where $R^7$ is hydrogen, alkyl, or alkenyl, and $R^{7a}$ and $R^{7b}$ are independently hydrogen, alkyl, alkenyl, hydroxyalkyl, haloalkyl, alkoxy, alkoxyalkyl, aminoalkyl, alkylaminoalkyl, dialkylaminoalkyl, cycloalkyl, cycloalkylalkyl, heterocycloalkyl, heterocycloalkylalkyl, heteroaryl, heteroarylalkyl, aryl, arylalkyl, or arylalkyloxy, and where the aryl, cycloalkyl, heterocycloalkyl and heteroaryl rings in $R^{7a}$ and $R^{7b}$ (either alone or as part of arylalkyl, cycloalkylalkyl, heterocycloalkylalkyl, and heteroarylalkyl) are independently optionally substituted with 1, 2, or 3 groups independently selected from alkyl, amino, alkylamino, dialkylamino, hydroxy, halo, alkoxy, alkylthio, and oxo;

b) —C(O)N$R^8R^{8a}$, where $R^8$ is hydrogen, hydroxy, alkoxy, alkyl, alkenyl, haloalkyl, or haloalkoxy, and $R^{8a}$ is hydrogen, alkyl, alkenyl, hydroxyalkyl, cyanoalkyl, alkoxyalkyl, alkylthioalkyl, heterocycloalkyl, heterocycloalkylalkyl, cycloalkyl, cycloalkylalkyl, heteroaryl, heteroarylalkyl, aryl, or arylalkyl, and where the aryl, cycloalkyl, heteroaryl, and heterocycloalkyl rings in $R^{8a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, halo, haloalkyl, haloalkoxy, hydroxy, hydroxyalkyl, oxo, amino, alkylamino, dialkylamino, alkylcarbonyl, aminoalkyl, alkylaminoalkyl, dialkylaminoalkyl, alkoxycarbonyl, and —C(O)H;

c) —N$R^9$C(O)$R^{9a}$, where $R^9$ is hydrogen, hydroxy, alkoxy, alkyl, alkenyl, haloalkyl, or haloalkoxy, and $R^{9a}$ is hydrogen, $C_2$-$C_6$-alkyl, alkenyl, hydroxyalkyl, alkoxyalkyl, cycloalkyl, cycloalkylalkyl, heterocycloalkyl, heterocycloalkylalkyl, heteroaryl, heteroarylalkyl, aryl, or arylalkyl, and where the aryl, cycloalkyl, heteroaryl, and heterocycloalkyl rings in $R^{9a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, hydroxy, hydroxyalkyl, halo, haloalkyl, haloalkoxy, oxo, amino, alkylamino, dialkylamino, alkylcarbonyl, alkoxycarbonyl, —C(O)H, aryl (optionally substituted with one or two halo), arylalkyl, heteroaryl, heteroarylalkyl, heterocycloalkyl, heterocycloalkylalkyl, cyloalkyl, cyloalkylalkyl, and cycloalkylcarbonyl;

d) —C(O)N($R^{10}$)—$C_1$-$C_6$-alkylene-N($R^{10a}$)$R^{10b}$, where $R^{10a}$ is hydrogen, hydroxy, alkoxy, alkyl, alkenyl, haloalkyl, or hydroxyalkyl, and $R^{10}$ and $R^{10b}$ are independently hydrogen, alkyl, alkenyl, haloalkyl, or hydroxyalkyl;

e) —N$R^{11}$C(O)N$R^{11a}R^{11b}$, where $R^{11a}$ is hydrogen, alkyl, alkenyl, hydroxy, or alkoxy, and $R^{11}$ and $R^{11b}$ are independently hydrogen, alkyl, alkenyl, aminoalkyl, alkylaminoalkyl, or dialkylaminoalkyl;

f) —C(O)$R^{12}$, where $R^{12}$ is heterocycloalkyl optionally substituted with 1, 2, or 3 groups selected from alkyl, oxo, amino, alkylamino, and heterocycloalkylalkyl;

g) —N$R^{13}$C(O)O$R^{13a}$, where $R^{13}$ is hydrogen, alkyl, or alkenyl and $R^{13a}$ is aminoalkyl, alkylaminoalkyl, dialkylaminoalkyl, aryl, or arylalkyl);

h) —C(O)N($R^{14}$)N($R^{14a}$)($R^{14b}$), where $R^{14}$, $R^{14a}$, and $R^{14b}$ are independently hydrogen, alkyl, or alkenyl;

i) —S(O)$_2$N($R^{15}$)—$C_1$-$C_6$-alkylene-N($R^{15a}$)$R^{15b}$, where $R^{15}$, $R^{15a}$, and $R^{15b}$ are independently hydrogen, alkyl, or alkenyl;

j) —C(O)N($R^{16}$)—$C_1$-$C_6$-alkylene-C(O)O$R^{16a}$, where $R^{16}$ is hydrogen, alkyl, or alkenyl, and $R^{16a}$ is alkyl or alkenyl;

k) heteroaryl optionally substituted with one or two aminoalkyl, alkylaminoalkyl, or dialkylaminoalkyl;

l) —N($R^{17}$)—C(=N($R^{17b}$)($R^{17a}$))(N$R^{17c}R^{17d}$), where $R^{17}$, $R^{17a}$, $R^{17b}$, $R^{17c}$, and $R^{17d}$ are independently hydrogen, alkyl, or alkenyl;

m) —N($R^{18}$)C(O)—$C_1$-$C_6$-alkylene-N($R^{18b}$)C(O)$R^{18a}$, where $R^{18a}$ is hydrogen, alkyl, alkenyl, or alkoxy, and $R^{18}$ and $R^{18b}$ are independently hydrogen, alkyl, or alkenyl;

n) —C(O)N($R^{19}$)—$C_1$-$C_6$-alkylene-C(O)$R^{19a}$, where $R^{19}$ is hydrogen, alkyl, or alkenyl, and $R^{19a}$ is amino, alkylamino, dialkylamino, or heterocycloalkyl;

o) —N($R^{20}$)C(O)—C-alkylene-C(O)$R^{20a}$, where $R^{20}$ is hydrogen, alkyl, or alkenyl, and $R^{20a}$ is cycloalkyl or heterocycloalkyl;

p) —N$R^{21}$S(O)$_2$—$C_1$-$C_6$-alkylene-N($R^{21b}$)$R^{21a}$, where $R^{21a}$ is hydrogen, alkyl, or alkenyl, and $R^{21a}$ and $R^{21b}$ are independently hydrogen, alkyl, or alkenyl;

q) —N($R^{22}$)C(O)—$C_1$-$C_6$-alkylene-N($R^{22b}$)—N($R^{22c}$)($R^{22a}$), where $R^{22}$, $R^{22a}$ and $R^{22b}$ are independently hydrogen, alkyl, or alkenyl;

r) —$C_0$-$C_6$-alkylene-N($R^{23}$)—$C_1$-$C_6$-alkylene-N($R^{23b}$)$R^{23a}$, where $R^{23}$, $R^{23a}$ and $R^{23b}$ are independently hydrogen, alkyl, or alkenyl; or s) —N$R^{24}$C(O)—$C_1$-$C_6$-alkylene-O$R^{24a}$, where $R^{24}$ is hydrogen, alkyl, or alkenyl, and $R^{24a}$ is alkoxyalkyl or aryl optionally substituted with one or two halo or alkyl;

wherein each of the alkylene in $R^3$ is independently optionally further substituted with 1, 2, 3, 4, or 5 groups selected from halo, hydroxy, amino, alkylamino, and dialkylamino; and provided that when $R^{50}$ and $R^{52}$ are hydrogen, $R^{15}$ is hydrogen or methyl, $R^{53}$ is hydrogen or methoxy, and $R^{54}$ is hydrogen or methoxy, then B is not 2,3-dihydro-1,4-benzodioxinyl, thien-2-yl, or thien-2-yl, substituted with one $R^3$, where $R^3$ is halo.

In one aspect, an inhibitor of HER3, MSPR, Axl, MAP3K (ERK, JNK, and p38 MAPK), or MEKK kinases/kinase receptors can be a functional nucleic acid, while in another it can be an antibody or protein display scaffold.

In another aspect, an inhibitor of HER3, HER2, MSPR, Axl, MAP3K (ERK, JNK, and p38 MAPK), MEKK kinases/kinase receptors, INSR, IGF-IR, or FGFR2 can be a functional nucleic acid, lapatinib, while in another it can be an antibody or protein display scaffold.

In one aspect, methods are provided for treating a patient with HER2 non-overexpressing cancer, comprising administering to the patient a therapeutically effective amount of compound A and a therapeutically effective amount of MM-121. In one embodiment, the cancer comprises a non-HER2 amplified tumor. In some embodiments, the combination exhibits therapeutic synergy in the treatment of HER2 non-overexpressing cancer. In other embodiments, the combination effects a $\log_{10}$ cell kill of at least 2.8, at least 2.9 or at least 3.0.

In another aspect, the cancer comprises a HER2 non-overexpressing cancer.

In another aspect, the cancer comprises a non-HER2 amplified tumor.

In another aspect, a therapeutically effective amount of Compound A is co-administered with a therapeutically effective amount of MM-121.

In another aspect, the combination of Compound A and MM121 exhibits therapeutic synergy in the treatment of cancer.

In another aspect, the combination of Compound A and MM121 exhibits effects a $\log_{10}$ cell kill of at least 2.8, at least 2.9 or at least 3.0.

In another aspect, the cancer is lung cancer.

LIST OF FIGURES

The patent or application file contains at least one drawing executed in color. Copies of this patent or patent application publication with color drawing(s) will be provided by the Office upon request and payment of the necessary fee.

FIG. 1A. siRNA screen to identify kinases that potentially compensate for PI3K inhibition. HCC1937 breast cancer cells were treated with the indicated amounts of compound A for 6, 24, or 72 hours in medium containing 2.5% FBS. Cell lysates analyzed by immunoblotting with the indicated antibodies.

FIG. 1B. siRNA screen to identify kinases that potentially compensate for PI3K inhibition. HCC1937 cells were seeded in triplicate in a 96-well plate and treated with DMSO or the indicated concentration of compound A for 72 hours. Cell viability was measured by the alamar blue assay.

FIG. 2. Scheme of the RNAi screen. The Dharmacon RTF Protein Kinase siRNA library, which contains SMARTpool siRNAs targeting 779 kinases, was used. HCC1937 cells were reverse-transfected in 96-well plates with 5 pmol siRNA/well. Plates were split 1:6 and treated with DMSO or 10 μM compound A for 72 hours. Cell viability was measured using the alamar blue assay. The screen has been performed twice.

FIGS. 3A and 3B. PI3K inhibition induces phosphorylation of RTKs and intracellular kinases. HCC1937 cells were treated with 10 μM compound A in medium containing 2.5% FBS for 0, 8, 24, or 48 hours. Media and drugs were replenished every 24 hours. Lysates were used to probe phospho-RTK arrays (FIG. 3A) or phospho-kinase arrays (FIG. 3B) (R&D systems). Corner spots are positive controls. Candidate kinases from the siRNA screen that are also phosphorylated upon treatment with compound A are shown in red.

FIGS. 4A and 4B. HCC1937 cells were treated with 10 μM compound A in medium containing 2.5% FBS for 0, 8, 24, or 48 hours. Media and drugs were replenished every 24 hours. Lysates were used to probe phospho-RTK arrays (A) or phospho-kinase arrays (B) (R&D systems). Corner spots are positive controls. Candidate kinases from the siRNA screen that are also phosphorylated upon treatment with compound A are shown in red.

FIG. 5. HCC1937 cells were treated with 10 μM compound A in medium containing 2.5% FBS for 0, 2, 8, or 24 hours. RNA was isolated with Trizol and purified using the RNeasy column (Qiagen). Gene expression from three independent experiments was measured using the Gene titan 3' microarray. *, $p<0.05$; **, $p<0.01$ versus 0 hours.

FIG. 6A. HER3 siRNA enhances the anti-proliferative effect of a PI3K inhibitor. BT474 Cells were transfected with control or HER3 siRNA oligonucleotides followed by treatment with 6 μM compound A in medium containing 2.5% FBS. Cells were harvested for proliferation assay (A).

FIG. 6B. HER3 siRNA enhances the anti-proliferative effect of a PI3K inhibitor. Crystal violet staining on day 6 post-transfection.

FIG. 7. BT-474 cells were treated with 6 uM compound A. Fresh medium and inhibitor were replenished every 24 hours. At the indicated times, cells were harvested in NP-40 lysis buffer containing protease and phosphatase inhibitors. Lysates were prepared, separated by SDS-PAGE, and subjected to immunoblot analysis with the indicated antibodies.

FIGS. 8A and 8B. MDA-453 (A) and SKBR-3 (B) cells were transfected with 10 nM HER3 or control siRNA duplexes in the presence of lipofectamine RNAiMAX as described in FIG. 7. Left panels: Following transfection, cells were maintained in medium containing 5% serum±2 uM compound A and harvested 24 hours later. Cell lysates were prepared and subjected to immunoblot analysis with the indicated antibodies. Actin was used as a control. Right panels: Following transfection, $2.5\times10^4$ cells/well were seeded on 12-well plates and maintained in medium containing 5% FCS±2 uM compound A. On day 6 post-transfection, cells were trypsinized and their numbers quantified in a Coulter counter. Each bar represents the mean cell number±SE of 3 wells (*, $p<0.001$ for MDA-453, $p<0.01$ for SKBR-3).

Figure 10A:
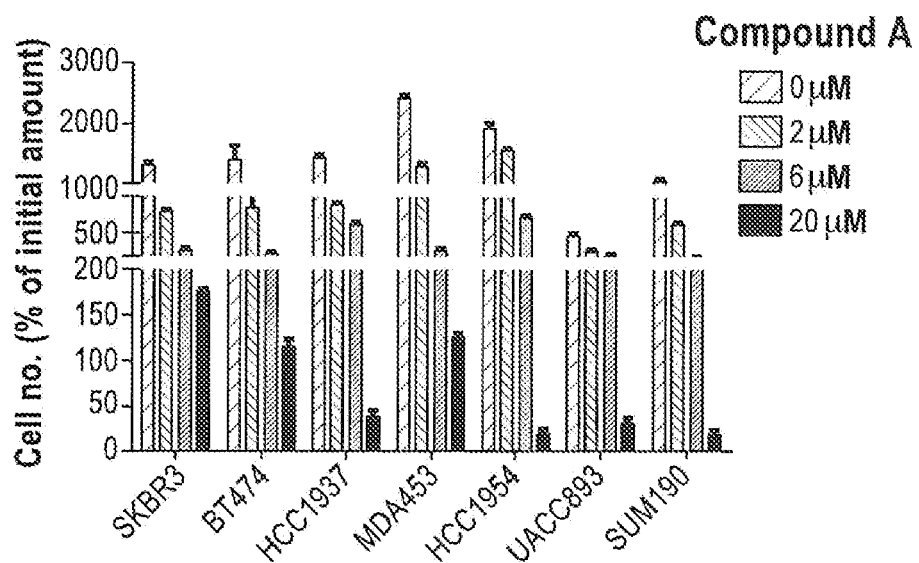
FIG. 10A depicts a bar graph of percent of cell number relative to the initial amount of plated cells as provided in FIG. 9A above was calculated for each breast cancer cell line treated with the indicated concentrations of compound A. Numbers below 100% (straight black line) are indicative of apoptosis.
Figure 10B:
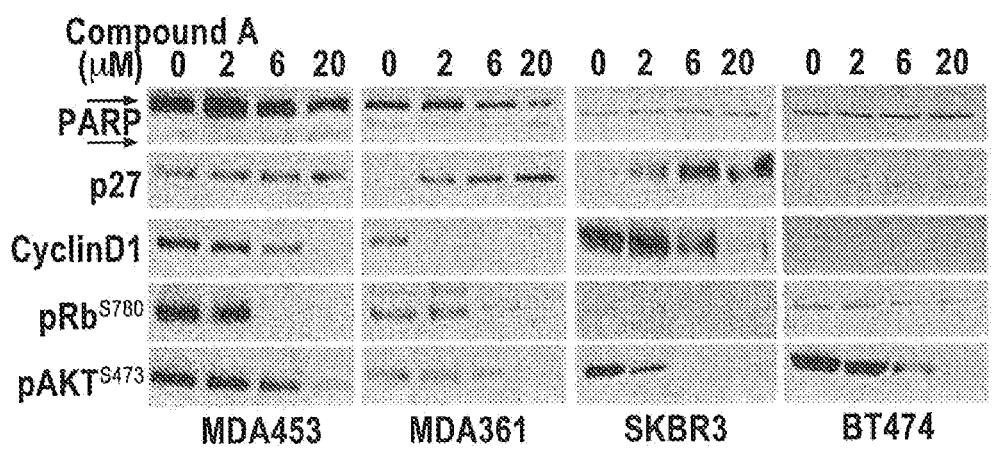

FIG. 10B depicts immunoblots wherein cells were treated with 0-20 μM compound A for 24 hours. Cell lysates were prepared and subjected to immunoblotting with the antibodies indicated to the left of the panels. The upper arrow indicates total PARP and lower arrow indicates cleaved PARP.

Figure 11:
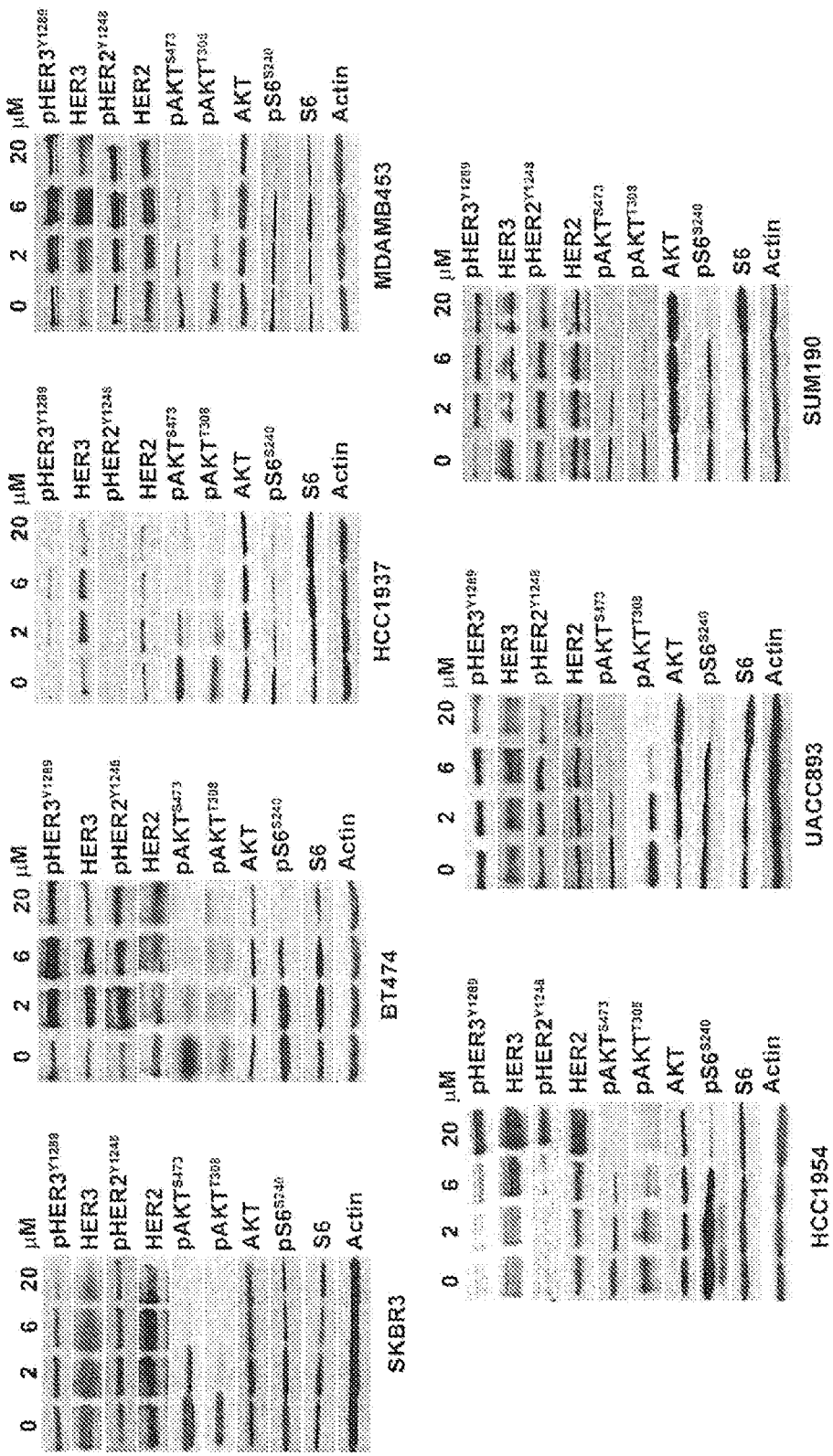

FIG. 11 depicts immunoblots of various cell lines treated overnight in serum-free medium with 0-20 μM compound A. Cells were harvested and lysates were used for immunoblotting analysis with the indicated antibodies.

FIG. 12A depicts a bar chart of timed HER3 mRNA transcription in BT474 cells which were treated with 6 μM compound A for the indicated times prior to RNA isolation and real-time qPCR analysis with HER3-specific primers.

FIG. 12B depicts a bar chart of timed HER3 mRNA transcription in BT474 cells which were treated with 2 μM 5J8, 20 μM LY294002, and 50 nM rapamycin for 10 hours prior to RNA isolation and qPCR analysis with HER3-specific primers.

FIG. 12C depicts a bar chart of HER3 mRNA transcription in MDA453 and SKBR3 cells which were treated with 6 μM compound A over the indicated time course up to 48 hours prior to RNA isolation and qPCR analysis with HER3-specific primers.

FIG. 12D depicts a photomicrrograph of immunoblots of cell lysates from BT474 and MDA453 cells which were treated with DMSO (control), 6 μM compound A, or 2 μM 5J8 for 4 hours. Nuclear (Nu) and cytoplasmic (Cy) extracts were isolated and subjected to immunoblotting with FoxO1 and FoxO3a antibodies. Loading controls for Nu: HDAC3; for Cy: RhoA (BT474) and MEK1/2 (MDA453). Arrow indicates the FoxO3a-specific band.

FIG. 12E depicts a bar chart representing BT474, MDA453, and SKBR3 cells which were transfected with either control or FoxO1 and FoxO3a-specific siRNA duplexes. Two days after transfection cells were treated with compound A for 6 hours prior to harvesting, RNA preparation, and qPCR analysis for HER3.

FIG. 12F depicts a bar chart representing BT474, MDA453 and SKBR3 cells which were transfected with either control or FoxO1 and FoxO3a-specific siRNA duplexes. Two days after transfection cells were treated with compound A for 6 hours prior to harvesting, RNA preparation, and qPCR analysis for FoxO1 and FoxO3a.

FIG. 13A depicts a photomicrrograph of immunoblots of cell lysates from BT474 cells which were treated with 6 μM compound A over a time course up to 72 hours and subjected to immunoblotting using the various antibodies listed on the Y-axis. compound A and media were replenished every 24 hours.

FIG. 13B depicts a photomicrrograph of immunoblots of cell lysates from BT474 cells which were treated with 6 μM or 20 μM compound A for 0-48 hours. Cell lysates were subjected to immunobloting with the indicated antibodies.

FIG. 13C depicts a photomicrrograph of immunoblots of cell lysates from BT474 cells which were treated with 0-20 μM compound A for 24 hours. Cells were then lysed, and 0.5 mg of lysate subjected to immunoprecipitation (IP) with a p85 antibody followed by p85 and pTyr.

FIG. 13D depicts a photomicrrograph of immunoblots of cell lysates from BT474 cells which were treated with 0-20 μM compound A for 24 hours. Cells were then lysed, and 0.5 mg of lysate subjected to immunoprecipitation (IP) with a p85 antibody followed by p85 and HER3.

FIG. 13E depicts a photomicrrograph of immunoblots of cell lysates from BT474 cells which were transfected with control or HER3-specific siRNA duplexes, followed by treatment with 6 μM compound A for 24 hours. Cell lysates were prepared, and 0.5 mg subjected to IP with a p85 antibody. Immune complexes were separated by SDS-PAGE and immunoblotted with p85 and HER3 antibodies.

FIG. 13F depicts a photomicrrograph of immunoblots of cell lysates from BT474 cells which were transfected with control or HER3-specific siRNA duplexes, followed by treatment with 6 μM compound A for 24 hours. Cell lysates were prepared, and 0.5 mg subjected to IP with a p85 antibody. Immune complexes were separated by SDS-PAGE and immunoblotted with p85 and pHER3$^{Y1197}$ antibodies.

FIG. 13G depicts a bar-graph representing BT474 cells which were transfected with HER3-specific siRNA and one day post-transfection treated with DMSO or 2 μM compound A. Growth medium and inhibitor were replenished every 3 days. Cells were harvested for counting on day 6.

FIG. 13H depicts a photomicrograph representing BT474 cells which were transfected with HER3-specific siRNA and one day post-transfection treated with DMSO or 2 μM compound A. Growth medium and inhibitor were replenished every 3 days. Cells were crystal violet stained on day 6 and photographed.

Figure 14A:
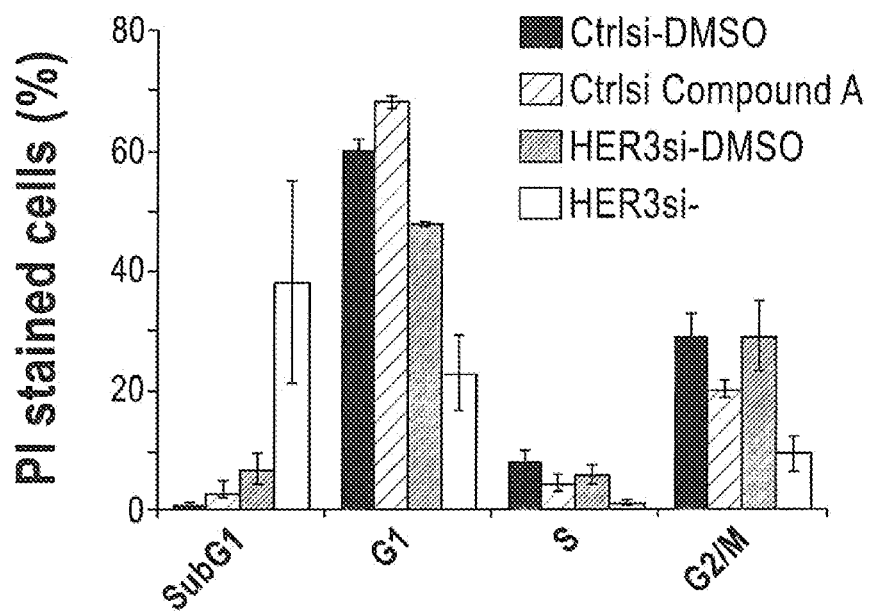

FIG. 14A depicts a bar-graph representing number of PI stained BT474 cells after transfection with HER3 siRNA or control duplexes and then treated with 6 μM compound A for 3 days. At this time, cells were washed, harvested, and prepared for cell cycle analysis.

Figure 14B:
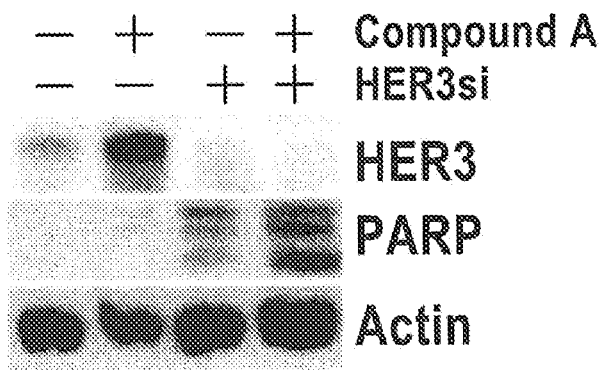

FIG. 14B depicts a photomicrograph of an immunoblot of cell lysates from BT474 cells which were transfected with control or HER3-specific siRNA duplexes, followed by treatment with 6 μM compound A and then immunoblotted with HER3 and PARP antibodies.

FIG. 15A depicts a photomicrograph of immunoblots of cell lysates from MDA453 cells which were transfected with control or HER3-specific siRNA duplexes, followed by treatment with 6 μM compound A for 24 hours. Cell lysates were prepared and subjected to immunoblotting with the indicated antibodies on the Y-axis.

FIG. 15B depicts a bar graph illustrating the growth or decline of MDA453 cells as indicated in FIG. 7A, except cells were allowed to grow while replenishing fresh medium and compound A (2 μM) every 3 days and counted on day 10.

FIG. 15C depicts a photomicrograph of immunoblots of cell lysates from SKBR3 cells which were transfected with control or HER3-specific siRNA duplexes, followed by treatment with 6 μM compound A for 24 hours. Cell lysates were prepared and subjected to immunoblotting with the indicated antibodies on the Y-axis.

FIG. 15D depicts a bar graph illustrating the growth or decline of SKBR3 cells as indicated in FIG. 7C, except cells were allowed to grow while replenishing fresh medium and compound A (2 μM) every 3 days and counted on day 10.

FIG. 16A depicts a bar-graph illustrating the cell growth or inhibition of BT474 cells which were treated in the absence or presence of 2 μM compound A alone or in combination with 0.1 μM lapatinib (Lap).

FIG. 16B depicts a bar-graph illustrating the cell growth or inhibition of BT474 cells which were treated in the absence or presence of 2 μM compound A alone or in combination with 10 μg/ml trastuzumab (Tras).

FIG. 16C depicts a photomicrograph of immunoblots for biomarkers of apoptosis and $G_1$-S phase transition with lysates from BT474 cells treated with the indicated inhibitors for 72 hours.

FIG. 16D depicts a bar-graph indicating real-time qPCR analysis of HER3 mRNA in cells treated with compound A (6 μM), lapatinib (1 μM), trastuzumab (10 μg/ml), or the indicated combinations for 10 hours.

FIG. 16E depicts photomicrograph of an immunoblot of cell lysates from BT474 cells which measured the presence of HER3 and phosphorylated HER3 in the cell lysates after treatment with compound A (6 μM), lapatinib (1 μM), trastuzumab (10 μg/ml), or the indicated combinations over a time course (0-24 hours).

Figures 17A, 17B:
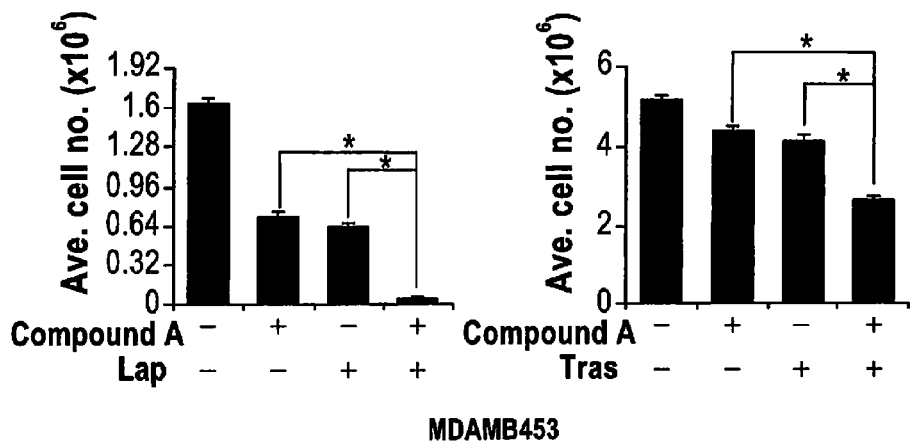

FIG. 17A depicts a bar-graph illustrating the cell growth or inhibition of HER2-dependent MDAMB453 cells treated with 0.1 μM lapatinib, or 2 μM compound A either alone or in the indicated combinations for a total of 6 days.

FIG. 17B depicts a bar-graph illustrating the cell growth or inhibition of HER2-dependent MDAMB453 cells treated with 10 μg/ml trastuzumab, or 2 μM compound A either alone or in the indicated combinations for a total of 6 days.

Figures 17C, 17D:
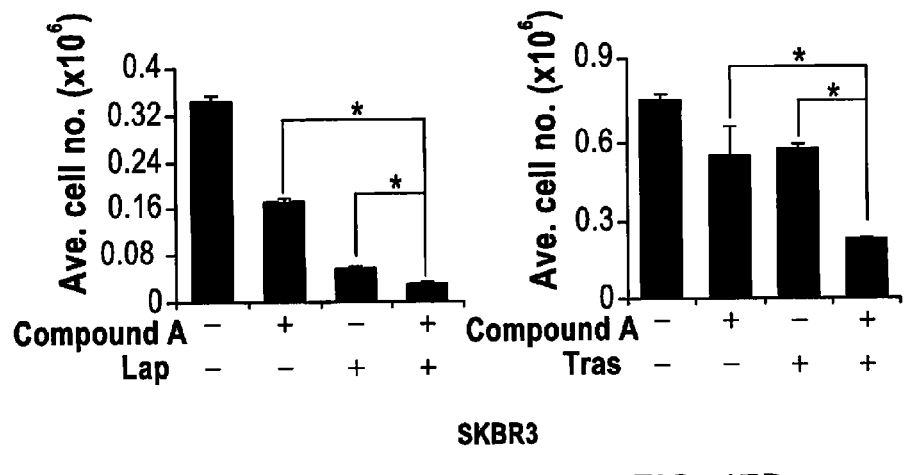

FIG. 17C depicts a bar-graph illustrating the cell growth or inhibition of HER2-dependent SKBR3 cells treated with 0.1 μM lapatinib, or 2 μM compound A either alone or in the indicated combinations for a total of 6 days.

FIG. 17D depicts a bar-graph illustrating the cell growth or inhibition of HER2-dependent SKBR3 cells treated with 10 μg/ml trastuzumab, or 2 μM compound A either alone or in the indicated combinations for a total of 6 days.

Figure 18A:
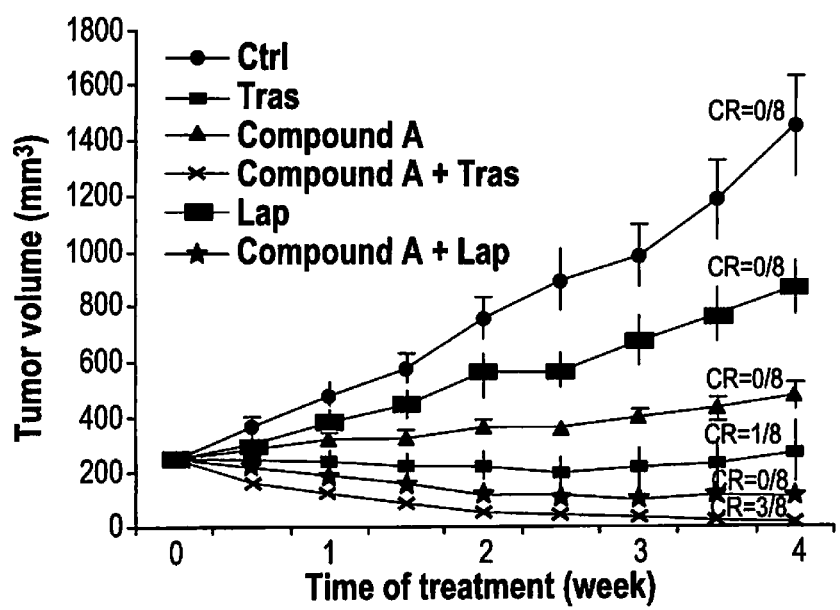

FIG. 18A depicts a graph illustrating the suppression of BT474 cells which were injected s.c. into estrogen-supplemented female athymic mice as described in Methods. Once tumors reached a volume ≥200 mm$^3$, mice were randomized to vehicle (control), compound A, lapatinib, trastuzumab, or the indicated combinations for 28 days. Tumor volumes were recorded twice-a-week. Each data point represents the mean tumor volume in mm$^3$±SE of 8 mice per type of treatment. CR=complete response to treatment.

Figure 18B:
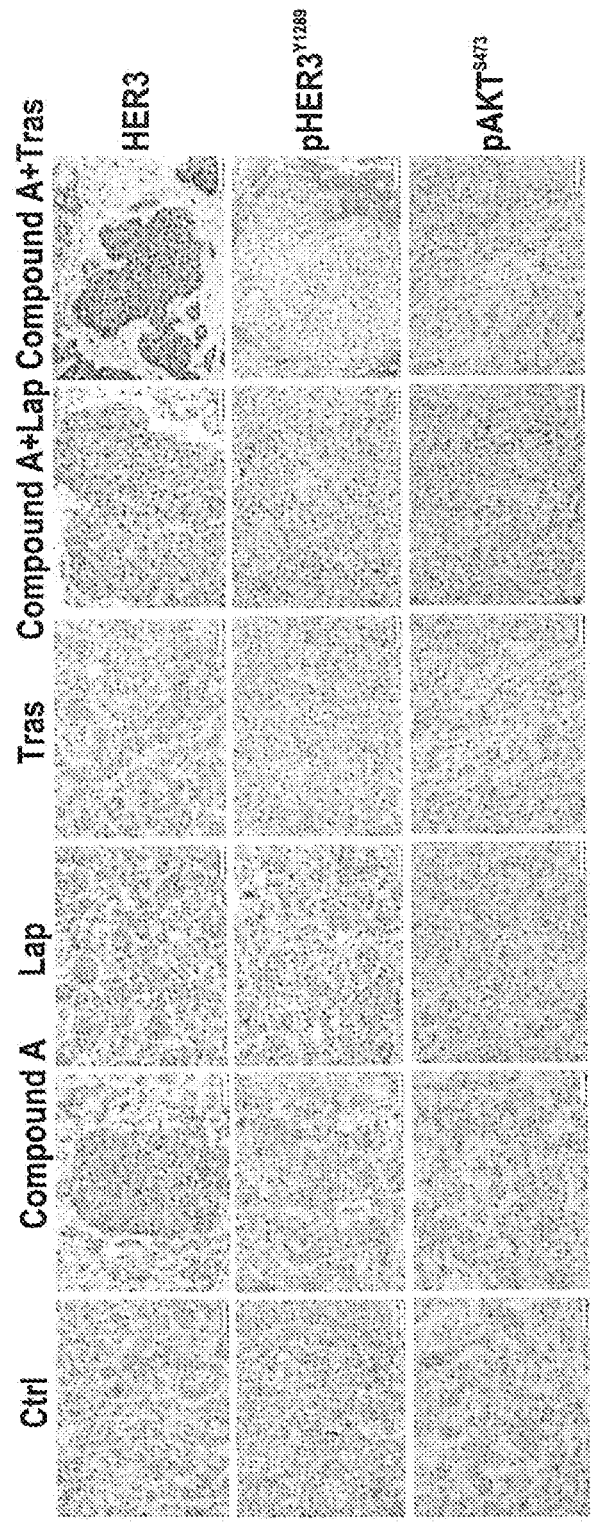

FIG. 18B depicts photomicrographs of immunohistochemistry sections from formalin-fixed, paraffin-embedded tumor blocks. Xenografts were harvested on day 28, 1 hour after the last dose of lapatinib and/or compound A. Antibodies used were against HER3, pHER3$^{Y1289}$, and pAKT$^{S473}$. Photographs were taken at 400× magnification (scale bar: 50 μm).

Figure 18C:
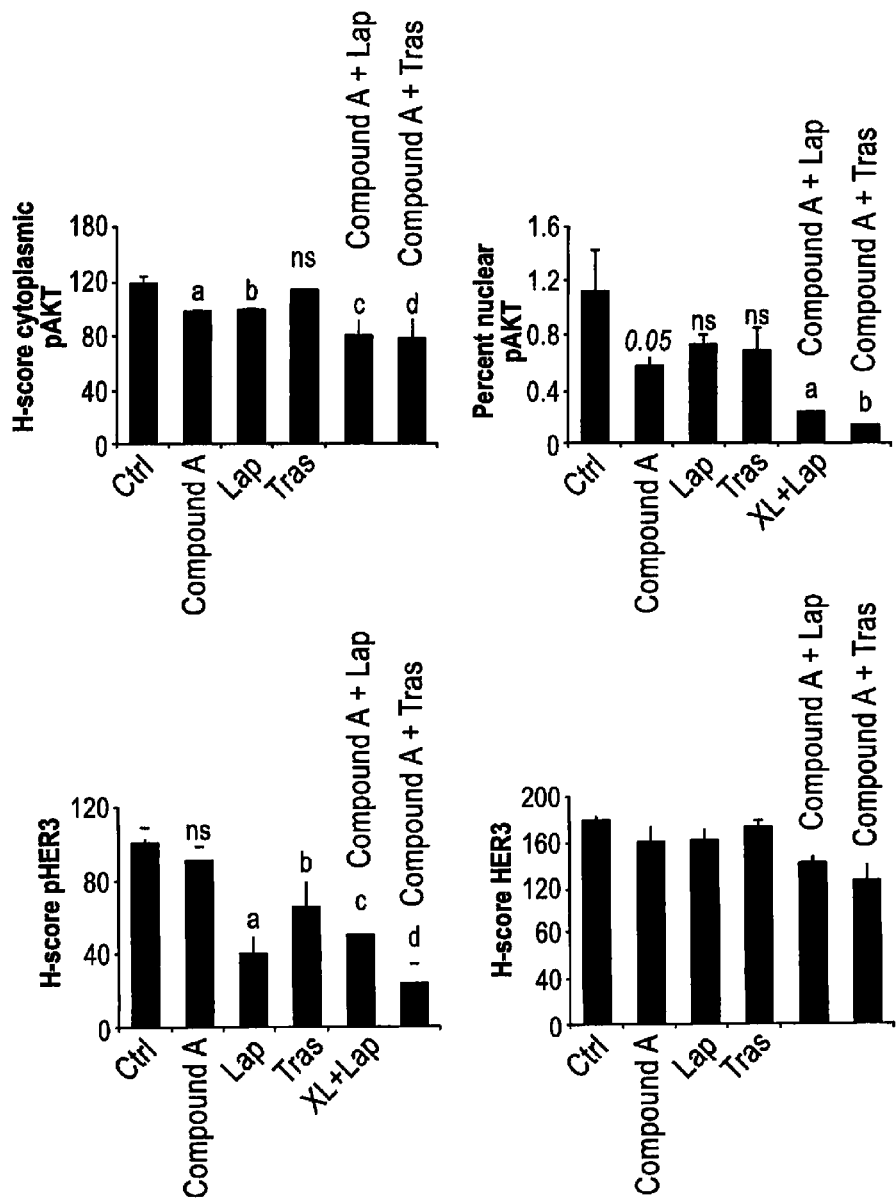

FIG. 18C depicts bar graphs representing the Histoscore (H-score) analysis of immunostained sections as provided in FIG. 18B.

Figure 19A:
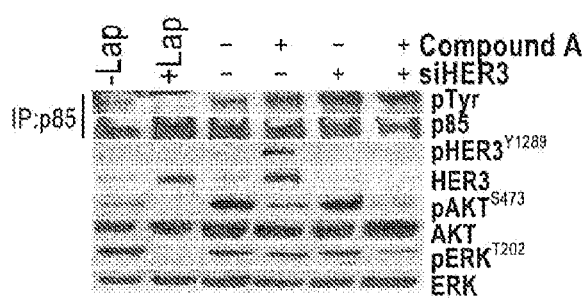

FIG. 19A depicts a photomicrograph of an immunoblot representing BT474 cells which were transfected with HER3 siRNA duplexes and treated with compound A for 24 hours. Cell lysates were prepared and 0.5 mg was immunoprecipitated with a p85 antibody. Immune complexes were next subjected to immunoblotting with antibodies indicated to the right of the panel. Cell lysates from BT474 cells treated with and without 1 μM lapatinib for 6 hours were used as controls (lanes 1 & 2).

Figure 19B:
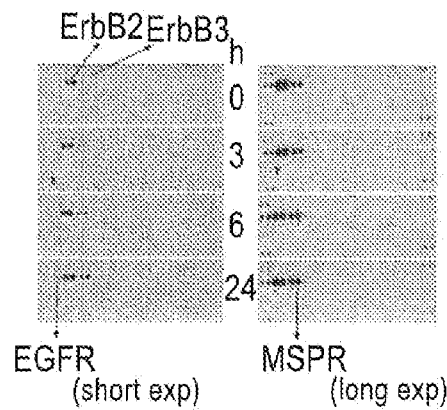

FIG. 19B depicts a photomicrograph of BT474 cells were treated with 6 μM compound A over a time course up to 24 hours as indicated. Cell lysates were prepared, and 200 μg of total protein were hybridized to arrays containing probes for 42 different receptors of tyrosine kinase (RTKs). Arrows indicate RTKs whose phosphorylation were upregulated upon treatment with the PI3K inhibitor.

Figure 19C:
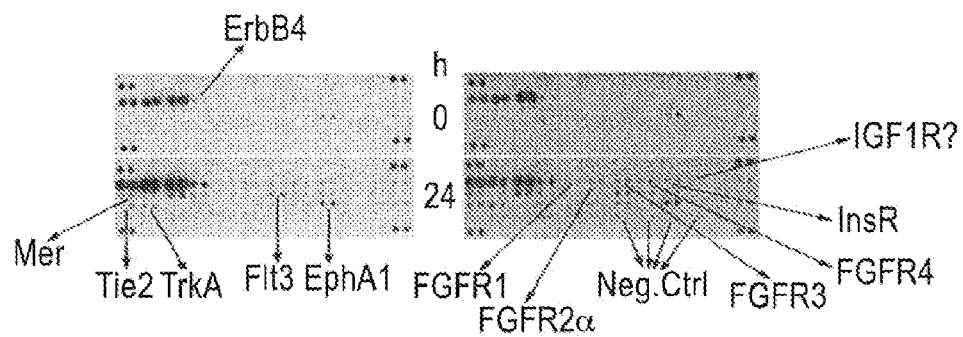

FIG. 19C depicts a photomicrograph of BT474 cells were treated with 6 μM compound A over a time course up to 24 hours as indicated. Cell lysates were prepared, and 500 μg of total protein were hybridized to arrays containing probes for 42 different receptors of tyrosine kinase (RTKs) Arrows indicate RTKs whose phosphorylation were upregulated upon treatment with the PI3K inhibitor.

Figure 19D:
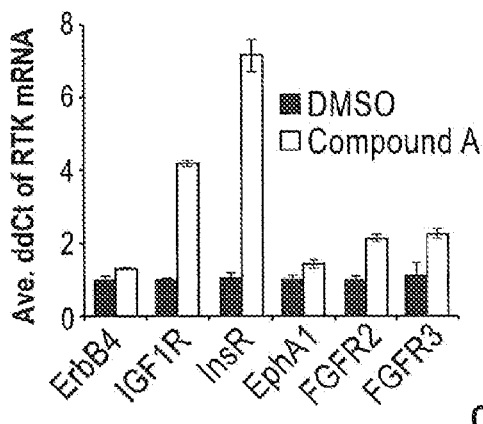

FIG. 19D depicts a bar-graph representing the amount of RTK mRNA as identified using real-time qPCR analysis of the indicated RTKs in RNA collected from BT474 cells treated with either DMSO or 10 μM compound A for 6 hours.

Figure 19E:
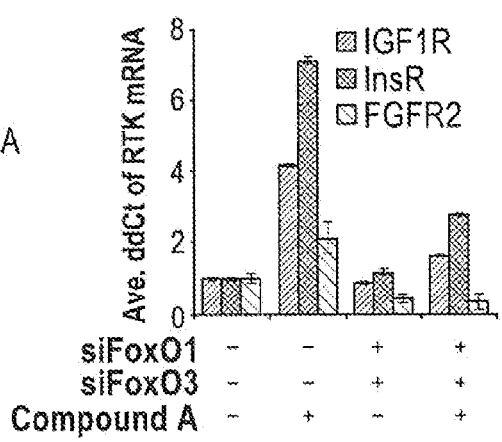

FIG. 19E depicts a bar-graph representing the amount of IGF-IR, InsR, and FGFR2 mRNA as identified using real-time qPCR in RNA extracted from BT474 cells transfected with FoxO1 and FoxO3a siRNA duplexes and then treated with 10 μM compound A for 6 hours.

FIG. 20A depicts a bar-graph representing IGF1R mRNA levels in BT474, MDA453, and MCF7 cells which were transfected with IGF-IR siRNA or control duplexes. Forty-eight hours later, RNA was isolated and subjected to qPCR analysis for IGF-IRmRNA levels.

FIG. 20B depicts a bar-graph representing InsR mRNA levels in BT474, MDA453, and MCF7 cells which were transfected with InsR siRNA or control duplexes. Forty-eight hours later, RNA was isolated and subjected to qPCR analysis for InsR mRNA levels.

FIG. 20C depicts a bar-graph representing inhibition of BT474 cells which were transfected with either IGF-IR siRNA or InsR siRNA or control duplexes. Forty-eight hours later they were treated with 10 μM compound A for a total of 4 days. At this time, the cells were counted.

FIG. 20D depicts a bar-graph representing inhibition of MDAMB453 cells which were transfected with either IGF-IR siRNA, InsR siRNA, or control duplexes. Forty-eight hours later they were treated with 10 μM compound A for a total of 4 days. At this time, the cells were counted.

FIG. 20E depicts a bar-graph representing inhibition of MCF7 cells which were transfected with either IGF-IR siRNA, InsR siRNA, or control duplexes. Forty-eight hours later they were treated with 10 μM compound A for a total of 4 days. At this time, the cells were counted.

DETAILED DESCRIPTION

Abbreviations and Definitions

The following abbreviations and terms have the indicated meanings throughout:

| Abbreviation | Meaning |
| --- | --- |
| Ab | Antibody |
| br | Broad |
| ° C. | Degrees Celsius |
| CBZ | CarboBenZoxy = benzyloxycarbonyl |
| d | Doublet |
| dd | Doublet of doublet |
| dt | Doublet of triplet |
| EI | Electron Impact ionization |
| Et | Ethyl |
| g | Gram(s) |
| GC | Gas chromatography |
| h or hr | Hour(s) |
| HPLC | High pressure liquid chromatography |
| L | Liter(s) |
| M | Molar or molarity |
| m | Multiplet |
| mg | Milligram(s) |
| MHz | Megahertz (frequency) |
| Min | Minute(s) |
| mL | Milliliter(s) |
| mM | Millimolar |
| mmol | Millimole(s) |
| mol | Mole(s) |
| MS | Mass spectral analysis |
| N | Normal or normality |
| nM | Nanomolar |
| NMR | Nuclear magnetic resonance spectroscopy |
| q | Quartet |
| RT | Room temperature |
| s | Singlet |
| s- | Secondary |
| t- | Tertiary |
| t or tr | Triplet |
| TFA | Trifluoroacetic acid |
| THF | Tetrahydrofuran |
| μL | Microliter(s) |
| μM | Micromole(s) or micromolar |

Definitions

The symbol "—" means a single bond, "=" means a double bond, "≡" means a triple bond, and " --- " means a single bond and optionally a double bond. When chemical structures are depicted or described, unless explicitly stated otherwise, all carbons are assumed to have hydrogen substitution to conform to a valence of four.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, chemotherapy, etc.), "administration" and its variants are each understood to include concurrent and sequential introduction of the compound or prodrug thereof and other agents.

"Alkenyl" or "lower alkenyl" means a straight or branched hydrocarbon radical having from 2 to 6 carbon atoms and at least one double bond. Representative examples include ethenyl, propenyl, 1-but-3-enyl, 1-pent-3-enyl, 1-hex-5-enyl, and the like.

"Alkenylcarbonyl" means a C(O)R group, where R is alkenyl, as defined herein.

"Alkenyloxy" or "lower alkenyloxy" means an —OR group where R is alkenyl, as defined herein. Representative examples include methoxy, ethoxy, 1-methoxyprop-1-en-3-yl, propoxy, isopropoxy, cyclopropyloxy, cyclohexyloxy, and the like.

"Alkoxy" or "lower alkoxy" means an —OR group where R is alkyl, as defined herein. Representative examples include methoxy, ethoxy, 1-methoxyprop-1-en-3-yl, propoxy, isopropoxy, cyclopropyloxy, cyclohexyloxy, and the like.

"Alkoxyalkyl" means an alkyl group, as defined herein, substituted with one, two, or three alkoxy groups, as defined herein.

"Akoxycarbonyl" means a —C(O)OR group, where R is alkyl, as defined herein.

"Alkoxyycarbonylalkyl" means an alkyl group, as defined herein, substituted with one, two, or three alkoxycarbonyl groups, as defined herein.

"Alkyl" or "lower alkyl" means a linear or branched hydrocarbon group having one to six carbon atoms. Examples of lower alkyl groups include methyl, ethyl, propyl, isopropyl, butyl, s-butyl, t-butyl, isobutyl, pentyl, hexyl, and the like. A "$C_0$" alkyl (as in "$C_0$-$C_6$-alkyl") is a covalent bond. "$C_6$ alkyl" refers to, for example, n-hexyl, iso-hexyl, and the like.

"Alkylamino" means a —NHR radical, where R is alkyl, as defined herein, or an N-oxide derivative thereof, e.g., methylamino, ethylamino, n-, iso-propylamino, n-, iso-, tert-butylamino, methylamino-N-oxide, and the like.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a C(O)R group where R is alkyl, as defined herein.

"Alkylcarbonylamino" means a —NRC(O)R' group, where R is hydrogen or alkyl, as defined herein, and R' is alkyl, as defined herein.

"Alkylene" refers to straight or branched divalent hydrocarbon, containing no unsaturation and having from two to eight carbon atoms. Examples of alkylene include eth-diyl (—CH₂CH₂—), prop-1,3-diyl (—CH₂CH₂CH₂—), 2,2-dimethylprop-1,3-diyl (—CH₂C(CH₃)₂CH₂—), and the like.

"Alkylsulfonyl" means a —S(O)₂R group, where R is alkyl, as defined herein.

"Alkylthio" means a —SR group, where R is alkyl, as defined herein. Examples of alkylthio include methylthio, ethylthio, and the like.

"Alkylthioalkyl" means an alkyl group substituted with one or two alkylthio groups, as defined herein, e.g. 2-(methylthio)-ethyl and 2-(ethylthio)-ethyl.

"Alkynyl" or "lower alkynyl" means a straight or branched hydrocarbon radical having from 2 to 6 carbon atoms and at least one triple bond. Representative examples include ethynyl, propynyl, butynyl, pentyn-2-yl, and the like.

"Amino" means a —NH₂ group.

"Aminoalkyl" means an alkyl group substituted with at least one, for example one, two, or three, amino groups.

"Aminoalkyloxy" means an —OR group, where R is aminoalkyl, as defined herein.

"Antisense" or "antisense oligonucleotide" refers to a nucleic acid molecule complementary to a portion of a particular gene transcript that can hybridize to the transcript and block its translation. An antisense oligonucleotide may comprise RNA or DNA.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Arylalkyl" means an alkyl group, as defined herein, substituted with one or two aryl groups, as defined herein. Examples include benzyl, phenethyl, phenylvinyl, phenylallyl, and the like.

"Aryloxy" means a —OR group, where R is aryl, as defined herein.

"Arylalkyloxy" means a —OR group, where R is arylalkyl, as defined herein.

"Arylsulfonyl" means a —SO₂R group, where R is aryl, as defined herein.

"Carboxyalkyl" means an alkyl group, as defined herein, substituted with one, two, or three —C(O)OH groups.

"Carboxy ester" means a —C(O)OR group, where R is lower alkyl, lower alkenyl, lower alkynyl, cycloalkyl, aryl, or arylalkyl, each of which is defined herein. Representative examples include methoxycarbonyl, ethoxycarbonyl, benzyloxycarbonyl, and the like.

"Compound A" is a compound of formula I and of Table I, having the structure:

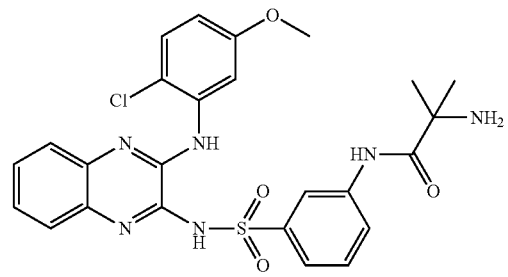 [SMILES: COc1ccc(Cl)c(Nc2nc3ccccc3nc2NS(=O)(=O)c2cccc(NC(=O)C(C)(C)N)c2)c1]

"Cyanoalkyl" means an alkyl, alkenyl, or alkynyl radical, as defined herein, substituted with at least one, for example one, two, or three, cyano groups.

"Cycloalkyl" means a monocyclic or polycyclic hydrocarbon radical having three to thirteen carbon atoms. The cycloalkyl can be saturated or partially unsaturated, but cannot contain an aromatic ring. Cycloalkyl includes fused, bridged, and spiro ring systems. Examples of such radicals include cyclopropyl, cyclobutyl, cyclopentyl, and cyclohexyl.

"Cycloalkylalkyl" means alkyl group substituted with one or two cycloalkyl groups, as defined herein. Representative examples include cyclopropylmethyl, 2-cyclobutyl-ethyl, and the like.

"Cycloalkylcarbonyl" means a —C(O)R group, where R is cycloalkyl, as defined herein.

"Dialkylamino" means a —NRR' radical, where R and R' are independently alkyl, as defined herein, or an N-oxide derivative, or a protected derivative thereof, e.g., dimethylamino, diethylamino, N,N-methylpropylamino, N,N-methylethylamino, and the like.

"Dialkylaminoalkyl" means an alkyl group substituted with one or dialkylamino groups, as defined herein.

"Dialkylaminoalkyloxy" means an —OR group, where R is dialkylaminoalkyl, as defined herein.

"Fused ring system" and "fused ring" refer to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydronaphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Haloalkoxy" means an —OR' group, where R' is haloalkyl as defined herein, e.g., trifluoromethoxy, 2,2,2-trifluoroethoxy, and the like.

"Haloalkoxyalkyl" means an alkyl group, as defined herein, substituted with one, two, or three haloalkoxy, as defined herein.

"Halogen" or "halo" means fluoro, chloro, bromo, or iodo.

"Haloalkenyl means an alkenyl group, as defined herein, substituted with one or more halogens, for example one to five halo atoms.

"Haloalkyl" means an alkyl group, as defined herein, substituted with one or more halogens, for example one to five halo atoms. Representative examples includes 2,2-difluoroethyl, trifluoromethyl, 2-chloro-1-fluoroethyl, and the like.

"Heteroaryl" means a monocyclic, fused bicyclic, or fused tricyclic, monovalent radical of 5 to 14 ring atoms containing one or more, for example one, two, three, or four ring heteroatoms independently selected from —O—, —S(O)$_n$— (n is 0, 1, or 2), —N—, —N(R$^x$)—, and the remaining ring atoms being carbon, wherein the ring comprising a monocyclic radical is aromatic, and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. In particular, when the point of valency is located on the nitrogen, R$^x$ is absent. In another embodiment, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl, 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl, tetrahydroisoquinolin-6-yl, and the like), pyrrolo[3,2-c]pyridinyl (including, for example, pyrrolo[3,2-c]pyridin-2-yl, pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Hetereoarylalkyl" means an alkyl group substituted with one or two heteroaryl groups, as defined herein.

"Heterocycloalkyl" means a saturated or partially unsaturated monovalent monocyclic group of 3 to 8 ring atoms or a saturated or partially unsaturated monovalent fused bicyclic group of 5 to 12 ring atoms in which one or more, for example one, two, three, or four ring heteroatoms independently selected from —O—, —S(O)$_n$— (n is 0, 1, or 2), —N=, —N(R$^y$)— (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. In particular, when the point of valency is located on a nitrogen atom, R$^y$ is absent. In another embodiment the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof, and N-oxide or a protected derivative thereof.

"Heterocycloalkylalkyl" means an alkyl group, as defined herein, substituted with one or two heterocycloalkyl groups, as defined herein.

"Hydroxyalkyl" means an alkyl radical, as defined herein, substituted with at least one, for example one, two, or three, hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, for example 2-hydroxyethyl, 2,3-dihydroxypropyl, 1-(hydroxymethyl)-2-hydroxyethyl, and the like.

"Hydroxyamino" means a —NH(OH) group.

The phrase "nucleic acid molecules" and the term "polynucleotides" denote polymeric forms of nucleotides of any length, either ribonucleotides or deoxynucleotides. They include single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of a polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. A polynucleotide may be further modified, such as by conjugation with a labeling component. Other types of modifications include caps, substitution of one or more of the naturally occurring nucleotides with an analog, and introduction of means for attaching the polynucleotide to proteins, metal ions, labeling components, other polynucleotides, or a solid support.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl $C_{1-8}$ alkyl," both the "$C_{1-8}$ alkyl" portion and the "aryl" portion of the molecule may or may not be substituted. A list of exemplary optional substitutions is presented below in the definition of "substituted."

"Optionally substituted alkyl" means an alkyl radical, as defined herein, optionally substituted with one or more groups, for example one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$ (where $R^c$ is hydrogen, alkyl, optionally substituted alkenyl, optionally substituted alkynyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —$C(O)NR^aR^b$ (where $R^a$ and $R^b$ are independently hydrogen, alkyl, optionally substituted alkenyl, optionally substituted alkynyl, hydroxy, alkoxy, alkenyloxy, or cyanoalkyl).

"Optionally substituted alkenyl" means an alkenyl radical, as defined herein, optionally substituted with one or more groups, for example one, two, or three groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$ (where $R^c$ is hydrogen, optionally substituted alkyl, optionally substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —$C(O)NR^aR^b$ (where $R^a$ and $R^b$ are independently hydrogen, optionally substituted alkyl, alkenyl, optionally substituted alkynyl, hydroxy, alkoxy, or alkenyloxy).

"Optionally substituted aryl" means an aryl group, as defined herein, which is optionally substituted with one, two, three, four, or five groups selected from halo, haloalkyl, haloalkoxy, hydroxy, lower alkyl, lower alkenyl, lower alkynyl, alkoxy, carboxy, carboxy ester, amino, alkylamino, dialkylamino, optionally substituted cycloalkyl, optionally substituted heterocycloalkyl, optionally substituted heteroaryl, —C(O)NR'R" (where R' is hydrogen or alkyl, and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —$NHS(O)_2R'$ (where R' is alkyl, aryl, or heteroaryl).

"Optionally substituted heteroaryl" means a heteroaryl group, as defined herein, optionally substituted with one, two, three, four, or five groups selected from halo, haloalkyl, haloalkoxy, lower alkyl, lower alkenyl, lower alkynyl, alkoxy, hydroxy, oxo (valency rules permitting), carboxy, carboxy ester, amino, alkylamino, dialkylamino, optionally substituted cycloalkyl, optionally substituted heterocycloalkyl, heteroaryl, optionally substituted aryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —$NHS(O)_2R'$ (where R' is alkyl, aryl, or heteroaryl).

"Optionally substituted heterocycloalkyl" means a heterocycloalkyl, as defined herein, optionally substituted with one, two, three, four, or five groups selected from halo, haloalkyl, haloalkoxy, hydroxy, oxo, lower alkyl, lower alkenyl, lower alkynyl, alkoxy, optionally substituted cycloalkyl, heterocycloalkyl, optionally substituted aryl, optionally substituted heteroaryl, alkylaminoalkyl, dialkylaminoalkyl, carboxy, carboxy ester, —C(O)NR'R" (where R' is hydrogen or alkyl, and R" is hydrogen, alkyl, aryl, heteroaryl, or heterocycloalkyl), —NR'C(O)R" (where R' is hydrogen or alkyl, and R" is alkyl, aryl, heteroaryl, or heterocycloalkyl), amino, alkylamino, dialkylamino, and —$NHS(O)_2R'$ (where R' is alkyl, aryl, or heteroaryl).

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Short interfering RNA" (siRNA) refers to double-stranded RNA molecules, generally, from about 10 to about 30 nucleotides long, that are capable of mediating RNA interference (RNAi).

"Spirocyclyl" or "spirocyclic ring" refers to a ring originating from a particular annular carbon of another ring. For example, as depicted below, a ring atom of a saturated bridged ring system (rings C and C'), but not a bridgehead atom, can be a shared atom between the saturated bridged ring system and a spirocyclyl (ring D) attached thereto. A spirocyclyl can be carbocyclic or heteroalicyclic.

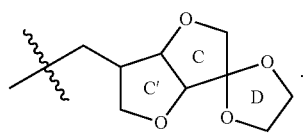

"Yield" for each of the reactions described herein is expressed as a percentage of the theoretical yield.

"Antibody" includes any immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', $F(ab')_2$, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as cytotoxics, toxins, radioisotopes, etc.

"Antibody fragment" can refer to a portion of an intact antibody. Examples of antibody fragments include, but are not limited to, linear antibodies, single-chain antibody molecules, Fc or Fc' peptides, Fab and Fab fragments, and multispecific antibodies formed from antibody fragments.

"Chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

"Humanized" forms of non-human (e.g., rabbit) antibodies include chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. Most often, the humanized antibody can comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Methods used to generate humanized antibodies are well known in the field of immunology and molecular biology.

"Hybrid antibodies" can include immunoglobulin molecules in which pairs of heavy and light chains from antibodies with different antigenic determinant regions are assembled together so that two different epitopes or two different antigens can be recognized and bound by the resulting tetramer.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3-5, and more usually, at least 5 or 8-10, amino acids in a unique spatial conformation.

The term "protein display scaffold" refers to binding reagents such as affibodies, immunity proteins, defensin A, T-cell receptors and the like, as described in Hosse et al., Protein Sci., 15(1):14-27 (2006), which is incorporated herein by reference.

"Specifically binds" to or shows "specific binding" towards an epitope means that the antibody reacts or associates more frequently, and/or more rapidly, and/or greater duration, and/or with greater affinity with the epitope than with alternative substances. Inhibitors of HER2 (also known as NEU, NGL, Human Epidermal growth factor Receptor 2 (or ErbB2), p185 and CD340), HER3 (also known as c-ErbB3), ERBB4 (also known as HER4, p180erbB4), Macrophage-stimulating protein receptor (MSPR), AXL Receptor Tyrosine Kinase (Axl), Mitogen-activated protein kinase (MAP3K), extracellular signal-regulated kinase (ERK), C-jun N-terminal kinase (JNK), p38 mitogen-activated protein kinase (p38MAPK), MEK kinase-1 (MEKK), Insulin growth factor 1 receptor (IGF-IR, or CD221), Insulin receptor 1 (InsR or INS-IR), EphA1 (also known as ephrin type-A receptor 1, EPH receptor A1, EPH, EPHT1, tyrosine-protein kinase receptor EPH, EPHT), Fibroblast growth factor receptor 2 (FGFR2), and Fibroblast growth factor receptor 3 (FGFR3) generally refer to molecules that have the capacity to inhibit the expression and/or the activity of the specific kinase or kinase receptor of interest, which include: HER3, HER2, MSPR, Axl, MAP3K (ERK, JNK, and p38 MAPK), MEKK kinases/kinase receptors, INSR, IGF-IR, and FGFR2. These inhibitors can be species specific or may be xenogenic in nature.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Breast: ductal carcinoma in situ, infiltrating ductal carcinoma, medullary carcinoma, infiltrating lobular carcinoma, tubular carcinoma, mucinous carcinoma, inflammatory breast cancer; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma. Thus, the term "cancerous cell" as provided herein, includes a cell afflicted by any one of the above-identified conditions.

While not wishing to be bound to theory, phosphatases can also play a role in "kinase-dependent diseases or conditions" as cognates of kinases; that is, kinases phosphorylate and phosphatases dephosphorylate, for example lipid substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention when used with the combination of other kinase receptor inhibitors, are useful for treating diseases characterized in part by abnormal levels of cell proliferation (i.e., tumor growth), programmed cell death (apoptosis), cell migration and invasion and angiogenesis associated with tumor growth.

A cancer which "overexpresses" an HER receptor is one which has significantly higher levels of an HER receptor, such as HER2, at the cell surface thereof, compared to a noncancerous cell of the same tissue type. Such overexpression may be caused by gene amplification or by increased transcription or translation. HER receptor overexpression may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479, published October 1998), Southern blotting, or polymerase chain reaction (PCR) techniques, such as real time quantitative PCR (RT-PCR). One may also study HER receptor overexpression by measuring shed antigen (e.g., HER extracellular domain) in a biological fluid such as serum (see, e.g., U.S. Pat. No. 4,933,294, issued Jun. 12, 1990; WO91/05264, published Apr. 18, 1991; U.S. Pat. No. 5,401,638, issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

The tumors overexpressing HER2 can be rated by immunohistochemical scores corresponding to the number of copies of HER2 molecules expressed per cell, and can been determined biochemically: 0=0 10,000 copies/cell, 1+=at least about 200,000 copies/cell, 2+=at least about 500,000 copies/cell, 3+=at least about 2,000,000 copies/cell. Overexpression of HER2 at the 3+ level, which leads to ligand-independent activation of the tyrosine kinase (Hudziak et al., Proc. Natl. Acad. Sci. USA 84: 7159 7163 [1987]), occurs in approximately 30% of breast cancers, and in these patients, relapse-free survival and overall survival are diminished (Slamon et al., Science 244: 707 712 [1989]; Slamon et al., Science 235: 177 182 [1987]).

"Non-HER2 amplified" tumors consist essentially of cells possessing a normal (i.e. wildtype) copy number of the HER2 gene.

"Patient," for the purposes of the present invention, includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, or S. M. Berge, et al., "Pharmaceutical Salts," J. Pharm. Sci., 1977; 66:1-19, both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, salicylic acid, and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example, with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The term "therapeutic synergy" is used when the combination of two products at given doses is more efficacious than the best of the two products alone considering the same doses. In one aspect, therapeutic synergy can be evaluated by comparing a combination to the best single agent using estimates obtained from a two-way analysis of variance with repeated measurements (Time factor) on parameter tumor volume. In other aspects, the maximum tolerated dose of the combination can be compared with the maximum tolerated dose of each of the isolated constituents in the study under consideration. This effectiveness can be quantified, for example, by the $\log_{10}$ cell kill, which is determined according to the following equation:

$$\log_{10} \text{cell kill} = T - C \text{ (days)}/3.32 \times T_d$$

in which T-C represents the delay in growth of the cells, which is the average time, in days, for the tumors of the treated group (T) and the tumors of the control group (C) to have reached a predetermined value (1 g for example), and $T_d$ represents the time, in days, necessary for the volume of the tumor to double in the control animals [T. H. Corbett et al., Cancer, 40, 2660.2680 (1977); F. M. Schabel et al., Cancer Drug Development, Part B, Methods in Cancer Research, 17, 3-51, New York, Academic Press Inc. (1979)]. A product is considered to be active if $\log_{10}$ cell kill is greater than or equal to 0.7. A product is considered to be very active if $\log_{10}$ cell kill is greater than 2.8. The combination, used at its own maximum tolerated dose, in which each of the constituents is present at a dose generally less than or equal to its maximum tolerated dose, will show therapeutic synergy when the $\log_{10}$ cell kill is greater than the value of the $\log_{10}$ cell kill of the best constituent when it is administered alone, and in particular has a superiority of at least one log cell kill.

"Therapeutically effective amount" is an amount of a compound of formula I and/or an inhibitor of a kinase or receptor, for example, HER3, HER2, MSPR, Axl, MAP3K (ERK, JNK, and p38 MAPK), MEKK kinases/kinase receptors, INSR, IGF-IR, and FGFR2, that when co-administered to a patient, ameliorates a symptom of the disease. The amount of a compound of formula I, or inhibitor of a kinase of the invention, which constitutes a "therapeutically effective amount" will vary depending on the compound, inhibitor, the disease state and its severity, the bioavailability characteristics of the compound and/or inhibitor, the age of the patient to be treated, and the like. The therapeutically effective amount can be determined routinely by one of ordinary skill in the art having regard to their knowledge and to this disclosure. The dosage or dosages comprising the therapeutically effective amounts are not toxic and confer to accepted medical practices commensurate with an appropriate risk/benefit ratio.

"Treating" or "treatment" of a disease, disorder, or syndrome, as used herein, includes: (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction, and the severity of the condition may be necessary, and will be ascertainable with routine experimentation by one of ordinary skill in the art.

"Co-administration," "combined administration," or the like, as utilized herein, are meant to include modes of administration of the selected active, therapeutic agents to a single patient and are intended to include treatment regimens in which the agents are not necessarily administered by the same route of administration or at the same time. Co-administration can also include delivery of the active ingredients in a "fixed combination," e.g. a compound of formula I and an inhibitor (for example, a functional nucleic acid, lapatinib, and/or an antibody against any one of kinases or kinase receptors: HER3, HER2, MSPR, Axl, MAP3K (ERK, JNK, and p38 MAPK), MEKK kinases/kinase receptors, INSR, IGF-IR, and FGFR2, are both administered to a patient simultaneously in the form of a single entity or dosage. The term "non-fixed combination" means that the active ingredients, e.g. a compound of formula I and an inhibitor (for example, a functional nucleic acid or an antibody) against any one or more of the kinases or receptors: HER3, HER2, MSPR, Axl, MAP3K (ERK, JNK, and p38 MAPK), MEKK kinases/kinase receptors, INSR, IGF-IR, and FGFR2, are both administered to a patient as separate entities either simultaneously, concurrently, or sequentially with no specific time limits, such that the administration provides therapeutically effective levels of the combination of active agents in the body of the patient.

Embodiments of the Invention

The following paragraphs present a number of embodiments of compounds of the invention. In each instance, the embodiment includes both the recited compounds as well as individual isomers and mixtures of isomers. In addition, in each instance, the embodiment optionally includes the pharmaceutically acceptable salts, hydrates, and/or solvates of the recited compounds and any individual isomers or mixture of isomers thereof.

For each of the following embodiments, the compound of formula I can, for example, be compound A or be selected from a compound in Table 1.

In another embodiment, the invention is directed to a method of treating cancer, comprising administering to a patient a therapeutically effective amount of a compound of formula I, as defined in the Summary, where growth and/or survival of tumor cells of the cancer is enhanced, at least in part, by the activity of PI3K; in combination with one or more inhibitors of HER3, MSPR, Axl, MAP3K (ERK, JNK, and p38 MAPK), and MEKK kinases/kinase receptors. In one aspect, the inhibitor can be a functional nucleic acid, while in another it is an antibody.

In another embodiment, the invention is directed to a method of treating cancer, comprising administering to a patient a therapeutically effective amount of a compound of formula I, as defined in the Summary, in combination with one or more inhibitors of HER3, MSPR, Axl, MAP3K (ERK, JNK, and p38 MAPK) and MEKK kinases/kinase receptors; where the cancer is selected from breast cancer, colon cancer, rectal cancer, endometrial cancer, gastric carcinoma (including gastrointestinal carcinoid tumors and gastrointestinal stromal tumors), glioblastoma, hepatocellular carcinoma, small cell lung cancer, non-small cell lung cancer (NSCLC), melanoma, ovarian cancer, cervical cancer, pancreatic cancer, prostate carcinoma, acute myelogenous leukemia (AML), chronic myelogenous leukemia (CML), non-Hodgkin's lymphoma, and thyroid carcinoma. In one aspect, the inhibitor can be a functional nucleic acid, while in another it is an antibody.

In another embodiment, the invention is directed to a method of treating cancer, comprising administering to a patient a therapeutically effective amount of a compound of formula I, as defined in the Summary, in combination with one or more inhibitors of HER3, MSPR, Axl, MAP3K (ERK, JNK, and p38 MAPK), and MEKK kinases/kinase receptors; where the cancer is selected from prostate cancer, NSCLC, ovarian cancer, cervical cancer, breast cancer, colon cancer, rectal cancer, and glioblastoma. In one aspect, the inhibitor can be a functional nucleic acid, while in another it is an antibody.

In another embodiment, the invention is directed to a method of treating cancer, comprising administering to a patient a therapeutically effective amount of a compound of formula I, as defined in the Summary, in combination with one or more inhibitors of HER3, MSPR, Axl, MAP3K (ERK, JNK, and p38 MAPK), and MEKK kinases/kinase receptors; where the cancer is selected from NSCLC, breast cancer, prostate cancer, glioblastoma, and ovarian cancer. In one aspect, the inhibitor can be a functional nucleic acid, while in another it is an antibody.

In another embodiment, the invention is directed to a method of treating cancer, comprising administering to a patient a therapeutically effective amount of a compound of formula I, as defined in the Summary, in combination with a treatment where the treatment includes a therapeutically effective amount of one or more antibodies operable to inhibit the activity and/or expression of HER3 receptor tyrosine kinase.

In another embodiment, the invention is directed to a method of treating cancer, comprising administering to a patient a therapeutically effective amount of a compound of formula I, as defined in the Summary, where growth and/or survival of tumor cells of the cancer is enhanced, at least in part, by the activity of PI3K; in combination with one or more inhibitors of HER3, HER2, MSPR, Axl, MAP3K (ERK, JNK, and p38 MAPK), MEKK kinases/kinase receptors, INSR, IGF-IR, and FGFR2 kinases/kinase receptors. In one aspect, the inhibitor can be a functional nucleic acid, or lapatanib, while in another it is an antibody.

In another aspect, the method of the invention comprises administering to a patient a therapeutically effective amount of a compound of formula I in combination with a HER3 inhibitor.

In another aspect, the method of the invention comprises administering to a patient a therapeutically effective amount of a compound of formula I in combination with a HER2 inhibitor.

In another aspect, the method of the invention comprises administering to a patient a therapeutically effective amount of a compound of formula I in combination with a HER3 inhibitor and a HER2 inhibitor.

In another aspect, the method of the invention comprises administering to a patient a therapeutically effective amount of a compound of formula I in combination with lapatinib.

In another aspect, the method of the invention comprises administering to a patient a therapeutically effective amount of a compound of formula I in combination with trastuzumab.

In another aspect, the method of the invention comprises administering to a patient a therapeutically effective amount of a compound of formula I in combination with lapatinib and trastuzumab.

In another aspect, the method of the invention comprises administering to a patient a therapeutically effective amount of a compound of formula I in combination with a HER3 inhibitor and lapatinib.

In another aspect, the method of the invention comprises administering to a patient a therapeutically effective amount of a compound of formula I in combination with a HER3 inhibitor and trastuzumab.

In another aspect, the method of the invention comprises administering to a patient a therapeutically effective amount of a compound of formula I in combination with a HER2 inhibitor and lapatinib.

In another aspect, the method of the invention comprises administering to a patient a therapeutically effective amount of a compound of formula I in combination with a HER2 inhibitor and trastuzumab.

In another aspect, the method of the invention comprises administering to a patient a therapeutically effective amount of a compound of formula I in combination with a HER3 inhibitor, a HER2 inhibitor, and lapatinib.

In another aspect, the method of the invention comprises administering to a patient a therapeutically effective amount of a compound of formula I in combination with a HER3 inhibitor, a HER2 inhibitor, and trastuzumab.

In another aspect, the method of the invention comprises administering to a patient a therapeutically effective amount of a compound of formula I in combination with a HER3 inhibitor, a HER2 inhibitor, lapatinib, and trastuzumab.

In another embodiment, the invention is directed to a method of treating cancer, comprising administering to a patient a therapeutically effective amount of a compound of formula I, as defined in the Summary, in combination with one or more inhibitors of HER3, HER2, MSPR, Axl, MAP3K (ERK, JNK, and p38 MAPK), MEKK kinases/kinase receptors, INSR, IGF-IR, and FGFR2 kinases/kinase receptors; where the cancer is selected from the group consisting of breast cancer (including HER2+ or HER2 overexpressing breast cancer), colon cancer, rectal cancer, endometrial cancer, gastric carcinoma (including gastrointestinal carcinoid tumors and gastrointestinal stromal tumors), glioblastoma, hepatocellular carcinoma, small cell lung cancer, non-small cell lung cancer (NSCLC), melanoma, ovarian cancer, cervical cancer, pancreatic cancer, prostate carcinoma, acute myelogenous leukemia (AML), chronic myelogenous leukemia (CML), non-Hodgkin's lymphoma, and thyroid carcinoma. In one aspect, the inhibitor can be a functional nucleic acid, while in another, the inhibitor can be lapatinib. In another embodiment, it is an antibody, while in another, the inhibitor can include a combination of functional nucleic acids, and/or lapatinib, and/or a combination of antibodies.

In another embodiment, the invention is directed to a method of treating cancer, comprising administering to a patient a therapeutically effective amount of a compound of formula I, as defined in the Summary, in combination with one or more inhibitors of HER3, HER2, MSPR, Axl, MAP3K (ERK, JNK, and p38 MAPK), MEKK kinases/kinase receptors, INSR, IGF-IR, and FGFR2 kinases/kinase receptors; where the cancer is selected from the group consisting of prostate cancer, NSCLC, ovarian cancer, cervical cancer, gastric cancer, breast cancer (including HER2+ or HER2 overexpressing breast cancer), colon cancer, rectal cancer, and glioblastoma. In one aspect, the inhibitor can be a functional nucleic acid, while in another, the inhibitor can be lapatinib. In another embodiment, it is an antibody, while in another, the inhibitor can include a combination of functional nucleic acids, and/or lapatinib, and/or a combination of antibodies.

In another embodiment, the invention is directed to a method of treating cancer, comprising administering to a patient a therapeutically effective amount of a compound of formula I, as defined in the Summary, in combination with one or more inhibitors of HER3, HER2, MSPR, Axl, MAP3K (ERK, JNK, and p38 MAPK), MEKK kinases/kinase receptors, INSR, IGF-IR, and FGFR2 kinases/kinase receptors; where the cancer is selected from the group consisting of NSCLC, breast cancer, prostate cancer, glioblastoma, and ovarian cancer. In one aspect, the inhibitor can be a functional nucleic acid, in another, the inhibitor can be lapatinib, while in another it is an antibody, while in another embodiment, the inhibitor can include a combination of functional nucleic acids, and/or lapatinib and/or a combination of antibodies.

In another embodiment, the invention is directed to a method of treating cancer, comprising administering to a patient a therapeutically effective amount of a compound of formula I, as defined in the Summary, in combination with a treatment that includes a therapeutically effective amount of one or more functional nucleic acids and/or a therapeutically effective amount of one or more antibodies operable to inhibit the activity and/or expression of HER2 receptor tyrosine kinase.

Compound of Formula I

For each of the foregoing embodiments, the compound of formula I is selected from any of the following embodiments, including from the representative compounds in Table 1.

One embodiment is directed to a compound of formula I, where $W^1$, $W^2$, $W^3$, and $W^4$ are —C($R^1$)=; or one or two of $W^1$, $W^2$, $W^3$, and $W^4$ are independently —N= and the remaining are —C($R^1$)=; where each $R^1$ is independently hydrogen, alkyl, haloalkyl, nitro, alkoxy, haloalkoxy, halo, hydroxy, cyano, amino, alkylamino, or dialkylamino; and all other groups are as defined in the Summary. In another embodiment, $W^1$, $W^2$, $W^3$, and $W^4$ are —C($R^1$)=, and each $R^1$ is independently hydrogen or alkyl; or one of $W^1$ and $W^4$ is —N= and the other is —C(H)=. In a further embodiment, $W^1$, $W^2$, $W^3$, and $W^4$ are —C($R^1$)=, where each $R^1$ is independently hydrogen or alkyl. More particularly, $R^1$ is hydrogen.

In another embodiment, $R^{50}$ is hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$N$R^{55}$$R^{55a}$, or alkylcarbonylamino; where $R^{55}$ and $R^{55b}$ are independently hydrogen, alkyl, or alkenyl, and $R^{55a}$ is hydrogen, alkyl, alkenyl, hydroxy, or alkoxy; and all other groups are as defined in the Summary. In a further embodiment, $R^{50}$ is hydrogen.

In another embodiment, $R^{51}$ is hydrogen or alkyl; and all other groups are as defined in the Summary. In a further embodiment, $R^{51}$ is alkyl. More particularly, $R^{51}$ is methyl.

In another embodiment, $R^{52}$ is hydrogen or halo; and all other groups are as defined in the Summary. In a further embodiment $R^{52}$ is hydrogen or fluoro. More particularly, $R^{52}$ is hydrogen.

In another embodiment, $R^{53}$ is hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$N$R^{55}$$R^{55a}$, or alkylcarbonylamino; where $R^{55}$ and $R^{55b}$ are independently hydrogen, alkyl, or alkenyl, and $R^{55a}$ is hydrogen, alkyl, alkenyl, hydroxy, or alkoxy; and all other groups are as defined in the Summary. In a further embodiment, $R^{53}$ is hydrogen, alkoxy, nitro, amino, or —N($R^{55}$)C(O)—$C_1$-$C_6$-alkylene-N($R^{55a}$)$R^{55b}$. In yet another embodiment, $R^{53}$ is hydrogen, methoxy, nitro, amino, or —NHC(O)CH$_2$N(CH$_3$)$_2$. More particularly, $R^{53}$ is hydrogen or methoxy.

In another embodiment, $R^{54}$ is hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$N$R^{55}$$R^{55a}$, or alkylcarbonylamino; where $R^{55}$ and $R^{55b}$ are independently hydrogen, alkyl, or alkenyl, and $R^{55a}$ is hydrogen, alkyl, alkenyl, hydroxy, or alkoxy; and all other groups are as defined in the Summary. In a further embodiment, $R^{54}$ is hydrogen, alkyl, alkoxy, or halo. In yet another embodiment, $R^{54}$ is hydrogen, methyl, methoxy, bromo, or chloro. More particularly, $R^{54}$ is hydrogen, methoxy, or chloro.

In another embodiment, $R^{50}$, $R^{52}$, and $R^{53}$ are hydrogen, and $R^{54}$ is halo or alkoxy; $R^{50}$, $R^{52}$, and $R^5$ are hydrogen, and $R^{53}$ is alkoxy; or $R^{50}$ and $R^{52}$ are hydrogen, and $R^{53}$ and $R^{54}$ together with the carbons to which they are attached form a 6-membered heteroaryl; and all other groups are as defined in the Summary. In another embodiment, $R^{50}$, $R^{52}$, and $R^{53}$ are hydrogen, and $R^{54}$ is chloro or methoxy; $R^{50}$, $R^{52}$, and $R^{54}$ are hydrogen, and $R^{53}$ is methoxy; or $R^{50}$ and $R^{52}$ are hydrogen, and $R^{53}$ and $R^{54}$ together with the carbons to which they are attached form pyridinyl. In a further embodiment, $R^{50}$, $R^{52}$, and $R^{53}$ are hydrogen, and $R^{54}$ is chloro or methoxy; or $R^{50}$, $R^{52}$, and $R^{54}$ is hydrogen and $R^{53}$ is methoxy. More particularly, $R^{51}$ is methyl.

In one embodiment, B is phenyl substituted with $R^{3a}$ and optionally further substituted with one, two, or three $R^3$; and all other groups are as defined in the Summary. In a further embodiment, B is phenyl substituted with $R^{3a}$. More particularly, the compound of formula I is a compound of formula I(a):

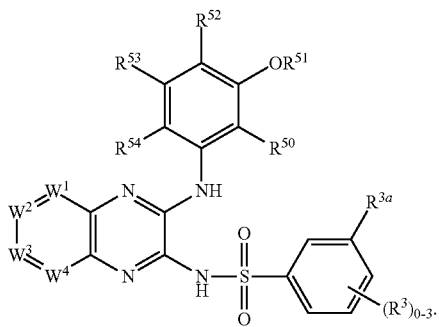

In another embodiment, B is phenyl substituted with $R^{3a}$, as depicted in formula I(a), and is not further substituted with $R^3$.

In another embodiment, B is heteroaryl optionally substituted with one, two, or three $R^3$. In a further embodiment, B is thien-3-yl, pyridinyl, pyrimidinyl, pyridazinyl, pyrazinyl, oxazolyl, isoxazolyl, pyrrolyl, imidazolyl, pyrazolyl, or thiazolyl, each of which is optionally substituted with one or two $R^3$. In yet another embodiment, B is thien-3-yl, pyridin-2-yl, pyridin-3-yl, pyridin-4-yl, oxazol-2-yl, oxazol-4-yl, oxazol-5-yl, isoxazol-3-yl, isoxazol-4-yl, isoxazol-5-yl, imidazol-2-yl, pyrrol-2-yl, pyrrol-3-yl, imidazol-4-yl, imidazol-5-yl, pyrazol-3-yl, pyrazol-4-yl, or pyrazol-5-yl, each of which is optionally substituted with one or two $R^3$. More particularly, B is thien-3-yl, pyridin-3-yl, pyridin-4-yl, isoxazol-4-yl, or pyrazol-4-yl, each of which is optionally substituted with one or two $R^3$. In a further embodiment, B is pyridin-3-yl, 2-hydroxy-pyridin-5-yl, isoxazol-4-yl, or pyrazol-4-yl, each of which is optionally substituted with one or two $R^3$.

In one embodiment, $R^{3a}$ is cyano, hydroxyamino, carboxy, alkylsulfonyl, aminoalkyloxy, alkylaminoalkyloxy, dialkylaminoalkyloxy, —N($R^7$)C(O)—$C_1$-$C_6$-alkylene-N($R^{7a}$)($R^{7b}$), —C(O)NR$^8$R$^{8a}$, —NR$^9$C(O)R$^{9a}$, —C(O)N($R^{10}$)—$C_1$-$C_6$-alkylene-N($R^{10a}$)$R^{10b}$, —NR$^{11}$C(O)NR$^{11a}$R$^{11b}$ where $R^{11a}$, —C(O)R$^{12}$, —NR$^{13}$C(O)OR$^{13a}$, —C(O)N($R^{14}$)N($R^{14a}$)($R^{14b}$), —S(O)$_2$N($R^{15}$)—$C_1$-$C_6$-alkylene-N($R^{15a}$)$R^{15b}$, —C(O)N($R^{16}$)—$C_1$-$C_6$-alkylene-C(O)OR$^{16a}$, heteroaryl optionally substituted with one or two aminoalkyl, alkylaminoalkyl, or dialkylaminoalkyl, —N($R^{17}$)—C(=N($R^{17b}$)($R^{17a}$))(NR$^{17c}$R$^{17d}$), —N($R^{18}$)C(O)—$C_1$-$C_6$-alkylene-N($R^{18b}$)C(O)R$^{18a}$, —C(O)N($R^{19}$)—$C_1$-$C_6$-alkylene-C(O)R$^{19a}$, —N($R^{22}$)C(O)—$C_1$-$C_6$-alkylene-N($R^{22b}$)—N($R^{22c}$)($R^{22a}$), —$C_0$-$C_6$-alkylene-N($R^{23}$)—$C_1$-$C_6$-alkylene-N($R^{23b}$)$R^{23a}$, or —NR$^{24}$C(O)—$C_1$-$C_6$-alkylene-OR$^{24a}$; where each of the alkylene in $R^{3a}$ is independently optionally further substituted with 1, 2, 3, 4, or 5 groups selected from halo, hydroxy, amino, alkylamino, and dialkylamino; and all other groups are as defined in the Summary.

In another embodiment, $R^{3a}$ is: —NHC(O)CH$_2$NH(CH$_3$), —NHC(O)CH$_2$NH(CH$_2$CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, —NHC(O)CH(CH$_3$)NH(CH$_3$), —NHC(O)CH$_2$NH$_2$, —NHC(O)H, —NHC(O)CH$_2$(azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH(CH$_2$CH$_3$), —NHC(O)CH$_2$CH$_2$NH$_2$, —NHOH, —NHC(O)(piperidin-3-yl), —NHC(O)CH$_2$(4-methyl-1,4-diazepan-1-yl), —NHC(O)CH(NH$_2$)(CH$_2$CH$_3$), —NHC(O)CH$_2$NH(CH$_2$CH(OH)(CH$_3$)), —NHC(O)CH$_2$NHCH$_2$CH$_2$F, —NHC(O)CH$_2$NH(OCH$_2$CH(CH$_3$)$_2$), —NHC(O)(1-aminocycloprop-1-yl), —NHC(O)CH$_2$NH(CH$_2$cyclopropyl), —NHC(O)CH$_2$(3-(dimethylamino)-azetidin-1-yl), —NHC(O)(piperidin-2-yl), —NHC(O)(morpholin-4-yl), —NHC(O)CH$_2$(pyrrolidin-1-yl), —NHC(O)CH(NH$_2$)CH$_2$CH$_2$CH$_2$CH$_2$N(CH$_3$)$_2$, —NHC(O)CH$_2$N(CH$_3$)(CH$_2$CH$_3$), —NHC(O)CH$_2$(imidazol-5-yl), —NHC(O)(1-aminocyclopent-1-yl), —NHC(O)CH$_2$NH(CH$_2$CH(CH$_3$)$_2$), —NHC(O)CH$_2$N(CH$_3$)(CH$_2$CH$_3$), —NHC(O)(N-(imidazol-4-ylmethyl)-azetidin-3-yl), —NHC(O)(N-ethyl-azetidin-3-yl), —NHCH$_2$N(CH$_3$)CH$_2$CH$_2$N(CH$_3$)$_2$, —NHC(O)CH$_2$N(CH$_3$)(N-methyl-pyrrolidin-3-yl), —NHC(O)CH$_2$N(CH$_3$)(CH$_2$CH$_2$N(CH$_3$)$_2$), —NHC(O)CH$_2$(3-hydroxy-pyrrolidin-1-yl), —NHC(O)(1-amino-cyclobut-1-yl), —NHC(O)CH$_2$NH(CH$_2$)$_3$CH$_3$, —NHC(O)CH$_2$(3-piperidin-1-ylazetidin-1yl), —NHC(O)NH$_2$, —NHC(O)(1-hydroxycyclopropyl), —NHC(O)CH$_2$NHN(CH$_3$)$_2$, —NHC(O)NH(CH$_2$)$_2$N(CH$_3$)$_2$, —NHC(O)CH$_2$OH, —NHC(O)(pyridazin-4-yl), —NHC(O)(N-methyl-piperidin-4-yl), —NHC(O)CH$_2$NHCH(CH$_3$)$_3$, —NHC(O)CH$_2$(3-dimethylamino-pyrrolidin-1yl), —NHC(O)CH$_2$NH(CH$_2$)$_2$N(CH$_3$)$_2$, —NHC(O)(1-cyclopropylmethyl-azetidin-3-yl), —NHC(O)CH$_2$NH(CH$_3$)$_3$, —NHC(O)(imidazol-2-yl), —NHC(O)(imidazol-4-yl), —NHC(O)(1,2-oxazol-5-yl), —NHC(O)CH$_2$NHCH$_2$CF$_3$, —NHC(O)CH$_2$CH$_2$(piperidin-1-yl), —NHC(O)(3-oxo-cyclopent-1-yl), —NHC(O)(2-hydroxy-pyridin-6-yl), —NHC(O)CH$_2$NH(3-fluoro-4-hydroxyphenyl), —NHC(O)(CH$_2$)$_3$N(CH$_3$)$_2$, —NHC(O)(1-(furan-2-ylmethyl)-azetidin-3-yl), —NHC(O)(pyrimidin-5-yl), —NHC(O)(pyrrol-2-yl), —NHC(O)CH$_2$N(CH$_3$)CH(CH$_3$)$_2$, —NHC(O)CH$_2$N(CH$_2$CH$_3$)$_2$, —NHC(O)CH$_2$(3-methyl-1,2-oxazol-5-yl), —NHC(O)CH$_2$NHCH$_2$(3-hydroxyphenyl), —NHC(O)(N-methyl-pyrrol-2-yl), —NHC(O)(2-amino-tetrahydropyran-2-yl), —NHC(O)CH$_2$(4-methylamino-piperidin-1-yl), —NHC(O)(piperidin-1-yl), —NHC(O)(N-methyl-pyrrolidin-2-yl), —NHC(O)(thien-3-yl), —NHC(O)(N-(cyclopropylcarbonyl)azetidin-3-yl), —NHC(O)CH$_2$(4-methylpiperazin-1-yl), —NHC(O)(N-benzylazetidin-3-yl), —NHC(O)(2-chloro-pyridin-3-yl), —NHC(O)CH$_2$(pyridin-4-yl), —NHC(O)CH$_2$N(CH$_3$)(CH$_2$CH=CH$_2$), —NHC(O)CH$_2$NH(benzyl), —NHC(O)CH$_2$OCH$_3$, —NHC(O)[1-(C(O)CH$_2$CH$_3$)-azetidin-3-yl], —NHC(O)(pyridin-3-yl), —NHC(O)CH$_2$NHCH$_2$CH$_2$OCH$_3$, —NHC(O)(1-[C(O)CH$_3$]piperidin-4-yl), —NHC(O)CH$_2$(2-methyl-pyrrolidin-1-yl), —NHC(O)(furan-3-yl), —NHC(O)CH$_2$N(CH$_3$)$_2$, —NHC(O)(2-chloro-pyridin-5-yl), —NHC(O)(2-chlorophenyl), —NHC(O)CH$_2$(pyridin-2-yl), —NHC(O)CH$_2$(3-dimethylamino-azetidin-1-yl), —NHC(O)CH$_2$(pyridin-3-yl), —NHC(O)CH$_2$(2-chlorophenyl), —NHC(O)CH$_2$N(CH$_3$)CH$_2$CH$_2$CH$_2$N(CH$_3$)$_2$, —NHC(O)CH$_2$N(CH$_2$CH$_3$)CH$_2$CH$_2$OH, —NHC(O)CH$_2$(2-benzyl-pyrrolidin-1-yl), —NHC(O)(furan-2-yl, —NHC(O)(2-chloro-pyridin-4-yl), —NHC(O)CH$_2$NHC(O)CH$_3$, —NHC(O)CH$_2$CH$_3$, —NHC(O)(4-chlorophenyl), —NHC(O)(4-methyl-phenyl), —NHC(O)CH$_2$NHC(O)O(CH$_3$)$_3$, —NHC(O)(benzo[d][1,3]dioxol-5-yl), —NHC(O)CH$_2$NHOCH$_2$(2-methoxyphenyl), —NHC(O)(pyridin-4-yl), —NHC(O)CH$_2$[4-(3,4-dichlorophenyl)-piperazin-1-yl], —NHC(O)CH$_2$CH$_2$(pyridin-3-yl), —NHC(O)(tetrahydrofuran-3-yl), —NHC(O)CH$_2$NHCH$_2$(2-methylphenyl), —NHC(O)CH(CH$_3$)CH$_2$CH$_3$, —NHC(O)CH$_2$(3-fluorophenyl), —NHC(O)CH$_2$C(CH$_3$)$_2$-phenyl, —NHC(O)(2-methyl-cycloprop-1-yl), —NHC(O)(2-methyl-4-methoxyphenyl), —NHC(O)(2-methylpyridin-3-yl), —NHC(O)(4-methoxyphenyl), —NHC(O)CH$_2$(4-ethylpiperazin-1-yl), —NHC(O)(thien-2-yl), —NHC(O)(3-fluoro-2-methylphenyl), —NHC(O)(2- bromo-thien-3-yl), —NHC(O)(4-fluorophenyl), —NHC(O)CH₂(3-methylpiperidin-1-yl), —NHC(O)CH(CH₃)₂, —NHC(O)(CH₂)₃CH₃, —NHC(O)CH₂OCH₂CH₃, —NHC(O)CH₂NH(2-fluorophenyl), —NHC(O)(3-dimethylaminophenyl), —NHC(O)CH₂(4-methylpiperidin-1-yl), —NHC(O)CH₂NH(2-n-propylphenyl), —NHC(O)phenyl, —NHC(O)(pyrazin2-yl), —NHC(O)(3-fluoro-4-methoxyphenyl), —NHC(O)C(CH₃)₂CH₂CH₃, —NHC(O)CH₂O(4-fluorophenyl), —NHC(O)(1-methylcarbonyl-azetidin-3-yl), —NHC(O)CH₂NH(4-methylphenyl), —NHC(O)CH₂NH(phenyl), —NHC(O)CH₂(4-allyl-piperazin-1-yl), —NHC(O)(2-methylphenyl), —NHC(O)CH₂CH₂OCH₃, —NHC(O)(3-methyl-furan-2-yl), —NHC(O)C(CH₃)₃, —NHC(O)CH₂NHbenzyl, —NHC(O)CH₂NH(3-chlorophenyl), —NHC(O)cyclobutyl, —NHC(O)CH₂(3-methoxyphenyl), —NHC(O)(1-methylcycloprop-1-yl), —NHC(O)(3-fluorophenyl), —NHC(O)(4-dimethylaminophenyl), —NHC(O)(3,4-dichlorophenyl), —NHC(O)CH₂NHCH₂(2-methylthiophenyl), —NHC(O)CH₂(2-fluorophenyl), —NHC(O)CH₂N(CH₂CH₃)CH(CH₃)₂, —NHC(O)(thiazol-4-yl), —NHC(O)CH₂N(CH₃)benzyl, —NHC(O)CH₂NHCH₂(thien-2-yl), —NHC(O)CH₂NHCH₂(pyridin-2-yl), —NHC(O)(3-methoxyphenyl), —NHC(O)CH₂NHCH₂(3-chloro-4-methylphenyl), —NHC(O)CH(CH₃)CH₂CH₃, —NHC(O)CH₂(4-chlorophenyl), —NHC(O)(3-fluoro-4-methylphenyl), —NHC(O)CH₂O(2-methylphenyl), —NHC(O)CH₂(cyclohexyl), —NHC(O)(2-phenyl-cycloprop-1-yl), —NHC(O)(3-chlorophenyl), —NHC(O)CH₂(2-methoxyphenyl), —NHC(O)CH₂CH₂(3-methoxyphenyl), —NHC(O)CH₂NH(2-fluoro-4-methylphenyl), —NHC(O)CH₂NHCH₂(3-fluoro-phenyl), —NHC(O)CH₂(4-methoxy-phenyl), —NHC(O)benzyl, —NHC(O)(2,4-dichlorophenyl), —NHC(O)(3-oxo-cyclohex-1-yl), —NHC(O)CH₂NH(3-fluorophenyl), —NHC(O)CH₂(3-chlorophenyl), —NHC(O)CH₂NHCH₂CH(CH₃)phenyl, —NHC(O)CH₂NHCH₂(2,4-dimethylphenyl), —NHC(O)CH₂(2-methyl-piperidin-1-yl), —NHC(O)CH₂NH(2-methoxyphenyl), —NHC(O)CH₂(1,2,3,4-tetrahydroisoquinolin-2-yl), —NHC(O)CH₂CH₂CH=CH₂, —NHC(O)CH₂NH(2-methylphenyl), —NHC(O)CH₂(4-oxo-piperidin-1-yl), —NHC(O)(2-fluorophenyl), —NHC(O)CH₂NHCH(CH₃)phenyl, —NHC(O)(2-fluoro-6-methoxyphenyl), —NHC(O)CH₂NH(2-isopropylphenyl), —NHC(O)CH₂CH₂(2-methoxyphenyl), —NHC(O)CH₂CH₂CH(CH₃)₂, —NHC(O)CH₂(2-phenyl-morpholin-4-yl), —NHC(O)CH₂CH₂(4-methoxyphenyl), —NHC(O)CH₂N(allyl)cyclopentyl, —NHC(O)CH₂N(CH₃)CH₂CH₂OCH₃, —NHC(O)CH₂CH₂C(O)cyclopropyl, —NHC(O)CH₂NH(3-tert-butylphenyl), —NHC(O)CH₂N(n-propyl)(cyclopropylmethyl), —NHC(O)CH₂(2-oxo-cyclopentyl), —NHC(O)CH₂NH(4-chlorophenyl), —NHC(O)CH₂(4-piperidin-1-ylpiperidin-1-yl), —NHC(O)CH₂(4-cyclopentylpiperazin-1-yl), —NHC(O)CH₂(2-methylphenyl), —NHC(O)CH₂NHCH₂(3-fluoro-6-methylphenyl), —NHC(O)CH₂C(CH₃)₃, —NHC(O)CH₂NH(2-chlorophenyl), —NHC(O)(3-fluoro-6-methylphenyl), —NHC(O)(4-fluoro-3-methylphenyl), —NHC(O)(2,3-dichlorophenyl), —NHC(O)CH₂Ophenyl, —NHC(O)CH₂NH(2,3-dimethylphenyl), —NHC(O)(2-fluoro-5-methylphenyl), —NHC(O)CH₂NHOCH₂(4-methylphenyl), —NHC(O)CH₂(4-isopropylpiperazin-1-yl), —NHC(O)CH₂(4-fluorophenyl), —NHC(O)CH₂CH(CH₃)₂, —NHC(O)(2-methoxy-4-methylphenyl), —NHC(O)CH₂(4-n-propylpiperidin-1-yl), —NHC(O)CH₂O(3-methylphenyl), —NHC(O)(tetrahydrofuran-2-yl), —NHC(O)CH₂(3-hydroxymethylpiperidin-1-yl), —NHC(O)(1-tert-butoxycarbonylpiperidin-2-yl), —NHC(O)CH₂N(CH₃)CH₂(pyridin-3-yl), —NHC(O)CH₂N(CH₂CH₃)phenyl, —NHC(O)CH₂OCH₂CH₂OCH₃, —NHC(O)CH₂CH₂(cyclopentyl), —NHC(O)(2,5-dichlorophenyl), —NHC(O)CH₂(4-methylcarbonylpiperazin-1-yl), —NHC(O)(5-fluoro-2-methoxyphenyl), —NHC(O)CH₂N(CH₂CH₃)cyclohexyl, —NHC(O)(5-methyl-1,2-oxazol-3-yl), —NHC(O)(3-methylpyridin-3-yl), —NHC(O)(2-methoxypyridin-3-yl), —NHC(O)(3,5-dichlorophenyl), —NHC(O)CH₂(thiazolidin3-yl), —NHC(O)CH₂(4-[C(O)H]-piperazin-1-yl), —NHC(O)CH₂(2-pyridin-4-ylpiperidin-1-yl), —NHC(O)(2-methoxyphenyl), —NHC(O)CH₂N(CH₃)CH₂CH(CH₃)₂, —NHC(O)CH₂(4-[C(O)H]-homopiperazin-1-yl), —NHC(O)(1-phenylcycloprop-1-yl), —NHC(O)CH₂(2,6-dimethylmorpholin-4-yl), NHC(O)CH₂(2-phenylpyrrolidin-1-yl), —NHC(O)CH₂(morpholin-4-yl), —C(O)NHCH(CH₃)CH₂N(CH₃)₂, —C(O)NHCH₂CH₂N(CH₃)₂, —C(O)NH(pyrrolidin-3-yl), —C(O)NHCH₂CH₂(pyrrolidin-1-yl), —C(O)NHCH₂CH₂NH₂, —C(O)N(CH₃)CH₂CH₂N(CH₃)₂, —C(O)NHCH₂(piperidin-2-yl), —C(O)NH(1-methylazetidin-3-yl), —C(O)NHCH₂CH₂(piperidin-1-yl), —C(O)NHCH₂CH₂N(CH₂CH₃)₂, —C(O)NH(1-methylpiperidin-3-yl), —C(O)NH(piperidin-3-yl), —C(O)NHCH₂(1-methylpiperidin-3-yl), —C(O)NHCH₂CH₂N(CH₂CH₂OH)₂, —C(O)NH(1-ethylpiperidin-3-yl), —C(O)NH₂, —C(O)(3-aminopyrrolidin-1-yl), —C(O)(3-methylaminopyrrolidin-1-yl), —C(O)OH, —C(O)NHCH₂CH₂(morpholin-4-yl), —C(O)NHCH₂(1-ethylpyrrolidin-2-yl), —C(O)(4-amino-3-oxo-pyrazolidin-1-yl), —C(O)NHCH₃, —C(O)(3-aminocyclobut-1-yl), —C(O)NHCH₂(pyridin-3-yl), —C(O)NHCH₂CH₂OH, —C(O)NH(3-oxo-pyrazolidin-4-yl), —NHCH₂CH₂(imidazol-4-yl), —C(O)(3-dimethylaminopyrrolidin-1-yl), —C(O)NHCH₂(pyridin-4-yl), —C(O)N(CH₃)(1-methyl-pyrrolidin-3-yl), —C(O)(3-diethylaminopyrrolidin-1-yl), —C(O)NH(pyrrol-1-yl), —C(O)NHCH₂CH₂CH₂(pyrrolidin-1-yl), —C(O)N(CH₃)CH₂CH₂CN, —C(O)NHCH₂CH₂OCH₃, —C(O)N(CH₂CH₃)CH₂CH₂CN, —C(O)(3-aminopiperidin-1-yl), —C(O)NHCH₂CH₂CH₂N(CH₃)₂, —C(O)NH(morpholin-4-yl), —C(O)NHN(CH₃)₂, —C(O)NHCH₂CH₂CH₂(imidazol-1-yl), —C(O)NHCH₂CH₂CH₂N(CH₂CH₃)₂, —C(O)NHCH₂CH₂CN, —C(O)NHCH₂CH₂C(O)OCH₃, —C(O)NHCH₂CH₂SCH₃, —(O)NHCH₂CH₂SCH₂CH₃, —C(O)N(CH₂CH₃)CH₂CH₂N(CH₃)₂, —C(O)NHCH₂CH₂CH₂(2-oxo-pyrrolidin-1-yl), —C(O)NHCH₂CH₂(pyridin-4-yl), —C(O)NHCH₂CH₂OCH₂CH₃, —C(O)NHCH₂CH₂CH₂(morpholin-4-yl), —C(O)NHCH₂CH₂CH₂OCH₃, —C(O)N(CH₃)CH₂CH₂CH₂N(CH₃)₂, —C(O)NHCH₂CH₂CH₂OCH₂CH₂OCH₃, —C(O)NHCH₂CH₂C(O)OCH₂CH₃, —C(O)NHCH₂CH₂OCH(CH₃)₂, —C(O)NHCH(CH₃)₂CH₂(piperidin-1-yl), —C(O)N(CH₃)CH₂CH₂CH₃, —C(O)NH(piperidin-1-yl), C(O)NHCH(CH₃)CH₂OCH₃, —C(O)NHC(CH₃)₂CH₂(morpholin-4-yl), —C(O)(2-dimethylaminomethylpiperidin-1-yl), —C(O)NH(CH₂)₃O(CH₂)₃CH₃, —C(O)NHCH(CH₃)(CH₂)₃N(CH₂CH₃)₂, —C(O)NHC(CH₃)₂C(O)(piperidin-1-yl), —C(O)(4-methylpiperazin-1-yl), —C(O)(2-piperidin-1-ylmethyl-piperidin-1-yl), cyano, —NHCH₃, —CH(CH₃)NHCH₂CH₂N(CH₃)₂, —C(O)CH₃, —S(O)₂NHCH₂CH₂N(CH₃)₂, —S(O)₂NH(CH₂)₃N(CH₃)₂, 5-(N,N-dimethylaminomethyl)-1,3,4-oxadiazol-2-yl, —NHCH₂CH₂N(CH₃)₂, —N(CH₃)₂, —OCH₂CH₂N(CH₃)₂, —NHC[N(CH₃)₂][=N(CH₃)₂], —OCHF₂, —S(O)₂CH₃, —OCF₃, or —NHC(O)CH₂(4-dimethylaminopiperidin-1-yl).

In another embodiment, $R^{3a}$ is hydroxyamino, —N($R^7$)C(O)—$C_1$-$C_6$-alkylene-N($R^{7a}$)($R^{7b}$), —C(O)N$R^8R^{8a}$, —N$R^9$C(O)$R^{9a}$, —C(O)N($R^{10}$)—$C_1$-$C_6$-alkylene-N($R^{10a}$)

$R^{10b}$, —$NR^{11}C(O)NR^{11a}R^{11b}$, —$N(R^{22})C(O)$—$C_1$-$C_6$-alkylene-$N(R^{22b})$—$N(R^{22c})(R^{22a})$, —$NR^{13}C(O)OR^{13a}$, —$N(R^{18})C(O)$—$C_1$-$C_6$-alkylene-$N(R^{18b})C(O)R^{18a}$, —$NR^{24}C(O)$—$C_1$-$C_6$-alkylene-$OR^{24a}$, or —$N(R^{20})C(O)$—$C_1$-$C_6$-alkylene-$C(O)R^{20a}$; where each of the alkylene in $R^{3a}$ is independently optionally further substituted with 1, 2, 3, 4, or 5 groups selected from halo, hydroxy, and amino; and all other groups are as defined in the Summary. In a further embodiment, $R^{3a}$ is —$NHC(O)CH_2NH(CH_3)$, —$NHC(O)CH(CH_3)NH_2$, —$NHC(O)C(CH_3)_2NH_2$, —$NHC(O)CH_2N(CH_3)_2$, —$NHC(O)CH_2N(CH_3)CH_2CH_2N(CH_3)_2$, —$NHC(O)CH(NH_2)CH_2CH_3$, —$NHC(O)CH_2N(CH_3)CH_2CH_2N(CH_3)_2$, —$NHC(O)CH(CH_3)NH(CH_3)$, —$NHC(O)H$, —$NHC(O)CH_2(azetidin-1-yl)$, —$NHC(O)(pyrrolidin-2-yl)$, —$NHC(O)CH(NH_2)CH_2OH$, —$NHC(O)(azetidin-4-yl)$, —$NHC(O)C(CH_3)_2NH(CH_3)$, —$NH_2$, —$NHC(O)CH_2NH(CH_2CH_2CH_3)$, —$NHC(O)CH_2CH_2NH_2$, —$NHOH$, or —$NHC(O)(piperidin-3-yl)$.

In another embodiment, $R^{3a}$—$N(R^7)C(O)$—$C_1$-$C_6$-alkylene-$N(R^{7a})(R^{7b})$; and $R^7$ is hydrogen or alkyl, and $R^{7a}$ and $R^{7b}$ are independently hydrogen, alkyl, aminoalkyl, alkylaminoalkyl, or dialkylaminoalkyl; and all other groups are as defined in the Summary. In a further embodiment, $R^{3a}$ is —$NHC(O)CH_2NH(CH_3)$, —$NHC(O)CH(CH_3)NH_2$, —$NHC(O)C(CH_3)_2NH_2$, —$NHC(O)CH_2N(CH_3)_2$, —$NHC(O)CH_2N(CH_3)CH_2CH_2N(CH_3)_2$, —$NHC(O)CH(NH_2)CH_2CH_3$, —$NHC(O)CH_2N(CH_3)CH_2CH_2N(CH_3)_2$, or —$NHC(O)CH(CH_3)NH(CH_3)$.

In one embodiment, each $R^3$ is independently halo, cyano, alkyl, alkenyl, alkoxy, hydroxyamino, carboxy, alkylsulfonyl, aminoalkyloxy, alkylaminoalkyloxy, dialkylaminoalkyloxy, —$N(R^7)C(O)$—$C_1$-$C_6$-alkylene-$N(R^{7a})(R^{7b})$, —$C(O)NR^8R^{8a}$, —$NR^9C(O)R^{9a}$, —$C(O)N(R^{10})$—$C_1$-$C_6$-alkylene-$N(R^{10a})R^{10b}$, —$NR^{11}C(O)NR^{11a}R^{11b}$ where $R^{11a}$, —$C(O)R^{12}$, —$NR^{13}C(O)OR^{13a}$, —$C(O)N(R^{14}N(R^{14a})(R^{14b})$, —$S(O)_2N(R^{15})$—$C_1$-$C_6$-alkylene-$N(R^{15a})R^{15b}$, —$C(O)N(R^{16})$—$C_1$-$C_6$-alkylene-$C(O)OR^{6a}$, heteroaryl optionally substituted with one or two aminoalkyl, alkylaminoalkyl, or dialkylaminoalkyl, —$N(R^{17})$—$C(=N(R^{17b})(R^{17a}))(NR^{17c}R^{17d})$, —$N(R^{18})C(O)$—$C_1$-$C_6$-alkylene-$N(R^{18b})C(O)R^{18a}$, —$C(O)N(R^{19})$—$C_1$-$C_6$-alkylene-$C(O)R^{19a}$, —$N(R^{22})C(O)$—$C_1$-$C_6$-alkylene-$N(R^{22b})$—$N(R^{22c})(R^{22a})$, —$C_0$-$C_6$-alkylene-$N(R^{23})$—$C_1$-$C_6$-alkylene-$N(R^{23b})R^{23a}$, or —$NR^{24}C(O)$—$C_1$-$C_6$-alkylene-$OR^{24a}$; where each of the alkylene in $R^3$ is independently optionally further substituted with 1, 2, 3, 4, or 5 groups selected from halo, hydroxy, amino, alkylamino, and dialkylamino; and all other groups are as defined in the Summary.

In a further embodiment, each $R^3$ is independently methyl, bromo, chloro, fluoro, —$NHC(O)CH_2NH(CH_3)$, —$NHC(O)CH_2NH(CH_2CH_3)$, —$NHC(O)CH(CH_3)NH_2$, —$NHC(O)C(CH_3)_2NH_2$, —$NHC(O)CH_2N(CH_3)_2$, —$NHC(O)CH_2N(CH_3)CH_2CH_2N(CH_3)_2$, —$NHC(O)CH(NH_2)CH_2CH_3$, —$NHC(O)CH_2N(CH_3)CH_2CH_2N(CH_3)_2$, —$NHC(O)CH(CH_3)NH(CH_3)$, —$NHC(O)CH_2NH_2$, —$NHC(O)H$, —$NHC(O)CH_2(azetidin-1-yl)$, —$NHC(O)(pyrrolidin-2-yl)$, —$NHC(O)CH(NH_2)CH_2OH$, —$NHC(O)(azetidin-4-yl)$, —$NHC(O)C(CH_3)_2NH(CH_3)$, —$NH_2$, —$NHC(O)CH_2NH(CH_2CH_2CH_3)$, —$NHC(O)CH_2CH_2NH_2$, —$NHOH$, —$NHC(O)(piperidin-3-yl)$, —$NHC(O)CH_2(4-methyl-1,4-diazepan-1-yl)$, —$NHC(O)CH(NH_2)(CH_2CH_3)$, —$NHC(O)CH_2NH(CH_2CH(OH)(CH_3))$, —$NHC(O)CH_2NHCH_2CH_2F$, —$NHC(O)CH_2NH(OCH_2CH(CH_3)_2)$, —$NHC(O)(1-aminocycloprop-1-yl)$, —$NHC(O)CH_2NH(CH_2cyclopropyl)$, —$NHC(O)CH_2(3-(dimethylamino)-azetidin-1-yl)$, —$NHC(O)(piperidin-2-yl)$, —$NHC(O)(morpholin-4-yl)$, —$NHC(O)CH_2(pyrrolidin-1-yl)$, —$NHC(O)CH(NH_2)CH_2CH_2CH_2N(CH_3)_2$, —$NHC(O)CH_2N(CH_3)(CH_2CH_3)$, —$NHC(O)CH_2(imidazol-5-yl)$, —$NHC(O)(1-aminocyclopent-1-yl)$, —$NHC(O)CH_2NH(CH_2CH(CH_3)_2)$, —$NHC(O)CH_2N(CH_3)(CH_2CH_3)$, —$NHC(O)(N-(imidazol-4-ylmethyl)-azetidin-3-yl)$, —$NHC(O)(N-ethyl-azetidin-3-yl)$, —$NHCH_2N(CH_3)CH_2CH_2N(CH_3)_2$, —$NHC(O)CH_2N(CH_3)(N-methyl-pyrrolidin-3-yl)$, —$NHC(O)CH_2N(CH_3)(CH_2CH_2N(CH_3)_2)$, —$NHC(O)CH_2(3-hydroxypyrrolidin-1-yl)$, —$NHC(O)(1-amino-cyclobut-1-yl)$, —$NHC(O)CH_2NH(CH_2)_3CH_3$, —$NHC(O)CH_2(3-piperidin-1-ylazetidin-1yl)$, —$NHC(O)NH_2$, —$NHC(O)(1-hydroxycyclopropyl)$, —$NHC(O)CH_2NH(CH_3)_2$, —$NHC(O)NH(CH_2)_2N(CH_3)_2$, —$NHC(O)CH_2OH$, —$NHC(O)(pyridazin-4-yl)$, —$NHC(O)(N-methyl-piperidin-4-yl)$, —$NHC(O)CH_2NHCH(CH_3)_3$, —$NHC(O)CH_2(3-dimethylamino-pyrrolidin-1-yl)$, —$NHC(O)CH_2NH(CH_2)_2N(CH_3)_2$, —$NHC(O)(1-cyclopropylmethyl-azetidin-3-yl)$, —$NHC(O)CH_2NH(CH_3)_3$, —$NHC(O)(imidazol-2-yl)$, —$NHC(O)(imidazol-4-yl)$, —$NHC(O)(1,2-oxazol-5-yl)$, —$NHC(O)CH_2NHCH_2CF_3$, —$NHC(O)CH_2CH_2(piperidin-1-yl)$, —$NHC(O)(3-oxo-cyclopent-1-yl)$, —$NHC(O)(2-hydroxy-pyridin-6-yl)$, —$NHC(O)CH_2NH(3-fluoro-4-hydroxyphenyl)$, —$NHC(O)(CH_2)_3N(CH_3)_2$, —$NHC(O)(1-(furan-2-ylmethyl)-azetidin-3-yl)$, —$NHC(O)(pyrimidin-5-yl)$, —$NHC(O)(pyrrol-2-yl)$, —$NHC(O)CH_2N(CH_3)CH(CH_3)_2$, —$NHC(O)CH_2N(CH_2CH_3)_2$, —$NHC(O)CH_2(3-methyl-1,2-oxazol-5-yl)$, —$NHC(O)CH_2NHCH_2(3-hydroxyphenyl)$, —$NHC(O)(N-methyl-pyrrol-2-yl)$, —$NHC(O)(2-amino-tetrahydropyran-2-yl)$, —$NHC(O)CH_2(4-methylamino-piperidin-1-yl)$, —$NHC(O)(piperidin-1-yl)$, —$NHC(O)(N-methyl-pyrrolidin-2-yl)$, —$NHC(O)(thien-3-yl)$, —$NHC(O)(N-(cyclopropylcarbonyl)azetidin-3-yl)$, —$NHC(O)CH_2(4-methylpiperazin-1-yl)$, —$NHC(O)(N-benzylazetidin-3-yl)$, —$NH$—$C(O)(2-chloro-pyridin-3-yl)$, —$NHC(O)CH_2(pyridin-4-yl)$, —$NHC(O)CH_2N(CH_3)(CH_2CH=CH_2)$, —$NHC(O)CH_2NH(benzyl)$, —$NHC(O)CH_2OCH_3$, —$NHC(O)[1-(C(O)CH_2CH_3)-azetidin-3-yl]$, —$NHC(O)(pyridin-3-yl)$, —$NHC(O)CH_2NHCH_2CH_2OCH_3$, —$NHC(O)(1-[C(O)CH_3]piperidin-4-yl)$, —$NHC(O)CH_2(2-methyl-pyrrolidin-1-yl)$, —$NHC(O)(furan-3-yl)$, —$NHC(O)CH_2N(CH_3)_2$, —$NHC(O)(2-chloro-pyridin-5-yl)$, —$NHC(O)(2-chlorophenyl)$, —$NHC(O)CH_2(pyridin-2-yl)$, —$NHC(O)CH_2(3-dimethylamino-azetidin-1-yl)$, —$NHC(O)CH_2(pyridin-3-yl)$, —$NHC(O)CH_2(2-chlorophenyl)$, —$NHC(O)CH_2N(CH_3)CH_2CH_2N(CH_3)_2$, —$NHC(O)CH_2N(CH_3)CH_2CH_2OH$, —$NHC(O)CH_2(2-benzyl-pyrrolidin-1-yl)$, —$NHC(O)(furan-2-yl$, —$NHC(O)(2-chloro-pyridin-4-yl)$, —$NHC(O)CH_2NHC(O)CH_3$, —$NHC(O)CH_2CH_2CH_3$, —$NHC(O)(4-chlorophenyl)$, —$NHC(O)(4-methyl-phenyl)$, —$NHC(O)CH_2NHC(O)O(CH_3)_3$, —$NHC(O)(benzo[d][1,3]dioxol-5-yl)$, —$NHC(O)CH_2NHOCH_2(2-methoxyphenyl)$, —$NHC(O)(pyridin-4-yl)$, —$NHC(O)CH_2[4-(3,4-dichlorophenyl)-piperazin-1-yl]$, —$NHC(O)CH_2CH_2(pyridin-3-yl)$, —$NHC(O)(tetrahydrofuran-3-yl)$, —$NHC(O)CH_2NHCH_2(2-methylphenyl)$, —$NHC(O)CH(CH_3)CH_2CH_3$, —$NHC(O)CH_2(3-fluorophenyl)$, —$NHC(O)CH_2C(CH_3)_2$-phenyl, —$NHC(O)(2-methyl-cycloprop-1-yl)$, —$NHC(O)(2-methyl-4-methoxyphenyl)$, —$NHC(O)(2-methylpyridin-3-yl)$, —$NHC(O)(4-methoxyphenyl)$, —$NHC(O)CH_2(4-ethylpiperazin-1-yl)$, —$NHC(O)(thien-2-yl)$, —$NHC(O)(3-fluoro-2-methylphenyl)$, —$NHC(O)(2-bromo-thien-3-yl)$, —$NHC(O)(4-fluorophenyl)$, —$NHC(O)CH_2(3-methylpiperidin-1-yl)$, —$NHC(O)CH(CH_3)_2$, —$NHC(O)CH_2)_3CH_3$, —$NHC(O)CH_2OCH_2CH_3$, —$NHC(O)CH_2NH(2-fluorophenyl)$, —$NHC(O)(3-dimethylaminophenyl)$, —$NH$—$C(O)CH_2(4-methylpiperidin-1-yl)$, —$NHC(O)CH_2NH(2-n-propylphenyl)$, —$NHC(O)phenyl, —NHC(O)(pyrazin2-yl), —NHC(O)(3-fluoro-4-methoxyphenyl), —NHC(O)C(CH$_3$)$_2$CH$_2$CH$_3$, —NHC(O)CH$_2$O (4-fluorophenyl), —NHC(O)(1-methylcarbonyl-azetidin-3-yl), —NHC(O)CH$_2$NH(4-methylphenyl), —NHC(O)CH$_2$NH(phenyl), —NHC(O)CH$_2$(4-allyl-piperazin-1-yl), —NHC(O)(2-methylphenyl), —NHC(O)CH$_2$CH$_2$OCH$_3$, —NHC(O)(3-methyl-furan-2-yl), —NHC(O)C(CH$_3$)$_3$, —NHC(O)CH$_2$NHObenzyl, —NHC(O)CH$_2$NH(3-chlorophenyl), —NHC(O)cyclobutyl, —NHC(O)CH$_2$(3-methoxyphenyl), —NHC(O)(1-methylcycloprop-1-yl), —NHC(O)(3-fluorophenyl), —NHC(O)(4-dimethylaminophenyl), —NHC(O)(3,4-dichlorophenyl), —NHC(O)CH$_2$NHCH$_2$(2-methylthiophenyl), —NHC(O)CH$_2$(2-fluorophenyl), —NHC(O)CH$_2$N(CH$_2$CH$_3$)CH(CH$_3$)$_2$, —NHC(O)(thiazol-4-yl), —NHC(O)CH$_2$N(CH$_3$)benzyl, —NHC(O)CH$_2$NHCH$_2$(thien-2-yl), —NHC(O)CH$_2$NHCH$_2$(pyridin-2-yl), —NHC(O)(3-methoxyphenyl), —NHC(O)CH$_2$NHCH$_2$(3-chloro-4-methylphenyl), —NHC(O)CH(CH$_3$)CH$_2$CH$_2$CH$_3$, —NHC(O)CH$_2$(4-chlorophenyl), —NHC(O)(3-fluoro-4-methylphenyl), —NHC(O)CH$_2$O(2-methylphenyl), —NHC(O)CH$_2$(cyclohexyl), —NHC(O)(2-phenyl-cycloprop-1-yl), —NHC(O)(3-chlorophenyl), —NHC(O)CH$_2$(2-methoxyphenyl), —NHC(O)CH$_2$CH$_2$(3-methoxyphenyl), —NHC(O)CH$_2$NH(2-fluoro-4-methylphenyl), —NHC(O)CH$_2$NHCH$_2$(3-fluoro-phenyl), —NHC(O)CH$_2$(4-methoxy-phenyl), —NHC(O)benzyl, —NHC(O)(2,4-dichlorophenyl), —NHC(O)(3-oxo-cyclohex-1-yl), —NHC(O)CH$_2$NH(3-fluorophenyl), —NHC(O)CH$_2$(3-chlorophenyl), —NHC(O)CH$_2$NHCH$_2$CH(CH$_3$)phenyl, —NHC(O)CH$_2$NHCH$_2$(2,4-dimethylphenyl), —NHC(O)CH$_2$(2-methyl-piperidin-1-yl), —NHC(O)CH$_2$NH(2-methoxyphenyl), —NHC(O)CH$_2$(1,2,3,4-tetrahydroisoquinolin-2-yl), —NHC(O)CH$_2$CH=CH$_2$, —NHC(O)CH$_2$NH(2-methylphenyl), —NHC(O)CH$_2$(4-oxo-piperidin-1-yl), —NHC(O)(2-fluorophenyl), —NHC(O)CH$_2$NHCH(CH$_3$)phenyl, —NHC(O)(2-fluoro-6-methoxyphenyl), —NHC(O)CH$_2$NH(2-isopropylphenyl), —NHC(O)CH$_2$CH$_2$(2-methoxyphenyl), —NHC(O)CH$_2$CH$_2$CH(CH$_3$)$_2$, —NHC(O)CH$_2$(2-phenyl-morpholin-4-yl), —NHC(O)CH$_2$CH$_2$(4-methoxyphenyl), —NHC(O)CH$_2$N(allyl)cyclopentyl, —NHC(O)CH$_2$N(CH$_3$)CH$_2$CH$_2$OCH$_3$, —NHC(O)CH$_2$CH$_2$C(O)cyclopropyl, —NHC(O)CH$_2$NH(3-tert-butylphenyl), —NHC(O)CH$_2$N(n-propyl)(cyclopropylmethyl), —NHC(O)CH$_2$(2-oxo-cyclopentyl), —NHC(O)CH$_2$NH(4-chlorophenyl), —NHC(O)CH$_2$(4-piperidin-1-ylpiperidin-1-yl), —NHC(O)CH$_2$(4-cyclopentylpiperazin-1-yl), —NHC(O)CH$_2$(2-methylphenyl), —NHC(O)CH$_2$NHCH$_2$(3-fluoro-6-methylphenyl), —NHC(O)CH$_2$C(CH$_3$)$_3$, —NHC(O)CH$_2$NH(2-chlorophenyl), —NHC(O)(3-fluoro-6-methylphenyl), —NHC(O)(4-fluoro-3-methylphenyl), —NHC(O)(2,3-dichlorophenyl), —NHC(O)CH$_2$Ophenyl, —NHC(O)CH$_2$NH(2,3-dimethylphenyl), —NHC(O)(2-fluoro-5-methylphenyl), —NHC(O)CH$_2$NHOCH$_2$(4-methylphenyl), —NHC(O)CH$_2$(4-isopropylpiperazin-1-yl), —NHC(O)CH$_2$(4-fluorophenyl), —NHC(O)CH$_2$CH(CH$_3$)$_2$, —NHC(O)(2-methoxy-4-methylphenyl), —NHC(O)CH$_2$(4-n-propylpiperidin-1-yl), —NHC(O)CH$_2$O(3-methylphenyl), —NHC(O)(tetrahydrofuran-2-yl), —NHC(O)CH$_2$(3-hydroxymethylpiperidin-1-yl), —NHC(O)(1-tert-butoxycarbonylpiperidin-2-yl), —NHC(O)CH$_2$N(CH$_3$)CH$_2$(pyridin-3-yl), —NHC(O)CH$_2$N(CH$_2$CH$_3$)phenyl, —NHC(O)CH$_2$OCH$_2$CH$_2$OCH$_3$, —NHC(O)CH$_2$CH$_2$(cyclopentyl), —NHC(O)(2,5-dichlorophenyl), —NHC(O)CH$_2$(4-methylcarbonylpiperazin-1-yl), —NHC(O)(5-fluoro-2-methoxyphenyl), —NHC(O)CH$_2$N(CH$_2$CH$_3$)cyclohexyl, —NHC(O)(5-methyl-1,2-oxazol-3-yl), —NHC(O)(3-methylpyridin-3-yl), —NHC(O)(2-methoxypyridin-3-yl), —NHC(O)(3,5-dichlorophenyl), —NHC(O)CH$_2$(thiazolidin3-yl), —NHC(O)CH$_2$(4-[C(O)H]-piperazin-1-yl), —NHC(O)CH$_2$(2-pyridin-4-ylpiperidin-1-yl), —NHC(O)(2-methoxyphenyl), —NHC(O)CH$_2$N(CH$_3$)CH$_2$CH(CH$_3$)$_2$, —NHC(O)CH$_2$(4-[C(O)H]-homopiperazin-1-yl), —NHC(O)(1-phenylcycloprop-1-yl), —NHC(O)CH$_2$(2,6-dimethylmorpholin-4-yl), NHC(O)CH$_2$(2-phenylpyrrolidin-1-yl), —NHC(O)CH$_2$(morpholin-4-yl), —C(O)NHCH(CH$_3$)CH$_2$N(CH$_3$)$_2$, —C(O)NHCH$_2$CH$_2$N(CH$_3$)$_2$, —C(O)NH(pyrrolidin-3-yl), —C(O)NHCH$_2$CH$_2$(pyrrolidin-1-yl), —C(O)NHCH$_2$CH$_2$NH$_2$, —C(O)N(CH$_3$)CH$_2$CH$_2$N(CH$_3$)$_2$, —C(O)NHCH$_2$(piperidin-2-yl), —C(O)NH(1-methylazetidin-3-yl), —C(O)NHCH$_2$CH$_2$(piperidin-1-yl), —C(O)NHCH$_2$CH$_2$N(CH$_2$CH$_3$)$_2$, —C(O)NH(1-methylpiperidin-3-yl), —C(O)NH(piperidin-3-yl), —C(O)NHCH$_2$(1-methylpiperidin-3-yl), —C(O)NHCH$_2$CH$_2$N(CH$_2$CH$_2$OH)$_2$, —C(O)NH(1-ethylpiperidin-3-yl), —C(O)NH$_2$, —C(O)(3-aminopyrrolidin-1-yl), —C(O)(3-methylaminopyrrolidin-1-yl), —C(O)OH, —C(O)NHCH$_2$CH$_2$(morpholin-4-yl), —C(O)NHCH$_2$(1-ethylpyrrolidin-2-yl), —C(O)(4-amino-3-oxo-pyrazolidin-1-yl), —C(O)NHCH$_3$, —C(O)(3-aminocyclobut-1-yl), —C(O)NHCH$_2$(pyridin-3-yl), —C(O)NHCH$_2$CH$_2$OH, —C(O)NH(3-oxo-pyrazolidin-4-yl), —NHCH$_2$CH$_2$(imidazol-4-yl), —C(O)(3-dimethylaminopyrrolidin-1-yl), —C(O)NHCH$_2$(pyridin-4-yl), —C(O)N(CH$_3$)(1-methyl-pyrrolidin-3-yl), —C(O)(3-diethylaminopyrrolidin-1-yl), —C(O)NH(pyrrol-1-yl), —C(O)NHCH$_2$CH$_2$CH$_2$(pyrrolidin-1-yl), —C(O)N(CH$_3$)CH$_2$CH$_2$CN, —C(O)NHCH$_2$CH$_2$OCH$_3$, —C(O)N(CH$_2$CH$_3$)CH$_2$CH$_2$CN, —C(O)(3-aminopiperidin-1-yl), —C(O)NHCH$_2$CH$_2$CH$_2$N(CH$_3$)$_2$, —C(O)NH(morpholin-4-yl), —C(O)NHN(CH$_3$)$_2$, —C(O)NHCH$_2$CH$_2$CH$_2$(imidazol-1-yl), —C(O)NHCH$_2$CH$_2$N(CH$_2$CH$_3$)$_2$, —C(O)NHCH$_2$CH$_2$CN, —C(O)NHCH$_2$C(O)OCH$_3$, —C(O)NHCH$_2$CH$_2$SCH$_3$, —C(O)NHCH$_2$CH$_2$SCH$_2$CH$_3$, —C(O)N(CH$_2$CH$_3$)CH$_2$CH$_2$N(CH$_3$)$_2$, —C(O)NHCH$_2$CH$_2$(2-oxo-pyrrolidin-1-yl), —C(O)NHCH$_2$(pyridin-4-yl), —C(O)NHCH$_2$CH$_2$CH$_2$OCH$_2$CH$_3$, —C(O)NHCH$_2$CH$_2$CH$_2$(morpholin-4-yl), —C(O)NHCH$_2$CH$_2$OCH$_3$, —C(O)N(CH$_3$)CH$_2$CH$_2$CH$_2$N(CH$_3$)$_2$, —C(O)NHCH$_2$CH$_2$CH$_2$OCH$_2$CH$_3$, C(O)NHCH$_2$CH$_2$C(O)OCH$_2$CH$_3$, —C(O)NHCH$_2$CH$_2$OCH(CH$_3$)$_2$, —C(O)NHC(CH$_3$)$_2$CH$_2$(piperidin-1-yl), —C(O)N(CH$_3$)CH$_2$CH$_2$CH$_3$, —C(O)NH(piperidin-1-yl), —C(O)NHCH(CH$_3$)CH$_2$OCH$_3$, —C(O)NHC(CH$_3$)$_2$CH$_2$(morpholin-4-yl), —C(O)(2-dimethylaminomethylpiperidin-1-yl), —C(O)NH(CH$_2$)$_3$O(CH$_2$)$_3$CH$_3$, —C(O)NHCH(CH$_3$)(CH$_2$)$_3$N(CH$_2$CH$_3$)$_2$, —C(O)NHCH(CH$_3$)$_2$C(O)(piperidin-1-yl), —C(O)(4-methylpiperazin-1-yl), —C(O)(2-piperidin-1-yl-methyl-piperidin-1-yl), cyano, —NHCH$_3$, —CH(CH$_3$)NHCH$_2$CH$_2$N(CH$_3$)$_2$, —C(O)CH$_3$, —S(O)$_2$NHCH$_2$CH$_2$N(CH$_3$)$_2$, —S(O)$_2$NH(CH$_2$)$_3$N(CH$_3$)$_2$, 5-(N,N-dimethylaminomethyl)-1,3,4-oxadiazol-2-yl, —NHCH$_2$CH$_2$N(CH$_3$)$_2$, —N(CH$_3$)$_2$, —OCH$_2$CH$_2$N(CH$_3$)$_2$, —NHC[N(CH$_3$)$_2$][=N(CH$_3$)$_2$], —OCHF$_2$, —CF$_3$, —S(O)$_2$CH$_3$, —OCF$_3$, —NHC(O)CH$_2$(4-dimethylaminopiperidin-1-yl), or methoxy.

In another embodiment, each $R^3$ is independently halo, alkyl, hydroxyamino, —N(R$^7$)C(O)—C$_1$-C$_6$-alkylene-N(R$^{7a}$)(R$^{7b}$), —C(O)NR$^8$R$^{8a}$, —NR$^9$C(O)R$^{9a}$, —C(O)N(R$^{10}$)—C$_1$-C$_6$-alkylene-N(R$^{10a}$)R$^{10b}$—NR$^{11}$C(O)NR$^{11a}$R$^{11b}$, —N(R$^{22}$)C(O)—C$_1$-C$_6$-alkylene-N(R$^{22b}$)—N(R$^{22c}$)(R$^{22a}$), —NR$^{13}$C(O)OR$^{13a}$, —N(R$^{18}$)C(O)—C$_1$-C$_6$-alkylene-N(R$^{18b}$)C(O)R$^{18a}$, —NR$^{24}$C(O)—C$_1$-C$_6$-alkylene-OR$^{24a}$, or —N(R$^{20}$)C(O)—C$_1$-C$_6$-alkylene-C(O)R$^{20a}$; where each of the alkylene in R$^3$ is independently optionally further substituted with 1, 2, 3, 4, or 5 groups selected from halo, hydroxy, and amino; and all other groups are as defined in the Summary. More particularly, each $R^3$ is independently methyl, chloro, —NHC(O)CH$_2$NH(CH$_3$), —NHC(O)CH (CH$_3$)NH$_2$, —NHC(O)C(CH$_3$)$_2$NH$_2$, —NHC(O)CH$_2$N (CH$_3$)$_2$, —NHC(O)CH$_2$N(CH$_3$)CH$_2$CH$_2$N(CH$_3$)$_2$, —NHC (O)CH(NH$_2$)CH$_2$CH$_3$, —NHC(O)CH$_2$N(CH$_3$)CH$_2$CH$_2$N (CH$_3$)$_2$, —NHC(O)CH(CH$_3$)NH(CH$_3$), —NHC(O)H, —NHC(O)CH$_2$(azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH (CH$_2$CH$_2$CH$_3$), —NHC(O)CH$_2$CH$_2$NH$_2$, —NHOH, or —NHC(O)(piperidin-3-yl).

In one embodiment, $R^3$ is alkyl or —N($R^7$)C(O)—C$_1$-C$_6$-alkylene-N($R^{7a}$)($R^{7b}$); and $R^7$ is hydrogen or alkyl, and $R^{7a}$ and $R^{7b}$ are independently hydrogen, alkyl, aminoalkyl, alkylaminoalkyl, or dialkylaminoalkyl; and all other groups are as defined in the Summary. More particularly, each $R^3$ is independently methyl, —NHC(O)CH$_2$NH(CH$_3$), —NHC(O)CH (CH$_3$)NH$_2$, —NHC(O)C(CH$_3$)$_2$NH$_2$, —NHC(O)—CH$_2$N (CH$_3$)$_2$, —NHC(O)CH$_2$N(CH$_3$)CH$_2$CH$_2$N(CH$_3$)$_2$, —NHC (O)CH(NH$_2$)CH$_2$CH$_3$, —NHC(O)CH$_2$N(CH$_3$)CH$_2$CH$_2$N (CH$_3$)$_2$, or —NHC(O)CH(CH$_3$)NH(CH$_3$).

In another embodiment, B is phenyl, $R^3$ is not present or $R^3$ is halo, alkyl, or alkoxy; $R^{3a}$ is —C(O)NR$^8$R$^{8a}$, —NR$^9$C(O) R$^{9a}$, —N($R^7$)C(O)—C$_1$-C$_6$-alkylene-N($R^{7a}$)($R^{7b}$), or C(O)N ($R^{10}$)—C$_1$-C$_6$-alkylene-N($R^{10a}$)R$^{10b}$; where each of the alkylene in $R^{3a}$ is independently optionally further substituted with 1, 2, 3, 4, or 5 groups selected from halo, hydroxy, and amino; and all other groups are as defined in the Summary.

In a further embodiment, $R^{50}$, $R^{52}$, and $R^{53}$ are hydrogen, and $R^{54}$ is halo or alkoxy; $R^{50}$, $R^{52}$, and $R^{54}$ are hydrogen, and $R^{53}$ is alkoxy; or $R^{50}$ and $R^{52}$ are hydrogen, and $R^{53}$ and $R^{54}$ together with the carbons to which they are attached form a 6-membered heteroaryl; and all other groups are as defined in the Summary. In yet another embodiment, $R^{50}$, $R^{52}$, and $R^{53}$ are hydrogen, and $R^{54}$ is halo or alkoxy; or $R^{50}$, $R^{52}$, and $R^{54}$ are hydrogen, and $R^{53}$ is alkoxy. More particularly, $R^{51}$ is methyl.

In another embodiment of the compound of formula I(a):

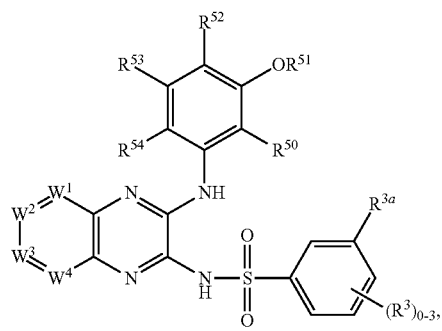

I(a)

wherein $R^3$ is not present or $R^3$ is alkyl, and $R^{3a}$ is —N($R^7$) C(O)—C$_1$-C$_6$-alkylene-N($R^{7a}$)($R^{7b}$), —C(O)NR$^8$R$^{8a}$, —NR$^9$C(O)R$^{9a}$, or —C(O)N($R^{10}$)—C$_1$-C$_6$-alkylene-N ($R^{10a}$)R$^{10b}$; where each of the alkylene in $R^{3a}$ is independently optionally further substituted with 1, 2, 3, 4, or 5 groups selected from halo, hydroxy, and amino; and all other groups are as defined in the Summary. In a further embodiment, $R^3$ is not present or is methyl. More particularly, $R^3$ is not present.

In another embodiment, $R^7$ is hydrogen or alkyl, and $R^{7a}$ and $R^{7b}$ are independently hydrogen, alkyl, hydroxyalkyl, aminoalkyl, alkylaminoalkyl, or dialkylaminoalkyl; $R^8$ is hydrogen or alkyl, and $R^{8a}$ is heterocycloalkyl or heterocycloalkylalkyl; $R^9$ is hydrogen or alkyl, and $R^{9a}$ is hydrogen, heterocycloalkyl, or heterocycloalkylalkyl; and $R^{10}$, $R^{10a}$, and $R^{10b}$ are independently hydrogen, alkyl, hydroxyalkyl, aminoalkyl, alkylaminoalkyl, or dialkylaminoalkyl.

In a further embodiment, $R^{50}$, $R^{52}$, and $R^{53}$ are hydrogen, and $R^{54}$ is halo or alkoxy; or $R^{50}$, $R^{52}$, and $R^{54}$ are hydrogen, and $R^{53}$ is alkoxy; or $R^{50}$ and $R^{52}$ are hydrogen, and $R^{53}$ and $R^{54}$ together with the carbons to which they are attached form a 6-membered heteroaryl. In yet another embodiment, $R^{50}$, $R^{52}$, and $R^{53}$ are hydrogen, and $R^{54}$ is halo or alkoxy; or $R^{50}$, $R^{52}$, and $R^{54}$ are hydrogen, and $R^{53}$ is alkoxy. More particularly, $R^{51}$ is methyl.

In one embodiment, B is heteroaryl, one $R^3$ is halo, alkyl, or alkoxy, and a second $R^3$ is —C(O)NR$^8$R$^{8a}$, —NR$^9$C(O)R$^{9a}$, —N($R^7$)C(O)—C$_1$-C$_6$-alkylene-N($R^{7a}$)($R^{7b}$), or —C(O)N ($R^{10}$)—C$_1$-C$_6$-alkylene-N($R^{10a}$)R$^{10b}$, where each of the alkylene in $R^3$ is independently optionally further substituted with 1, 2, 3, 4, or 5 groups selected from halo, hydroxy, and amino; and all other groups are as defined in the Summary.

In a further embodiment, $R^7$ is hydrogen or alkyl, and $R^{7a}$ and $R^{7b}$ are independently hydrogen, alkyl, hydroxyalkyl, aminoalkyl, alkylaminoalkyl, or dialkylaminoalkyl; $R^8$ is hydrogen or alkyl, and $R^{8a}$ is heterocycloalkyl or heterocycloalkylalkyl; $R^9$ is hydrogen or alkyl, and $R^{9a}$ is hydrogen, heterocycloalkyl, or heterocycloalkylalkyl; $R^{10}$, $R^{10a}$, and $R^{10b}$ are independently hydrogen, alkyl, hydroxyalkyl, aminoalkyl, alkylaminoalkyl, or dialkylaminoalkyl.

In another embodiment, B is:

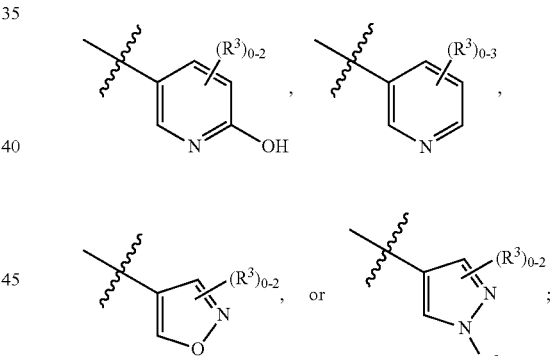

each $R^3$ (when $R^3$ is present) is independently halo, alkyl, alkoxy, aminoalkyloxy, alkylaminoalkyloxy, dialkylaminoalkyloxy, alkylamino, dialkylamino, —C(O)NR$^8$R$^{8a}$, —NR$^9$C(O)R$^{9a}$, —N($R^7$)C(O)—C$_1$-C$_6$-alkylene-N($R^{7a}$) ($R^{7b}$), or —C(O)N($R^{10}$)—C$_1$-C$_6$-alkylene-N($R^{10a}$)R$^{10b}$; and all other groups are as defined in the Summary.

In another embodiment, $R^{50}$, $R^{52}$, and $R^{53}$ are hydrogen, and $R^{54}$ is halo or alkoxy; $R^{50}$, $R^{52}$, and $R^{54}$ are hydrogen, and $R^{53}$ is alkoxy; or $R^{50}$ and $R^{52}$ are hydrogen, and $R^{53}$ and $R^{54}$ together with the carbons to which they are attached form a 6-membered heteroaryl; and all other groups are as defined in the Summary. In a further embodiment, $R^{50}$, $R^{52}$, and $R^{53}$ are hydrogen, and $R^{54}$ is halo or alkoxy; or $R^{50}$, $R^{52}$, and $R^{54}$ are hydrogen and $R^{53}$ is alkoxy. More particularly, $R^{51}$ is methyl.

In yet another embodiment, $R^7$ is hydrogen or alkyl, and $R^{7a}$ and $R^{7b}$ are independently hydrogen, alkyl, hydroxyalkyl, aminoalkyl, alkylaminoalkyl, or dialkylaminoalkyl; $R^8$ is hydrogen or alkyl, and $R^{8a}$ is heterocycloalkyl or heterocycloalkylalkyl; $R^9$ is hydrogen or alkyl, and $R^{9a}$ is hydrogen, heterocycloalkyl, or heterocycloalkylalkyl; and $R^{10}$, $R^{10a}$, and $R^{10b}$ are independently hydrogen, alkyl, hydroxyalkyl, aminoalkyl, alkylaminoalkyl, or dialkylaminoalkyl In one embodiment, $W^1$, $W^2$, $W^3$, and $W^4$ are —C(H)=; or $W^2$ and $W^3$ are —C(H)=, and one of $W^1$ and $W^4$ is —N= and the other is —C(H)=;

$R^{50}$ is hydrogen;

$R^{51}$ is hydrogen or alkyl;

$R^{52}$ is hydrogen;

$R^{53}$ is hydrogen, alkoxy, nitro, amino, or —N($R^{55}$)C(O)—$C_1$-$C_6$-alkylene-N($R^{55a}$)$R^{55b}$; and $R^{54}$ is hydrogen, alkyl, alkoxy, or halo; or $R^{53}$ and $R^{54}$ together with the carbons to which they are attached form a 6-membered heteroaryl;

B is phenyl substituted with $R^{3a}$ and optionally further substituted with one $R^3$; or B is heteroaryl optionally substituted with one or two $R^3$;

$R^{3a}$ is cyano, hydroxyamino, carboxy, alkylsulfonyl, aminoalkyloxy, alkylaminoalkyloxy, dialkylaminoalkyloxy, —N($R^7$)C(O)—$C_1$-$C_6$-alkylene-N($R^{7a}$)($R^{7b}$), —C(O)NR$^8$R$^{8a}$, —NR$^9$C(O)R$^{9a}$, —C(O)N($R^{10}$)—$C_1$-$C_6$-alkylene-N($R^{10a}$)$R^{10b}$, —NR$^{11}$C(O)NR$^{11a}$R$^{11b}$ where R$^{11a}$, —C(O)R$^{12}$; —NR$^{13}$C(O)OR$^{13a}$, —C(O)N($R^{14}$)N($R^{14a}$)($R^{14b}$), —S(O)$_2$N($R^{15}$)—$C_1$-$C_6$-alkylene-N($R^{15a}$)$R^{15b}$, —C(O)N($R^{16}$)—$C_1$-$C_6$-alkylene-C(O)OR$^{16a}$, heteroaryl optionally substituted with one or two aminoalkyl, alkylaminoalkyl, or dialkylaminoalkyl, —N($R^{17}$)—C(=N($R^{17b}$)($R^{17a}$))(NR$^{17c}$R$^{17d}$), —N($R^{18}$)C(O)—$C_1$-$C_6$-alkylene-N($R^{18b}$)C(O)R$^{18a}$, —C(O)N($R^{19}$)—$C_1$-$C_6$-alkylene-C(O)R$^{19a}$, —N($R^{22}$)C(O)—$C_1$-$C_6$-alkylene-N($R^{22b}$)—N($R^{22c}$)($R^{22a}$), —$C_0$-$C_6$-alkylene-N($R^{23}$)—$C_1$-$C_6$-alkylene-N($R^{23b}$)$R^{23a}$, or —NR$^{24}$C(O)—$C_1$-$C_6$-alkylene-OR$^{24a}$; where each of the alkylene in $R^{3a}$ is independently optionally further substituted with 1, 2, 3, 4, or 5 groups selected from halo, hydroxy, and amino;

each $R^3$ (when $R^3$ is present) is independently halo, cyano, alkyl, alkenyl, alkoxy, hydroxyamino, carboxy, alkylsulfonyl, aminoalkyloxy, alkylaminoalkyloxy, dialkylaminoalkyloxy, —N($R^7$)C(O)—$C_1$-$C_6$-alkylene-N($R^{7a}$)($R^{7b}$), —C(O)NR$^8$R$^{8a}$, —NR$^9$C(O)R$^{9a}$, —C(O)N($R^{10}$)—$C_1$-$C_6$-alkylene-N($R^{10a}$)$R^{10b}$, —NR$^{11}$C(O)NR$^{11a}$R$^{11b}$ where R$^{11a}$, —C(O)R$^{12}$, —NR$^{13}$C(O)OR$^{13}$, —C(O)N($R^{14}$)N($R^{14a}$)($R^{14b}$), —S(O)$_2$N($R^{15}$)—$C_1$-$C_6$-alkylene-N($R^{15a}$)$R^{15b}$, —C(O)N($R^{16}$)—$C_1$-$C_6$-alkylene-C(O)OR$^{16a}$, heteroaryl optionally substituted with one or two aminoalkyl, alkylaminoalkyl, or dialkylaminoalkyl, —N($R^{17}$)—C(=N($R^{17b}$)($R^{17a}$))(NR$^{17c}$R$^{17d}$), —N($R^{18}$)C(O)—$C_1$-$C_6$-alkylene-N($R^{18b}$)C(O)R$^{18a}$, —C(O)N($R^{19}$)—$C_1$-$C_6$-alkylene-C(O)R$^{19a}$, —N($R^{22}$)C(O)—$C_1$-$C_6$-alkylene-N($R^{22b}$)—N($R^{22c}$)($R^{22a}$), —$C_0$-$C_6$-alkylene-N($R^{23}$)—$C_1$-$C_6$-alkylene-N($R^{23b}$)$R^{23a}$, or —NR$^{24}$C(O)—$C_1$-$C_6$-alkylene-OR$^{24a}$; where each of the alkylene in $R^3$ is independently optionally further substituted with 1, 2, 3, 4, or 5 groups selected from halo, hydroxy, and amino;

provided that when $R^{50}$ and $R^{52}$ are hydrogen, $R^{51}$ is hydrogen or methyl, $R^{53}$ is hydrogen or methoxy, and $R^{54}$ is hydrogen or methoxy, then B is not 2,3-dihydro-1,4-benzodioxinyl, thien-2-yl, or thien-2-yl, substituted with one $R^3$, where $R^3$ is halo.

In another embodiment, $R^{50}$, $R^{53}$, and $R^{54}$ are independently hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$NR$^{55}$R$^{55a}$, or alkylcarbonylamino and where $R^{55}$ and $R^{55b}$ are independently hydrogen, alkyl, or alkenyl and $R^{55a}$ is hydrogen, alkyl, alkenyl, hydroxy, or alkoxy; or $R^{53}$ and $R^{54}$ together with the carbons to which they are attached form a 5- or 6-membered heteroaryl or 5- or 6-membered heterocycloalkyl.

More particularly, $R^{53}$ and $R^{54}$ together with the carbons to which they are attached form a 5- or 6-membered heteroaryl or 5- or 6-membered heterocycloalkyl.

In another embodiment of the compound of Formula I(a):

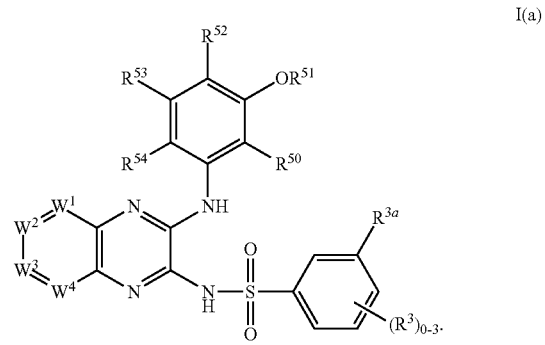

I(a)

$W^1$, $W^2$, $W^3$, and $W^4$ are —C(H)—;

$R^{50}$ is hydrogen;

$R^{51}$ is methyl;

$R^{52}$ is hydrogen;

$R^{53}$ is hydrogen or alkoxy; and $R^{54}$ is hydrogen, alkyl, alkoxy, or halo; or $R^{53}$ and $R^{54}$ together with the carbons to which they are attached form a 6-membered heteroaryl; and $R^3$ is halo or methyl; and $R^{3a}$ is —N($R^7$)C(O)—$C_1$-$C^6$-alkylene-N($R^{7a}$)($R^{7b}$) where $R^7$ is hydrogen and $R^{7a}$ and $R^{7b}$ are independently hydrogen, alkyl, aminoalkyl, alkylaminoalkyl, or dialkylaminoalkyl.

In another embodiment of the compound of Formula I(a), $R^{51}$ is methyl; and $R^{50}$, $R^{52}$, and $R^{53}$ are hydrogen and $R^{54}$ is halo or alkoxy or $R^{50}$, $R^{52}$, and $R^{54}$ are hydrogen and $R^{53}$ is alkoxy; or a single stereoisomer or mixture of stereoisomers thereof and optionally as a pharmaceutically acceptable salt thereof.

In another embodiment of the compound of Formula I(a), $R^{3a}$ is

—NHHC(O)CH$_2$NH(CH$_3$),

—NHC(O)CH(CH$_3$)NH$_2$,

—NHC(O)C(CH$_3$)$_2$NH$_2$,

—NHC(O)CH$_2$N(CH$_3$)$_2$,

—NHC(O)CH$_2$N(CH$_3$)CH$_2$CH$_2$N(CH$_3$)$_2$,

—NHC(O)CH(NH$_2$)CH$_2$CH$_3$,

—NHC(O)CH$_2$N(CH$_3$)CH$_2$CH$_2$N(CH$_3$)$_2$, or

—NHC(O)CH(CH$_3$)NH(CH$_3$), or geometric isomer thereof and optionally as a pharmaceutically acceptable salt thereof.

In another embodiment, the compound of Formula I(a) is:

| Structure | Name |
|---|---|
| 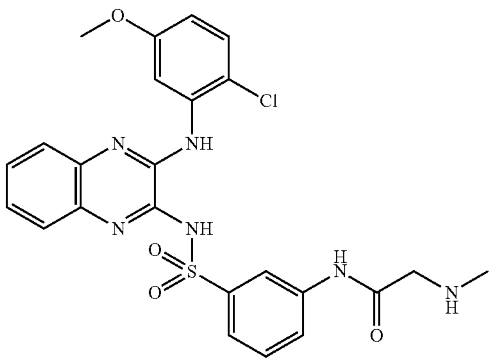 [SMILES: CNCC(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}-phenyl)-N-2-methylglycinamide |
| 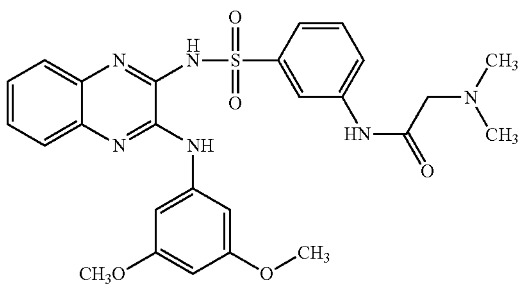 | N-(3-{[(3-{[3,5-bis(methoxy)phenyl]amino)quinoxalin-2-yl)amino]sulfonyl}phenyl)-N-2-,N-2-dimethylglycinamide |
| 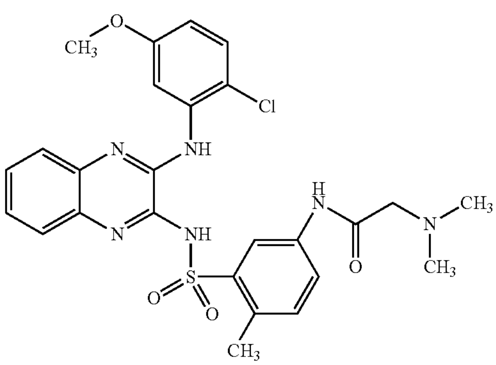 [SMILES: COc1ccc(Cl)c(Nc2nc3ccccc3nc2NS(=O)(=O)c2cc(NC(=O)CN(C)C)ccc2C)c1] | N-(3-{[(3-{[2-chloro-5-(methoxy)phenyl]amino}quinoxalin-2-yl)amino]sulfonyl}-4-methylphenyl)-N-2-,N-2-dimethylglycinamide |
| 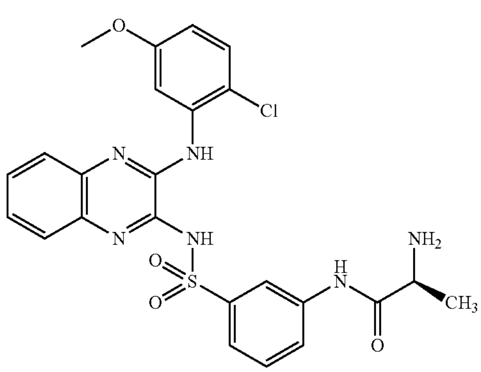 [SMILES: COc1ccc(Cl)c(Nc2nc3ccccc3nc2NS(=O)(=O)c2cccc(NC(=O)[C@H](C)N)c2)c1] | N-(3-{[(3-{[2-chloro-5-(methoxy)phenyl]amino}quinoxalin-2-yl)amino]sulfonyl}phenyl)-L-alaninamide |

| Structure | Name |
|---|---|
| 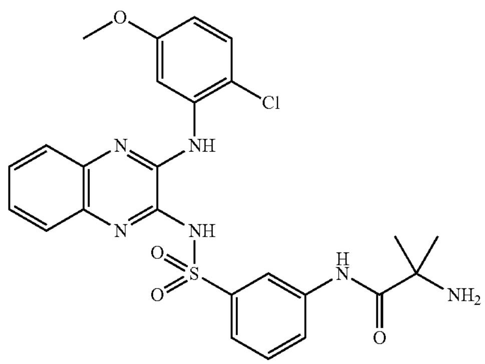 [SMILES: COc1ccc(Cl)c(Nc2nc3ccccc3nc2NS(=O)(=O)c2cccc(NC(=O)C(C)(C)N)c2)c1] | N-(3-{[(3-{[2-chloro-5-(methoxy)phenyl]amino}quinoxalin-2-yl)amino]sulfonyl}phenyl)-2-methylalaninamide |
| 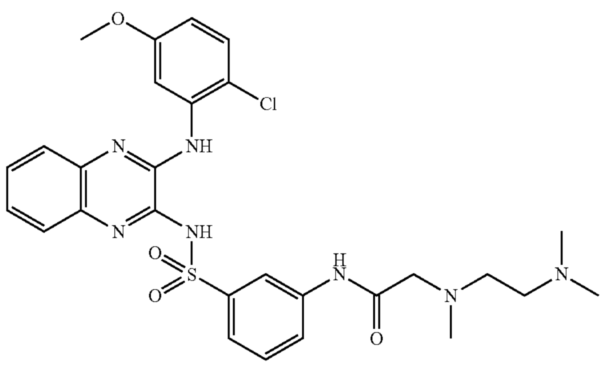 [SMILES: COc1ccc(Cl)c(Nc2nc3ccccc3nc2NS(=O)(=O)c2cccc(NC(=O)CN(C)CCN(C)C)c2)c1] | N-(3-{[(3-{[2-chloro-5-(methoxy)phenyl]amino}quinoxalin-2-yl)amino]sulfonyl}phenyl)-N-2-[2-(dimethylamino)ethyl]-N-2-methylglycinamide |
| 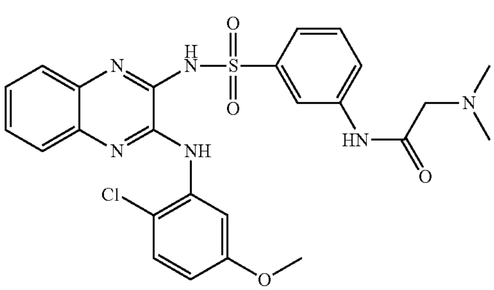 [SMILES: COc1ccc(Cl)c(Nc2nc3ccccc3nc2NS(=O)(=O)c2cccc(NC(=O)CN(C)C)c2)c1] | N-(3-{[(3-{[2-chloro-5-(methoxy)phenyl]amino)quinoxalin-2-yl)amino]sulfonyl}phenyl)-N-2-,N-2-dimethylglycinamide |
| 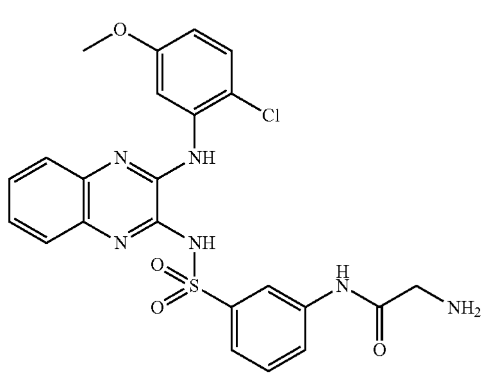 [SMILES: COc1ccc(Cl)c(Nc2nc3ccccc3nc2NS(=O)(=O)c2cccc(NC(=O)CN)c2)c1] | N-(3-{[(3-{[2-chloro-5-(methoxy)phenyl]amino}quinoxalin-2-yl)amino]sulfonyl}phenyl)glycinamide |

-continued

| Structure | Name |
|---|---|
| 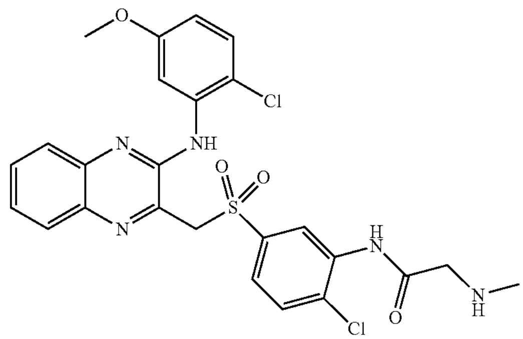 [SMILES: CNCC(=O)Nc1cc(S(=O)(=O)Cc2nc3ccccc3nc2Nc2cc(OC)ccc2Cl)ccc1Cl] | N-(2-chloro-5-{[(3-{[2-chloro-5-(methoxy)phenyl]amino)quinoxalin-2-yl)amino]sulfonyl}phenyl-N-2-methylglycinamide |
| 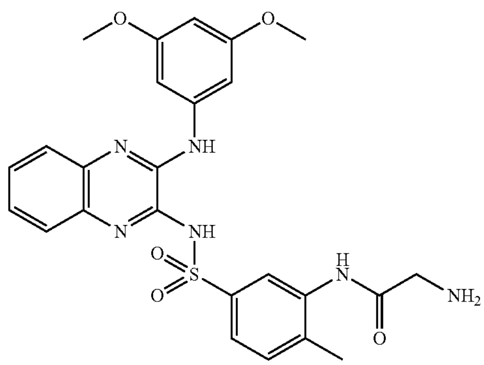 [SMILES: COc1cc(Nc2nc3ccccc3nc2NS(=O)(=O)c2ccc(C)c(NC(=O)CN)c2)cc(OC)c1] | N-(5-{[(3-{[3,5-bis(methoxy)phenyl]amino}quinoxalin-2-yl)amino]sulfonyl}-2-methylphenyl)glycinamide |
| 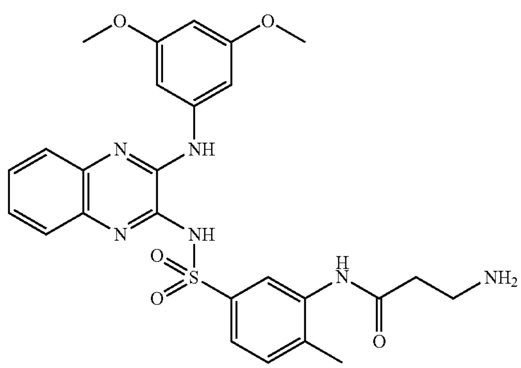 [SMILES: COc1cc(Nc2nc3ccccc3nc2NS(=O)(=O)c2ccc(C)c(NC(=O)CCN)c2)cc(OC)c1] | N-(5-{[(3-{[3,5-bis(methoxy)phenyl]amino}quinoxalin-2-yl)amino]sulfonyl}-2-methylphenyl)-beta-alaninamide |
| | N-(5-{[(3-{[2-chloro-5-(methoxy)phenyl]amino}quinoxalin-2-yl)amino]sulfonyl}-2-methylphenyl)-N-2-,N-2-dimethylglycinamide | or a pharmaceutically acceptable salt thereof.

In another embodiment, the compound of Formula I(a) is:

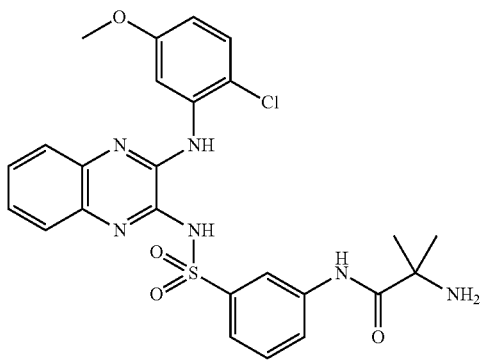 [SMILES: COc1ccc(Cl)c(Nc2nc3ccccc3nc2NS(=O)(=O)c2cccc(NC(=O)C(C)(C)N)c2)c1]

or a pharmaceutically acceptable salt thereof.

Representative Compounds

Representative compounds of formula I and/or I(a) are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Names in Table 1 were generated using ACD/Labs naming software 8.00 release, product version 8.08 with the exception of compound 374 which was named using ChemDraw v. 9.0.1.

Table 1

Representative PI3K-Alpha Inhibitors

The compounds in Table 1 can be prepared as pharmaceutically acceptable salts, solvates, hydrates, and/or isomers thereof. All such salt, solvate, hydrate, and isomer combinations of the compounds in Table 1 can be used to practice the invention. In particular, the invention can be practiced with one or two pharmaceutically acceptable salts of a compound of Table 1, wherein the salt(s) are formed with one or two acids independently selected from hydrochloric acid, hydrobromic acid, sulfuric acid, nitric acid, phosphoric acid, acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid. In particular, the invention can be practiced with one or two pharmaceutically acceptable salts of a compound of Table 1, wherein the salt(s) are formed with one or two bases independently selected from sodium, potassium, lithium, ammonium, calcium, magnesium, iron, zinc, copper, manganese, aluminum, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, and N-methylglucamine. Any individual compound (and any optional salt, optional solvate, and optional hydrate thereof) in Table 1 can be used in combination with any of the above embodiments.

TABLE 1

| Cpd. No. | Structure | Name |
|---|---|---|
| 1 | 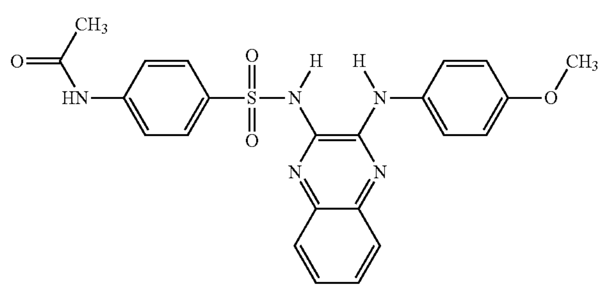 [SMILES: COc1ccc(Nc2nc3ccccc3nc2NS(=O)(=O)c2ccc(NC(C)=O)cc2)cc1] | N-(4-{[(3-{[4-(methoxy)phenyl]amino}quinoxalin-2-yl)amino]sulfonyl}phenyl)acetamide |
| 2 | 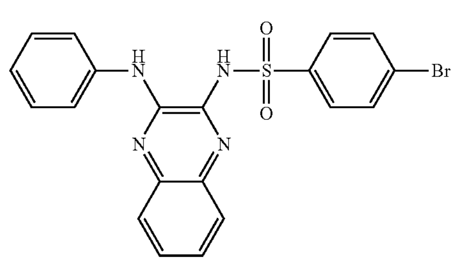 [SMILES: O=S(=O)(Nc1nc2ccccc2nc1Nc1ccccc1)c1ccc(Br)cc1] | 4-bromo-N-[3-(phenylamino)quinoxalin-2-yl]benzene sulfonamide |

TABLE 1-continued

| Cpd. No. | Structure | Name |
|---|---|---|
| 3 | 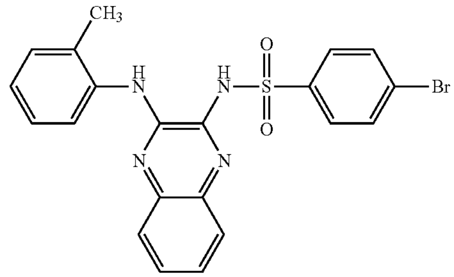 [SMILES: Cc1ccccc1Nc1nc2ccccc2nc1NS(=O)(=O)c1ccc(Br)cc1] | 4-bromo-N-{3-[(2-methylphenyl)amino]quinoxalin-2-yl}benzene sulfonamide |
| 4 | 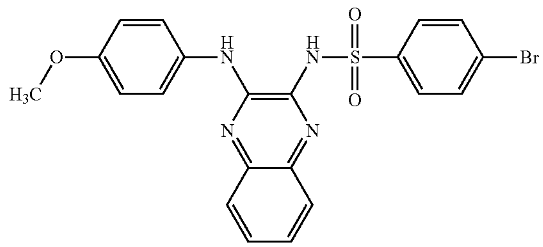 [SMILES: COc1ccc(Nc2nc3ccccc3nc2NS(=O)(=O)c2ccc(Br)cc2)cc1] | 4-bromo-N-(3-{[4-(methoxy)phenyl]amino}quinoxalin-2-yl)benzene sulfonamide |
| 5 | 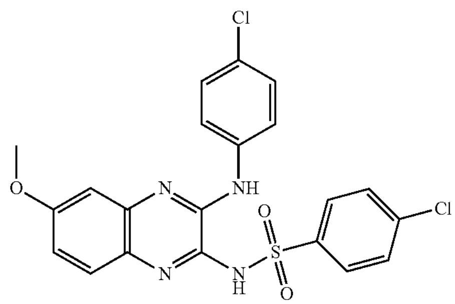 [SMILES: COc1ccc2nc(NS(=O)(=O)c3ccc(Cl)cc3)c(Nc3ccc(Cl)cc3)nc2c1] | 4-chloro-N-{3-[(4-chlorophenyl)amino]-6-(methoxy)quinoxalin-2-yl}benzenesulfonamide |
| 6 | 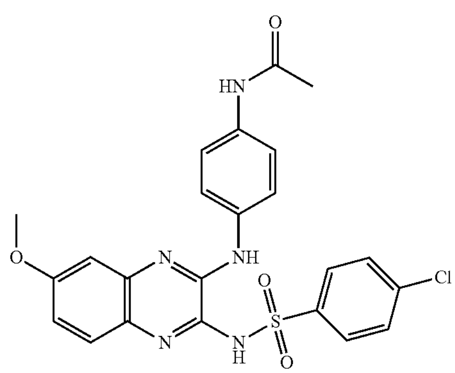 [SMILES: COc1ccc2nc(NS(=O)(=O)c3ccc(Cl)cc3)c(Nc3ccc(NC(C)=O)cc3)nc2c1] | N-(4-{[3-{[(4-chlorophenyl)sulfonyl]amino)-7-(methoxy)quinoxalin-2-yl]amino}phenyl)acetamide |
| 7 | 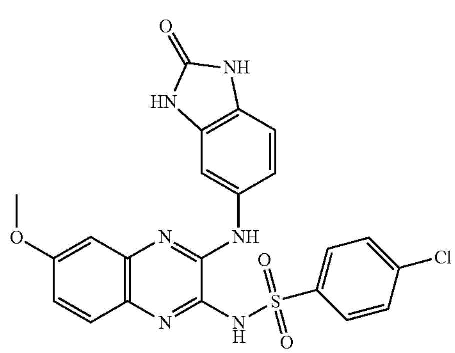 [SMILES: COc1ccc2nc(NS(=O)(=O)c3ccc(Cl)cc3)c(Nc3ccc4[nH]c(=O)[nH]c4c3)nc2c1] | 4-chloro-N-{6-(methoxy)-3-[(2-oxo-2,3-dihydro-1H-benzimidazol-5-yl)amino]quinoxalin-2-yl}benzenesulfonamide |

TABLE 1-continued

| Cpd. No. | Structure | Name |
|---|---|---|
| 8 | 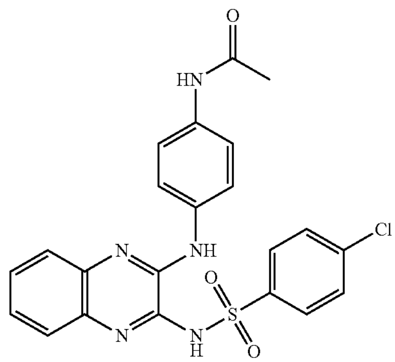 [SMILES: CC(=O)Nc1ccc(Nc2nc3ccccc3nc2NS(=O)(=O)c2ccc(Cl)cc2)cc1] | N-{4-[(3-{[(4-chloro-phenyl)sulfonyl]amino}quinoxalin-2-yl)amino]phenyl}acetamide |
| 9 | 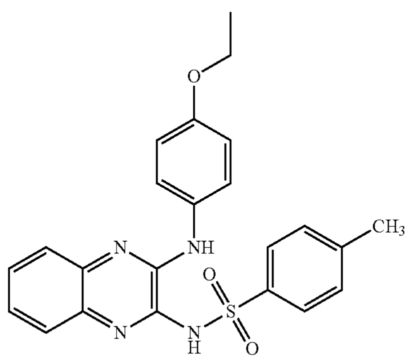 [SMILES: CCOc1ccc(Nc2nc3ccccc3nc2NS(=O)(=O)c2ccc(C)cc2)cc1] | N-(3-{[4-(ethyloxy)phen-yl]amino}quinoxalin-2-yl)-4-methylbenzene sulfonamide |
| 10 | 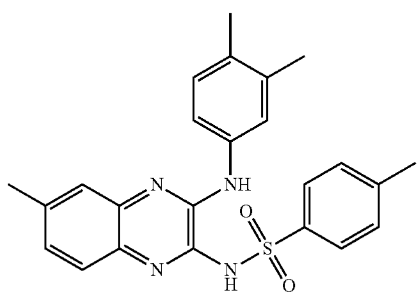 | N-{3-[(3,4-dimethylphenyl)amino]-6-methylquinoxalin-2-yl}-4-methylbenzene sulfonamide |
| 11 | 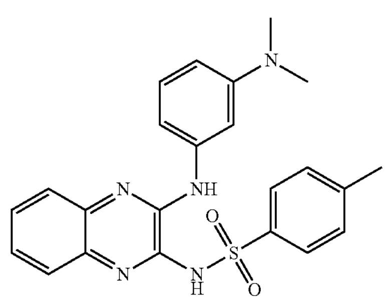 [SMILES: Cc1ccc(S(=O)(=O)Nc2nc3ccccc3nc2Nc2cccc(N(C)C)c2)cc1] | N-(3-{[3-(dimethyl-amino)phenyl]amino}quinoxalin-2-yl)-4-methylbenzene sulfonamide |
| 12 | 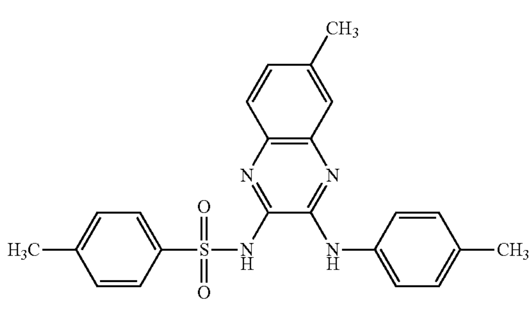 | 4-methyl-N-{6-methyl-3-[(4-methylphenyl)amino]quinoxalin-2-yl}benzenesulfonamide |

TABLE 1-continued

| Cpd. No. | Structure | Name |
| --- | --- | --- |
| 13 | 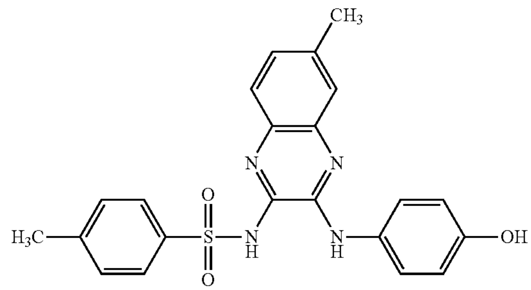 [SMILES: Cc1ccc(S(=O)(=O)Nc2nc3ccc(C)cc3nc2Nc2ccc(O)cc2)cc1] | N-{3-[(4-hydroxyphenyl)amino]-6-methylquinoxalin-2-yl}-4-methylbenzenesulfonamide |
| 14 | 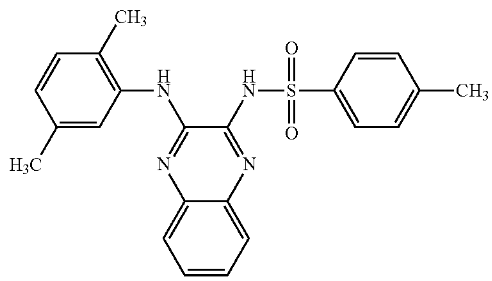 [SMILES: Cc1ccc(S(=O)(=O)Nc2nc3ccccc3nc2Nc2cc(C)ccc2C)cc1] | N-{3-[(2,5-dimethylphenyl)amino]quinoxalin-2-yl}-4-methylbenzenesulfonamide |
| 15 | 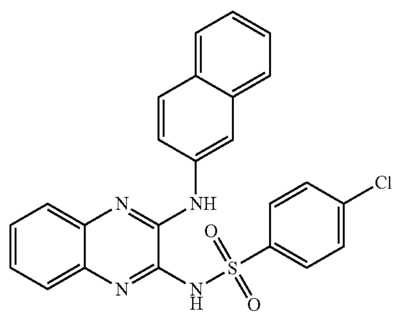 [SMILES: O=S(=O)(Nc1nc2ccccc2nc1Nc1ccc2ccccc2c1)c1ccc(Cl)cc1] | 4-chloro-N-[3-(naphthalen-2-ylamino)quinoxalin-2-yl]benzenesulfonamide |
| 16 | 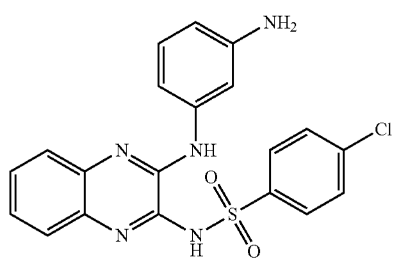 [SMILES: Nc1cccc(Nc2nc3ccccc3nc2NS(=O)(=O)c2ccc(Cl)cc2)c1] | N-{3-[(3-aminophenyl)amino]quinoxalin-2-yl}-4-chlorobenzenesulfonamide |
| 17 | 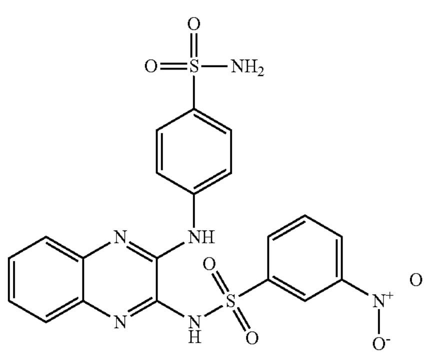 | N-(3-{[4-(amino-sulfonyl)phenyl)amino}quinoxalin-2-yl)-3-nitrobenzenesulfonamide |

TABLE 1-continued

| Cpd. No. | Structure | Name |
| --- | --- | --- |
| 18 | 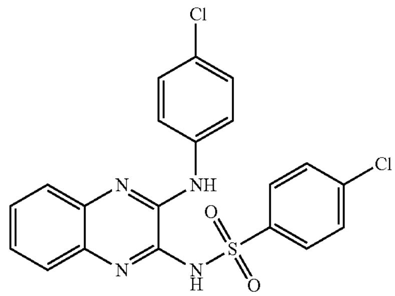 [SMILES: O=S(=O)(Nc1nc2ccccc2nc1Nc1ccc(Cl)cc1)c1ccc(Cl)cc1] | 4-chloro-N-{3-[(4-chlorophenyl)amino]quinoxalin-2-yl}benzenesulfonamide |
| 19 | 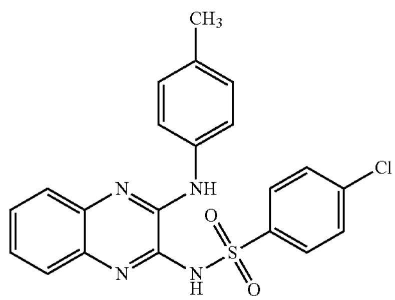 [SMILES: Cc1ccc(Nc2nc3ccccc3nc2NS(=O)(=O)c2ccc(Cl)cc2)cc1] | 4-chloro-N-{3-[(4-methylphenyl)amino]quinoxalin-2-yl}benzenesulfonamide |
| 20 | 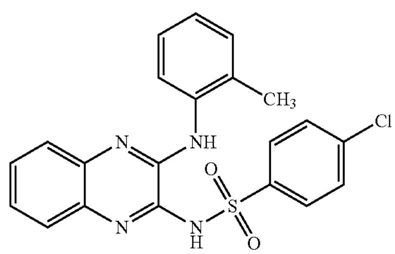 [SMILES: Cc1ccccc1Nc1nc2ccccc2nc1NS(=O)(=O)c1ccc(Cl)cc1] | 4-chloro-N-{3-[(2-methylphenyl)amino]quinoxalin-2-yl}benzenesulfonamide |
| 21 | 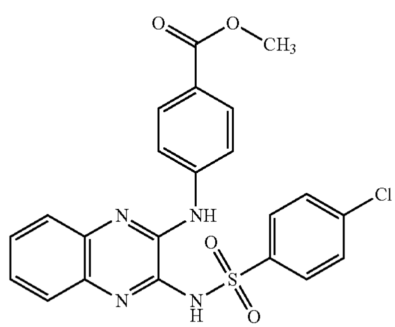 [SMILES: COC(=O)c1ccc(Nc2nc3ccccc3nc2NS(=O)(=O)c2ccc(Cl)cc2)cc1] | methyl 4-[(3-{[(4-chloro-phenyl)sulfonyl]amino}quinoxalin-2-yl)amino]benzoate |
| 22 | 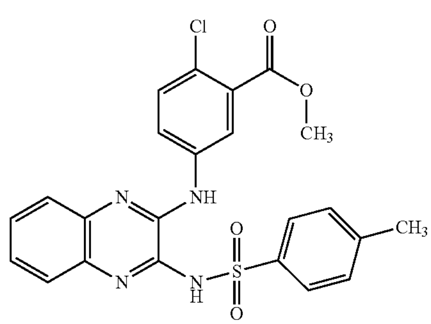 [SMILES: COC(=O)c1cc(Nc2nc3ccccc3nc2NS(=O)(=O)c2ccc(C)cc2)ccc1Cl] | methyl 2-chloro-5-[(3-{[(4-methyl-phenyl)sulfonyl]amino}quinoxalin-2-yl)amino]benzoate |

TABLE 1-continued

| Cpd. No. | Structure | Name |
| --- | --- | --- |
| 23 | 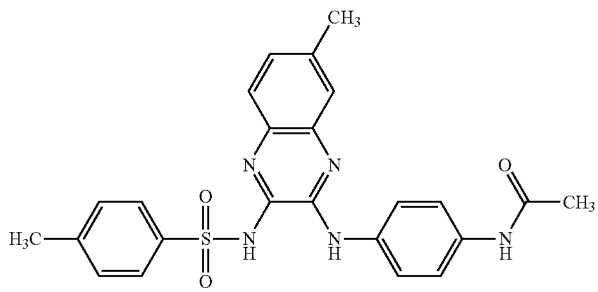 [SMILES: CC(=O)Nc1ccc(Nc2nc3cc(C)ccc3nc2NS(=O)(=O)c2ccc(C)cc2)cc1] | N-{4-[(7-methyl-3-{[(4-methyl-phenyl)sulfonyl]amino}quinoxalin-2-yl)amino]phenyl}acetamide |
| 24 | 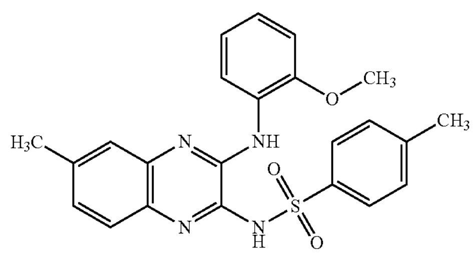 | 4-methyl-N-(6-methyl-3-{[2-(methoxy)phenyl]amino}quinoxalin-2-yl)benzenesulfonamide |
| 25 | 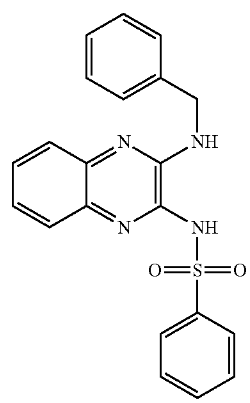 [SMILES: O=S(=O)(Nc1nc2ccccc2nc1NCc1ccccc1)c1ccccc1] | N-{3-[(phenylmethyl)amino]quinoxalin-2-yl}benzenesulfonamide |
| 26 | 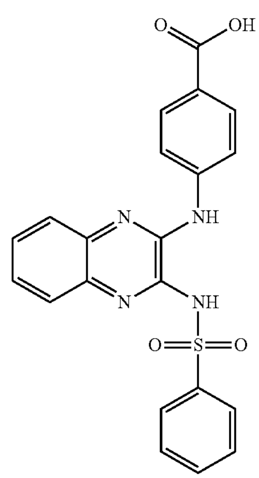 [SMILES: O=C(O)c1ccc(Nc2nc3ccccc3nc2NS(=O)(=O)c2ccccc2)cc1] | 4-({3-[(phenylsulfonyl)amino]quinoxalin-2-yl}amino)benzoic acid |

TABLE 1-continued

| Cpd. No. | Structure | Name |
|---|---|---|
| 27 | 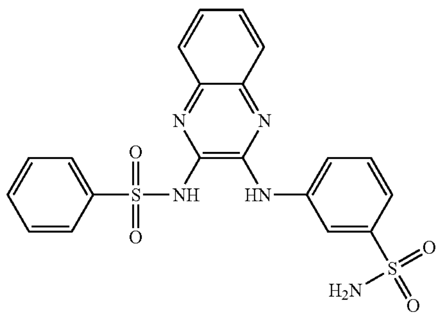 [SMILES: NS(=O)(=O)c1cccc(Nc2nc3ccccc3nc2NS(=O)(=O)c2ccccc2)c1] | 3-({3-[(phenylsulfonyl)amino]quinoxalin-2-yl}amino)benzenesulfonamide |
| 28 | 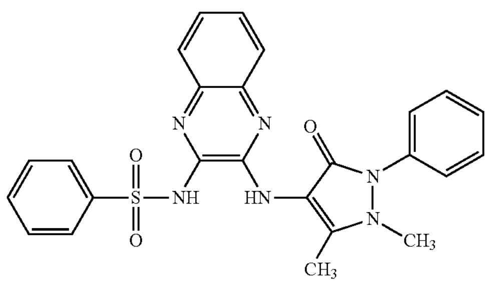 [SMILES: Cc1c(Nc2nc3ccccc3nc2NS(=O)(=O)c2ccccc2)c(=O)n(-c2ccccc2)n1C] | N-{3-[(1,5-dimethyl-3-oxo-2-phenyl-2,3-dihydro-1H-pyrazol-4-yl)amino]quinoxalin-2-yl}benzenesulfonamide |
| 29 | 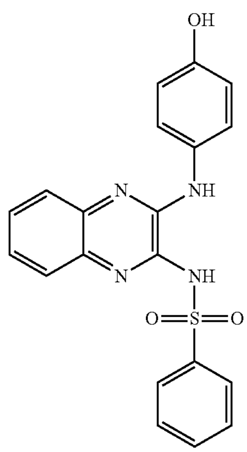 [SMILES: O=S(=O)(Nc1nc2ccccc2nc1Nc1ccc(O)cc1)c1ccccc1] | N-{3-[(4-hydroxyphenyl)amino]quinoxalin-2-yl}benzenesulfonamide |
| 30 | 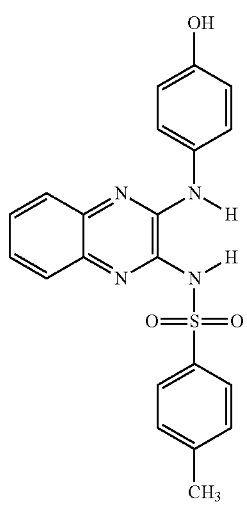 | N-{3-[(4-hydroxyphenyl)amino]quinoxalin-2-yl}-4-methylbenzenesulfonamide |

TABLE 1-continued

| Cpd. No. | Structure | Name |
|---|---|---|
| 31 | 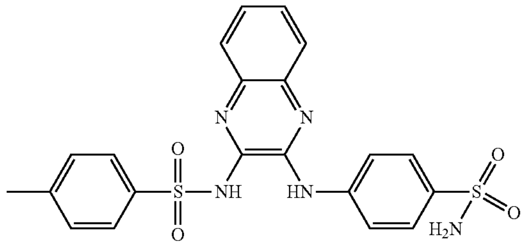 [SMILES: Cc1ccc(S(=O)(=O)Nc2nc3ccccc3nc2Nc2ccc(S(N)(=O)=O)cc2)cc1] | N-(3-{[4-(amino-sulfonyl)phenyl]amino}quinoxalin-2-yl)-4-methylbenzenesulfonamide |
| 32 | 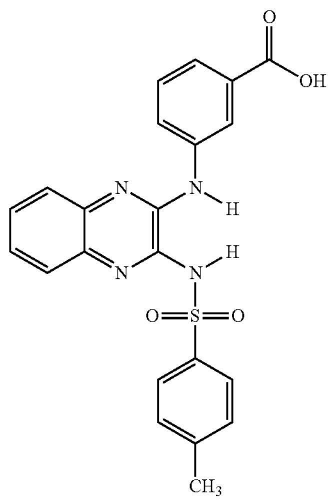 [SMILES: Cc1ccc(S(=O)(=O)Nc2nc3ccccc3nc2Nc2cccc(C(=O)O)c2)cc1] | 3-[(3-{[(4-methyl-phenyl)sulfonyl]amino}quinoxalin-2-yl)amino]benzoic acid |
| 33 | 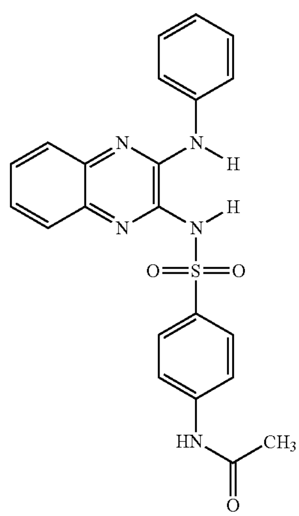 [SMILES: CC(=O)Nc1ccc(S(=O)(=O)Nc2nc3ccccc3nc2Nc2ccccc2)cc1] | N-[4-({[3-(phenylamino)quinoxalin-2-yl]amino}sulfonyl)phenyl]acetamide |
| 34 | 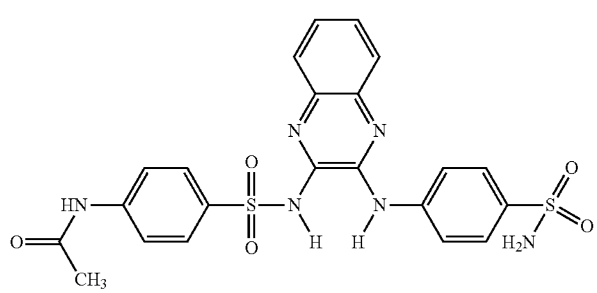 [SMILES: CC(=O)Nc1ccc(S(=O)(=O)Nc2nc3ccccc3nc2Nc2ccc(S(N)(=O)=O)cc2)cc1] | N-(4-{[(3-{[4-(amino-sulfonyl)phenyl]amino}quinoxalin-2-yl)amino]sulfonyl}phenyl)aceta-mide |

TABLE 1-continued

| Cpd. No. | Structure | Name |
|---|---|---|
| 35 | 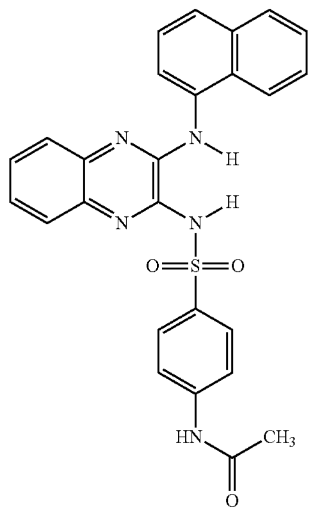 [SMILES: CC(=O)Nc1ccc(S(=O)(=O)Nc2nc3ccccc3nc2Nc2cccc3ccccc23)cc1] | N-[4-({[3-(naphthalen-1-ylamino)quinoxalin-2-yl]amino}sulfonyl)phenyl]acetamide |
| 36 | 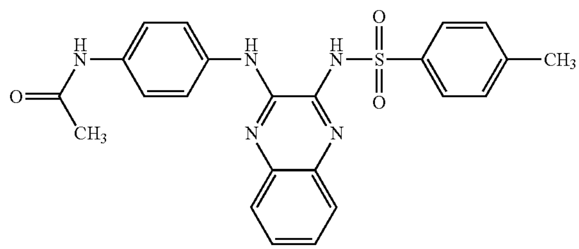 [SMILES: CC(=O)Nc1ccc(Nc2nc3ccccc3nc2NS(=O)(=O)c2ccc(C)cc2)cc1] | N-{4-[(3-{[(4-methylphenyl)sulfonyl]amino}quinoxalin-2-yl)amino]phenyl}acetamide |
| 37 | 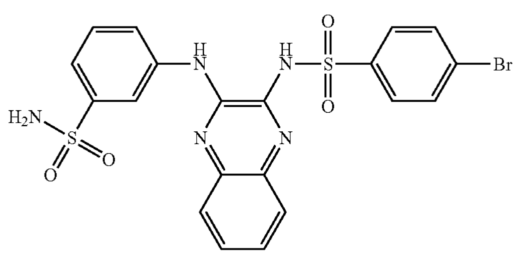 [SMILES: NS(=O)(=O)c1cccc(Nc2nc3ccccc3nc2NS(=O)(=O)c2ccc(Br)cc2)c1] | N-(3-{[3-(aminosulfonyl)phenyl]amino}quinoxalin-2-yl)-4-bromobenzenesulfonamide |
| 38 | 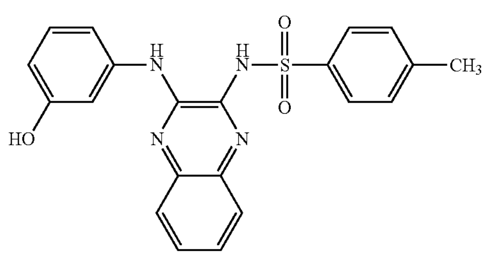 [SMILES: Cc1ccc(S(=O)(=O)Nc2nc3ccccc3nc2Nc2cccc(O)c2)cc1] | N-{3-[(3-hydroxyphenyl)amino]quinoxalin-2-yl}-4-methylbenzenesulfonamide |
| 39 | 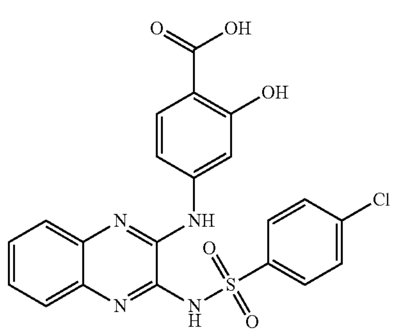 [SMILES: O=C(O)c1ccc(Nc2nc3ccccc3nc2NS(=O)(=O)c2ccc(Cl)cc2)cc1O] | 4-[(3-{[(4-chlorophenyl)sulfonyl]amino}quinoxalin-2-yl)amino]-2-hydroxybenzoic acid |

TABLE 1-continued

| Cpd. No. | Structure | Name |
| --- | --- | --- |
| 40 | 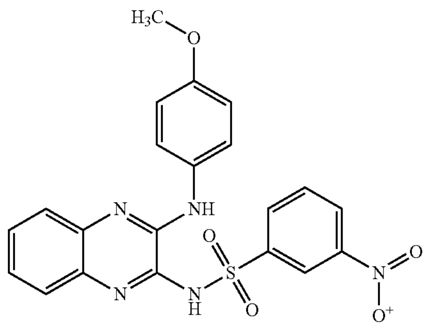 | N-(3-{[4-(methoxy)phenyl]amino}quinoxalin-2-yl)-3-nitrobenzenesulfonamide |
| 41 | 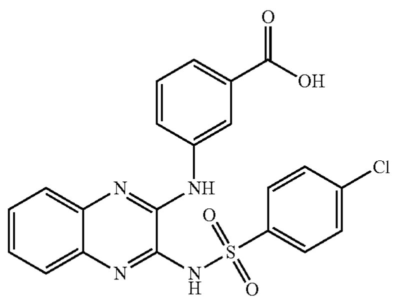 [SMILES: O=C(O)c1cccc(Nc2nc3ccccc3nc2NS(=O)(=O)c2ccc(Cl)cc2)c1] | 3-[(3-{[(4-chlorophenyl)sulfonyl]amino}quinoxalin-2-yl)amino]benzoic acid |
| 42 | 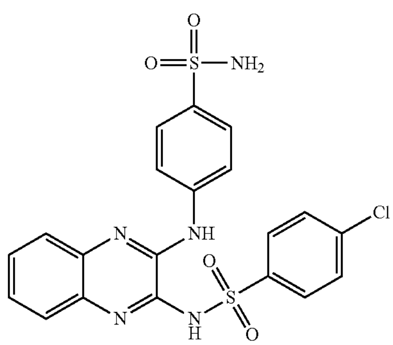 [SMILES: NS(=O)(=O)c1ccc(Nc2nc3ccccc3nc2NS(=O)(=O)c2ccc(Cl)cc2)cc1] | N-(3-{[4-(aminosulfonyl)phenyl]amino}quinoxalin-2-yl)-4-chlorobenzenesulfonamide |
| 43 | 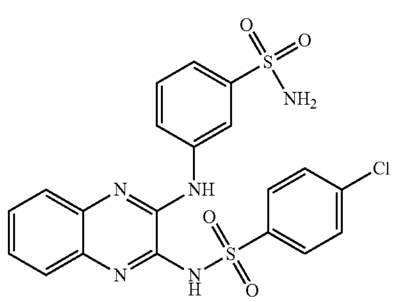 [SMILES: NS(=O)(=O)c1cccc(Nc2nc3ccccc3nc2NS(=O)(=O)c2ccc(Cl)cc2)c1] | N-(3-{[3-(aminosulfonyl)phenyl]amino}quinoxalin-2-yl)-4-chlorobenzenesulfonamide |
| 44 | 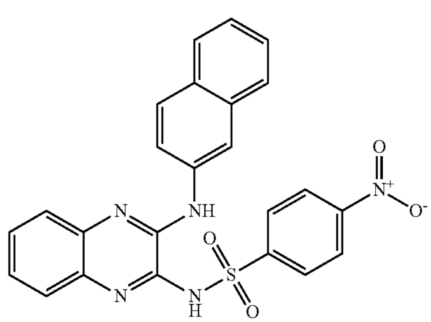 [SMILES: O=[N+]([O-])c1ccc(S(=O)(=O)Nc2nc3ccccc3nc2Nc2ccc3ccccc3c2)cc1] | N-[3-(naphthalen-2-ylamino)quinoxalin-2-yl]-4-nitrobenzenesulfonamide |

TABLE 1-continued

| Cpd. No. | Structure | Name |
| --- | --- | --- |
| 45 | 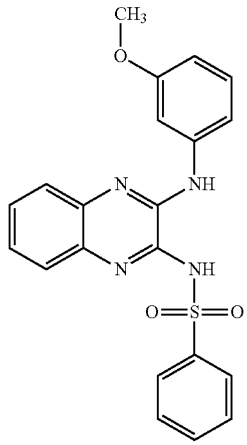 [SMILES: COc1cccc(Nc2nc3ccccc3nc2NS(=O)(=O)c2ccccc2)c1] | N-(3-{[3-(methoxy)phenyl]amino}quinoxalin-2-yl)benzenesulfonamide |
| 46 | 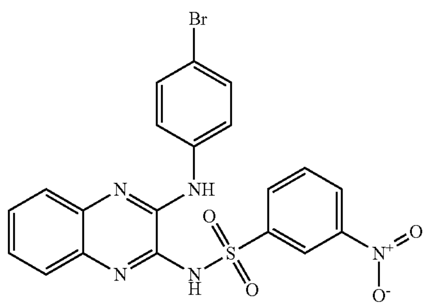 [SMILES: O=[N+]([O-])c1cccc(S(=O)(=O)Nc2nc3ccccc3nc2Nc2ccc(Br)cc2)c1] | N-{3-[(4-bromophenyl)amino]quinoxalin-2-yl}-3-nitrobenzenesulfonamide |
| 47 | 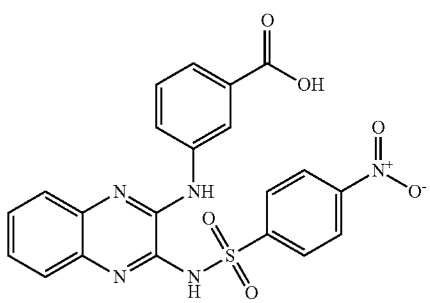 [SMILES: O=C(O)c1cccc(Nc2nc3ccccc3nc2NS(=O)(=O)c2ccc([N+](=O)[O-])cc2)c1] | 3-[(3-{[(4-nitrophenyl)sulfonyl]amino}quinoxalin-2-yl)amino]benzoic acid |
| 48 | 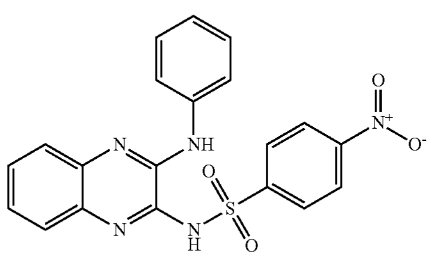 [SMILES: O=[N+]([O-])c1ccc(S(=O)(=O)Nc2nc3ccccc3nc2Nc2ccccc2)cc1] | 4-nitro-N-[3-(phenylamino)quinoxalin-2-yl]benzenesulfonamide |
| 49 | 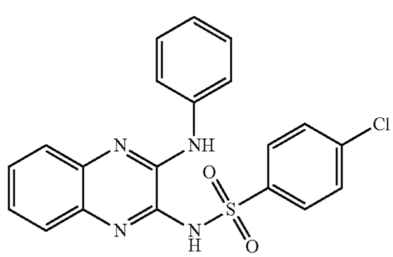 [SMILES: O=S(=O)(Nc1nc2ccccc2nc1Nc1ccccc1)c1ccc(Cl)cc1] | 4-chloro-N-[3-(phenylamino)quinoxalin-2-yl]benzenesulfonamide |

TABLE 1-continued

| Cpd. No. | Structure | Name |
|---|---|---|
| 50 | 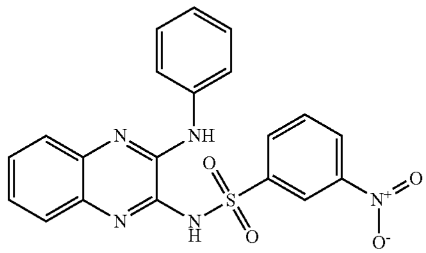 [SMILES: O=[N+]([O-])c1cccc(S(=O)(=O)Nc2nc3ccccc3nc2Nc2ccccc2)c1] | 3-nitro-N-[3-(phenylamino)quinoxalin-2-yl]benzenesulfonamide |
| 51 | 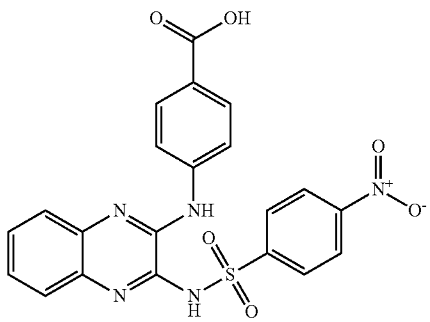 [SMILES: O=C(O)c1ccc(Nc2nc3ccccc3nc2NS(=O)(=O)c2ccc([N+](=O)[O-])cc2)cc1] | 4-[(3-{[(4-nitrophenyl)sulfonyl]amino}quinoxalin-2-yl)amino]benzoic acid |
| 52 | 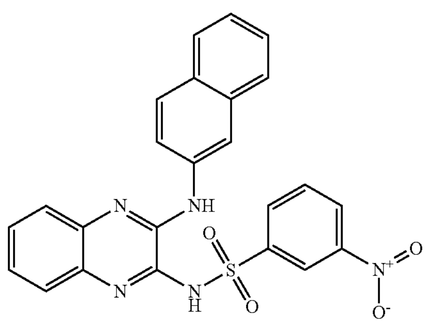 [SMILES: O=[N+]([O-])c1cccc(S(=O)(=O)Nc2nc3ccccc3nc2Nc2ccc3ccccc3c2)c1] | N-[3-(naphthalen-2-ylamino)quinoxalin-2-yl]-3-nitrobenzenesulfonamide |
| 53 | 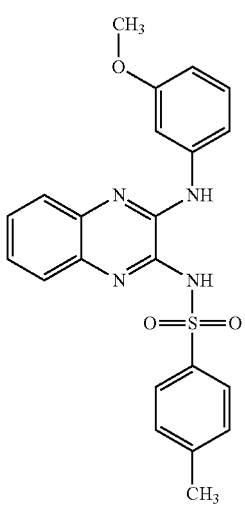 [SMILES: COc1cccc(Nc2nc3ccccc3nc2NS(=O)(=O)c2ccc(C)cc2)c1] | 4-methyl-N-(3-{[3-(methoxy)phenyl]amino}quinoxalin-2-yl)benzenesulfonamide |

TABLE 1-continued

| Cpd. No. | Structure | Name |
|---|---|---|
| 54 | 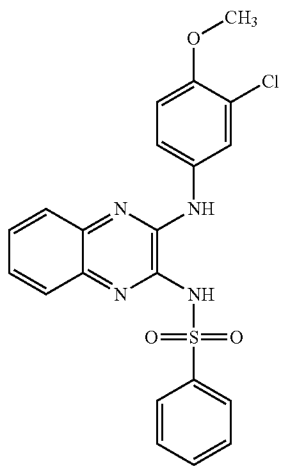 [SMILES: COc1ccc(Nc2nc3ccccc3nc2NS(=O)(=O)c2ccccc2)cc1Cl] | N-(3-{[3-chloro-4-(methoxy)phenyl]amino}quinoxalin-2-yl)benzenesulfonamide |
| 55 | 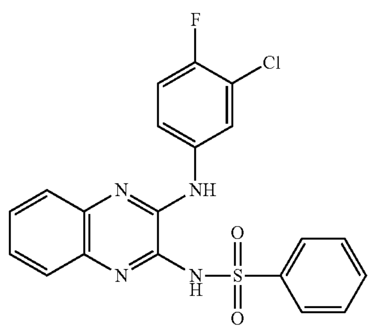 [SMILES: O=S(=O)(Nc1nc2ccccc2nc1Nc1ccc(F)c(Cl)c1)c1ccccc1] | N-{3-[(3-chloro-4-fluorophenyl)amino]quinoxalin-2-yl}benzenesulfonamide |
| 56 | 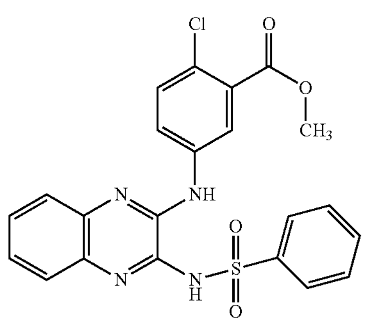 [SMILES: COC(=O)c1cc(Nc2nc3ccccc3nc2NS(=O)(=O)c2ccccc2)ccc1Cl] | methyl 2-chloro-5-({3-[(phenylsulfonyl)amino]quinoxalin-2-yl}amino)benzoate |
| 57 | 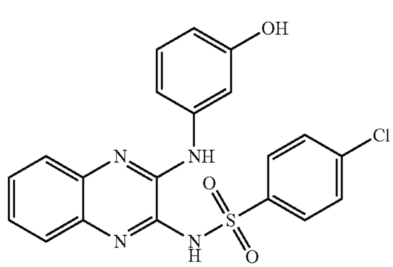 | 4-chloro-N-{3-[(3-hydroxyphenyl)amino]quinoxalin-2-yl}benzenesulfonamide |

TABLE 1-continued

| Cpd. No. | Structure | Name |
|---|---|---|
| 58 | 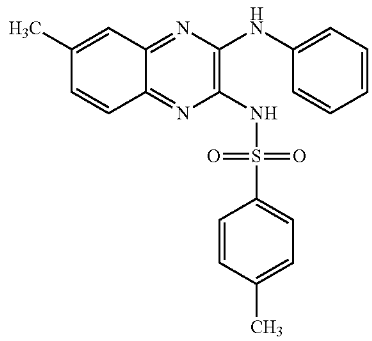 [SMILES: Cc1ccc(S(=O)(=O)Nc2nc3ccc(C)cc3nc2Nc2ccccc2)cc1] | 4-methyl-N-[6-methyl-3-(phenylamino)quinoxalin-2-yl]benzenesulfonamide |
| 59 | 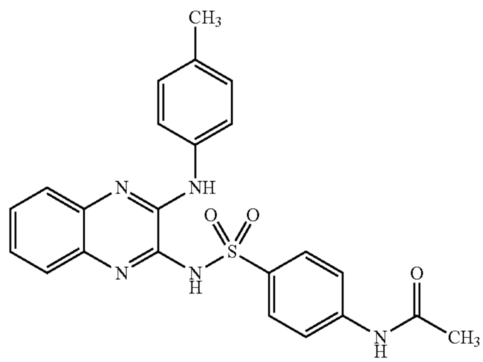 [SMILES: CC(=O)Nc1ccc(S(=O)(=O)Nc2nc3ccccc3nc2Nc2ccc(C)cc2)cc1] | N-{4-[({3-[(4-methylphenyl)amino]quinoxalin-2-yl}amino)sulfonyl]phenyl}acetamide |
| 60 | 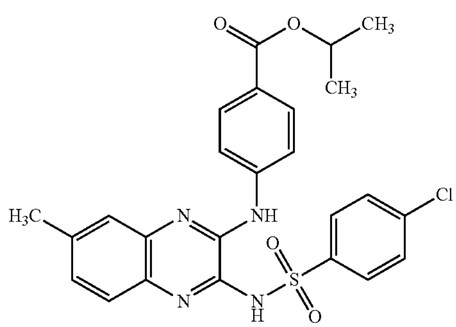 [SMILES: Cc1ccc2nc(NS(=O)(=O)c3ccc(Cl)cc3)c(Nc3ccc(C(=O)OC(C)C)cc3)nc2c1] | 1-methylethyl 4-[(3-{[(4-chlorophenyl)sulfonyl]amino}-7-methylquinoxalin-2-yl)amino]benzoate |
| 61 | 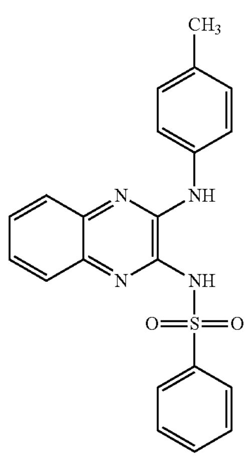 [SMILES: Cc1ccc(Nc2nc3ccccc3nc2NS(=O)(=O)c2ccccc2)cc1] | N-{3-[(4-methylphenyl)amino]quinoxalin-2-yl}benzenesulfonamide |

TABLE 1-continued
| Cpd. No. | Structure | Name |
| --- | --- | --- |
| 62 | 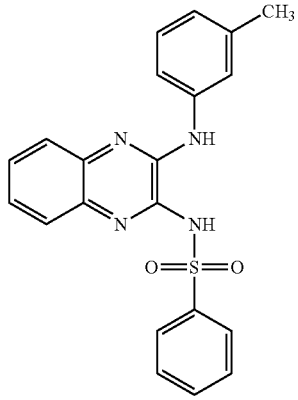 [SMILES: Cc1cccc(Nc2nc3ccccc3nc2NS(=O)(=O)c2ccccc2)c1] | N-{3-[(3-methylphenyl)amino]quinoxalin-2-yl}benzenesulfonamide |
| 63 | 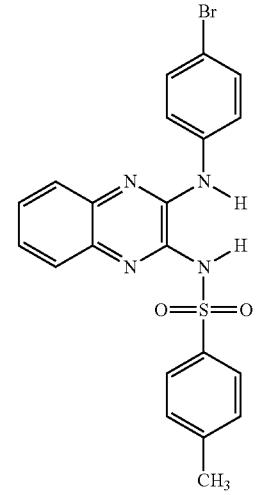 [SMILES: Cc1ccc(S(=O)(=O)Nc2nc3ccccc3nc2Nc2ccc(Br)cc2)cc1] | N-{3-[(4-bromophenyl)amino]quinoxalin-2-yl}-4-methylbenzenesulfonamide |
| 64 | 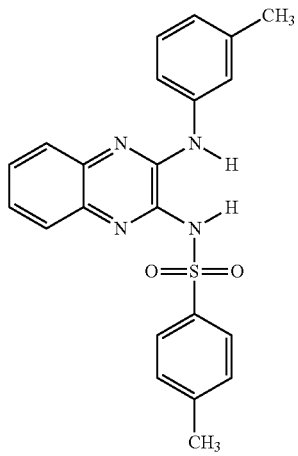 [SMILES: Cc1ccc(S(=O)(=O)Nc2nc3ccccc3nc2Nc2cccc(C)c2)cc1] | 4-methyl-N-{3-[(3-methylphenyl)amino]quinoxalin-2-yl}benzenesulfonamide |

TABLE 1-continued

| Cpd. No. | Structure | Name |
|---|---|---|
| 65 | 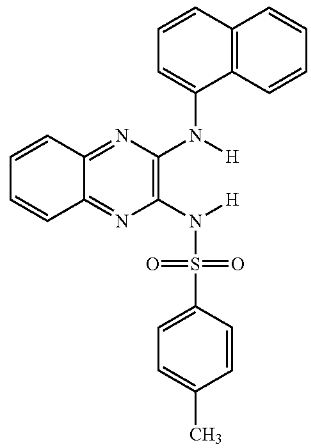 [SMILES: Cc1ccc(S(=O)(=O)Nc2nc3ccccc3nc2Nc2cccc3ccccc23)cc1] | 4-methyl-N-[3-(naphthalen-1-ylamino)quinoxalin-2-yl]benzenesulfonamide |
| 66 | 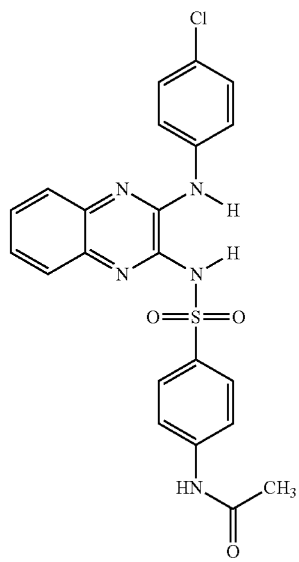 [SMILES: CC(=O)Nc1ccc(S(=O)(=O)Nc2nc3ccccc3nc2Nc2ccc(Cl)cc2)cc1] | N-{4-[({3-[(4-chlorophenyl)amino]quinoxalin-2-yl}amino)sulfonyl]phenyl}acetamide |
| 67 | 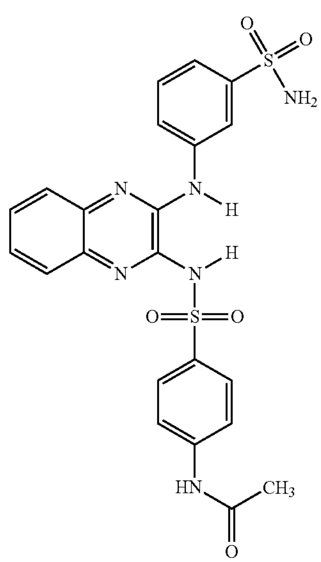 [SMILES: CC(=O)Nc1ccc(S(=O)(=O)Nc2nc3ccccc3nc2Nc2cccc(S(N)(=O)=O)c2)cc1] | N-(4-{[(3-{[3-(aminosulfonyl)phenyl]amino}quinoxalin-yl)amino]sulfonyl}phenyl)acetamide |

TABLE 1-continued

| Cpd. No. | Structure | Name |
|---|---|---|
| 68 | 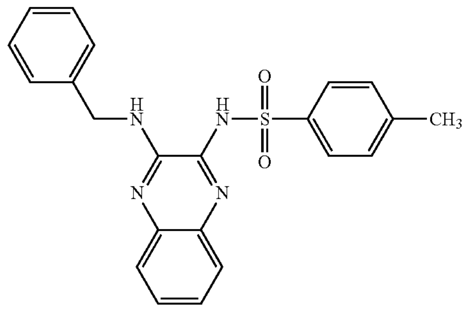 [SMILES: Cc1ccc(S(=O)(=O)Nc2nc3ccccc3nc2NCc2ccccc2)cc1] | 4-methyl-N-{3-[(phenylmethyl)amino]quinoxalin-2-yl}benzenesulfonamide |
| 69 | 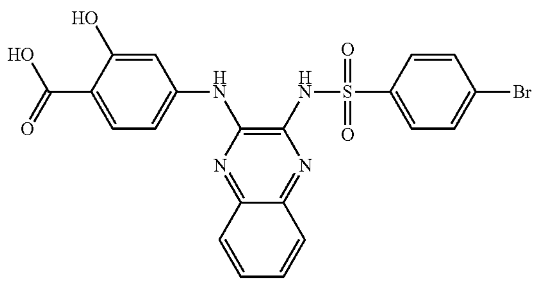 [SMILES: O=C(O)c1ccc(Nc2nc3ccccc3nc2NS(=O)(=O)c2ccc(Br)cc2)cc1O] | 4-[(3-{[(4-bromo-phenyl)sulfonyl]amino}quinoxalin-2-yl)amino]-2-hydroxybenzoic acid |
| 70 | 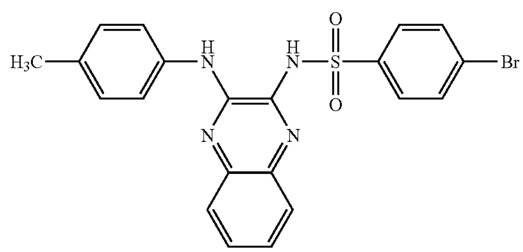 [SMILES: Cc1ccc(Nc2nc3ccccc3nc2NS(=O)(=O)c2ccc(Br)cc2)cc1] | 4-bromo-N-{3-[(4-methylphenyl)amino]quinoxalin-2-yl}benzenesulfonamide |
| 71 | 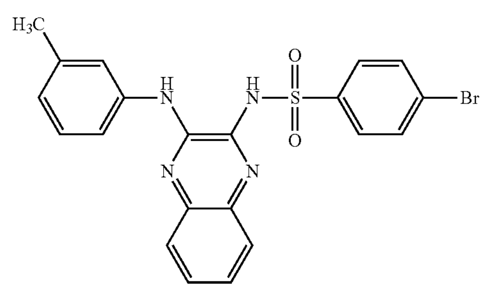 [SMILES: Cc1cccc(Nc2nc3ccccc3nc2NS(=O)(=O)c2ccc(Br)cc2)c1] | 4-bromo-N-{3-[(3-methylphenyl)amino]quinoxalin-2-yl}benzenesulfonamide |
| 72 | 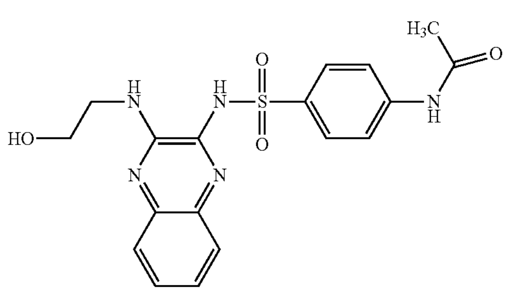 [SMILES: CC(=O)Nc1ccc(S(=O)(=O)Nc2nc3ccccc3nc2NCCO)cc1] | N-{4-[({3-[(2-hydroxyethyl)amino]quinoxalin-2-yl}amino)sulfonyl]phenyl}acetamide |

| Cpd. No. | Structure | Name |
|---|---|---|
| 73 | 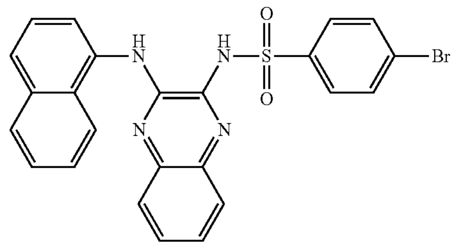 [SMILES: O=S(=O)(Nc1nc2ccccc2nc1Nc1cccc2ccccc12)c1ccc(Br)cc1] | 4-bromo-N-[3-(naphthalen-1-ylamino)quinoxalin-2-yl]benzenesulfonamide |
| 74 | 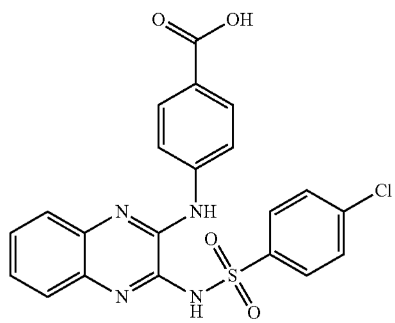 [SMILES: O=C(O)c1ccc(Nc2nc3ccccc3nc2NS(=O)(=O)c2ccc(Cl)cc2)cc1] | 4-[(3-{[(4-chloro-phenyl)sulfonyl]amino}quinoxalin-2-yl)amino]benzoic acid |
| 75 | 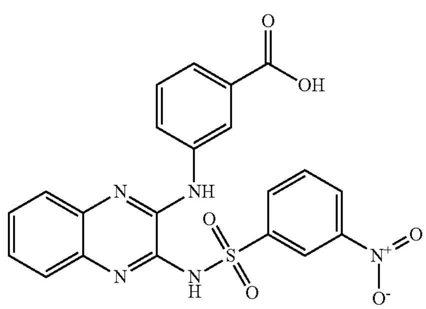 [SMILES: O=C(O)c1cccc(Nc2nc3ccccc3nc2NS(=O)(=O)c2cccc([N+](=O)[O-])c2)c1] | 3-[(3-{[(3-nitro-phenyl)sulfonyl]amino}quinoxalin-2-yl)amino]benzoic acid |
| 76 | 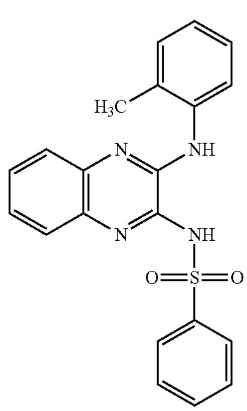 [SMILES: Cc1ccccc1Nc1nc2ccccc2nc1NS(=O)(=O)c1ccccc1] | N-{3-[(2-methylphenyl)amino]quinoxalin-2-yl}benzenesulfonamide |

TABLE 1-continued

| Cpd. No. | Structure | Name |
|---|---|---|
| 77 | 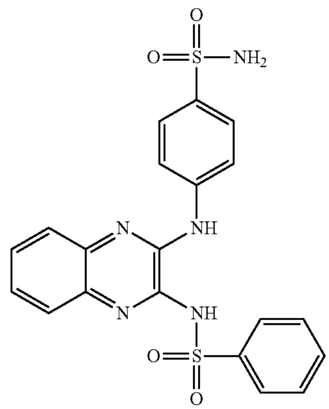 [SMILES: NS(=O)(=O)c1ccc(Nc2nc3ccccc3nc2NS(=O)(=O)c2ccccc2)cc1] | 4-({3-[(phenylsulfonyl)amino]quinoxalin-2-yl}amino)benzenesulfonamide |
| 78 | 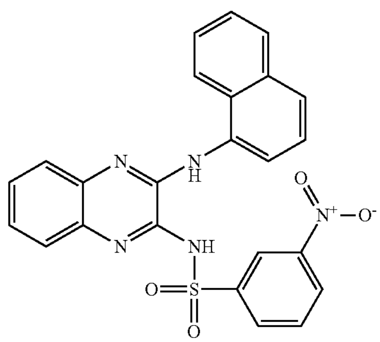 [SMILES: O=[N+]([O-])c1cccc(S(=O)(=O)Nc2nc3ccccc3nc2Nc2cccc3ccccc23)c1] | N-[3-(naphthalen-1-ylamino)quinoxalin-2-yl]-3-nitrobenzenesulfonamide |
| 79 | 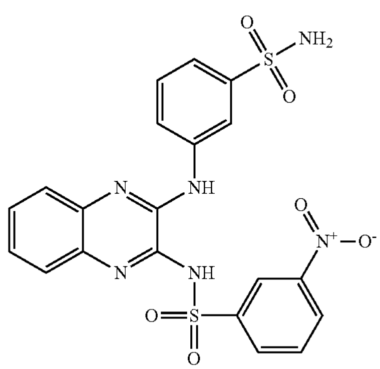 [SMILES: NS(=O)(=O)c1cccc(Nc2nc3ccccc3nc2NS(=O)(=O)c2cccc([N+](=O)[O-])c2)c1] | N-(3-{[3-(aminosulfonyl)phenyl]amino}quinoxalin-2-yl)-3-nitrobenzenesulfonamide |
| 80 | 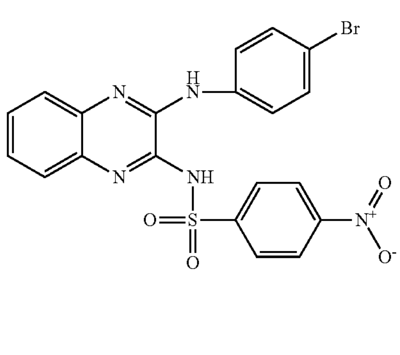 [SMILES: O=[N+]([O-])c1ccc(S(=O)(=O)Nc2nc3ccccc3nc2Nc2ccc(Br)cc2)cc1] | N-{3-[(4-bromophenyl)amino]quinoxalin-2-yl}-4-nitrobenzenesulfonamide |

TABLE 1-continued
| Cpd. No. | Structure | Name |
|---|---|---|
| 81 | 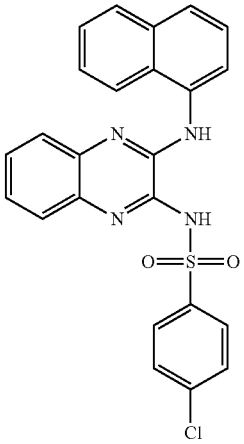 [SMILES: O=S(=O)(Nc1nc2ccccc2nc1Nc1cccc2ccccc12)c1ccc(Cl)cc1] | 4-chloro-N-[3-(naphthalen-1-ylamino)quinoxalin-2-yl]benzenesulfonamide |
| 82 | 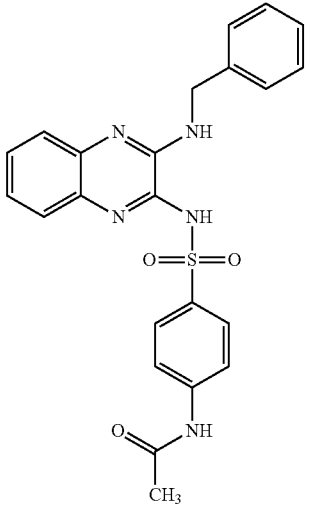 [SMILES: CC(=O)Nc1ccc(S(=O)(=O)Nc2nc3ccccc3nc2NCc2ccccc2)cc1] | N-{4-[({3-[(phenylmethyl)amino]quinoxalin-2-yl}amino)sulfonyl]phenyl}acetamide |
| 83 | 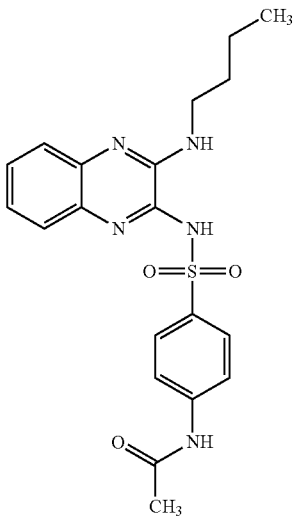 [SMILES: CCCCNc1nc2ccccc2nc1NS(=O)(=O)c1ccc(NC(C)=O)cc1] | N-[4-({[3-(butylamino)quinoxalin-2-yl]amino}sulfonyl)phenyl]acetamide |

TABLE 1-continued

| Cpd. No. | Structure | Name |
| --- | --- | --- |
| 84 | 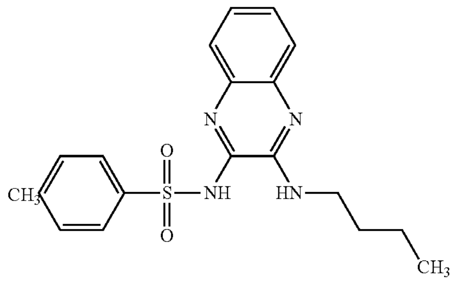 | N-{3-(butylamino)quinoxalin-2-yl]-4-methylbenzenesulfonamide |
| 85 | 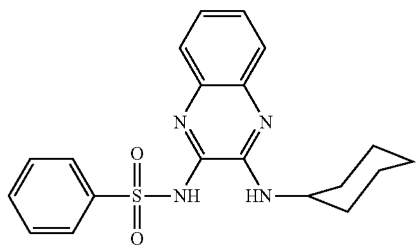 [SMILES: O=S(=O)(Nc1nc2ccccc2nc1NC1CCCCC1)c1ccccc1] | N-[3-(cyclohexylamino)quinoxalin-2-yl]benzenesulfonamide |
| 86 | 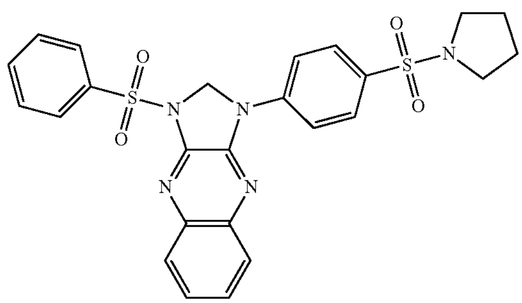 [SMILES: O=S(=O)(c1ccc(N2CN(S(=O)(=O)c3ccccc3)c3nc4ccccc4nc32)cc1)N1CCCC1] | 1-(phenylsulfonyl)-3-[4-(pyrrolidin-1-ylsulfonyl)phenyl]-2,3-dihydro-1H-imidazo[4,5-b]quinoxaline |
| 87 | 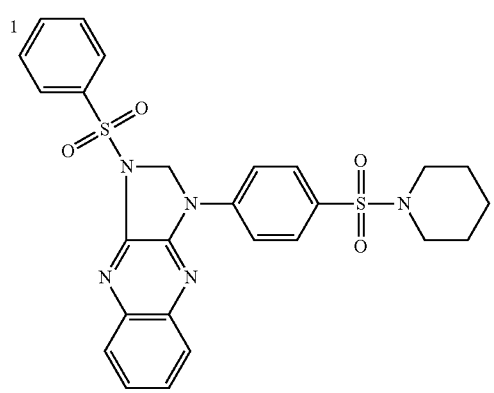 | 1-(phenylsulfonyl)-3-[4-(piperidin-1-ylsulfonyl)phenyl]-2,3-dihydro-1H-imidazo[4,5-b]quinoxaline |

TABLE 1-continued

| Cpd. No. | Structure | Name |
|---|---|---|
| 88 | 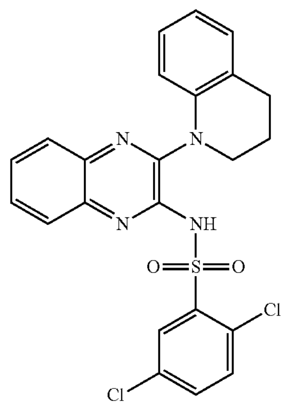 [SMILES: O=S(=O)(Nc1nc2ccccc2nc1N1CCCc2ccccc21)c1cc(Cl)ccc1Cl] | 2,5-dichloro-N-[3-(3,4-dihydroquinolin-1(2H)-yl)quinoxalin-2-yl]benzenesulfonamide |
| 89 | 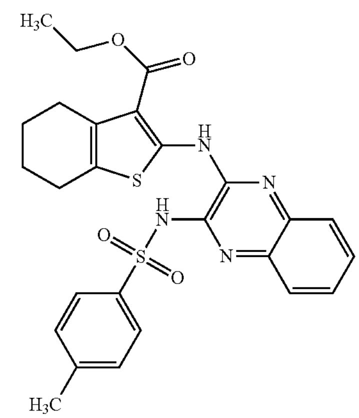 [SMILES: CCOC(=O)c1c(Nc2nc3ccccc3nc2NS(=O)(=O)c2ccc(C)cc2)sc2c1CCCC2] | ethyl 2-[(3-{[(4-methylphenyl)sulfonyl]amino}quinoxalin-2-yl)amino]-4,5,6,7-tetrahydro-1-benzothiophene-3-carboxylate |
| 90 | 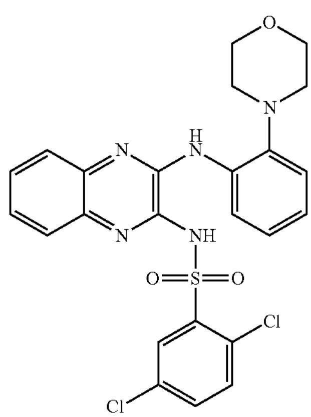 [SMILES: O=S(=O)(Nc1nc2ccccc2nc1Nc1ccccc1N1CCOCC1)c1cc(Cl)ccc1Cl] | 2,5-dichloro-N-{3-[(2-morpholin-4-ylphenyl)amino]quinoxalin-2-yl}benzenesulfonamide |
| 91 | 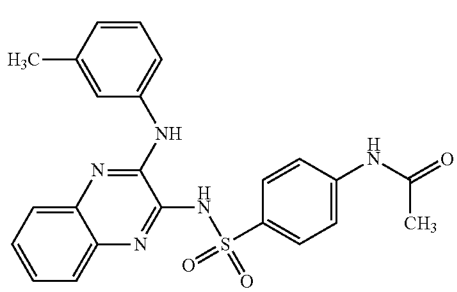 [SMILES: CC(=O)Nc1ccc(S(=O)(=O)Nc2nc3ccccc3nc2Nc2cccc(C)c2)cc1] | N-{4-[({3-[(3-methylphenyl)amino]quinoxalin-2-yl}amino)sulfonyl]phenyl}acetamide |

TABLE 1-continued

| Cpd. No. | Structure | Name |
| --- | --- | --- |
| 92 | 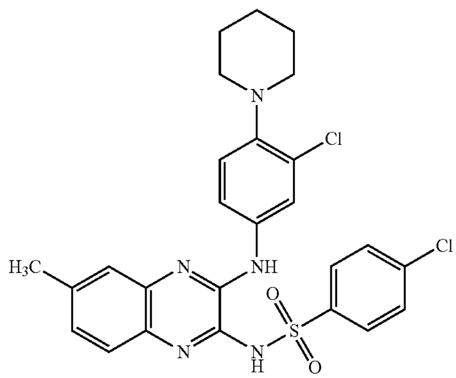 [SMILES: Cc1ccc2nc(NS(=O)(=O)c3ccc(Cl)cc3)c(Nc3ccc(N4CCCCC4)c(Cl)c3)nc2c1] | 4-chloro-N-{3-[(3-chloro-4-piperidin-1-ylphenyl)amino]-6-methylquinoxalin-2-yl}benzenesulfonamide |
| 93 | 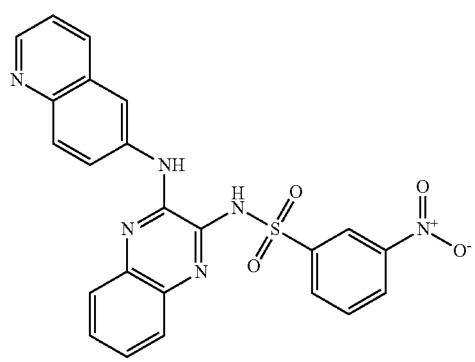 [SMILES: O=[N+]([O-])c1cccc(S(=O)(=O)Nc2nc3ccccc3nc2Nc2ccc3ncccc3c2)c1] | 3-nitro-N-[3-(quinolin-6-ylamino)quinoxalin-2-yl]benzenesulfonamide |
| 94 | 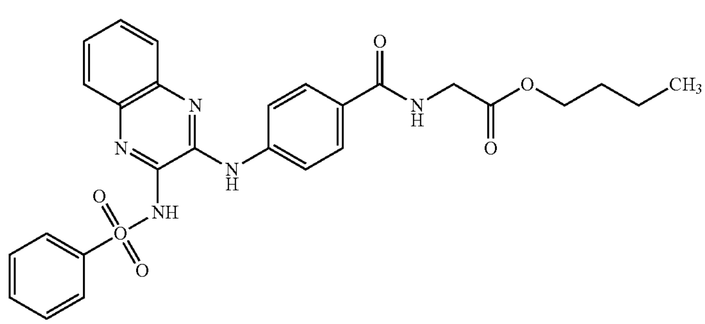 | butyl N-{[4-({3-[(phenyl-sulfonyl)amino]quinoxalin-2-yl}amino)phenyl]carbonyl}glycinate |
| 95 | 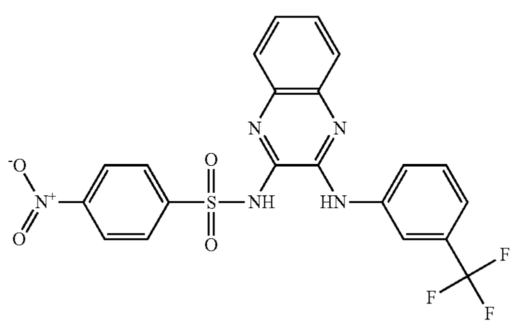 | 4-nitro-N-(3-{[3-(trifluoro-methyl)phenyl]amino}quinoxalin-2-yl)benzenesulfonamide |

TABLE 1-continued

| Cpd. No. | Structure | Name |
| --- | --- | --- |
| 96 | 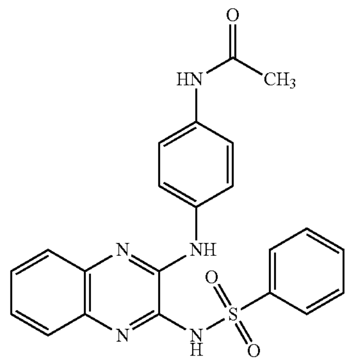 [SMILES: CC(=O)Nc1ccc(Nc2nc3ccccc3nc2NS(=O)(=O)c2ccccc2)cc1] | N-[4-({3-[(phenyl-sulfonyl)amino]quinoxalin-2-yl}amino)phenyl]acetamide |
| 97 | 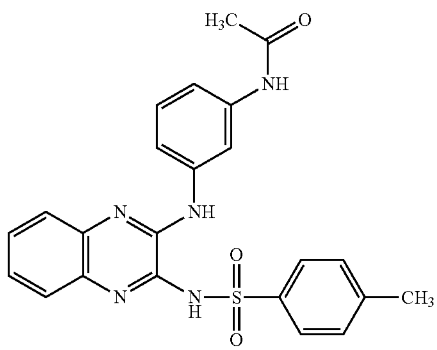 [SMILES: CC(=O)Nc1cccc(Nc2nc3ccccc3nc2NS(=O)(=O)c2ccc(C)cc2)c1] | N-{3-[(3-{[(4-methyl-phenyl)sulfonyl]amino}quinoxalin-2-yl)amino]phenyl}acetamide |
| 98 | 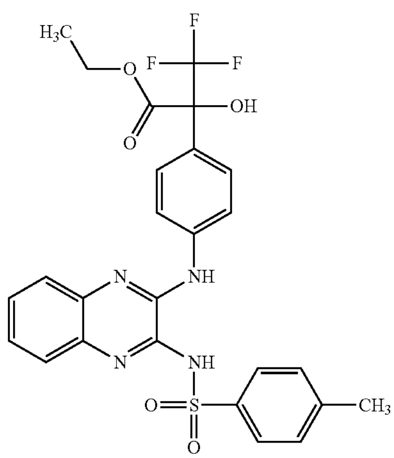 [SMILES: CCOC(=O)C(O)(c1ccc(Nc2nc3ccccc3nc2NS(=O)(=O)c2ccc(C)cc2)cc1)C(F)(F)F] | ethyl 3,3,3-trifluoro-2-hydroxy-2-{4-[(3-{[(4-methylphenyl)sulfonyl]amino}quinoxalin-2-yl)amino]phenyl}propanoate |
| 99 | 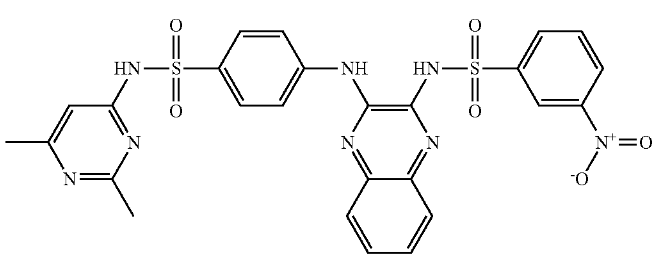 | N-{3-[(4-{[(2,6-dimethylpyrimidin-4-yl)amino]sulfonyl}phenyl)amino]quinoxalin-2-yl}-3-nitrobenzenesulfonamide |

TABLE 1-continued

| Cpd. No. | Structure | Name |
|---|---|---|
| 100 | 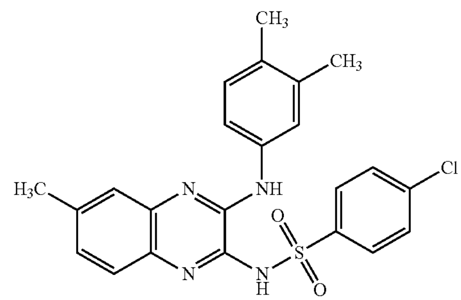 [SMILES: Cc1ccc2nc(NS(=O)(=O)c3ccc(Cl)cc3)c(Nc3ccc(C)c(C)c3)nc2c1] | 4-chloro-N-{3-[(3,4-dimethylphenyl)amino]-6-methylquinoxalin-2-yl}benzenesulfonamide |
| 101 | 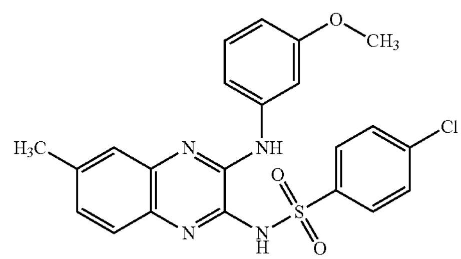 [SMILES: COc1cccc(Nc2nc3cc(C)ccc3nc2NS(=O)(=O)c2ccc(Cl)cc2)c1] | 4-chloro-N-(6-methyl-3-{[3-(methoxy)phenyl]amino}quinoxalin-2-yl)benzenesulfonamide |
| 102 | 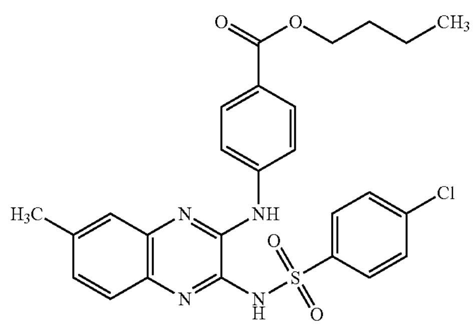 [SMILES: CCCCOC(=O)c1ccc(Nc2nc3cc(C)ccc3nc2NS(=O)(=O)c2ccc(Cl)cc2)cc1] | butyl 4-[(3-{[(4-chlorophenyl)sulfonyl]amino}-7-methylquinoxalin-2-yl)amino]benzoate |
| 103 | 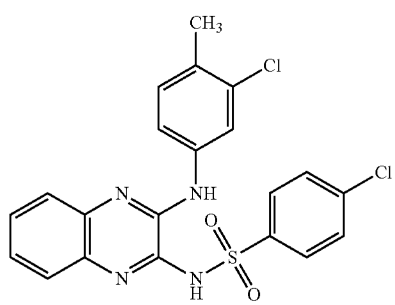 [SMILES: Cc1ccc(Nc2nc3ccccc3nc2NS(=O)(=O)c2ccc(Cl)cc2)cc1Cl] | 4-chloro-N-{3-[(3-chloro-4-methylphenyl)amino]quinoxalin-2-yl}benzenesulfonamide |
| 104 | 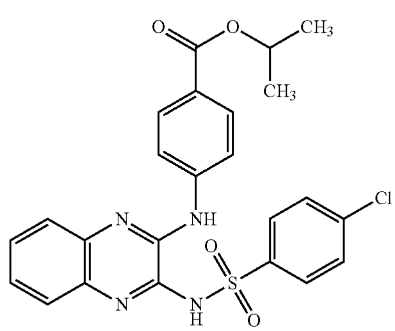 [SMILES: CC(C)OC(=O)c1ccc(Nc2nc3ccccc3nc2NS(=O)(=O)c2ccc(Cl)cc2)cc1] | 1-methylethyl 4-[(3-{[(4-chlorophenyl)sulfonyl]amino}quinoxalin-2-yl)amino]benzoate |

TABLE 1-continued

| Cpd. No. | Structure | Name |
|---|---|---|
| 105 | 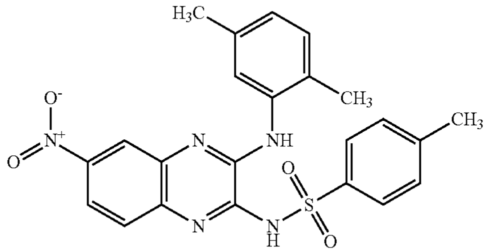 [SMILES: Cc1ccc(S(=O)(=O)Nc2nc3ccc([N+](=O)[O-])cc3nc2Nc2cc(C)ccc2C)cc1] | N-{3-[(2,5-dimethylphenyl)amino]-6-nitroquinoxalin-2-yl}-4-methylbenzenesulfonamide |
| 106 | 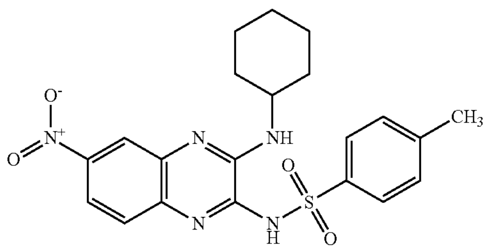 [SMILES: Cc1ccc(S(=O)(=O)Nc2nc3ccc([N+](=O)[O-])cc3nc2NC2CCCCC2)cc1] | N-[3-(cyclohexylamino)-6-nitroquinoxalin-2-yl]-4-methylbenzenesulfonamide |
| 107 | 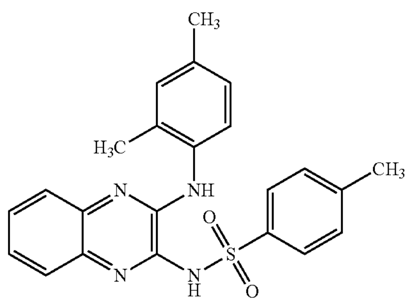 [SMILES: Cc1ccc(S(=O)(=O)Nc2nc3ccccc3nc2Nc2ccc(C)cc2C)cc1] | N-{3-[(2,4-dimethylphenyl)amino]quinoxalin-2-yl}-4-methylbenzenesulfonamide |
| 108 | 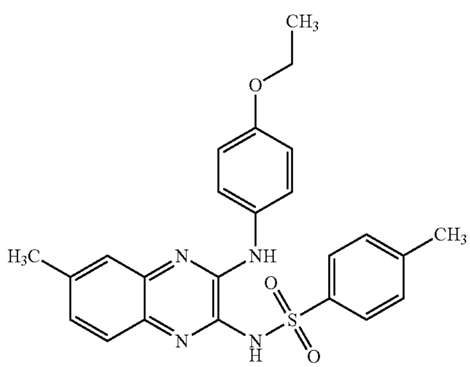 | N-(3-{[4-(ethyloxy)phenyl]amino}-6-methylquinoxalin-2-yl)-4-methylbenzenesulfonamide |
| 109 | 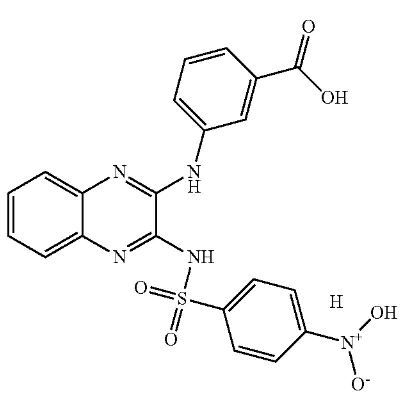 | 3-({3-[({4-[hydroxy(oxido)amino]phenyl}sulfonyl)amino]quinoxalin-2-yl}amino)benzoic acid |

TABLE 1-continued

| Cpd. No. | Structure | Name |
|---|---|---|
| 110 | 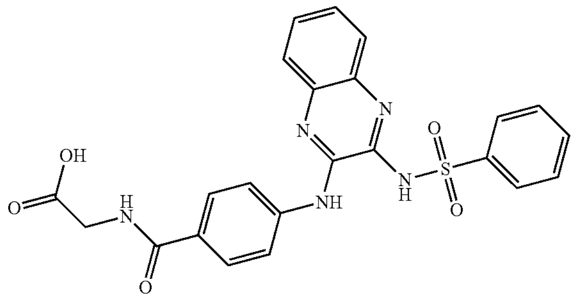 [SMILES: O=C(O)CNC(=O)c1ccc(Nc2nc3ccccc3nc2NS(=O)(=O)c2ccccc2)cc1] | N-{[4-({3-[(phenyl-sulfonyl)amino]quinoxalin-2-yl}amino)phenyl]carbonyl}glycine |
| 111 | 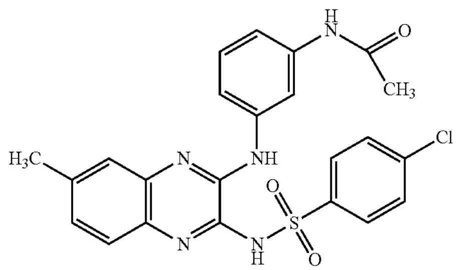 [SMILES: CC(=O)Nc1cccc(Nc2nc3cc(C)ccc3nc2NS(=O)(=O)c2ccc(Cl)cc2)c1] | N-{3-[(3-{[(4-chlorophenyl)sulfonyl]amino}-7-methylquinoxalin-2-yl)amino]phenyl}acetamide |
| 112 | 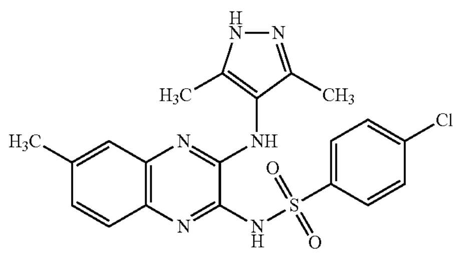 [SMILES: Cc1ccc2nc(NS(=O)(=O)c3ccc(Cl)cc3)c(Nc3c(C)n[nH]c3C)nc2c1] | 4-chloro-N-{3-[(3,5-dimethyl-1H-pyrazol-4-yl)amino]-6-methylquinoxalin-2-yl}benzenesulfonamide |
| 113 | 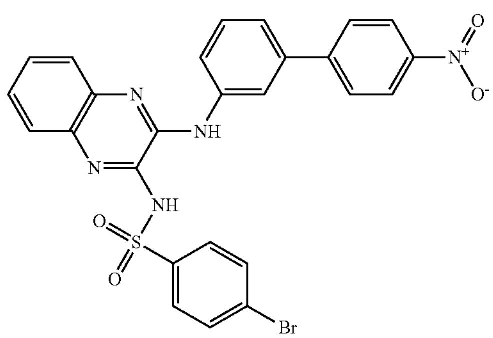 [SMILES: O=[N+]([O-])c1ccc(-c2cccc(Nc3nc4ccccc4nc3NS(=O)(=O)c3ccc(Br)cc3)c2)cc1] | 4-bromo-N-{3-[(4'-nitrobiphenyl-3-yl)amino]quinoxalin-2-yl}benzenesulfonamide |
| 114 | 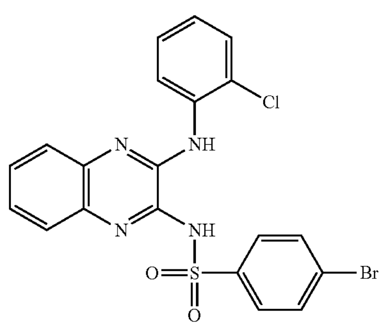 [SMILES: O=S(=O)(Nc1nc2ccccc2nc1Nc1ccccc1Cl)c1ccc(Br)cc1] | 4-bromo-N-{3-[(2-chlorophenyl)amino]quinoxalin-2-yl}benzenesulfonamide |

TABLE 1-continued

| Cpd. No. | Structure | Name |
| --- | --- | --- |
| 115 | 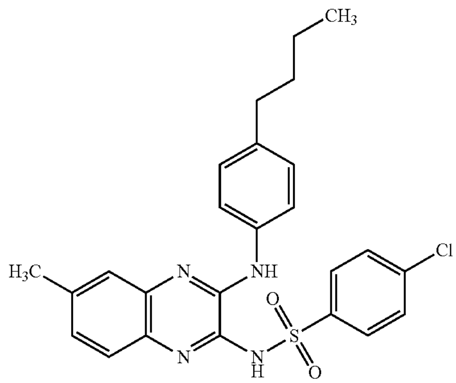 [SMILES: CCCCc1ccc(Nc2nc3cc(C)ccc3nc2NS(=O)(=O)c2ccc(Cl)cc2)cc1] | N-{3-[(4-butylphenyl)amino]-6-methylquinoxalin-2-yl}-4-chlorobenzenesulfonamide |
| 116 | 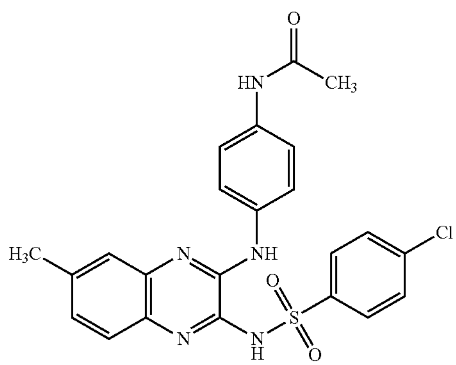 [SMILES: CC(=O)Nc1ccc(Nc2nc3cc(C)ccc3nc2NS(=O)(=O)c2ccc(Cl)cc2)cc1] | N-{4-[(3-{[(4-chlorophenyl)sulfonyl]amino}-7-methylquinoxalin-2-yl)amino]phenyl}acetamide |
| 117 | 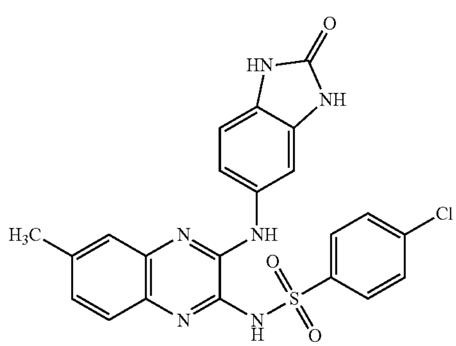 [SMILES: Cc1ccc2nc(NS(=O)(=O)c3ccc(Cl)cc3)c(Nc3ccc4[nH]c(=O)[nH]c4c3)nc2c1] | 4-chloro-N-{6-methyl-3-[(2-oxo-2,3-dihydro-1H-benzimidazol-5-yl)amino]quinoxalin-2-yl}benzenesulfonamide |
| 118 | 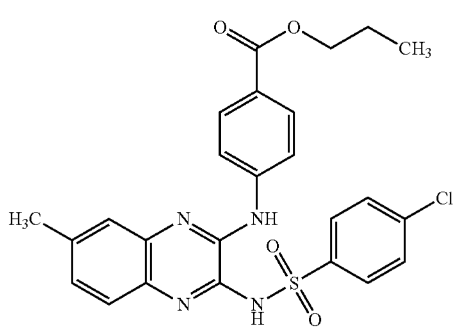 [SMILES: CCCOC(=O)c1ccc(Nc2nc3cc(C)ccc3nc2NS(=O)(=O)c2ccc(Cl)cc2)cc1] | propyl 4-[(3-{[(4-chlorophenyl)sulfonyl]amino}-7-methylquinoxalin-2-yl)amino]benzoate |

TABLE 1-continued

| Cpd. No. | Structure | Name |
| --- | --- | --- |
| 119 | 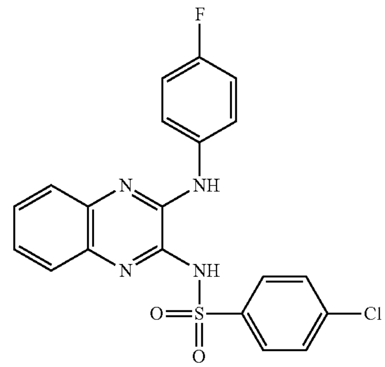 [SMILES: O=S(=O)(Nc1nc2ccccc2nc1Nc1ccc(F)cc1)c1ccc(Cl)cc1] | 4-chloro-N-{3-[(4-fluorophenyl)amino]quinoxalin-2-yl}benzenesulfonamide |
| 120 | 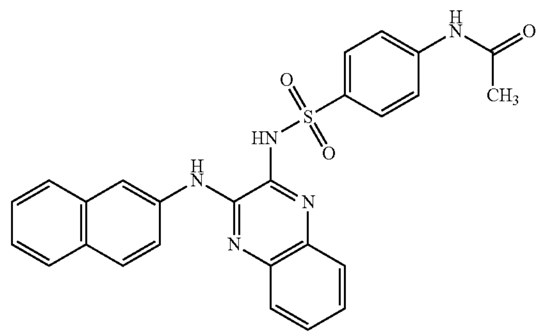 [SMILES: CC(=O)Nc1ccc(S(=O)(=O)Nc2nc3ccccc3nc2Nc2ccc3ccccc3c2)cc1] | N-[4-({[3-(naphthalen-2-ylamino)quinoxalin-2-yl]amino}sulfonyl)phenyl]acetamide |
| 121 | 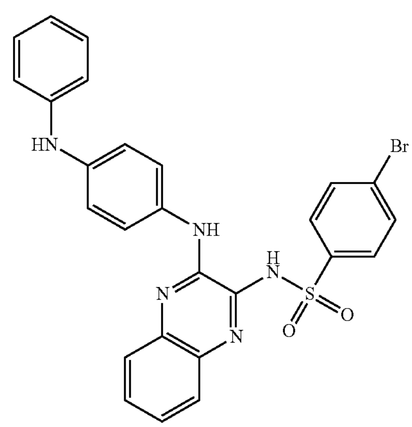 [SMILES: O=S(=O)(Nc1nc2ccccc2nc1Nc1ccc(Nc2ccccc2)cc1)c1ccc(Br)cc1] | 4-bromo-N-(3-{[4-(phenylamino)phenyl]amino}quinoxalin-2-yl)benzenesulfonamide |
| 122 | 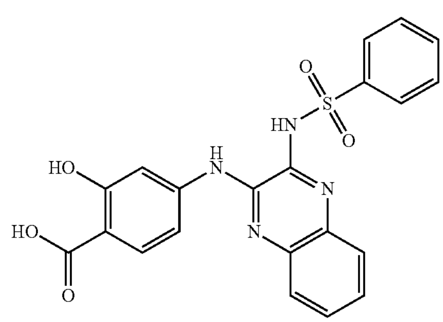 [SMILES: O=C(O)c1ccc(Nc2nc3ccccc3nc2NS(=O)(=O)c2ccccc2)cc1O] | 2-hydroxy-4-({3-[(phenylsulfonyl)amino]quinoxalin-2-yl}amino)benzoic acid |

TABLE 1-continued

| Cpd. No. | Structure | Name |
|---|---|---|
| 123 | 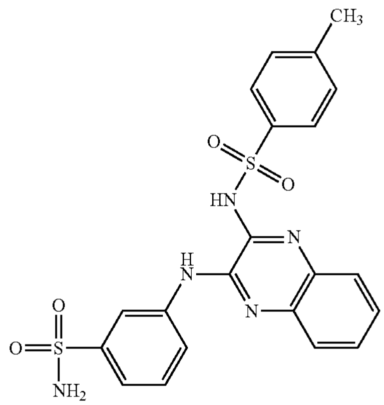 [SMILES: Cc1ccc(S(=O)(=O)Nc2nc3ccccc3nc2Nc2cccc(S(N)(=O)=O)c2)cc1] | N-(3-{[3-(amino-sulfonyl)phenyl]amino}quinoxalin-2-yl)-4-methylbenzenesulfonamide |
| 124 | 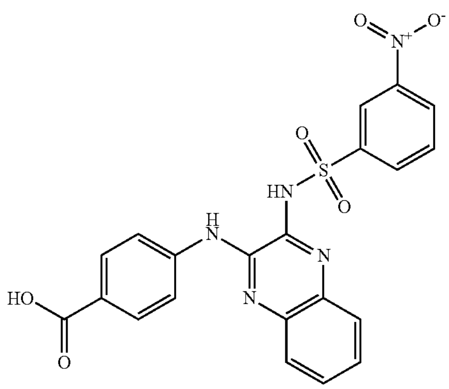 [SMILES: O=C(O)c1ccc(Nc2nc3ccccc3nc2NS(=O)(=O)c2cccc([N+](=O)[O-])c2)cc1] | 4-[(3-{[(3-nitro-phenyl)sulfonyl]amino}quinoxalin-2-yl)amino]benzoic acid |
| 125 | 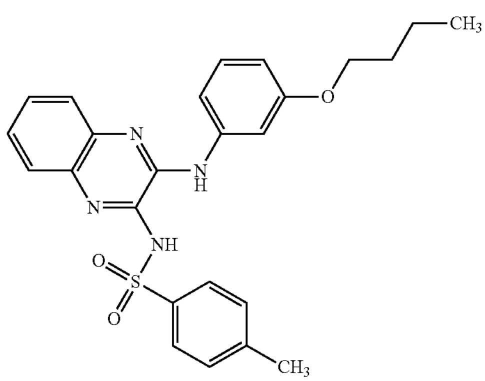 [SMILES: CCCCOc1cccc(Nc2nc3ccccc3nc2NS(=O)(=O)c2ccc(C)cc2)c1] | N-(3-{[3-(butyloxy)phenyl]amino}quinoxalin-2-yl)-4-methylbenzenesulfonamide |
| 126 | 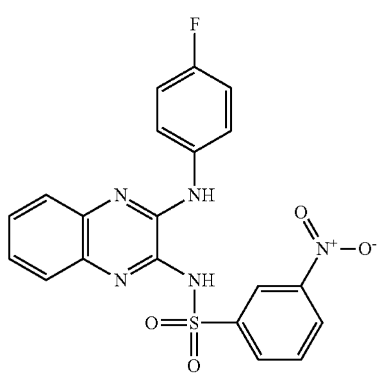 [SMILES: O=[N+]([O-])c1cccc(S(=O)(=O)Nc2nc3ccccc3nc2Nc2ccc(F)cc2)c1] | N-{3-[(4-fluorophenyl)amino]quinoxalin-2-yl}-3-nitrobenzenesulfonamide |

| Cpd. No. | Structure | Name |
|---|---|---|
| 127 | 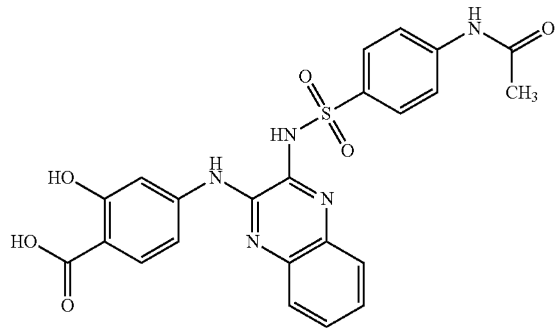 [SMILES: CC(=O)Nc1ccc(S(=O)(=O)Nc2nc3ccccc3nc2Nc2ccc(C(=O)O)c(O)c2)cc1] | 4-{[3-({[4-(acetylamino)phenyl]sulfonyl}amino)quinoxalin-2-yl]amino}-2-hydroxybenzoic acid |
| 128 | 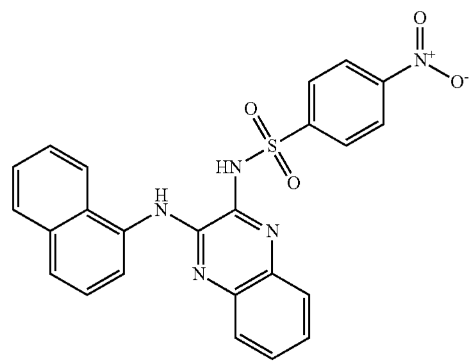 [SMILES: O=[N+]([O-])c1ccc(S(=O)(=O)Nc2nc3ccccc3nc2Nc2cccc3ccccc23)cc1] | N-[3-(naphthalen-1-ylamino)quinoxalin-2-yl]-4-nitrobenzenesulfonamide |
| 129 | 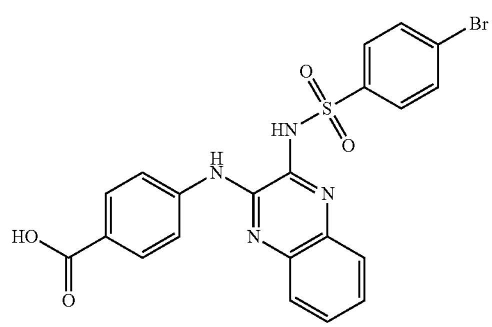 [SMILES: O=C(O)c1ccc(Nc2nc3ccccc3nc2NS(=O)(=O)c2ccc(Br)cc2)cc1] | 4-[(3-{[(4-bromophenyl)sulfonyl]amino}quinoxalin-2-yl)amino]benzoic acid |
| 130 | 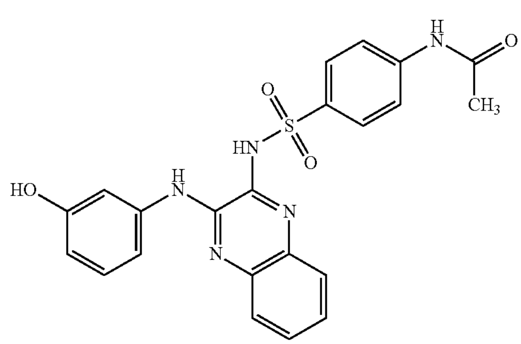 [SMILES: CC(=O)Nc1ccc(S(=O)(=O)Nc2nc3ccccc3nc2Nc2cccc(O)c2)cc1] | N-{4-[({3-[(3-hydroxyphenyl)amino]quinoxalin-2-yl}amino)sulfonyl]phenyl}acetamide |

TABLE 1-continued

| Cpd. No. | Structure | Name |
| --- | --- | --- |
| 131 | 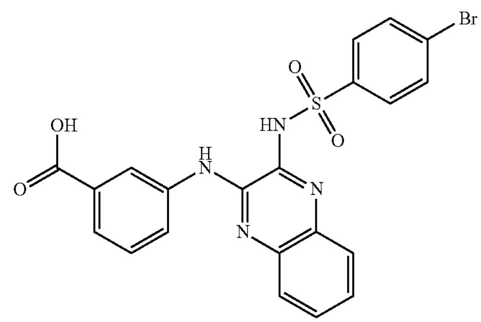 [SMILES: O=C(O)c1cccc(Nc2nc3ccccc3nc2NS(=O)(=O)c2ccc(Br)cc2)c1] | 3-[(3-{[(4-bromophenyl)sulfonyl]amino}quinoxalin-2-yl)amino]benzoic acid |
| 132 | 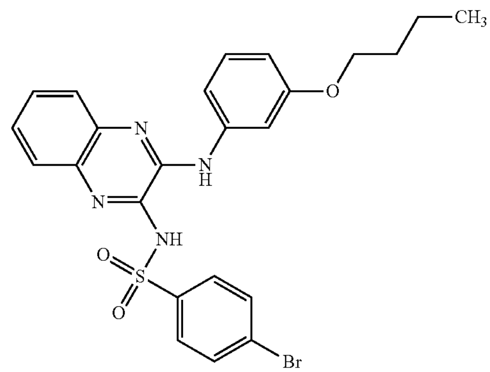 [SMILES: CCCCOc1cccc(Nc2nc3ccccc3nc2NS(=O)(=O)c2ccc(Br)cc2)c1] | 4-bromo-N-(3-{[3-(butyloxy)phenyl]amino}quinoxalin-2-yl)benzenesulfonamide |
| 133 | 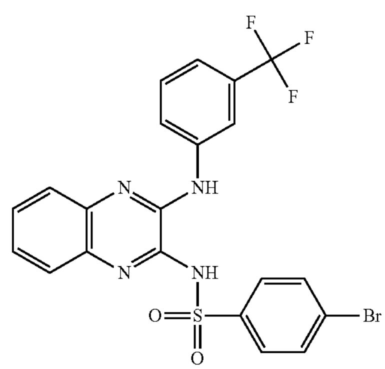 [SMILES: O=S(=O)(Nc1nc2ccccc2nc1Nc1cccc(C(F)(F)F)c1)c1ccc(Br)cc1] | 4-bromo-N-(3-{[3-(trifluoromethyl)phenyl]amino}quinoxalin-2-yl)benzenesulfonamide |
| 134 | 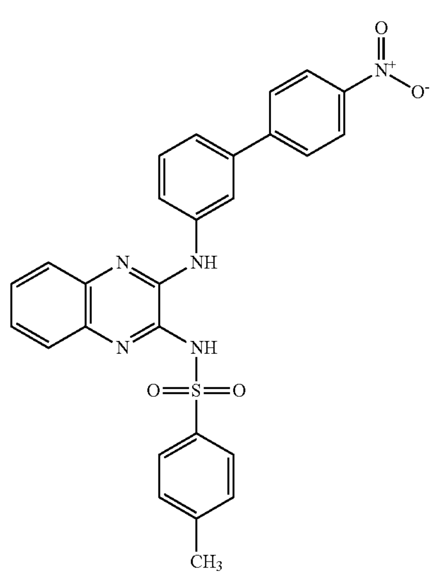 [SMILES: Cc1ccc(S(=O)(=O)Nc2nc3ccccc3nc2Nc2cccc(-c3ccc([N+](=O)[O-])cc3)c2)cc1] | 4-methyl-N-{3-[(4'-nitrobiphenyl-3-yl)amino]quinoxalin-2-yl}benzenesulfonamide |

TABLE 1-continued

| Cpd. No. | Structure | Name |
|---|---|---|
| 135 | 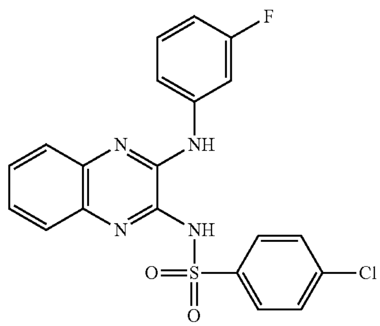 [SMILES: O=S(=O)(Nc1nc2ccccc2nc1Nc1cccc(F)c1)c1ccc(Cl)cc1] | 4-chloro-N-{3-[(3-fluorophenyl)amino]quinoxalin-2-yl}benzenesulfonamide |
| 136 | 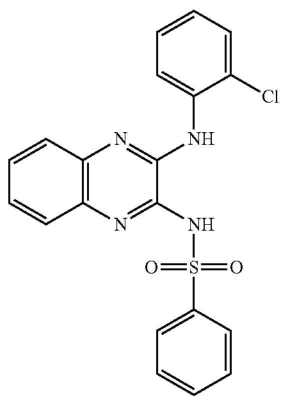 [SMILES: O=S(=O)(Nc1nc2ccccc2nc1Nc1ccccc1Cl)c1ccccc1] | N-{3-[(2-chlorophenyl)amino]quinoxalin-2-yl}benzenesulfonamide |
| 137 | 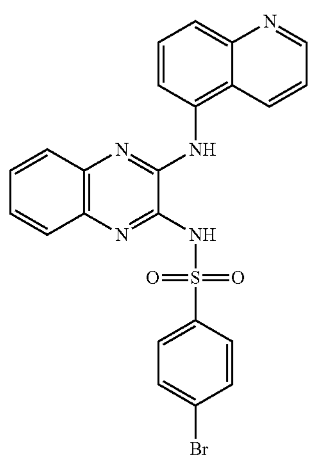 [SMILES: O=S(=O)(Nc1nc2ccccc2nc1Nc1cccc2ncccc12)c1ccc(Br)cc1] | 4-bromo-N-[3-(quinolin-5-ylamino)quinoxalin-2-yl]benzenesulfonamide |
| 138 | 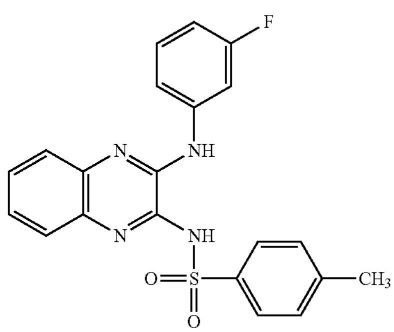 [SMILES: Cc1ccc(S(=O)(=O)Nc2nc3ccccc3nc2Nc2cccc(F)c2)cc1] | N-{3-[(3-fluorophenyl)amino]quinoxalin-2-yl}-4-methylbenzenesulfonamide |

TABLE 1-continued
| Cpd. No. | Structure | Name |
|---|---|---|
| 139 | 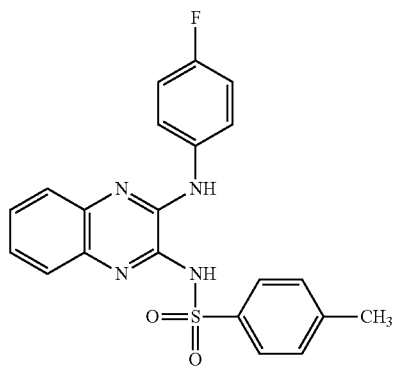 [SMILES: Cc1ccc(S(=O)(=O)Nc2nc3ccccc3nc2Nc2ccc(F)cc2)cc1] | N-{3-[(3-fluorophenyl)amino]quinoxalin-2-yl}-4-methylbenzenesulfonamide |
| 140 | 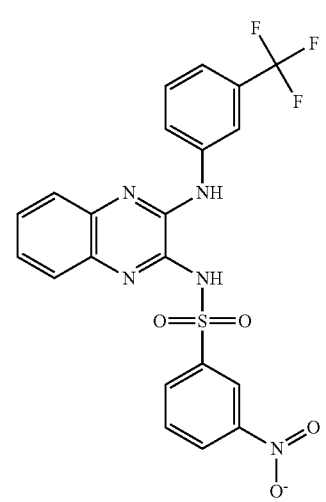 | 3-nitro-N-(3-{[3-(trifluoromethyl)phenyl]amino}quinoxalin-2-yl)benzenesulfonamide |
| 141 | 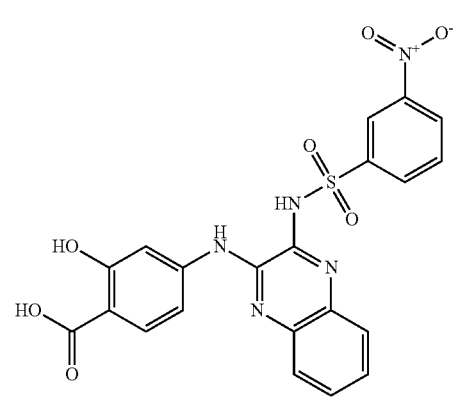 [SMILES: O=C(O)c1ccc(Nc2nc3ccccc3nc2NS(=O)(=O)c2cccc([N+](=O)[O-])c2)cc1O] | 2-hydroxy-4-[(3-{[(3-nitrophenyl)sulfonyl]amino}quinoxalin-2-yl)amino]benzoic acid |
| 142 | 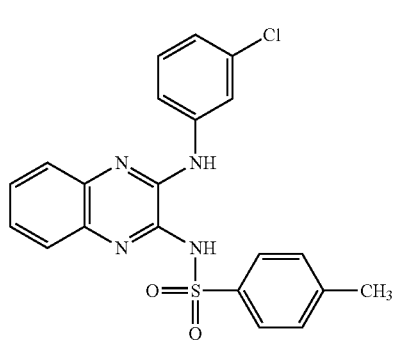 | N-{3-[(3-chloropheny)amino]quinoxalin-2-yl}-4-methylbenzenesulfonamide |

TABLE 1-continued
| Cpd. No. | Structure | Name |
|---|---|---|
| 143 | 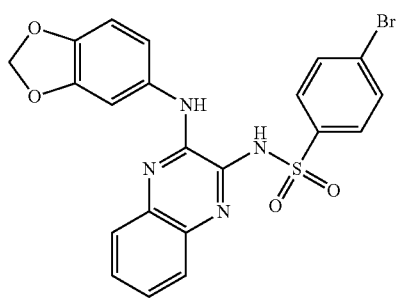 [SMILES: O=S(=O)(Nc1nc2ccccc2nc1Nc1ccc2c(c1)OCO2)c1ccc(Br)cc1] | N-[3-(1,3-benzodioxol-5-ylamino)quinoxalin-2-yl]-4-bromobenzenesulfonamide |
| 144 | 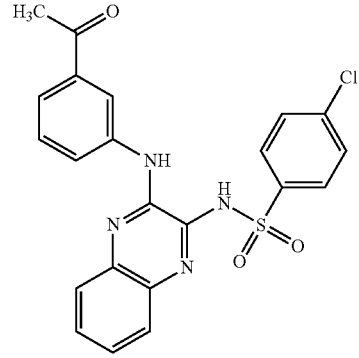 [SMILES: CC(=O)c1cccc(Nc2nc3ccccc3nc2NS(=O)(=O)c2ccc(Cl)cc2)c1] | N-{3-[(3-acetylphenyl)amino]quinoxalin-2-yl}-4-chlorobenzenesulfonamide |
| 145 | 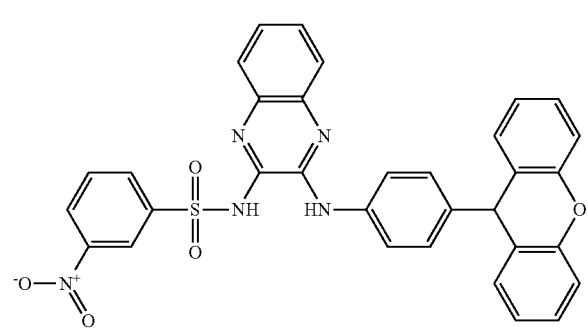 | 3-nitro-N-(3-{[4-(9H-xanthen-9-yl)phenyl]amino}quinoxalin-2-yl)benzenesulfonamide |
| 146 | 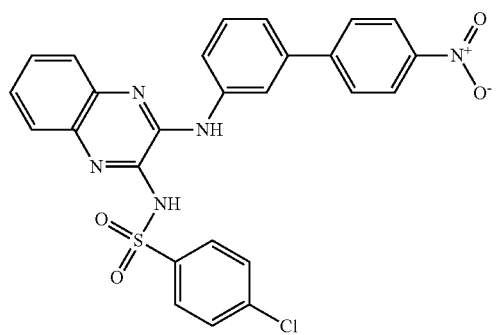 | 4-chloro-N-{3-[(4'-nitrobiphenyl-3-yl)amino]quinoxalin-2-yl}benzenesulfonamide |

TABLE 1-continued

| Cpd. No. | Structure | Name |
|---|---|---|
| 147 | 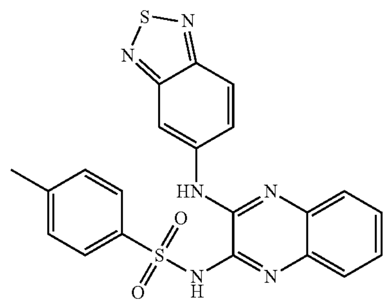 [SMILES: Cc1ccc(S(=O)(=O)Nc2nc3ccccc3nc2Nc2ccc3nsnc3c2)cc1] | N-[3-(2,1,3-benzothiadiazol-5-ylamino)quinoxalin-2-yl]-4-tolylsulfonamide |
| 148 | 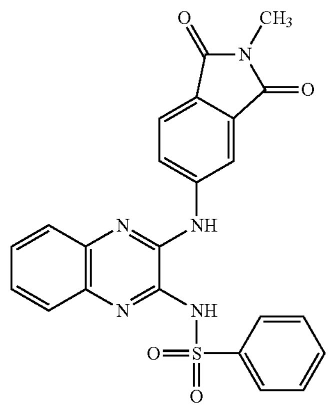 [SMILES: CN1C(=O)c2ccc(Nc3nc4ccccc4nc3NS(=O)(=O)c3ccccc3)cc2C1=O] | N-{3-[(2-methyl-1,3-dioxo-2,3-dihydro-1H-isoindol-5-yl)amino]quinoxalin-2-yl}benzenesulfonamide |
| 149 | 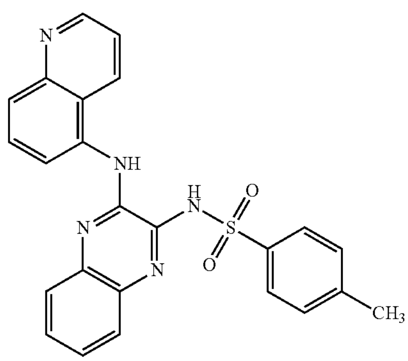 [SMILES: Cc1ccc(S(=O)(=O)Nc2nc3ccccc3nc2Nc2cccc3ncccc23)cc1] | 4-methyl-N-[3-(quinolin-5-ylamino)quinoxalin-2-yl]benzenesulfonamide |
| 150 | 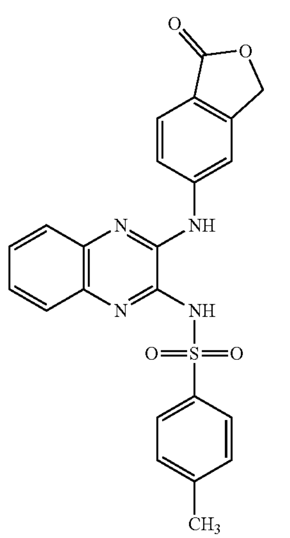 [SMILES: Cc1ccc(S(=O)(=O)Nc2nc3ccccc3nc2Nc2ccc3c(c2)COC3=O)cc1] | 4-methyl-N-{3-[(1-oxo-1,3-dihydro-2-benzofuran-5-yl)amino]quinoxalin-2-yl}benzenesulfonamide |

TABLE 1-continued

| Cpd. No. | Structure | Name |
|---|---|---|
| 151 | 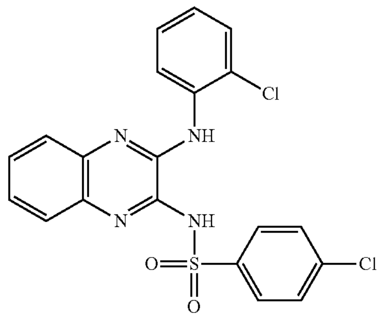 [SMILES: O=S(=O)(Nc1nc2ccccc2nc1Nc1ccccc1Cl)c1ccc(Cl)cc1] | 4-chloro-N-{3-[(2-chlorophenyl)amino]quinoxalin-2-yl}benzenesulfonamide |
| 152 | 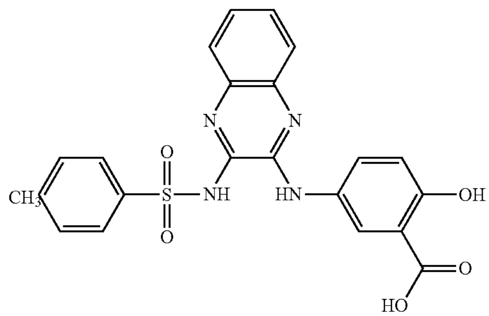 | 2-hydroxy-5-[(3-{[(4-methylphenyl)sulfonyl]amino}quinoxalin-2-yl)amino]benzoic acid |
| 153 | 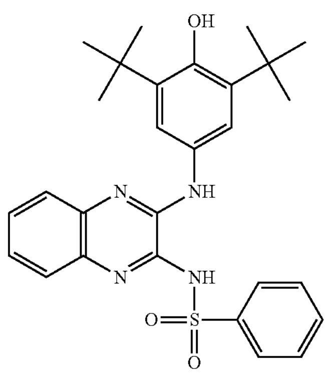 [SMILES: CC(C)(C)c1cc(Nc2nc3ccccc3nc2NS(=O)(=O)c2ccccc2)cc(C(C)(C)C)c1O] | N-(3-{[3,5-bis(1,1-dimethylethyl)-4-hydroxyphenyl]amino}quinoxalin-2-yl)benzenesulfonamide |
| 154 | 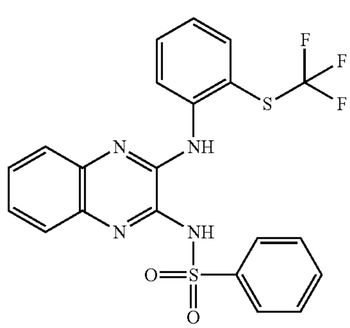 [SMILES: O=S(=O)(Nc1nc2ccccc2nc1Nc1ccccc1SC(F)(F)F)c1ccccc1] | N-[3-({2-[(trifluoromethyl)thio]phenyl}amino)quinoxalin-2-yl]benzenesulfonamide |

TABLE 1-continued

| Cpd. No. | Structure | Name |
|---|---|---|
| 155 | 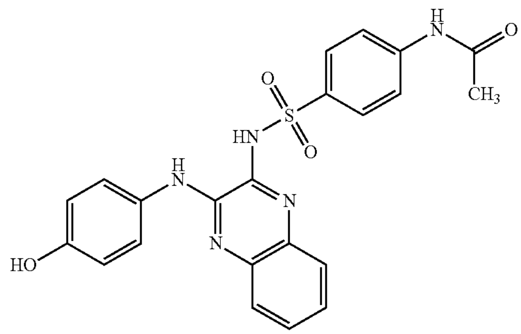 [SMILES: CC(=O)Nc1ccc(S(=O)(=O)Nc2nc3ccccc3nc2Nc2ccc(O)cc2)cc1] | N-{4-[({3-[(4-hydroxyphenyl)amino]quinoxalin-2-yl}amino)sulfonyl]phenyl}acetamide |
| 156 | 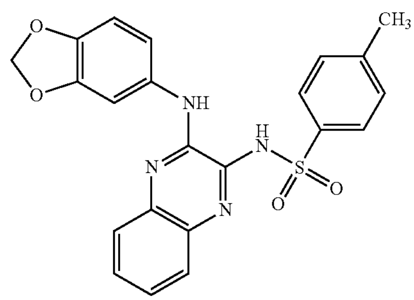 [SMILES: Cc1ccc(S(=O)(=O)Nc2nc3ccccc3nc2Nc2ccc3c(c2)OCO3)cc1] | N-[3-(1,3-benzodioxol-5-ylamino)quinoxalin-2-yl]-4-methylbenzenesulfonamide |
| 157 | 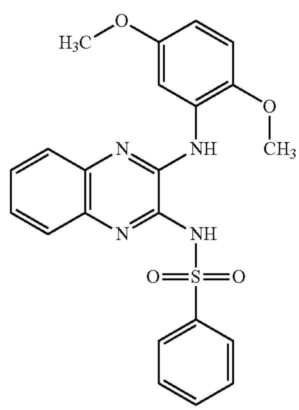 [SMILES: COc1ccc(OC)c(Nc2nc3ccccc3nc2NS(=O)(=O)c2ccccc2)c1] | N-(3-{[2,5-bis(methoxy)phenyl]amino}quinoxalin-2-yl)benzenesulfonamide |
| 158 | 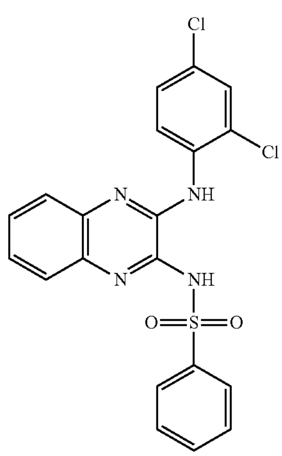 [SMILES: O=S(=O)(Nc1nc2ccccc2nc1Nc1ccc(Cl)cc1Cl)c1ccccc1] | N-{3-[(2,4-dichlorophenyl)amino]quinoxalin-2-yl}benzenesulfonamide |

TABLE 1-continued

| Cpd. No. | Structure | Name |
|---|---|---|
| 159 | 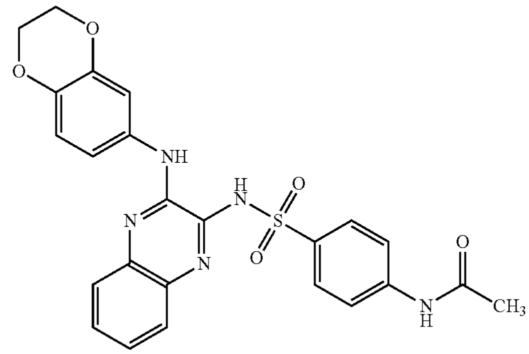 [SMILES: CC(=O)Nc1ccc(S(=O)(=O)Nc2nc3ccccc3nc2Nc2ccc3c(c2)OCCO3)cc1] | N-[4-({[3-(2,3-dihydro-1,4-benzodioxin-6-ylamino)quinoxalin-2-yl]amino}sulfonyl)phenyl]acetamide |
| 160 | 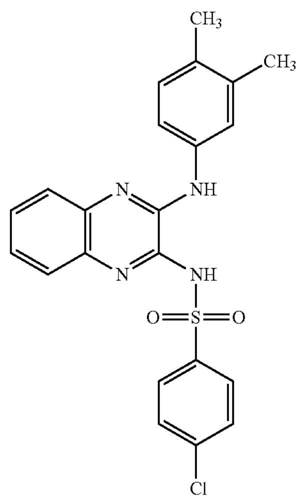 [SMILES: Cc1ccc(Nc2nc3ccccc3nc2NS(=O)(=O)c2ccc(Cl)cc2)cc1C] | 4-chloro-N-{3-[(3,4-dimethylphenyl)amino]quinoxalin-2-yl}benzenesulfonamide |
| 161 | 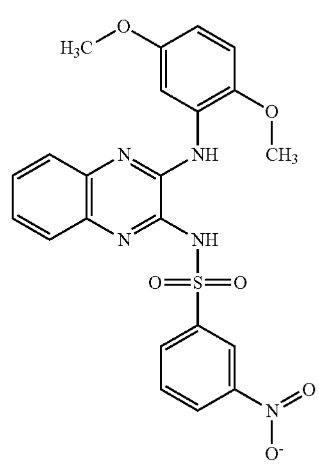 | N-(3-{[2,5-bis(methoxy)phenyl]amino}quinoxalin-2-yl)-3-nitrobenzenesulfonamide |

TABLE 1-continued
| Cpd. No. | Structure | Name |
|---|---|---|
| 162 | 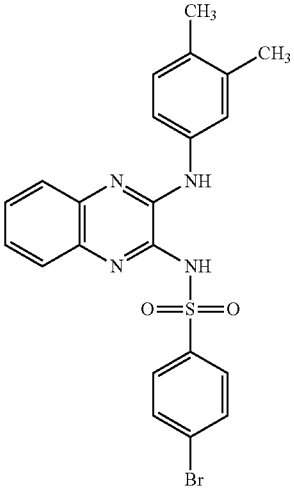 | 4-bromo-N-{3-[(3,4-dimethyl-phenyl)amino]quinoxalin-2-yl}benzenesulfonamide |
| 163 | 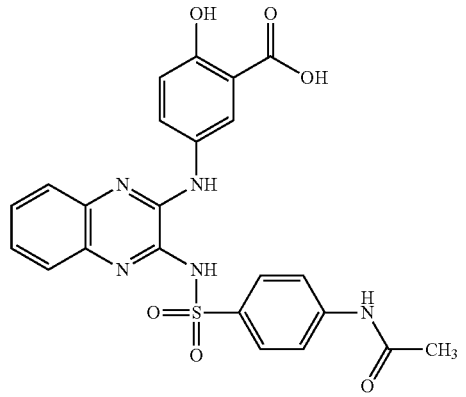 [SMILES: CC(=O)Nc1ccc(S(=O)(=O)Nc2nc3ccccc3nc2Nc2ccc(O)c(C(=O)O)c2)cc1] | 5-{[3-({[4-(acetylamino)phenyl]sulfon-yl}amino)quinoxalin-2-yl]amino}-2-hydroxybenzoic acid |
| 164 | 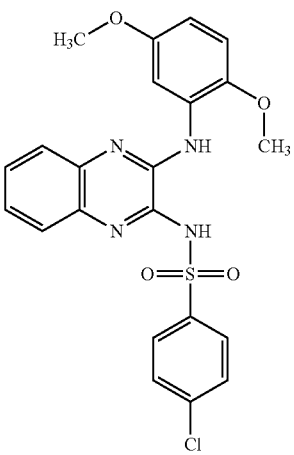 [SMILES: COc1ccc(OC)c(Nc2nc3ccccc3nc2NS(=O)(=O)c2ccc(Cl)cc2)c1] | N-(3-{[2,5-bis(methoxy)phen-yl]amino}quinoxalin-2-yl)-4-chlorobenzenesulfonamide |

TABLE 1-continued
| Cpd. No. | Structure | Name |
| --- | --- | --- |
| 165 | 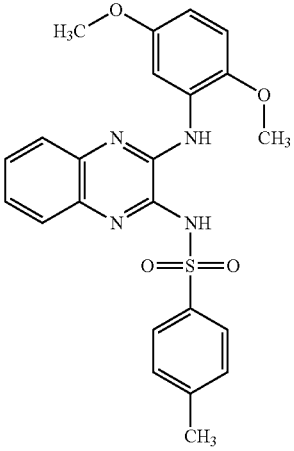 [SMILES: COc1ccc(OC)c(Nc2nc3ccccc3nc2NS(=O)(=O)c2ccc(C)cc2)c1] | N-(3-{[2,5-bis(methoxy)phenyl]amino}quinoxalin-2-yl)-4-methylbenzenesulfonamide |
| 166 | 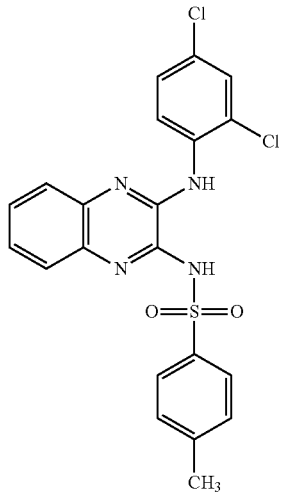 [SMILES: Cc1ccc(S(=O)(=O)Nc2nc3ccccc3nc2Nc2ccc(Cl)cc2Cl)cc1] | N-{3-[(2,4-dichlorophenyl)amino]quinoxalin-2-yl}-4-methylbenzenesulfonamide |
| 167 | 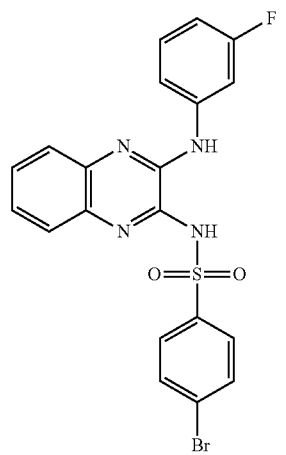 [SMILES: O=S(=O)(Nc1nc2ccccc2nc1Nc1cccc(F)c1)c1ccc(Br)cc1] | 4-bromo-N-{3-[(3-fluorophenyl)amino]quinoxalin-2-yl}benzenesulfonamide |

TABLE 1-continued

| Cpd. No. | Structure | Name |
|---|---|---|
| 168 | 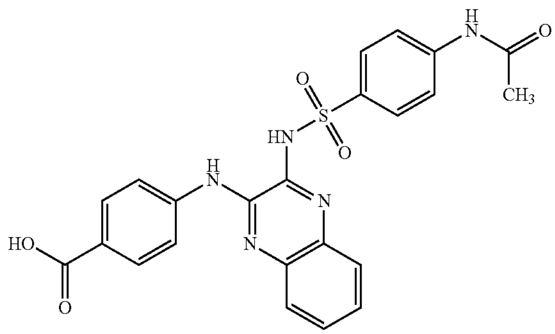 [SMILES: CC(=O)Nc1ccc(S(=O)(=O)Nc2nc3ccccc3nc2Nc2ccc(C(=O)O)cc2)cc1] | 4-{[3-({[4-(acetylamino)phenyl]sulfonyl}amino)quinoxalin-2-yl]amino}benzoic acid |
| 169 | 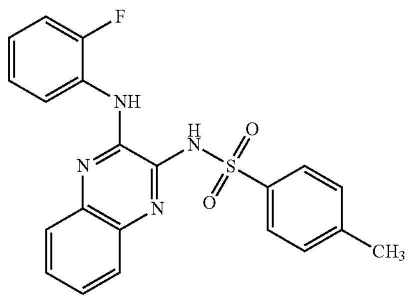 [SMILES: Cc1ccc(S(=O)(=O)Nc2nc3ccccc3nc2Nc2ccccc2F)cc1] | N-{3-[(2-fluorophenyl)amino]quinoxalin-2-yl}-4-methylbenzenesulfonamide |
| 170 | 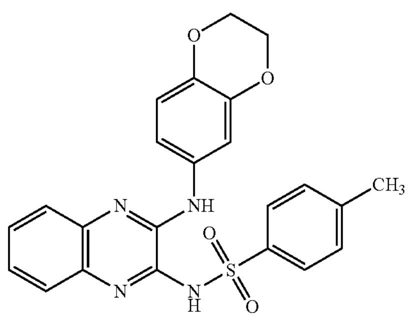 [SMILES: Cc1ccc(S(=O)(=O)Nc2nc3ccccc3nc2Nc2ccc3c(c2)OCCO3)cc1] | N-[3-(2,3-dihydro-1,4-benzodioxin-6-ylamino)quinoxalin-2-yl]-4-methylbenzenesulfonamide |
| 171 | 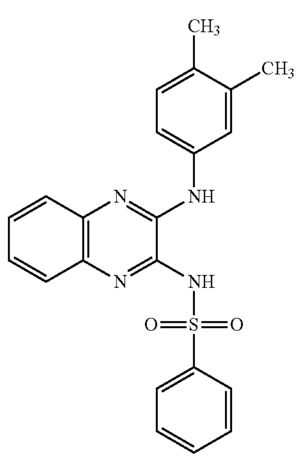 [SMILES: Cc1ccc(Nc2nc3ccccc3nc2NS(=O)(=O)c2ccccc2)cc1C] | N-{3-[(3,4-dimethylphenyl)amino]quinoxalin-2-yl}benzenesulfonamide |

TABLE 1-continued

| Cpd. No. | Structure | Name |
|---|---|---|
| 172 | 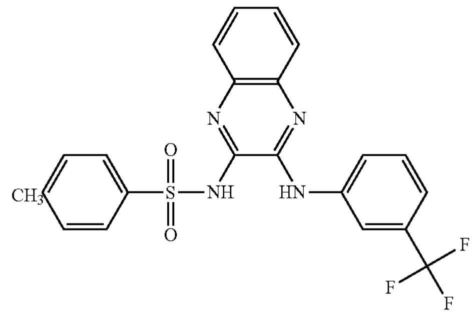 | 4-methyl-N-(3-{[3-(trifluoromethyl)phenyl]amino}quinoxalin-2-yl)benzenesulfonamide |
| 173 | 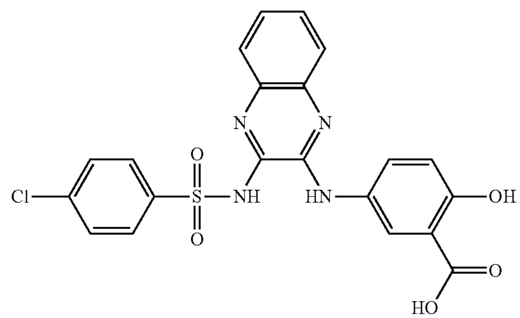 [SMILES: O=C(O)c1cc(Nc2nc3ccccc3nc2NS(=O)(=O)c2ccc(Cl)cc2)ccc1O] | 5-[(3-{[(4-chlorophenyl)sulfonyl]amino}quinoxalin-2-yl)amino]-2-hydroxybenzoic acid |
| 174 | 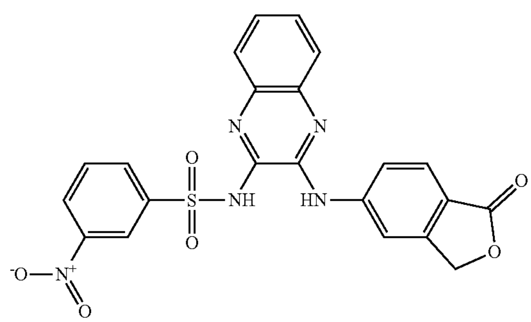 | 3-nitro-N-{3-[(1-oxo-1,3-dihydro-2-benzofuran-5-yl)amino]quinoxalin-2-yl}benzenesulfonamide |
| 175 | 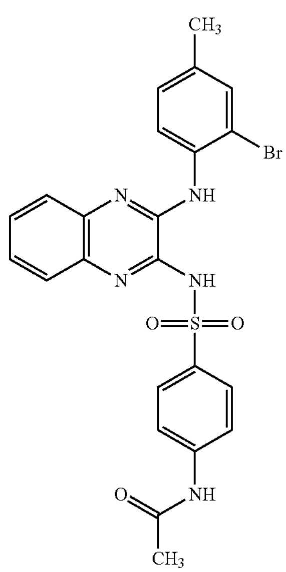 [SMILES: CC(=O)Nc1ccc(S(=O)(=O)Nc2nc3ccccc3nc2Nc2ccc(C)cc2Br)cc1] | N-{4-[({3-[(2-bromo-4-methylphenyl)amino]quinoxalin-2-yl}amino)sulfonyl]phenyl}acetamide |

| Cpd. No. | Structure | Name |
|---|---|---|
| 176 | 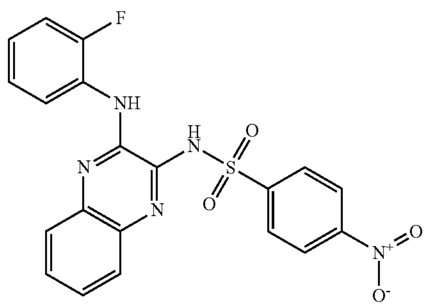 [SMILES: O=[N+]([O-])c1ccc(S(=O)(=O)Nc2nc3ccccc3nc2Nc2ccccc2F)cc1] | N-{3-[(2-fluorophenyl)amino]quinoxalin-2-yl}-4-nitrobenzenesulfonamide |
| 177 | 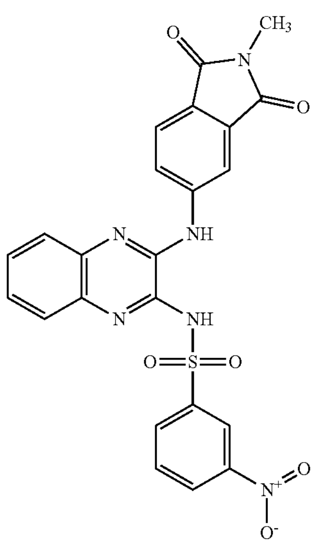 [SMILES: CN1C(=O)c2ccc(Nc3nc4ccccc4nc3NS(=O)(=O)c3cccc([N+](=O)[O-])c3)cc2C1=O] | N-{3-[(2-methyl-1,3-dioxo-2,3-dihydro-1H-isoindol-5-yl)amino]quinoxalin-2-yl}-3-nitrobenzenesulfonamide |
| 178 | 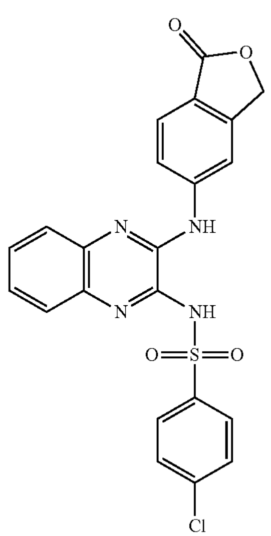 [SMILES: O=C1OCc2cc(Nc3nc4ccccc4nc3NS(=O)(=O)c3ccc(Cl)cc3)ccc21] | 4-chloro-N-{3-[(1-oxo-1,3-dihydro-2-benzofuran-5-yl)amino]quinoxalin-2-yl}benzenesulfonamide |

TABLE 1-continued

| Cpd. No. | Structure | Name |
| --- | --- | --- |
| 179 | 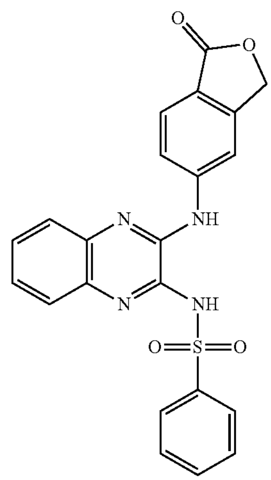 [SMILES: O=C1OCc2cc(Nc3nc4ccccc4nc3NS(=O)(=O)c3ccccc3)ccc21] | N-{3-[(1-oxo-1,3-dihydro-2-benzofuran-5-yl)amino]quinoxalin-2-yl}benzenesulfonamide |
| 180 | 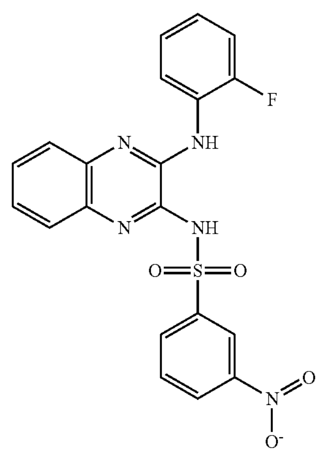 | N-{3-[(2-fluorophenyl)amino]quinoxalin-2-yl}-3-nitrobenzenesulfonamide |
| 181 | 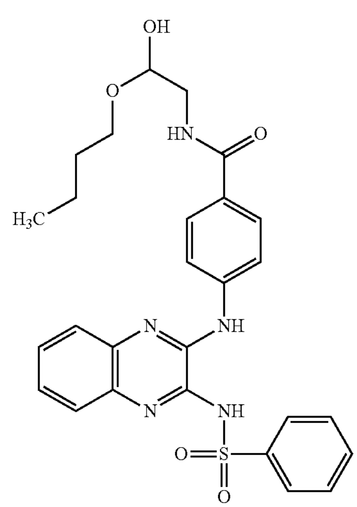 [SMILES: CCCCOC(O)CNC(=O)c1ccc(Nc2nc3ccccc3nc2NS(=O)(=O)c2ccccc2)cc1] | N-[2-(butyloxy)-2-hydroxyethyl]-4-({3-[(phenylsulfonyl)amino]quinoxalin-2-yl}amino)benzamide |

TABLE 1-continued

| Cpd. No. | Structure | Name |
|---|---|---|
| 182 | 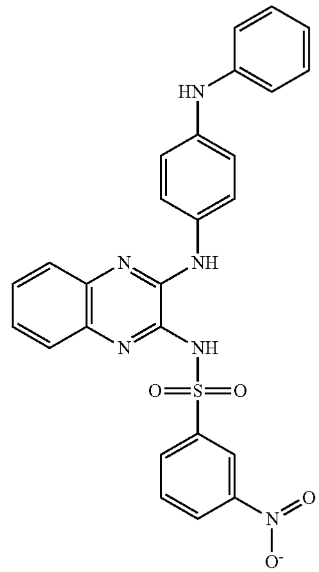 | 3-nitro-N-(3-{[4-(phenylamino)phenyl]amino}quinoxalin-2-yl)benzenesulfonamide |
| 183 | 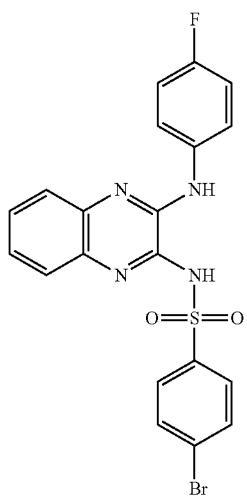 [SMILES: O=S(=O)(Nc1nc2ccccc2nc1Nc1ccc(F)cc1)c1ccc(Br)cc1] | 4-bromo-N-{3-[(4-fluorophenyl)amino]quinoxalin-2-yl}benzenesulfonamide |
| 184 | 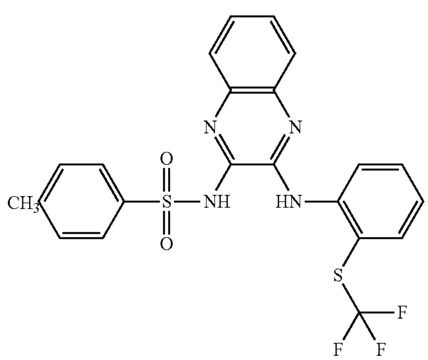 | 4-methyl-N-[3-({2-[(trifluoromethyl)thio]phenyl}amino)quinoxalin-2-yl]benzenesulfonamide |

TABLE 1-continued

| Cpd. No. | Structure | Name |
|---|---|---|
| 185 | 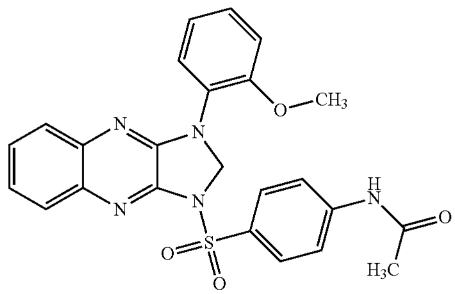 [SMILES: COc1ccccc1N1CN(S(=O)(=O)c2ccc(NC(C)=O)cc2)c2nc3ccccc3nc21] | N-[4-({3-[2-(methoxy)phenyl]-2,3-dihydro-1H-imidazo[4,5-b]quinoxalin-1-yl}sulfonyl)phenyl]acetamide |
| 186 | 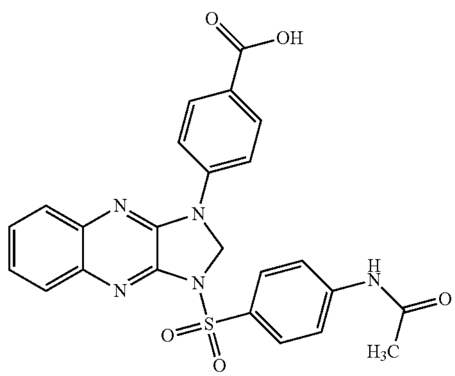 [SMILES: CC(=O)Nc1ccc(S(=O)(=O)N2CN(c3ccc(C(=O)O)cc3)c3nc4ccccc4nc32)cc1] | 4-(3-{[4-(acetylamino)phenyl]sulfonyl}-2,3-dihydro-1H-imidazo[4,5-b]quinoxalin-1-yl)benzoic acid |
| 187 | 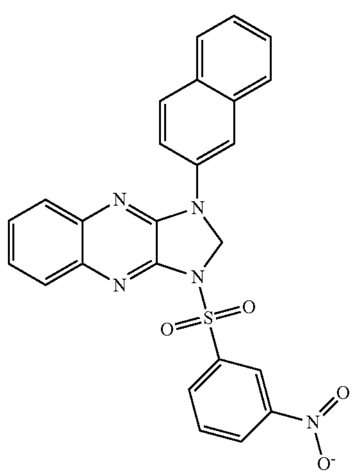 | 1-naphthalen-2-yl-3-[(3-nitrophenyl)sulfonyl]-2,3-dihydro-1H-imidazo[4,5-b]quinoxaline |

TABLE 1-continued
| Cpd. No. | Structure | Name |
|---|---|---|
| 188 | 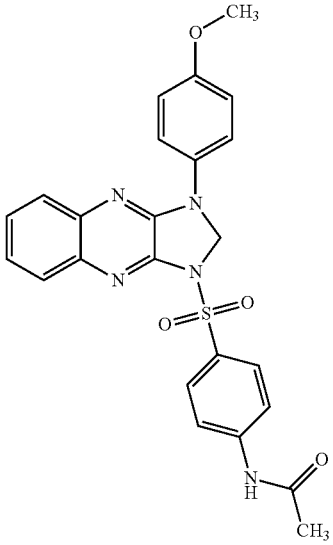 [SMILES: COc1ccc(N2CN(S(=O)(=O)c3ccc(NC(C)=O)cc3)c3nc4ccccc4nc32)cc1] | N-[4-({3-[4-(methoxy)phenyl]-2,3-dihydro-1H-imidazo[4,5-b]quinoxalin-1-yl}sulfonyl)phenyl]acetamide |
| 189 | 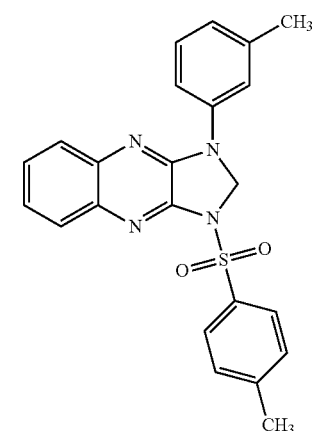 [SMILES: Cc1ccc(S(=O)(=O)N2CN(c3cccc(C)c3)c3nc4ccccc4nc32)cc1] | 1-(3-methylphenyl)-3-((4-methylphenyl)sulfonyl]-2,3-dihydro-1H-imidazo[4,5-b)quinoxaline |
| 190 | 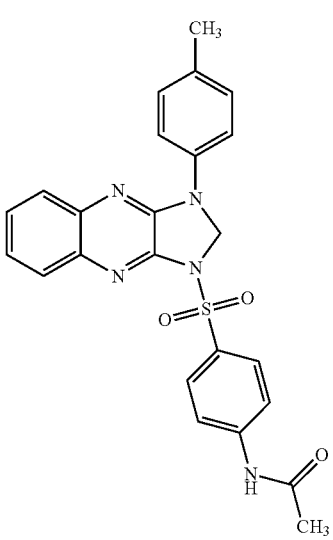 [SMILES: CC(=O)Nc1ccc(S(=O)(=O)N2CN(c3ccc(C)cc3)c3nc4ccccc4nc32)cc1] | N-(4-{[3-(4-methylphenyl)-2,3-dihydro-1H-imidazo[4,5-b]quinoxalin-1-yl]sulfonyl}phenyl)acetamide |

TABLE 1-continued

| Cpd. No. | Structure | Name |
|---|---|---|
| 191 | 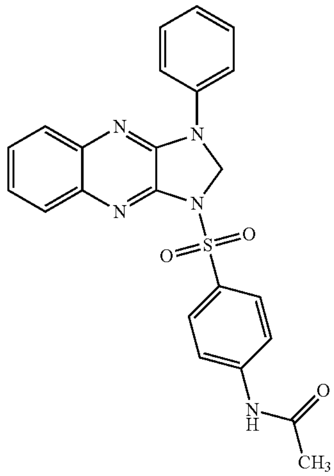 [SMILES: CC(=O)Nc1ccc(S(=O)(=O)N2CN(c3ccccc3)c3nc4ccccc4nc32)cc1] | N-{4-[(3-phenyl-2,3-dihydro-1H-imidazo[4,5-b]quinoxalin-1-yl)sulfonyl]phenyl}acetamide |
| 192 | 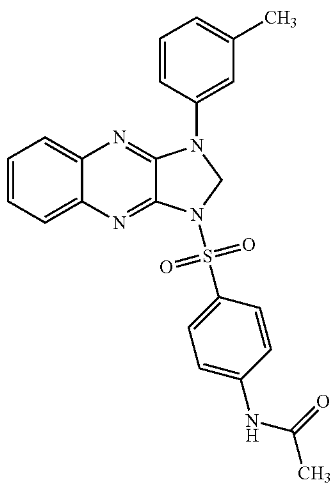 [SMILES: CC(=O)Nc1ccc(S(=O)(=O)N2CN(c3cccc(C)c3)c3nc4ccccc4nc32)cc1] | N-(4-{[3-(3-methylphenyl)-2,3-dihydro-1H-imidazo[4,5-b]quinoxalin-1-yl]sulfonyl}phenyl)acetamide |
| 193 | 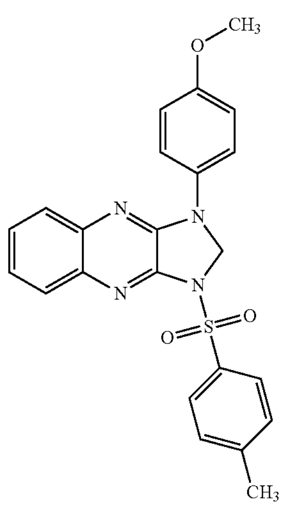 [SMILES: COc1ccc(N2CN(S(=O)(=O)c3ccc(C)cc3)c3nc4ccccc4nc32)cc1] | 1-[4-(methoxy)phenyl]-3-[(4-methylphenyl)sulfonyl]-2,3-dihydro-1H-imidazo[4,5-b]quinoxaline |

TABLE 1-continued

| Cpd. No. | Structure | Name |
|---|---|---|
| 194 | 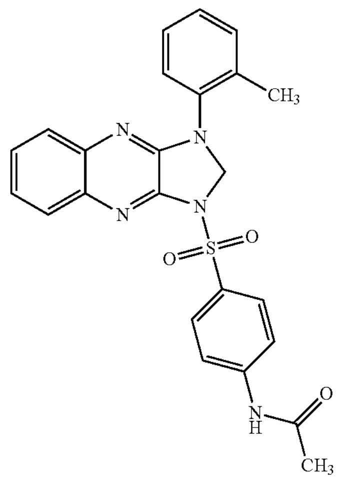 [SMILES: CC(=O)Nc1ccc(S(=O)(=O)N2CN(c3ccccc3C)c3nc4ccccc4nc32)cc1] | N-(4-{[3-(2-methylphenyl)-2,3-dihydro-1H-imidazo[4,5-b]quinoxalin-1-yl]sulfonyl}phenyl)acetamide |
| 195 | 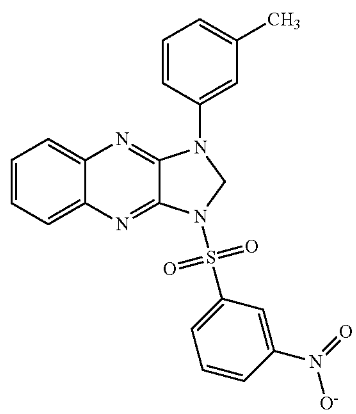 | 1-(3-methylphenyl)-3-[(3-nitrophenyl)sulfonyl]-2,3-dihydro-1H-imidazo[4,5-b]quinoxaline |
| 196 | 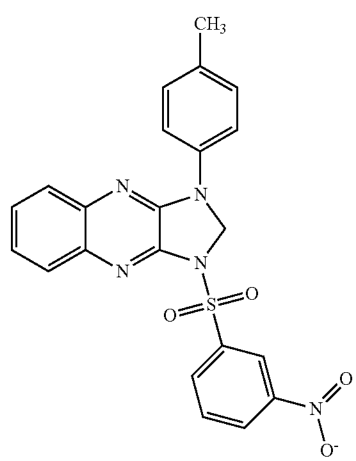 | 1-(4-methylphenyl)-3-[(3-nitrophenyl)sulfonyl]-2,3-dihydro-1H-imidazo[4,5-b]quinoxaline |

TABLE 1-continued

| Cpd. No. | Structure | Name |
|---|---|---|
| 197 | 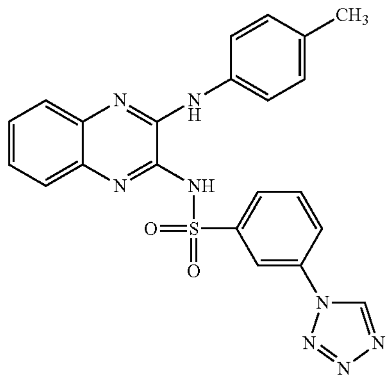 [SMILES: Cc1ccc(Nc2nc3ccccc3nc2NS(=O)(=O)c2cccc(-n3cnnn3)c2)cc1] | N-{3-[(4-methylphenyl)amino]quinoxalin-2-yl}-3-(1H-tetrazol-1-yl)benzenesulfonamide |
| 198 | 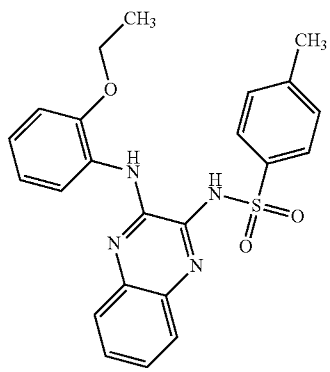 [SMILES: CCOc1ccccc1Nc1nc2ccccc2nc1NS(=O)(=O)c1ccc(C)cc1] | N-(3-{[2-(ethyloxy)phenyl]amino}quinoxalin-2-yl)-4-methylbenzenesulfonamide |
| 199 | 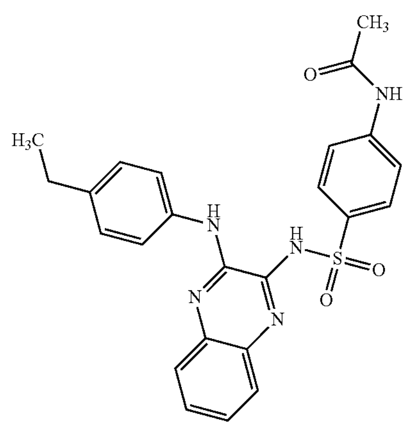 [SMILES: CCc1ccc(Nc2nc3ccccc3nc2NS(=O)(=O)c2ccc(NC(C)=O)cc2)cc1] | N-{4-[({3-[(4-ethylphenyl)amino]quinoxalin-2-yl}amino)sulfonyl]phenyl}acetamide |
| 200 | 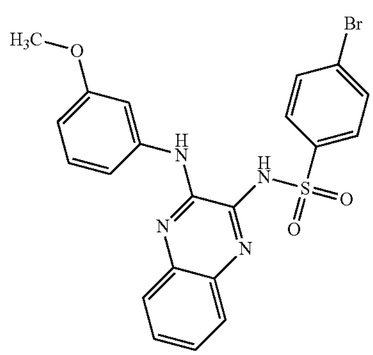 [SMILES: COc1cccc(Nc2nc3ccccc3nc2NS(=O)(=O)c2ccc(Br)cc2)c1] | 4-bromo-N-(3-{[3-(methoxy)phenyl]amino}quinoxalin-2-yl)benzenesulfonamide |

TABLE 1-continued

| Cpd. No. | Structure | Name |
| --- | --- | --- |
| 201 | 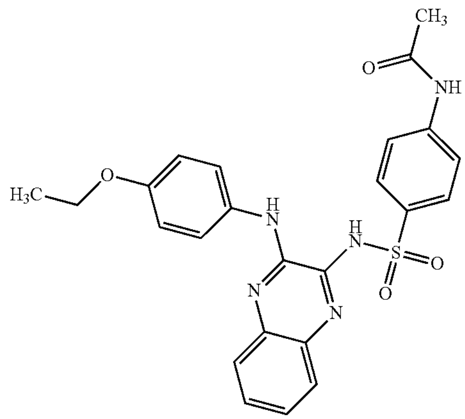 [SMILES: CCOc1ccc(Nc2nc3ccccc3nc2NS(=O)(=O)c2ccc(NC(C)=O)cc2)cc1] | N-(4-{[(3-{[4-(ethyloxy)phenyl]amino}quinoxalin-2-yl)amino]sulfonyl}phenyl)acetamide |
| 202 | 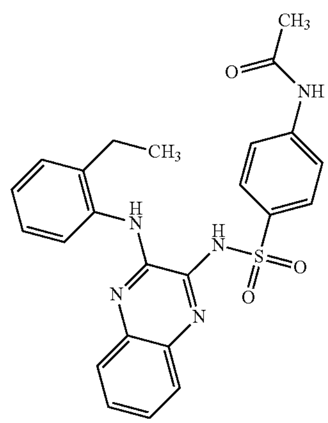 [SMILES: CCc1ccccc1Nc1nc2ccccc2nc1NS(=O)(=O)c1ccc(NC(C)=O)cc1] | N-{4-[({3-[(2-ethylphenyl)amino]quinoxalin-2-yl}amino)sulfonyl]phenyl}acetamide |
| 203 | 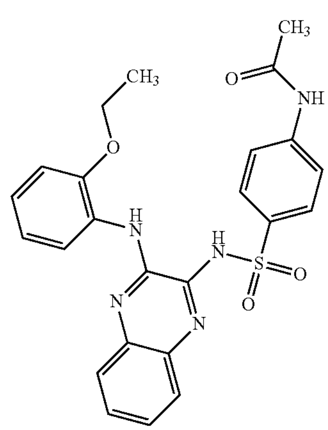 [SMILES: CCOc1ccccc1Nc1nc2ccccc2nc1NS(=O)(=O)c1ccc(NC(C)=O)cc1] | N-(4-{[(3-{[2-(ethyloxy)phenyl]amino}quinoxalin-2-yl)amino]sulfonyl}phenyl)acetamide |

TABLE 1-continued
| Cpd. No. | Structure | Name |
|---|---|---|
| 204 | 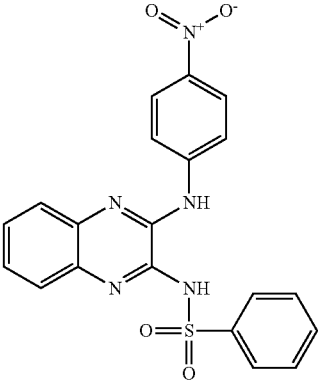 [SMILES: O=[N+]([O-])c1ccc(Nc2nc3ccccc3nc2NS(=O)(=O)c2ccccc2)cc1] | N-{3-[(4-nitrophenyl)amino]quinoxalin-2-yl}benzenesulfonamide |
| 205 | 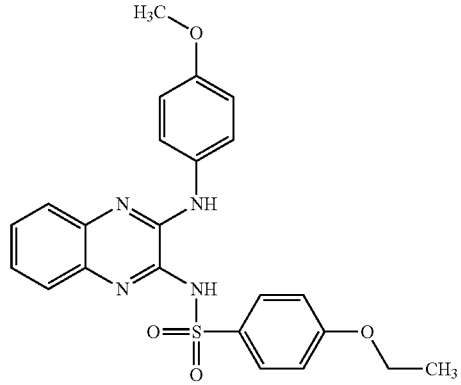 [SMILES: CCOc1ccc(S(=O)(=O)Nc2nc3ccccc3nc2Nc2ccc(OC)cc2)cc1] | 4-(ethyloxy)-N-(3-{[4-(methoxy)phenyl]amino}quinoxalin-2-yl)benzenesulfonamide |
| 206 | 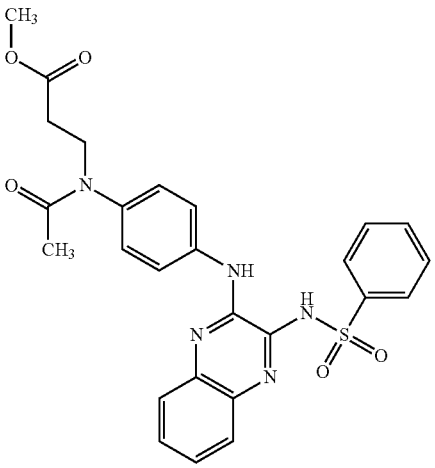 [SMILES: COC(=O)CCN(C(C)=O)c1ccc(Nc2nc3ccccc3nc2NS(=O)(=O)c2ccccc2)cc1] | methyl N-acetyl-N-[4-({3-[(phenylsulfonyl)amino]quinoxalin-2-yl}amino)phenyl]-beta-alaninate |

TABLE 1-continued
| Cpd. No. | Structure | Name |
|---|---|---|
| 207 | 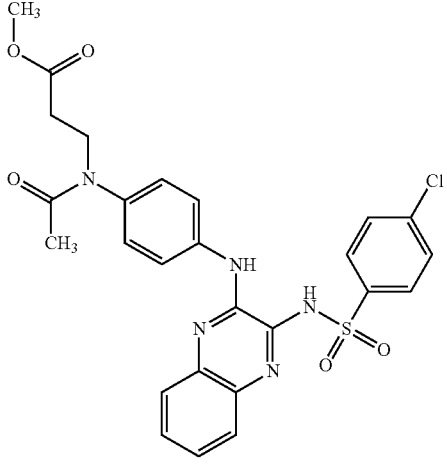 [SMILES: COC(=O)CCN(C(C)=O)c1ccc(Nc2nc3ccccc3nc2NS(=O)(=O)c2ccc(Cl)cc2)cc1] | methyl N-acetyl-N-{4-[(3-{[(4-chlorophenyl)sulfonyl]amino}quinoxalin-2-yl)amino]phenyl}-beta-alaninate |
| 208 | 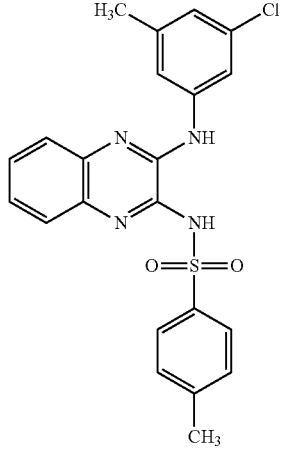 [SMILES: Cc1ccc(S(=O)(=O)Nc2nc3ccccc3nc2Nc2cc(C)cc(Cl)c2)cc1] | N-{3-[(3-chloro-5-methylphenyl)amino]quinoxalin-2-yl}-4-methylbenzenesulfonamide |
| 209 | 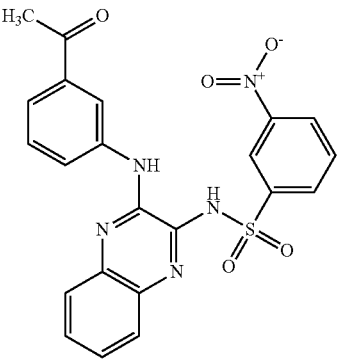 [SMILES: CC(=O)c1cccc(Nc2nc3ccccc3nc2NS(=O)(=O)c2cccc([N+](=O)[O-])c2)c1] | N-{3-[(3-acetylphenyl)amino]quinoxalin-2-yl}-3-nitrobenzenesulfonamide |

TABLE 1-continued
| Cpd. No. | Structure | Name |
|---|---|---|
| 210 | 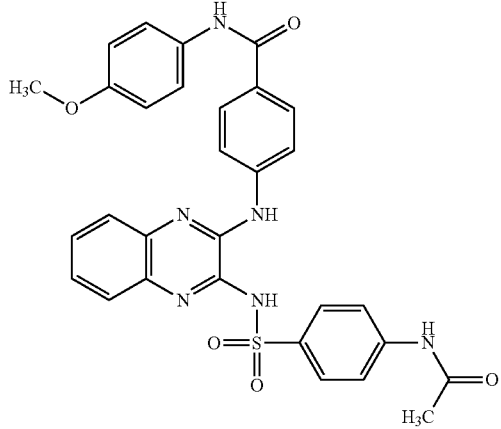 [SMILES: COc1ccc(NC(=O)c2ccc(Nc3nc4ccccc4nc3NS(=O)(=O)c3ccc(NC(C)=O)cc3)cc2)cc1] | 4-{[3-({[4-(acetylamino)phenyl]sulfonyl}amino)quinoxalin-2-yl]amino}-N-[4-(methoxy)phenyl]benzamide |
| 211 | 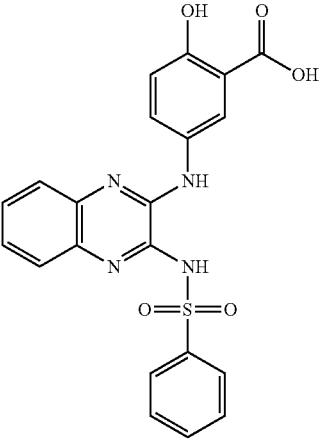 [SMILES: O=C(O)c1cc(Nc2nc3ccccc3nc2NS(=O)(=O)c2ccccc2)ccc1O] | 2-hydroxy-5-({3-[(phenylsulfonyl)amino]quinoxalin-2-yl}amino)benzoic acid |
| 212 | 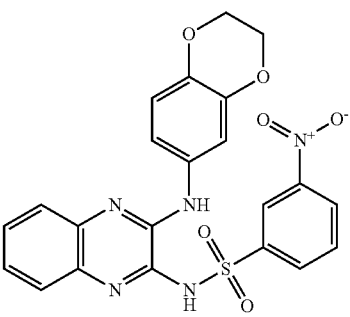 [SMILES: O=[N+]([O-])c1cccc(S(=O)(=O)Nc2nc3ccccc3nc2Nc2ccc3c(c2)OCCO3)c1] | N-[3-(2,3-dihydro-1,4-benzodioxin-6-ylamino)quinoxalin-2-yl]-3-nitrobenzenesulfonamide |

TABLE 1-continued

| Cpd. No. | Structure | Name |
|---|---|---|
| 213 | 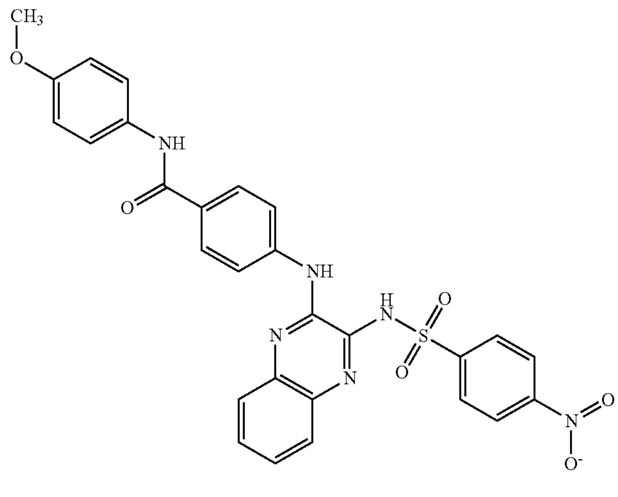 | N-[4-(methoxy)phenyl]-4-[(3-{[(4-nitrophenyl)sulfonyl]amino}quinoxalin-2-yl)amino]benzamide |
| 214 | 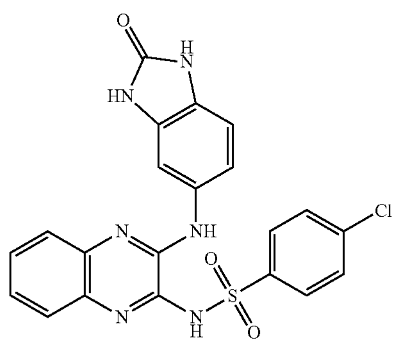 [SMILES: O=c1[nH]c2ccc(Nc3nc4ccccc4nc3NS(=O)(=O)c3ccc(Cl)cc3)cc2[nH]1] | 4-chloro-N-{3-[(2-oxo-2,3-dihydro-1H-benzimidazol-5-yl)amino]quinoxalin-2-yl}benzenesulfonamide |
| 215 | 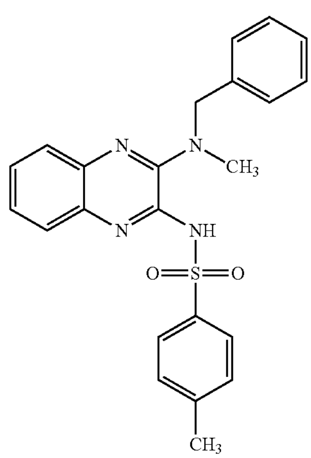 [SMILES: Cc1ccc(S(=O)(=O)Nc2nc3ccccc3nc2N(C)Cc2ccccc2)cc1] | 4-methyl-N-{3-[methyl(phenylmethyl)amino]quinoxalin-2-yl}benzenesulfonamide |

TABLE 1-continued

| Cpd. No. | Structure | Name |
|---|---|---|
| 216 | 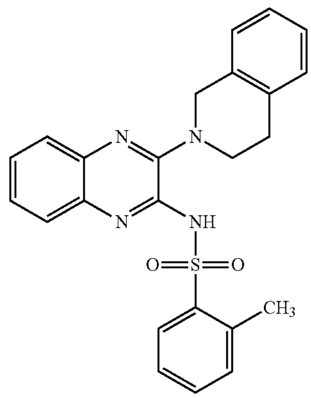 [SMILES: Cc1ccccc1S(=O)(=O)Nc1nc2ccccc2nc1N1CCc2ccccc2C1] | N-[3-(3,4-dihydroisoquinolin-2(1H)-yl)quinoxalin-2-yl]-2-methylbenzenesulfonamide |
| 217 | 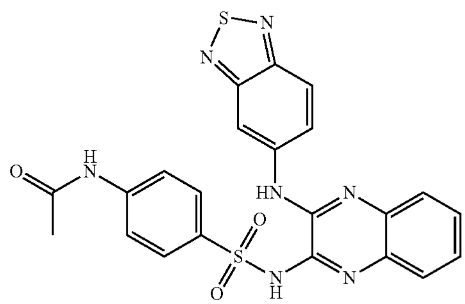 [SMILES: CC(=O)Nc1ccc(S(=O)(=O)Nc2nc3ccccc3nc2Nc2ccc3nsnc3c2)cc1] | N-[4-({[3-(2,1,3-benzothiadiazol-5-ylamino)quinoxalin-2-yl]amino}sulfonyl)phenyl]acetamide |
| 218 | 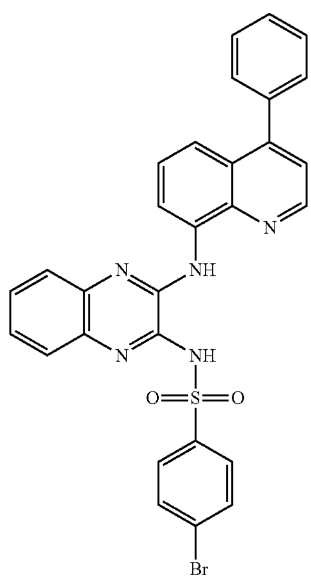 [SMILES: O=S(=O)(Nc1nc2ccccc2nc1Nc1cccc2c(-c3ccccc3)ccnc12)c1ccc(Br)cc1] | 4-bromo-N-{3-[(4-phenylquinolin-8-yl)amino]quinoxalin-2-yl}benzenesulfonamide |
| 219 | 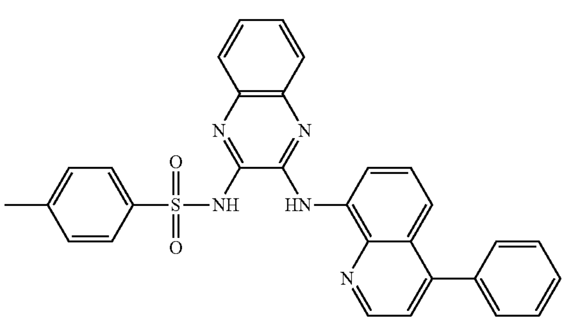 [SMILES: Cc1ccc(S(=O)(=O)Nc2nc3ccccc3nc2Nc2cccc3c(-c4ccccc4)ccnc23)cc1] | 4-methyl-N-{3-[(4-phenylquinolin-8-yl)amino]quinoxalin-2-yl}benzenesulfonamide |

TABLE 1-continued

| Cpd. No. | Structure | Name |
| --- | --- | --- |
| 220 | 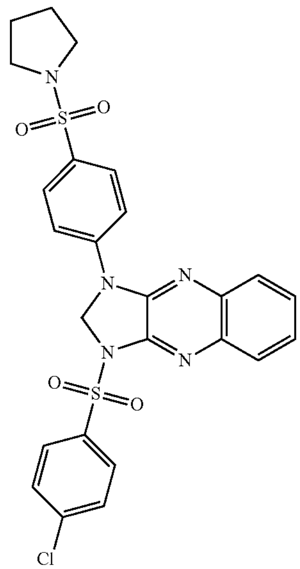 [SMILES: O=S(=O)(c1ccc(N2CN(S(=O)(=O)c3ccc(Cl)cc3)c3nc4ccccc4nc32)cc1)N1CCCC1] | 1-[(4-chlorophenyl)sulfonyl]-3-[4-(pyrrolidin-1-ylsulfonyl)phenyl]-2,3-dihydro-1H-imidazo[4,5-b]quinoxaline |
| 221 | 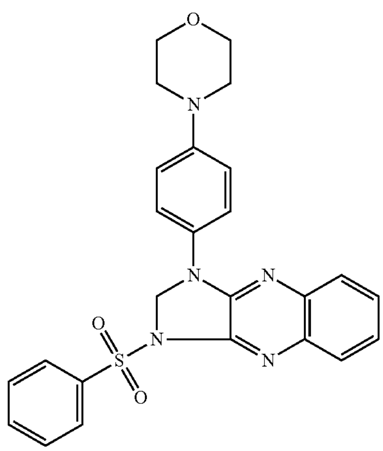 [SMILES: O=S(=O)(c1ccccc1)N1CN(c2ccc(N3CCOCC3)cc2)c2nc3ccccc3nc21] | 1-(4-morpholin-4-ylphenyl)-3-(phenylsulfonyl)-2,3-dihydro-1H-imidazo[4,5-b]quinoxaline |
| 222 | 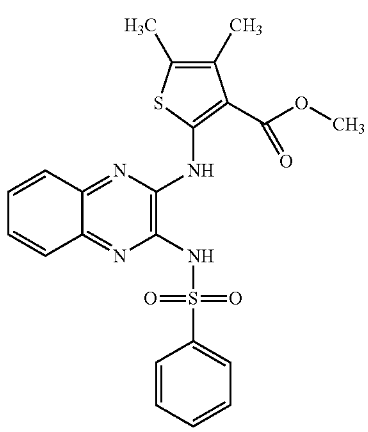 [SMILES: COC(=O)c1c(Nc2nc3ccccc3nc2NS(=O)(=O)c2ccccc2)sc(C)c1C] | methyl 4,5-dimethyl-2-({3-[(phenylsulfonyl)amino]quinoxalin-2-yl}amino)thiophene-3-carboxylate |

TABLE 1-continued

| Cpd. No. | Structure | Name |
|---|---|---|
| 223 | 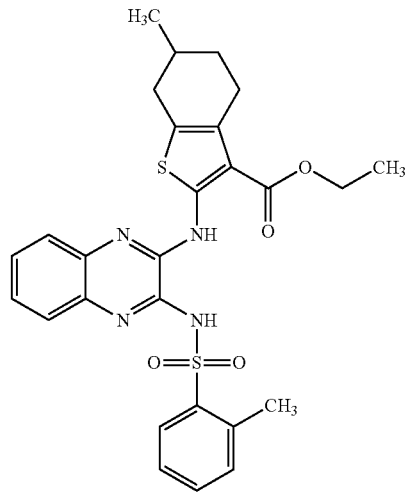 [SMILES: CCOC(=O)c1c(Nc2nc3ccccc3nc2NS(=O)(=O)c2ccccc2C)sc2c1CCC(C)C2] | ethyl 6-methyl-2-[(3-{[(2-methylphenyl)sulfonyl]amino}quinoxalin-2-yl)amino]-4,5,6,7-tetrahydro-1-benzothiophene-3-carboxylate |
| 224 | 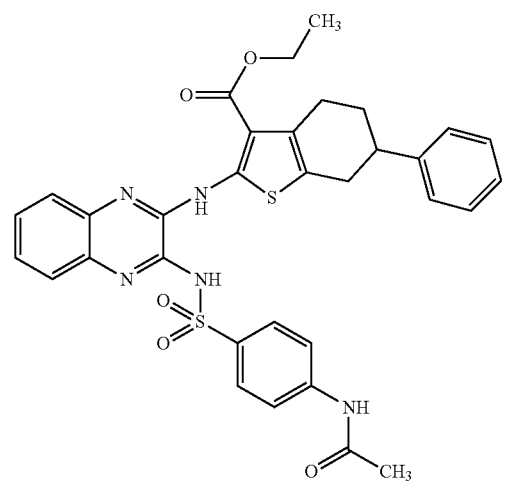 [SMILES: CCOC(=O)c1c(Nc2nc3ccccc3nc2NS(=O)(=O)c2ccc(NC(C)=O)cc2)sc2c1CCC(c1ccccc1)C2] | ethyl 2-{[3-({[4-(acetylamino)phenyl]sulfonyl}amino)quinoxalin-2-yl]amino}-6-phenyl-4,5,6,7-tetrahydro-1-benzothiophene-3-carboxylate |
| 225 | 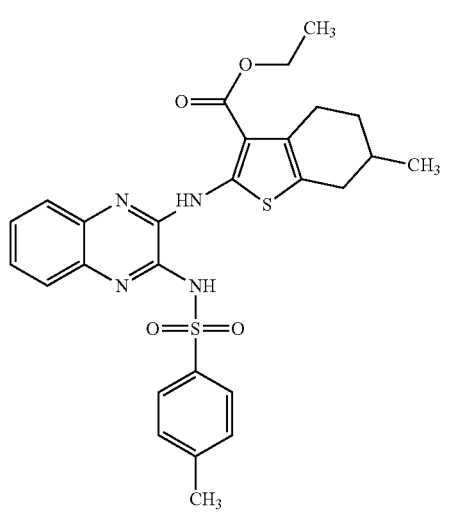 [SMILES: CCOC(=O)c1c(Nc2nc3ccccc3nc2NS(=O)(=O)c2ccc(C)cc2)sc2c1CCC(C)C2] | ethyl 6-methyl-2-[(3-{[(4-methylphenyl)sulfonyl]amino}quinoxalin-2-yl)amino]-4,5,6,7-tetrahydro-1-benzothiophene-3-carboxylate |

TABLE 1-continued
| Cpd. No. | Structure | Name |
|---|---|---|
| 226 | 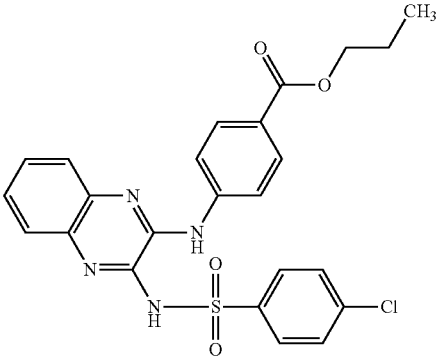 [SMILES: CCCOC(=O)c1ccc(Nc2nc3ccccc3nc2NS(=O)(=O)c2ccc(Cl)cc2)cc1] | propyl 4-[(3-{[(4-chlorophenyl)sulfonyl]amino}quinoxalin-2-yl)amino]benzoate |
| 227 | 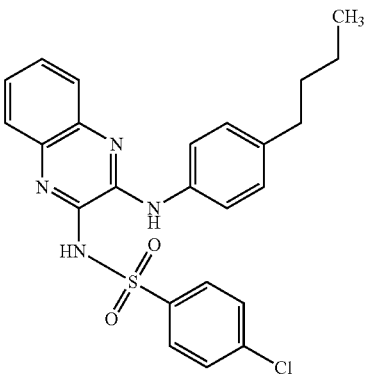 [SMILES: CCCCc1ccc(Nc2nc3ccccc3nc2NS(=O)(=O)c2ccc(Cl)cc2)cc1] | N-{3-[(4-butylphenyl)amino]quinoxalin-2-yl}-4-chlorobenzenesulfonamide |
| 228 | 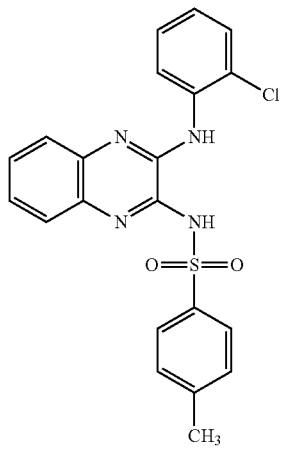 [SMILES: Cc1ccc(S(=O)(=O)Nc2nc3ccccc3nc2Nc2ccccc2Cl)cc1] | N-{3-[(2-chlorophenyl)amino]quinoxalin-2-yl}-4-methylbenzenesulfonamide |

TABLE 1-continued

| Cpd. No. | Structure | Name |
|---|---|---|
| 229 | 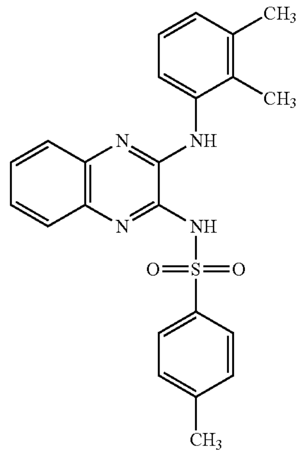 [SMILES: Cc1ccc(S(=O)(=O)Nc2nc3ccccc3nc2Nc2cccc(C)c2C)cc1] | N-{3-[(2,3-dimethylphenyl)amino]quinoxalin-2-yl}-4-methylbenzenesulfonamide |
| 230 | 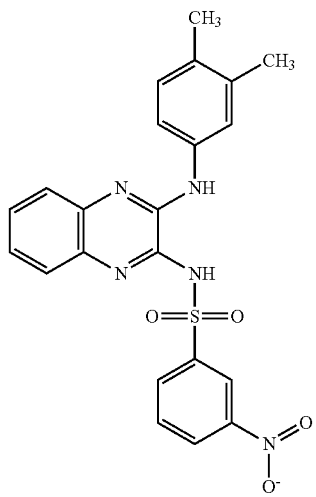 | N-{3-[(3,4-dimethylphenyl)amino]quinoxalin-2-yl}-3-nitrobenzenesulfonamide |
| 231 | 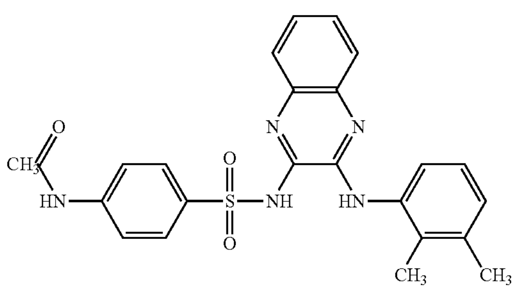 | N-{4-[({3-[(2,3-dimethylphenyl)amino]quinoxalin-2-yl}amino)sulfonyl]phenyl}acetamide |
| 232 | 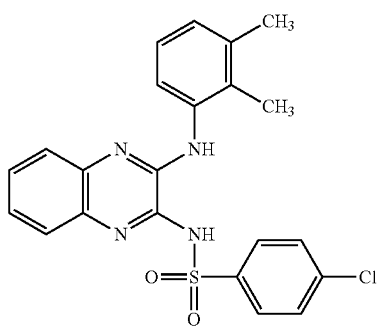 [SMILES: Cc1cccc(Nc2nc3ccccc3nc2NS(=O)(=O)c2ccc(Cl)cc2)c1C] | 4-chloro-N-{3-[(2,3-dimethylphenyl)amino]quinoxalin-2-yl}benzenesulfonamide |

TABLE 1-continued

| Cpd. No. | Structure | Name |
|---|---|---|
| 233 | 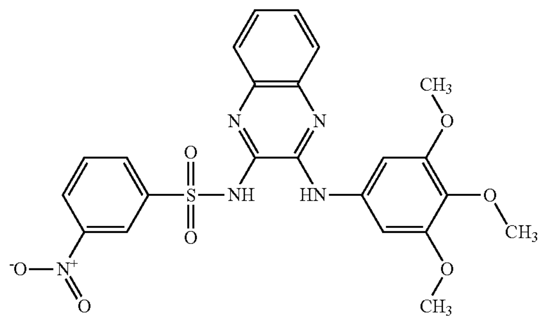 | 3-nitro-N-(3-{[3,4,5-tris(methoxy)phenyl]amino}quinoxalin-2-yl)benzenesulfonamide |
| 234 | 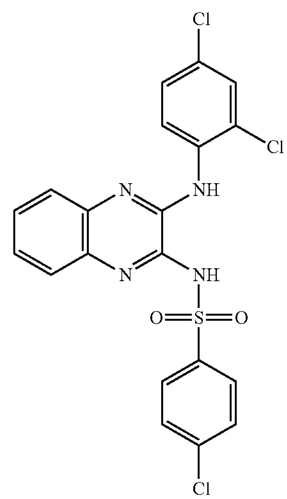 [SMILES: O=S(=O)(Nc1nc2ccccc2nc1Nc1ccc(Cl)cc1Cl)c1ccc(Cl)cc1] | 4-chloro-N-{3-[(2,4-dichlorophenyl)amino]quinoxalin-2-yl}benzenesulfonamide |
| 235 | 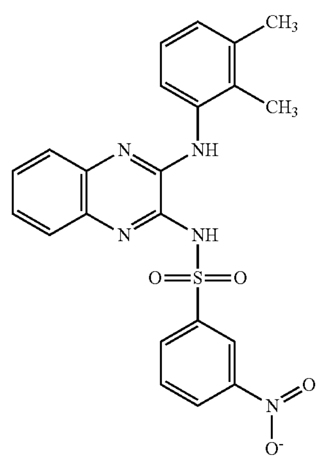 | N-{3-[(2,3-dimethylphenyl)amino]quinoxalin-2-yl}-3-nitrobenzenesulfonamide |
| 236 | 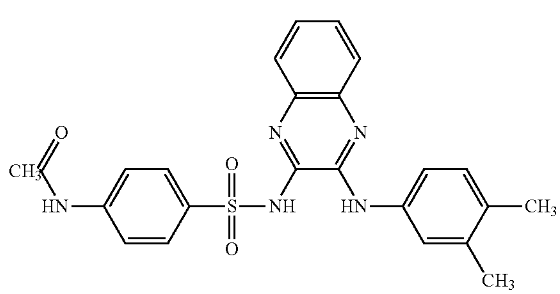 | N-{4-[({3-[(3,4-dimethylphenyl)amino]quinoxalin-2-yl}amino)sulfonyl]phenyl}acetamide |

TABLE 1-continued

| Cpd. No. | Structure | Name |
|---|---|---|
| 237 | 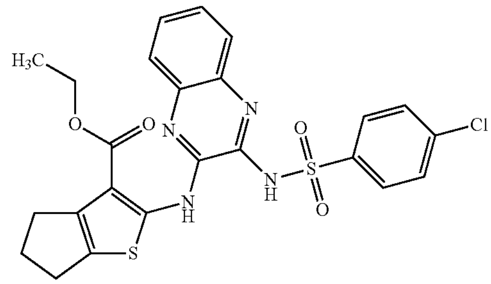 [SMILES: CCOC(=O)c1c(Nc2nc3ccccc3nc2NS(=O)(=O)c2ccc(Cl)cc2)sc2c1CCC2] | ethyl 2-[(3-{[(4-chloro-phenyl)sulfonyl]amino}quinoxalin-2-yl)amino]-5,6-dihydro-4H-cyclopenta[b]thiophene-3-carboxylate |
| 238 | 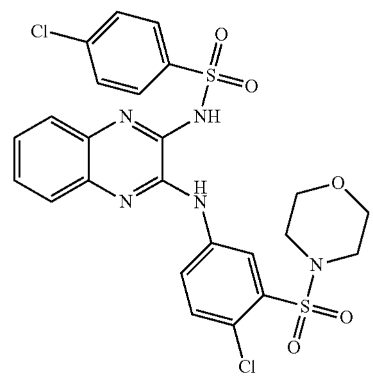 [SMILES: O=S(=O)(Nc1nc2ccccc2nc1Nc1ccc(Cl)c(S(=O)(=O)N2CCOCC2)c1)c1ccc(Cl)cc1] | 4-chloro-N-(3-{[4-chloro-3-(morpholin-4-ylsulfonyl)phenyl]amino}quinoxalin-2-yl)benzenesulfonamide |
| 239 | 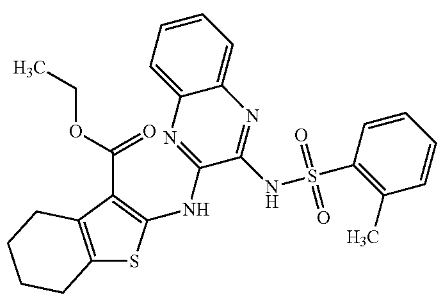 [SMILES: CCOC(=O)c1c(Nc2nc3ccccc3nc2NS(=O)(=O)c2ccccc2C)sc2c1CCCC2] | ethyl 2-[(3-{[(2-methylphenyl)sulfonyl]amino}quinoxalin-2-yl)amino]-4,5,6,7-tetrahydro-1-benzothiophene-3-carboxylate |
| 240 | 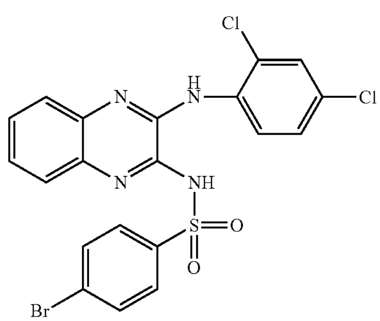 [SMILES: O=S(=O)(Nc1nc2ccccc2nc1Nc1ccc(Cl)cc1Cl)c1ccc(Br)cc1] | 4-bromo-N-{3-[(2,4-dichlorophenyl)amino]quinoxalin-2-yl}benzenesulfonamide |
| 241 | 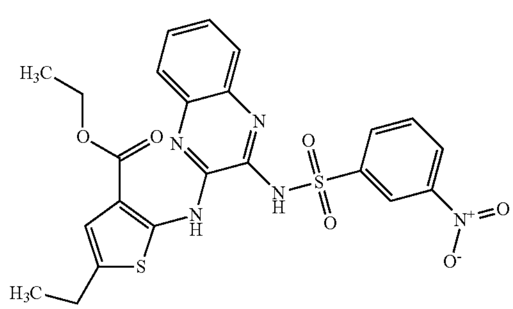 [SMILES: CCOC(=O)c1cc(CC)sc1Nc1nc2ccccc2nc1NS(=O)(=O)c1cccc([N+](=O)[O-])c1] | ethyl 5-ethyl-2-[(3-{[(3-nitrophenyl)sulfonyl]amino}quinoxalin-2-yl)amino]thiophene-3-carboxylate |

TABLE 1-continued

| Cpd. No. | Structure | Name |
|---|---|---|
| 242 | 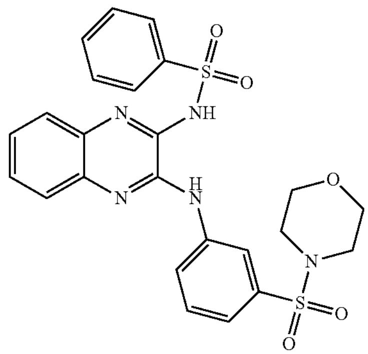 [SMILES: O=S(=O)(Nc1nc2ccccc2nc1Nc1cccc(S(=O)(=O)N2CCOCC2)c1)c1ccccc1] | N-(3-{[3-(morpholin-4-ylsulfonyl)phenyl]amino}quinoxalin-2-yl)benzene-sulfonamide |
| 243 | 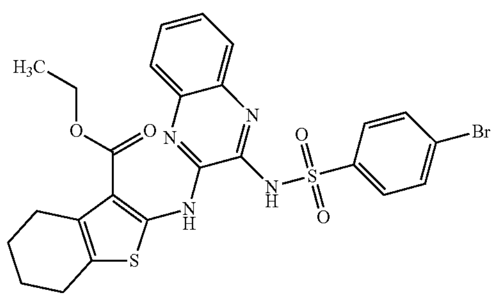 [SMILES: CCOC(=O)c1c(Nc2nc3ccccc3nc2NS(=O)(=O)c2ccc(Br)cc2)sc2c1CCCC2] | ethyl 2-[(3-{[(4-bromophenyl)sulfonyl]amino}quinoxalin-2-yl)amino]-4,5,6,7-tetrahydro-1-benzothiophene-3-carboxylate |
| 244 | 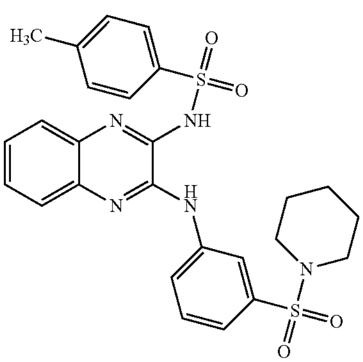 [SMILES: Cc1ccc(S(=O)(=O)Nc2nc3ccccc3nc2Nc2cccc(S(=O)(=O)N3CCCCC3)c2)cc1] | 4-methyl-N-(3-{[3-(piperidin-1-ylsulfonyl)phenyl]amino}quinoxalin-2-yl)benzenesulfonamide |
| 245 | 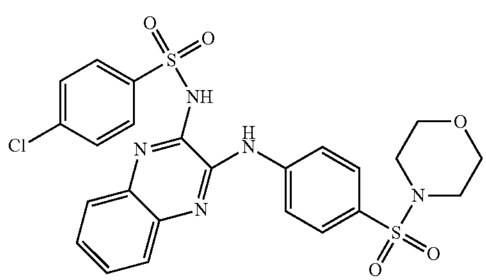 [SMILES: O=S(=O)(Nc1nc2ccccc2nc1Nc1ccc(S(=O)(=O)N2CCOCC2)cc1)c1ccc(Cl)cc1] | 4-chloro-N-(3-{[4-(morpholin-4-ylsulfonyl)phenyl]amino}quinoxalin-2-yl)benzenesulfonamide |

TABLE 1-continued

| Cpd. No. | Structure | Name |
| --- | --- | --- |
| 246 | 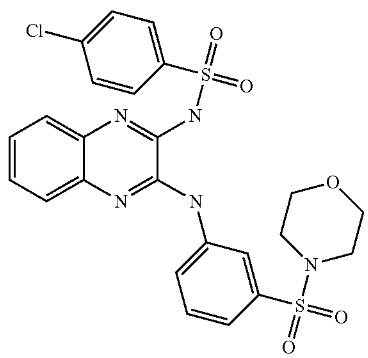 [SMILES: O=S(=O)(Nc1nc2ccccc2nc1Nc1cccc(S(=O)(=O)N2CCOCC2)c1)c1ccc(Cl)cc1] | 4-chloro-N-(3-{[3-(morpholin-4-ylsulfonyl)phenyl]amino}quinoxalin-2-yl)benzenesulfonamide |
| 247 | 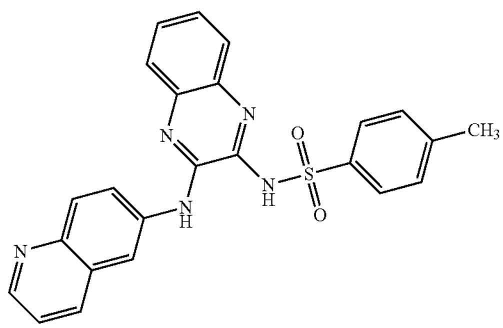 [SMILES: Cc1ccc(S(=O)(=O)Nc2nc3ccccc3nc2Nc2ccc3ncccc3c2)cc1] | 4-methyl-N-[3-(quinolin-6-ylamino)quinoxalin-2-yl]benzenesulfonamide |
| 248 | 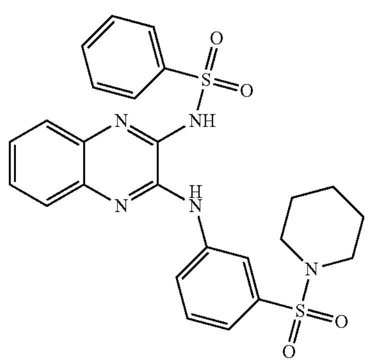 [SMILES: O=S(=O)(Nc1nc2ccccc2nc1Nc1cccc(S(=O)(=O)N2CCCCC2)c1)c1ccccc1] | N-(3-{[3-(piperidin-1-ylsulfonyl)phenyl]amino}quinoxalin-2-yl)benzenesulfonamide |
| 249 | 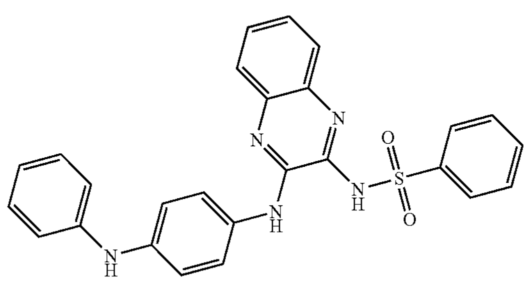 [SMILES: O=S(=O)(Nc1nc2ccccc2nc1Nc1ccc(Nc2ccccc2)cc1)c1ccccc1] | N-(3-{[4-(phenylamino)phenyl]amino}quinoxalin-2-yl)benzenesulfonamide |

TABLE 1-continued

| Cpd. No. | Structure | Name |
|---|---|---|
| 250 | 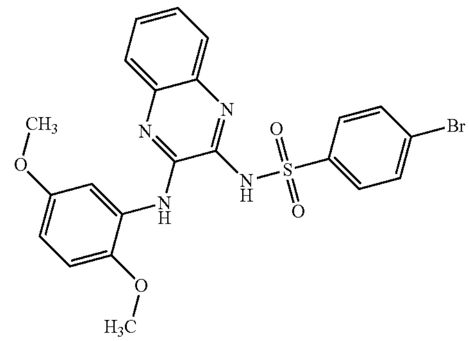 [SMILES: COc1ccc(OC)c(Nc2nc3ccccc3nc2NS(=O)(=O)c2ccc(Br)cc2)c1] | N-(3-{[2,5-bis(methoxy)phenyl]amino}quinoxalin-2-yl)-4-bromobenzenesulfonamide |
| 251 | 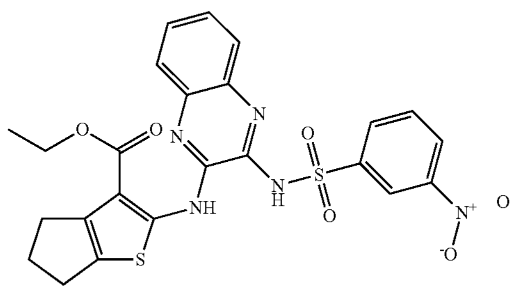 | ethyl 2-[(3-{[(3-nitrophenyl)sulfonyl]amino}quinoxalin-2-yl)amino]-5,6-dihydro-4H-cyclopenta[b]thiophene-3-carboxylate |
| 252 | 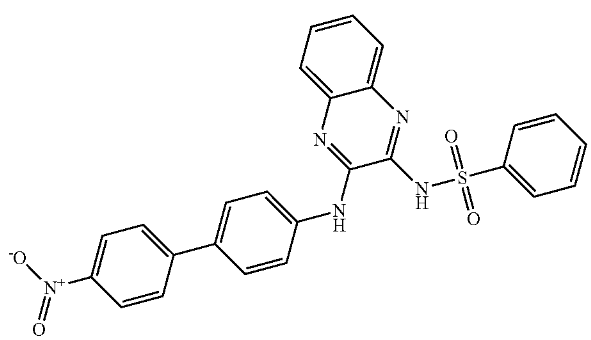 | N-{3-[(4'-nitrobiphenyl-4-yl)amino]quinoxalin-2-yl}benzenesulfonamide |
| 253 | 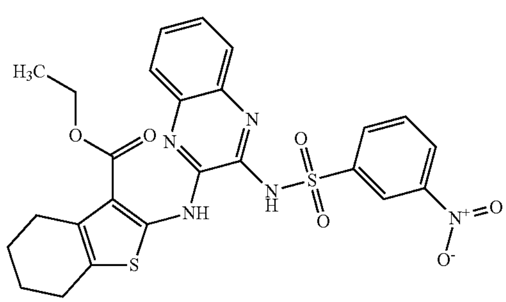 [SMILES: CCOC(=O)c1c(Nc2nc3ccccc3nc2NS(=O)(=O)c2cccc([N+](=O)[O-])c2)sc2c1CCCC2] | ethyl 2-[(3-{[(3-nitrophenyl)sulfonyl]amino}quinoxalin-2-yl)amino]-4,5,6,7-tetrahydro-1-benzothiophene-3-carboxylate |

TABLE 1-continued

| Cpd. No. | Structure | Name |
|---|---|---|
| 254 | 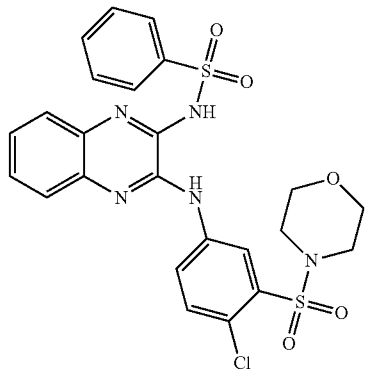 [SMILES: O=S(=O)(Nc1nc2ccccc2nc1Nc1ccc(Cl)c(S(=O)(=O)N2CCOCC2)c1)c1ccccc1] | N-(3-{[4-chloro-3-(morpholin-4-yl-sulfonyl)phenyl]amino}quinoxalin-2-yl)benzenesulfonamide |
| 255 | 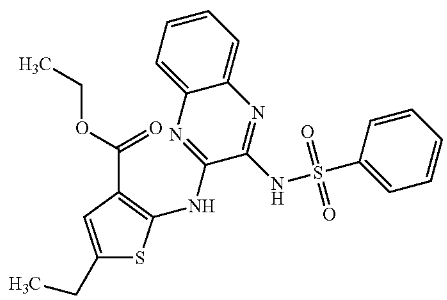 [SMILES: CCOC(=O)c1cc(CC)sc1Nc1nc2ccccc2nc1NS(=O)(=O)c1ccccc1] | ethyl 5-ethyl-2-({3-[(phenylsulfonyl)amino]quinoxalin-2-yl}amino)thiophene-3-carboxylate |
| 256 | 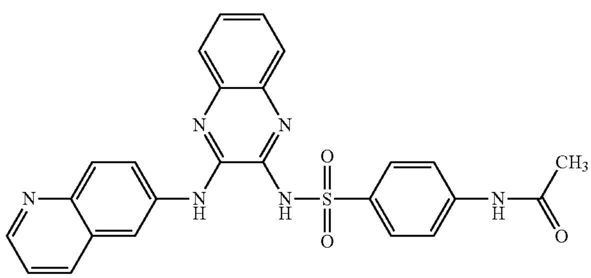 [SMILES: CC(=O)Nc1ccc(S(=O)(=O)Nc2nc3ccccc3nc2Nc2ccc3ncccc3c2)cc1] | N-[4-({[3-(quinolin-6-ylamino)quinoxalin-2-yl]amino}sulfonyl)phenyl]acetamide |
| 257 | 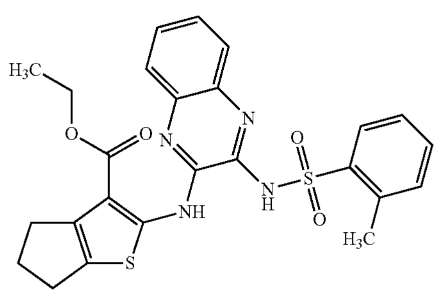 [SMILES: CCOC(=O)c1c(Nc2nc3ccccc3nc2NS(=O)(=O)c2ccccc2C)sc2c1CCC2] | ethyl 2-[(3-{[(2-methylphenyl)sulfonyl]amino}quinoxalin-2-yl)amino]-5,6-dihydro-4H-cyclopenta[b]thiophene-3-carboxylate |
| 258 | 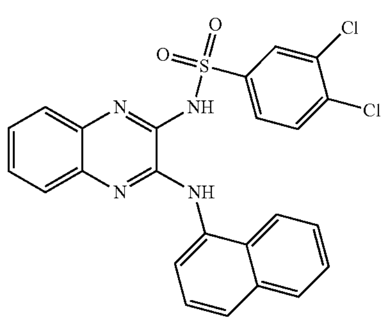 [SMILES: O=S(=O)(Nc1nc2ccccc2nc1Nc1cccc2ccccc12)c1ccc(Cl)c(Cl)c1] | 3,4-dichloro-N-[3-(naphthalen-1-ylamino)quinoxalin-2-yl]benzenesulfonamide |

TABLE 1-continued

| Cpd. No. | Structure | Name |
|---|---|---|
| 259 | 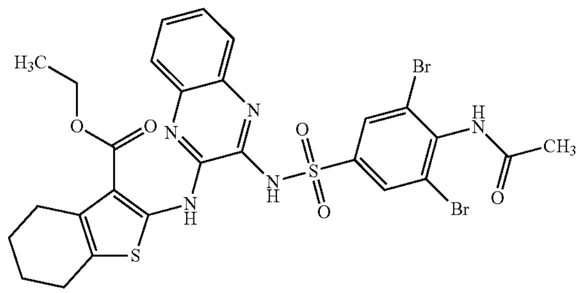 [SMILES: CCOC(=O)c1c(Nc2nc3ccccc3nc2NS(=O)(=O)c2cc(Br)c(NC(C)=O)c(Br)c2)sc2c1CCCC2] | ethyl 2-{[3-({[4-(acetylamino)-3,5-dibromophenyl]sulfonyl}amino)quinoxalin-2-yl]amino}-4,5,6,7-tetrahydro-1-benzothiophene-3-carboxylate |
| 260 | 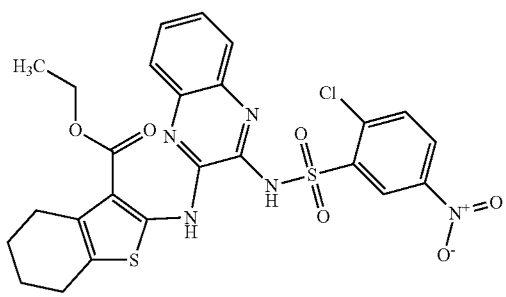 [SMILES: CCOC(=O)c1c(Nc2nc3ccccc3nc2NS(=O)(=O)c2cc([N+](=O)[O-])ccc2Cl)sc2c1CCCC2] | ethyl 2-[(3-{[(2-chloro-5-nitrophenyl)sulfonyl]amino}quinoxalin-2-yl)amino]-4,5,6,7-tetrahydro-1-benzothiophene-3-carboxylate |
| 261 | 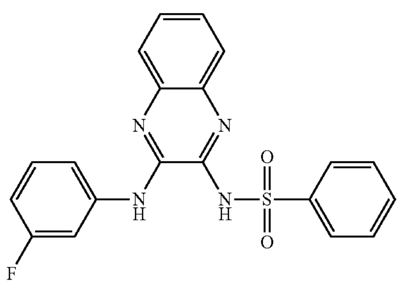 [SMILES: O=S(=O)(Nc1nc2ccccc2nc1Nc1cccc(F)c1)c1ccccc1] | N-{3-[(3-fluorophenyl)amino)quinoxalin-2-yl}benzenesulfonamide |
| 262 | 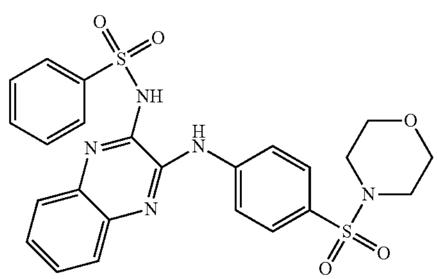 [SMILES: O=S(=O)(Nc1nc2ccccc2nc1Nc1ccc(S(=O)(=O)N2CCOCC2)cc1)c1ccccc1] | N-(3-{[4-(morpholin-4-ylsulfonyl)phenyl]amino}quinoxalin-2-yl)benzenesulfonamide |
| 263 | 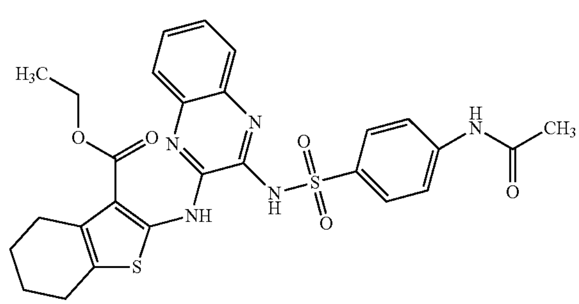 [SMILES: CCOC(=O)c1c(Nc2nc3ccccc3nc2NS(=O)(=O)c2ccc(NC(C)=O)cc2)sc2c1CCCC2] | ethyl 2-{[3-({[4-(acetylamino)phenyl]sulfonyl}amino)quinoxalin-2-yl]amino}-4,5,6,7-tetrahydro-1-benzothiophene-3-carboxylate |

TABLE 1-continued

| Cpd. No. | Structure | Name |
| --- | --- | --- |
| 264 | 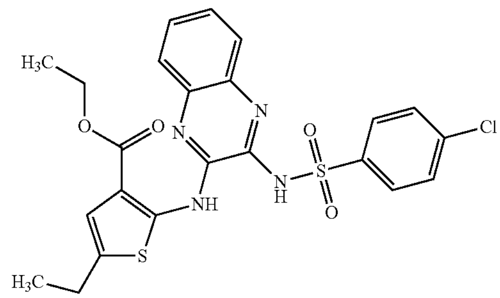 [SMILES: CCOC(=O)c1cc(CC)sc1Nc1nc2ccccc2nc1NS(=O)(=O)c1ccc(Cl)cc1] | ethyl 2-[(3-{[(4-chlorophenyl)sulfonyl]amino}quinoxalin-2-yl)amino]-5-ethylthiophene-3-carboxylate |
| 265 | 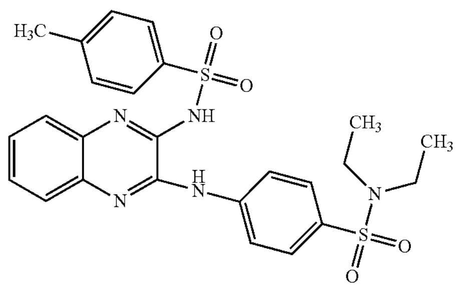 [SMILES: CCN(CC)S(=O)(=O)c1ccc(Nc2nc3ccccc3nc2NS(=O)(=O)c2ccc(C)cc2)cc1] | N,N-diethyl-4-[(3-{[(4-methylphenyl)sulfonyl]amino}quinoxalin-2-yl)amino]benzenesulfonamide |
| 266 | 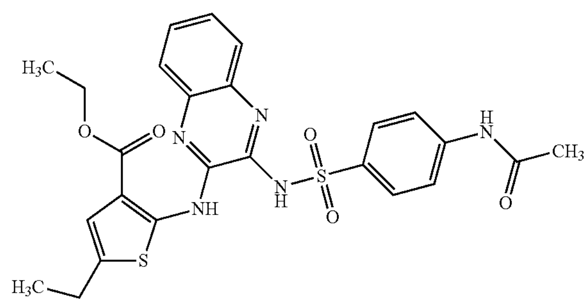 [SMILES: CCOC(=O)c1cc(CC)sc1Nc1nc2ccccc2nc1NS(=O)(=O)c1ccc(NC(C)=O)cc1] | ethyl 2-{[3-({[4-(acetylamino)phenyl]sulfonyl}amino)quinoxalin-2-yl]amino}-5-ethylthiophene-3-carboxylate |
| 267 | 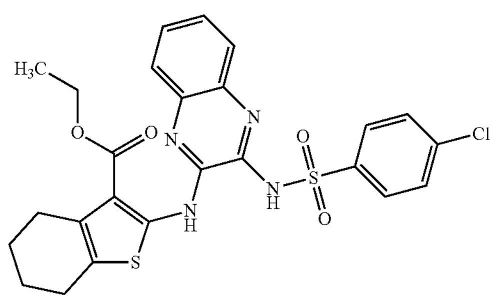 [SMILES: CCOC(=O)c1c(Nc2nc3ccccc3nc2NS(=O)(=O)c2ccc(Cl)cc2)sc2c1CCCC2] | ethyl 2-[(3-{[(4-chlorophenyl)sulfonyl]amino}quinoxalin-2-yl)amino]-4,5,6,7-tetrahydro-1-benzothiophene-3-carboxylate |
| 268 | 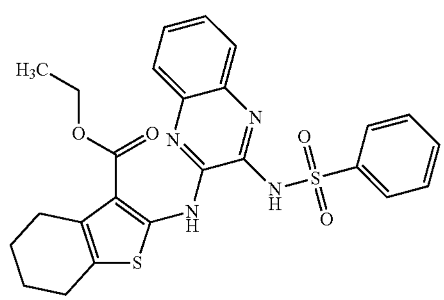 [SMILES: CCOC(=O)c1c(Nc2nc3ccccc3nc2NS(=O)(=O)c2ccccc2)sc2c1CCCC2] | ethyl 2-({3-[(phenylsulfonyl)amino]quinoxalin-2-yl}amino)-4,5,6,7-tetrahydro-1-benzothiophene-3-carboxylate |

TABLE 1-continued

| Cpd. No. | Structure | Name |
| --- | --- | --- |
| 269 | 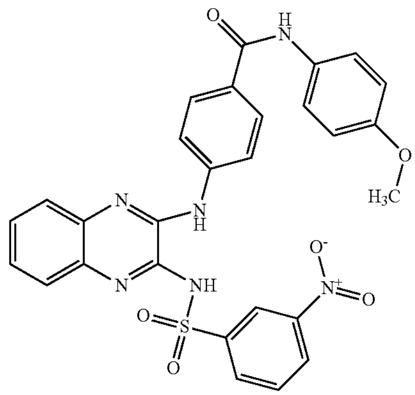 [SMILES: COc1ccc(NC(=O)c2ccc(Nc3nc4ccccc4nc3NS(=O)(=O)c3cccc([N+](=O)[O-])c3)cc2)cc1] | N-[4-(methoxy)phenyl]-4-[(3-{[(3-nitrophenyl)sulfonyl]amino}quinoxalin-2-yl)amino]benzamide |
| 270 | 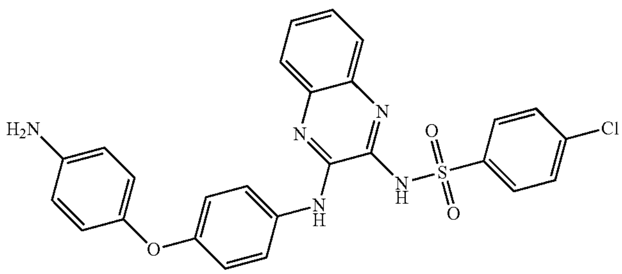 [SMILES: Nc1ccc(Oc2ccc(Nc3nc4ccccc4nc3NS(=O)(=O)c3ccc(Cl)cc3)cc2)cc1] | N-[3-({4-[(4-aminophenyl)oxy]phenyl}amino)quinoxalin-2-yl]-4-chlorobenzenesulfonamide |
| 271 | 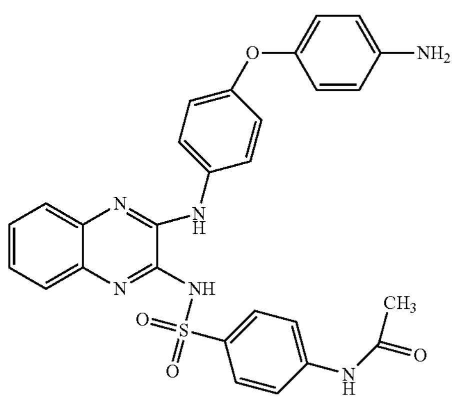 [SMILES: CC(=O)Nc1ccc(S(=O)(=O)Nc2nc3ccccc3nc2Nc2ccc(Oc3ccc(N)cc3)cc2)cc1] | N-[4-({[3-({4-[(4-aminophenyl)oxy]phenyl}amino)quinoxalin-2-yl]amino}sulfonyl)phenyl]acetamide |
| 272 | 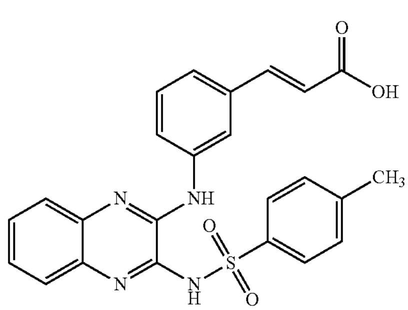 [SMILES: Cc1ccc(S(=O)(=O)Nc2nc3ccccc3nc2Nc2cccc(/C=C/C(=O)O)c2)cc1] | (2E)-3-{3-[(3-{[(4-methylphenyl)sulfonyl]amino}quinoxalin-2-yl)amino]phenyl}prop-2-enoic acid |

TABLE 1-continued
| Cpd. No. | Structure | Name |
|---|---|---|
| 273 | 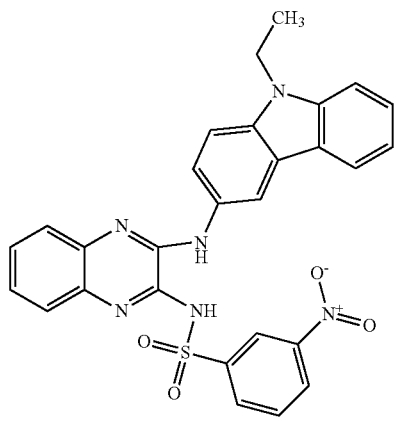 [SMILES: CCn1c2ccccc2c2cc(Nc3nc4ccccc4nc3NS(=O)(=O)c3cccc([N+](=O)[O-])c3)ccc21] | N-{3-[(9-ethyl-9H-carbazol-3-yl)amino]quinoxalin-2-yl}-3-nitrobenzenesulfonamide |
| 274 | 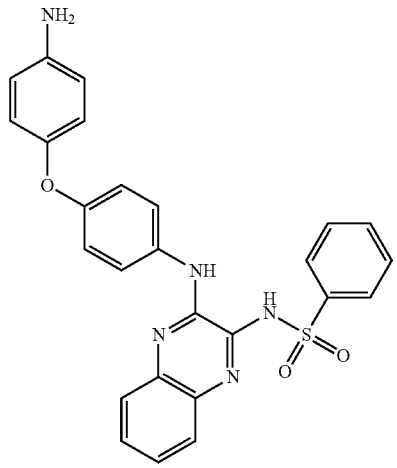 [SMILES: Nc1ccc(Oc2ccc(Nc3nc4ccccc4nc3NS(=O)(=O)c3ccccc3)cc2)cc1] | N-[3-({4-[(4-aminophenyl)oxy]phenyl}amino)quinoxalin-2-yl]benzenesulfonamide |
| 275 | 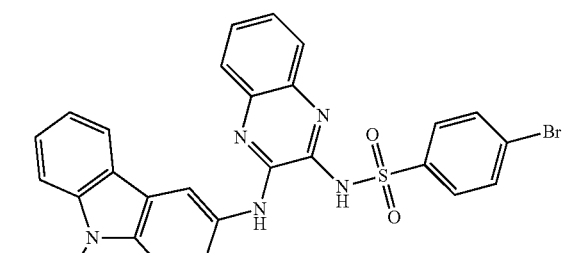 | 4-bromo-N-{3-[(9-ethyl-9H-carbazol-3-yl)amino]quinoxalin-2-yl}benzenesulfonamide |
| 276 | 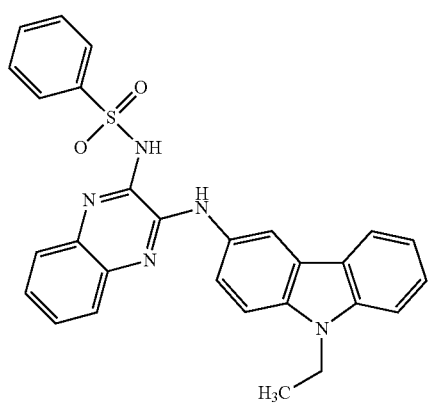 | N-{3-[(9-ethyl-9H-carbazol-3-yl)amino]quinoxalin-2-yl}benzenesulfonamide |

TABLE 1-continued

| Cpd. No. | Structure | Name |
|---|---|---|
| 277 | 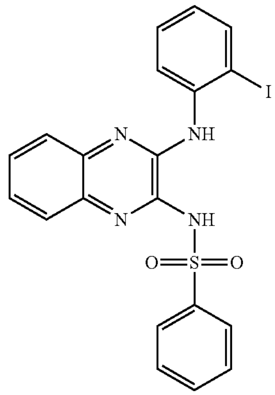 [SMILES: O=S(=O)(Nc1nc2ccccc2nc1Nc1ccccc1I)c1ccccc1] | N-{3-[(2-iodophenyl)amino]quinoxalin-2-yl}benzenesulfonamide |
| 278 | 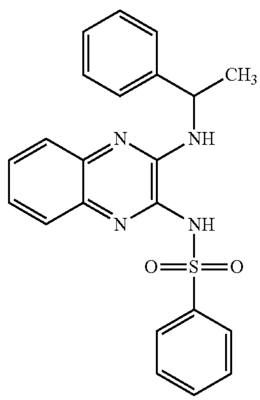 [SMILES: CC(Nc1nc2ccccc2nc1NS(=O)(=O)c1ccccc1)c1ccccc1] | N-{3-[(1-phenylethyl)amino]quinoxalin-2-yl}benzenesulfonamide |
| 279 | 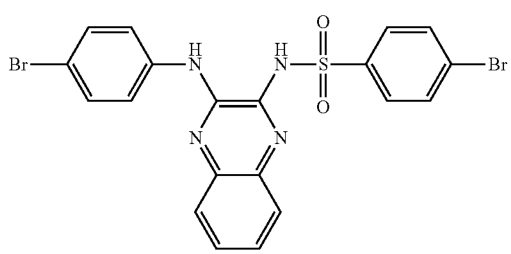 [SMILES: O=S(=O)(Nc1nc2ccccc2nc1Nc1ccc(Cl)cc1)c1ccc(Br)cc1] | 4-bromo-N-{3-[(4-bromophenyl)amino]quinoxalin-2-yl}benzenesulfonamide |
| 280 | 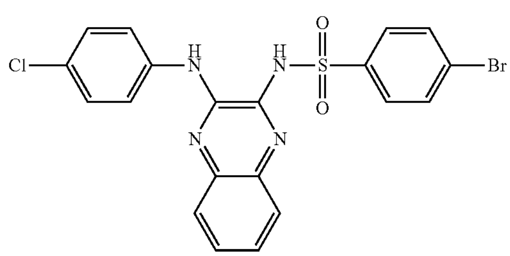 | 4-bromo-N-{3-[(4-chlorophenyl)amino]quinoxalin-2-yl}benzenesulfonamide |
| 281 | 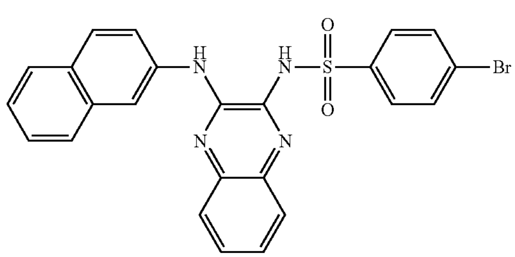 [SMILES: O=S(=O)(Nc1nc2ccccc2nc1Nc1ccc2ccccc2c1)c1ccc(Br)cc1] | 4-bromo-N-[3-(naphthalen-2-ylamino)quinoxalin-2-yl]benzenesulfonamide |

TABLE 1-continued

| Cpd. No. | Structure | Name |
|---|---|---|
| 282 | 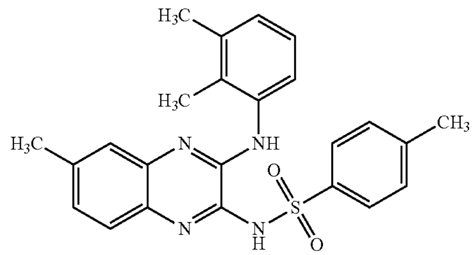 | N-{3-[(2,3-dimethylphenyl)amino]-6-methylquinoxalin-2-yl}-4-methylbenzenesulfonamide |
| 283 | 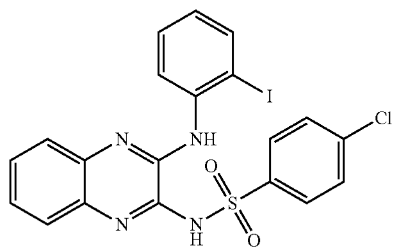 [SMILES: O=S(=O)(Nc1nc2ccccc2nc1Nc1ccccc1I)c1ccc(Cl)cc1] | 4-chloro-N-{3-[(2-iodophenyl)amino]quinoxalin-2-yl}benzenesulfonamide |
| 284 | 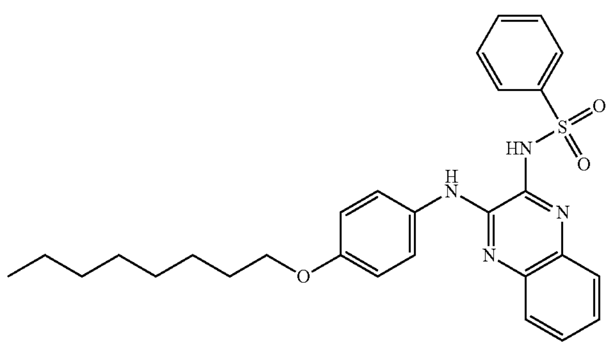 [SMILES: CCCCCCCCOc1ccc(Nc2nc3ccccc3nc2NS(=O)(=O)c2ccccc2)cc1] | N-(3-{[4-(octyloxy)phenyl]amino}quinoxalin-2-yl)benzenesulfonamide |
| 285 | 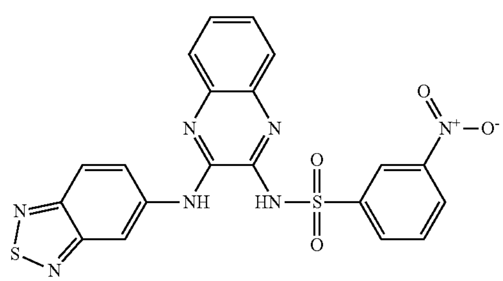 [SMILES: O=[N+]([O-])c1cccc(S(=O)(=O)Nc2nc3ccccc3nc2Nc2ccc3nsnc3c2)c1] | N-[3-(2,1,3-benzothiadiazol-5-ylamino)quinoxalin-2-yl]-3-nitrobenzenesulfonamide |
| 286 | 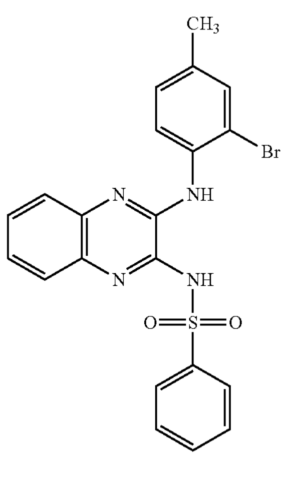 [SMILES: Cc1ccc(Nc2nc3ccccc3nc2NS(=O)(=O)c2ccccc2)c(Br)c1] | N-{3-[(2-bromo-4-methylphenyl)amino]quinoxalin-2-yl}benzenesulfonamide |

TABLE 1-continued

| Cpd. No. | Structure | Name |
|---|---|---|
| 287 | 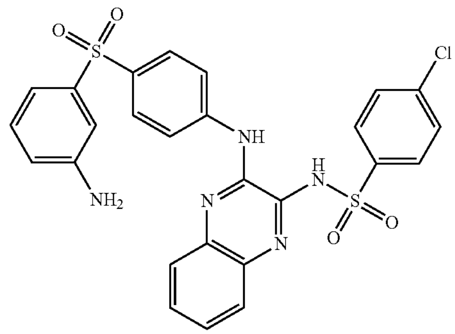 [SMILES: Nc1cccc(S(=O)(=O)c2ccc(Nc3nc4ccccc4nc3NS(=O)(=O)c3ccc(Cl)cc3)cc2)c1] | N-[3-({4-[(3-aminophenyl)sulfonyl]phenyl}amino)quinoxalin-2-yl]-4-chlorobenzenesulfonamide |
| 288 | 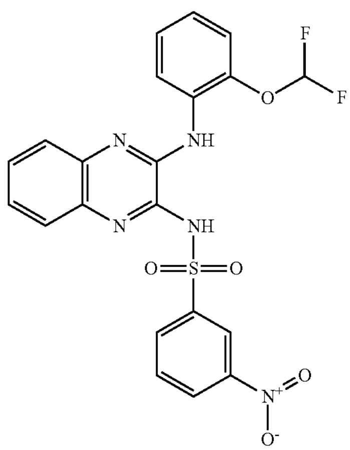 [SMILES: O=[N+]([O-])c1cccc(S(=O)(=O)Nc2nc3ccccc3nc2Nc2ccccc2OC(F)F)c1] | N-[3-({2-[(difluoromethyl)oxy]phenyl}amino)quinoxalin-2-yl]-3-nitrobenzenesulfonamide |
| 289 | 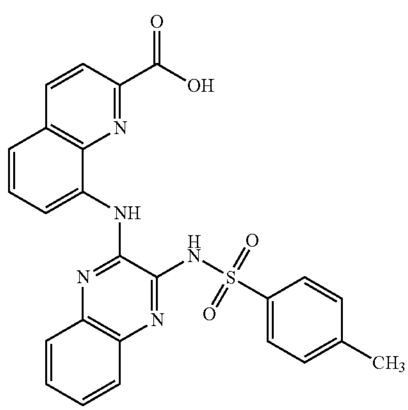 [SMILES: Cc1ccc(S(=O)(=O)Nc2nc3ccccc3nc2Nc2cccc3ccc(C(=O)O)nc23)cc1] | 8-[(3-{[(4-methylphenyl)sulfonyl]amino}quinoxalin-2-yl)amino]quinoline-2-carboxylic acid |

TABLE 1-continued
| Cpd. No. | Structure | Name |
|---|---|---|
| 290 | 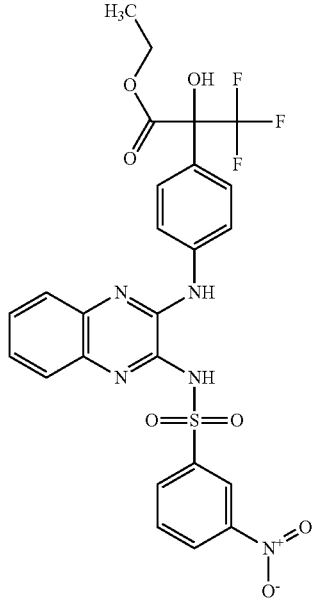 [SMILES: CCOC(=O)C(O)(c1ccc(Nc2nc3ccccc3nc2NS(=O)(=O)c2cccc([N+](=O)[O-])c2)cc1)C(F)(F)F] | ethyl 3,3,3-trifluoro-2-hydroxy-2-{4-[(3-{[(3-nitrophenyl)sulfonyl]amino}quinoxalin-2-yl)amino]phenyl}propanoate |
| 291 | 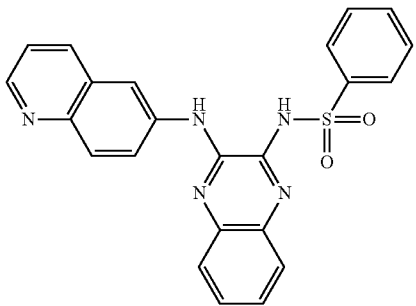 [SMILES: O=S(=O)(Nc1nc2ccccc2nc1Nc1ccc2ncccc2c1)c1ccccc1] | N-[3-(quinolin-6-ylamino)quinoxalin-2-yl]benzenesulfonamide |
| 292 | 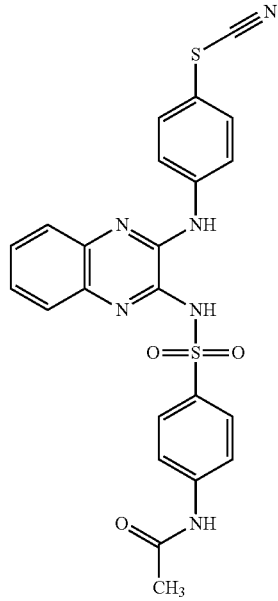 [SMILES: CC(=O)Nc1ccc(S(=O)(=O)Nc2nc3ccccc3nc2Nc2ccc(SC#N)cc2)cc1] | 4-{[3-({[4-(acetylamino)phenyl]sulfonyl}amino)quinoxalin-2-yl]amino}phenyl thiocyanate |

| Cpd. No. | Structure | Name |
| --- | --- | --- |
| 293 | 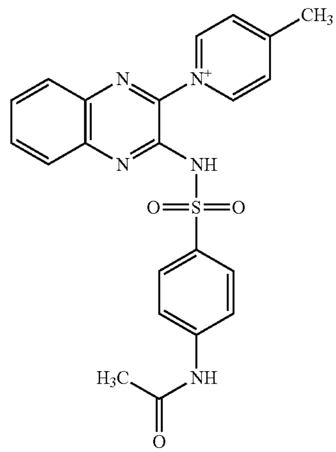 [SMILES: CC(=O)Nc1ccc(S(=O)(=O)Nc2nc3ccccc3nc2-[n+]2ccc(C)cc2)cc1] | 1-[3-({[4-(acetylamino)phenyl]sulfonyl}amino)quinoxalin-2-yl]-4-methylpyridinium |
| 294 | 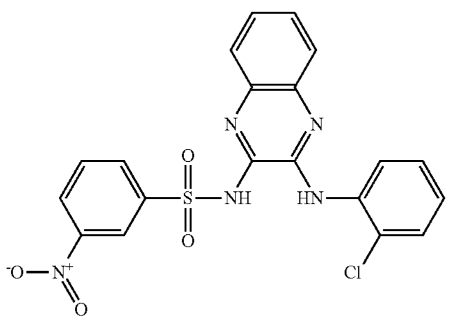 | N-{3-[(2-chlorophenyl)amino]quinoxalin-2-yl}-3-nitrobenzenesulfonamide |
| 295 | 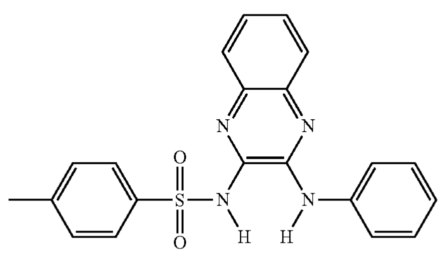 [SMILES: Cc1ccc(S(=O)(=O)Nc2nc3ccccc3nc2Nc2ccccc2)cc1] | 4-methyl-N-[3-(phenylamino)quinoxalin-2-yl]benzenesulfonamide |
| 296 | 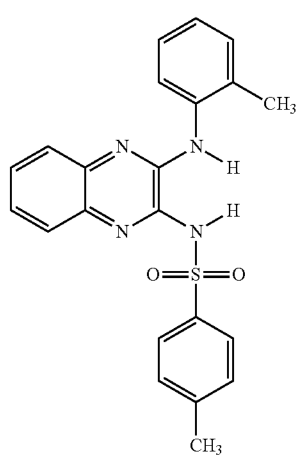 [SMILES: Cc1ccc(S(=O)(=O)Nc2nc3ccccc3nc2Nc2ccccc2C)cc1] | 4-methyl-N-{3-[(2-methylphenyl)amino]quinoxalin-2-yl}benzenesulfonamide |

TABLE 1-continued

| Cpd. No. | Structure | Name |
|---|---|---|
| 297 | 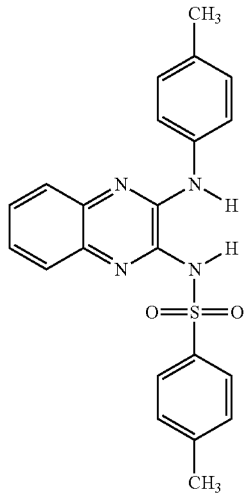 [SMILES: Cc1ccc(Nc2nc3ccccc3nc2NS(=O)(=O)c2ccc(C)cc2)cc1] | 4-methyl-N-{3-[(4-methylphenyl)amino]quinoxalin-2-yl}benzenesulfonamide |
| 298 | 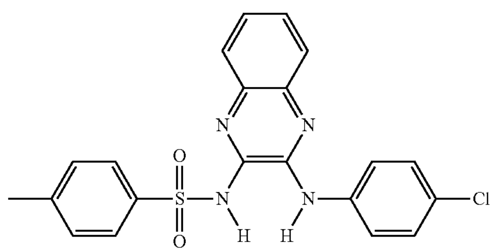 [SMILES: Cc1ccc(S(=O)(=O)Nc2nc3ccccc3nc2Nc2ccc(Cl)cc2)cc1] | N-{3-[(4-chlorophenyl)amino]quinoxalin-2-yl}-4-methylbenzenesulfonamide |
| 299 | 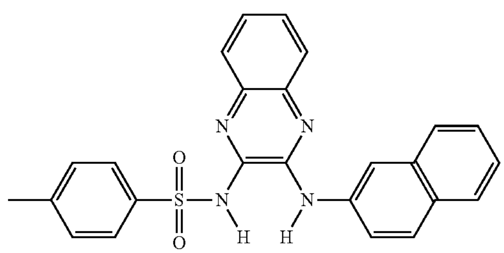 [SMILES: Cc1ccc(S(=O)(=O)Nc2nc3ccccc3nc2Nc2ccc3ccccc3c2)cc1] | 4-methyl-N-[3-(naphthalen-2-ylamino)quinoxalin-2-yl]benzenesulfonamide |
| 300 | 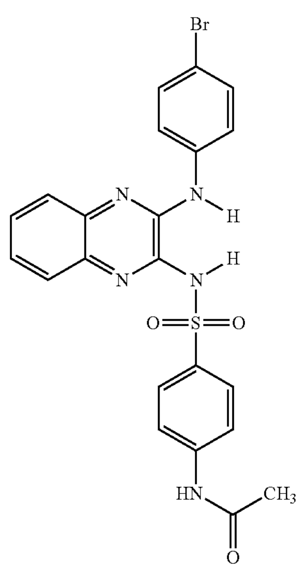 | N-{4-[({3-[(4-bromophenyl)amino]quinoxalin-2-yl}amino)sulfonyl]phenyl}acetamide |

TABLE 1-continued

| Cpd. No. | Structure | Name |
|---|---|---|
| 301 | 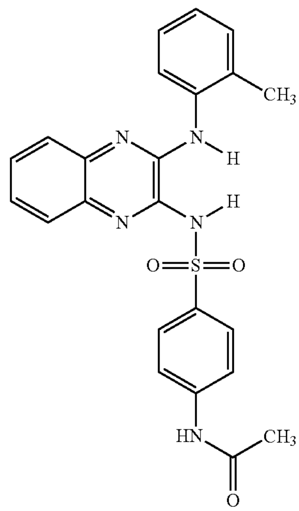 [SMILES: CC(=O)Nc1ccc(S(=O)(=O)Nc2nc3ccccc3nc2Nc2ccccc2C)cc1] | N-{4-[({3-[(2-methylphenyl)amino]quinoxalin-2-yl}amino)sulfonyl]phenyl}acetamide |
| 302 | 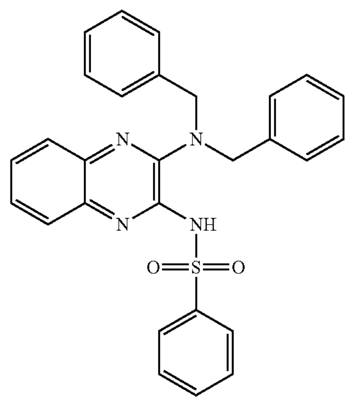 [SMILES: O=S(=O)(Nc1nc2ccccc2nc1N(Cc1ccccc1)Cc1ccccc1)c1ccccc1] | N-{3-[bis(phenylmethyl)amino]quinoxalin-2-yl}benzenesulfonamide |
| 303 | 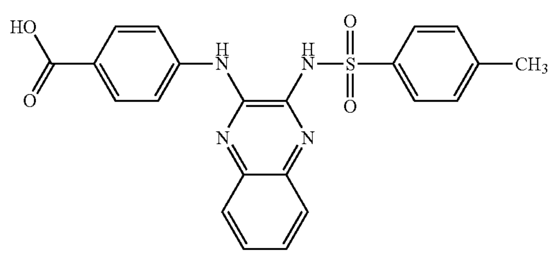 [SMILES: Cc1ccc(S(=O)(=O)Nc2nc3ccccc3nc2Nc2ccc(C(=O)O)cc2)cc1] | 4-[(3-{[(4-methylphenyl)sulfonyl]amino}quinoxalin-2-yl)amino]benzoic acid |
| 304 | 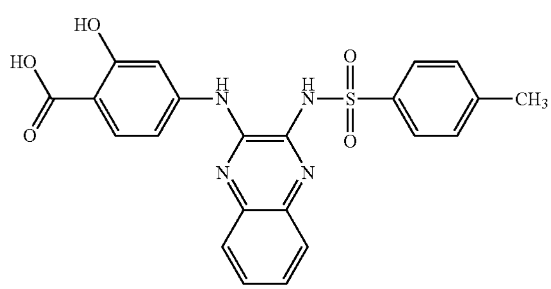 [SMILES: Cc1ccc(S(=O)(=O)Nc2nc3ccccc3nc2Nc2ccc(C(=O)O)c(O)c2)cc1] | 2-hydroxy-4-[(3-{[(4-methylphenyl)sulfonyl]amino}quinoxalin-2-yl)amino]benzoic acid |

TABLE 1-continued

| Cpd. No. | Structure | Name |
|---|---|---|
| 305 | 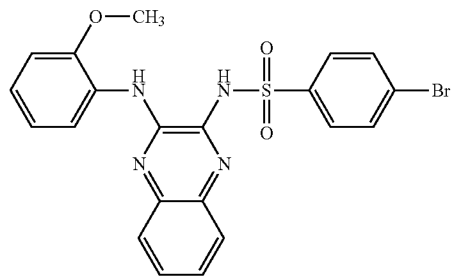 [SMILES: COc1ccccc1Nc1nc2ccccc2nc1NS(=O)(=O)c1ccc(Br)cc1] | 4-bromo-N-(3-{[2-(methoxy)phenyl]amino}quinoxalin-2-yl)benzenesulfonamide |
| 306 | 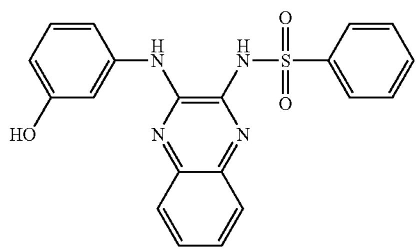 [SMILES: O=S(=O)(Nc1nc2ccccc2nc1Nc1cccc(O)c1)c1ccccc1] | N-{3-[(3-hydroxyphenyl)amino]quinoxalin-2-yl}benzenesulfonamide |
| 307 | 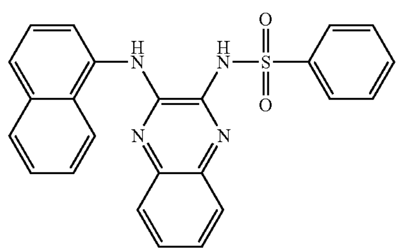 [SMILES: O=S(=O)(Nc1nc2ccccc2nc1Nc1cccc2ccccc12)c1ccccc1] | N-[3-(naphthalen-1-ylamino)quinoxalin-2-yl]benzenesulfonamide |
| 308 | 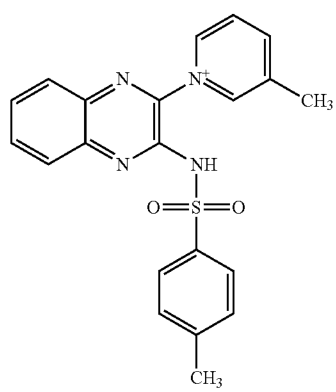 [SMILES: Cc1ccc(S(=O)(=O)Nc2nc3ccccc3nc2-[n+]2cccc(C)c2)cc1] | 3-methyl-1-(3-{[(4-methylphenyl)sulfonyl]amino}quinoxalin-2-yl)pyridinium |
| 309 | 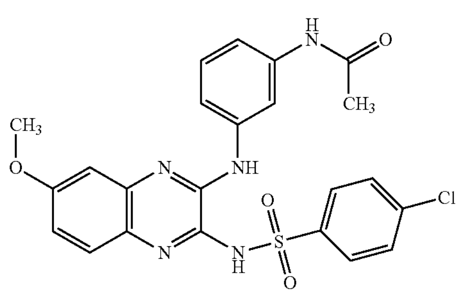 [SMILES: COc1ccc2nc(NS(=O)(=O)c3ccc(Cl)cc3)c(Nc3cccc(NC(C)=O)c3)nc2c1] | N-(3-{[3-{[(4-chlorophenyl)sulfonyl]amino}-7-(methoxy)quinoxalin-2-yl]amino}phenyl)acetamide |

TABLE 1-continued

| Cpd. No. | Structure | Name |
| --- | --- | --- |
| 310 | 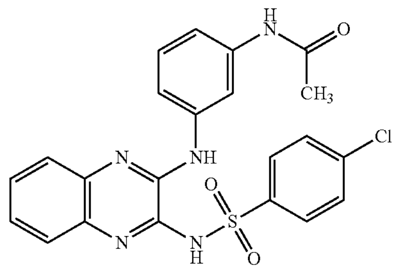 [SMILES: CC(=O)Nc1cccc(Nc2nc3ccccc3nc2NS(=O)(=O)c2ccc(Cl)cc2)c1] | N-{3-[(3-{[(4-chloro-phenyl)sulfonyl]amino}quinoxalin-2-yl)amino]phenyl}acetamide |
| 311 | 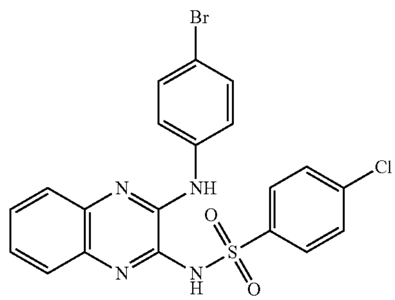 [SMILES: O=S(=O)(Nc1nc2ccccc2nc1Nc1ccc(Br)cc1)c1ccc(Cl)cc1] | N-{3-[(4-bromophenyl)amino]quinoxalin-2-yl}-4-chlorobenzenesulfonamide |
| 312 | 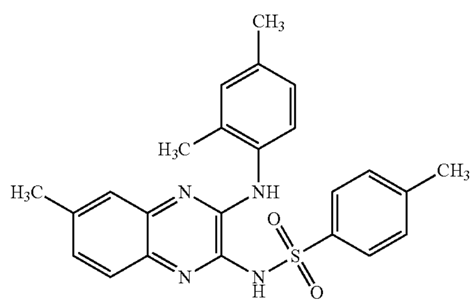 | N-{3-[(2,4-dimethylphenyl)amino]-6-methylquinoxalin-2-yl}-4-methylbenzenesulfonamide |
| 313 | 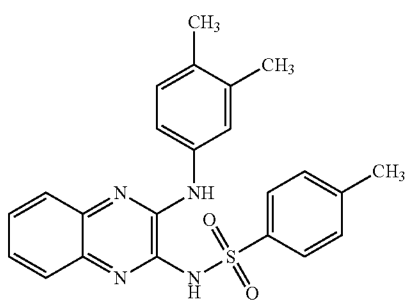 [SMILES: Cc1ccc(S(=O)(=O)Nc2nc3ccccc3nc2Nc2ccc(C)c(C)c2)cc1] | N-{3-[(3,4-dimethylphenyl)amino]quinoxalin-2-yl}-4-methylbenzenesulfonamide |
| 314 | 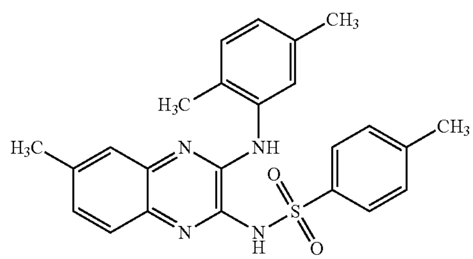 | N-{3-[(2,5-dimethylphenyl)amino]-6-methylquinoxalin-2-yl}-4-methylbenzenesulfonamide |

TABLE 1-continued

| Cpd. No. | Structure | Name |
|---|---|---|
| 315 | 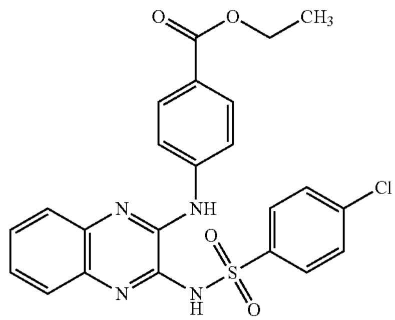 [SMILES: CCOC(=O)c1ccc(Nc2nc3ccccc3nc2NS(=O)(=O)c2ccc(Cl)cc2)cc1] | ethyl 4-[(3-{[(4-chloro-phenyl)sulfonyl]amino}quinoxalin-2-yl)amino]benzoate |
| 316 | 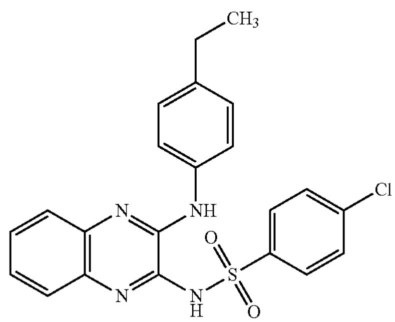 [SMILES: CCc1ccc(Nc2nc3ccccc3nc2NS(=O)(=O)c2ccc(Cl)cc2)cc1] | 4-chloro-N-{3-[(4-ethylphenyl)amino]quinoxalin-2-yl}benzenesulfonamide |
| 317 | 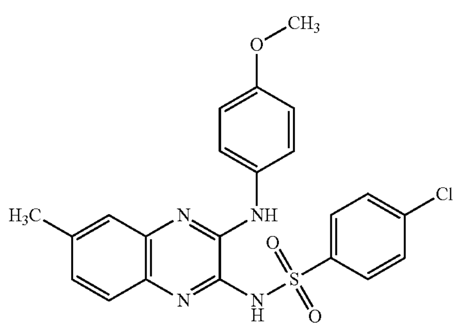 [SMILES: COc1ccc(Nc2nc3cc(C)ccc3nc2NS(=O)(=O)c2ccc(Cl)cc2)cc1] | 4-chloro-N-(6-methyl-3-{[4-(methoxy)phenyl]amino}quinoxalin-2-yl)benzenesulfonamide |
| 318 | 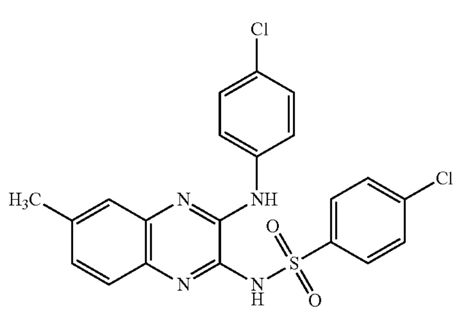 [SMILES: Cc1ccc2nc(NS(=O)(=O)c3ccc(Cl)cc3)c(Nc3ccc(Cl)cc3)nc2c1] | 4-chloro-N-{3-[(4-chlorophenyl)amino]-6-methylquinoxalin-2-yl}benzenesulfonamide |

TABLE 1-continued

| Cpd. No. | Structure | Name |
|---|---|---|
| 319 | 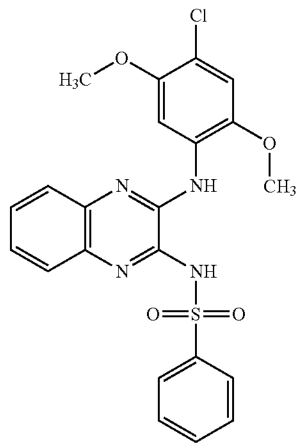 [SMILES: COc1cc(Nc2nc3ccccc3nc2NS(=O)(=O)c2ccccc2)c(OC)cc1Cl] | N-(3-{[4-chloro-2,5-bis(methoxy)phenyl]amino}quinoxalin-2-yl)benzenesulfonamide |
| 320 | 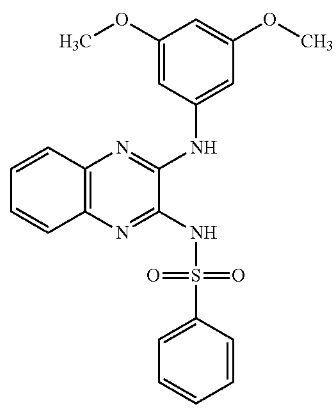 [SMILES: COc1cc(Nc2nc3ccccc3nc2NS(=O)(=O)c2ccccc2)cc(OC)c1] | N-(3-{[3,5-bis(methoxy)phenyl]amino}quinoxalin-2-yl)benzenesulfonamide |
| 321 | 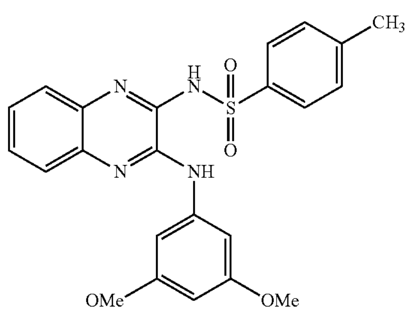 [SMILES: COc1cc(Nc2nc3ccccc3nc2NS(=O)(=O)c2ccc(C)cc2)cc(OC)c1] | N-(3-{[3,5-bis(methoxy)phenyl]amino}quinoxalin-2-yl)-4-methylbenzenesulfonamide |
| 322 | 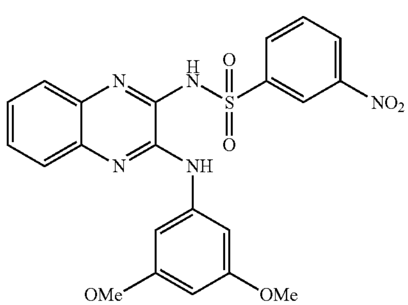 [SMILES: COc1cc(Nc2nc3ccccc3nc2NS(=O)(=O)c2cccc([N+](=O)[O-])c2)cc(OC)c1] | N-(3-{[3,5-bis(methoxy)phenyl]amino}quinoxalin-2-yl)-3-nitrobenzenesulfonamide |

TABLE 1-continued

| Cpd. No. | Structure | Name |
| --- | --- | --- |
| 323 | 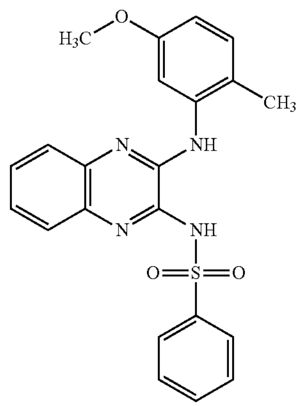 [SMILES: COc1ccc(C)c(Nc2nc3ccccc3nc2NS(=O)(=O)c2ccccc2)c1] | N-(3-{[2-methyl-5-(methoxy)phenyl]amino}quinoxalin-2-yl)benzenesulfonamide |
| 324 | 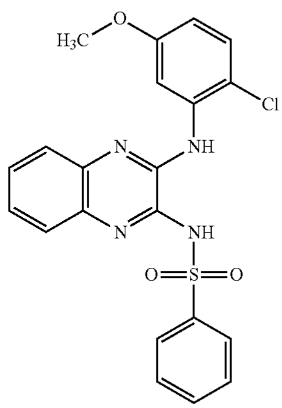 [SMILES: COc1ccc(Cl)c(Nc2nc3ccccc3nc2NS(=O)(=O)c2ccccc2)c1] | N-[3-(2-Chloro-5-methoxy-phenylamino)-quinoxalin-2-yl]-benzensulfonamide |
| 325 | 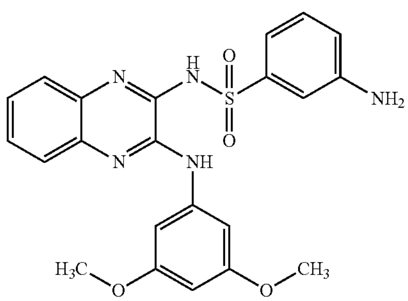 [SMILES: COc1cc(Nc2nc3ccccc3nc2NS(=O)(=O)c2cccc(N)c2)cc(OC)c1] | 3-amino-N-(3-{[3,5-bis(methoxy)phenyl]amino}quinoxalin-2-yl)benzenesulfonamide |
| 326 | 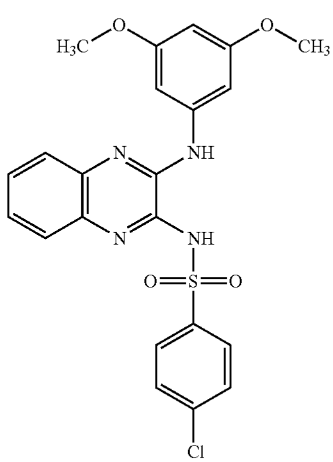 [SMILES: COc1cc(Nc2nc3ccccc3nc2NS(=O)(=O)c2ccc(Cl)cc2)cc(OC)c1] | N-(3-{[3,5-bis(methoxy)phenyl]amino}quinoxalin-2-yl)-4-chlorobenzenesulfonamide |

TABLE 1-continued

| Cpd. No. | Structure | Name |
| --- | --- | --- |
| 327 | 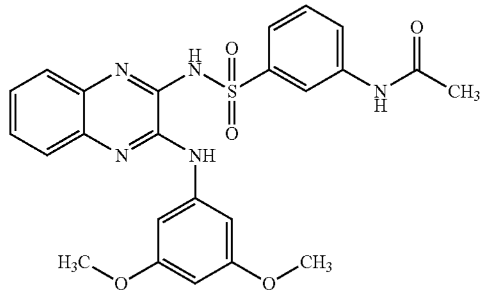 [SMILES: COc1cc(Nc2nc3ccccc3nc2NS(=O)(=O)c2cccc(NC(C)=O)c2)cc(OC)c1] | N-(3-{[(3-{[3,5-bis(methoxy)phenyl]amino}quinoxalin-2-yl)amino]sulfonyl}phenyl)acetamide |
| 328 | 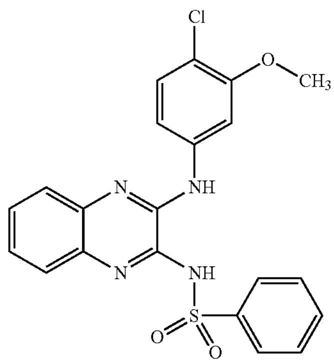 [SMILES: COc1cc(Nc2nc3ccccc3nc2NS(=O)(=O)c2ccccc2)ccc1Cl] | N-(3-{[4-chloro-3-(methoxy)phenyl]amino}quinoxalin-2-yl)benzenesulfonamide |
| 329 | 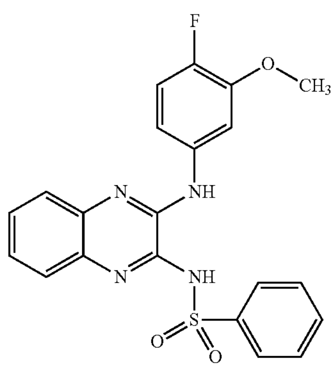 [SMILES: COc1cc(Nc2nc3ccccc3nc2NS(=O)(=O)c2ccccc2)ccc1F] | N-(3-{[4-fluoro-3-(methoxy)phenyl]amino}quinoxalin-2-yl)benzenesulfonamide |
| 330 | 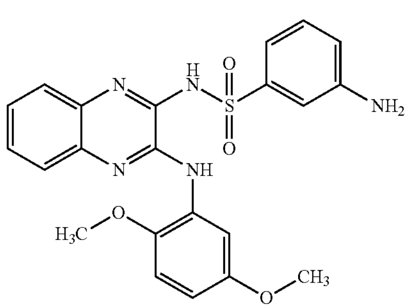 [SMILES: COc1ccc(OC)c(Nc2nc3ccccc3nc2NS(=O)(=O)c2cccc(N)c2)c1] | 3-amino-N-(3-{[2,5-bis(methoxy)phenyl]amino}quinoxalin-2-yl)benzenesulfonamide |

TABLE 1-continued

| Cpd. No. | Structure | Name |
|---|---|---|
| 331 | 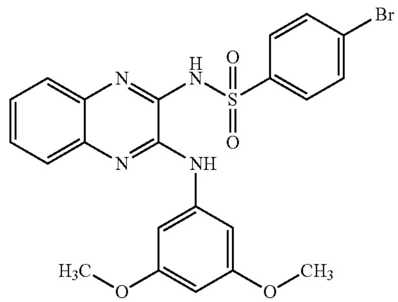 [SMILES: COc1cc(Nc2nc3ccccc3nc2NS(=O)(=O)c2ccc(Br)cc2)cc(OC)c1] | N-(3-{[3,5-bis(methoxy)phenyl]amino}quinoxalin-2-yl)-4-bromobenzenesulfonamide |
| 332 | 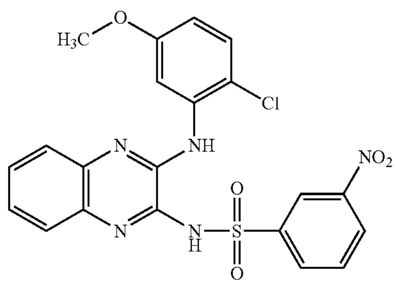 | N-(3-{[2-chloro-5-(methoxy)phenyl]amino}quinoxalin-2-yl)-3-nitrobenzenesulfonamide |
| 333 | 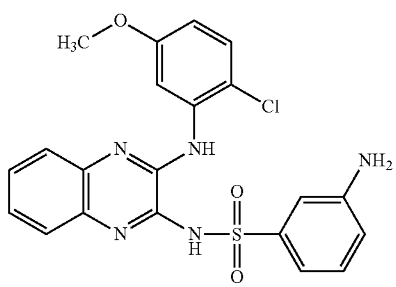 [SMILES: COc1ccc(Cl)c(Nc2nc3ccccc3nc2NS(=O)(=O)c2cccc(N)c2)c1] | 3-amino-N-(3-{[2-chloro-5-(methoxy)phenyl]amino}quinoxalin-2-yl)benzenesulfonamide |
| 334 | 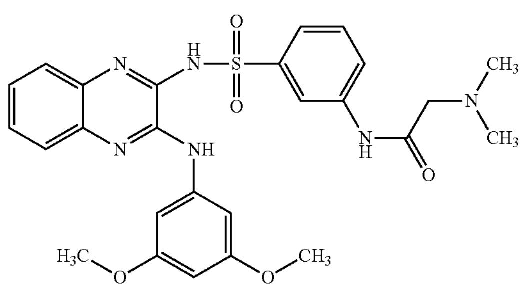 [SMILES: COc1cc(Nc2nc3ccccc3nc2NS(=O)(=O)c2cccc(NC(=O)CN(C)C)c2)cc(OC)c1] | N-(3-{[(3-{[3,5-bis(methoxy)phenyl]amino}quinoxalin-2-yl)amino]sulfonyl}phenyl)-N-2-,N-2-dimethylglycinamide |
| 335 | 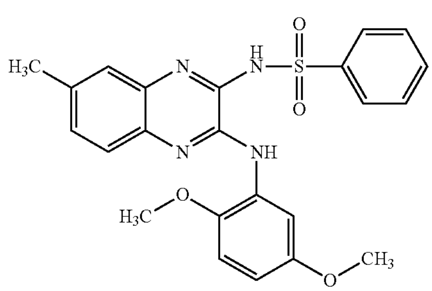 [SMILES: COc1ccc(OC)c(Nc2nc3ccc(C)cc3nc2NS(=O)(=O)c2ccccc2)c1] | N-(3-{[2,5-bis(methoxy)phenyl]amino}-7-methylquinoxalin-2-yl)benzenesulfonamide |

TABLE 1-continued

| Cpd. No. | Structure | Name |
|---|---|---|
| 336 | 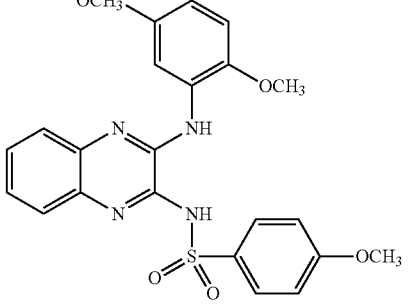 | N-(3-{[2,5-bis(methoxy)phenyl]amino}quinoxalin-2-yl)-4-(methoxy)benzenesulfonamide |
| 337 | 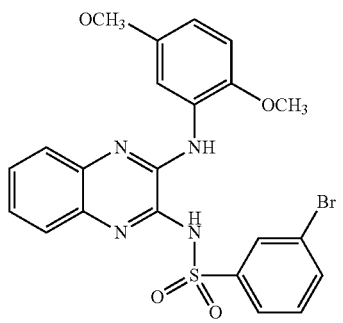 [SMILES: COc1ccc(OC)c(Nc2nc3ccccc3nc2NS(=O)(=O)c2cccc(Br)c2)c1] | N-(3-{[2,5-bis(methoxy)phenyl]amino}quinoxalin-2-yl)-3-bromobenzenesulfonamide |
| 338 | 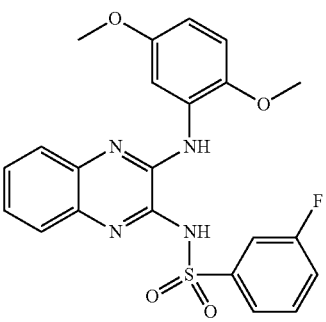 [SMILES: COc1ccc(OC)c(Nc2nc3ccccc3nc2NS(=O)(=O)c2cccc(F)c2)c1] | N-(3-{[2,5-bis(methoxy)phenyl]amino}quinoxalin-2-yl)-3-fluorobenzenesulfonamide |
| 339 | 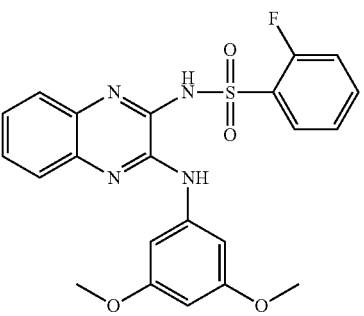 [SMILES: COc1cc(Nc2nc3ccccc3nc2NS(=O)(=O)c2ccccc2F)cc(OC)c1] | N-(3-{[3,5-bis(methoxy)phenyl]amino}quinoxalin-2-yl)-2-fluorobenzenesulfonamide |
| 340 | 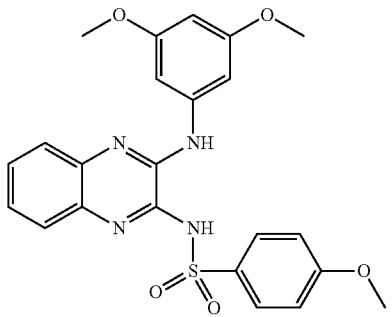 [SMILES: COc1ccc(S(=O)(=O)Nc2nc3ccccc3nc2Nc2cc(OC)cc(OC)c2)cc1] | N-(3-{[3,5-bis(methoxy)phenyl]amino}quinoxalin-2-yl)-4-(methoxy)benzenesulfonamide |

TABLE 1-continued

| Cpd. No. | Structure | Name |
|---|---|---|
| 341 | 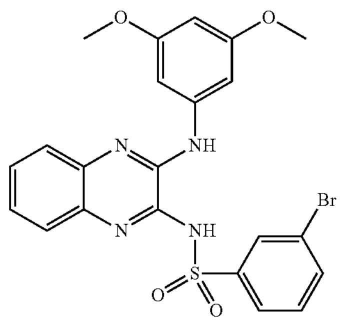 [SMILES: COc1cc(Nc2nc3ccccc3nc2NS(=O)(=O)c2cccc(Br)c2)cc(OC)c1] | N-(3-{[3,5-bis(methoxy)phenyl]amino}quinoxalin-2-yl)-3-bromobenzenesulfonamide |
| 342 | 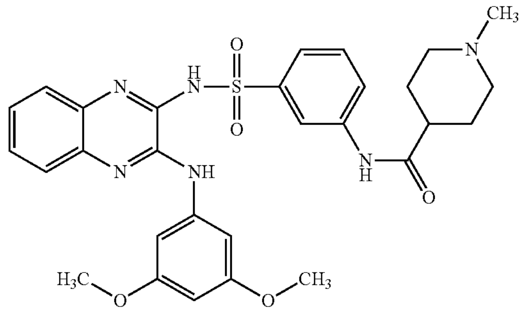 [SMILES: COc1cc(Nc2nc3ccccc3nc2NS(=O)(=O)c2cccc(NC(=O)C3CCN(C)CC3)c2)cc(OC)c1] | N-(3-{[(3-{[3,5-bis(methoxy)phenyl]amino}quinoxalin-2-yl)amino]sulfonyl}phenyl)-1-methylpiperidine-4-carboxamide |
| 343 | 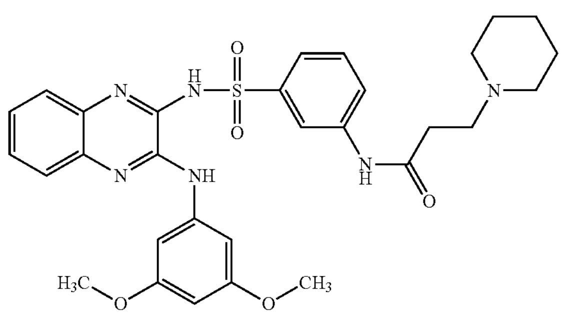 [SMILES: COc1cc(Nc2nc3ccccc3nc2NS(=O)(=O)c2cccc(NC(=O)CCN3CCCCC3)c2)cc(OC)c1] | N-(3-{[(3-{[3,5-bis(methoxy)phenyl]amino}quinoxalin-2-yl)amino]sulfonyl}phenyl)-3-piperidin-1-ylpropanamide |
| 344 | 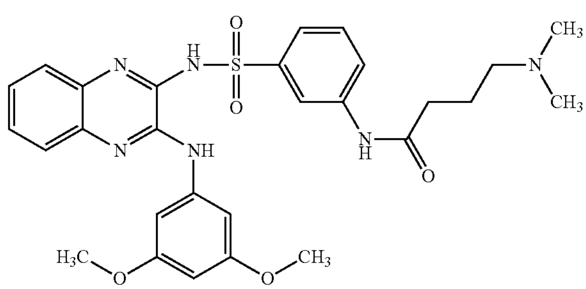 [SMILES: COc1cc(Nc2nc3ccccc3nc2NS(=O)(=O)c2cccc(NC(=O)CCCN(C)C)c2)cc(OC)c1] | N-(3-{[(3-{[3,5-bis(methoxy)phenyl]amino}quinoxalin-2-yl)amino]sulfonyl}phenyl)-4-(dimethylamino)butanamide |
| 345 | 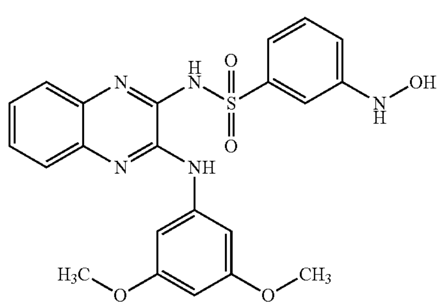 [SMILES: COc1cc(Nc2nc3ccccc3nc2NS(=O)(=O)c2cccc(NO)c2)cc(OC)c1] | N-(3-{[3,5-bis(methoxy)phenyl]amino}quinoxalin-2-yl)-3-(hydroxyamino)benzenesulfonamide |

TABLE 1-continued

| Cpd. No. | Structure | Name |
|---|---|---|
| 346 | 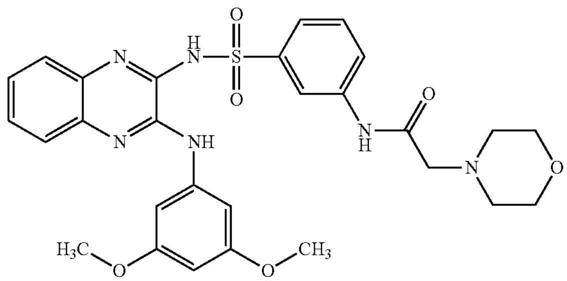 [SMILES: COc1cc(Nc2nc3ccccc3nc2NS(=O)(=O)c2cccc(NC(=O)CN3CCOCC3)c2)cc(OC)c1] | N-(3-{[(3-{[3,5-bis(methoxy)phenyl]amino}quinoxalin-2-yl)amino]sulfonyl}phenyl)-2-morpholin-4-ylacetamide |
| 347 | 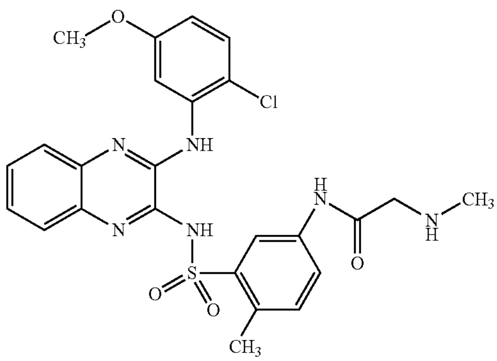 [SMILES: CNCC(=O)Nc1ccc(C)c(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}-4-methylphenyl)-N-2-methylglycinamide |
| 348 | 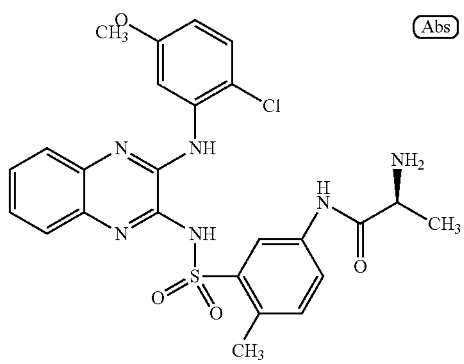 | N-(3-{[(3-{[2-chloro-5-(methoxy)phenyl]amino}quinoxalin-2-yl)amino]sulfonyl}-4-methylphenyl)-L-alaninamide |
| 349 | 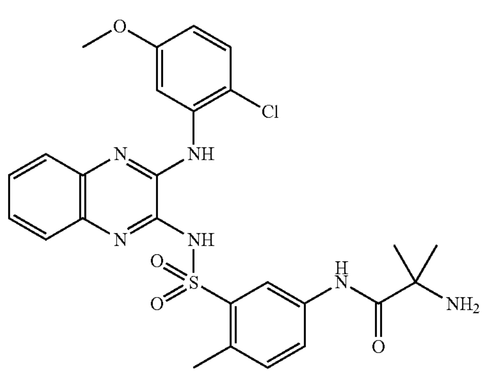 [SMILES: COc1ccc(Cl)c(Nc2nc3ccccc3nc2NS(=O)(=O)c2cc(NC(=O)C(C)(C)N)ccc2C)c1] | N-(3-{[(3-{[2-chloro-5-(methoxy)phenyl]amino}quinoxalin-2-yl)amino]sulfonyl}-4-methylphenyl)-2-methylalaninamide |

TABLE 1-continued

| Cpd. No. | Structure | Name |
| --- | --- | --- |
| 350 | 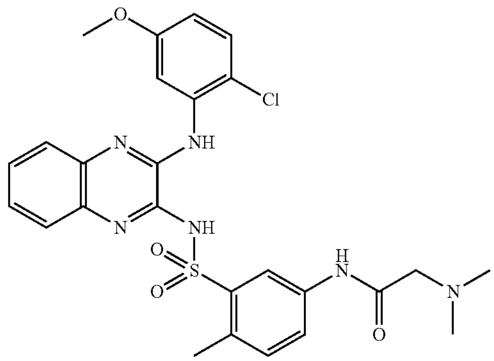 [SMILES: COc1ccc(Cl)c(Nc2nc3ccccc3nc2NS(=O)(=O)c2cc(NC(=O)CN(C)C)ccc2C)c1] | N-(3-{[(3-{[2-chloro-5-(methoxy)phenyl]amino}quinoxalin-2-yl)amino]sulfonyl}-4-methylphenyl)-N-2-,N-2-dimethylglycinamide |
| 351 | 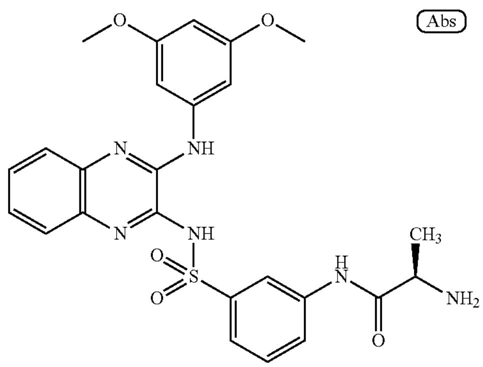 [SMILES: COc1cc(Nc2nc3ccccc3nc2NS(=O)(=O)c2cccc(NC(=O)[C@@H](C)N)c2)cc(OC)c1] | N-(3-{[(3-{[3,5-bis(methoxy)phenyl]amino}quinoxalin-2-yl)amino]sulfonyl}phenyl)-D-alaninamide |
| 352 | 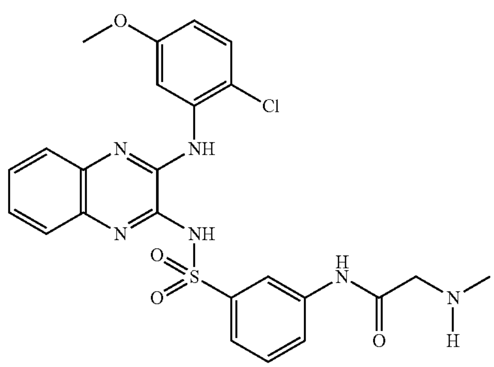 [SMILES: CNCC(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-methylglycinamide<br>N-(3-{[(3-{[2-chloro-5-(methoxy)phenyl]amino}quinoxalin-2-yl)amino]sulfonyl}-4-methylphenyl)-D-alaninamide |
| 353 | 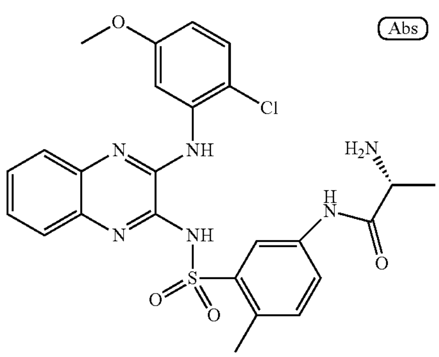 [SMILES: COc1ccc(Cl)c(Nc2nc3ccccc3nc2NS(=O)(=O)c2cc(NC(=O)[C@@H](C)N)ccc2C)c1] | N-(3-{[(3-{[2-chloro-5-(methoxy)phenyl]amino}quinoxalin-2-yl)amino]sulfonyl}-4-methylphenyl)-D-alaninamide |

TABLE 1-continued

| Cpd. No. | Structure | Name |
|---|---|---|
| 354 | 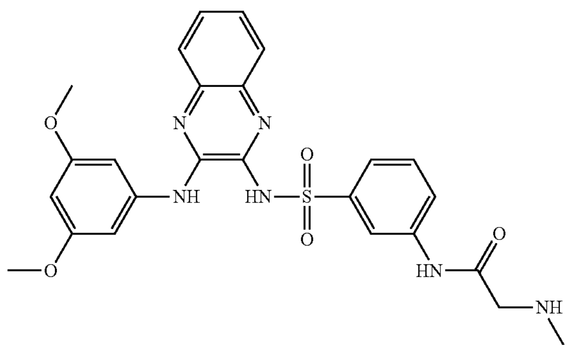 | N-(3-{[(3-{[3,5-bis(methoxy)phenyl]amino}quinoxalin-2-yl)amino]sulfonyl}phenyl)-N-2-methylglycinamide |
| 355 | 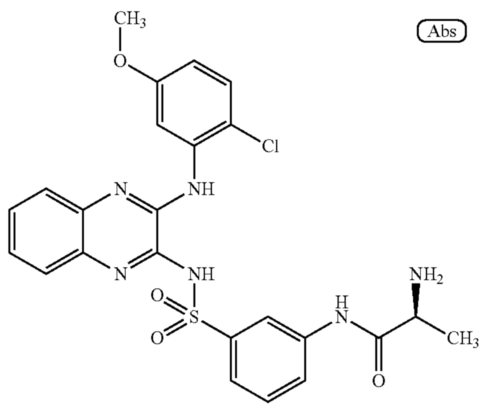 [SMILES: COc1ccc(Cl)c(Nc2nc3ccccc3nc2NS(=O)(=O)c2cccc(NC(=O)[C@H](C)N)c2)c1] | N-(3-{[(3-{[2-chloro-5-(methoxy)phenyl]amino}quinoxalin-2-yl)amino]sulfonyl}phenyl)-L-alaninamide |
| 356 | 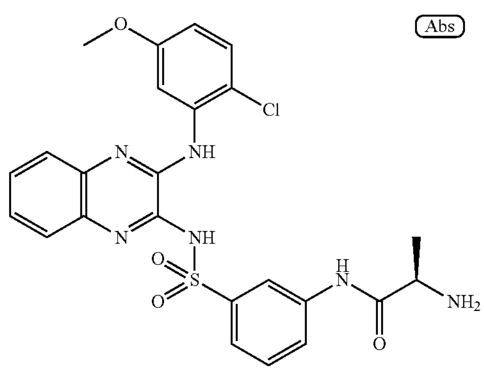 [SMILES: COc1ccc(Cl)c(Nc2nc3ccccc3nc2NS(=O)(=O)c2cccc(NC(=O)[C@@H](C)N)c2)c1] | N-(3-{[(3-{[2-chloro-5-(methoxy)phenyl]amino}quinoxalin-2-yl)amino]sulfonyl}phenyl)-D-alaninamide |
| 357 | 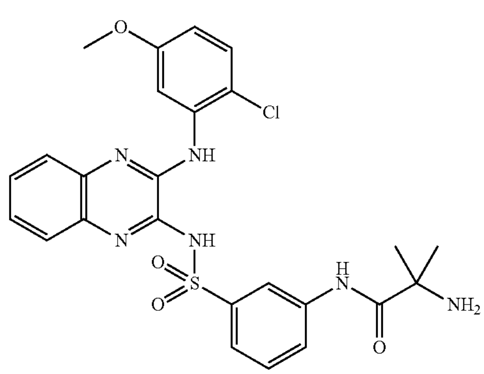 [SMILES: COc1ccc(Cl)c(Nc2nc3ccccc3nc2NS(=O)(=O)c2cccc(NC(=O)C(C)(C)N)c2)c1] | N-(3-{[(3-{[2-chloro-5-(methoxy)phenyl]amino}quinoxalin-2-yl)amino]sulfonyl}phenyl)-2-methylalaninamide |

TABLE 1-continued

| Cpd. No. | Structure | Name |
|---|---|---|
| 358 | 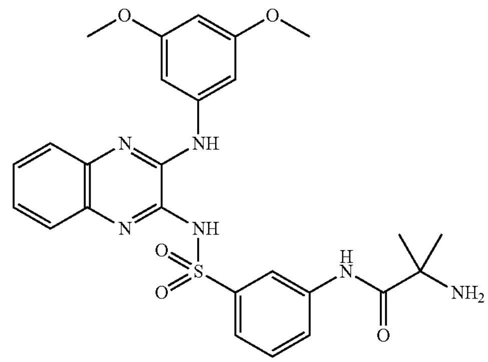 [SMILES: COc1cc(Nc2nc3ccccc3nc2NS(=O)(=O)c2cccc(NC(=O)C(C)(C)N)c2)cc(OC)c1] | N-(3-{[(3,5-bis(methoxy)phenyl]amino}quinoxalin-2-yl)amino]sulfonyl}phenyl)-2-methylalaninamide |
| 359 | 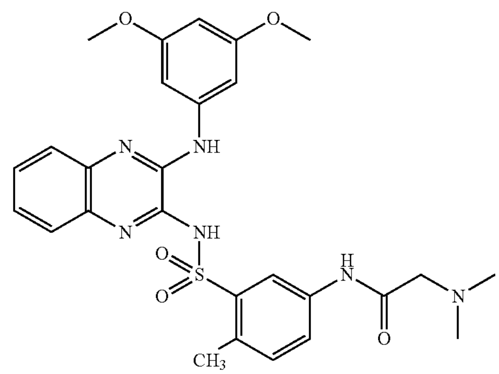 [SMILES: COc1cc(Nc2nc3ccccc3nc2NS(=O)(=O)c2cc(NC(=O)CN(C)C)ccc2C)cc(OC)c1] | N-(3-{[(3-{[3,5-bis(methoxy)phenyl]amino}quinoxalin-2-yl)amino]sulfonyl}-4-methylphenyl)-N-2-,N-2-dimethylglycinamide |
| 360 | 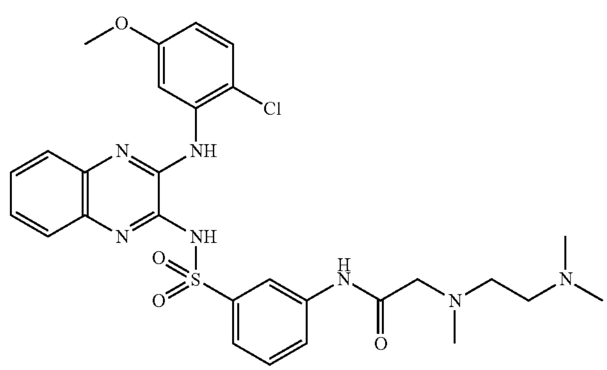 [SMILES: COc1ccc(Cl)c(Nc2nc3ccccc3nc2NS(=O)(=O)c2cccc(NC(=O)CN(C)CCN(C)C)c2)c1] | N-(3-{[(3-{[2-chloro-5-(methoxy)phenyl]amino}quinoxalin-2-yl)amino]sulfonyl}phenyl)-N-2-[2-(dimethylamino)ethyl]-N-2-methylglycinamide |
| 361 | (Abs) | (2S)-2-amino-N-(3-{[(3-{[2-chloro-5-(methoxy)phenyl]amino}quinoxalin-2-yl)amino]sulfonyl}phenyl)butanamide |

| Cpd. No. | Structure | Name |
|---|---|---|
| 362 | 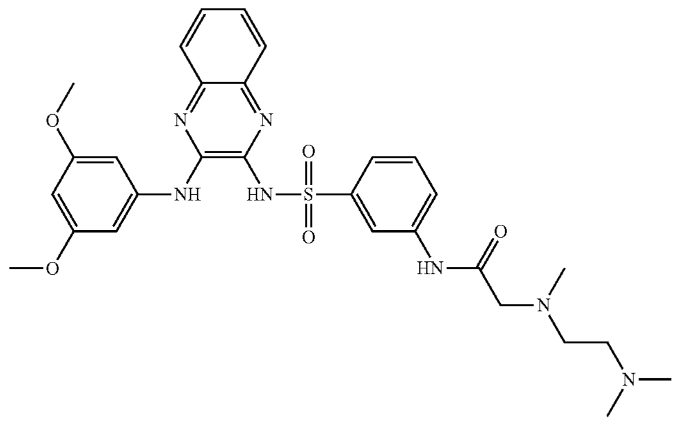 | N-(3-{[(3-{[3,5-bis(methoxy)phenyl]amino}quinoxalin-2-yl)amino]sulfonyl}phenyl)-N-2-[2-(dimethylamino)ethyl]-N-2-methylglycinamide |
| 363 | 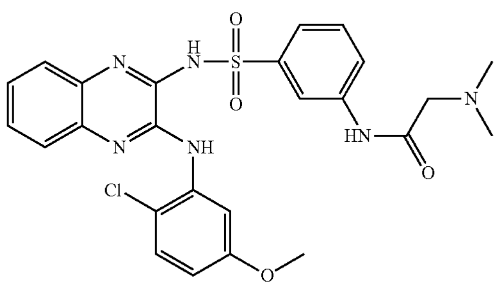 [SMILES: COc1ccc(Cl)c(Nc2nc3ccccc3nc2NS(=O)(=O)c2cccc(NC(=O)CN(C)C)c2)c1] | N-(3-{[(3-{[2-chloro-5-(methoxy)phenyl]amino}quinoxalin-2-yl)amino]sulfonyl}phenyl)-N-2-,N-2-dimethylglycinamide |
| 364 | 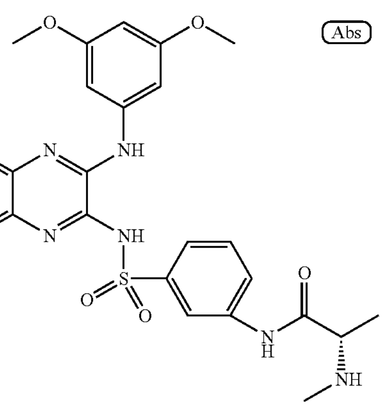 | N-(3-{[(3-{[3,5-bis(methoxy)phenyl]amino}quinoxalin-2-yl)amino]sulfonyl}phenyl)-N-2-methyl-L-alaninamide |
| 365 | 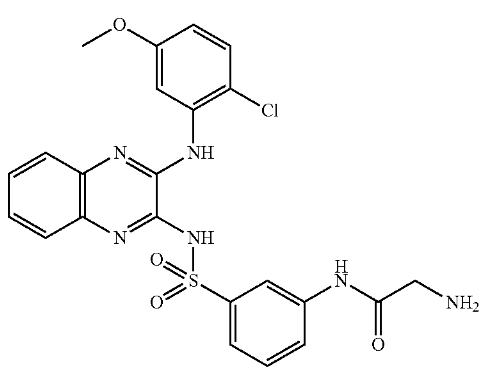 [SMILES: COc1ccc(Cl)c(Nc2nc3ccccc3nc2NS(=O)(=O)c2cccc(NC(=O)CN)c2)c1] | N-(3-{[(3-{[2-chloro-5-(methoxy)phen-yl]amino}quinoxalin-2-yl)amino]sulfonyl}phenyl)glycinamide |

TABLE 1-continued

| Cpd. No. | Structure | Name |
|---|---|---|
| 366 | 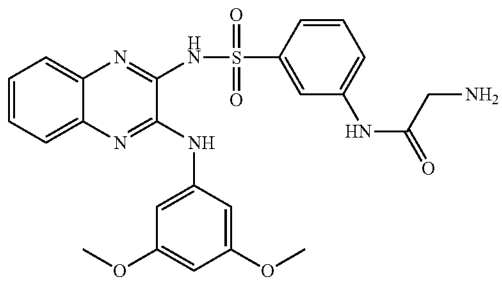 [SMILES: COc1cc(Nc2nc3ccccc3nc2NS(=O)(=O)c2cccc(NC(=O)CN)c2)cc(OC)c1] | N-(3-{[(3-{[3,5-bis(methoxy)phenyl]amino}quinoxahn-2-yl)amino]sulfonyl}phenyl)glycinamide |
| 367 | 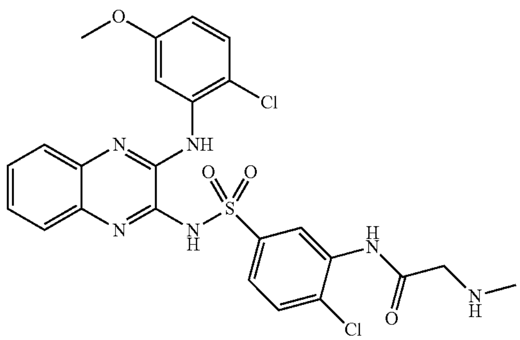 [SMILES: CNCC(=O)Nc1cc(S(=O)(=O)Nc2nc3ccccc3nc2Nc2cc(OC)ccc2Cl)ccc1Cl] | N-(2-chloro-5-{[(3-{[2-chloro-5-(methoxy)phenyl]amino}quinoxalin-2-yl)amino]sulfonyl}phenyl)-N-2-methylglycinamide |
| 368 | 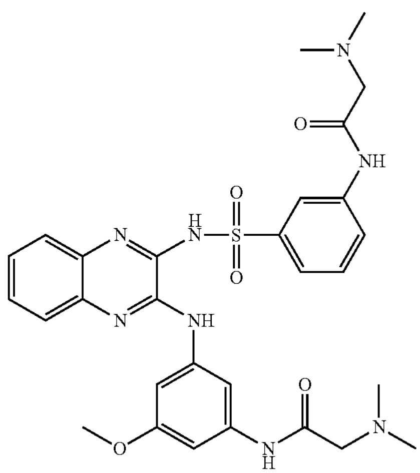 [SMILES: COc1cc(NC(=O)CN(C)C)cc(Nc2nc3ccccc3nc2NS(=O)(=O)c2cccc(NC(=O)CN(C)C)c2)c1] | 2-(dimethylamino)-N-(3-(N-(3-(3-(2-(dimethylamino)acetamido)-5-methoxyphenylamino)quinoxalin-2-yl)sulfamoyl)phenyl)acetamide |
| 369 | 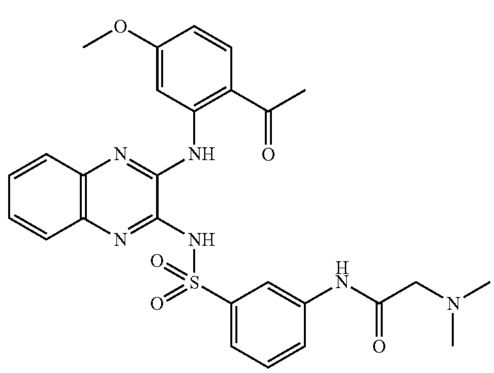 [SMILES: COc1ccc(C(C)=O)c(Nc2nc3ccccc3nc2NS(=O)(=O)c2cccc(NC(=O)CN(C)C)c2)c1] | N-(3-{[(3-{[2-acetyl-5-(methoxy)phenyl]amino}quinoxalin-2-yl)amino]sulfonyl}phenyl)-N-2-,N-2-dimethylglycinamide |

TABLE 1-continued

| Cpd. No. | Structure | Name |
| --- | --- | --- |
| 370 | 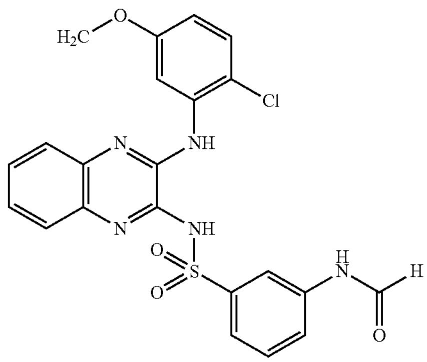 [SMILES: COc1ccc(Cl)c(Nc2nc3ccccc3nc2NS(=O)(=O)c2cccc(NC=O)c2)c1] | N-(3-{[2-chloro-5-(methoxy)phenyl]amino}quinoxalin-2-yl)-3-(formylamino)benzenesulfonamide |
| 371 | 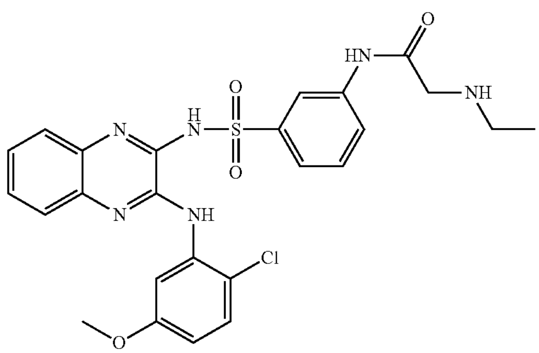 [SMILES: CCNCC(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-ethylglycinamide |
| 372 | 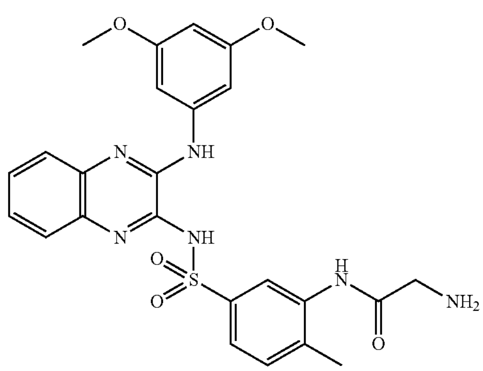 [SMILES: COc1cc(Nc2nc3ccccc3nc2NS(=O)(=O)c2ccc(C)c(NC(=O)CN)c2)cc(OC)c1] | N-(5-{[(3-{[3,5-bis(methoxy)phenyl]amino}quinoxalin-2-yl)amino]sulfonyl}-2-methylphenyl)glycinamide |
| 373 | 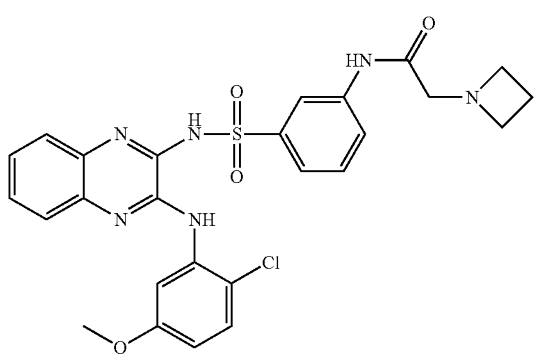 [SMILES: COc1ccc(Cl)c(Nc2nc3ccccc3nc2NS(=O)(=O)c2cccc(NC(=O)CN3CCC3)c2)c1] | 2-azetidin-1-yl-N-(3-{[(3-{[2-chloro-5-(methoxy)phenyl]amino}quinoxalin-2-yl)amino]sulfonyl}phenyl)acetamide |

TABLE 1-continued

| Cpd. No. | Structure | Name |
|---|---|---|
| 374 | 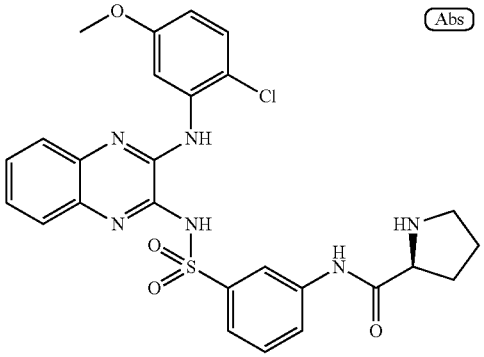 [SMILES: COc1ccc(Cl)c(Nc2nc3ccccc3nc2NS(=O)(=O)c2cccc(NC(=O)[C@@H]3CCCN3)c2)c1] | N-(3-{[(3-{[2-chloro-5-(methoxy)phenyl]amino}quinoxalin-2-yl)amino]sulfonyl}phenyl)-L-prolinamide |
| 375 | 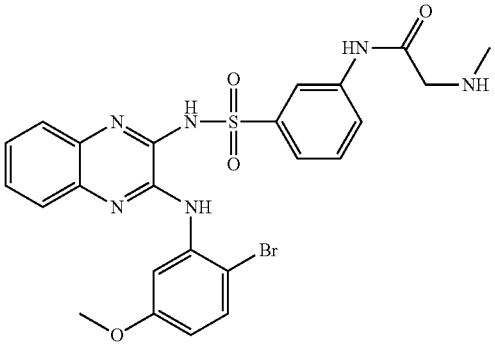 [SMILES: CNCC(=O)Nc1cccc(S(=O)(=O)Nc2nc3ccccc3nc2Nc2cc(OC)ccc2Br)c1] | N-(3-{[(3-{[2-bromo-5-(methoxy)phenyl]amino}quinoxalin-2-yl)amino]sulfonyl}phenyl)-N-2-methylglycinamide |
| 376 | 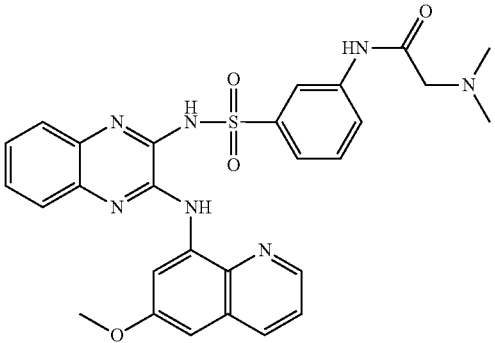 [SMILES: COc1cc(Nc2nc3ccccc3nc2NS(=O)(=O)c2cccc(NC(=O)CN(C)C)c2)c2ncccc2c1] | N-2-,N-2-dimethyl-N-(3-{[(3-{[6-(methoxy)quinolin-8-yl]amino}quinoxalin-2-yl)amino]sulfonyl}phenyl)glycinamide |
| 377 | 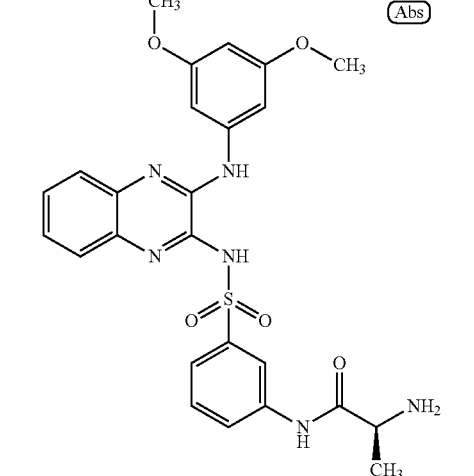 | N-(3-{[(3-{[3,5-bis(methoxy)phenyl]amino}quinoxalin-2-yl)amino]sulfonyl}phenyl)-L-alaninamide |

TABLE 1-continued
| Cpd. No. | Structure | Name |
|---|---|---|
| 378 | 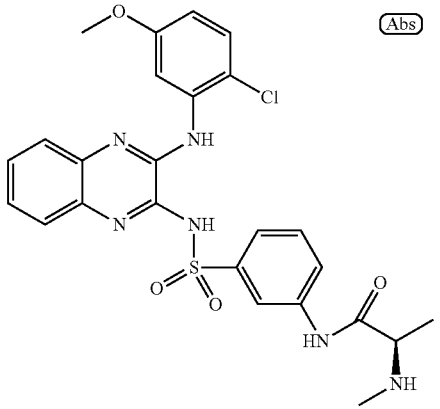 [SMILES: CN[C@H](C)C(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-methyl-D-alaninamide |
| 379 | 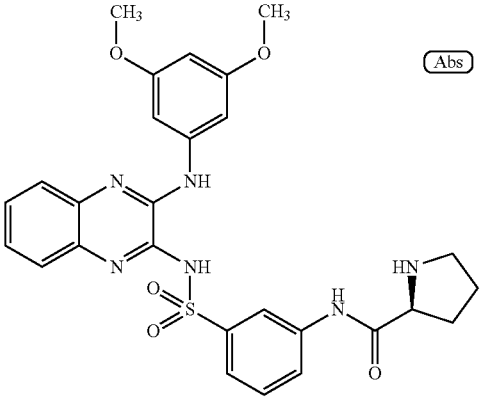 [SMILES: COc1cc(Nc2nc3ccccc3nc2NS(=O)(=O)c2cccc(NC(=O)[C@@H]3CCCN3)c2)cc(OC)c1] | N-(3-{[(3-{[3,5-bis(methoxy)phenyl]amino}quinoxalin-2-yl)amino]sulfonyl}phenyl)-L-prolinamide |
| 380 | 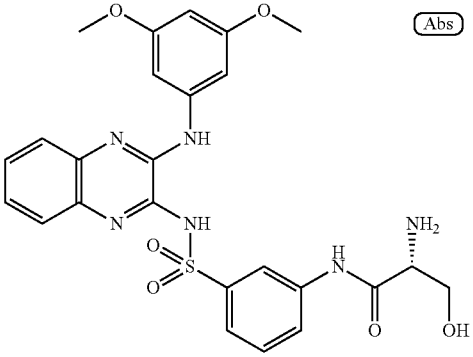 [SMILES: COc1cc(Nc2nc3ccccc3nc2NS(=O)(=O)c2cccc(NC(=O)[C@H](N)CO)c2)cc(OC)c1] | N-(3-{[(3-{[3,5-bis(methoxy)phenyl]amino}quinoxalin-2-yl)amino]sulfonyl}phenyl)-D-serinamide |

TABLE 1-continued

| Cpd. No. | Structure | Name |
|---|---|---|
| 381 | 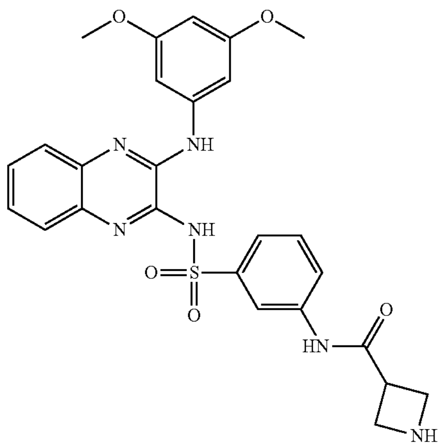 [SMILES: COc1cc(Nc2nc3ccccc3nc2NS(=O)(=O)c2cccc(NC(=O)C3CNC3)c2)cc(OC)c1] | N-(3-{[(3-{[3,5-bis(methoxy)phenyl]amino}quinoxalin-2-yl)amino]sulfonyl}phenyl)azetidine-3-carboxamide |
| 382 | 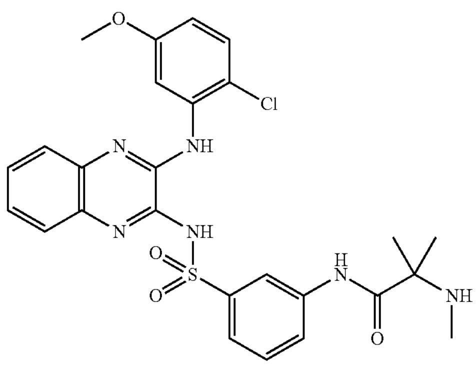 [SMILES: CNC(C)(C)C(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-,2-dimethylalaninamide |
| 383 | 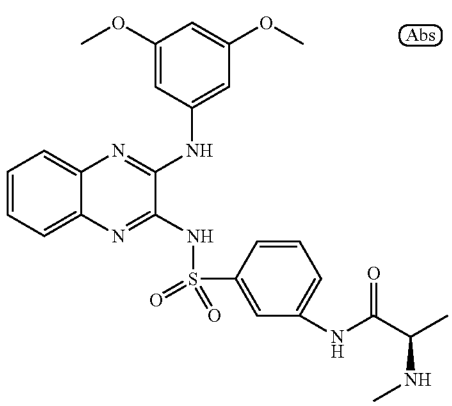 [SMILES: CN[C@H](C)C(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-methyl-D-alaninamide |
| 384 | 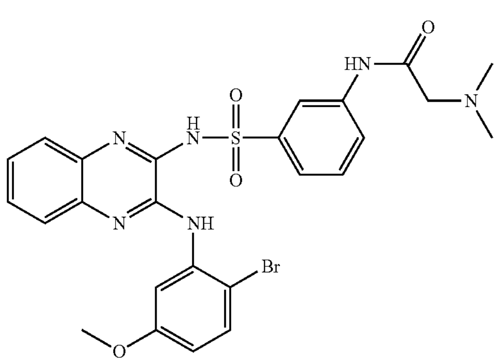 [SMILES: COc1ccc(Br)c(Nc2nc3ccccc3nc2NS(=O)(=O)c2cccc(NC(=O)CN(C)C)c2)c1] | N-(3-{[(3-{[2-bromo-5-(methoxy)phenyl]amino}quinoxalin-2-yl)amino]sulfonyl}phenyl)-N-2-,N-2-dimethylglycinamide |

TABLE 1-continued

| Cpd. No. | Structure | Name |
| --- | --- | --- |
| 385 | 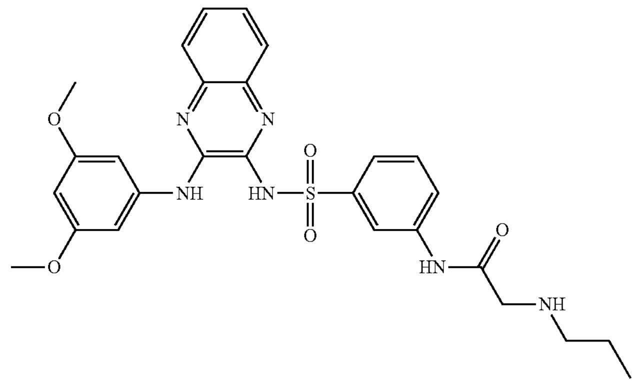 [SMILES: CCCNCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-propylglycinamide |
| 386 | 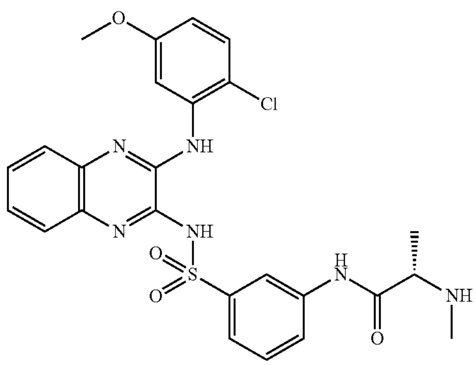 [SMILES: CN[C@@H](C)C(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-methyl-L-alaninamide |
| 387 | 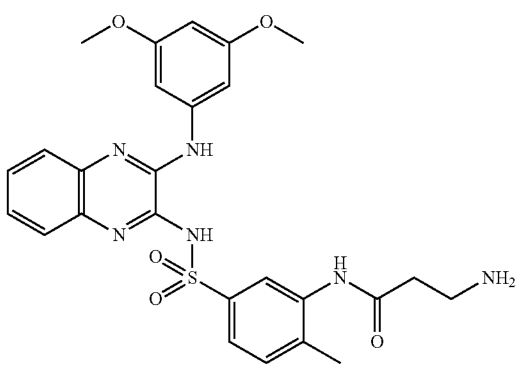 [SMILES: COc1cc(Nc2nc3ccccc3nc2NS(=O)(=O)c2ccc(C)c(NC(=O)CCN)c2)cc(OC)c1] | N-(5-{[(3-{[3,5-bis(methoxy)phenyl]amino}quinoxalin-2-yl)amino]sulfonyl}-2-methylphenyl)-beta-alaninamide |
| 388 | 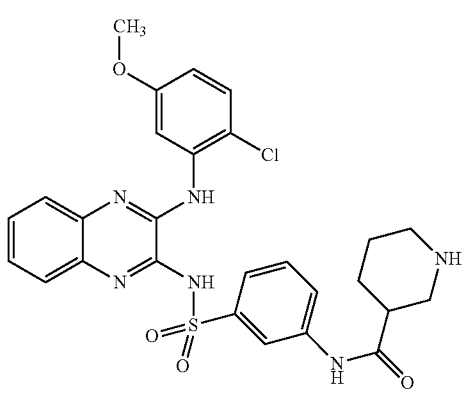 [SMILES: COc1ccc(Cl)c(Nc2nc3ccccc3nc2NS(=O)(=O)c2cccc(NC(=O)C3CCCNC3)c2)c1] | N-(3-{[(3-{[2-chloro-5-(methoxy)phenyl]amino}quinoxalin-2-yl)amino]sulfonyl}phenyl)piperidine-3-carboxamide |

TABLE 1-continued

| Cpd. No. | Structure | Name |
|---|---|---|
| 389 | 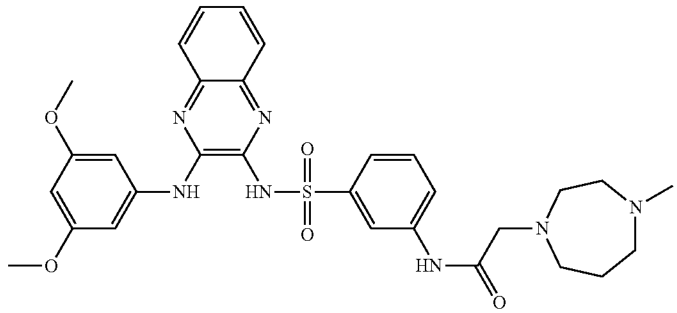 | N-(3-{[(3-{[3,5-bis(methoxy)phenyl]amino}quinoxalin-2-yl)amino]sulfonyl}phenyl)-2-(4-methyl-1,4-diazepan-1-yl)acetamide |
| 390 | 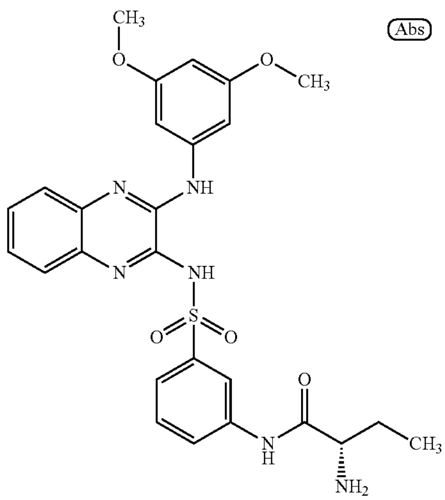 [SMILES: CC[C@H](N)C(=O)Nc1cccc(S(=O)(=O)Nc2nc3ccccc3nc2Nc2cc(OC)cc(OC)c2)c1] | (2S)-2-amino-N-(3-{[(3-{[3,5-bis(methoxy)phenyl]amino}quinoxalin-2-yl)amino]sulfonyl}phenyl)butanamide |
| 391 | 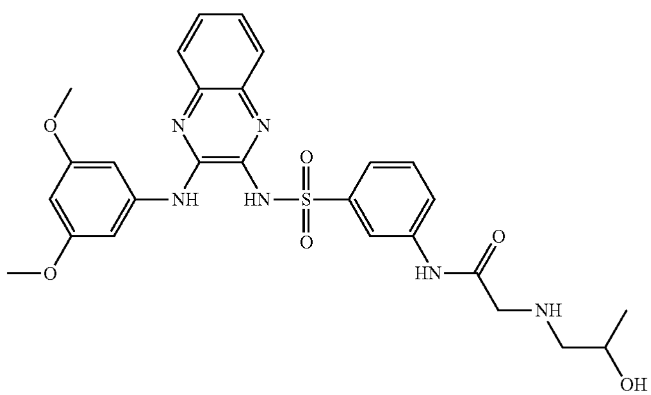 [SMILES: COc1cc(Nc2nc3ccccc3nc2NS(=O)(=O)c2cccc(NC(=O)CNCC(C)O)c2)cc(OC)c1] | N-(3-{[(3-{[3,5-bis(methoxy)phenyl]amino}quinoxalin-2-yl)amino]sulfonyl}phenyl)-N-2-(2-hydroxypropyl)glycinamide |
| 392 | 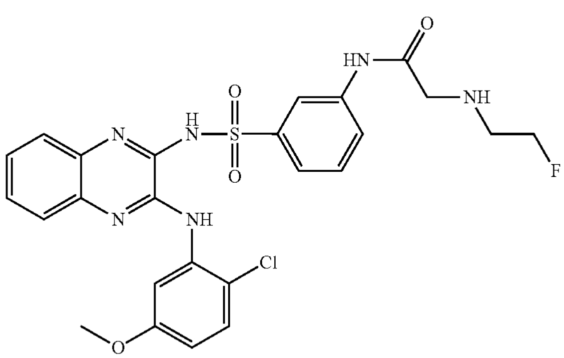 [SMILES: COc1ccc(Cl)c(Nc2nc3ccccc3nc2NS(=O)(=O)c2cccc(NC(=O)CNCCF)c2)c1] | N-(3-{[(3-{[2-chloro-5-(methoxy)phenyl]amino}quinoxalin-2-yl)amino]sulfonyl}phenyl)-N-2-(2-fluoroethyl)glycinamide |

TABLE 1-continued

| Cpd. No. | Structure | Name |
|---|---|---|
| 393 | 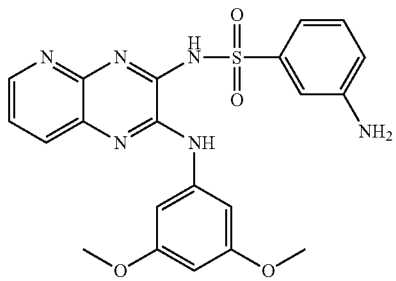 [SMILES: COc1cc(Nc2nc3cccnc3nc2NS(=O)(=O)c2cccc(N)c2)cc(OC)c1] | 3-amino-N-(2-{[3,5-bis(methoxy)phenyl]amino}pyrido[2,3-b]pyrazin-3-yl)benzenesulfonamide |
| 394 | 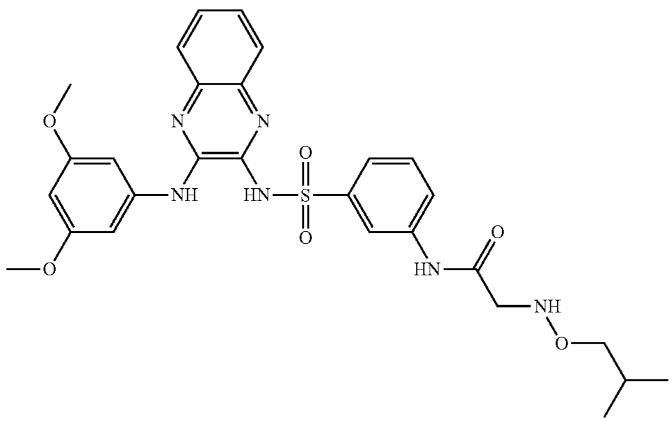 [SMILES: COc1cc(Nc2nc3ccccc3nc2NS(=O)(=O)c2cccc(NC(=O)CNOCC(C)C)c2)cc(OC)c1] | N-(3-{[(3-{[3,5-bis(methoxy)phenyl]animo}quinoxalin-2-yl)amino]sulfonyl}phenyl)-N-2-[(2-methylpropyl)oxy]glycinamide |
| 395 | 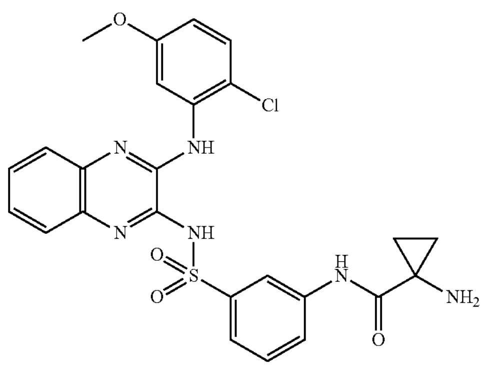 [SMILES: COc1ccc(Cl)c(Nc2nc3ccccc3nc2NS(=O)(=O)c2cccc(NC(=O)C3(N)CC3)c2)c1] | 1-amino-N-(3-{[(3-{[2-chloro-5-(methoxy)phenyl]amino}quinoxalin-2-yl)amino]sulfonyl}phenyl)cyclopropanecarboxamide |
| 396 | 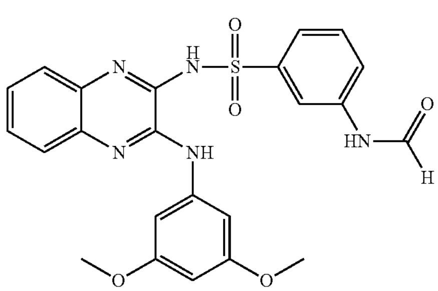 [SMILES: COc1cc(Nc2nc3ccccc3nc2NS(=O)(=O)c2cccc(NC=O)c2)cc(OC)c1] | N-(3-{[3,5-bis(methoxy)phenyl]amino}quinoxalin-2-yl)-3-(formylamino)benzenesulfonamide |

TABLE 1-continued

| Cpd. No. | Structure | Name |
|---|---|---|
| 397 | 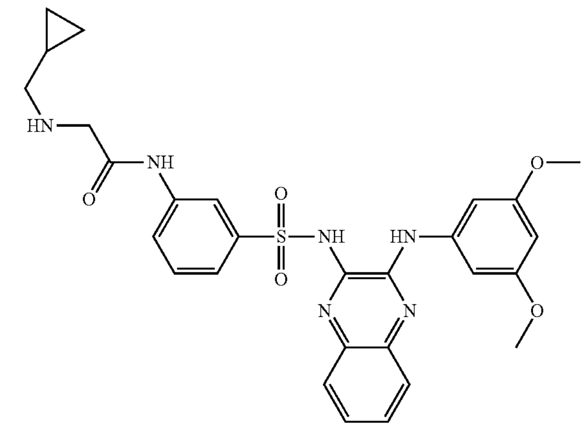 [SMILES: COc1cc(Nc2nc3ccccc3nc2NS(=O)(=O)c2cccc(NC(=O)CNCC3CC3)c2)cc(OC)c1] | N-(3-{[(3-{[3,5-bis(methoxy)phenyl]amino}quinoxalin-2-yl)amino]sulfonyl}phenyl)-N-2-(cyclopropylmethyl)glycinamide |
| 398 | 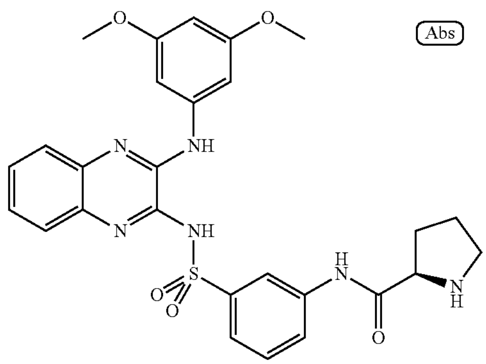 [SMILES: COc1cc(Nc2nc3ccccc3nc2NS(=O)(=O)c2cccc(NC(=O)[C@H]3CCCN3)c2)cc(OC)c1] | N-(3-{[(3-{[3,5-bis(methoxy)phenyl]amino}quinoxalin-2-yl)amino]sulfonyl}phenyl)-D-prolinamide |
| 399 | 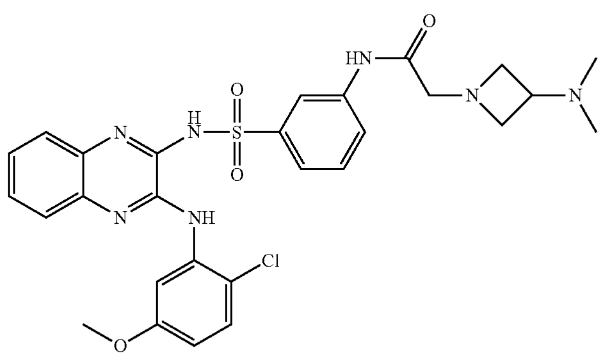 [SMILES: COc1ccc(Cl)c(Nc2nc3ccccc3nc2NS(=O)(=O)c2cccc(NC(=O)CN3CC(N(C)C)C3)c2)c1] | N-(3-{[(3-{[2-chloro-5-(methoxy)phenyl]amino}quinoxalin-2-yl)amino]sulfonyl}phenyl)-2-[3-(dimethylamino)azetidin-1-yl]acetamide |
| 400 | 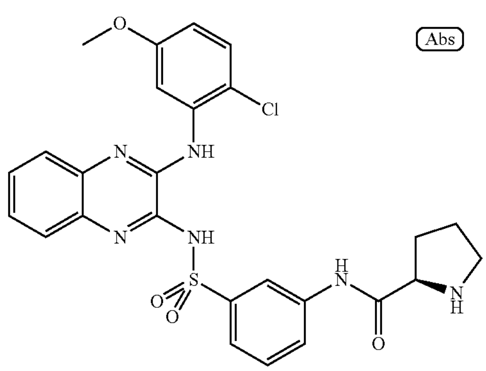 [SMILES: COc1ccc(Cl)c(Nc2nc3ccccc3nc2NS(=O)(=O)c2cccc(NC(=O)[C@H]3CCCN3)c2)c1] | N-(3-{[(3-{[2-chloro-5-(methoxy)phenyl]amino}quinoxalin-2-yl)amino]sulfonyl}phenyl)-D-prolinamide |

TABLE 1-continued

| Cpd. No. | Structure | Name |
| --- | --- | --- |
| 401 | 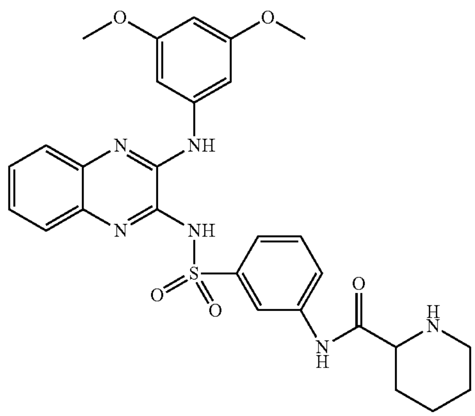 [SMILES: COc1cc(Nc2nc3ccccc3nc2NS(=O)(=O)c2cccc(NC(=O)C3CCCCN3)c2)cc(OC)c1] | N-(3-{[(3-{[3,5-bis(methoxy)phenyl]amino}quinoxalin-2-yl)amino]sulfonyl}phenyl)piperidine-2-carboxamide |
| 402 | 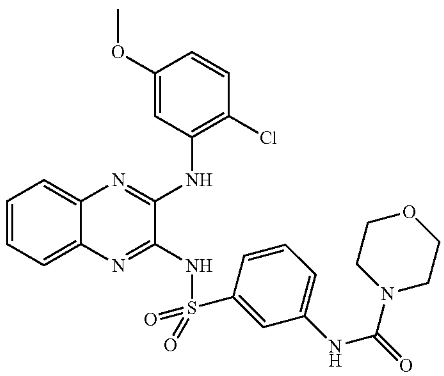 [SMILES: COc1ccc(Cl)c(Nc2nc3ccccc3nc2NS(=O)(=O)c2cccc(NC(=O)N3CCOCC3)c2)c1] | N-(3-{[(3-{[2-chloro-5-(methoxy)phenyl]amino}quinoxalin-2-yl)amino]sulfonyl}phenyl)morpholine-4-carboxamide |
| 403 | 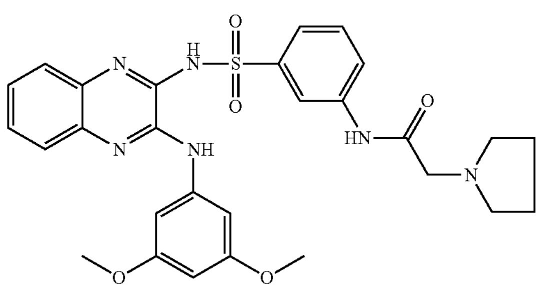 [SMILES: COc1cc(Nc2nc3ccccc3nc2NS(=O)(=O)c2cccc(NC(=O)CN3CCCC3)c2)cc(OC)c1] | N-(3-{[(3-{[3,5-bis(methoxy)phenyl]amino}quinoxalin-2-yl)amino]sulfonyl}phenyl)-2-pyrrolidin-1-ylacetamide |
| 404 | 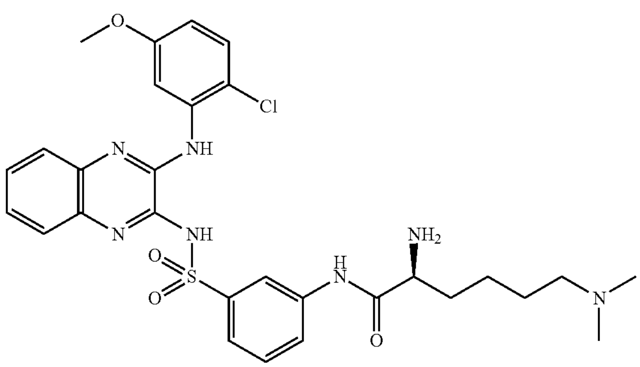 [SMILES: COc1ccc(Cl)c(Nc2nc3ccccc3nc2NS(=O)(=O)c2cccc(NC(=O)[C@@H](N)CCCCN(C)C)c2)c1] | N-(3-{[(3-{[2-chloro-5-(methoxy)phenyl]amino}quinoxalin-2-yl)amino]sulfonyl}phenyl)-N-6-,N-6-dimethyl-L-lysinamide |

TABLE 1-continued

| Cpd. No. | Structure | Name |
|---|---|---|
| 405 | 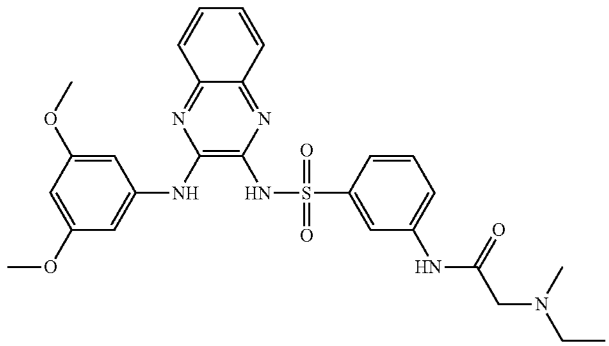 [SMILES: CCN(C)CC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-ethyl-N-2-methylglycinamide |
| 406 | 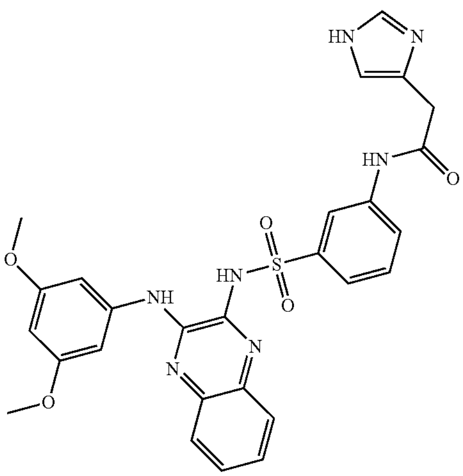 [SMILES: COc1cc(Nc2nc3ccccc3nc2NS(=O)(=O)c2cccc(NC(=O)Cc3c[nH]cn3)c2)cc(OC)c1] | N-(3-{[(3-{[3,5-bis(methoxy)phenyl]amino}quinoxalin-2-yl)amino]sulfonyl}phenyl)-2-(1H-imidazol-4-yl)acetamide |
| 407 | 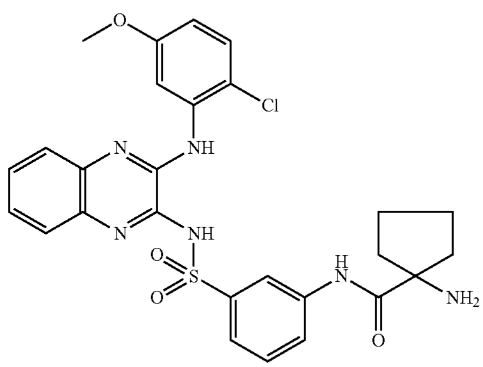 [SMILES: COc1ccc(Cl)c(Nc2nc3ccccc3nc2NS(=O)(=O)c2cccc(NC(=O)C3(N)CCCC3)c2)c1] | 1-amino-N-(3-{[(3-{[2-chloro-5-(methoxy)phenyl]amino}quinoxalin-2-yl)amino]sulfonyl}phenyl)cyclopentanecarboxamide |
| 408 | 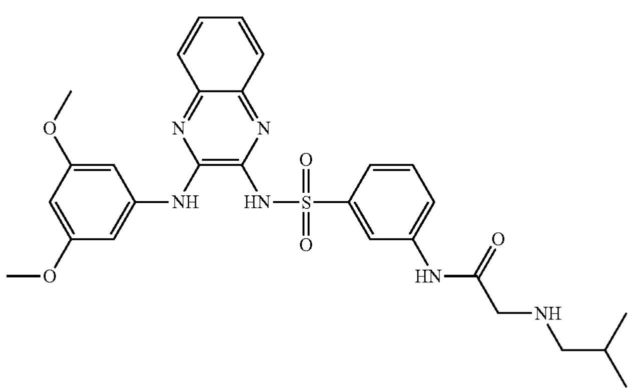 [SMILES: COc1cc(Nc2nc3ccccc3nc2NS(=O)(=O)c2cccc(NC(=O)CNCC(C)C)c2)cc(OC)c1] | N-(3-{[(3-{[3,5-bis(methoxy)phenyl]amino}quinoxalin-2-yl)amino]sulfonyl}phenyl)-N-2-(2-methylpropyl)glycinamide |

| Cpd. No. | Structure | Name |
| --- | --- | --- |
| 409 | 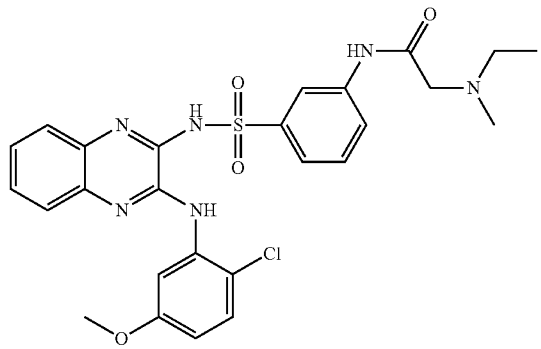 [SMILES: CCN(C)CC(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-ethyl-N-2-methylglycinamide |
| 410 | 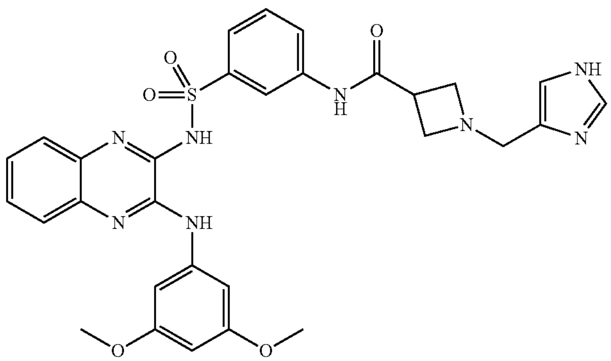 [SMILES: COc1cc(Nc2nc3ccccc3nc2NS(=O)(=O)c2cccc(NC(=O)C3CN(Cc4c[nH]cn4)C3)c2)cc(OC)c1] | N-(3-{[(3-{[3,5-bis(methoxy)phenyl]amino}quinoxalin-2-yl)amino]sulfonyl}phenyl)-1-(1H-imidazol-4-ylmethyl)azetidine-3-carboxamide |
| 411 | 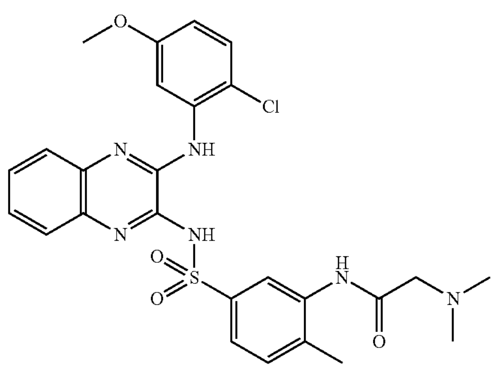 [SMILES: COc1ccc(Cl)c(Nc2nc3ccccc3nc2NS(=O)(=O)c2ccc(C)c(NC(=O)CN(C)C)c2)c1] | N-(5-{[(3-{[2-chloro-5-(methoxy)phenyl]amino}quinoxalin-2-yl)amino]sulfonyl}-2-methylphenyl)-N-2-,N-2-dimethylglycinamide |
| 412 | 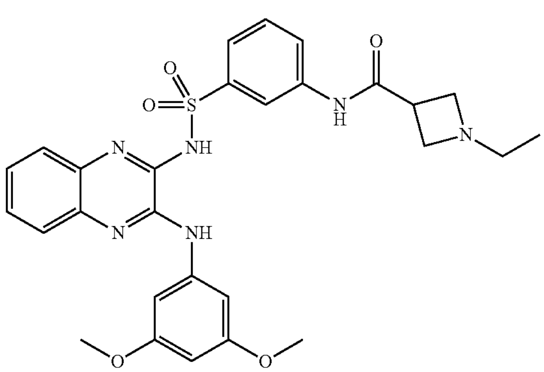 [SMILES: CCN1CC(C(=O)Nc2cccc(S(=O)(=O)Nc3nc4ccccc4nc3Nc3cc(OC)cc(OC)c3)c2)C1] | N-(3-{[(3-{[3,5-bis(methoxy)phenyl]amino}quinoxalin-2-yl)amino]sulfonyl}phenyl)-1-ethylazetidine-3-carboxamide |

| Cpd. No. | Structure | Name |
|---|---|---|
| 413 | 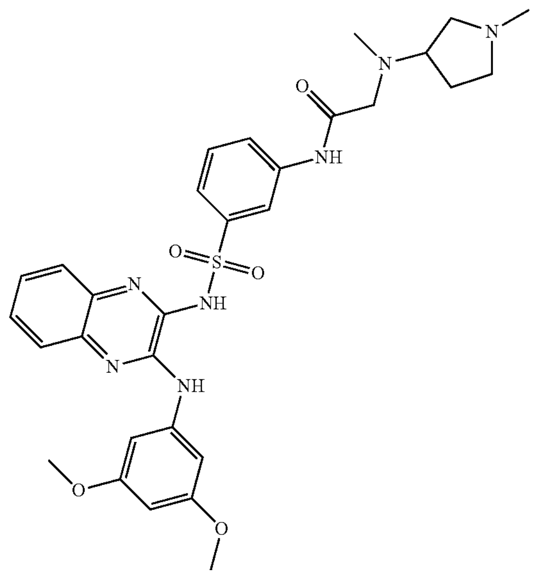 [SMILES: COc1cc(Nc2nc3ccccc3nc2NS(=O)(=O)c2cccc(NC(=O)CN(C)C3CCN(C)C3)c2)cc(OC)c1] | N-(3-{[(3-{[3,5-bis(methoxy)phenyl]amino}quinoxalin-2-yl)amino]sulfonyl}phenyl)-N-2-methyl-N-2-(1-methylpyrrolidin-3-yl)glycinamide |
| 414 | 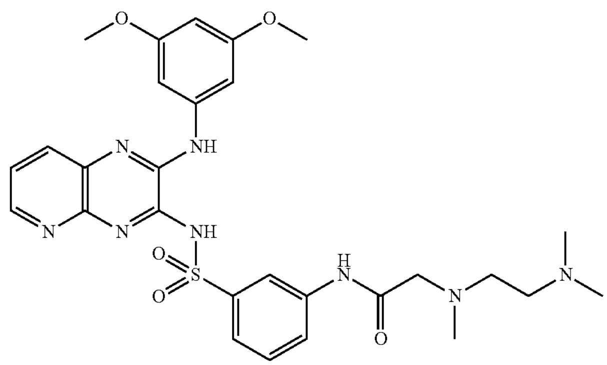 [SMILES: COc1cc(Nc2nc3cccnc3nc2NS(=O)(=O)c2cccc(NC(=O)CN(C)CCN(C)C)c2)cc(OC)c1] | N-(3-{[(2-{[3,5-bis(methoxy)phenyl]amino}pyrido[2,3-b]pyrazin-3-yl)amino]sulfonyl}phenyl)-N-2-[2-(dimethylamino)ethyl]-N-2-methylglycinamide |
| 415 | 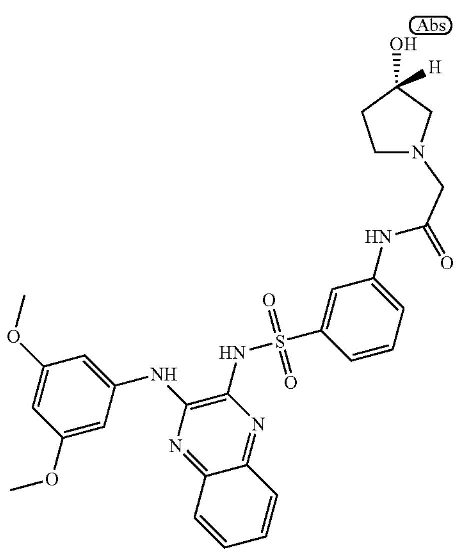 [SMILES: COc1cc(Nc2nc3ccccc3nc2NS(=O)(=O)c2cccc(NC(=O)CN3CC[C@H](O)C3)c2)cc(OC)c1] | N-(3-{[(3-{[3,5-bis(methoxy)phenyl]amino}quinoxalin-2-yl)amino]sulfonyl}phenyl)-2-[(3S)-3-hydroxypyrrolidin-1-yl]acetamide |

TABLE 1-continued

| Cpd. No. | Structure | Name |
|---|---|---|
| 416 | 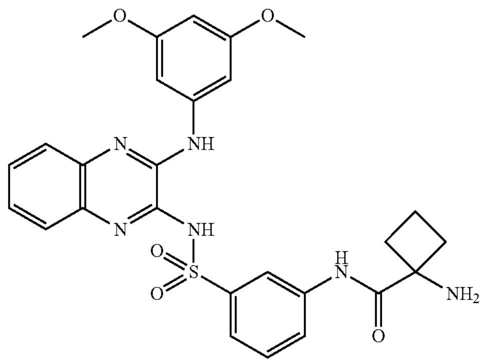 [SMILES: COc1cc(Nc2nc3ccccc3nc2NS(=O)(=O)c2cccc(NC(=O)C3(N)CCC3)c2)cc(OC)c1] | 1-amino-N-(3-{[(3-{[3,5-bis(methoxy)phenyl]amino}quinoxalin-2-yl)amino]sulfonyl}phenyl)cyclobutanecarboxamide |
| 417 | 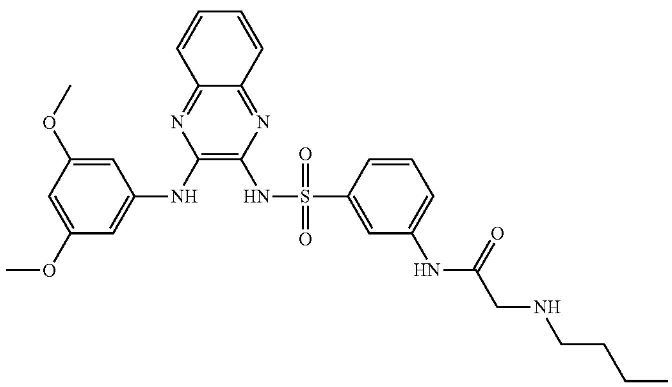 [SMILES: CCCCNCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-butylglycinamide |
| 418 | 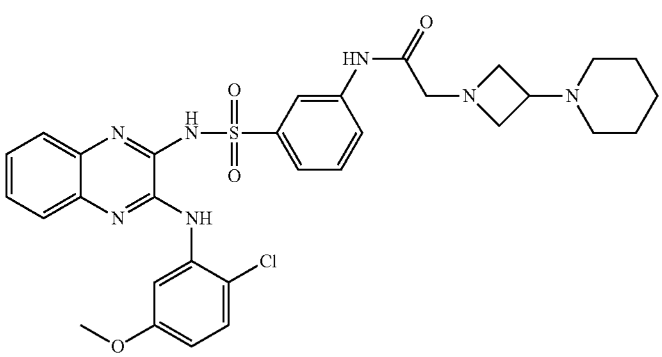 [SMILES: COc1ccc(Cl)c(Nc2nc3ccccc3nc2NS(=O)(=O)c2cccc(NC(=O)CN3CC(N4CCCCC4)C3)c2)c1] | N-(3-{[(3-{[2-chloro-5-(methoxy)phenyl]amino}quinoxalin-2-yl)amino]sulfonyl}phenyl)-2-(3-piperidin-1-ylazetidin-1-yl)acetamide |
| 419 | 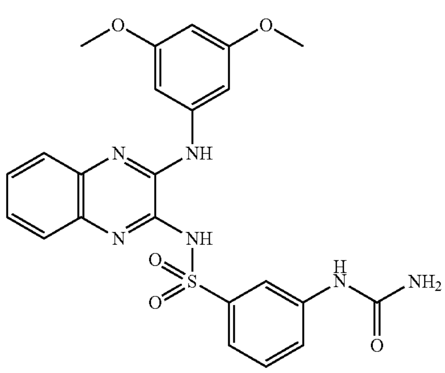 [SMILES: COc1cc(Nc2nc3ccccc3nc2NS(=O)(=O)c2cccc(NC(N)=O)c2)cc(OC)c1] | 3-[(aminocarbonyl)amino]-N-(3-{[3,5-bis(methoxy)phenyl]amino}quinoxalin-2-yl)benzenesulfonamide |

TABLE 1-continued

| Cpd. No. | Structure | Name |
|---|---|---|
| 420 | 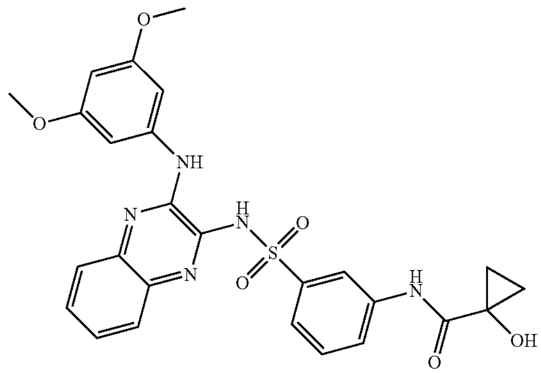 [SMILES: COc1cc(Nc2nc3ccccc3nc2NS(=O)(=O)c2cccc(NC(=O)C3(O)CC3)c2)cc(OC)c1] | N-(3-{[(3-{[3,5-bis(methoxy)phenyl]amino}quinoxalin-2-yl)amino]sulfonyl}phenyl)-1-hydroxycyclopropanecarboxamide |
| 421 | 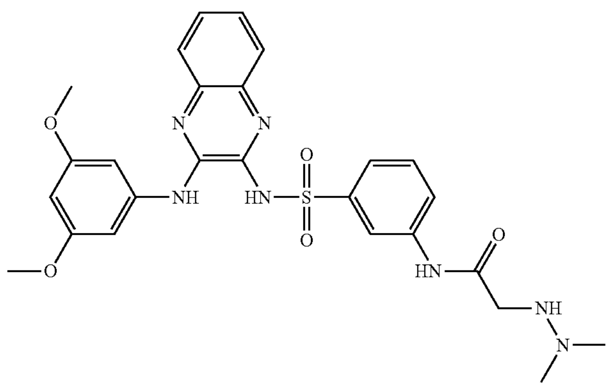 | N-(3-{[(3-{[3,5-bis(methoxy)phenyl]amino}quinoxalin-2-yl)amino]sulfonyl}phenyl)-2-(2,2-dimethylhydrazino)acetamide |
| 422 | 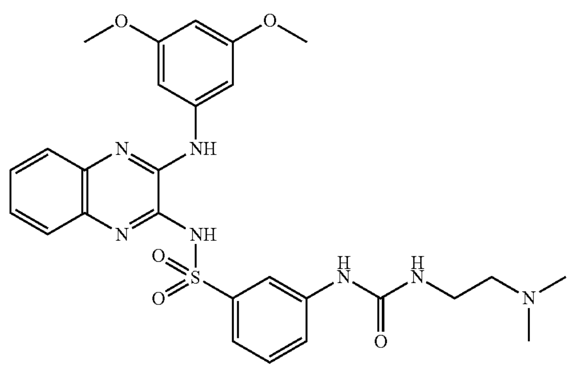 [SMILES: COc1cc(Nc2nc3ccccc3nc2NS(=O)(=O)c2cccc(NC(=O)NCCN(C)C)c2)cc(OC)c1] | N-(3-{[3,5-bis(methoxy)phenyl]amino}quinoxalin-2-yl)-3-[({[2-(dimethylamino)ethyl]amino}carbonyl)amino]benzenesulfonamide |
| 423 | 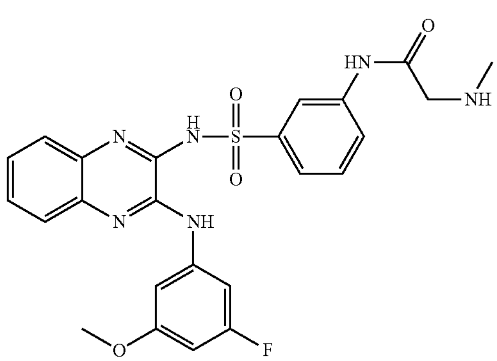 [SMILES: CNCC(=O)Nc1cccc(S(=O)(=O)Nc2nc3ccccc3nc2Nc2cc(F)cc(OC)c2)c1] | N-(3-{[(3-{[3-fluoro-5-(methoxy)phenyl]amino}quinoxalin-2-yl)amino]sulfonyl}phenyl)-N-2-methylglycinamide |

| Cpd. No. | Structure | Name |
|---|---|---|
| 424 | 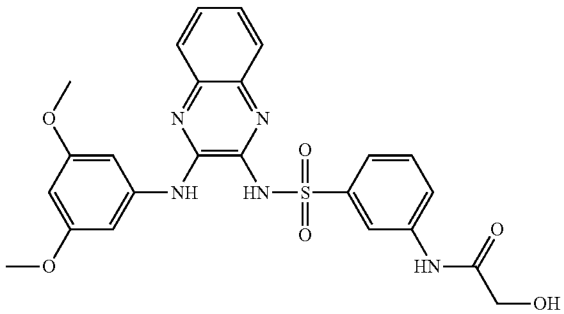 [SMILES: COc1cc(Nc2nc3ccccc3nc2NS(=O)(=O)c2cccc(NC(=O)CO)c2)cc(OC)c1] | N-(3-{[(3-{[3,5-bis(methoxy)phenyl]amino}quinoxalin-2-yl)amino]sulfonyl}phenyl)-2-hydroxyacetamide |
| 425 | 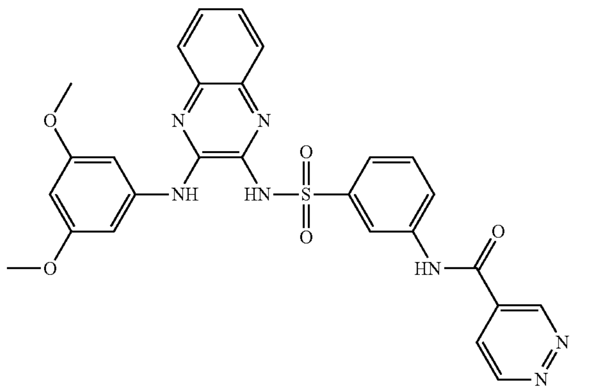 [SMILES: COc1cc(Nc2nc3ccccc3nc2NS(=O)(=O)c2cccc(NC(=O)c3ccnnc3)c2)cc(OC)c1] | N-(3-{[(3-{[3,5-bis(methoxy)phenyl]amino}quinoxalin-2-yl)amino]sulfonyl}phenyl)pyridazine-4-carboxamide |
| 426 | 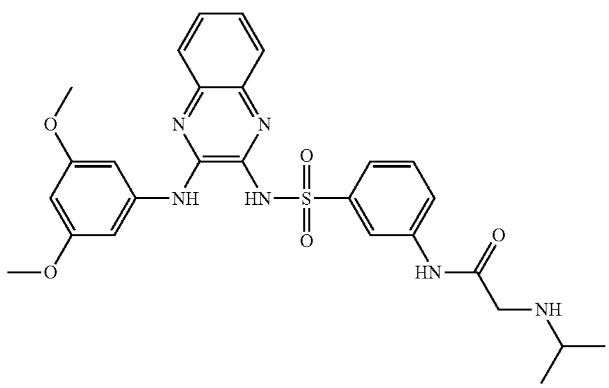 | N-(3-{[(3-{[3,5-bis(methoxy)phenyl]amino}quinoxalin-2-yl)amino]sulfonyl}phenyl)-N-2-(1-methylethyl)glycinamide |
| 427 | 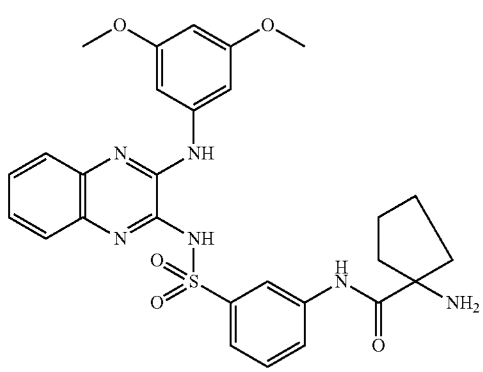 [SMILES: COc1cc(Nc2nc3ccccc3nc2NS(=O)(=O)c2cccc(NC(=O)C3(N)CCCC3)c2)cc(OC)c1] | 1-amino-N-(3-{[(3-{[3,5-bis(methoxy)phenyl]amino}quinoxalin-2-yl)amino]sulfonyl}phenyl)cyclopentanecarboxamide |

TABLE 1-continued

| Cpd. No. | Structure | Name |
|---|---|---|
| 428 | 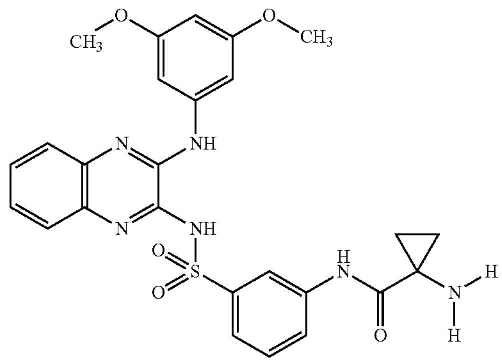 [SMILES: COc1cc(Nc2nc3ccccc3nc2NS(=O)(=O)c2cccc(NC(=O)C3(N)CC3)c2)cc(OC)c1] | 1-amino-N-(3-{[(3-{[3,5-bis(methoxy)phenyl]amino}quinoxalin-2-yl)amino]sulfonyl}phenyl)cyclopropanecarboxamide |
| 429 | 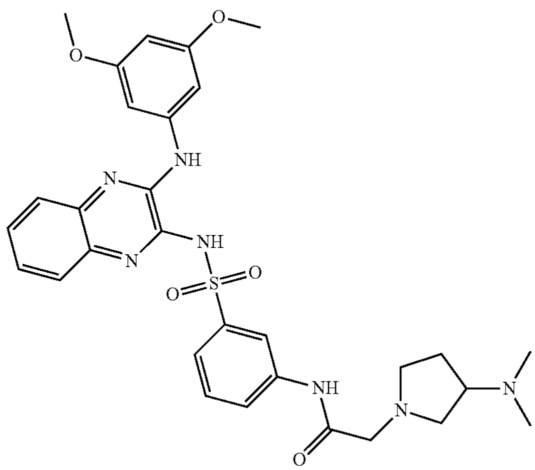 [SMILES: COc1cc(Nc2nc3ccccc3nc2NS(=O)(=O)c2cccc(NC(=O)CN3CCC(N(C)C)C3)c2)cc(OC)c1] | N-(3-{[(3-{(3,5-bis(methoxy)phenyl]amino}quinoxalin-2-yl)amino]sulfonyl}phenyl)-2-[3-(dimethylamino)pyrrolidin-1-yl]acetamide |
| 430 | 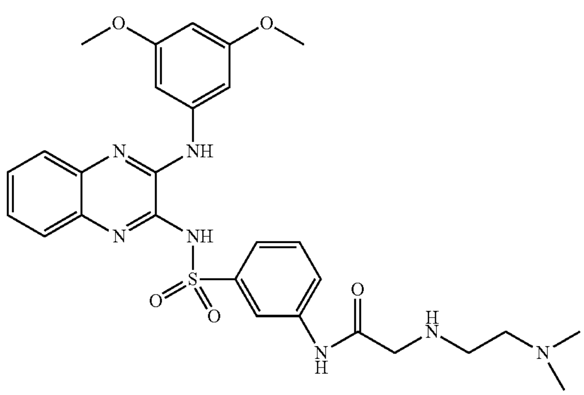 [SMILES: COc1cc(Nc2nc3ccccc3nc2NS(=O)(=O)c2cccc(NC(=O)CNCCN(C)C)c2)cc(OC)c1] | N-(3-{[(3-{[3,5-bis(methoxy)phenyl]amino}quinoxalin-2-yl)amino]sulfonyl}phenyl)-N-2-[2-(dimethylamino)ethyl)glycinamide |
| 431 | 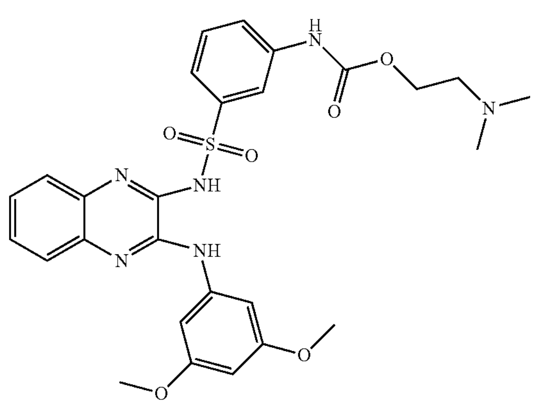 [SMILES: COc1cc(Nc2nc3ccccc3nc2NS(=O)(=O)c2cccc(NC(=O)OCCN(C)C)c2)cc(OC)c1] | 2-(dimethylamino)ethyl(3-{[(3-{[3,5-bis(methoxy)phenyl]amino}quinoxalin-2-yl)amino]sulfonyl}phenyl)carbamate |

TABLE 1-continued

| Cpd. No. | Structure | Name |
|---|---|---|
| 432 | 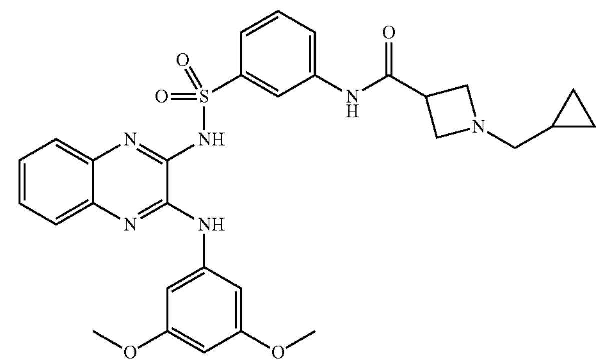 [SMILES: COc1cc(Nc2nc3ccccc3nc2NS(=O)(=O)c2cccc(NC(=O)C3CN(CC4CC4)C3)c2)cc(OC)c1] | N-(3-{[(3-{[3,5-bis(methoxy)phenyl]amino}quinoxalin-2-yl)amino]sulfonyl}phenyl)-1-(cyclopropylmethyl)azetidine-3-carboxamide |
| 433 | 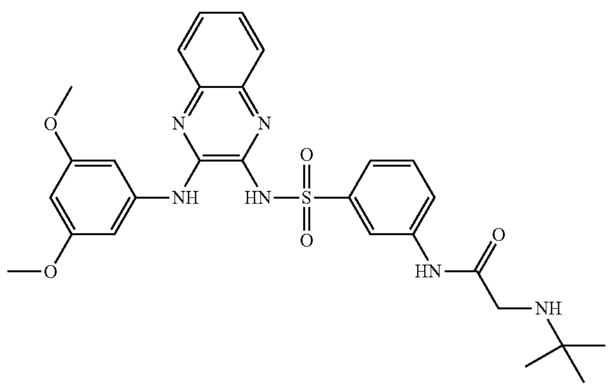 [SMILES: COc1cc(Nc2nc3ccccc3nc2NS(=O)(=O)c2cccc(NC(=O)CNC(C)(C)C)c2)cc(OC)c1] | N-(3-{[(3-{[3,5-bis(methoxy)phenyl]amino}quinoxalin-2-yl)amino]sulfonyl}phenyl)-N-2-(1,1-dimethylethyl)glycinamide |
| 434 | 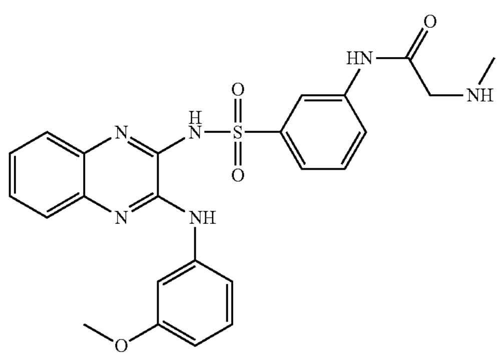 [SMILES: CNCC(=O)Nc1cccc(S(=O)(=O)Nc2nc3ccccc3nc2Nc2cccc(OC)c2)c1] | N-2-methyl-N-(3-{[(3-{[3-(methoxy)phenyl]amino}quinoxalin-2-yl)amino]sulfonyl}phenyl)glycinamide |
| 435 | 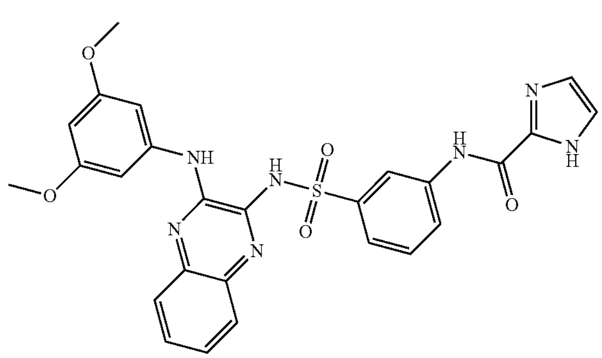 [SMILES: COc1cc(Nc2nc3ccccc3nc2NS(=O)(=O)c2cccc(NC(=O)c3ncc[nH]3)c2)cc(OC)c1] | N-(3-{[(3-{[3,5-bis(methoxy)phenyl]amino}quinoxalin-2-yl)amino]sulfonyl}phenyl)-1H-imidazole-2-carboxamide |

| Cpd. No. | Structure | Name |
| --- | --- | --- |
| 436 | 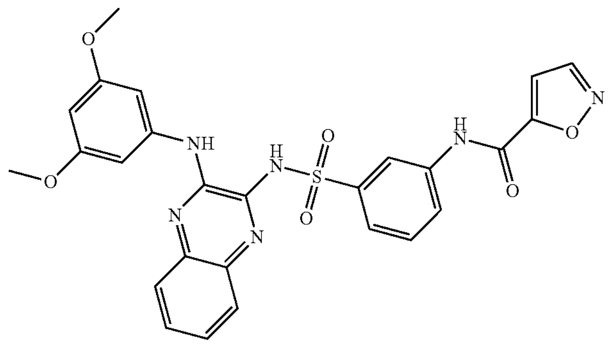 [SMILES: COc1cc(Nc2nc3ccccc3nc2NS(=O)(=O)c2cccc(NC(=O)c3ccno3)c2)cc(OC)c1] | N-(3-{[(3-{[3,5-bis(methoxy)phenyl]amino}quinoxalin-2-yl)amino]sulfonyl}phenyl)isoxazole-5-carboxamide |
| 437 | 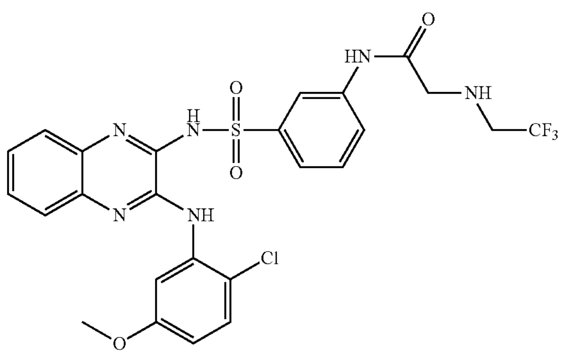 [SMILES: COc1ccc(Cl)c(Nc2nc3ccccc3nc2NS(=O)(=O)c2cccc(NC(=O)CNCC(F)(F)F)c2)c1] | N-(3-{[(3-{[2-chloro-5-(methoxy)phenyl]amino}quinoxalin-2-yl)amino]sulfonyl}phenyl)-N-2-(2,2,2-trifluoroethyl)glycinamide |
| 438 | 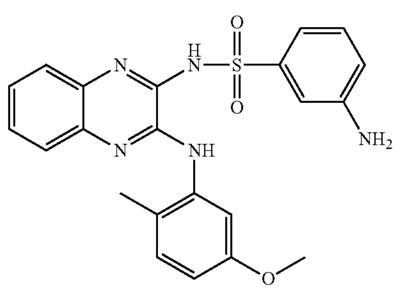 [SMILES: COc1ccc(C)c(Nc2nc3ccccc3nc2NS(=O)(=O)c2cccc(N)c2)c1] | 3-amino-N-(3-{[2-methyl-5-(methoxy)phenyl]amino}quinoxalin-2-yl)benzenesulfonamide |
| 439 | 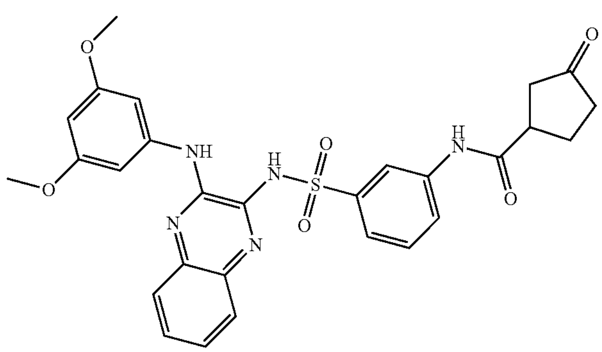 [SMILES: COc1cc(Nc2nc3ccccc3nc2NS(=O)(=O)c2cccc(NC(=O)C3CCC(=O)C3)c2)cc(OC)c1] | N-(3-{[(3-{[3,5-bis(methoxy)phenyl]amino}quinoxalin-2-yl)amino]sulfonyl}phenyl)-3-oxocyclopentanecarboxamide |

TABLE 1-continued

| Cpd. No. | Structure | Name |
|---|---|---|
| 440 | 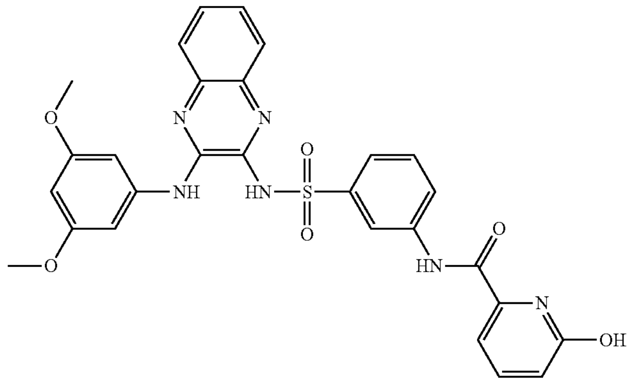 [SMILES: COc1cc(Nc2nc3ccccc3nc2NS(=O)(=O)c2cccc(NC(=O)c3cccc(O)n3)c2)cc(OC)c1] | N-(3-{[(3-{[3,5-bis(methoxy)phenyl]amino}quinoxalin-2-yl)amino]sulfonyl}phenyl)-6-hydroxypyridine-2-carboxamide |
| 441 | 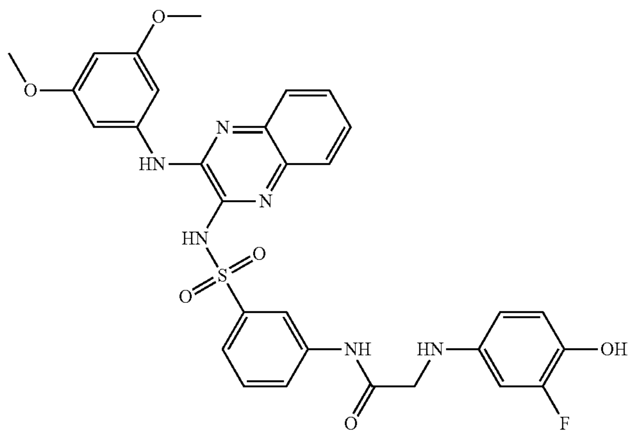 [SMILES: COc1cc(Nc2nc3ccccc3nc2NS(=O)(=O)c2cccc(NC(=O)CNc3ccc(O)c(F)c3)c2)cc(OC)c1] | N-(3-{[(3-{[3,5-bis(methoxy)phenyl]amino}quinoxalin-2-yl)amino]sulfonyl}phenyl)-N-2-(3-fluoro-4-hydroxyphenyl)glycinamide |
| 442 | 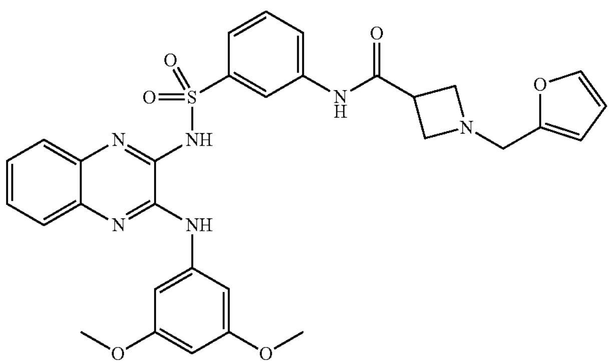 [SMILES: COc1cc(Nc2nc3ccccc3nc2NS(=O)(=O)c2cccc(NC(=O)C3CN(Cc4ccco4)C3)c2)cc(OC)c1] | N-(3-{[(3-{[3,5-bis(methoxy)phenyl]amino}quinoxalin-2-yl)amino]sulfonyl}phenyl)-1-(furan-2-ylmethyl)azetidine-3-carboxamide |
| 443 | 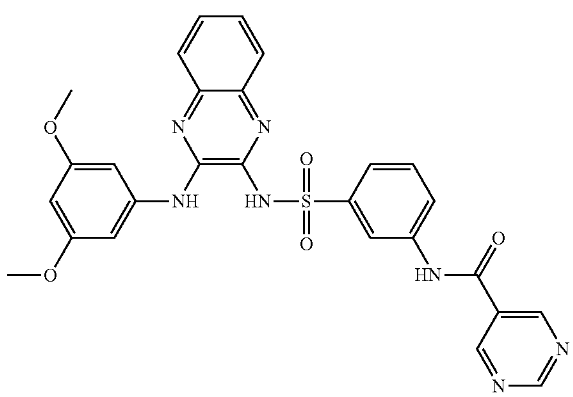 [SMILES: COc1cc(Nc2nc3ccccc3nc2NS(=O)(=O)c2cccc(NC(=O)c3cncnc3)c2)cc(OC)c1] | N-(3-{[(3-{[3,5-bis(methoxy)phenyl]amino}quinoxalin-2-yl)amino]sulfonyl}phenyl)pyrimidine-5-carboxamide |

TABLE 1-continued

| Cpd. No. | Structure | Name |
|---|---|---|
| 444 | 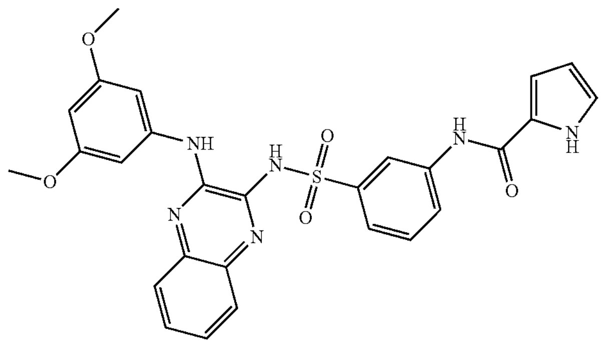 [SMILES: COc1cc(Nc2nc3ccccc3nc2NS(=O)(=O)c2cccc(NC(=O)c3ccc[nH]3)c2)cc(OC)c1] | N-(3-{[(3-{[3,5-bis(methoxy)phenyl]amino}quinoxalin-2-yl)amino]sulfonyl}phenyl)-1H-pyrrole-2-carboxamide |
| 445 | 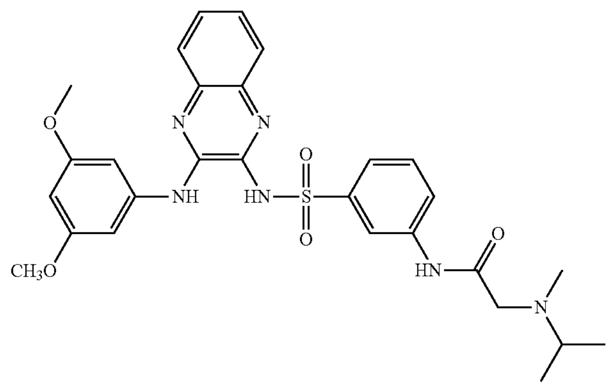 | N-(3-{[(3-{[3,5-bis(methoxy)phenyl]amino}quinoxalin-2-yl)amino]sulfonyl}phenyl)-N-2-methyl-N-2-(1-methylethyl)glycinamide |
| 446 | 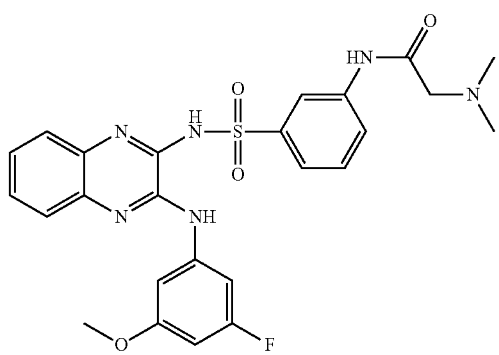 [SMILES: COc1cc(F)cc(Nc2nc3ccccc3nc2NS(=O)(=O)c2cccc(NC(=O)CN(C)C)c2)c1] | N-(3-{[(3-{[3-fluoro-5-(methoxy)phenyl]amino}quinoxalin-2-yl)amino]sulfonyl}phenyl)-N-2-,N-2-dimethylglycinamide |
| 447 | 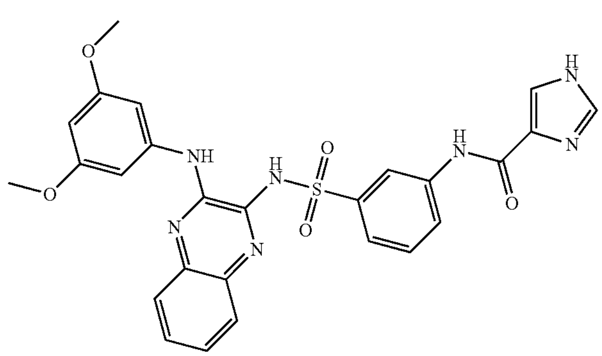 [SMILES: COc1cc(Nc2nc3ccccc3nc2NS(=O)(=O)c2cccc(NC(=O)c3c[nH]cn3)c2)cc(OC)c1] | N-(3-{[(3-{[3,5-bis(methoxy)phenyl]amino}quinoxalin-2-yl)amino]sulfonyl}phenyl)-1H-imidazole-4-carboxamide |

TABLE 1-continued

| Cpd. No. | Structure | Name |
|---|---|---|
| 448 | 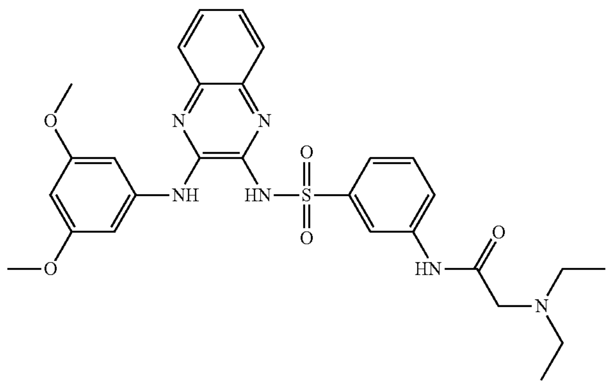 [SMILES: CCN(CC)CC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-,N-2-diethylglycinamide |
| 449 | 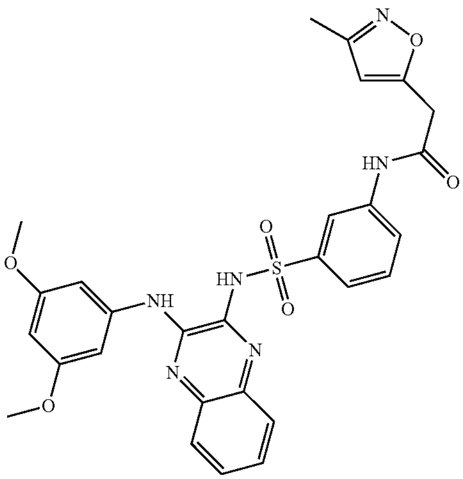 [SMILES: COc1cc(Nc2nc3ccccc3nc2NS(=O)(=O)c2cccc(NC(=O)Cc3cc(C)no3)c2)cc(OC)c1] | N-(3-{[(3-{[3,5-bis(methoxy)phenyl]amino}quinoxalin-2-yl)amino]sulfonyl}phenyl)-2-(3-methylisoxazol-5-yl)acetamide |
| 450 | 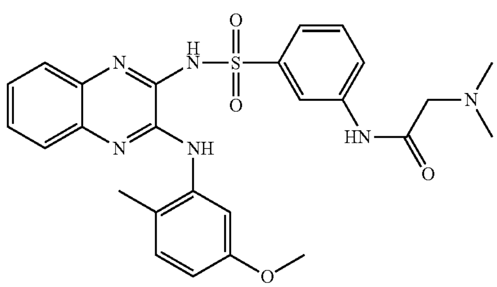 | N-2-,N-2-dimethyl-N-(3-{[(3-{[2-methyl-5-(methoxy)phenyl]amino}quinoxalin-2-yl)amino]sulfonyl}phenyl)glycinamide |
| 451 | 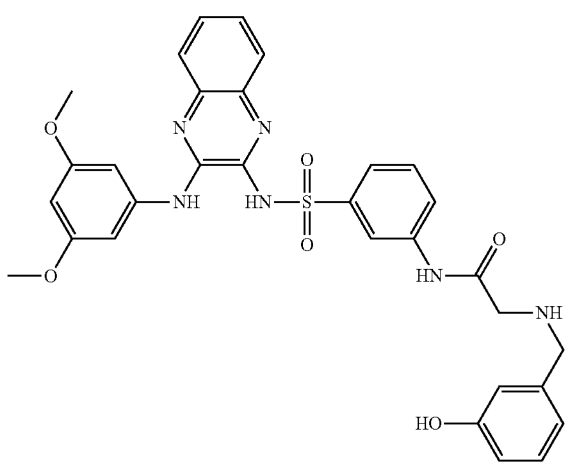 [SMILES: COc1cc(Nc2nc3ccccc3nc2NS(=O)(=O)c2cccc(NC(=O)CNCc3cccc(O)c3)c2)cc(OC)c1] | N-(3-{[(3-{[3,5-bis(methoxy)phenyl]amino}quinoxalin-2-yl)amino]sulfonyl}phenyl)-N-2-[(3-hydroxyphenyl)methyl]glycinamide |

TABLE 1-continued

| Cpd. No. | Structure | Name |
|---|---|---|
| 452 | 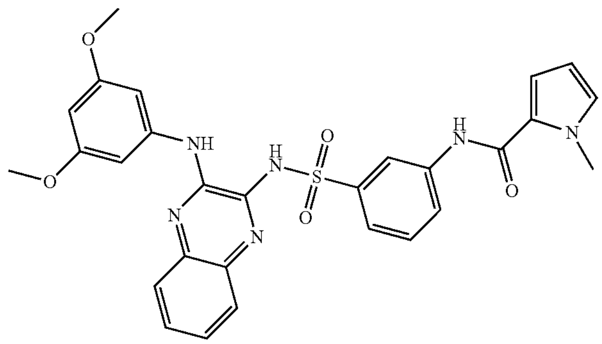 [SMILES: COc1cc(Nc2nc3ccccc3nc2NS(=O)(=O)c2cccc(NC(=O)c3cccn3C)c2)cc(OC)c1] | N-(3-{[(3-{[3,5-bis(methoxy)phenyl]amino}quinoxalin-2-yl)amino]sulfonyl}phenyl)-1-methyl-1H-pyrrole-2-carboxamide |
| 453 | 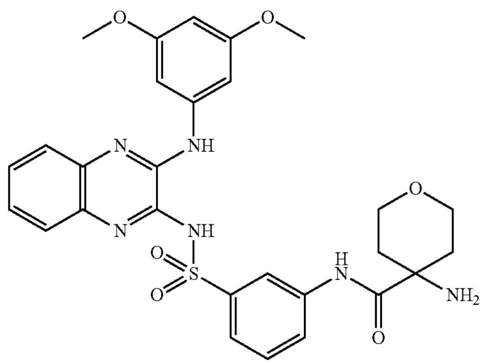 [SMILES: COc1cc(Nc2nc3ccccc3nc2NS(=O)(=O)c2cccc(NC(=O)C3(N)CCOCC3)c2)cc(OC)c1] | 4-amino-N-(3-{[(3-{[3,5-bis(methoxy)phenyl]amino}quinoxalin-2-yl)amino]sulfonyl}phenyl)tetrahydro-2H-pyran-4-carboxamide |
| 454 | 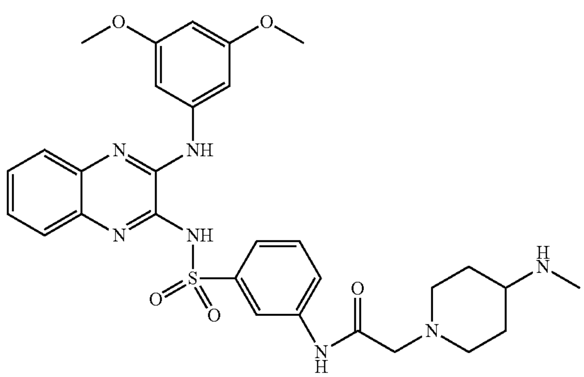 [SMILES: CNC1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methoxy)phenyl]amino}quinoxalin-2-yl)amino]sulfonyl}phenyl)-2-[4-(methylamino)piperidin-1-yl]acetamide |
| 455 | 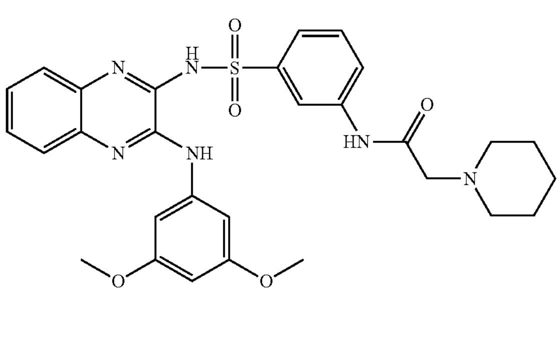 [SMILES: COc1cc(Nc2nc3ccccc3nc2NS(=O)(=O)c2cccc(NC(=O)CN3CCCCC3)c2)cc(OC)c1] | N-(3-{[(3-{[3,5-bis(methoxy)phenyl]amino}quinoxalin-2-yl)amino]sulfonyl}phenyl)-2-piperidin-1-ylacetamide |

TABLE 1-continued

| Cpd. No. | Structure | Name |
|---|---|---|
| 456 | 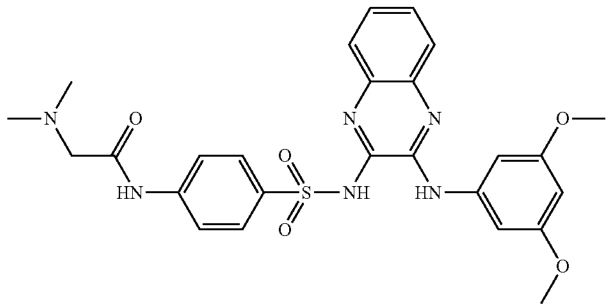 | N-(4-{[(3-{[3,5-bis(methoxy)phenyl]amino}quinoxalin-2-yl)amino]sulfonyl}phenyl)-N-2-,N-2-dimethylglycinamide |
| 457 | 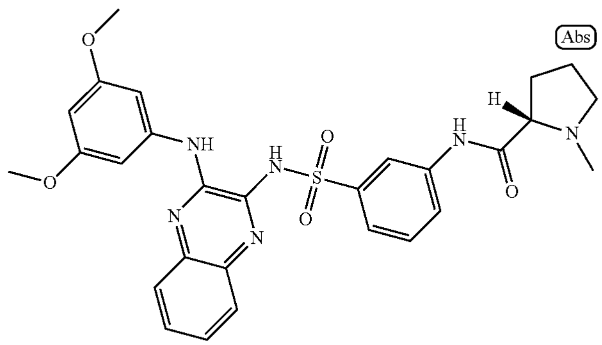 [SMILES: COc1cc(Nc2nc3ccccc3nc2NS(=O)(=O)c2cccc(NC(=O)[C@@H]3CCCN3C)c2)cc(OC)c1] | N-(3-{[(3-{[3,5-bis(methoxy)phenyl]amino}quinoxalin-2-yl)amino]sulfonyl}phenyl)-1-methyl-L-prolinamide |
| 458 | 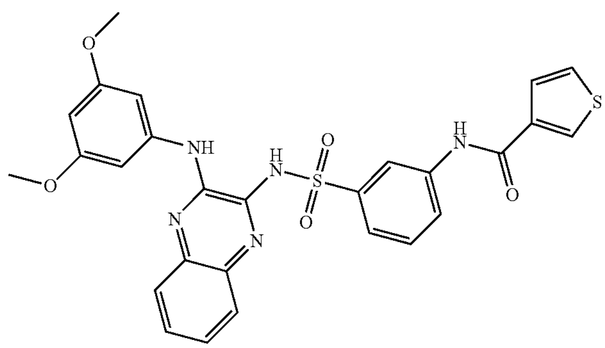 [SMILES: COc1cc(Nc2nc3ccccc3nc2NS(=O)(=O)c2cccc(NC(=O)c3ccsc3)c2)cc(OC)c1] | N-(3-{[(3-{[3,5-bis(methoxy)phenyl]amino}quinoxalin-2-yl)amino]sulfonyl}phenyl)thiophene-3-carboxamide |
| 459 | 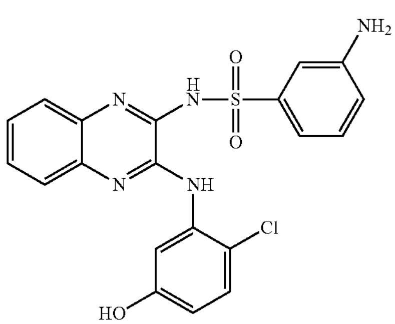 | 3-amino-N-{3-[(2-chloro-5-hydroxyphenyl)amino]quinoxalin-2-yl}benzenesulfonamide |

| Cpd. No. | Structure | Name |
|---|---|---|
| 460 | 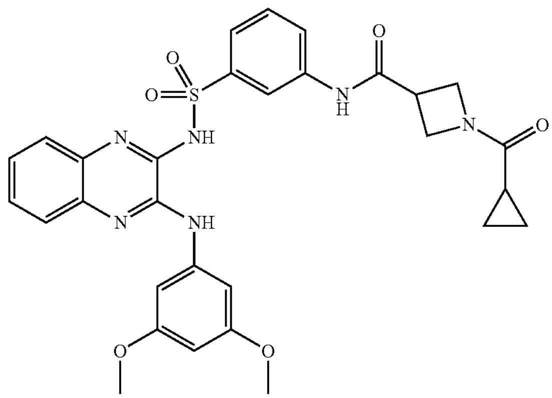 [SMILES: COc1cc(Nc2nc3ccccc3nc2NS(=O)(=O)c2cccc(NC(=O)C3CN(C(=O)C4CC4)C3)c2)cc(OC)c1] | N-(3-{[(3-{[3,5-bis(methoxy)phenyl]amino}quinoxalin-2-yl)amino]sulfonyl}phenyl)-1-(cyclopropylcarbonyl)azetidine-3-carboxamide |
| 461 | 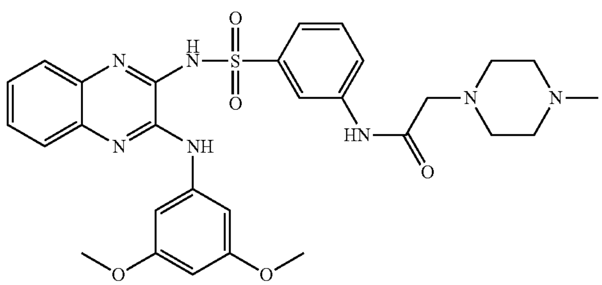 [SMILES: COc1cc(Nc2nc3ccccc3nc2NS(=O)(=O)c2cccc(NC(=O)CN3CCN(C)CC3)c2)cc(OC)c1] | N-(3-{[(3-{[3,5-bis(methoxy)phenyl]amino}quinoxalin-2-yl)amino]sulfonyl}phenyl)-2-(4-methylpiperazin-1-yl)acetamide |
| 462 | 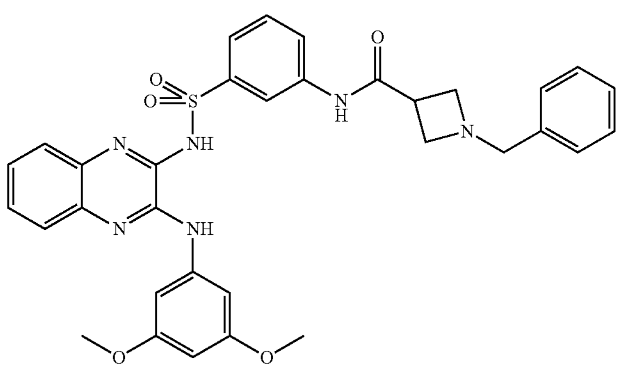 [SMILES: COc1cc(Nc2nc3ccccc3nc2NS(=O)(=O)c2cccc(NC(=O)C3CN(Cc4ccccc4)C3)c2)cc(OC)c1] | N-(3-{[(3-{[3,5-bis(methoxy)phenyl]amino}quinoxalin-2-yl)amino]sulfonyl}phenyl)-1-(phenylmethyl)azetidine-3-carboxamide |
| 463 | 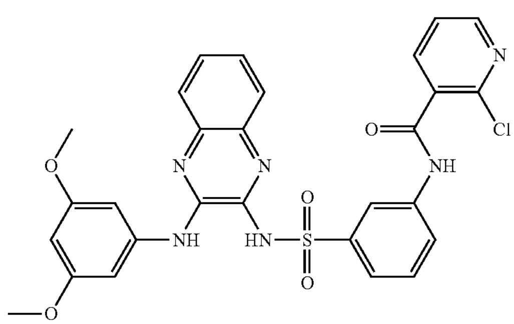 [SMILES: COc1cc(Nc2nc3ccccc3nc2NS(=O)(=O)c2cccc(NC(=O)c3cccnc3Cl)c2)cc(OC)c1] | N-(3-{[(3-{[3,5-bis(methoxy)phenyl]amino}quinoxalin-2-yl)amino]sulfonyl}phenyl)-2-chloropyridine-3-carboxamide |

TABLE 1-continued

| Cpd. No. | Structure | Name |
|---|---|---|
| 464 | 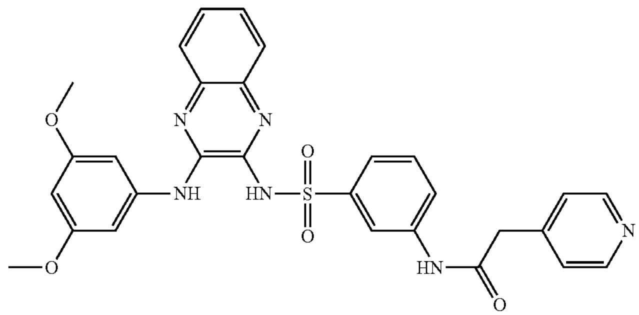 [SMILES: COc1cc(Nc2nc3ccccc3nc2NS(=O)(=O)c2cccc(NC(=O)Cc3ccncc3)c2)cc(OC)c1] | N-(3-{[(3-{[3,5-bis(methoxy)phenyl]amino}quinoxalin-2-yl)amino]sulfonyl}phenyl)-2-pyridin-4-ylacetamide |
| 465 | 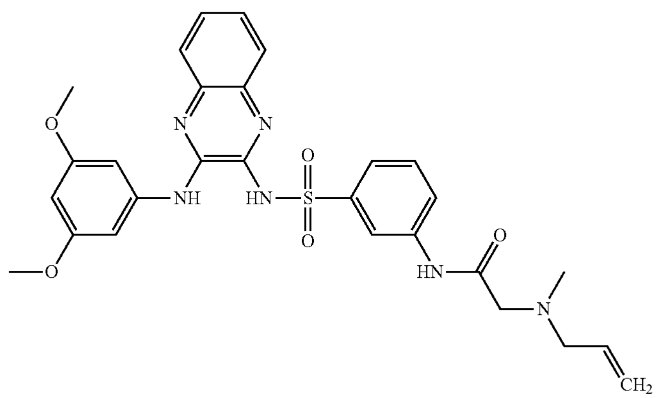 [SMILES: C=CCN(C)CC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-methyl-N-2-prop-2-en-1-ylglycinamide |
| 466 | 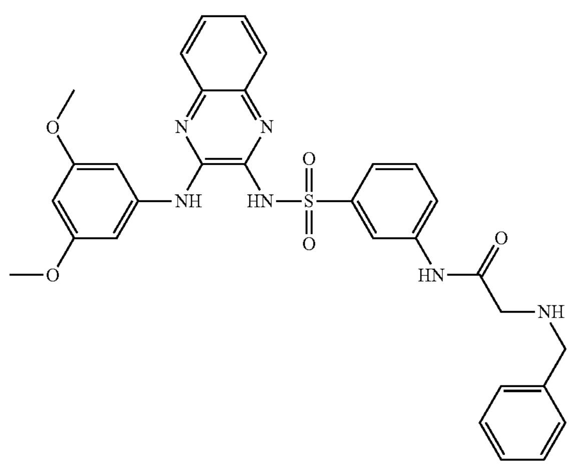 | N-(3-{[(3-{[3,5-bis(methoxy)phenyl]amino}quinoxalin-2-yl)amino]sulfonyl}phenyl)-N-2-(phenylmethyl)glycinamide |
| 467 | 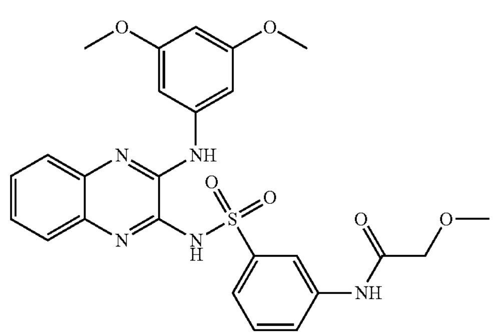 [SMILES: COCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-2-(methoxy)acetamide |

TABLE 1-continued

| Cpd. No. | Structure | Name |
|---|---|---|
| 468 | 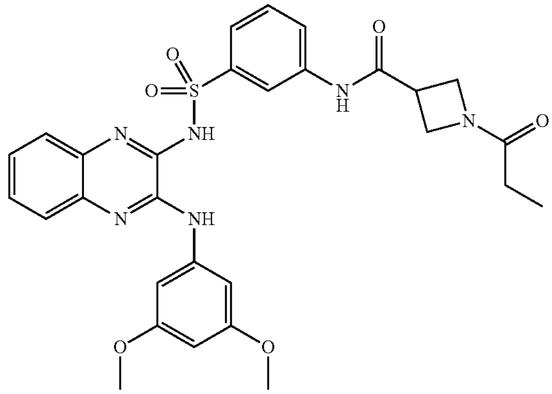 [SMILES: CCC(=O)N1CC(C(=O)Nc2cccc(S(=O)(=O)Nc3nc4ccccc4nc3Nc3cc(OC)cc(OC)c3)c2)C1] | N-(3-{[(3-{[3,5-bis(methoxy)phenyl]amino}quinoxalin-2-yl)amino]sulfonyl}phenyl)-1-propanoylazetidine-3-carboxamide |
| 469 | 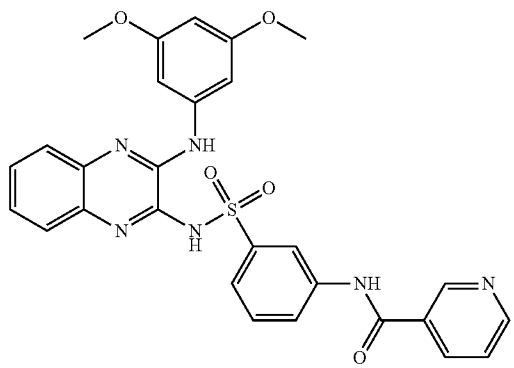 [SMILES: COc1cc(Nc2nc3ccccc3nc2NS(=O)(=O)c2cccc(NC(=O)c3cccnc3)c2)cc(OC)c1] | N-(3-{[(3-{[3,5-bis(methoxy)phenyl]amino}quinoxalin-2-yl)amino]sulfonyl}phenyl)pyridine-3-carboxamide |
| 470 | 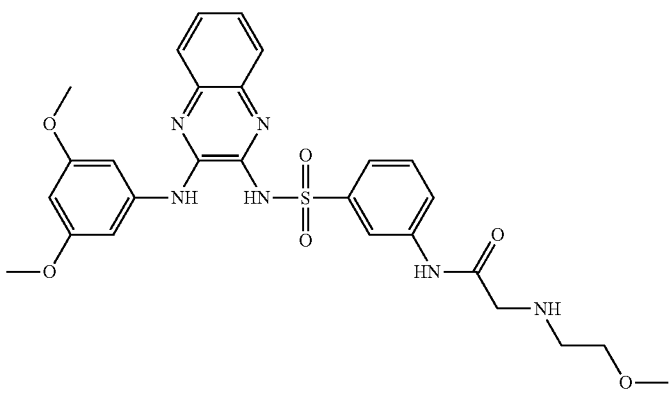 | N-(3-{[(3-{[3,5-bis(methoxy)phenyl]amino}quinoxalin-2-yl)amino]sulfonyl}phenyl)-N-2-[2-(methoxy)ethyl]glycinamide |
| 471 | 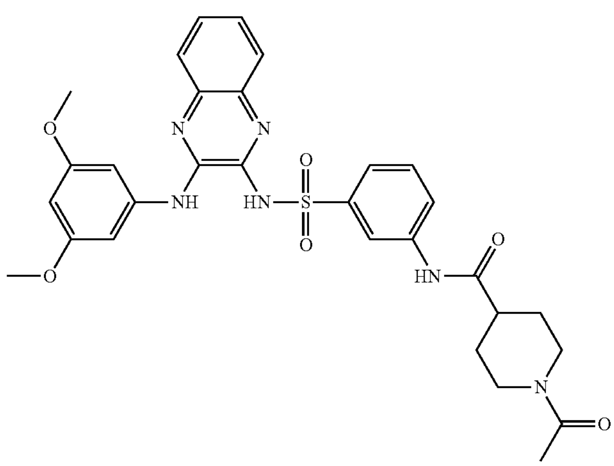 [SMILES: COc1cc(Nc2nc3ccccc3nc2NS(=O)(=O)c2cccc(NC(=O)C3CCN(C(C)=O)CC3)c2)cc(OC)c1] | 1-acetyl-N-(3-{[(3-{[3,5-bis(methoxy)phenyl]amino}quinoxalin-2-yl)amino]sulfonyl}phenyl)piperidine-4-carboxamide |

TABLE 1-continued

| Cpd. No. | Structure | Name |
|---|---|---|
| 472 | 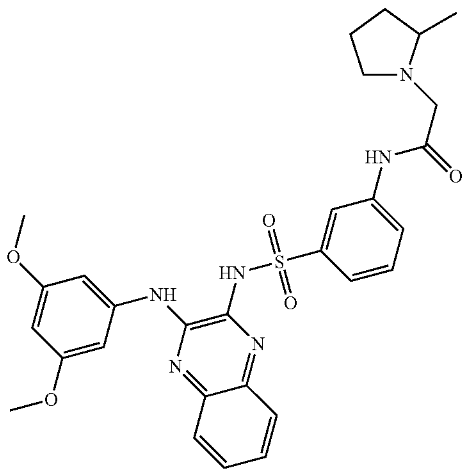 | N-(3-{[(3-{[3,5-his(methoxy)phenyl]amino}quinoxalin-2-yl)amino]sulfonyl}phenyl)-2-(2-methylpyrrolidin-1-yl)acetamide |
| 473 | 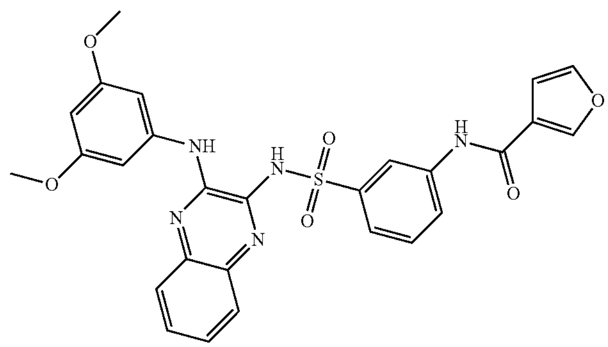 [SMILES: COc1cc(Nc2nc3ccccc3nc2NS(=O)(=O)c2cccc(NC(=O)c3ccoc3)c2)cc(OC)c1] | N-(3-{[(3-{[3,5-bis(methoxy)phenyl]amino}quinoxalin-2-yl)amino]sulfonyl}phenyl)furan-3-carboxamide |
| 474 | 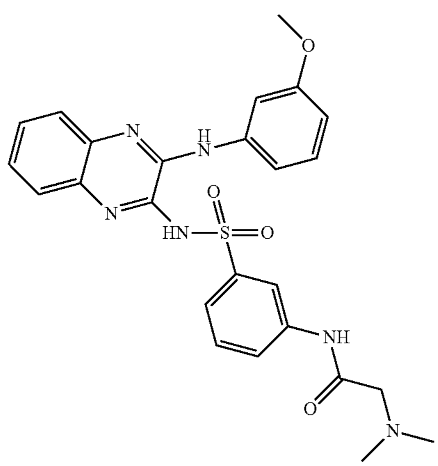 [SMILES: COc1cccc(Nc2nc3ccccc3nc2NS(=O)(=O)c2cccc(NC(=O)CN(C)C)c2)c1] | N-2-,N-2-dimethyl-N-(3-{[(3-{[3-(methoxy)phenyl]amino}quinoxalin-2-yl)amino]sulfonyl}phenyl)glycinamide |
| 475 | 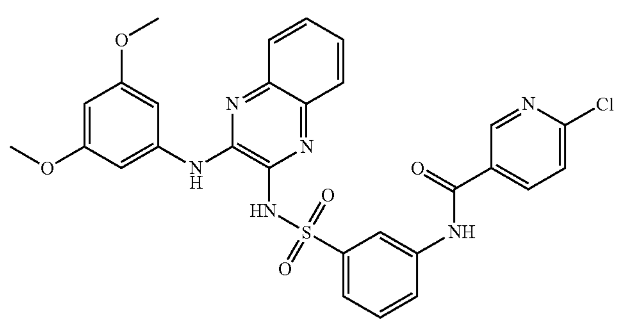 [SMILES: COc1cc(Nc2nc3ccccc3nc2NS(=O)(=O)c2cccc(NC(=O)c3ccc(Cl)nc3)c2)cc(OC)c1] | N-(3-{[(3-{[3,5-bis(methoxy)phenyl]amino}quinoxalin-2-yl)amino]sulfonyl}phenyl)-6-chloropyridine-3-carboxamide |

| Cpd. No. | Structure | Name |
|---|---|---|
| 476 | 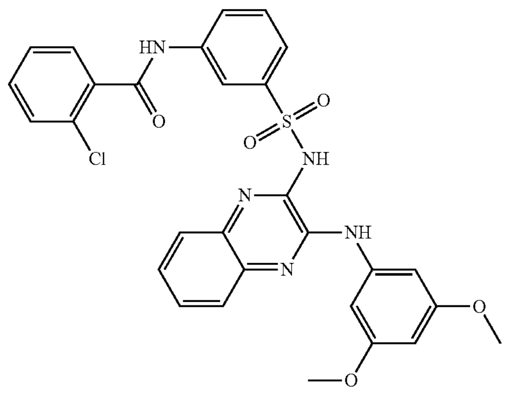 | N-(3-{[(3-{[3,5-bis(methoxy)phenyl]amino}quinoxalin-2-yl)amino]sulfonyl}phenyl)-2-chlorobenzamide |
| 477 | 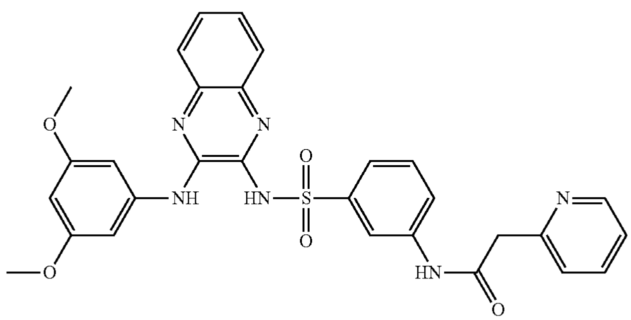 [SMILES: COc1cc(Nc2nc3ccccc3nc2NS(=O)(=O)c2cccc(NC(=O)Cc3ccccn3)c2)cc(OC)c1] | N-(3-{[(3-{[3,5-bis(methoxy)phenyl]amino}quinoxalin-2-yl)amino]sulfonyl}phenyl)-2-pyridin-2-ylacetamide |
| 478 | 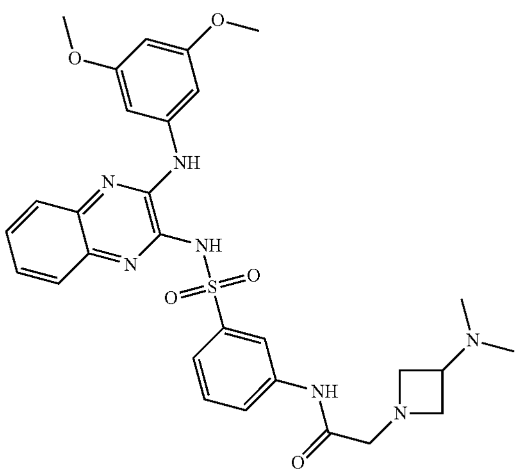 [SMILES: COc1cc(Nc2nc3ccccc3nc2NS(=O)(=O)c2cccc(NC(=O)CN3CC(N(C)C)C3)c2)cc(OC)c1] | N-(3-{[(3-{[3,5-bis(methoxy)phenyl]amino}quinoxalin-2-yl)amino]sulfonyl}phenyl)-2-[3-(dimethylamino)azetidin-1-yl]acetamide |
| 479 | 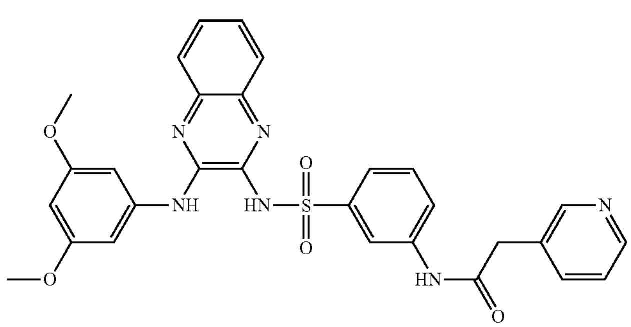 [SMILES: COc1cc(Nc2nc3ccccc3nc2NS(=O)(=O)c2cccc(NC(=O)Cc3cccnc3)c2)cc(OC)c1] | N-(3-{[(3-{[3,5-bis(methoxy)phenyl]amino}quinoxalin-2-yl)amino]sulfonyl}phenyl)-2-pyridin-3-ylacetamide |

TABLE 1-continued
| Cpd. No. | Structure | Name |
| --- | --- | --- |
| 480 | 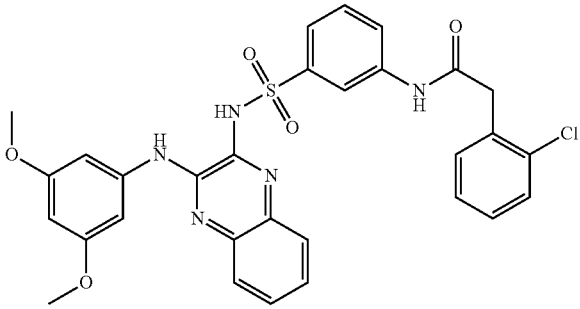 [SMILES: COc1cc(Nc2nc3ccccc3nc2NS(=O)(=O)c2cccc(NC(=O)Cc3ccccc3Cl)c2)cc(OC)c1] | N-(3-{[(3-{[3,5-bis(methoxy)phenyl]amino}quinoxalin-2-yl)amino]sulfonyl}phenyl)-2-(2-chlorophenyl)acetamide |
| 481 | 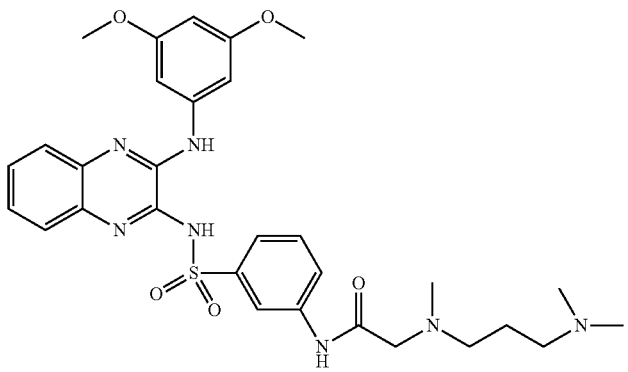 [SMILES: COc1cc(Nc2nc3ccccc3nc2NS(=O)(=O)c2cccc(NC(=O)CN(C)CCCN(C)C)c2)cc(OC)c1] | N-(3-{[(3-{[3,5-bis(methoxy)phenyl]amino}quinoxalin-2-yl)amino]sulfonyl}phenyl)-N-2-[3-(dimethylamino)propyl]-N-2-methylglycinamide |
| 482 | 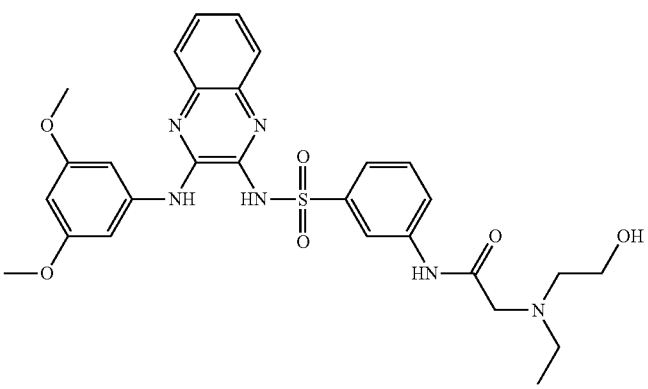 [SMILES: CCN(CCO)CC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-ethyl-N-2-(2-hydroxyethyl)glycinamide |

TABLE 1-continued

| Cpd. No. | Structure | Name |
|---|---|---|
| 483 | 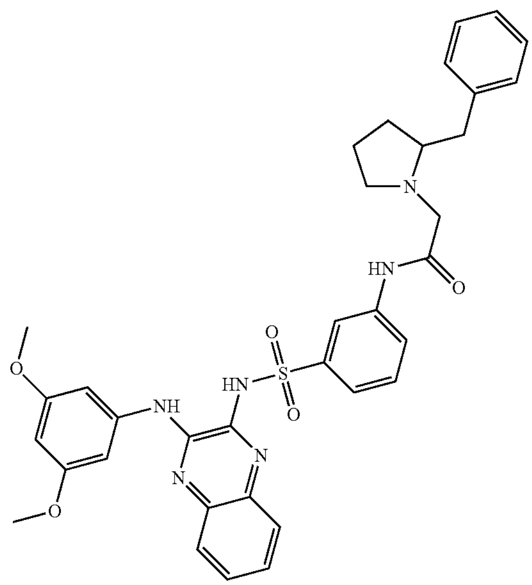 [SMILES: COc1cc(Nc2nc3ccccc3nc2NS(=O)(=O)c2cccc(NC(=O)CN3CCCC3Cc3ccccc3)c2)cc(OC)c1] | N-(3-{[(3-{[3,5-bis(methoxy)phenyl]amino}quinoxalin-2-yl)amino]sulfonyl}phenyl)-2-[2-(phenylmethyl)pyrrolidin-1-yl]acetamide |
| 484 | 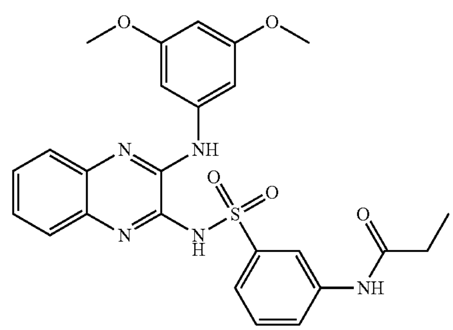 [SMILES: CCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)propanamide |
| 485 | 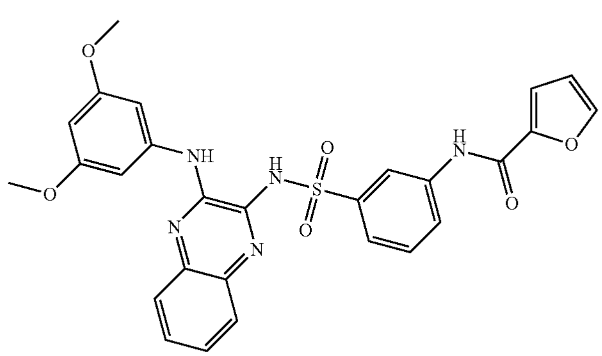 [SMILES: COc1cc(Nc2nc3ccccc3nc2NS(=O)(=O)c2cccc(NC(=O)c3ccco3)c2)cc(OC)c1] | N-(3-{[(3-{[3,5-bis(methoxy)phenyl]amino}quinoxalin-2-yl)amino]sulfonyl}phenyl)furan-2-carboxamide |

TABLE 1-continued

| Cpd. No. | Structure | Name |
|---|---|---|
| 486 | 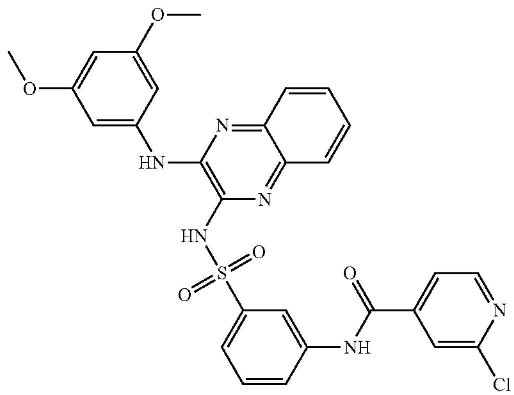 [SMILES: COc1cc(Nc2nc3ccccc3nc2NS(=O)(=O)c2cccc(NC(=O)c3ccnc(Cl)c3)c2)cc(OC)c1] | N-(3-{[(3-{[3,5-bis(methoxy)phenyl]amino}quinoxalin-2-yl)amino]sulfonyl}phenyl)-2-chloropyridine-4-carboxamide |
| 487 | 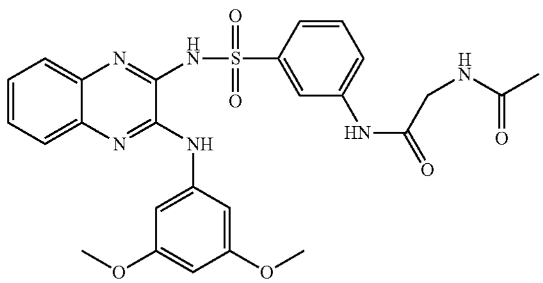 [SMILES: COc1cc(Nc2nc3ccccc3nc2NS(=O)(=O)c2cccc(NC(=O)CNC(C)=O)c2)cc(OC)c1] | N-2-acetyl-N-(3-{[(3-{[3,5-bis(methoxy)phenyl]amino}quinoxalin-2-yl)amino]sulfonyl}phenyl)glycinamide |
| 488 | 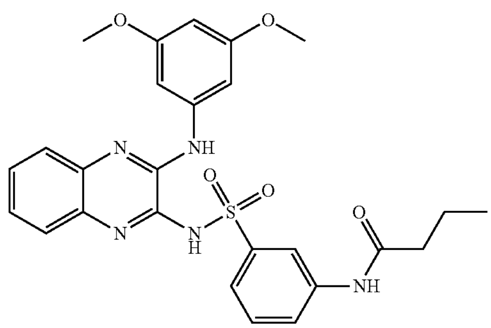 | N-(3-{[(3-{[3,5-bis(methoxy)phenyl]amino}quinoxalin-2-yl)amino]sulfonyl}phenyl)butanamide |
| 489 | 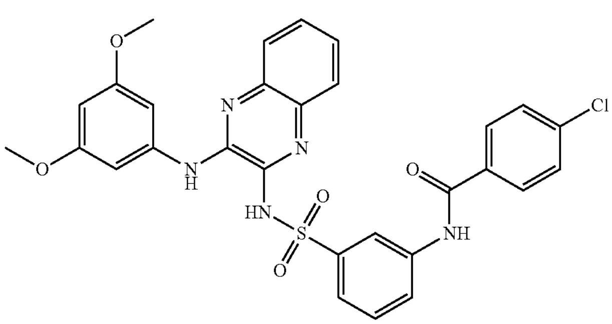 [SMILES: COc1cc(Nc2nc3ccccc3nc2NS(=O)(=O)c2cccc(NC(=O)c3ccc(Cl)cc3)c2)cc(OC)c1] | N-(3-{[(3-{[3,5-bis(methoxy)phenyl]amino}quinoxalin-2-yl)amino]sulfonyl}phenyl)-4-chlorobenzamide |

TABLE 1-continued

| Cpd. No. | Structure | Name |
|---|---|---|
| 490 | 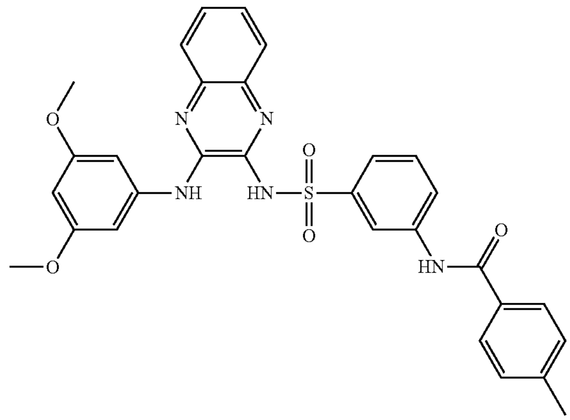 | N-(3-{[(3-{[3,5-bis(methoxy)phen-yl]amino}quinoxalin-2-yl)amino]sulfonyl}phenyl)-4-methylbenzamide |
| 491 | 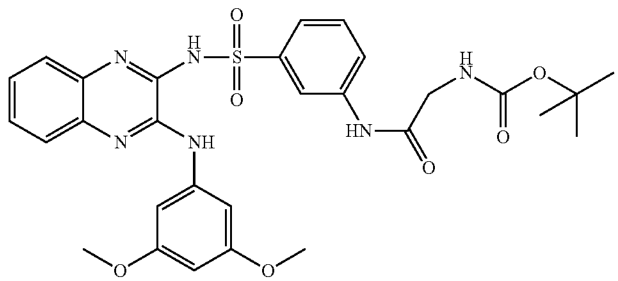 [SMILES: COc1cc(Nc2nc3ccccc3nc2NS(=O)(=O)c2cccc(NC(=O)CNC(=O)OC(C)(C)C)c2)cc(OC)c1] | 1,1-dimethylethyl{2-[(3-{[(3-{[3,5-bis(methoxy)phenyl]amino}quin-oxalin-2-yl)amino]sulfonyl}phen-yl)amino]-2-oxoethyl}carbamate |
| 492 | 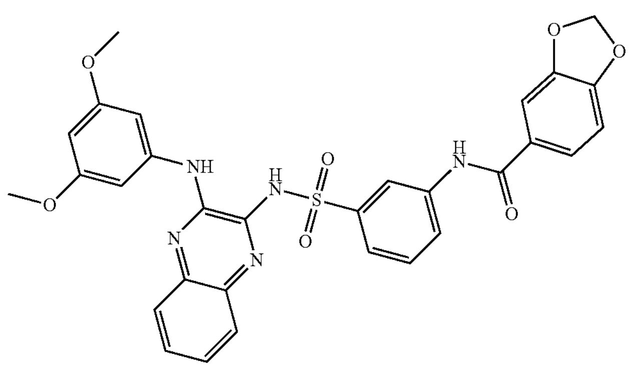 [SMILES: COc1cc(Nc2nc3ccccc3nc2NS(=O)(=O)c2cccc(NC(=O)c3ccc4c(c3)OCO4)c2)cc(OC)c1] | N-(3-{[(3-{[3,5-bis(methoxy)phen-yl]amino}quinoxalin-2-yl)amino]sulfonyl}phenyl)-1,3-benzodioxole-5-carboxamide |
| 493 | 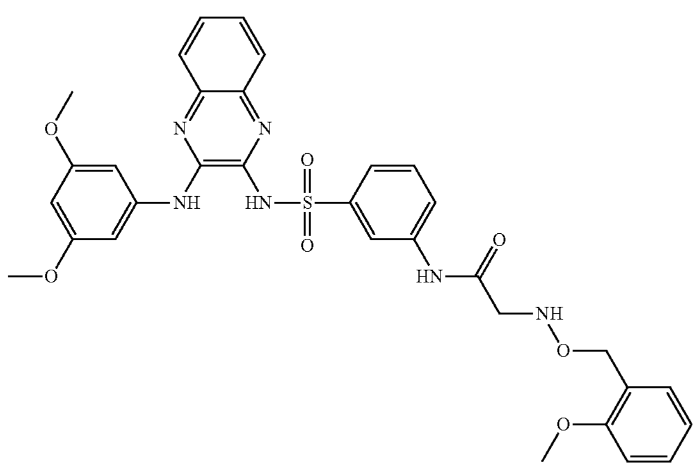 [SMILES: COc1cc(Nc2nc3ccccc3nc2NS(=O)(=O)c2cccc(NC(=O)CNOCc3ccccc3OC)c2)cc(OC)c1] | N-(3-{[(3-{[3,5-bis(methoxy)phen-yl]amino}quinoxalin-2-yl)amino]sulfonyl}phenyl)-N-2-({[2-(methoxy)phenyl]meth-yl}oxy)glycinamide |

TABLE 1-continued

| Cpd. No. | Structure | Name |
|---|---|---|
| 494 | 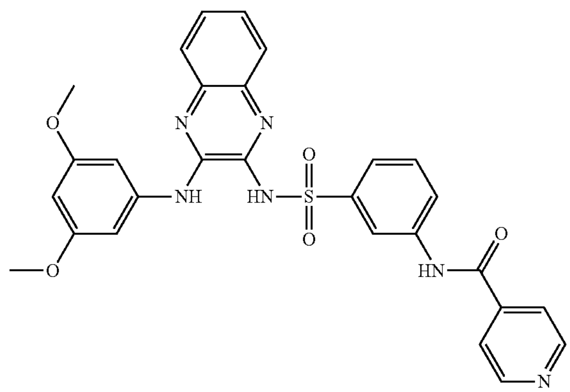 [SMILES: COc1cc(Nc2nc3ccccc3nc2NS(=O)(=O)c2cccc(NC(=O)c3ccncc3)c2)cc(OC)c1] | N-(3-{[(3-{[3,5-bis(methoxy)phenyl]amino}quinoxalin-2-yl)amino]sulfonyl}phenyl)pyridine-4-carboxamide |
| 495 | 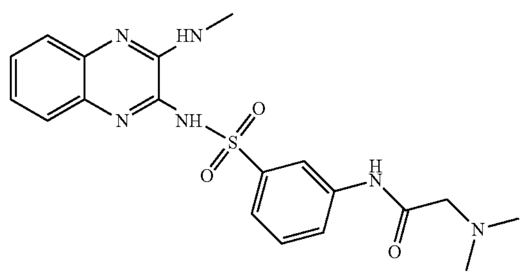 [SMILES: CNc1nc2ccccc2nc1NS(=O)(=O)c1cccc(NC(=O)CN(C)C)c1] | N-(3-{[(3-{[4-fluoro-3-(methoxy)phenyl]amino}quinoxalin-2-yl)amino]sulfonyl}phenyl)-N-2-,N-2-dimethylglycinamide |
| 496 | 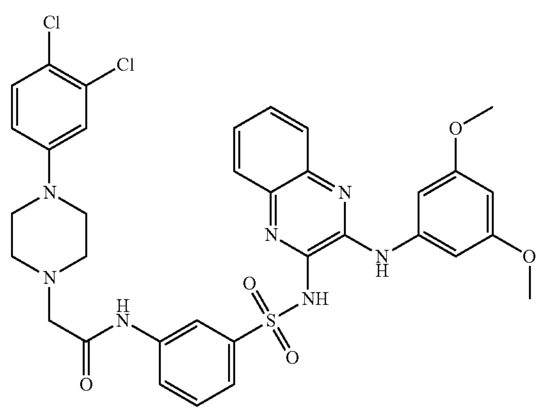 [SMILES: COc1cc(Nc2nc3ccccc3nc2NS(=O)(=O)c2cccc(NC(=O)CN3CCN(c4ccc(Cl)c(Cl)c4)CC3)c2)cc(OC)c1] | N-(3-{[(3-{[3,5-bis(methoxy)phenyl]amino}quinoxalin-2-yl)amino]sulfonyl}phenyl)-2-[4-(3,4-dichlorophenyl)piperazin-1-yl]acetamide |
| 497 | 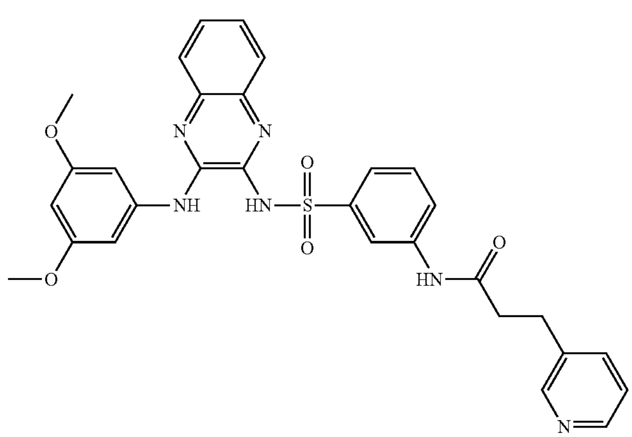 [SMILES: COc1cc(Nc2nc3ccccc3nc2NS(=O)(=O)c2cccc(NC(=O)CCc3cccnc3)c2)cc(OC)c1] | N-(3-{[(3-{[3,5-bis(methoxy)phenyl]amino}quinoxalin-2-yl)amino]sulfonyl}phenyl)-3-pyridin-3-ylpropanamide |

TABLE 1-continued

| Cpd. No. | Structure | Name |
|---|---|---|
| 498 | 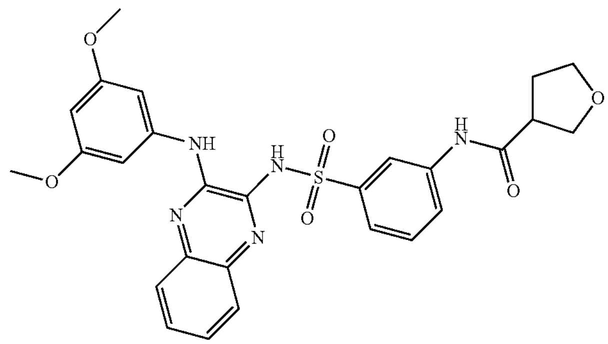 [SMILES: COc1cc(Nc2nc3ccccc3nc2NS(=O)(=O)c2cccc(NC(=O)C3CCOC3)c2)cc(OC)c1] | N-(3-{[(3-{[3,5-bis(methoxy)phenyl]amino}quinoxalin-2-yl)amino]sulfonyl}phenyl)tetrahydrofuran-3-carboxamide |
| 499 | 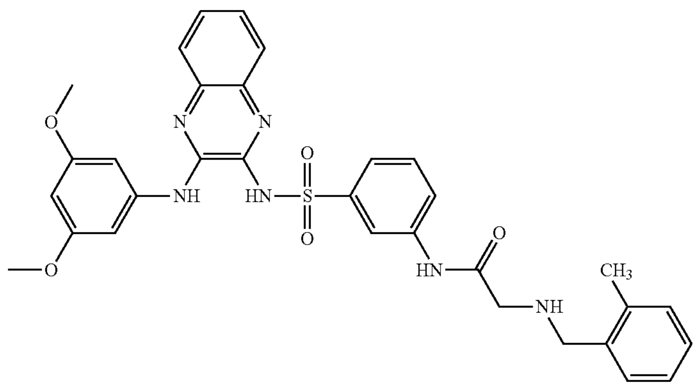 [SMILES: COc1cc(Nc2nc3ccccc3nc2NS(=O)(=O)c2cccc(NC(=O)CNCc3ccccc3C)c2)cc(OC)c1] | N-(3-{[(3-{[3,5-bis(methoxy)phenyl]amino}quinoxalin-2-yl)amino]sulfonyl}phenyl)-N-2-[(2-methylphenyl)methyl]glycinamide |
| 500 | 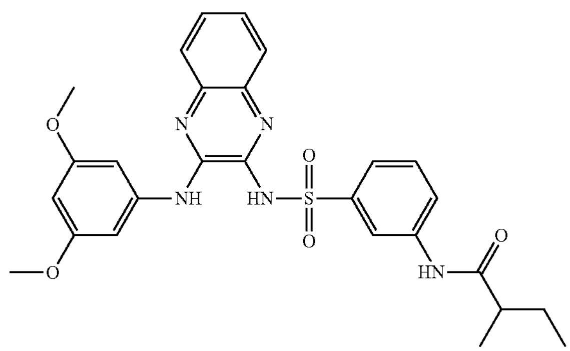 [SMILES: CCC(C)C(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-2-methylbutanamide |
| 501 | 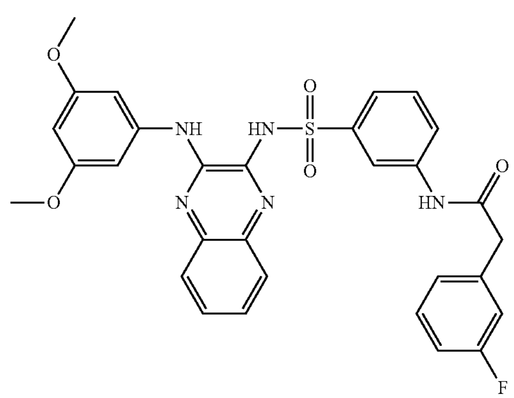 [SMILES: COc1cc(Nc2nc3ccccc3nc2NS(=O)(=O)c2cccc(NC(=O)Cc3cccc(F)c3)c2)cc(OC)c1] | N-(3-{[(3-{[3,5-bis(methoxy)phenyl]amino}quinoxalin-2-yl)amino]sulfonyl}phenyl)-2-(3-fluorophenyl)acetamide |

TABLE 1-continued

| Cpd. No. | Structure | Name |
|---|---|---|
| 502 | 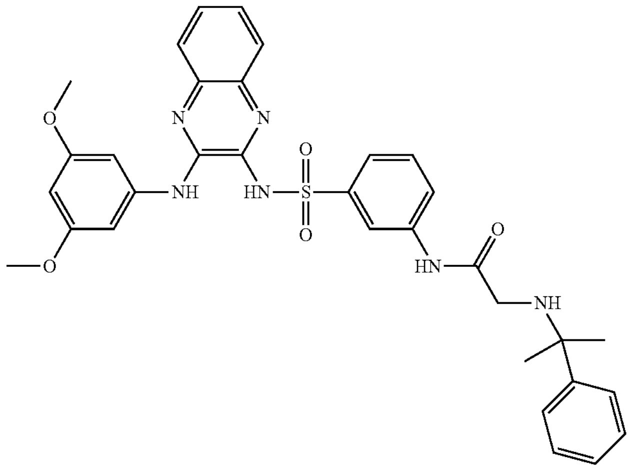 [SMILES: COc1cc(Nc2nc3ccccc3nc2NS(=O)(=O)c2cccc(NC(=O)CNC(C)(C)c3ccccc3)c2)cc(OC)c1] | N-(3-{[(3-{[3,5-bis(methoxy)phenyl]amino}quinoxalin-2-yl)amino]sulfonyl}phenyl)-N-2-(1-methyl-1-phenylethyl)glycinamide |
| 503 | 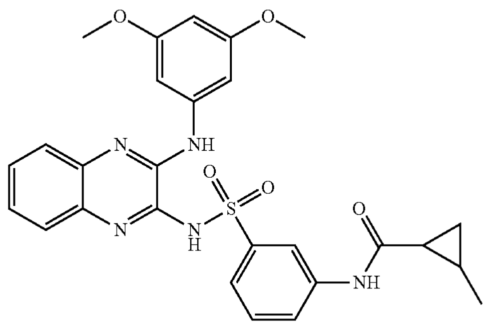 [SMILES: COc1cc(Nc2nc3ccccc3nc2NS(=O)(=O)c2cccc(NC(=O)C3CC3C)c2)cc(OC)c1] | N-(3-{[(3-{[3,5-bis(methoxy)phenyl]amino}quinoxalin-2-yl)amino]sulfonyl}phenyl)-2-methylcyclopropanecarboxamide |
| 504 | 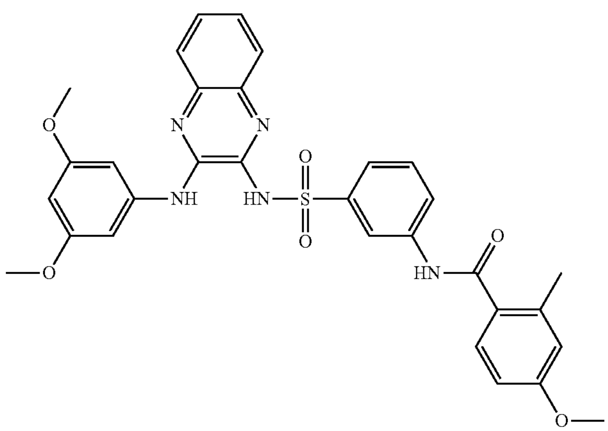 | N-(3-{[(3-{[3,5-bis(methoxy)phenyl]amino}quinoxalin-2-yl)amino]sulfonyl}phenyl)-2-methyl-4-(methoxy)benzamide |
| 505 | 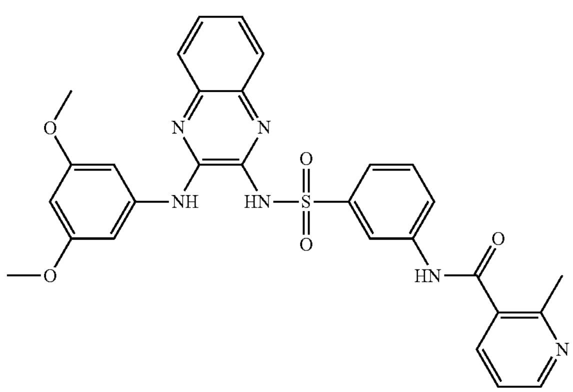 | N-(3-{[(3-{[3,5-bis(methoxy)phenyl]amino}quinoxalin-2-yl)amino]sulfonyl}phenyl)-2-methylpyridine-3-carboxamide |

TABLE 1-continued

| Cpd. No. | Structure | Name |
|---|---|---|
| 506 | 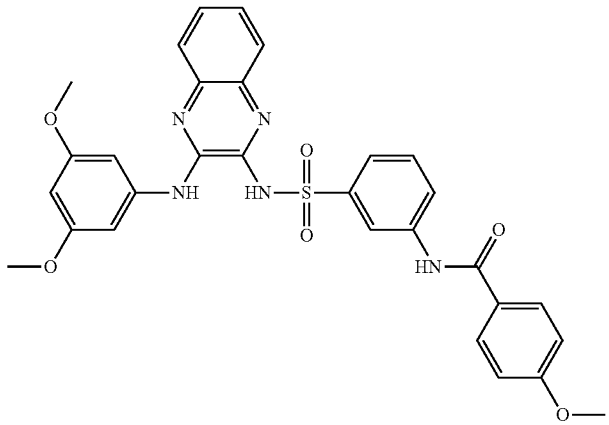 | N-{3-{[(3-{[3,5-bis(methoxy)phenyl]amino}quinoxalin-2-yl)amino]sulfonyl}phenyl)-4-(methoxy)benzamide |
| 507 | 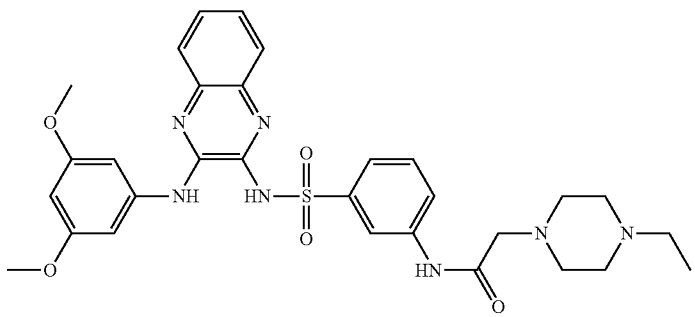 [SMILES: CCN1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methoxy)phenyl]amino}quinoxalin-2-yl)amino]sulfonyl}phenyl)-2-(4-ethylpiperazin-1-yl)acetamide |
| 508 | 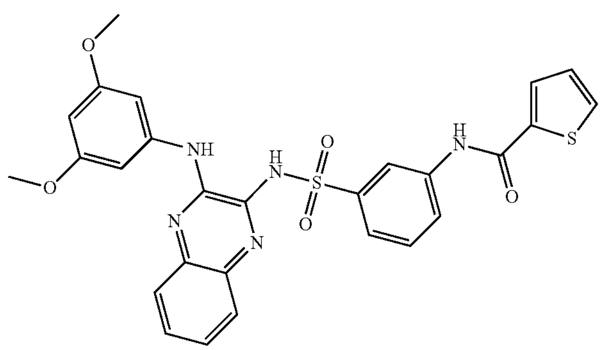 | N-(3-{[(3-{[3,5-bis(methoxy)phenyl]amino}quinoxalin-2-yl)amino]sulfonyl}phenyl)thiophene-2-carboxamide |
| 509 | 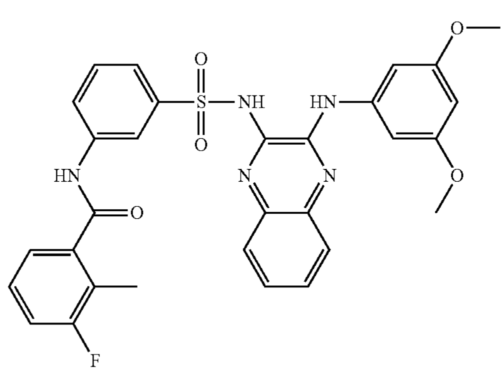 [SMILES: COc1cc(Nc2nc3ccccc3nc2NS(=O)(=O)c2cccc(NC(=O)c3cccc(F)c3C)c2)cc(OC)c1] | N-(3-{[(3-{[3,5-bis(methoxy)phenyl]amino}quinoxalin-2-yl)amino]sulfonyl}phenyl)-3-fluoro-2-methylbenzamide |

TABLE 1-continued

| Cpd. No. | Structure | Name |
|---|---|---|
| 510 | 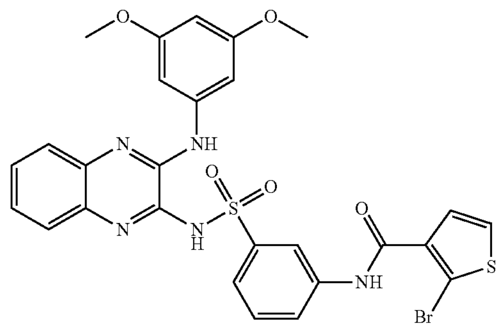 [SMILES: COc1cc(Nc2nc3ccccc3nc2NS(=O)(=O)c2cccc(NC(=O)c3ccsc3Br)c2)cc(OC)c1] | N-(3-{[(3-{[3,5-bis(methoxy)phenyl]amino}quinoxalin-2-yl)amino]sulfonyl}phenyl)-2-bromothiophene-3-carboxamide |
| 511 | 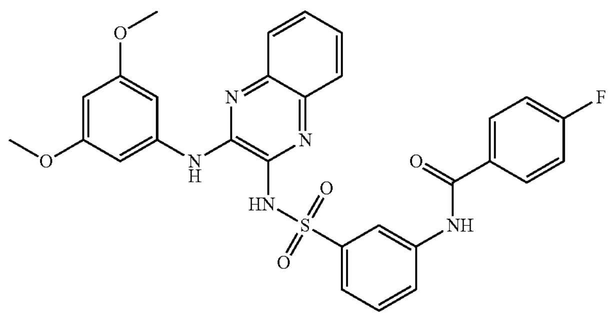 [SMILES: COc1cc(Nc2nc3ccccc3nc2NS(=O)(=O)c2cccc(NC(=O)c3ccc(F)cc3)c2)cc(OC)c1] | N-(3-{[(3-{[3,5-bis(methoxy)phenyl]amino}quinoxalin-2-yl)amino]sulfonyl}phenyl)-4-fluorobenzamide |
| 512 | 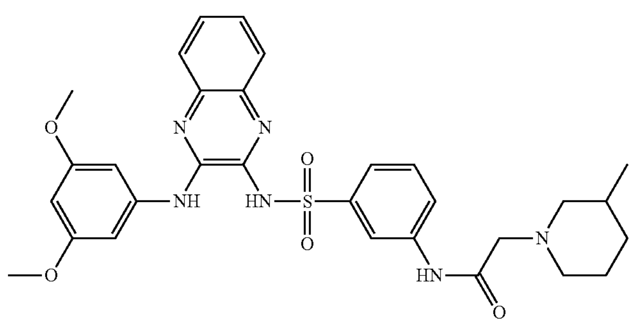 | N-(3-{[(3-{[3,5-bis(methoxy)phenyl]amino}quinoxalin-2-yl)amino]sulfonyl}phenyl)-2-(3-methylpiperidin-1-yl)acetamide |
| 513 | 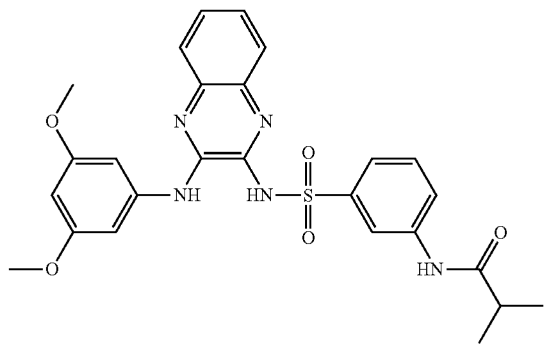 [SMILES: COc1cc(Nc2nc3ccccc3nc2NS(=O)(=O)c2cccc(NC(=O)C(C)C)c2)cc(OC)c1] | N-(3-{[(3-{[3,5-bis(methoxy)phenyl]amino}quinoxalin-2-yl)amino]sulfonyl}phenyl)-2-methylpropanamide |

TABLE 1-continued

| Cpd. No. | Structure | Name |
| --- | --- | --- |
| 514 | 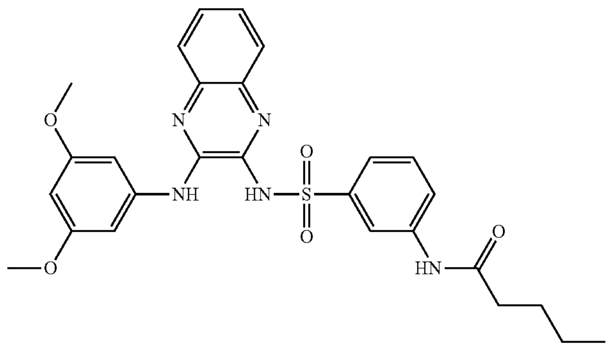 [SMILES: CCCCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)pentanamide |
| 515 | 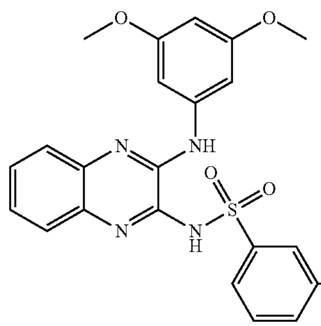 | N-(3-{[(3-{[3,5-bis(methoxy)phenyl]amino}quinoxalin-2-yl)amino]sulfonyl}phenyl)-2-(ethyloxy)acetamide |
| 516 | 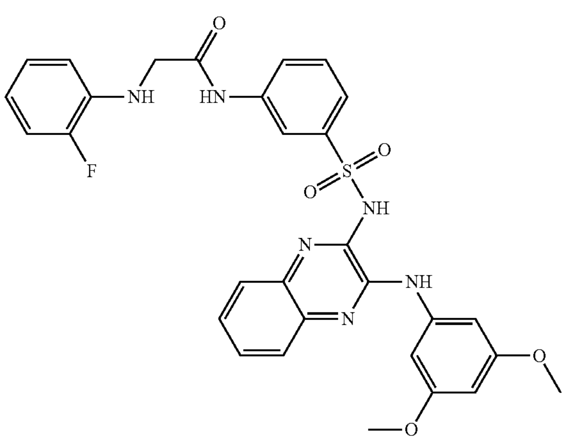 | N-(3-{[(3-{[3,5-bis(methoxy)phenyl]amino}quinoxalin-2-yl)amino]sulfonyl}phenyl)-N-2-(2-fluorophenyl)glycinamide |
| 517 | 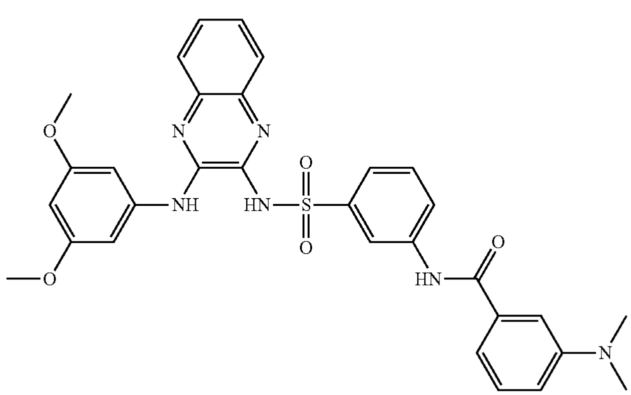 | N-(3-{[(3-{[3,5-bis(methoxy)phenyl]amino}quinoxalin-2-yl)amino]sulfonyl}phenyl)-3-(dimethylamino)benzamide |

| Cpd. No. | Structure | Name |
|---|---|---|
| 518 | 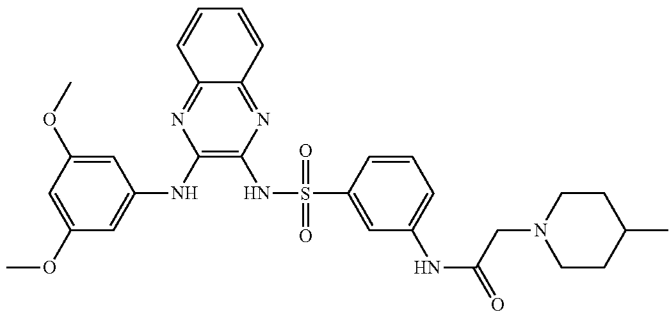 | N-(3-{[(3-{[3,5-bis(methoxy)phenyl]amino}quinoxalin-2-yl)amino]sulfonyl}phenyl)-2-(4-methylpiperidin-1-yl)acetamide |
| 519 | 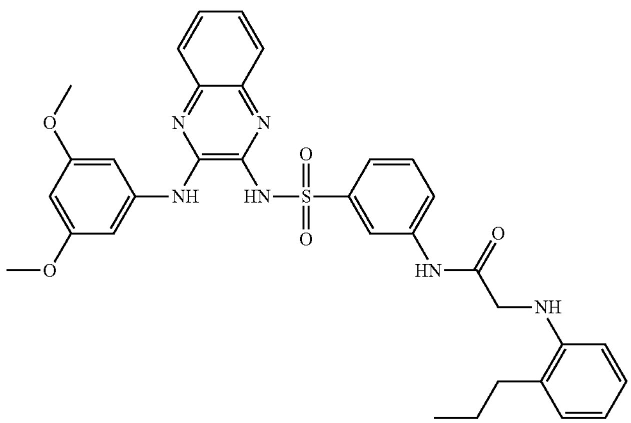 [SMILES: CCCc1ccccc1NCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-(2-propylphenyl)glycinamide |
| 520 | 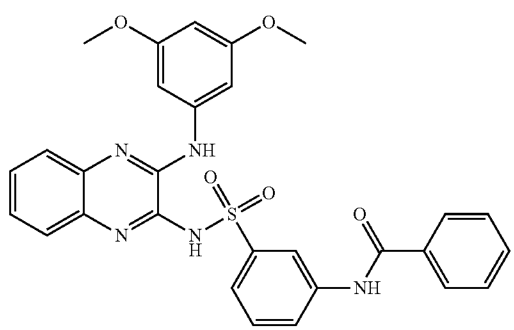 [SMILES: COc1cc(Nc2nc3ccccc3nc2NS(=O)(=O)c2cccc(NC(=O)c3ccccc3)c2)cc(OC)c1] | N-(3-{[(3-{[3,5-bis(methoxy)phenyl]amino}quinoxalin-2-yl)amino]sulfonyl}phenyl)benzamide |
| 521 | 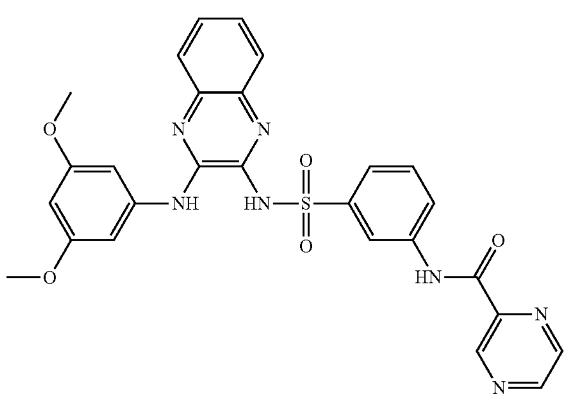 [SMILES: COc1cc(Nc2nc3ccccc3nc2NS(=O)(=O)c2cccc(NC(=O)c3cnccn3)c2)cc(OC)c1] | N-(3-{[(3-{[3,5-bis(methoxy)phenyl]amino}quinoxalin-2-yl)amino]sulfonyl}phenyl)pyrazine-2-carboxamide |

TABLE 1-continued

| Cpd. No. | Structure | Name |
| --- | --- | --- |
| 522 | 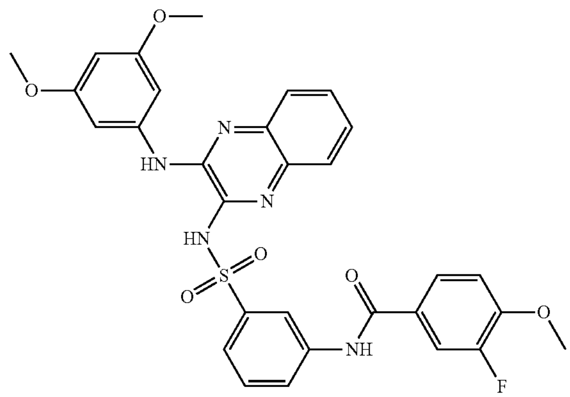 | N-(3-{[(3-{[3,5-bis(methoxy)phenyl]amino}quinoxalin-2-yl)amino]sulfonyl}phenyl)-3-fluoro-4-(methoxy)benzamide |
| 523 | 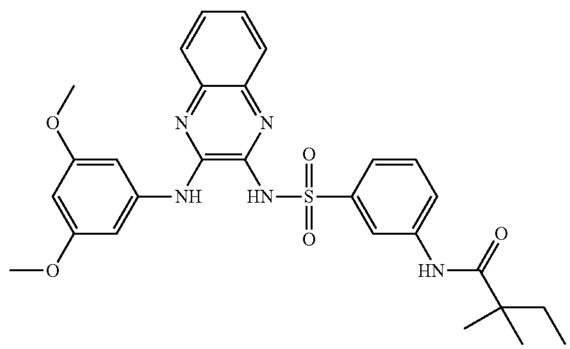 [SMILES: CCC(C)(C)C(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-2,2-dimethylbutanamide |
| 524 | 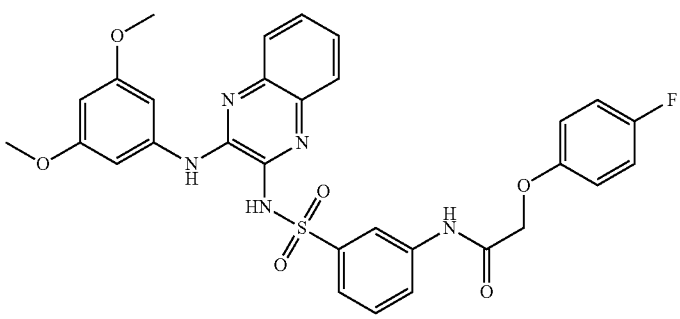 [SMILES: COc1cc(Nc2nc3ccccc3nc2NS(=O)(=O)c2cccc(NC(=O)COc3ccc(F)cc3)c2)cc(OC)c1] | N-(3-{[(3-{[3,5-bis(methoxy)phenyl]amino}quinoxalin-2-yl)amino]sulfonyl}phenyl)-2-[(4-fluorophenyl)oxy]acetamide |
| 525 | 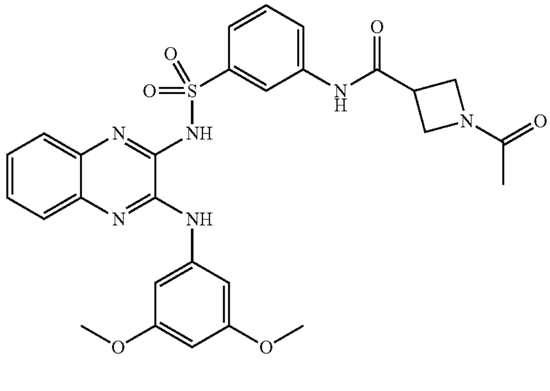 [SMILES: COc1cc(Nc2nc3ccccc3nc2NS(=O)(=O)c2cccc(NC(=O)C3CN(C(C)=O)C3)c2)cc(OC)c1] | 1-acetyl-N-(3-{[(3-{[3,5-bis(methoxy)phenyl]amino}quinoxalin-2-yl)amino]sulfonyl}phenyl)azetidine-3-carboxamide |

TABLE 1-continued

| Cpd. No. | Structure | Name |
|---|---|---|
| 526 | 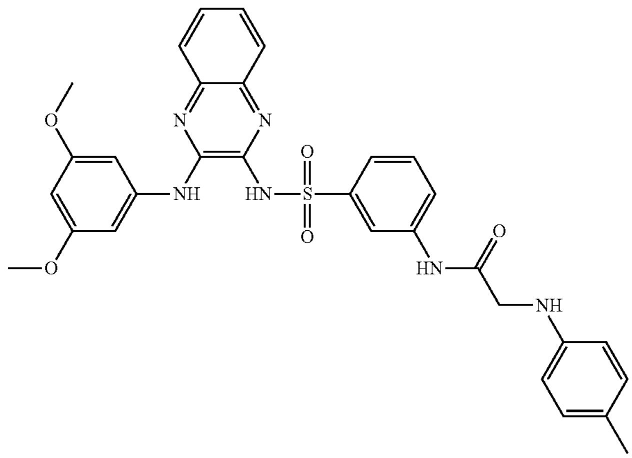 | N-(3-{[(3-{[3,5-bis(methoxy)phenyl]amino}quinoxalin-2-yl)amino]sulfonyl}phenyl)-N-2-(4-methylphenyl)glycinamide |
| 527 | 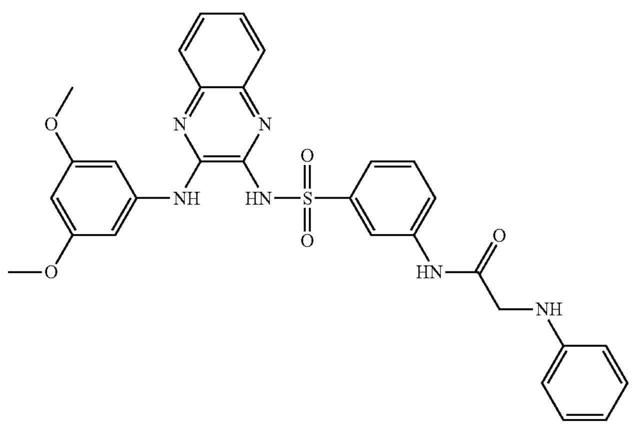 [SMILES: COc1cc(Nc2nc3ccccc3nc2NS(=O)(=O)c2cccc(NC(=O)CNc3ccccc3)c2)cc(OC)c1] | N-(3-{[(3-{[3,5-bis(methoxy)phenyl]amino}quinoxalin-2-yl)amino]sulfonyl}phenyl)-N-2-phenylglycinamide |
| 528 | 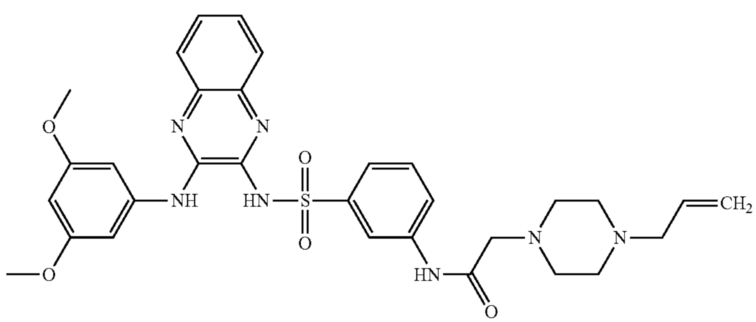 [SMILES: C=CCN1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methoxy)phenyl]amino}quinoxalin-2-yl)amino]sulfonyl}phenyl)-2-(4-prop-2-en-1-ylpiperazin-1-yl)acetamide |
| 529 | 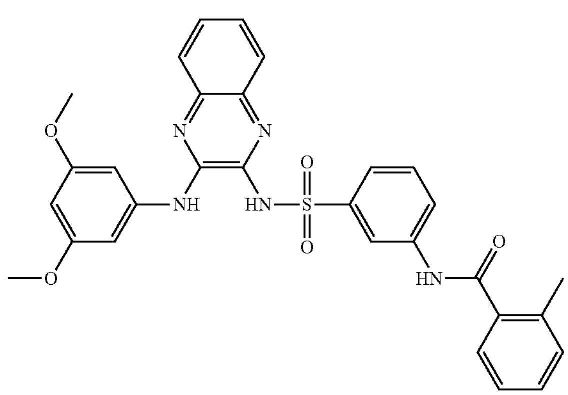 | N-(3-{[(3-{[3,5-bis(methoxy)phenyl]amino}quinoxalin-2-yl)amino]sulfonyl}phenyl)-2-methylbenzamide |

TABLE 1-continued

| Cpd. No. | Structure | Name |
| --- | --- | --- |
| 530 | 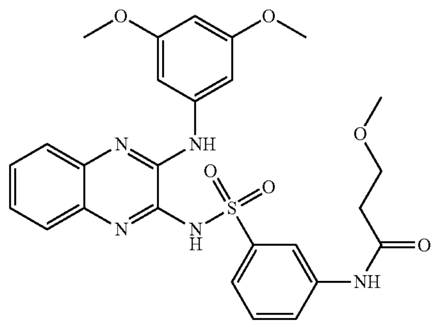 [SMILES: COCCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-3-(methoxy)propanamide |
| 531 | 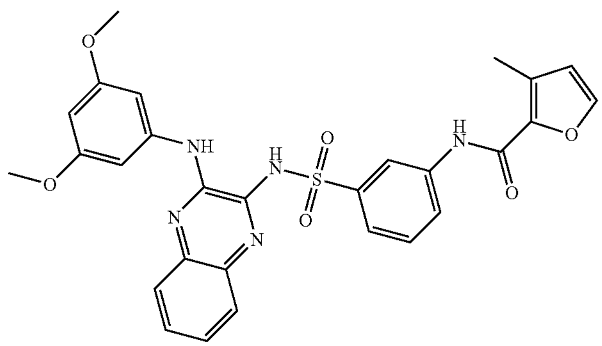 [SMILES: COc1cc(Nc2nc3ccccc3nc2NS(=O)(=O)c2cccc(NC(=O)c3occc3C)c2)cc(OC)c1] | N-(3-{[(3-{[3,5-bis(methoxy)phenyl]amino}quinoxalin-2-yl)amino]sulfonyl}phenyl)-3-methylfuran-2-carboxamide |
| 532 | 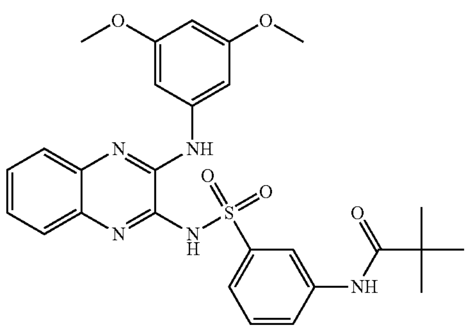 [SMILES: COc1cc(Nc2nc3ccccc3nc2NS(=O)(=O)c2cccc(NC(=O)C(C)(C)C)c2)cc(OC)c1] | N-(3-{[(3-{[3,5-bis(methoxy)phenyl]amino}quinoxalin-2-yl)amino]sulfonyl}phenyl)-2,2-dimethylpropanamide |
| 533 | 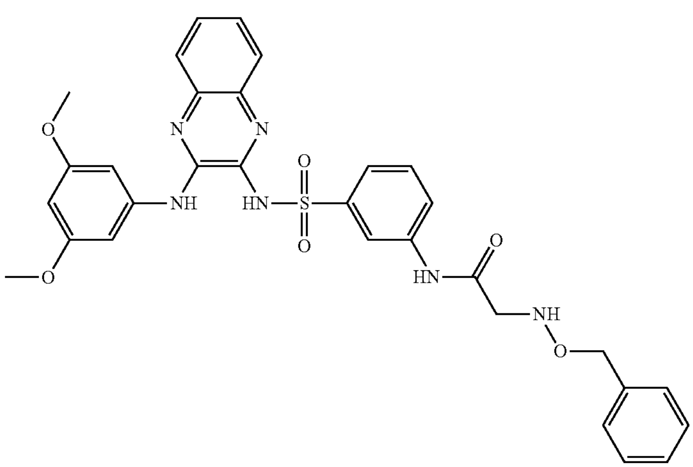 [SMILES: COc1cc(Nc2nc3ccccc3nc2NS(=O)(=O)c2cccc(NC(=O)CNOCc3ccccc3)c2)cc(OC)c1] | N-(3-{[(3-{[3,5-bis(methoxy)phenyl]amino}quinoxalin-2-yl)amino]sulfonyl}phenyl)-N-2-[(phenylmethyl)oxy]glycinamide |

TABLE 1-continued

| Cpd. No. | Structure | Name |
|---|---|---|
| 534 | 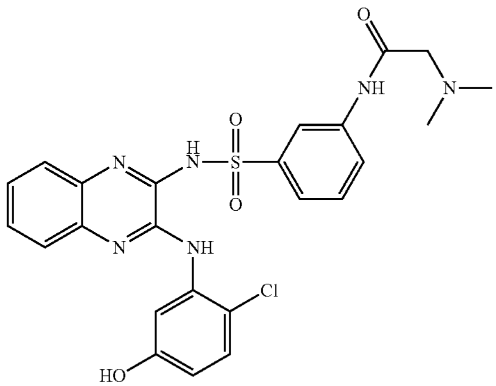 [SMILES: CN(C)CC(=O)Nc1cccc(S(=O)(=O)Nc2nc3ccccc3nc2Nc2cc(O)ccc2Cl)c1] | N-{3-[({3-[(2-chloro-5-hydroxy-phenyl)amino]quinoxalin-2-yl}amino)sulfonyl]phenyl}-N-2-,N-2-dimethylglycinamide |
| 535 | 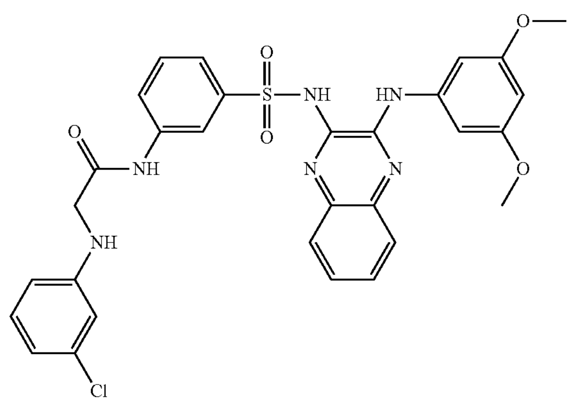 | N-(3-{[(3-{[3,5-bis(methoxy)phen-yl]amino}quinoxalin-2-yl)amino]sulfonyl}phenyl)-N-2-(3-chlorophenyl)glycinamide |
| 536 | 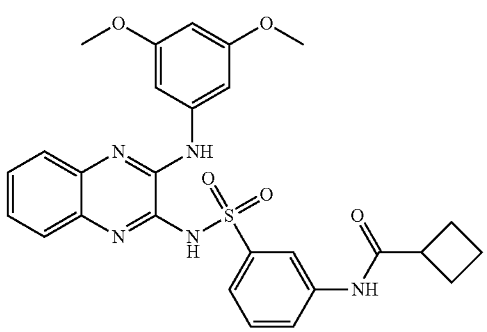 [SMILES: COc1cc(Nc2nc3ccccc3nc2NS(=O)(=O)c2cccc(NC(=O)C3CCC3)c2)cc(OC)c1] | N-(3-{[(3-{[3,5-bis(methoxy)phen-yl]amino}quinoxalin-2-yl)amino]sulfonyl}phenyl)cyclo-butanecarboxamide |
| 537 | 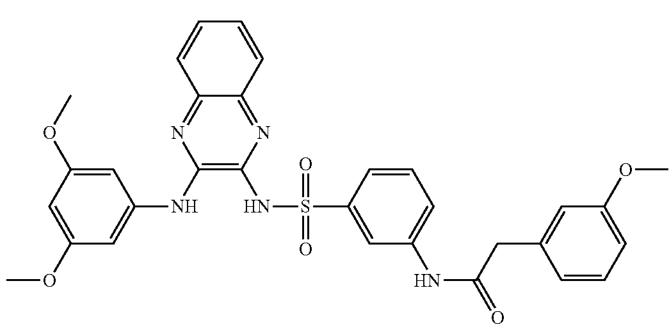 | N-(3-{[(3-{[3,5-bis(methoxy)phen-yl]amino}quinoxalin-2-yl)amino]sulfonyl}phenyl)-2-[3-(methoxy)phenyl]acetamide |

| Cpd. No. | Structure | Name |
|---|---|---|
| 538 | 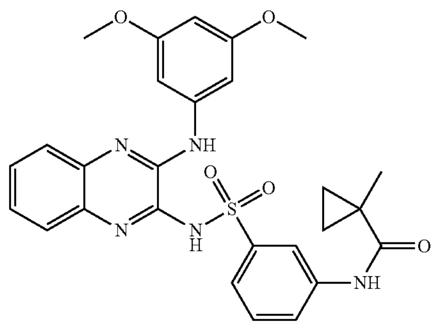 [SMILES: COc1cc(Nc2nc3ccccc3nc2NS(=O)(=O)c2cccc(NC(=O)C3(C)CC3)c2)cc(OC)c1] | N-(3-{[(3-{[3,5-bis(methoxy)phenyl]amino}quinoxalin-2-yl)amino]sulfonyl}phenyl)-1-methylcyclopropanecarboxamide |
| 539 | 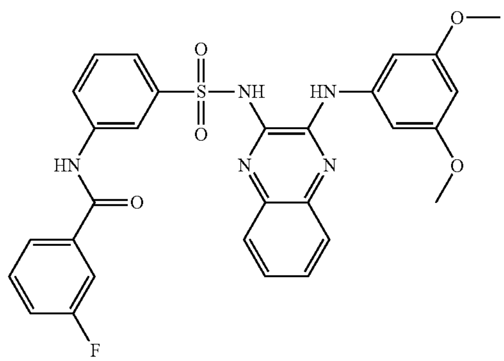 | N-(3-{[(3-{[3,5-bis(methoxy)phenyl]amino}quinoxalin-2-yl)amino]sulfonyl}phenyl)-3-fluorobenzamide |
| 540 | 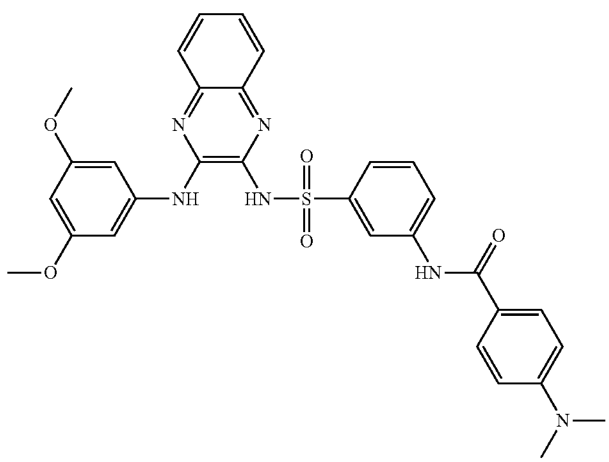 | N-(3-{[(3-{[3,5-bis(methoxy)phenyl]amino}quinoxalin-2-yl)amino]sulfonyl}phenyl)-4-(dimethylamino)benzamide |
| 541 | 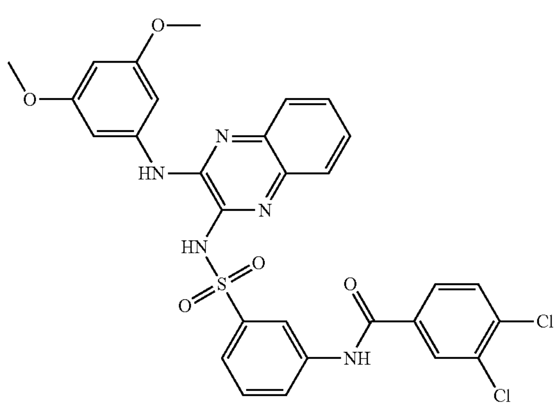 [SMILES: COc1cc(Nc2nc3ccccc3nc2NS(=O)(=O)c2cccc(NC(=O)c3ccc(Cl)c(Cl)c3)c2)cc(OC)c1] | N-(3-{[(3-{[3,5-bis(methoxy)phenyl]amino}quinoxalin-2-yl)amino]sulfonyl}phenyl)-3,4-dichlorobenzamide |

TABLE 1-continued

| Cpd. No. | Structure | Name |
| --- | --- | --- |
| 542 | 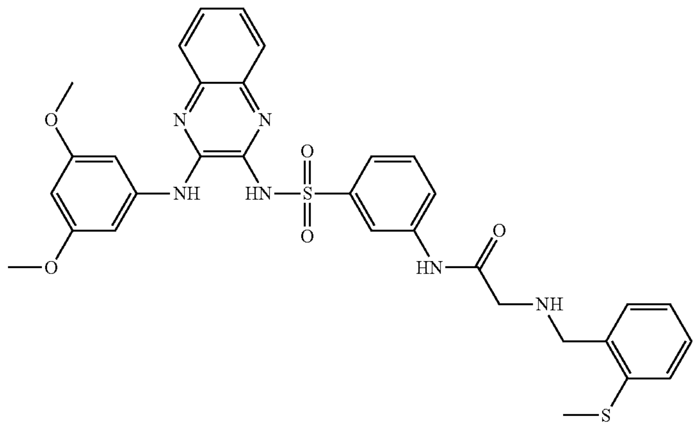 [SMILES: COc1cc(Nc2nc3ccccc3nc2NS(=O)(=O)c2cccc(NC(=O)CNCc3ccccc3SC)c2)cc(OC)c1] | N-(3-{[(3-{[3,5-bis(methoxy)phenyl]amino}quinoxalin-2-yl)amino]sulfonyl}phenyl)-N-2-{[2-(methylthio)phenyl]methyl}glycinamide |
| 543 | 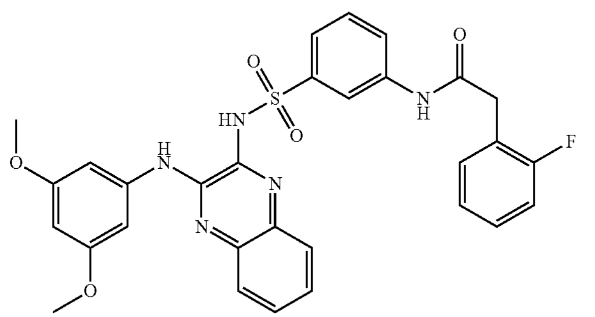 [SMILES: COc1cc(Nc2nc3ccccc3nc2NS(=O)(=O)c2cccc(NC(=O)Cc3ccccc3F)c2)cc(OC)c1] | N-(3-{[(3-{[3,5-bis(methoxy)phenyl]amino}quinoxalin-2-yl)amino]sulfonyl}phenyl)-2-(2-fluorophenyl)acetamide |
| 544 | 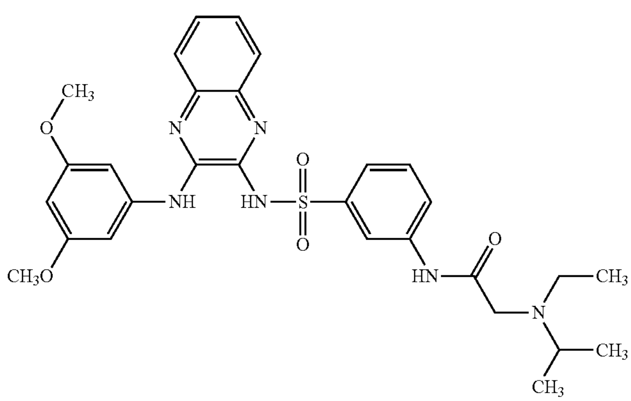 | N-(3-{[(3-{[3,5-bis(methoxy)phenyl]amino}quinoxalin-2-yl)amino]sulfonyl}phenyl)-N-2-ethyl-N-2-(1-methylethyl)glycinamide |
| 545 | 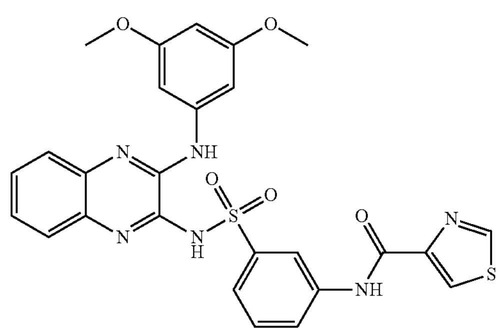 [SMILES: COc1cc(Nc2nc3ccccc3nc2NS(=O)(=O)c2cccc(NC(=O)c3cscn3)c2)cc(OC)c1] | N-(3-{[(3-{[3,5-bis(methoxy)phenyl]amino}quinoxalin-2-yl)amino]sulfonyl}phenyl)-1,3-thiazole-4-carboxamide |

TABLE 1-continued

| Cpd. No. | Structure | Name |
|---|---|---|
| 546 | 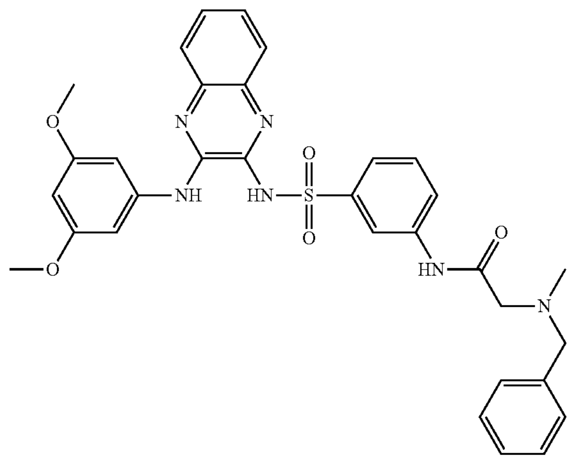 | N-(3-{[(3-{[3,5-bis(methoxy)phenyl]amino}quinoxalin-2-yl)amino]sulfonyl}phenyl)-N-2-methyl-N-2-(phenylmethyl)glycinamide |
| 547 | 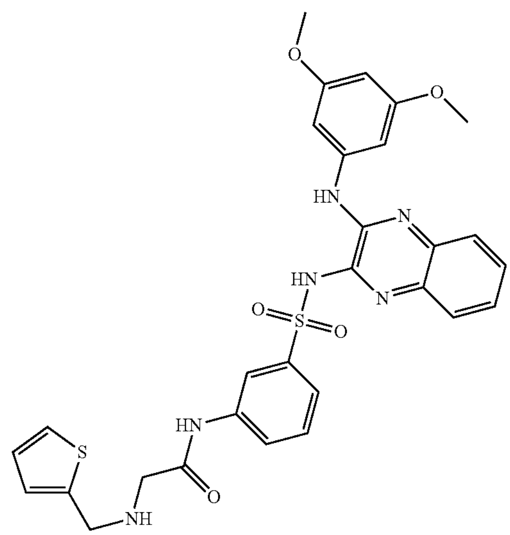 [SMILES: COc1cc(Nc2nc3ccccc3nc2NS(=O)(=O)c2cccc(NC(=O)CNCc3cccs3)c2)cc(OC)c1] | N-(3-{[(3-{[3,5-bis(methoxy)phenyl]amino}quinoxalin-2-yl)amino]sulfonyl}phenyl)-N-2-(2-thienylmethyl)glycinamide |
| 548 | 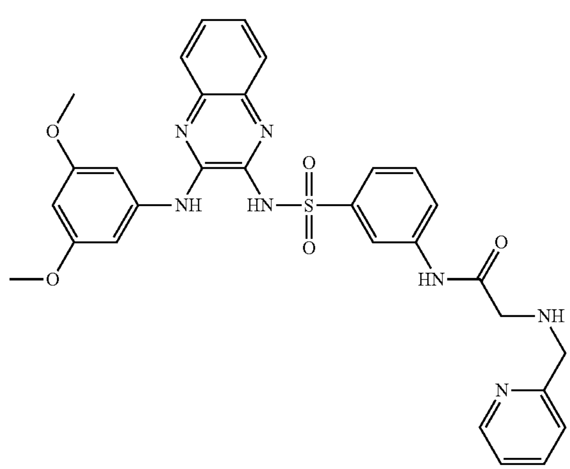 [SMILES: COc1cc(Nc2nc3ccccc3nc2NS(=O)(=O)c2cccc(NC(=O)CNCc3ccccn3)c2)cc(OC)c1] | N-(3-{[(3-{[3,5-bis(methoxy)phenyl]amino}quinoxalin-2-yl)amino]sulfonyl}phenyl)-N-2-(pyridin-2-ylmethyl)glycinamide |

TABLE 1-continued

| Cpd. No. | Structure | Name |
| --- | --- | --- |
| 549 | 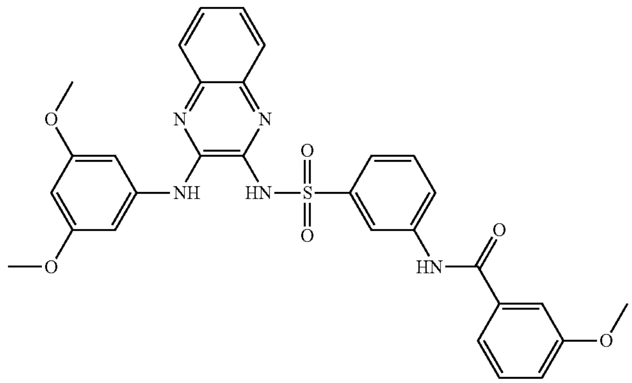 | N-(3-{[(3-{[3,5-bis(methoxy)phenyl]amino}quinoxalin-2-yl)amino]sulfonyl}phenyl)-3-(methoxy)benzamide |
| 550 | 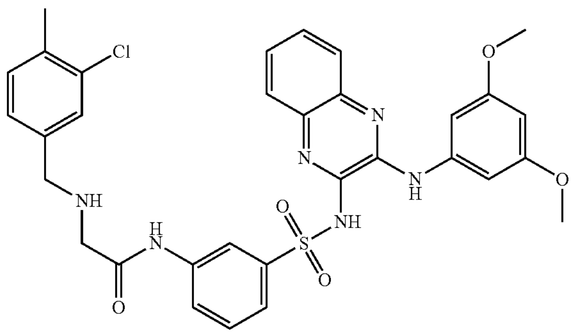 [SMILES: COc1cc(Nc2nc3ccccc3nc2NS(=O)(=O)c2cccc(NC(=O)CNCc3ccc(C)c(Cl)c3)c2)cc(OC)c1] | N-(3-{[(3-{[3,5-bis(methoxy)phenyl]amino}quinoxalin-2-yl)amino]sulfonyl}phenyl)-N-2-[(3-chloro-4-methylphenyl)methyl]glycinamide |
| 551 | 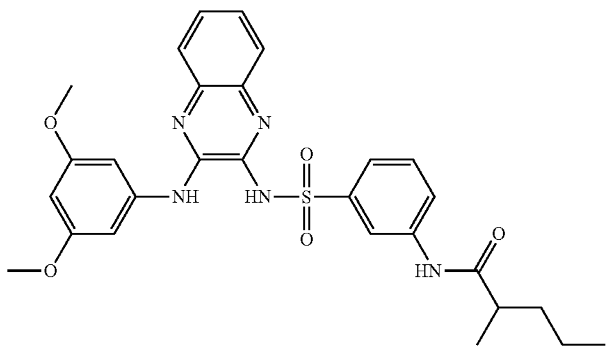 [SMILES: CCCC(C)C(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-2-methylpentanamide |
| 552 | 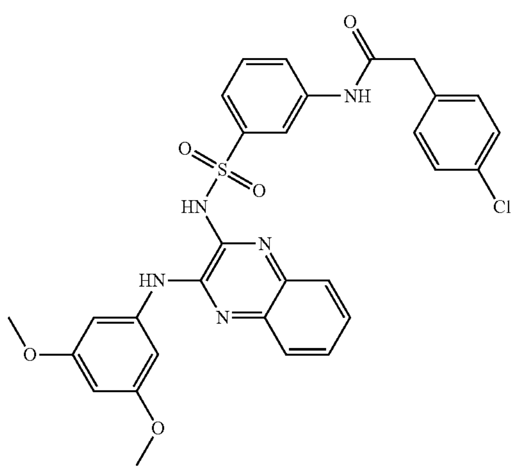 [SMILES: COc1cc(Nc2nc3ccccc3nc2NS(=O)(=O)c2cccc(NC(=O)Cc3ccc(Cl)cc3)c2)cc(OC)c1] | N-(3-{[(3-{[3,5-bis(methoxy)phenyl]amino}quinoxalin-2-yl)amino]sulfonyl}phenyl)-2-(4-chlorophenyl)acetamide |

TABLE 1-continued

| Cpd. No. | Structure | Name |
|---|---|---|
| 553 | 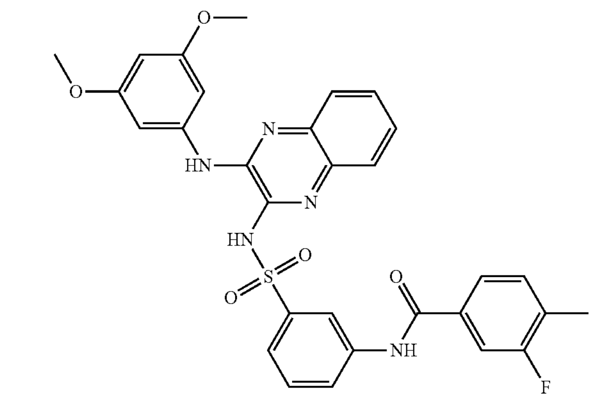 | N-(3-{[(3-{[3,5-bis(methoxy)phenyl]amino}quinoxalin-2-yl)amino]sulfonyl}phenyl)-3-fluoro-4-methylbenzamide |
| 554 | 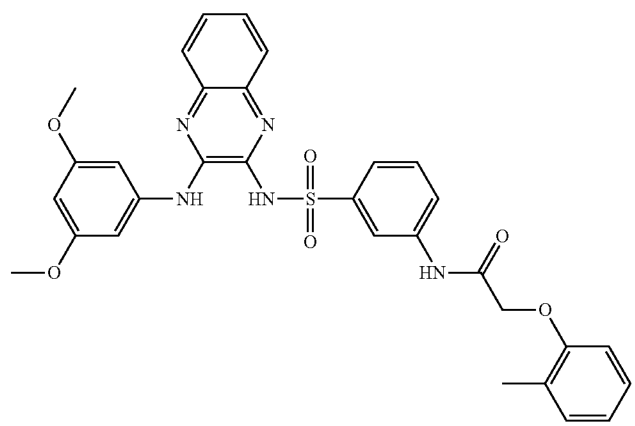 [SMILES: COc1cc(Nc2nc3ccccc3nc2NS(=O)(=O)c2cccc(NC(=O)COc3ccccc3C)c2)cc(OC)c1] | N-(3-{[(3-{(3,5-bis(methoxy)phenyl]amino}quinoxalin-2-yl)amino]sulfonyl}phenyl)-2-[(2-methylphenyl)oxy]acetamide |
| 555 | 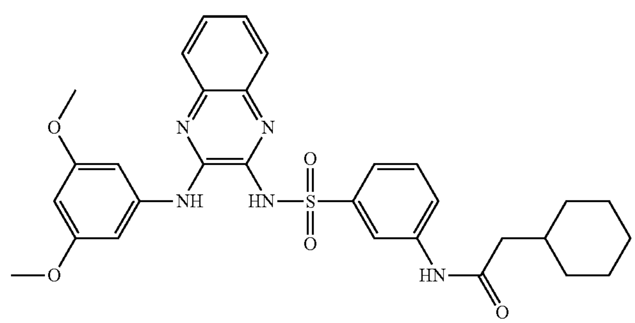 | N-(3-{[(3-{[3,5-bis(methoxy)phenyl]amino}quinoxalin-2-yl)amino]sulfonyl}phenyl)-2-cyclohexylacetamide |
| 556 | 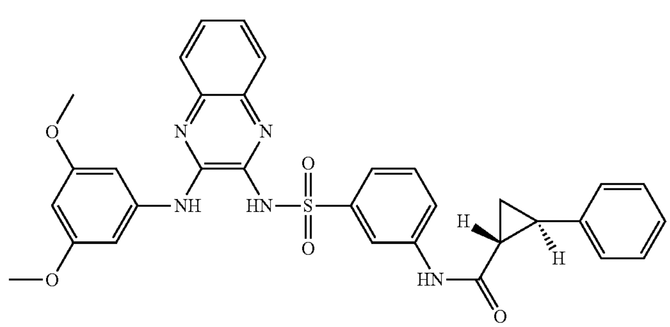 [SMILES: COc1cc(Nc2nc3ccccc3nc2NS(=O)(=O)c2cccc(NC(=O)[C@@H]3C[C@H]3c3ccccc3)c2)cc(OC)c1] | (1R,2R)-N-(3-{[(3-{[3,5-bis(methoxy)phenyl]amino}quinoxalin-2-yl)amino]sulfonyl}phenyl)-2-phenylcyclopropanecarboxamide |

TABLE 1-continued

| Cpd. No. | Structure | Name |
|---|---|---|
| 557 | 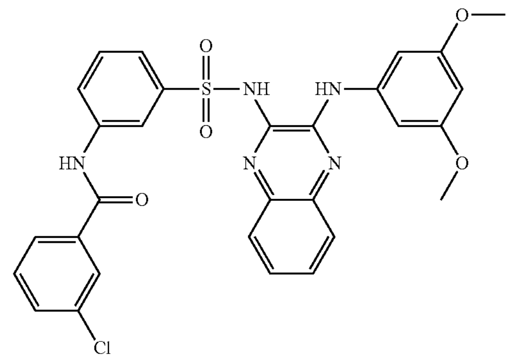 [SMILES: COc1cc(Nc2nc3ccccc3nc2NS(=O)(=O)c2cccc(NC(=O)c3cccc(Cl)c3)c2)cc(OC)c1] | N-(3-{[(3-{[3,5-bis(methoxy)phenyl]amino}quinoxalin-2-yl)amino]sulfonyl}phenyl)-3-chlorobenzamide |
| 558 | 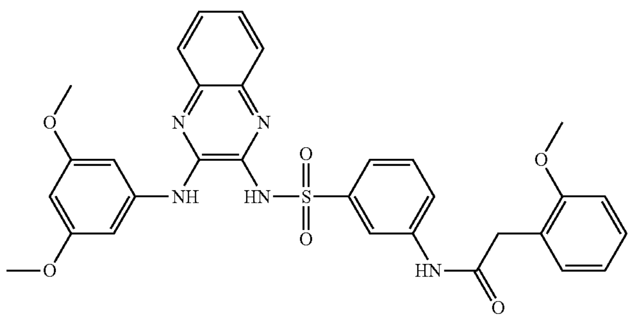 [SMILES: COc1cc(Nc2nc3ccccc3nc2NS(=O)(=O)c2cccc(NC(=O)Cc3ccccc3OC)c2)cc(OC)c1] | N-(3-{[(3-{[3,5-bis(methoxy)phenyl]amino}quinoxalin-2-yl)amino]sulfonyl}phenyl)-2-[2-(methoxy)phenyl]acetamide |
| 559 | 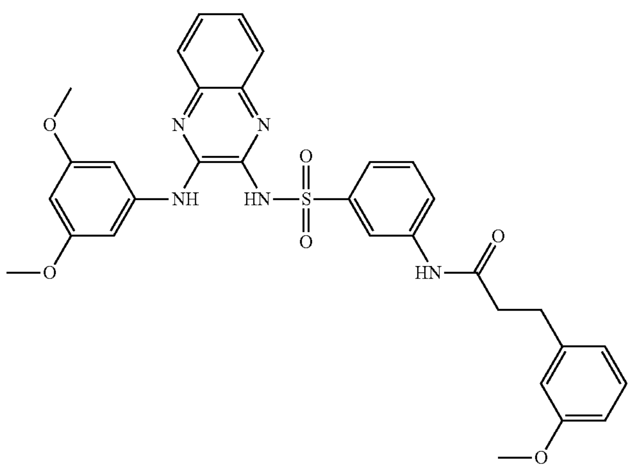 [SMILES: COc1cccc(CCC(=O)Nc2cccc(S(=O)(=O)Nc3nc4ccccc4nc3Nc3cc(OC)cc(OC)c3)c2)c1] | N-(3-{[(3-{[3,5-bis(methoxy)phenyl]amino}quinoxalin-2-yl)amino]sulfonyl}phenyl)-3-[3-(methoxy)phenyl]propanamide |
| 560 | 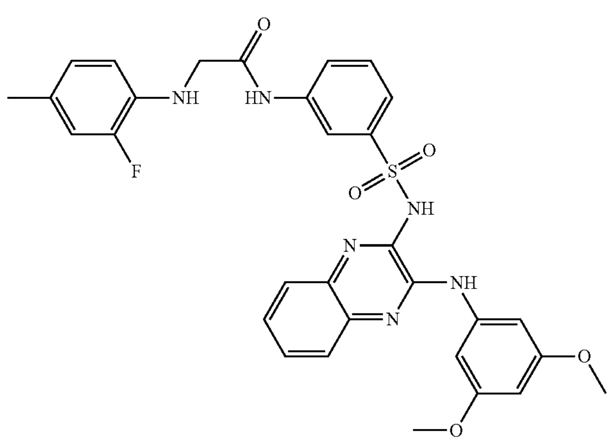 | N-(3-{[(3-{[3,5-bis(methoxy)phenyl]amino}quinoxalin-2-yl)amino]sulfonyl}phenyl)-N-2-(2-fluoro-4-methylphenyl)glycinamide |

TABLE 1-continued

| Cpd. No. | Structure | Name |
|---|---|---|
| 561 | 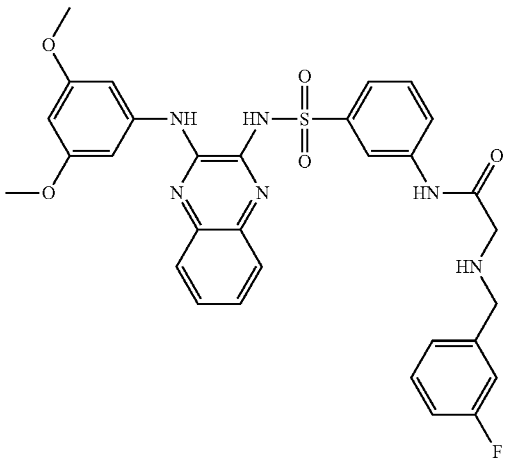 [SMILES: COc1cc(Nc2nc3ccccc3nc2NS(=O)(=O)c2cccc(NC(=O)CNCc3cccc(F)c3)c2)cc(OC)c1] | N-(3-{[(3-{[3,5-bis(methoxy)phenyl]amino}quinoxalin-2-yl)amino]sulfonyl}phenyl)-N-2-[(3-fluorophenyl)methyl]glycinamide |
| 562 | 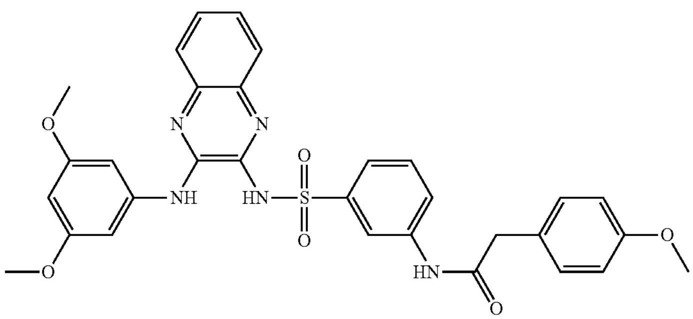 | N-(3-{[(3-{[3,5-bis(methoxy)phenyl]amino}quinoxalin-2-yl)amino]sulfonyl}phenyl)-2-[4-(methoxy)phenyl]acetamide |
| 563 | 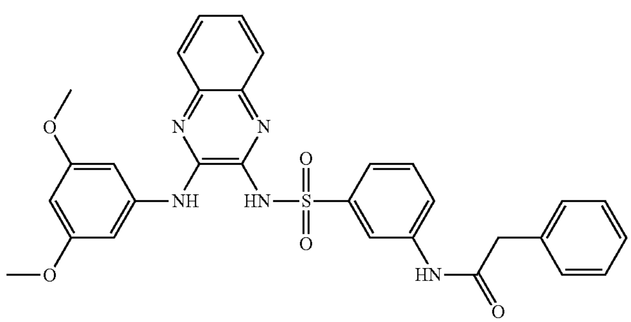 [SMILES: COc1cc(Nc2nc3ccccc3nc2NS(=O)(=O)c2cccc(NC(=O)Cc3ccccc3)c2)cc(OC)c1] | N-(3-{[(3-{[3,5-bis(methoxy)phenyl]amino}quinoxalin-2-yl)amino]sulfonyl}phenyl)-2-phenylacetamide |
| 564 | 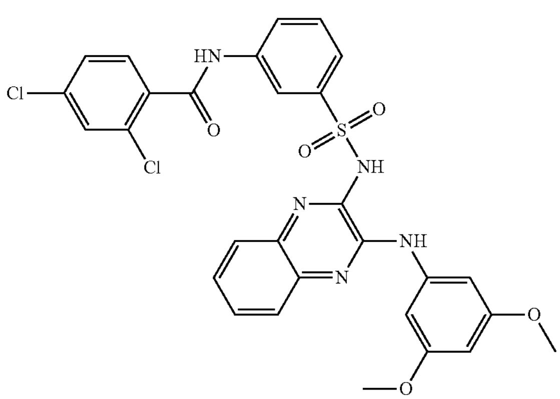 [SMILES: COc1cc(Nc2nc3ccccc3nc2NS(=O)(=O)c2cccc(NC(=O)c3ccc(Cl)cc3Cl)c2)cc(OC)c1] | N-(3-{[(3-{[3,5-bis(methoxy)phenyl]amino}quinoxalin-2-yl)amino]sulfonyl}phenyl)-2,4-dichlorobenzamide |

TABLE 1-continued

| Cpd. No. | Structure | Name |
|---|---|---|
| 565 | 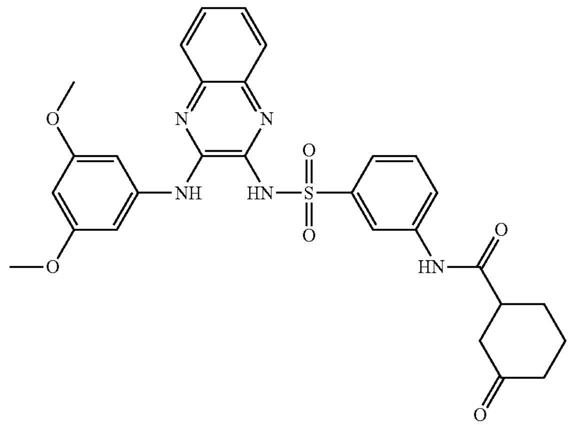 [SMILES: COc1cc(Nc2nc3ccccc3nc2NS(=O)(=O)c2cccc(NC(=O)C3CCCC(=O)C3)c2)cc(OC)c1] | N-(3-{[(3-{[3,5-bis(methoxy)phenyl]amino}quinoxalin-2-yl)amino]sulfonyl}phenyl)-3-oxocyclohexanecarboxamide |
| 566 | 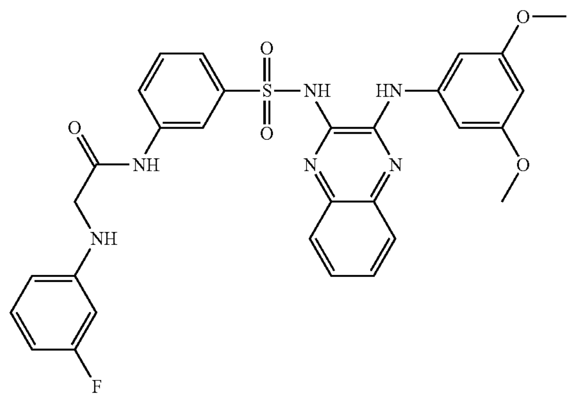 [SMILES: COc1cc(Nc2nc3ccccc3nc2NS(=O)(=O)c2cccc(NC(=O)CNc3cccc(F)c3)c2)cc(OC)c1] | N-(3-{[(3-{[3,5-bis(methoxy)phenyl]amino}quinoxalin-2-yl)amino]sulfonyl}phenyl)-N-2-(3-fluorophenyl)glycinamide |
| 567 | 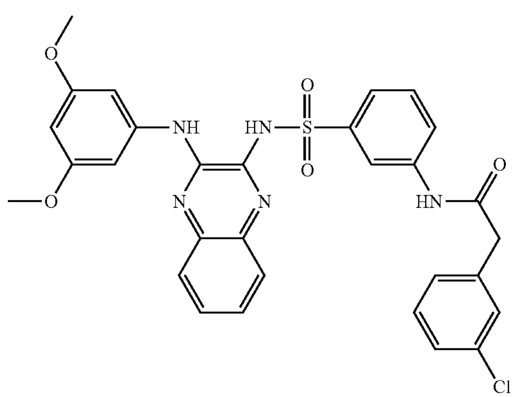 [SMILES: COc1cc(Nc2nc3ccccc3nc2NS(=O)(=O)c2cccc(NC(=O)Cc3cccc(Cl)c3)c2)cc(OC)c1] | N-(3-{[(3-{[3,5-bis(methoxy)phenyl]amino}quinoxalin-2-yl)amino]sulfonyl}phenyl)-2-(3-chlorophenyl)acetamide |
| 568 | 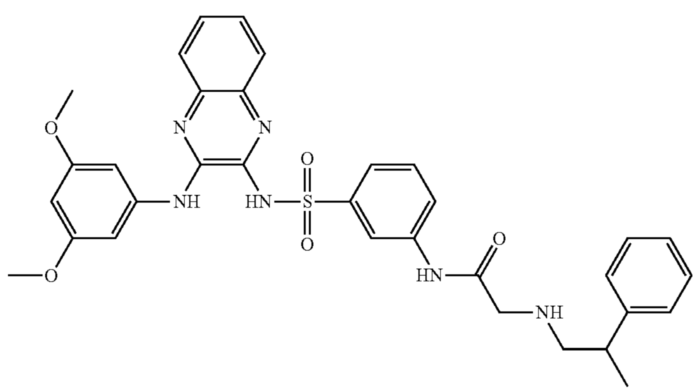 [SMILES: COc1cc(Nc2nc3ccccc3nc2NS(=O)(=O)c2cccc(NC(=O)CNCC(C)c3ccccc3)c2)cc(OC)c1] | N-(3-{[(3-{[3,5-bis(methoxy)phenyl]amino}quinoxalin-2-yl)amino]sulfonyl}phenyl)-N-2-(2-phenylpropyl)glycinamide |

TABLE 1-continued

| Cpd. No. | Structure | Name |
|---|---|---|
| 569 | 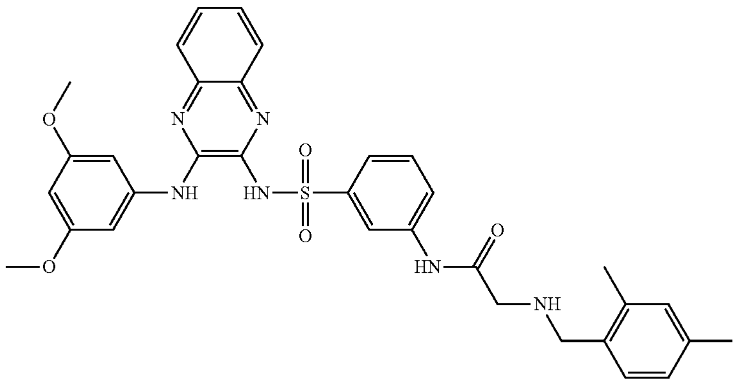 | N-(3-{[(3-{[3,5-bis(methoxy)phenyl]amino}quinoxalin-2-yl)amino]sulfonyl}phenyl)-N-2-[(2,4-dimethylphenyl)methyl]glycinamide |
| 570 | 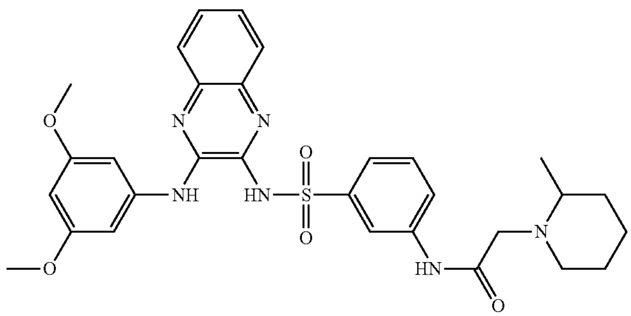 [SMILES: COc1cc(Nc2nc3ccccc3nc2NS(=O)(=O)c2cccc(NC(=O)CN3CCCCC3C)c2)cc(OC)c1] | N-(3-{[(3-{[3,5-bis(methoxy)phenyl]amino}quinoxalin-2-yl)amino]sulfonyl}phenyl)-2-(2-methylpiperidin-1-yl)acetamide |
| 571 | 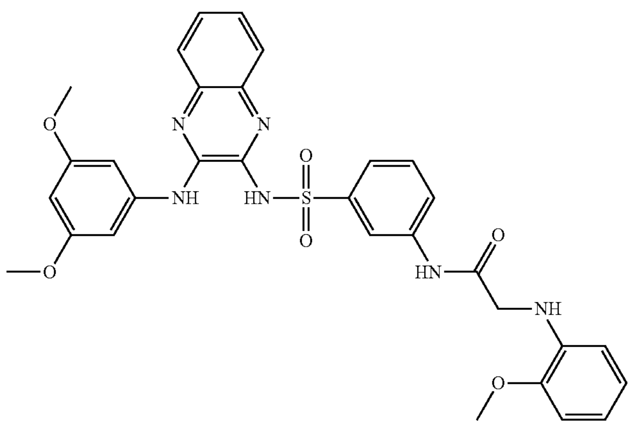 [SMILES: COc1cc(Nc2nc3ccccc3nc2NS(=O)(=O)c2cccc(NC(=O)CNc3ccccc3OC)c2)cc(OC)c1] | N-(3-{[(3-{[3,5-bis(methoxy)phenyl]amino}quinoxalin-2-yl)amino]sulfonyl}phenyl)-N-2-[2-(methoxy)phenyl]glycinamide |
| 572 | 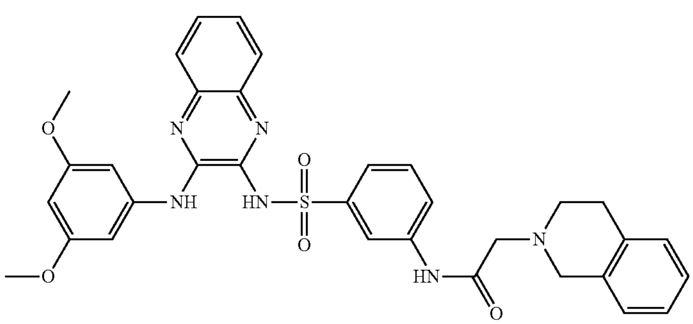 [SMILES: COc1cc(Nc2nc3ccccc3nc2NS(=O)(=O)c2cccc(NC(=O)CN3CCc4ccccc4C3)c2)cc(OC)c1] | N-(3-{[(3-{[3,5-bis(methoxy)phenyl]amino}quinoxalin-2-yl)amino]sulfonyl}phenyl)-2-(3,4-dihydroisoquinolin-2(1H)-yl)acetamide |

TABLE 1-continued

| Cpd. No. | Structure | Name |
|---|---|---|
| 573 | 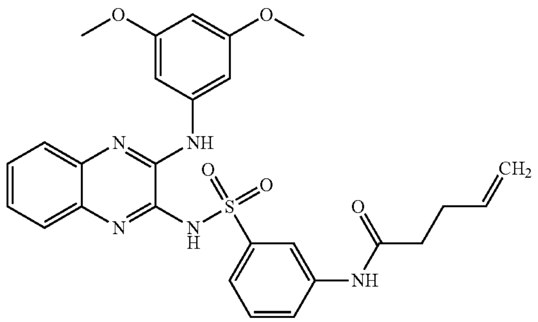 [SMILES: C=CCCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)pent-4-enamide |
| 574 | 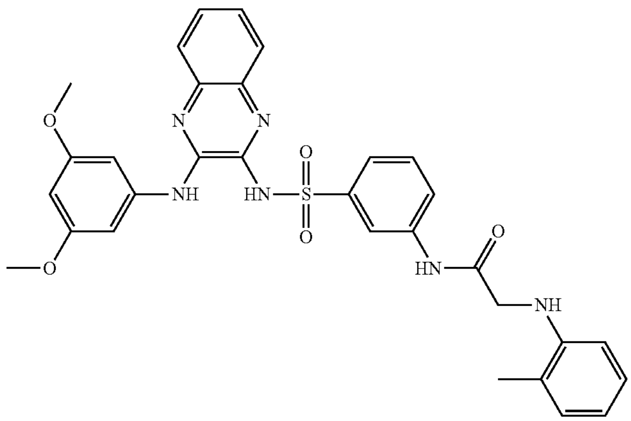 [SMILES: COc1cc(Nc2nc3ccccc3nc2NS(=O)(=O)c2cccc(NC(=O)CNc3ccccc3C)c2)cc(OC)c1] | N-(3-{[(3-{[3,5-bis(methoxy)phenyl]amino}quinoxalin-2-yl)amino]sulfonyl}phenyl)-N-2-(2-methylphenyl)glycinamide |
| 575 | 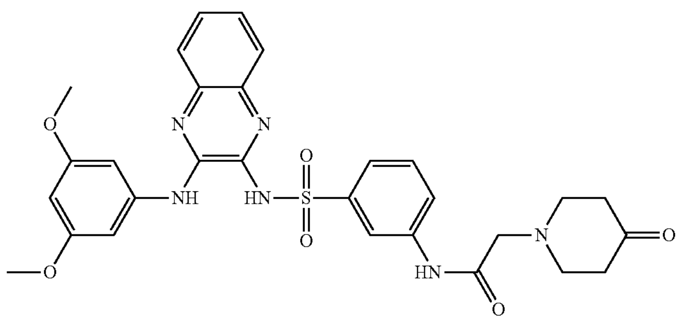 [SMILES: COc1cc(Nc2nc3ccccc3nc2NS(=O)(=O)c2cccc(NC(=O)CN3CCC(=O)CC3)c2)cc(OC)c1] | N-(3-{[(3-{[3,5-bis(methoxy)phenyl]amino}quinoxalin-2-yl)amino]sulfonyl}phenyl)-2-(4-oxopiperidin-1-yl)acetamide |
| 576 | 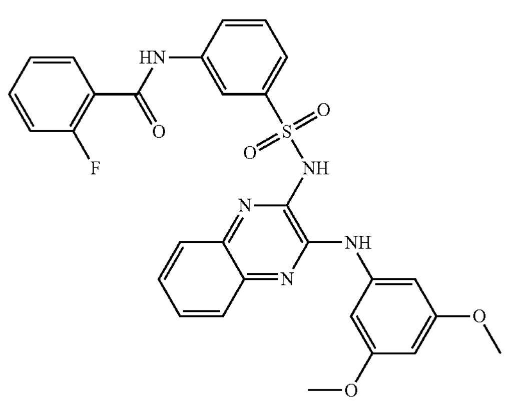 [SMILES: COc1cc(Nc2nc3ccccc3nc2NS(=O)(=O)c2cccc(NC(=O)c3ccccc3F)c2)cc(OC)c1] | N-(3-{[(3-{[3,5-bis(methoxy)phenyl]amino}quinoxalin-2-yl)amino]sulfonyl}phenyl)-2-fluorobenzamide |

TABLE 1-continued

| Cpd. No. | Structure | Name |
|---|---|---|
| 577 | 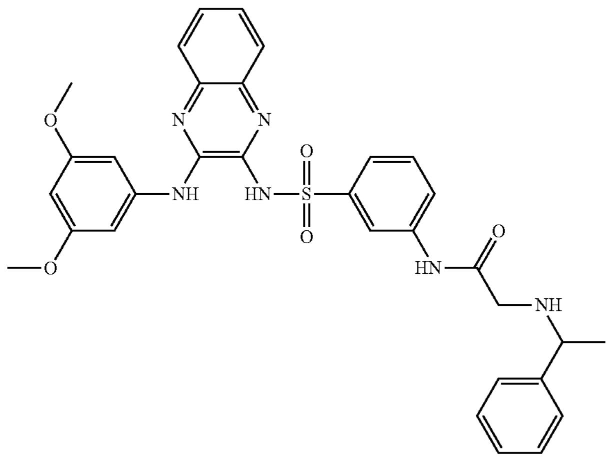 [SMILES: COc1cc(Nc2nc3ccccc3nc2NS(=O)(=O)c2cccc(NC(=O)CNC(C)c3ccccc3)c2)cc(OC)c1] | N-(3-{[(3-{[3,5-bis(methoxy)phenyl]amino}quinoxalin-2-yl)amino]sulfonyl}phenyl)-N-2-(1-phenylethyl)glycinamide |
| 578 | 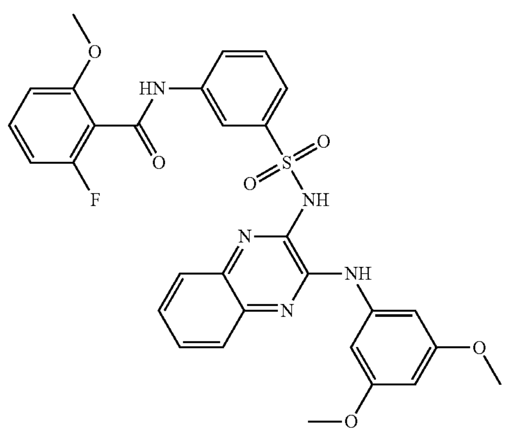 [SMILES: COc1cc(Nc2nc3ccccc3nc2NS(=O)(=O)c2cccc(NC(=O)c3c(F)cccc3OC)c2)cc(OC)c1] | N-(3-{[(3-{[3,5-bis(methoxy)phenyl]amino}quinoxalin-2-yl)amino]sulfonyl}phenyl)-2-fluoro-6-(methoxy)benzamide |
| 579 | 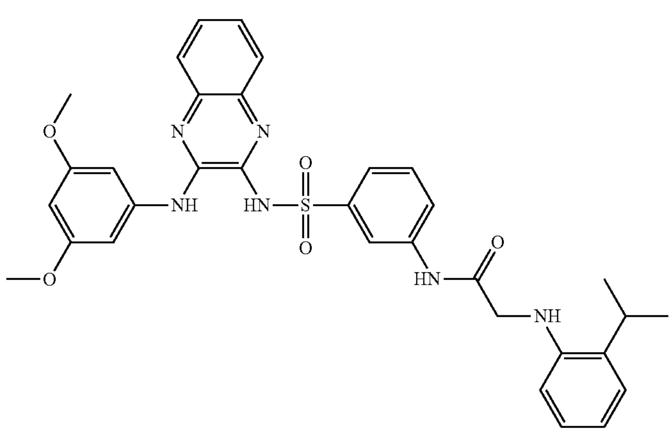 [SMILES: COc1cc(Nc2nc3ccccc3nc2NS(=O)(=O)c2cccc(NC(=O)CNc3ccccc3C(C)C)c2)cc(OC)c1] | N-(3-{[(3-{[3,5-bis(methoxy)phenyl]amino}quinoxalin-2-yl)amino]sulfonyl}phenyl)-N-2-[2-(1-methylethyl)phenyl]glycinamide |

TABLE 1-continued

| Cpd. No. | Structure | Name |
|---|---|---|
| 580 | 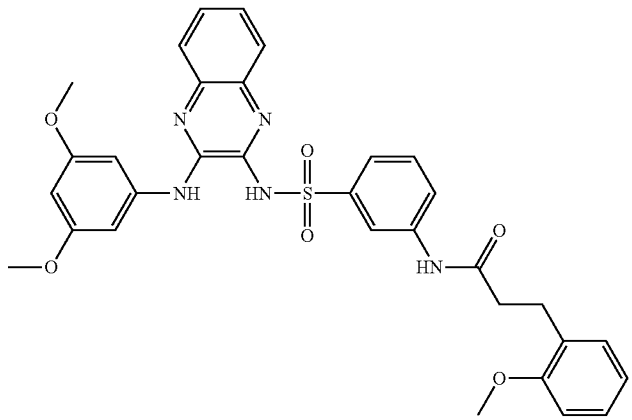 [SMILES: COc1cc(Nc2nc3ccccc3nc2NS(=O)(=O)c2cccc(NC(=O)CCc3ccccc3OC)c2)cc(OC)c1] | N-(3-{[(3-{[(3,5-bis(methoxy)phenyl]amino}quinoxalin-2-yl)amino]sulfonyl}phenyl)-3-[2-(methoxy)phenyl]propanamide |
| 581 | 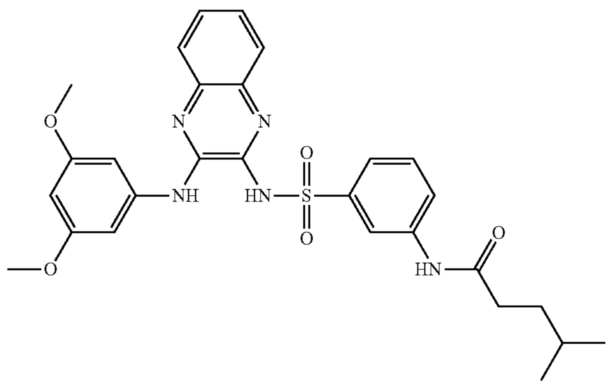 | N-(3-{[(3-{[3,5-bis(methoxy)phenyl]amino}quinoxalin-2-yl)amino]sulfonyl}phenyl)-4-methylpentanamide |
| 582 | 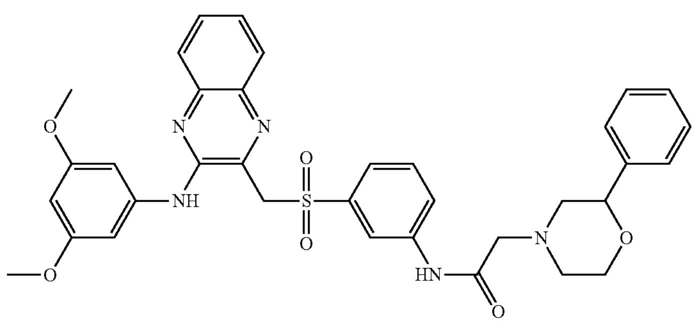 [SMILES: COc1cc(Nc2nc3ccccc3nc2CS(=O)(=O)c2cccc(NC(=O)CN3CCOC(c4ccccc4)C3)c2)cc(OC)c1] | N-(3-{[(3-{[3,5-bis(methoxy)phenyl]amino}quinoxalin-2-yl)amino]sulfonyl}phenyl)-2-(2-phenylmorpholin-4-yl)acetamide |
| 583 | 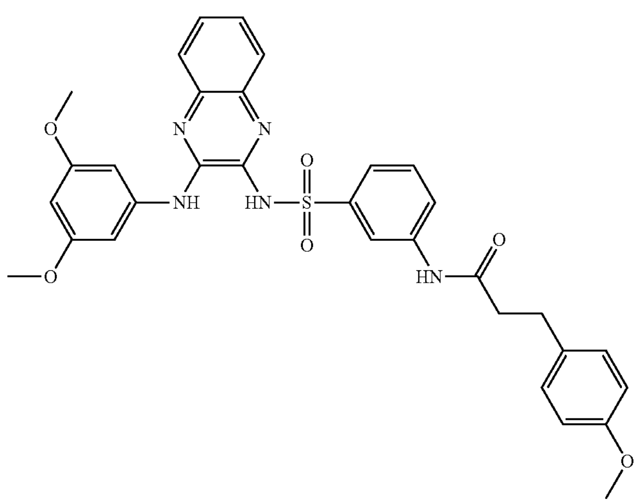 [SMILES: COc1ccc(CCC(=O)Nc2cccc(S(=O)(=O)Nc3nc4ccccc4nc3Nc3cc(OC)cc(OC)c3)c2)cc1] | N-(3-{[(3-{[3,5-bis(methoxy)phenyl]amino}quinoxalin-2-yl)amino]sulfonyl}phenyl)-3-[4-(methoxy)phenyl]propanamide |

TABLE 1-continued

| Cpd. No. | Structure | Name |
|---|---|---|
| 584 | 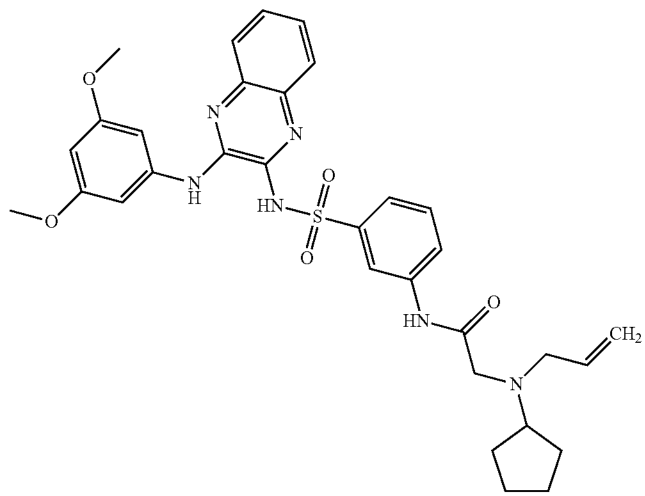 [SMILES: C=CCN(CC(=O)Nc1cccc(S(=O)(=O)Nc2nc3ccccc3nc2Nc2cc(OC)cc(OC)c2)c1)C1CCCC1] | N-(3-{[(3-{[3,5-bis(methoxy)phenyl]amino}quinoxalin-2-yl)amino]sulfonyl}phenyl)-N-2-cyclopentyl-N-2-prop-2-en-1-ylglycinamide |
| 585 | 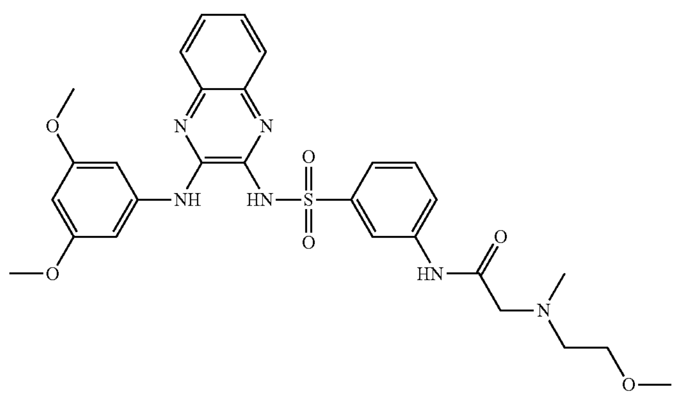 | N-(3-{[(3-{[3,5-bis(methoxy)phenyl]amino}quinoxalin-2-yl)amino]sulfonyl}phenyl)-N-2-methyl-N-2-[2-(methoxy)ethyl]glycinamide |
| 586 | 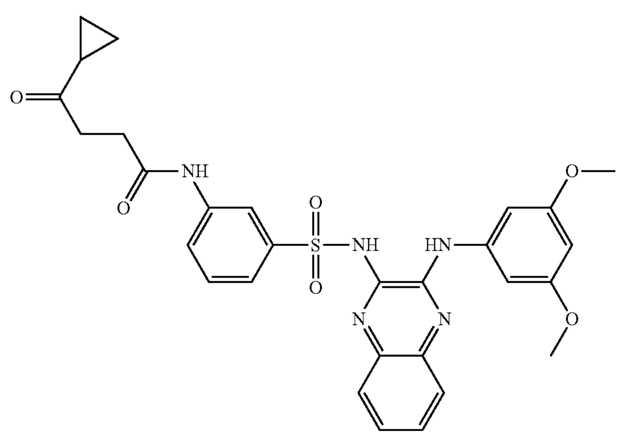 [SMILES: COc1cc(Nc2nc3ccccc3nc2NS(=O)(=O)c2cccc(NC(=O)CCC(=O)C3CC3)c2)cc(OC)c1] | N-(3-{[(3-{[3,5-bis(methoxy)phenyl]amino}quinoxalin-2-yl)amino]sulfonyl}phenyl)-4-cyclopropyl-4-oxobutanamide |

TABLE 1-continued

| Cpd. No. | Structure | Name |
| --- | --- | --- |
| 587 | 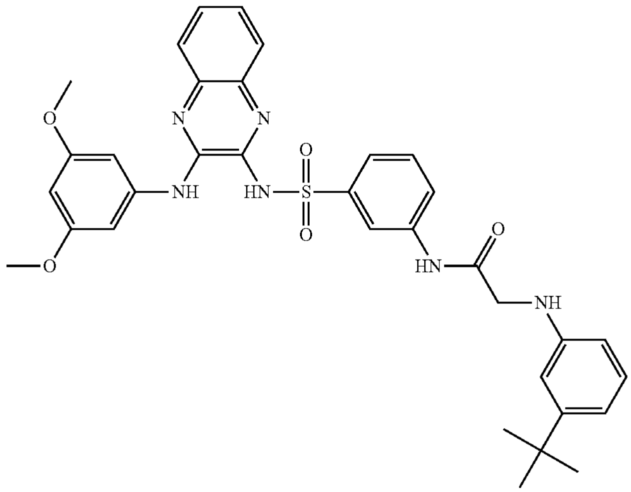 [SMILES: COc1cc(Nc2nc3ccccc3nc2NS(=O)(=O)c2cccc(NC(=O)CNc3cccc(C(C)(C)C)c3)c2)cc(OC)c1] | N-(3-{[(3-{[3,5-bis(methoxy)phenyl]amino}quinoxalin-2-yl)amino]sulfonyl}phenyl)-N-2-[3-(1,1-dimethylethyl)phenyl]glycinamide |
| 588 | 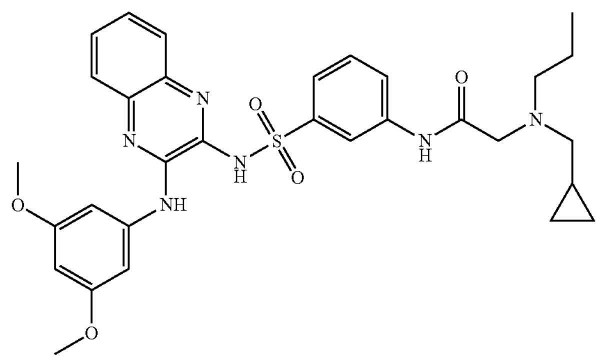 [SMILES: CCCN(CC(=O)Nc1cccc(S(=O)(=O)Nc2nc3ccccc3nc2Nc2cc(OC)cc(OC)c2)c1)CC1CC1] | N-(3-{[(3-{[3,5-bis(methoxy)phenyl]amino}quinoxalin-2-yl)amino]sulfonyl}phenyl)-N-2-(cyclopropylmethyl)-N-2-propylglycinamide |
| 589 | 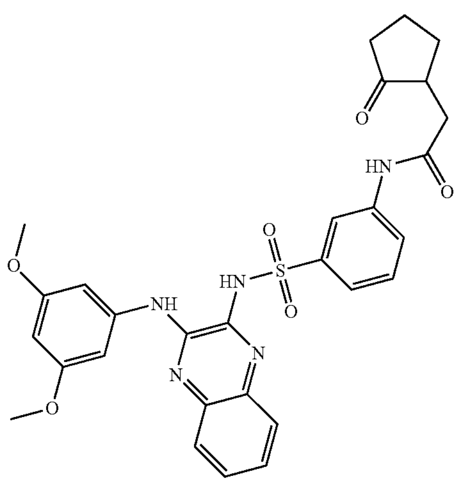 [SMILES: COc1cc(Nc2nc3ccccc3nc2NS(=O)(=O)c2cccc(NC(=O)CC3CCCC3=O)c2)cc(OC)c1] | N-(3-{[(3-{[3,5-bis(methoxy)phenyl]amino}quinoxalin-2-yl)amino]sulfonyl}phenyl)-2-(2-oxocyclopentyl)acetamide |

TABLE 1-continued

| Cpd. No. | Structure | Name |
| --- | --- | --- |
| 590 | 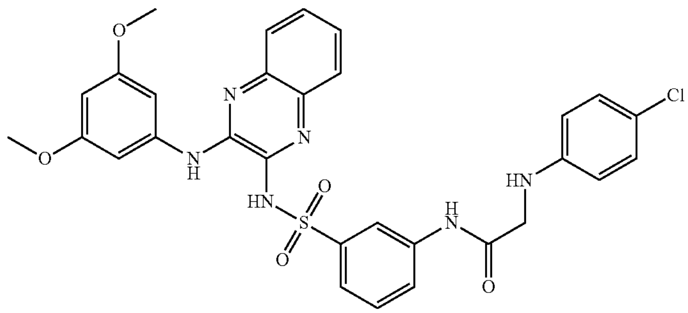 [SMILES: COc1cc(Nc2nc3ccccc3nc2NS(=O)(=O)c2cccc(NC(=O)CNc3ccc(Cl)cc3)c2)cc(OC)c1] | N-(3-{[(3-{[3,5-bis(methoxy)phenyl]amino}quinoxalin-2-yl)amino]sulfonyl}phenyl)-N-2-(4-chlorophenyl)glycinamide |
| 591 | 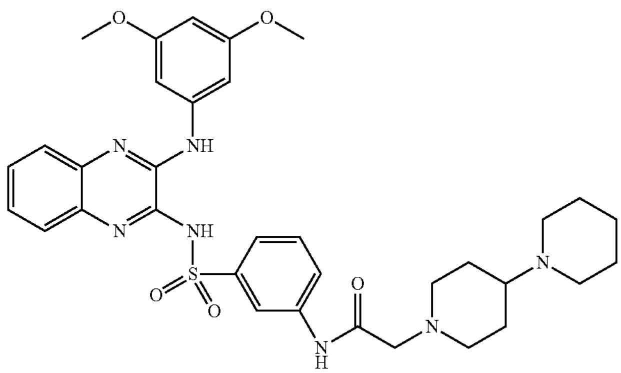 [SMILES: COc1cc(Nc2nc3ccccc3nc2NS(=O)(=O)c2cccc(NC(=O)CN3CCC(N4CCCCC4)CC3)c2)cc(OC)c1] | 2-(1,4'-bipiperidin-1'-yl)-N-(3-{[(3-{[3,5-bis(methoxy)phenyl]amino}quinoxalin-2-yl)amino]sulfonyl}phenyl)acetamide |
| 592 | 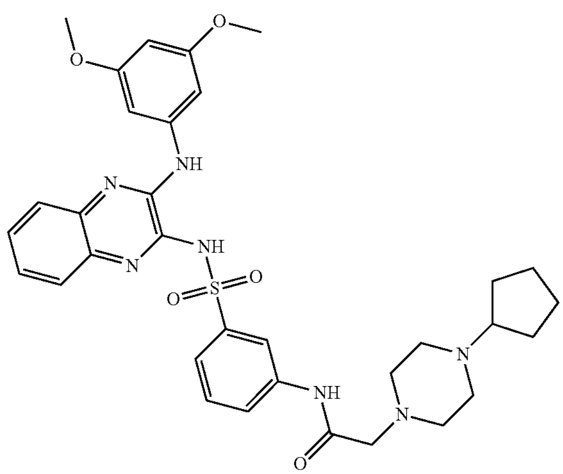 [SMILES: COc1cc(Nc2nc3ccccc3nc2NS(=O)(=O)c2cccc(NC(=O)CN3CCN(C4CCCC4)CC3)c2)cc(OC)c1] | N-(3-{[(3-{[3,5-bis(methoxy)phenyl]amino}quinoxalin-2-yl)amino]sulfonyl}phenyl)-2-(4-cyclopentylpiperazin-1-yl)acetamide |
| 593 | 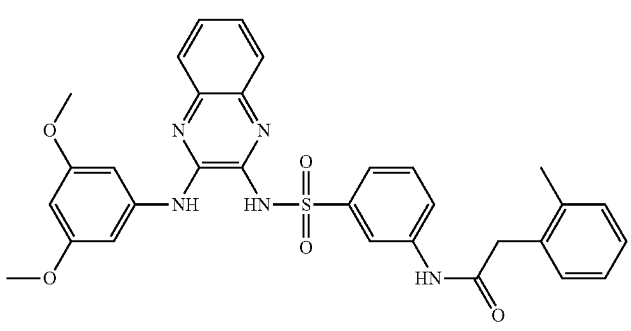 | N-(3-{[(3-{[3,5-bis(methoxy)phenyl]amino}quinoxalin-2-yl)amino]sulfonyl}phenyl)-2-(2-methylphenyl)acetamide |

| Cpd. No. | Structure | Name |
|---|---|---|
| 594 | 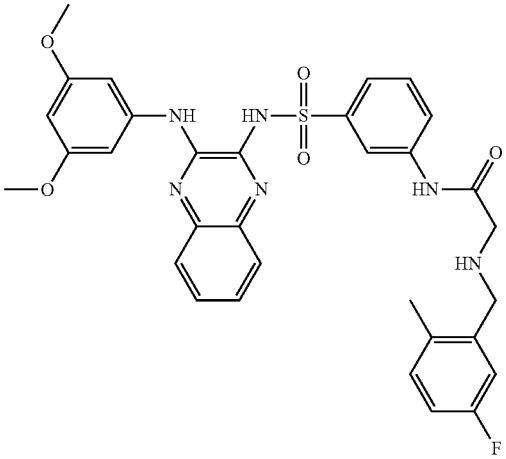 [SMILES: COc1cc(Nc2nc3ccccc3nc2NS(=O)(=O)c2cccc(NC(=O)CNCc3cc(F)ccc3C)c2)cc(OC)c1] | N-(3-{[(3-{[3,5-bis(methoxy)phenyl]amino}quinoxalin-2-yl)amino]sulfonyl}phenyl)-N-2-[(5-fluoro-2-methylphenyl)methyl)glycinamide |
| 595 | 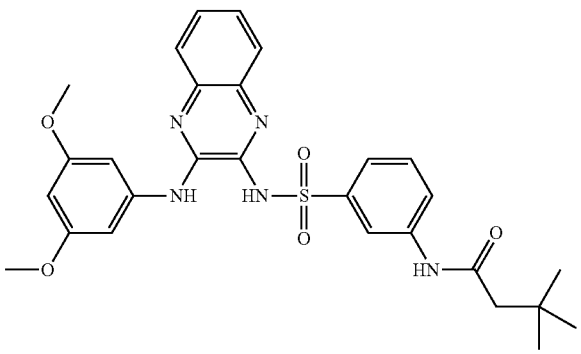 [SMILES: COc1cc(Nc2nc3ccccc3nc2NS(=O)(=O)c2cccc(NC(=O)CC(C)(C)C)c2)cc(OC)c1] | N-(3-{[(3-{[3,5-bis(methoxy)phenyl]amino}quinoxalin-2-yl)amino]sulfonyl}phenyl)-3,3-dimethylbutanamide |
| 596 | 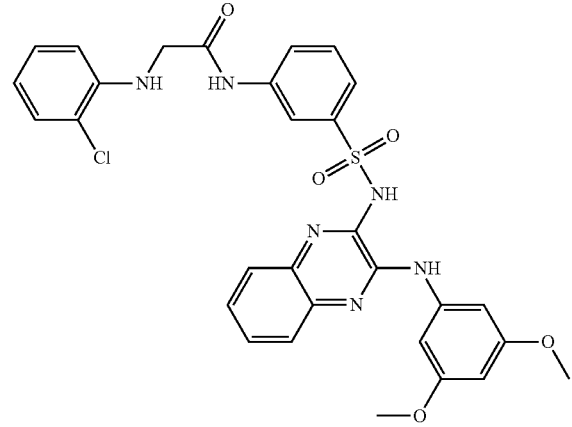 | N-(3-{[(3-{[3,5-bis(methyloxy)phenyl]amino}quinoxalin-2-yl)amino]sulfonyl}phenyl)-$N^2$-(2-chlorophenyl)glycinamide |
| 597 | 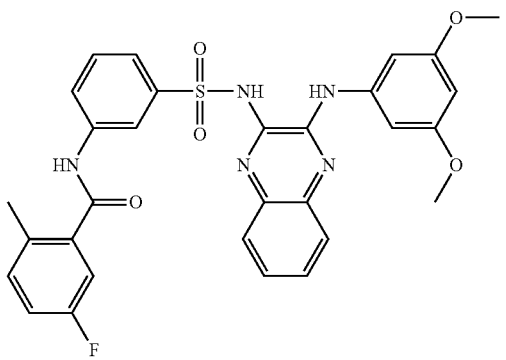 [SMILES: COc1cc(Nc2nc3ccccc3nc2NS(=O)(=O)c2cccc(NC(=O)c3cc(F)ccc3C)c2)cc(OC)c1] | N-(3-{[(3-{[3,5-bis(methoxy)phenyl]amino}quinoxalin-2-yl)amino]sulfonyl}phenyl)-5-fluoro-2-methylbenzamide |

TABLE 1-continued

| Cpd. No. | Structure | Name |
| --- | --- | --- |
| 598 | 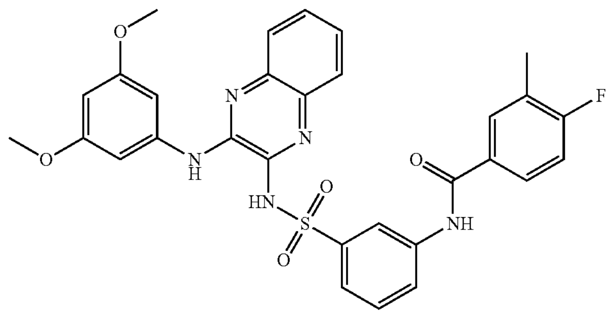 | N-(3-{[(3-{[3,5-bis(methoxy)phenyl]amino}quinoxalin-2-yl)amino]sulfonyl}phenyl)-4-fluoro-3-methylbenzamide |
| 599 | 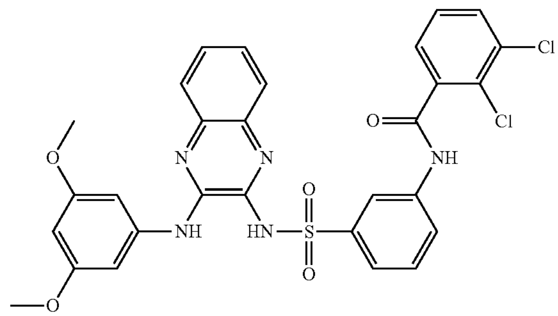 [SMILES: COc1cc(Nc2nc3ccccc3nc2NS(=O)(=O)c2cccc(NC(=O)c3cccc(Cl)c3Cl)c2)cc(OC)c1] | N-(3-{[(3-{[3,5-bis(methoxy)phenyl]amino}quinoxalin-2-yl)amino]sulfonyl}phenyl)-2,3-dichlorobenzamide |
| 600 | 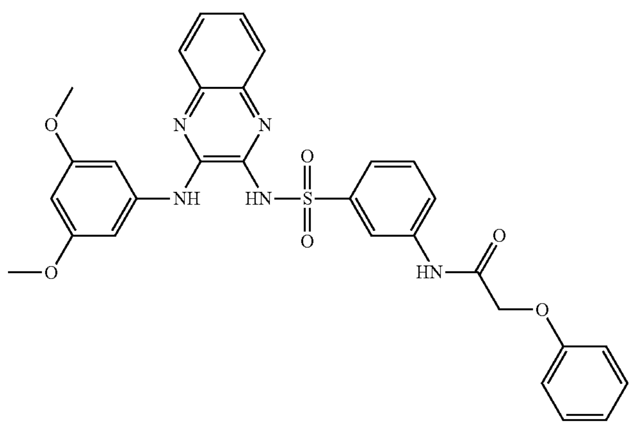 [SMILES: COc1cc(Nc2nc3ccccc3nc2NS(=O)(=O)c2cccc(NC(=O)COc3ccccc3)c2)cc(OC)c1] | N-(3-{[(3-{[3,5-bis(methoxy)phenyl]amino}quinoxalin-2-yl)amino]sulfonyl}phenyl)-2-(phenyloxy)acetamide |
| 601 | 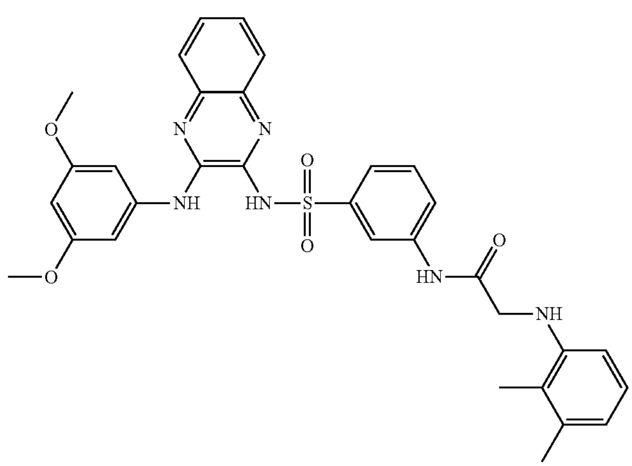 [SMILES: COc1cc(Nc2nc3ccccc3nc2NS(=O)(=O)c2cccc(NC(=O)CNc3cccc(C)c3C)c2)cc(OC)c1] | N-(3-{[(3-{[3,5-bis(methoxy)phenyl]amino}quinoxalin-2-yl)amino]sulfonyl}phenyl)-N-2-(2,3)-dimethylphenyl)glycinamide |

TABLE 1-continued

| Cpd. No. | Structure | Name |
|---|---|---|
| 602 | 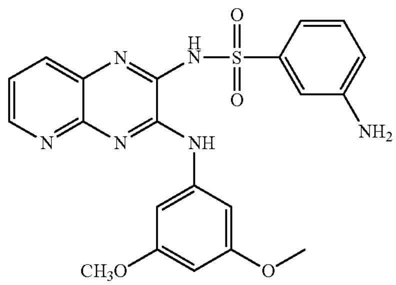 | 3-amino-N-(3-{[3,5-bis(methoxy)phenyl]amino}pyrido[2,3-b]pyrazin-2-yl)benzenesulfonamide |
| 603 | 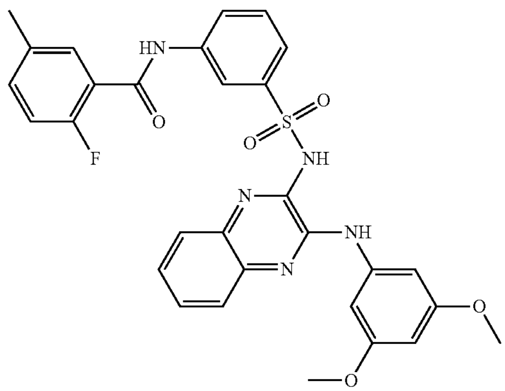 [SMILES: COc1cc(Nc2nc3ccccc3nc2NS(=O)(=O)c2cccc(NC(=O)c3cc(C)ccc3F)c2)cc(OC)c1] | N-(3-{[(3-{[3,5-bis(methoxy)phenyl]amino}quinoxalin-2-yl)amino]sulfonyl}phenyl)-2-fluoro-5-methylbenzamide |
| 604 | 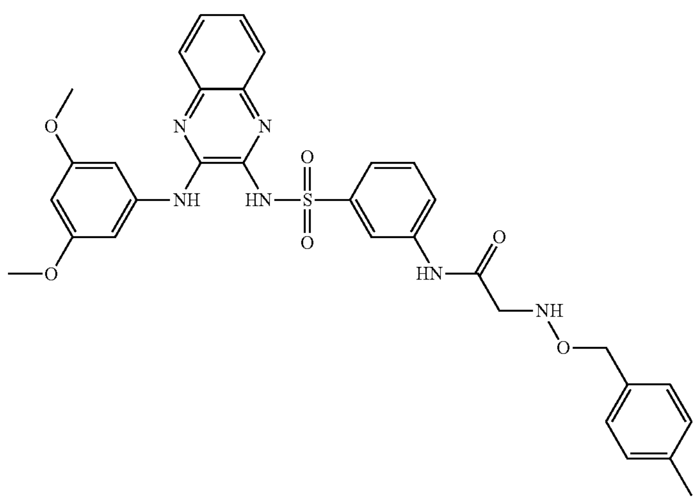 | N-(3-{[(3-{[3,5-bis(methoxy)phenyl]amino}quinoxalin-2-yl)amino]sulfonyl}phenyl)-N-2-{[(4-methylphenyl)methyl]oxy}glycinamide |
| 605 | 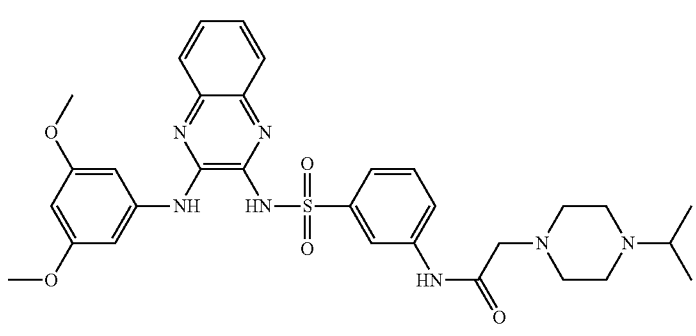 [SMILES: COc1cc(Nc2nc3ccccc3nc2NS(=O)(=O)c2cccc(NC(=O)CN3CCN(C(C)C)CC3)c2)cc(OC)c1] | N-(3-{[(3-{[3,5-bis(methoxy)phenyl]amino}quinoxalin-2-yl)amino]sulfonyl}phenyl)-2-[4-(1-methylethyl)piperazin-1-yl]acetamide |

TABLE 1-continued

| Cpd. No. | Structure | Name |
|---|---|---|
| 606 | 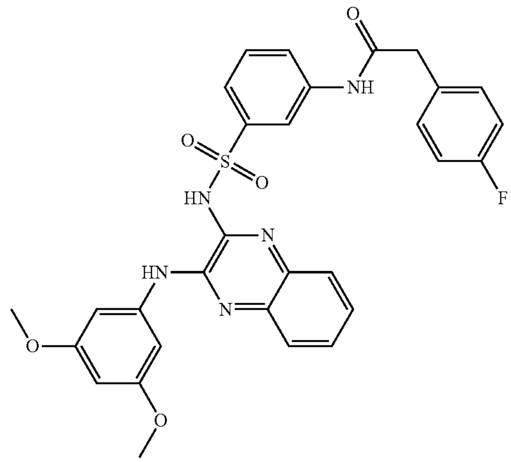 [SMILES: COc1cc(Nc2nc3ccccc3nc2NS(=O)(=O)c2cccc(NC(=O)Cc3ccc(F)cc3)c2)cc(OC)c1] | N-(3-{[(3-{[3,5-bis(methoxy)phenyl]amino}quinoxalin-2-yl)amino]sulfonyl}phenyl)-2-(4-fluorophenyl)acetamide |
| 607 | 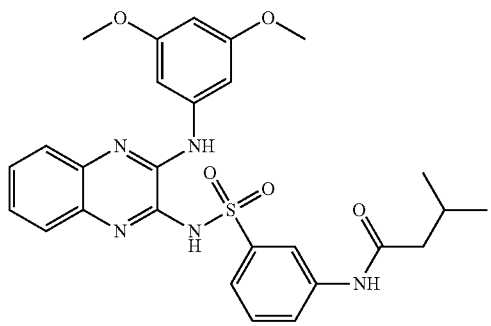 [SMILES: COc1cc(Nc2nc3ccccc3nc2NS(=O)(=O)c2cccc(NC(=O)CC(C)C)c2)cc(OC)c1] | N-(3-{[(3-{[3,5-bis(methoxy)phenyl]amino}quinoxalin-2-yl)amino]sulfonyl}phenyl)-3-methylbutanamide |
| 608 | 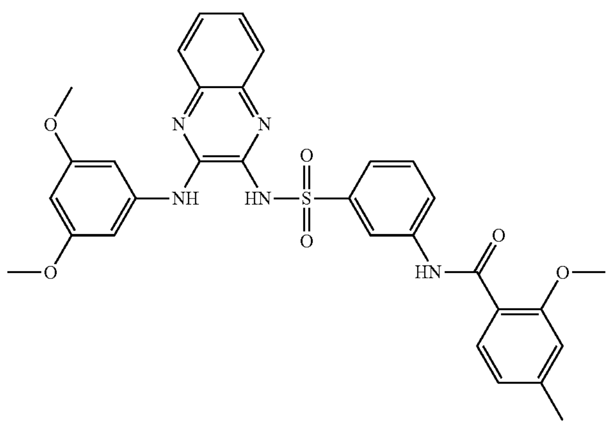 | N-(3-{[(3-{[3,5-bis(methoxy)phenyl]amino}quinoxalin-2-yl)amino]sulfonyl}phenyl)-4-methyl-2-(methoxy)benzamide |
| 609 | 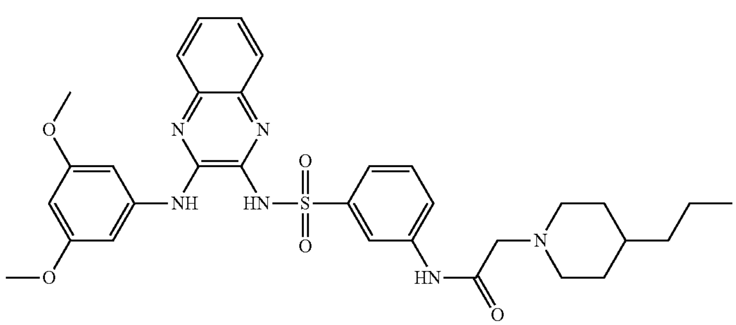 [SMILES: CCCC1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methoxy)phenyl]amino}quinoxalin-2-yl)amino]sulfonyl}phenyl)-2-(4-propylpiperidin-1-yl)acetamide |

TABLE 1-continued

| Cpd. No. | Structure | Name |
|---|---|---|
| 610 | 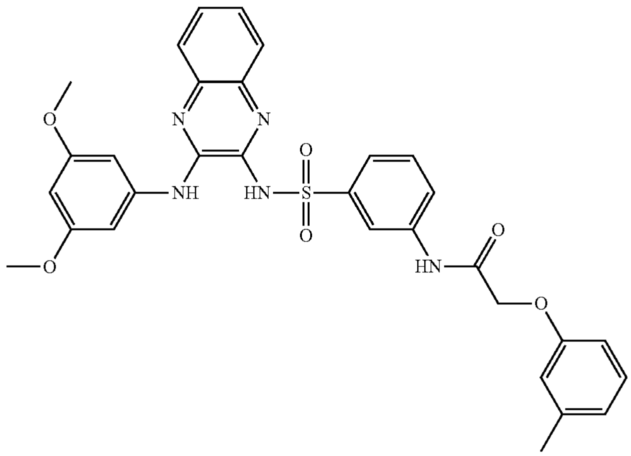 [SMILES: COc1cc(Nc2nc3ccccc3nc2NS(=O)(=O)c2cccc(NC(=O)COc3cccc(C)c3)c2)cc(OC)c1] | N-(3-{[(3-{[3,5-bis(methoxy)phenyl]amino}quinoxalin-2-yl)amino]sulfonyl}phenyl)-2-[(3-methylphenyl)oxy]acetamide |
| 611 | 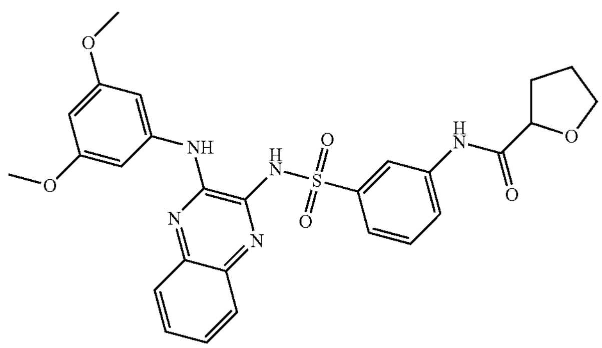 [SMILES: COc1cc(Nc2nc3ccccc3nc2NS(=O)(=O)c2cccc(NC(=O)C3CCCO3)c2)cc(OC)c1] | N-(3-{[(3-{[3,5-bis(methoxy)phenyl]amino}quinoxalin-2-yl)amino]sulfonyl}phenyl)tetrahydrofuran-2-carboxamide |
| 612 | 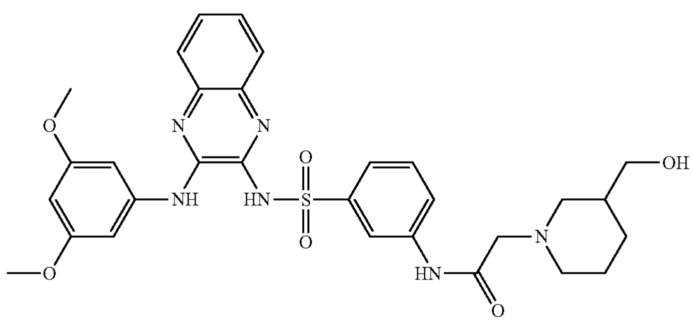 [SMILES: COc1cc(Nc2nc3ccccc3nc2NS(=O)(=O)c2cccc(NC(=O)CN3CCCC(CO)C3)c2)cc(OC)c1] | N-(3-{[(3-{[3,5-bis(methoxy)phenyl]amino}quinoxalin-2-yl)amino]sulfonyl}phenyl)-2-[3-(hydroxymethyl)piperidin-1-yl]acetamide |
| 613 | 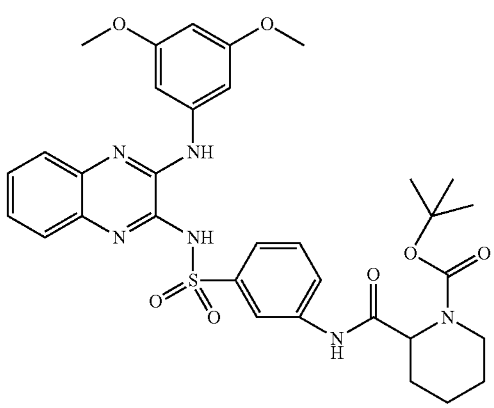 [SMILES: COc1cc(Nc2nc3ccccc3nc2NS(=O)(=O)c2cccc(NC(=O)C3CCCCN3C(=O)OC(C)(C)C)c2)cc(OC)c1] | 1,1-dimethylethyl2-{[(3-{[(3-{[3,5-bis(methoxy)phenyl]amino}quinoxalin-2-yl)amino]sulfonyl}phenyl)amino]carbonyl}piperidine-1-carboxylate |

TABLE 1-continued

| Cpd. No. | Structure | Name |
|---|---|---|
| 614 | 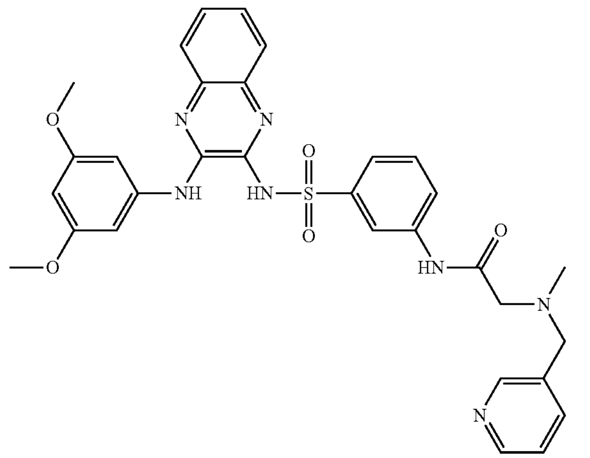 | N-(3-{[(3-{[3,5-bis(methoxy)phenyl]amino}quinoxalin-2-yl)amino]sulfonyl}phenyl)-N-2-methyl-N-2-(pyridin-3-ylmethyl)glycinamide |
| 615 | 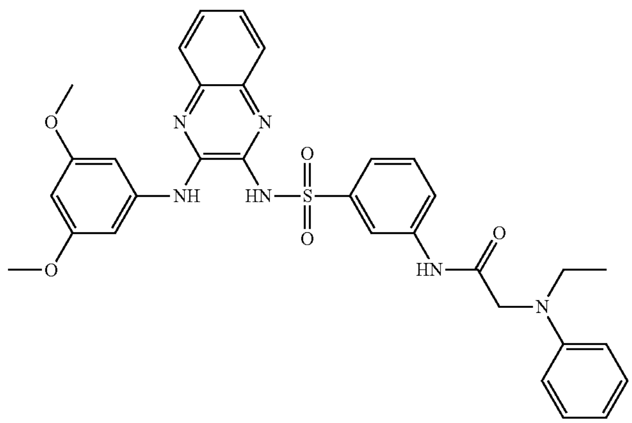 [SMILES: CCN(CC(=O)Nc1cccc(S(=O)(=O)Nc2nc3ccccc3nc2Nc2cc(OC)cc(OC)c2)c1)c1ccccc1] | N-(3-{[(3-{[3,5-bis(methoxy)phenyl]amino}quinoxalin-2-yl)amino]sulfonyl}phenyl)-N-2-ethyl-N-2-phenylglycinamide |
| 616 | 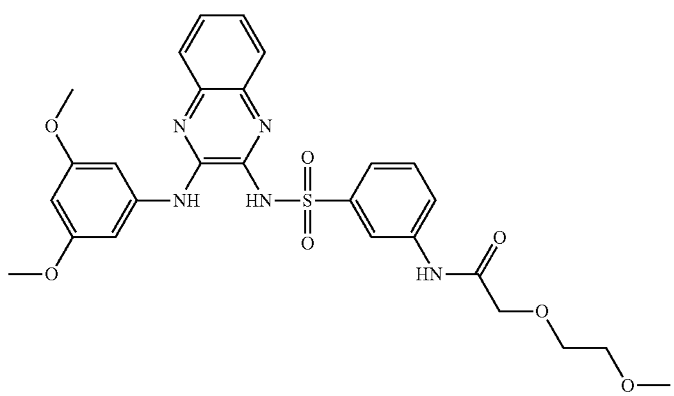 | N-(3-{[(3-{[3,5-bis(methoxy)phenyl]amino}quinoxalin-2-yl)amino]sulfonyl}phenyl)-2-{[2-(methoxy)ethyl]oxy}acetamide |
| 617 | 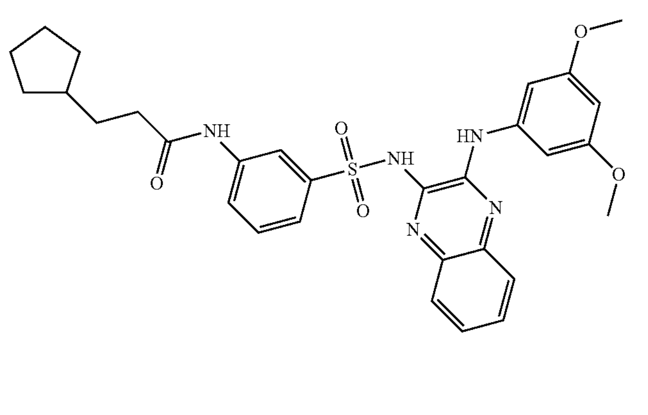 [SMILES: COc1cc(Nc2nc3ccccc3nc2NS(=O)(=O)c2cccc(NC(=O)CCC3CCCC3)c2)cc(OC)c1] | N-(3-{[(3-{[3,5-bis(methoxy)phenyl]amino}quinoxalin-2-yl)amino]sulfonyl}phenyl)-3-cyclopentylpropanamide |

TABLE 1-continued

| Cpd. No. | Structure | Name |
|---|---|---|
| 618 | 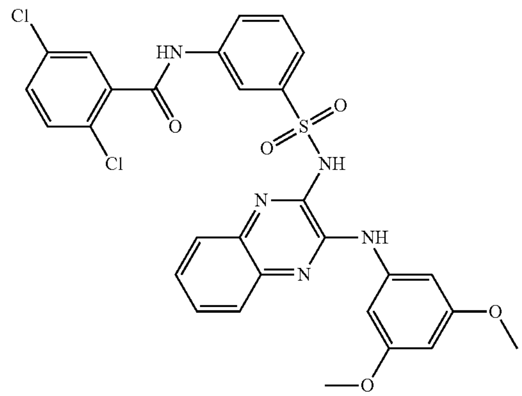 [SMILES: COc1cc(Nc2nc3ccccc3nc2NS(=O)(=O)c2cccc(NC(=O)c3cc(Cl)ccc3Cl)c2)cc(OC)c1] | N-(3-{[(3-{[3,5-bis(methoxy)phenyl]amino}quinoxalin-2-yl)amino]sulfonyl}phenyl)-2,5-dichlorobenzamide |
| 619 | 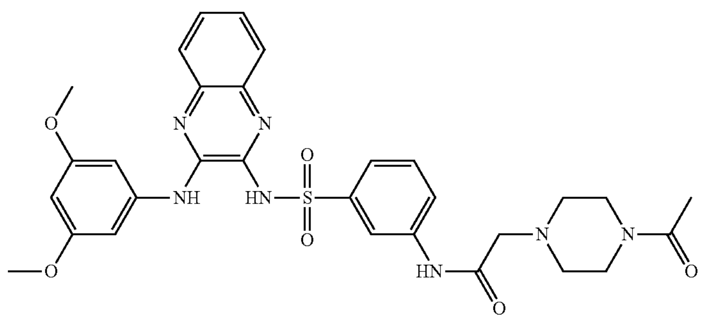 [SMILES: COc1cc(Nc2nc3ccccc3nc2NS(=O)(=O)c2cccc(NC(=O)CN3CCN(C(C)=O)CC3)c2)cc(OC)c1] | 2-(4-acetylpiperazin-1-yl)-N-(3-{[(3-{[3,5-bis(methoxy)phenyl]amino}quinoxalin-2-yl)amino]sulfonyl}phenyl)acetamide |
| 620 | 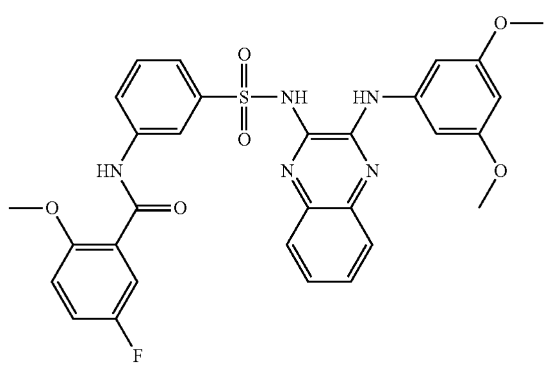 | N-(3-{[(3-{[3,5-bis(methoxy)phenyl]amino}quinoxalin-2-yl)amino]sulfonyl}phenyl)-5-fluoro-2-(methoxy)benzamide |
| 621 | 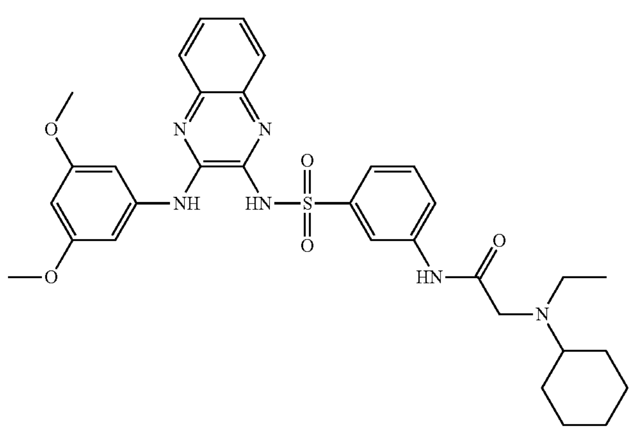 [SMILES: CCN(CC(=O)Nc1cccc(S(=O)(=O)Nc2nc3ccccc3nc2Nc2cc(OC)cc(OC)c2)c1)C1CCCCC1] | N-(3-{[(3-{[3,5-bis(methoxy)phenyl]amino}quinoxalin-2-yl)amino]sulfonyl}phenyl)-N-2-cyclohexyl-N-2-ethylglycinamide |

TABLE 1-continued

| Cpd. No. | Structure | Name |
|---|---|---|
| 622 | 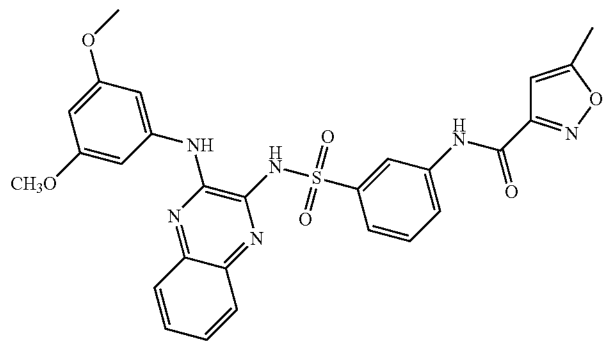 | N-(3-{[(3-{[3,5-bis(methoxy)phenyl]amino}quinoxalin-2-yl)amino]sulfonyl}phenyl)-5-methylisoxazole-3-carboxamide |
| 623 | 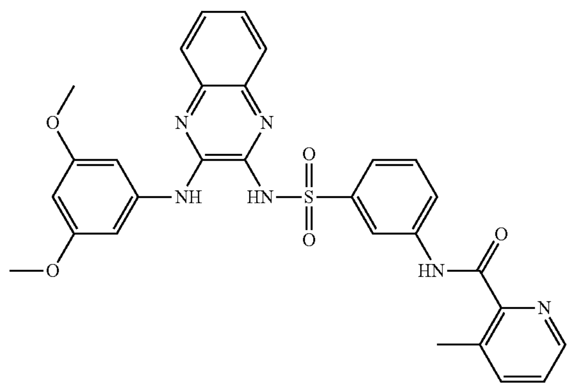 [SMILES: COc1cc(Nc2nc3ccccc3nc2NS(=O)(=O)c2cccc(NC(=O)c3ncccc3C)c2)cc(OC)c1] | N-(3-{[(3-{[3,5-bis(methoxy)phenyl]amino}quinoxalin-2-yl)amino]sulfonyl}phenyl)-3-methylpyridine-2-carboxamide |
| 624 | 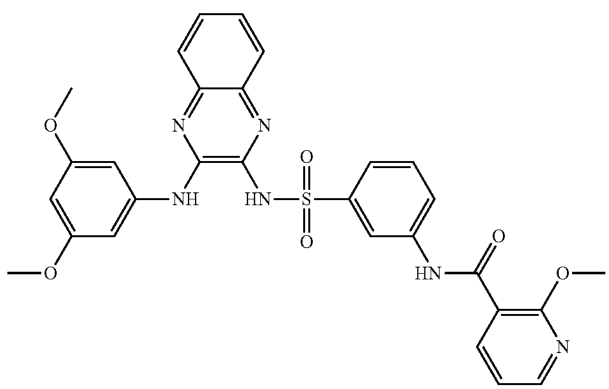 | N-(3-{[(3-{[3,5-bis(methoxy)phenyl]amino}quinoxalin-2-yl)amino]sulfonyl}phenyl)-2-(methoxy)pyridine-3-carboxamide |
| 625 | 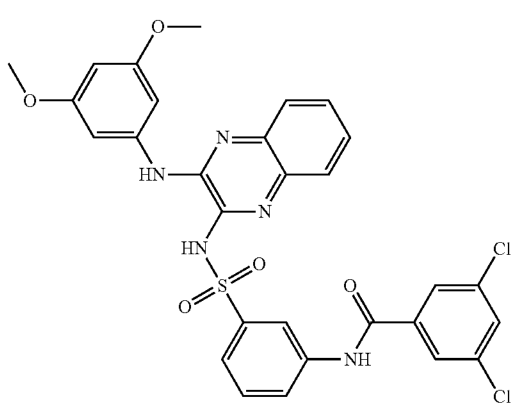 [SMILES: COc1cc(Nc2nc3ccccc3nc2NS(=O)(=O)c2cccc(NC(=O)c3cc(Cl)cc(Cl)c3)c2)cc(OC)c1] | N-(3-{[(3-{[3,5-bis(methoxy)phenyl]amino}quinoxalin-2-yl)amino]sulfonyl}phenyl)-3,5-dichlorobenzamide |

TABLE 1-continued

| Cpd. No. | Structure | Name |
|---|---|---|
| 626 | 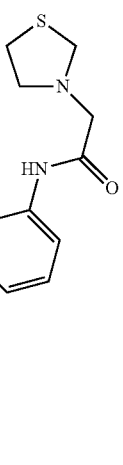 | N-(3-{[(3-{[3,5-bis(methoxy)phenyl]amino}quinoxalin-2-yl)amino]sulfonyl}phenyl)-2-(1,3-thiazolidin-3-yl)acetamide |
| 627 | 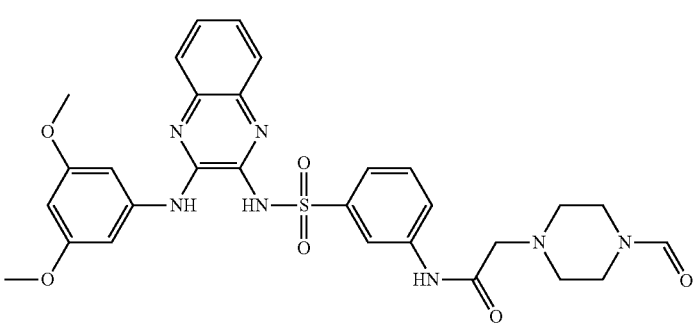 [SMILES: COc1cc(Nc2nc3ccccc3nc2NS(=O)(=O)c2cccc(NC(=O)CN3CCN(C=O)CC3)c2)cc(OC)c1] | N-(3-{[(3-{[3,5-bis(methoxy)phenyl]amino}quinoxalin-2-yl)amino]sulfonyl}phenyl)-2-(4-formylpiperazin-1-yl)acetamide |
| 628 | 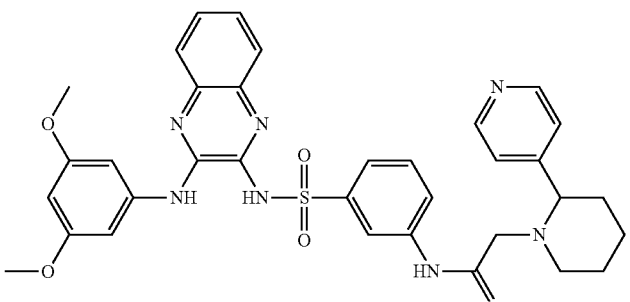 | N-(3-{[(3-{[3,5-bis(methoxy)phenyl]amino}quinoxalin-2-yl)amino]sulfonyl}phenyl)-2-(2-pyridin-4-ylpiperidin-1-yl)acetamide |
| 629 | 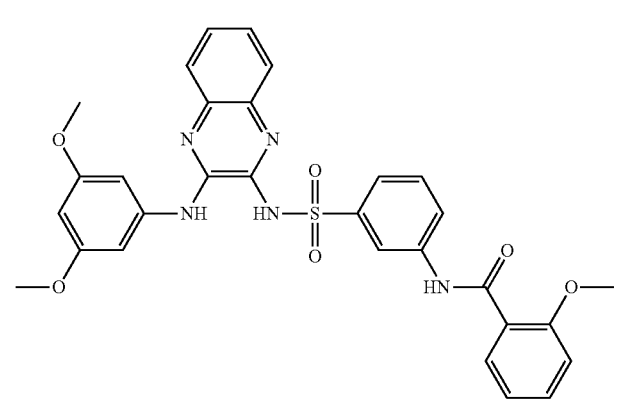 | N-(3-{[(3-{[3,5-bis(methoxy)phenyl]amino}quinoxalin-2-yl)amino]sulfonyl}phenyl)-2-(methoxy)benzamide |

TABLE 1-continued

| Cpd. No. | Structure | Name |
| --- | --- | --- |
| 630 | 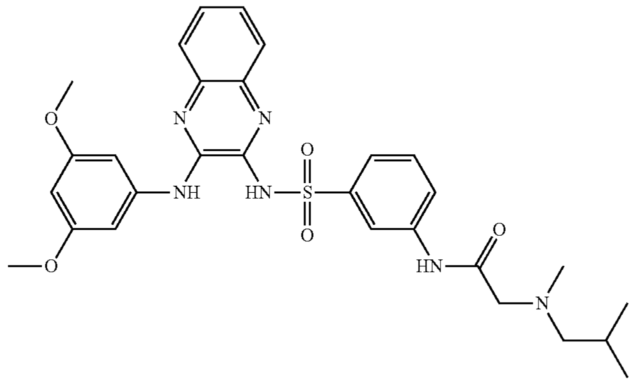 [SMILES: COc1cc(Nc2nc3ccccc3nc2NS(=O)(=O)c2cccc(NC(=O)CN(C)CC(C)C)c2)cc(OC)c1] | N-(3-{[(3-{[3,5-bis(methoxy)phenyl]amino}quinoxalin-2-yl)amino]sulfonyl}phenyl)-N-2-methyl-N-2-(2-methylpropyl)glycinamide |
| 631 | 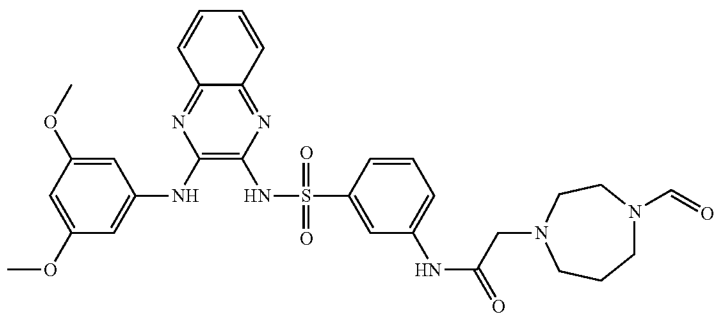 [SMILES: COc1cc(Nc2nc3ccccc3nc2NS(=O)(=O)c2cccc(NC(=O)CN3CCCN(C=O)CC3)c2)cc(OC)c1] | N-(3-{[(3-{[3,5-bis(methoxy)phenyl]amino}quinoxalin-2-yl)amino]sulfonyl}phenyl)-2-(4-formyl-1,4-diazepan-1-yl)acetamide |
| 632 | 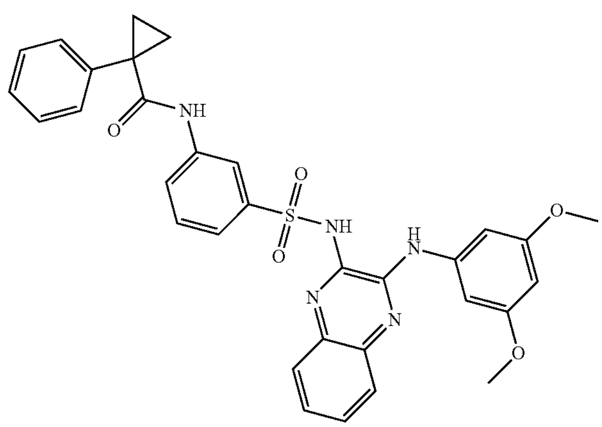 [SMILES: COc1cc(Nc2nc3ccccc3nc2NS(=O)(=O)c2cccc(NC(=O)C3(c4ccccc4)CC3)c2)cc(OC)c1] | N-(3-{[(3-{[3,5-bis(methoxy)phenyl]amino}quinoxalin-2-yl)amino]sulfonyl}phenyl)-1-phenylcyclopropanecarboxamide |
| 633 | 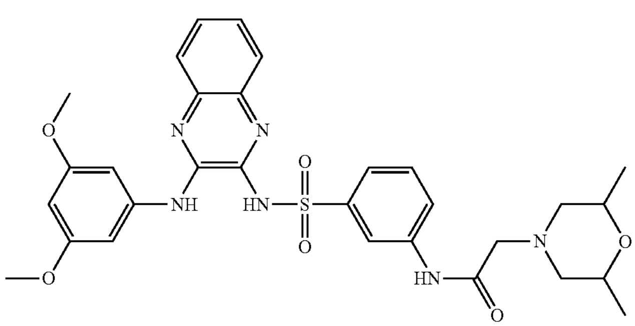 | N-(3-{[(3-{[3,5-bis(methoxy)phenyl]amino}quinoxalin-2-yl)amino]sulfonyl}phenyl)-2-(2,6-dimethylmorpholin-4-yl)acetamide |

| Cpd. No. | Structure | Name |
|---|---|---|
| 634 | 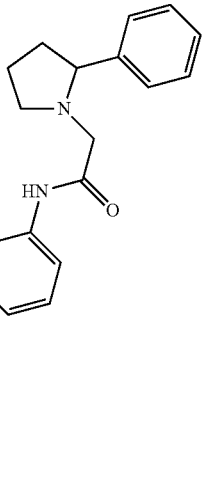 | N-(3-{[(3-{[3,5-bis(methoxy)phen-yl]amino}quinoxalin-2-yl)amino]sulfonyl}phenyl)-2-(2-phenylpyrrolidin-1-yl)acetamide |
| 635 | 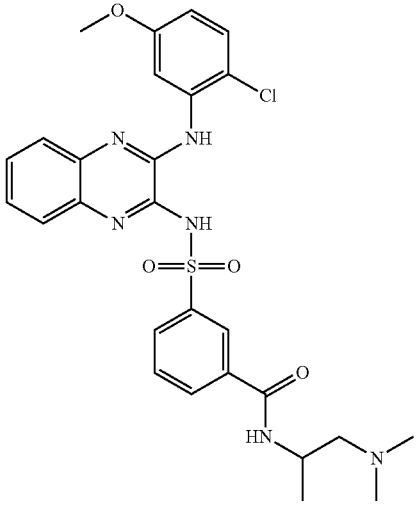 [SMILES: COc1ccc(Cl)c(Nc2nc3ccccc3nc2NS(=O)(=O)c2cccc(C(=O)NC(C)CN(C)C)c2)c1] | 3-{[(3-{[2-chloro-5-(methoxy)phen-yl]amino}quinoxalin-2-yl)amino]sulfonyl}-N-[2-(dimethylamino)-1-methylethyl]benzamide |
| 636 | 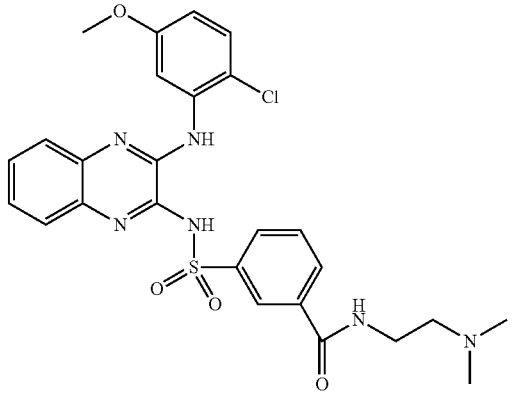 [SMILES: COc1ccc(Cl)c(Nc2nc3ccccc3nc2NS(=O)(=O)c2cccc(C(=O)NCCN(C)C)c2)c1] | 3-{[(3-{[2-chloro-5-(methoxy)phen-yl]amino}quinoxalin-2-yl)amino]sulfonyl}-N-[2-(dimethylamino)ethyl]benzamide |

TABLE 1-continued

| Cpd. No. | Structure | Name |
| --- | --- | --- |
| 637 | 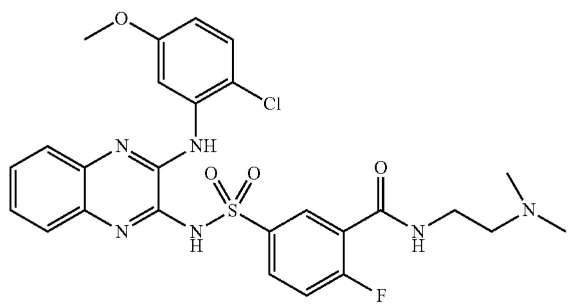 [SMILES: COc1ccc(Cl)c(Nc2nc3ccccc3nc2NS(=O)(=O)c2ccc(F)c(C(=O)NCCN(C)C)c2)c1] | 5-{[(3-{[2-chloro-5-(methoxy)phenyl]amino}quinoxalin-2-yl)amino]sulfonyl}-N-[2-(dimethylamino)ethyl]-2-fluorobenzamide |
| 638 | 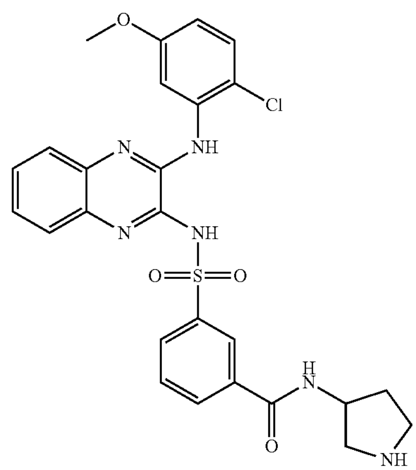 [SMILES: COc1ccc(Cl)c(Nc2nc3ccccc3nc2NS(=O)(=O)c2cccc(C(=O)NC3CCNC3)c2)c1] | 3-{[(3-{[2-chloro-5-(methoxy)phenyl]amino}quinoxalin-2-yl)amino]sulfonyl}-N-pyrrolidin-3-ylbenzamide |
| 639 | 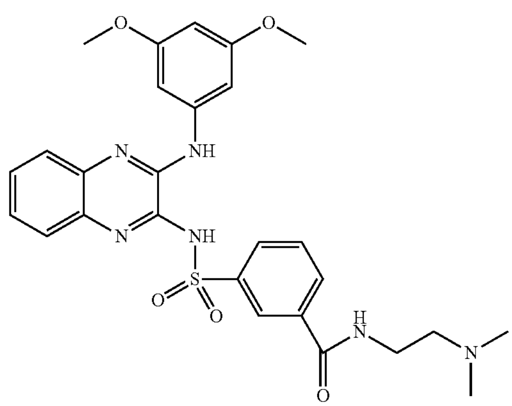 | 3-{[(3-{[3,5-bis(methoxy)phenyl]amino}quinoxalin-2-yl)amino]sulfonyl}-N-[2-(dimethylamino)ethyl)benzamide |
| 640 | 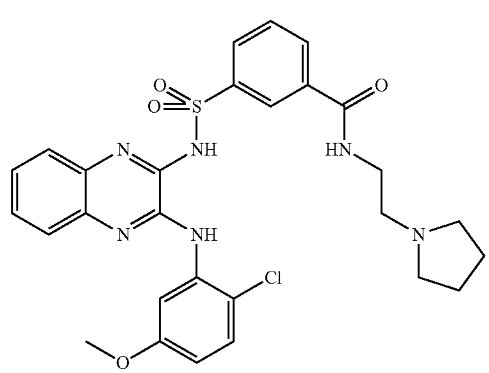 [SMILES: COc1ccc(Cl)c(Nc2nc3ccccc3nc2NS(=O)(=O)c2cccc(C(=O)NCCN3CCCC3)c2)c1] | 3-{[(3-{[2-chloro-5-(methoxy)phenyl]amino}quinoxalin-2-yl)amino]sulfonyl}-N-(2-pyrrolidin-1-ylethyl)benzamide |

TABLE 1-continued

| Cpd. No. | Structure | Name |
|---|---|---|
| 641 | 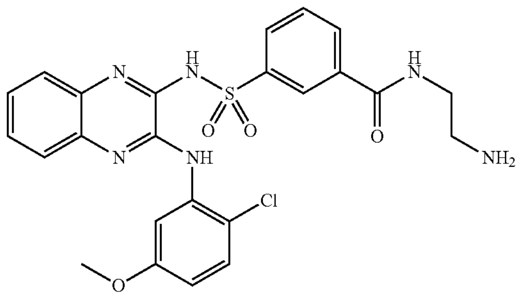 [SMILES: COc1ccc(Cl)c(Nc2nc3ccccc3nc2NS(=O)(=O)c2cccc(C(=O)NCCN)c2)c1] | N-(2-aminoethyl)-3-{[(3-{[2-chloro-5-(methoxy)phenyl]amino}quinoxalin-2-yl)amino]sulfonyl}benzamide |
| 642 | 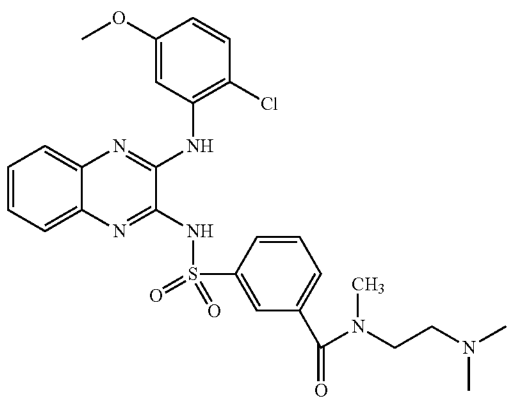 [SMILES: COc1ccc(Cl)c(Nc2nc3ccccc3nc2NS(=O)(=O)c2cccc(C(=O)N(C)CCN(C)C)c2)c1] | 3-{[(3-{[2-chloro-5-(methoxy)phenyl]amino}quinoxalin-2-yl)amino]sulfonyl}-N-[2-(dimethylamino)ethyl]-N-methylbenzamide |
| 643 | 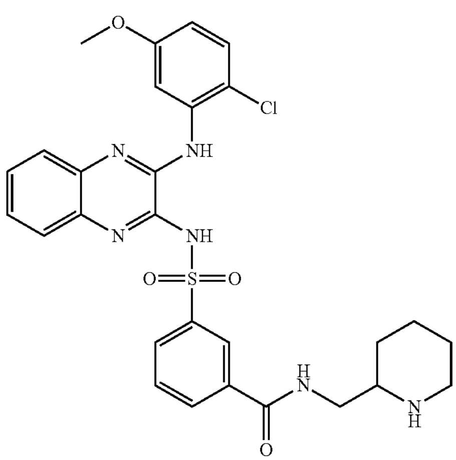 [SMILES: COc1ccc(Cl)c(Nc2nc3ccccc3nc2NS(=O)(=O)c2cccc(C(=O)NCC3CCCCN3)c2)c1] | 3-{[(3-{[2-chloro-5-(methoxy)phenyl]amino}quinoxalin-2-yl)amino]sulfonyl}-N-(piperidin-2-ylmethyl)benzamide |

TABLE 1-continued
| Cpd. No. | Structure | Name |
|---|---|---|
| 644 | 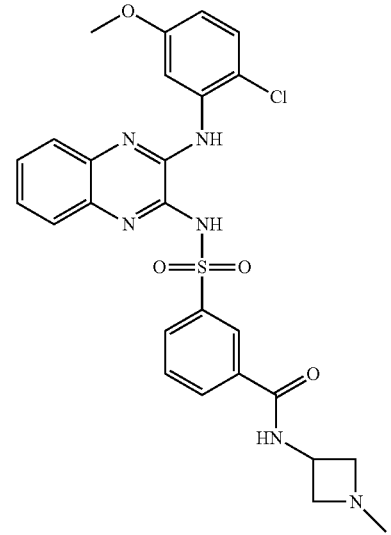 [SMILES: COc1ccc(Cl)c(Nc2nc3ccccc3nc2NS(=O)(=O)c2cccc(C(=O)NC3CN(C)C3)c2)c1] | 3-{[(3-{[2-chloro-5-(methoxy)phenyl]amino}quinoxalin-2-yl)amino]sulfonyl}-N-(1-methylazetidin-3-yl)benzamide |
| 645 | 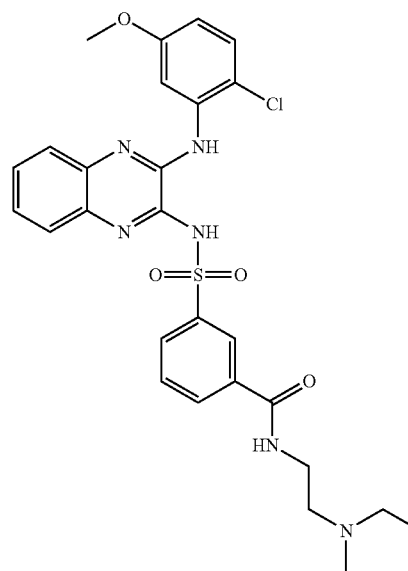 | 3-{[(3-{[2-chloro-5-(methoxy)phenyl]amino}quinoxalin-2-yl)amino]sulfonyl}-N-(2-piperidin-1-ylethyl)benzamide |

TABLE 1-continued
| Cpd. No. | Structure | Name |
|---|---|---|
| 646 | 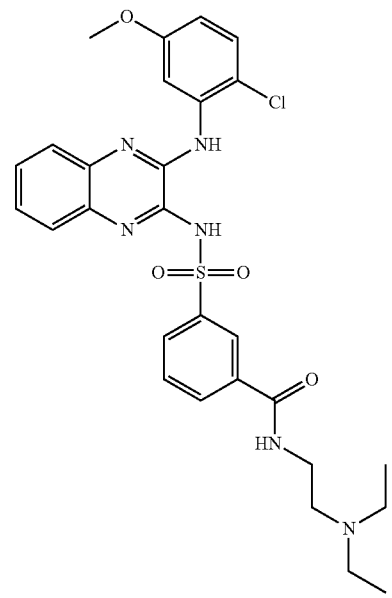 [SMILES: CCN(CC)CCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[2-(diethylamino)ethyl]benzamide |
| 647 | 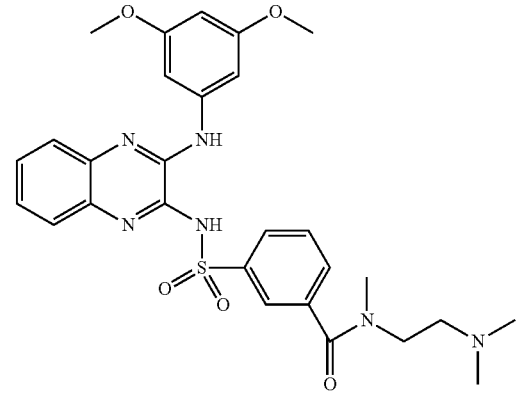 [SMILES: COc1cc(Nc2nc3ccccc3nc2NS(=O)(=O)c2cccc(C(=O)N(C)CCN(C)C)c2)cc(OC)c1] | 3-{[(3-{[3,5-bis(methoxy)phenyl]amino}quinoxalin-2-yl)amino]sulfonyl}-N-[2-(dimethylamino)ethyl]-N-methylbenzamide |
| 648 | 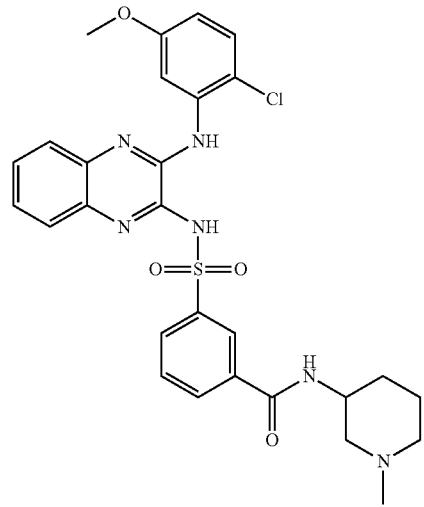 [SMILES: COc1ccc(Cl)c(Nc2nc3ccccc3nc2NS(=O)(=O)c2cccc(C(=O)NC3CCCN(C)C3)c2)c1] | 3-{[(3-{[2-chloro-5-(methoxy)phenyl]amino}quinoxalin-2-yl)amino]sulfonyl}-N-(1-methylpiperidin-3-yl)benzamide |

TABLE 1-continued

| Cpd. No. | Structure | Name |
| --- | --- | --- |
| 649 | 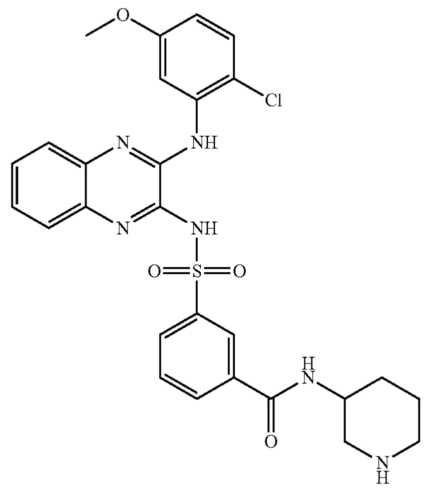 [SMILES: COc1ccc(Cl)c(Nc2nc3ccccc3nc2NS(=O)(=O)c2cccc(C(=O)NC3CCCNC3)c2)c1] | 3-{[(3-{[2-chloro-5-(methoxy)phenyl]amino}quinoxalin-2-yl)amino]sulfonyl}-N-piperidin-3-ylbenzamide |
| 650 | 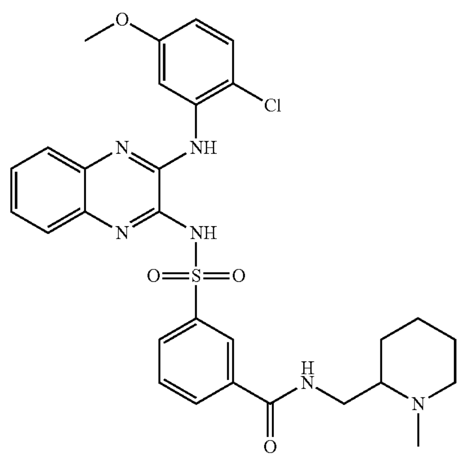 [SMILES: COc1ccc(Cl)c(Nc2nc3ccccc3nc2NS(=O)(=O)c2cccc(C(=O)NCC3CCCCN3C)c2)c1] | 3-{[(3-{[2-chloro-5-(methoxy)phenyl]amino}quinoxalin-2-yl)amino]sulfonyl}-N-(1-methylpiperidin-2-yl)methyl]benzamide |
| 651 | 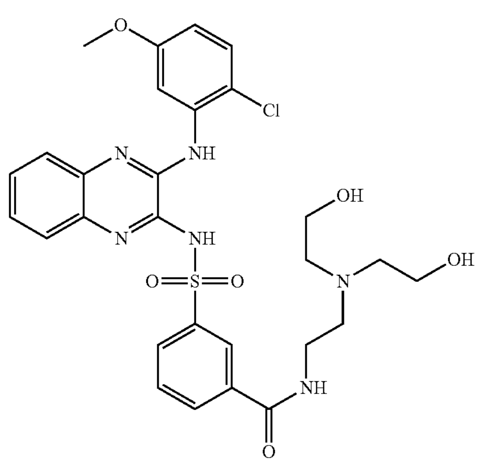 [SMILES: COc1ccc(Cl)c(Nc2nc3ccccc3nc2NS(=O)(=O)c2cccc(C(=O)NCCN(CCO)CCO)c2)c1] | N-{2-[bis(2-hydroxyethyl)amino]ethyl}-3-{[(3-{[2-chloro-5-(methoxy)phenyl]amino}quinoxalin-2-yl)amino]sulfonyl}benzamide |

| Cpd. No. | Structure | Name |
|---|---|---|
| 652 | 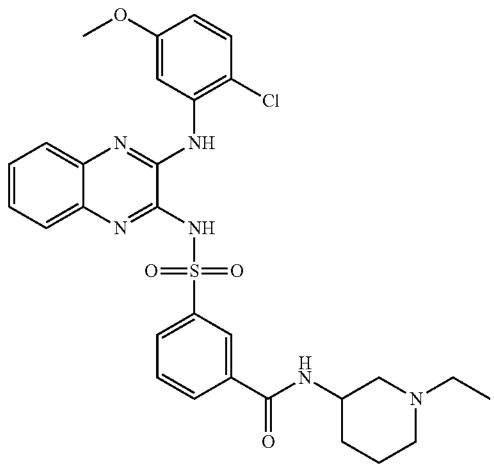 [SMILES: CCN1CCCC(NC(=O)c2cccc(S(=O)(=O)Nc3nc4ccccc4nc3Nc3cc(OC)ccc3Cl)c2)C1] | 3-{[(3-{[2-chloro-5-(methoxy)phen-yl]amino}quinoxalin-2-yl)amino]sulfonyl}-N-(1-ethylpiperidin-3-yl)benzamide |
| 653 | 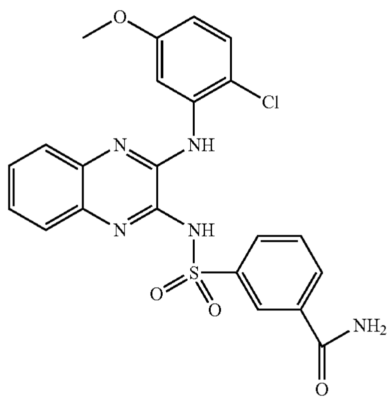 [SMILES: COc1ccc(Cl)c(Nc2nc3ccccc3nc2NS(=O)(=O)c2cccc(C(N)=O)c2)c1] | 3-{[(3-{[2-chloro-5-(methoxy)phen-yl]amino}quinoxalin-2-yl)amino]sulfonyl}benzamide |
| 654 | 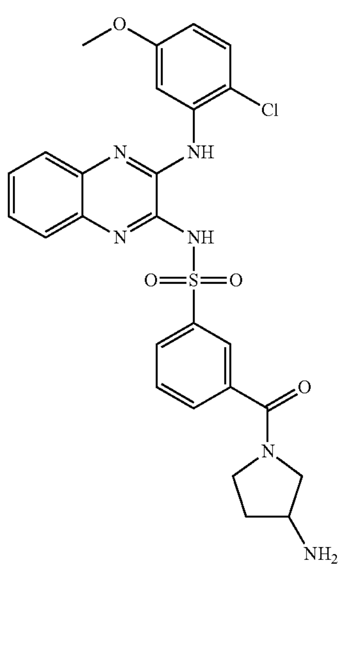 [SMILES: COc1ccc(Cl)c(Nc2nc3ccccc3nc2NS(=O)(=O)c2cccc(C(=O)N3CCC(N)C3)c2)c1] | 3-[(3-aminopyrrolidin-1-yl)carbonyl]-N-(3-{[2-chloro-5-(methoxy)phenyl]amino}quinoxalin-2-yl)benzenesulfonamide |

TABLE 1-continued

| Cpd. No. | Structure | Name |
|---|---|---|
| 655 | 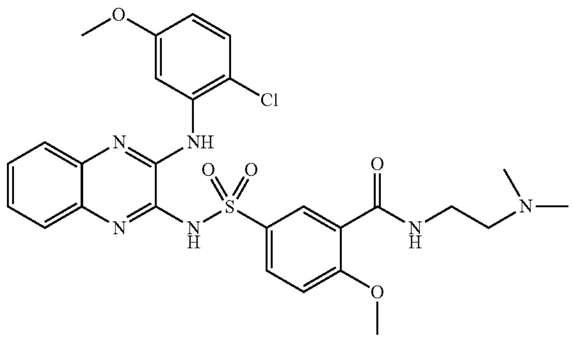 [SMILES: COc1ccc(Cl)c(Nc2nc3ccccc3nc2NS(=O)(=O)c2ccc(OC)c(C(=O)NCCN(C)C)c2)c1] | 5-{[(3-{[2-chloro-5-(methoxy)phenyl]amino}quinoxalin-2-yl)amino]sulfonyl}-N-[2-(dimethylamino)ethyl]-2-(methoxy)benzamide |
| 656 | 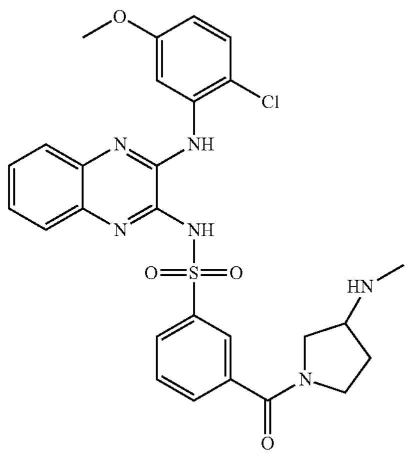 [SMILES: CNC1CCN(C(=O)c2cccc(S(=O)(=O)Nc3nc4ccccc4nc3Nc3cc(OC)ccc3Cl)c2)C1] | N-(3-{[2-chloro-5-(methoxy)phenyl]amino}quinoxalin-2-yl)-3-{[3-(methylamino)pyrrolidin-1-yl]carbonyl}benzenesulfonamide |
| 657 | 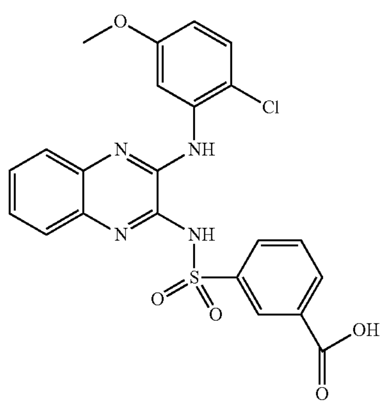 | 3-{[(3-{[2-chloro-5-(methoxy)phenyl]amino}quinoxalin-2-yl)amino]sulfonyl}benzoicacid |
| 658 | 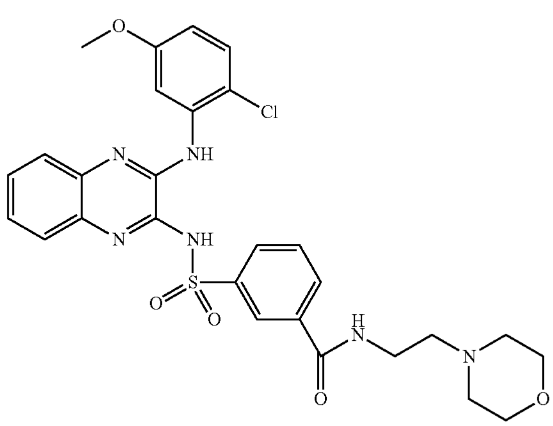 [SMILES: COc1ccc(Cl)c(Nc2nc3ccccc3nc2NS(=O)(=O)c2cccc(C(=O)NCCN3CCOCC3)c2)c1] | 3-{[(3-{[2-chloro-5-(methoxy)phenyl]amino}quinoxalin-2-yl)amino]sulfonyl}-N-(2-morpholin-4-ylethyl)benzamide |

| Cpd. No. | Structure | Name |
|---|---|---|
| 659 | 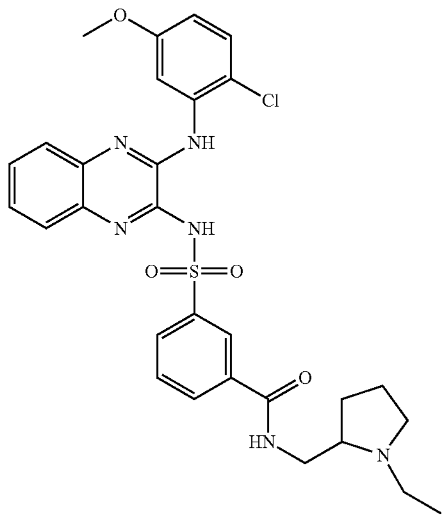 [SMILES: CCN1CCCC1CNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[(1-ethylpyrrolidin-2-yl)methyl]benzamide |
| 660 | 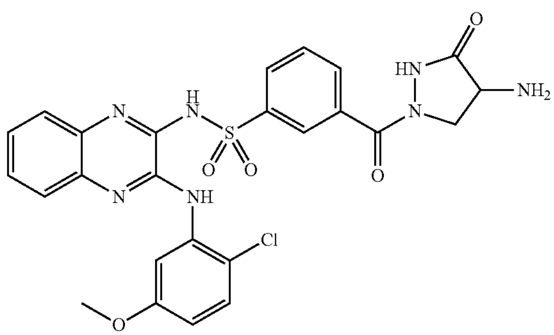 [SMILES: COc1ccc(Cl)c(Nc2nc3ccccc3nc2NS(=O)(=O)c2cccc(C(=O)N3CC(N)C(=O)N3)c2)c1] | 3-[(4-amino-3-oxopyrazolidin-1-yl)carbonyl]-N-(3-{[2-chloro-5-(methoxy)phenyl]amino}quinoxalin-2-yl)benzenesulfonamide |
| 661 | 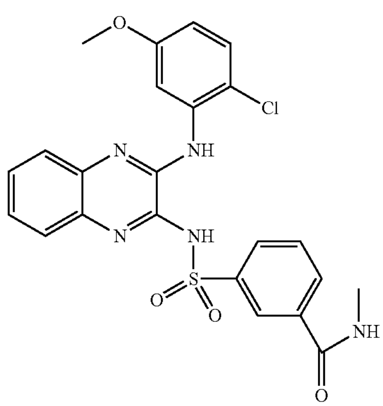 [SMILES: CNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-methylbenzamide |

TABLE 1-continued

| Cpd. No. | Structure | Name |
|---|---|---|
| 662 | 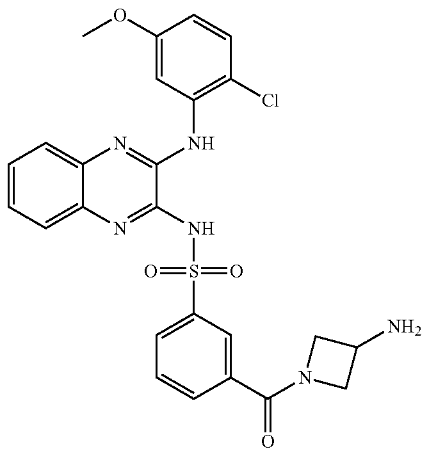 [SMILES: COc1ccc(Cl)c(Nc2nc3ccccc3nc2NS(=O)(=O)c2cccc(C(=O)N3CC(N)C3)c2)c1] | 3-[(3-aminoazetidin-1-yl)carbonyl]-N-(3-{[2-chloro-5-(methoxy)phenyl]amino}quinoxalin-2-yl)benzenesulfonamide |
| 663 | 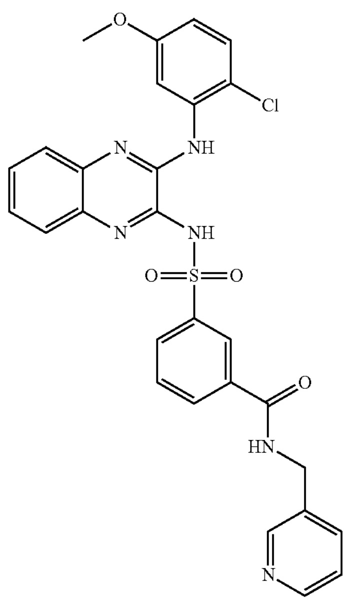 [SMILES: COc1ccc(Cl)c(Nc2nc3ccccc3nc2NS(=O)(=O)c2cccc(C(=O)NCc3cccnc3)c2)c1] | 3-{[(3-{[2-chloro-5-(methoxy)phenyl]amino}quinoxalin-2-yl)amino]sulfonyl}-N-(pyridin-3-ylmethyl)benzamide |
| 664 | 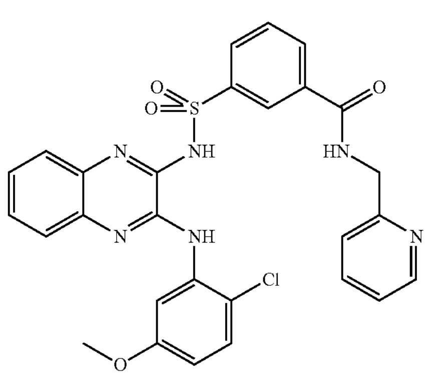 [SMILES: COc1ccc(Cl)c(Nc2nc3ccccc3nc2NS(=O)(=O)c2cccc(C(=O)NCc3ccccn3)c2)c1] | 3-{[(3-{[2-chloro-5-(methoxy)phenyl]amino}quinoxalin-2-yl)amino]sulfonyl}-N-(pyridin-2-ylmethyl)benzamide |

| Cpd. No. | Structure | Name |
|---|---|---|
| 665 | 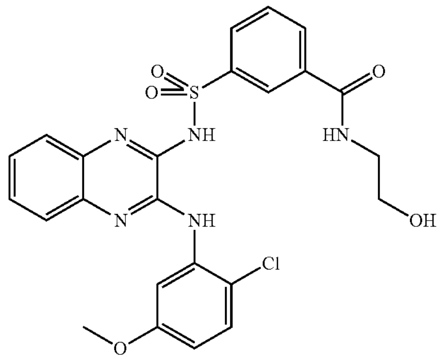 [SMILES: COc1ccc(Cl)c(Nc2nc3ccccc3nc2NS(=O)(=O)c2cccc(C(=O)NCCO)c2)c1] | 3-{[(3-{[2-chloro-5-(methoxy)phenyl]amino}quinoxalin-2-yl)amino]sulfonyl}-N-(2-hydroxyethyl)benzamide |
| 666 | 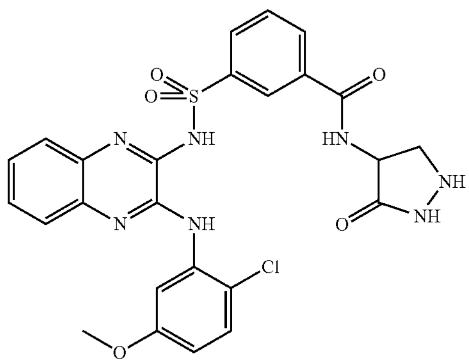 [SMILES: COc1ccc(Cl)c(Nc2nc3ccccc3nc2NS(=O)(=O)c2cccc(C(=O)NC3CNNC3=O)c2)c1] | 3-{[(3-{[2-chloro-5-(methoxy)phenyl]amino}quinoxalin-2-yl)amino]sulfonyl}-N-(3-oxopyrazolidin-4-yl)benzamide |
| 667 | 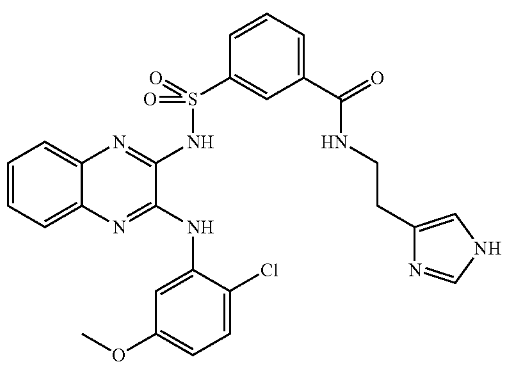 [SMILES: COc1ccc(Cl)c(Nc2nc3ccccc3nc2NS(=O)(=O)c2cccc(C(=O)NCCc3c[nH]cn3)c2)c1] | 3-{[(3-{[2-chloro-5-(methoxy)phenyl]amino}quinoxalin-2-yl)amino]sulfonyl}-N-[2-(1H-imidazol-4-yl)ethyl]benzamide |
| 668 | 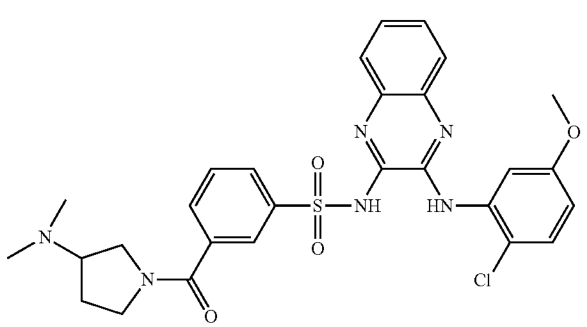 [SMILES: COc1ccc(Cl)c(Nc2nc3ccccc3nc2NS(=O)(=O)c2cccc(C(=O)N3CCC(N(C)C)C3)c2)c1] | N-(3-{[2-chloro-5-(methoxy)phenyl]amino}quinoxalin-2-yl)-3-{[3-(dimethylamino)pyrrolidin-1-yl]carbonyl}benzenesulfonamide |

TABLE 1-continued
| Cpd. No. | Structure | Name |
|---|---|---|
| 669 | 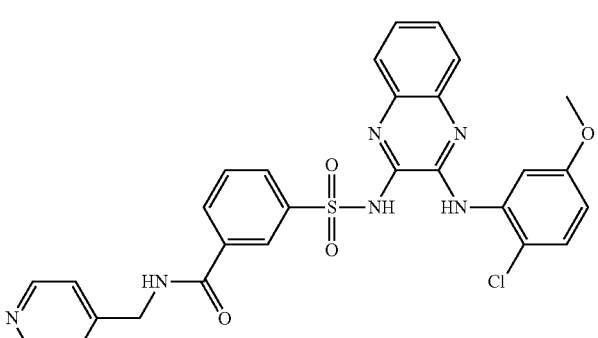 | 3-{[(3-{[2-chloro-5-(methoxy)phenyl]amino}quinoxalin-2-yl)amino]sulfonyl}-N-(pyridin-4-ylmethyl)benzamide |
| 670 | 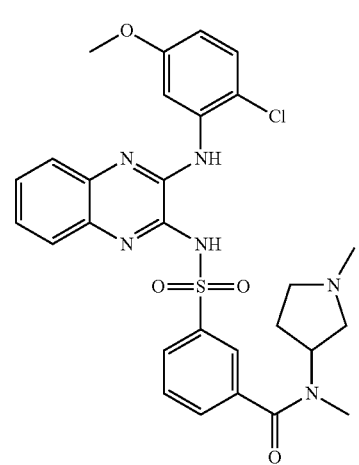 [SMILES: COc1ccc(Cl)c(Nc2nc3ccccc3nc2NS(=O)(=O)c2cccc(C(=O)N(C)C3CCN(C)C3)c2)c1] | 3-{[(3-{[2-chloro-5-(methoxy)phenyl]amino}quinoxalin-2-yl)amino]sulfonyl}-N-methyl-N-(1-methylpyrrolidin-3-yl)benzamide |
| 671 | 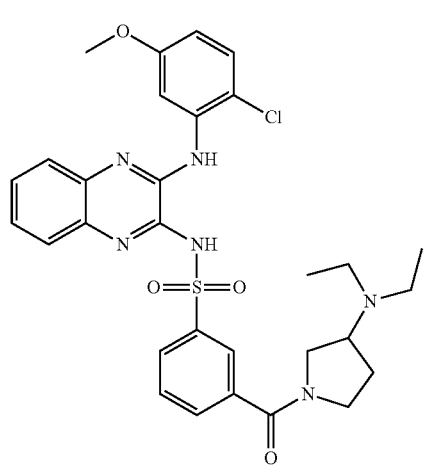 [SMILES: CCN(CC)C1CCN(C(=O)c2cccc(S(=O)(=O)Nc3nc4ccccc4nc3Nc3cc(OC)ccc3Cl)c2)C1] | N-(3-{[2-chloro-5-(methoxy)phenyl]amino}quinoxalin-2-yl)-3-{[3-(diethylamino)pyrrolidin-1-yl]carbonyl}benzenesulfonamide |

| Cpd. No. | Structure | Name |
|---|---|---|
| 672 | 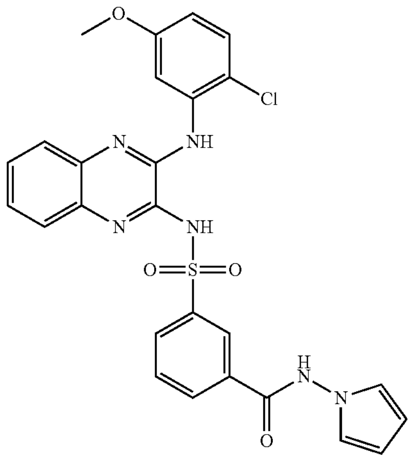 [SMILES: COc1ccc(Cl)c(Nc2nc3ccccc3nc2NS(=O)(=O)c2cccc(C(=O)Nn3cccc3)c2)c1] | 3-{[(3-{[2-chloro-5-(methoxy)phenyl]amino}quinoxalin-2-yl)amino]sulfonyl}-N-1H-pyrrol-1-ylbenzamide |
| 673 | 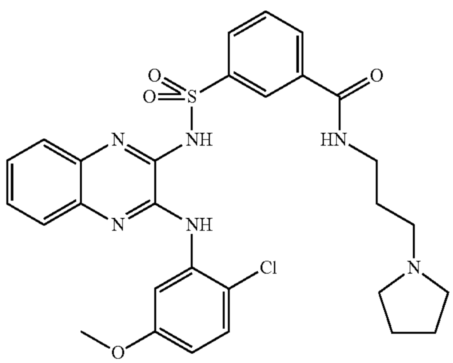 [SMILES: COc1ccc(Cl)c(Nc2nc3ccccc3nc2NS(=O)(=O)c2cccc(C(=O)NCCCN3CCCC3)c2)c1] | 3-{[(3-{[2-chloro-5-(methoxy)phenyl]amino}quinoxalin-2-yl)amino]sulfonyl}-N-(3-pyrrolidin-1-ylpropyl)benzamide |
| 674 | 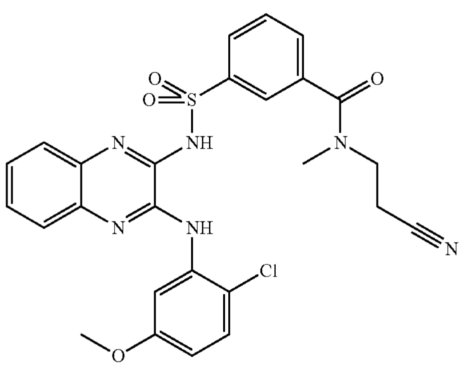 [SMILES: COc1ccc(Cl)c(Nc2nc3ccccc3nc2NS(=O)(=O)c2cccc(C(=O)N(C)CCC#N)c2)c1] | 3-{[(3-{[2-chloro-5-(methoxy)phenyl]amino}quinoxalin-2-yl)amino]sulfonyl}-N-(2-cyanoethyl)-N-methylbenzamide |
| 675 | 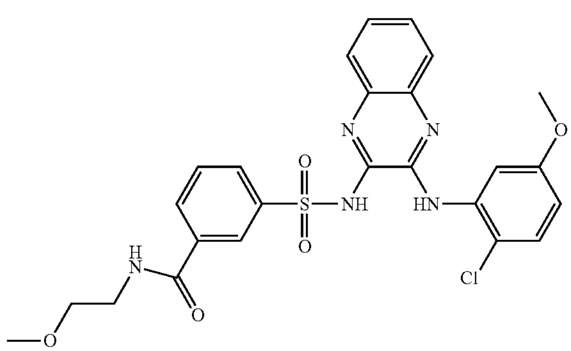 [SMILES: COCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[2-(methoxy)ethyl]benzamide |

TABLE 1-continued
| Cpd. No. | Structure | Name |
|---|---|---|
| 676 | 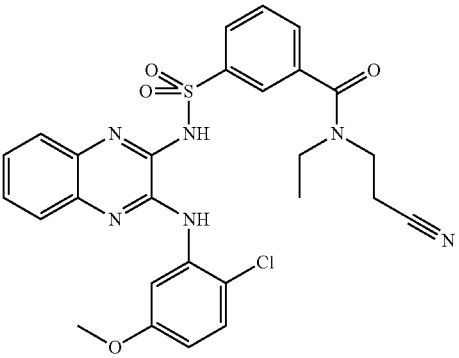 [SMILES: CCN(CCC#N)C(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-(2-cyanoethyl)-N-ethylbenzamide |
| 677 | 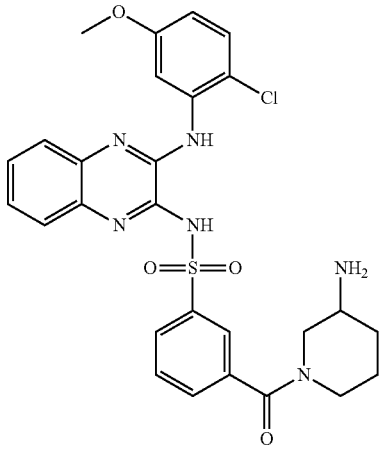 [SMILES: COc1ccc(Cl)c(Nc2nc3ccccc3nc2NS(=O)(=O)c2cccc(C(=O)N3CCCC(N)C3)c2)c1] | 3-[(3-aminopiperidin-1-yl)carbonyl]-N-(3-{[2-chloro-5-(methoxy)phenyl]amino}quinoxalin-2-yl)benzenesulfonamide |
| 678 | 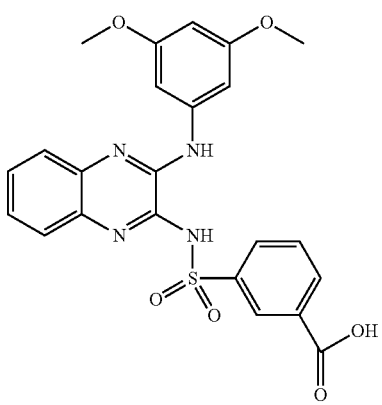 [SMILES: COc1cc(Nc2nc3ccccc3nc2NS(=O)(=O)c2cccc(C(=O)O)c2)cc(OC)c1] | 3-{[(3-{[3,5-bis(methoxy)phenyl]amino}quinoxalin-2-yl)amino]sulfonyl}benzoicacid |

TABLE 1-continued

| Cpd. No. | Structure | Name |
|---|---|---|
| 679 | 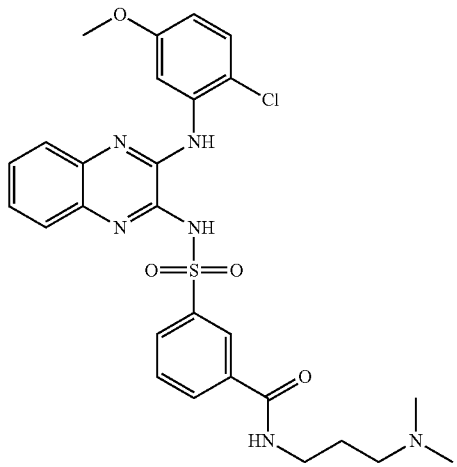 [SMILES: COc1ccc(Cl)c(Nc2nc3ccccc3nc2NS(=O)(=O)c2cccc(C(=O)NCCCN(C)C)c2)c1] | 3-{[(3-{[2-chloro-5-(methoxy)phenyl]amino}quinoxalin-2-yl)amino]sulfonyl}-N-[3-(dimethylamino)propyl]benzamide |
| 680 | 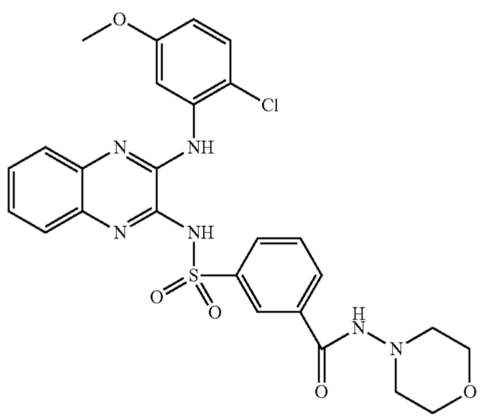 [SMILES: COc1ccc(Cl)c(Nc2nc3ccccc3nc2NS(=O)(=O)c2cccc(C(=O)NN3CCOCC3)c2)c1] | 3-{[(3-{[2-chloro-5-(methoxy)phenyl]amino}quinoxalin-2-yl)amino]sulfonyl}-N-morpholin-4-ylbenzamide |
| 681 | 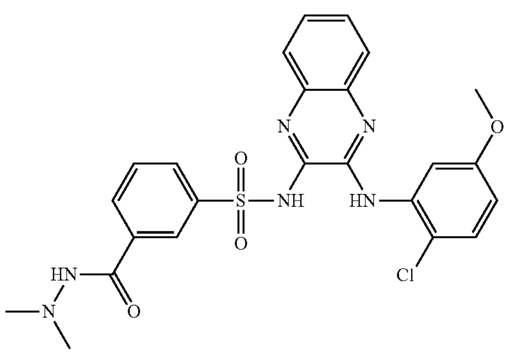 [SMILES: COc1ccc(Cl)c(Nc2nc3ccccc3nc2NS(=O)(=O)c2cccc(C(=O)NN(C)C)c2)c1] | N-(3-{[2-chloro-5-(methoxy)phenyl]amino}quinoxalin-2-yl)-3-[(2,2-dimethylhydrazino)carbonyl]benzenesulfonamide |
| 682 | 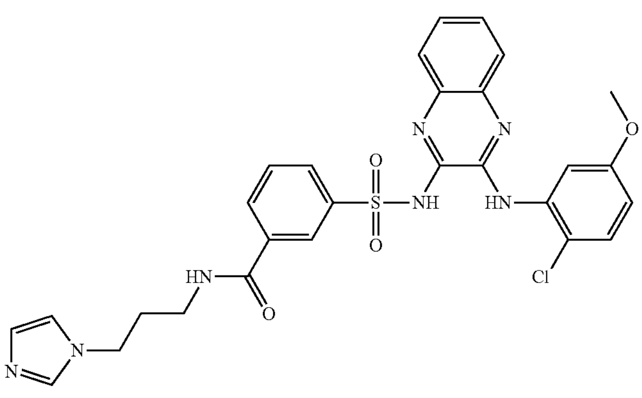 [SMILES: COc1ccc(Cl)c(Nc2nc3ccccc3nc2NS(=O)(=O)c2cccc(C(=O)NCCCn3ccnc3)c2)c1] | 3-{[(3-{[2-chloro-5-(methoxy)phenyl]amino}quinoxalin-2-yl)amino]sulfonyl}-N-[3-(1H-imidazol-1-yl)propyl]benzamide |

TABLE 1-continued

| Cpd. No. | Structure | Name |
|---|---|---|
| 683 | 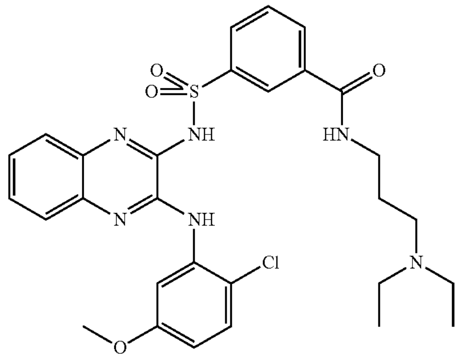 [SMILES: CCN(CC)CCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[3-(diethylamino)propyl]benzamide |
| 684 | 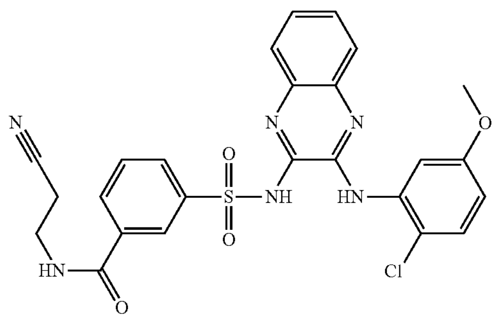 [SMILES: COc1ccc(Cl)c(Nc2nc3ccccc3nc2NS(=O)(=O)c2cccc(C(=O)NCCC#N)c2)c1] | 3-{[(3-{[2-chloro-5-(methoxy)phenyl]amino}quinoxalin-2-yl)amino]sulfonyl}-N-(2-cyanoethyl)benzamide |
| 685 | 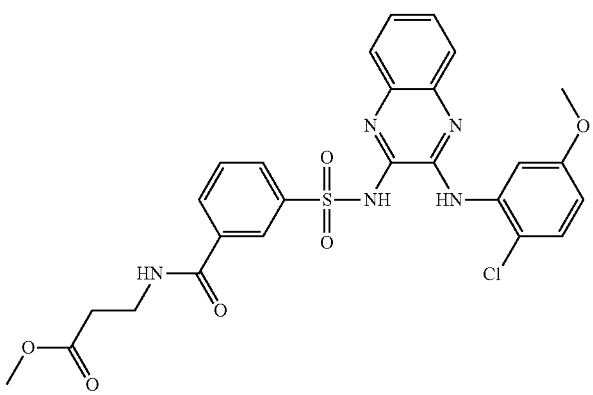 [SMILES: COC(=O)CCNC(=O)c1cccc(S(=O)(=O)Nc2nc3ccccc3nc2Nc2cc(OC)ccc2Cl)c1] | methyl N-[(3-{[(3-{[2-chloro-5-(methoxy)phenyl]amino}quinoxalin-2-yl)amino]sulfonyl}phenyl)carbonyl]-beta-alaninate |
| 686 | 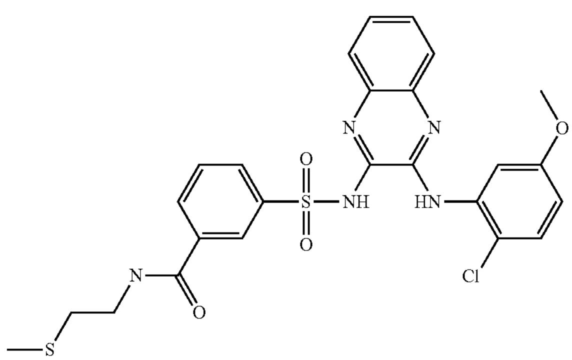 [SMILES: COc1ccc(Cl)c(Nc2nc3ccccc3nc2NS(=O)(=O)c2cccc(C(=O)NCCSC)c2)c1] | 3-{[(3-{[2-chloro-5-(methoxy)phenyl]amino}quinoxalin-2-yl)amino]sulfonyl}-N-[2-(methylthio)ethyl]benzamide |

TABLE 1-continued

| Cpd. No. | Structure | Name |
|---|---|---|
| 687 | 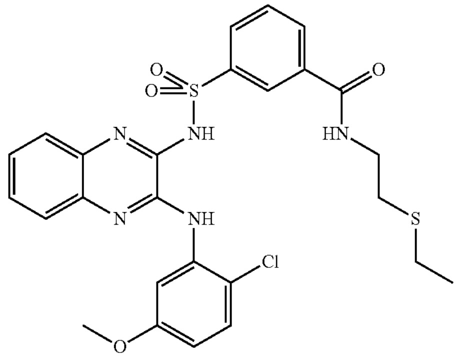 | 3-{[(3-{[2-chloro-5-(methoxy)phenyl]amino}quinoxalin-2-yl)amino]sulfonyl}-N-[2-(ethylthio)ethyl]benzamide |
| 688 | 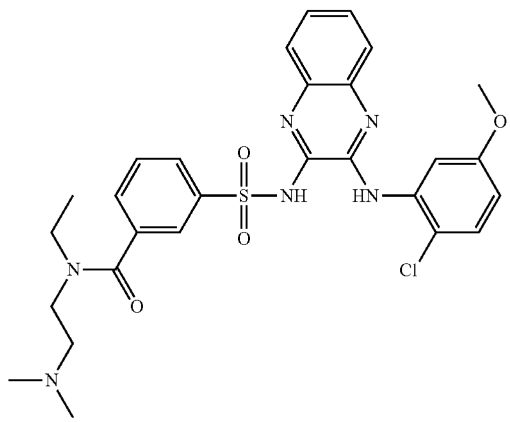 [SMILES: CCN(CCN(C)C)C(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[2-(dimethylamino)ethyl]-N-ethylbenzamide |
| 689 | 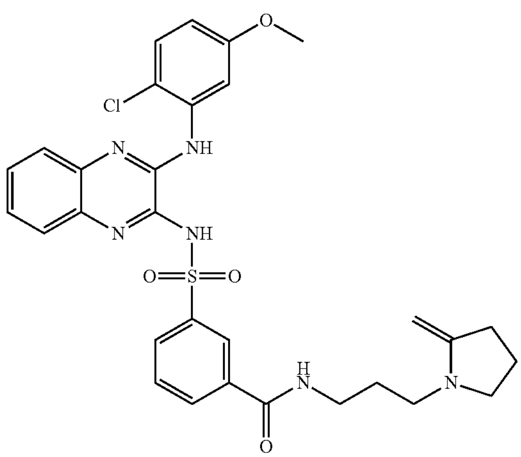 [SMILES: C=C1CCCN1CCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[3-(2-oxopyrrolidin-1-yl)propyl]benzamide |
| 690 | 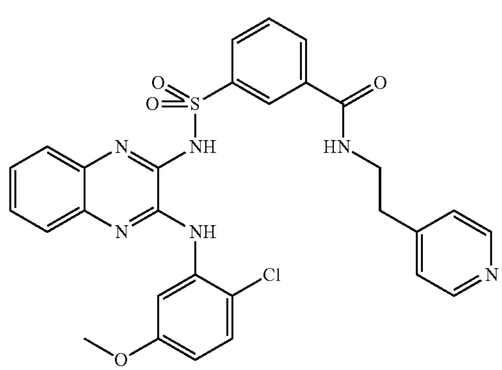 [SMILES: COc1ccc(Cl)c(Nc2nc3ccccc3nc2NS(=O)(=O)c2cccc(C(=O)NCCc3ccncc3)c2)c1] | 3-{[(3-{[2-chloro-5-(methoxy)phenyl]amino}quinoxalin-2-yl)amino]sulfonyl}-N-(2-pyridin-4-ylethyl)benzamide |

TABLE 1-continued

| Cpd. No. | Structure | Name |
|---|---|---|
| 691 | 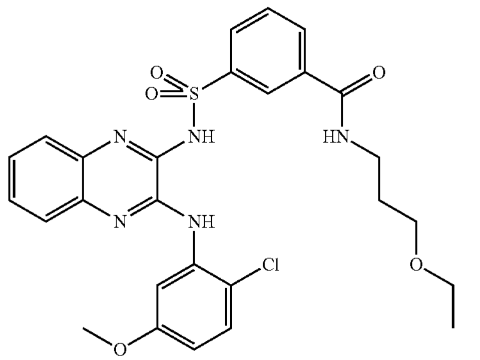 [SMILES: CCOCCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[3-(ethyloxy)propyl]benzamide |
| 692 | 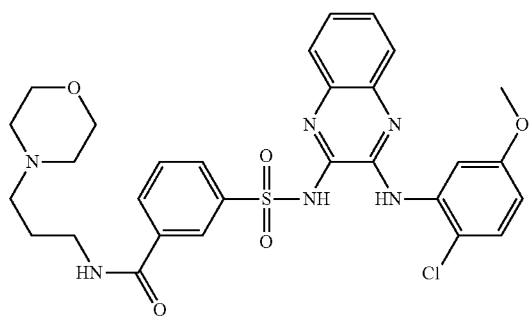 [SMILES: COc1ccc(Cl)c(Nc2nc3ccccc3nc2NS(=O)(=O)c2cccc(C(=O)NCCCN3CCOCC3)c2)c1] | 3-{[(3-{[2-chloro-5-(methoxy)phenyl]amino}quinoxalin-2-yl)amino]sulfonyl}-N-(3-morpholin-4-ylpropyl)benzamide |
| 693 | 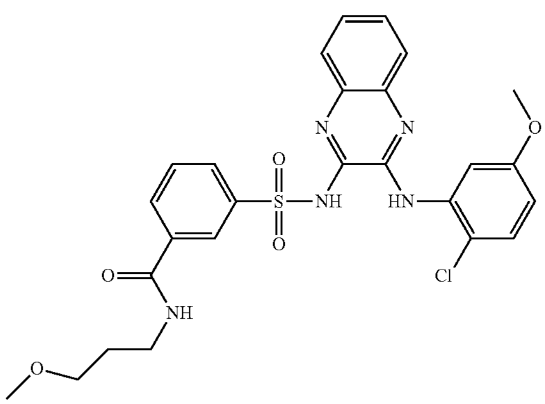 [SMILES: COCCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[3-(methoxy)propyl]benzamide |
| 694 | 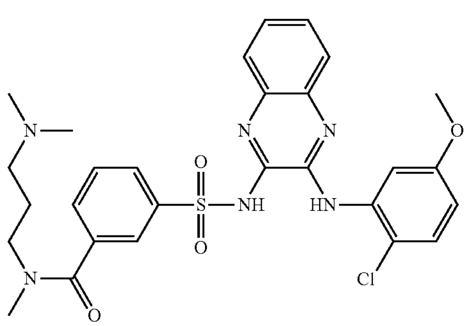 [SMILES: COc1ccc(Cl)c(Nc2nc3ccccc3nc2NS(=O)(=O)c2cccc(C(=O)N(C)CCCN(C)C)c2)c1] | 3-{[(3-{[2-chloro-5-(methoxy)phenyl]amino}quinoxalin-2-yl)amino]sulfonyl}-N-[3-(dimethylamino)propyl]-N-methylbenzamide |

TABLE 1-continued

| Cpd. No. | Structure | Name |
| --- | --- | --- |
| 695 | 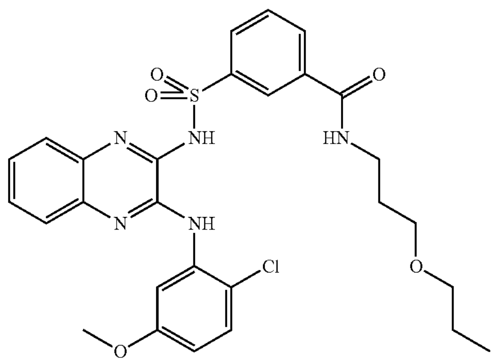 [SMILES: CCCOCCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[3-(propyloxy)propyl]benzamide |
| 696 | 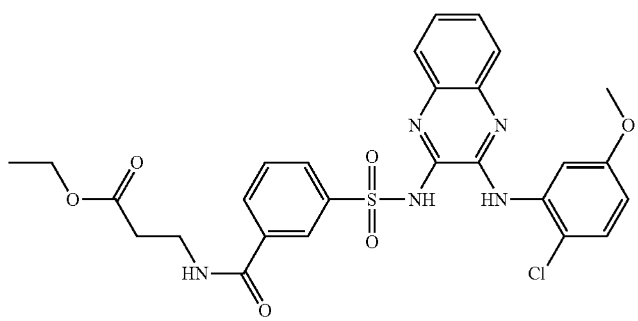 [SMILES: CCOC(=O)CCNC(=O)c1cccc(S(=O)(=O)Nc2nc3ccccc3nc2Nc2cc(OC)ccc2Cl)c1] | ethyl N-[(3-{[(3-{[2-chloro-5-(methoxy)phenyl]amino}quinoxalin-2-yl)amino]sulfonyl}phenyl)carbonyl]-beta-alaninate |
| 697 | 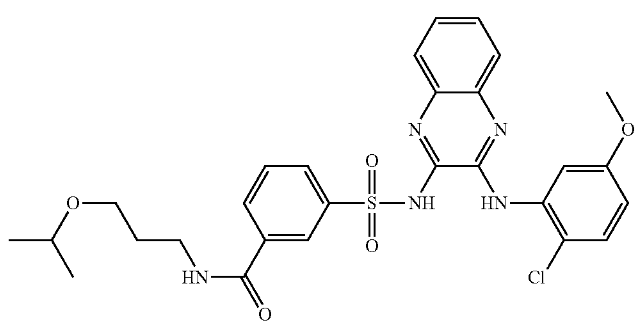 [SMILES: COc1ccc(Cl)c(Nc2nc3ccccc3nc2NS(=O)(=O)c2cccc(C(=O)NCCCOC(C)C)c2)c1] | 3-{[(3-{[2-chloro-5-(methoxy)phenyl]amino}quinoxalin-2-yl)amino]sulfonyl}-N-{3-[(1-methylethyl)oxy]propyl}benzamide |
| 698 | 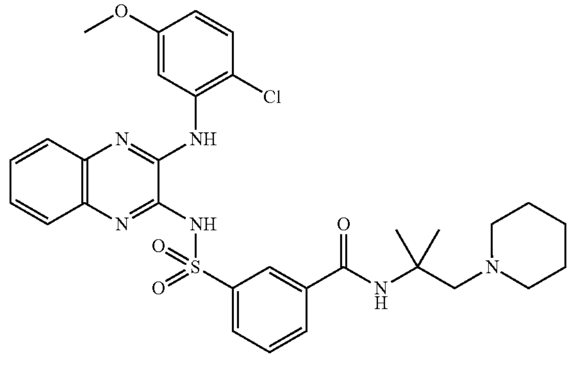 [SMILES: COc1ccc(Cl)c(Nc2nc3ccccc3nc2NS(=O)(=O)c2cccc(C(=O)NC(C)(C)CN3CCCCC3)c2)c1] | 3-{[(3-{[2-chloro-5-(methoxy)phenyl]amino}quinoxalin-2-yl)amino]sulfonyl}-N-(1,1-dimethyl-2-piperidin-1-ylethyl)benzamide |

| Cpd. No. | Name |
|---|---|
| 699 | 3-{[(3-{[2-chloro-5-(methoxy)phenyl]amino}quinoxalin-2-yl)amino]sulfonyl}-N-methyl-N-propylbenzamide |
| 700 | 3-{[(3-{[2-chloro-5-(methoxy)phenyl]amino}quinoxalin-2-yl)amino]sulfonyl}-N-piperidin-1-ylbenzamide |
| 701 | 3-{[(3-{[2-chloro-5-(methoxy)phenyl]amino}quinoxalin-2-yl)amino]sulfonyl}-N-[1-methyl-2-(methoxy)ethyl]benzamide |
| 702 | 3-{[(3-{[2-chloro-5-(methoxy)phenyl]amino}quinoxalin-2-yl)amino]sulfonyl}-N-(1,1-dimethyl-2-morpholin-4-ylethyl)benzamide |

| Cpd. No. | Structure | Name |
| --- | --- | --- |
| 703 | 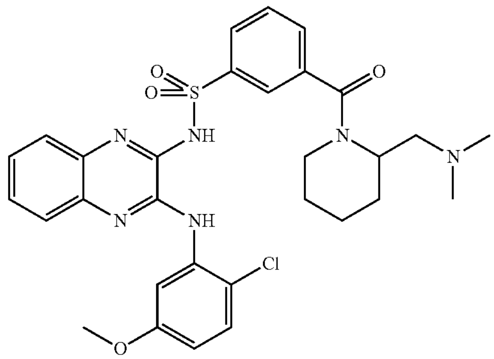 [SMILES: COc1ccc(Cl)c(Nc2nc3ccccc3nc2NS(=O)(=O)c2cccc(C(=O)N3CCCCC3CN(C)C)c2)c1] | N-(3-{[2-chloro-5-(methoxy)phenyl]amino}quinoxalin-2-yl)-3-({2-[(dimethylamino)methyl]piperidin-1-yl}carbonyl)benzenesulfonamide |
| 704 | 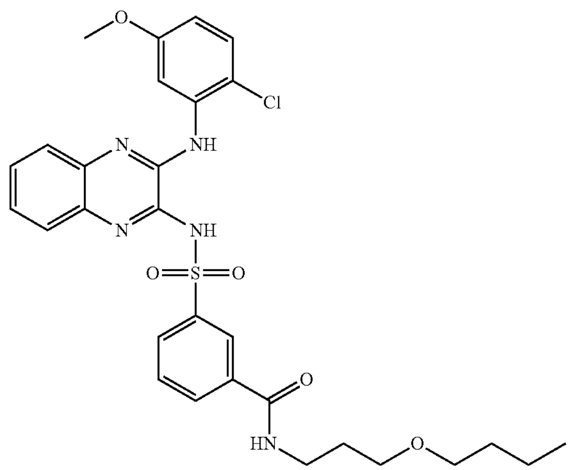 [SMILES: CCCCOCCCNC(=O)c1cccc(S(=O)(=O)Nc2nc3ccccc3nc2Nc2cc(OC)ccc2Cl)c1] | N-[3-(butyloxy)propyl]-3-{[(3-{[2-chloro-5-(methoxy)phenyl]amino}quinoxalin-2-yl)amino]sulfonyl}benzamide |
| 705 | 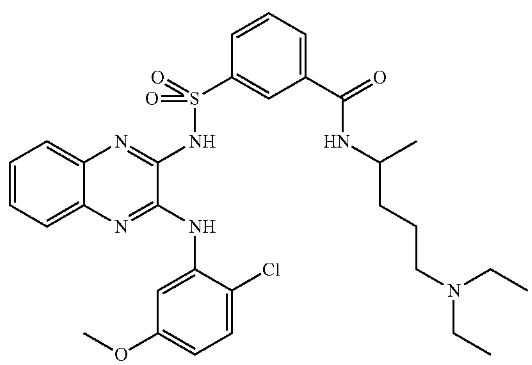 [SMILES: CCN(CC)CCCC(C)NC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[4-(diethylamino)-1-methylbutyl]benzamide |
| 706 | 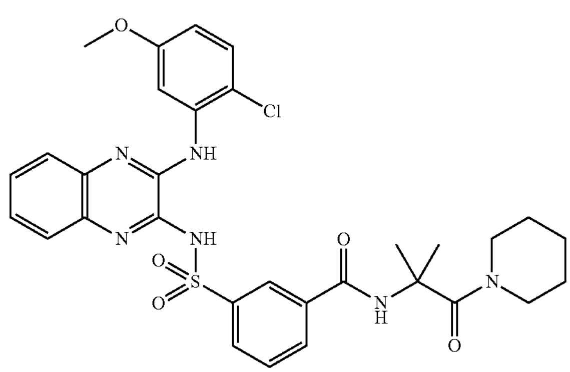 [SMILES: COc1ccc(Cl)c(Nc2nc3ccccc3nc2NS(=O)(=O)c2cccc(C(=O)NC(C)(C)C(=O)N3CCCCC3)c2)c1] | 3-{[(3-{[2-chloro-5-(methoxy)phenyl]amino}quinoxalin-2-yl)amino]sulfonyl}-N-(1,1-dimethyl-2-oxo-2-piperidin-1-ylethyl)benzamide |

TABLE 1-continued

| Cpd. No. | Structure | Name |
|---|---|---|
| 707 | 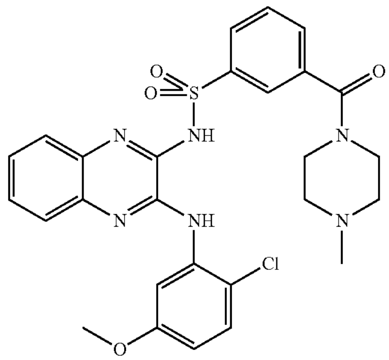 [SMILES: COc1ccc(Cl)c(Nc2nc3ccccc3nc2NS(=O)(=O)c2cccc(C(=O)N3CCN(C)CC3)c2)c1] | N-(3-{[2-chloro-5-(methoxy)phenyl]amino}quinoxalin-2-yl)-3-[(4-methylpiperazin-1-yl)carbonyl]benzenesulfonamide |
| 708 | 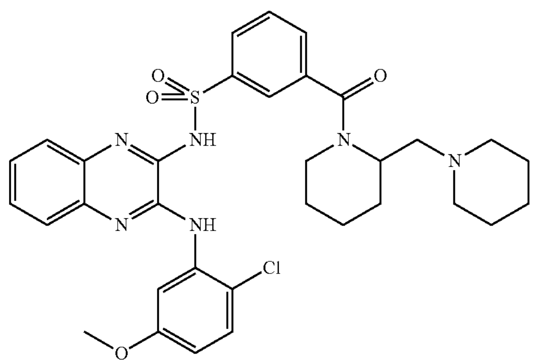 [SMILES: COc1ccc(Cl)c(Nc2nc3ccccc3nc2NS(=O)(=O)c2cccc(C(=O)N3CCCCC3CN3CCCCC3)c2)c1] | N-(3-{[2-chloro-5-(methoxy)phenyl]amino}quinoxalin-2-yl)-3-{[2-(piperidin-1-ylmethyl)piperidin-1-yl]carbonyl}benzenesulfonamide |
| 709 | 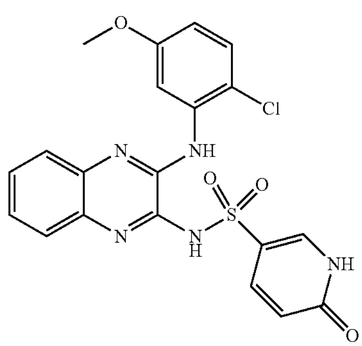 [SMILES: COc1ccc(Cl)c(Nc2nc3ccccc3nc2NS(=O)(=O)c2ccc(=O)[nH]c2)c1] | N-(3-{[2-chloro-5-(methoxy)phenyl]amino}quinoxalin-2-yl)-6-oxo-1,6-dihydropyridine-3-sulfonamide |
| 710 | 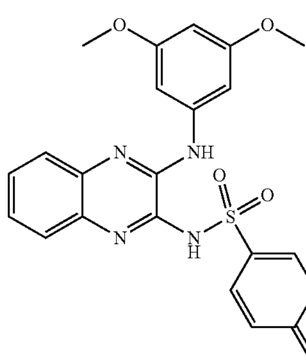 | N-(3-{[3,5-bis(methoxy)phenyl]amino}quinoxalin-2-yl)-6-oxo-1,6-dihydropyridine-3-sulfonamide |

TABLE 1-continued

| Cpd. No. | Structure | Name |
|---|---|---|
| 711 | 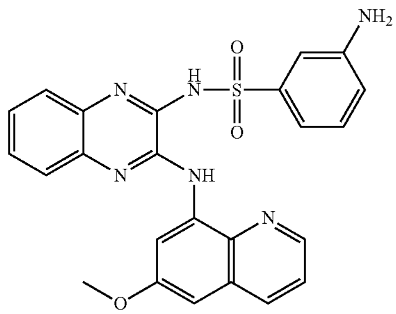 | 3-amino-N-(3-{[6-(methoxy)quinolin-8-yl]amino}quinoxalin-2-yl)benzenesulfonamide |
| 712 | 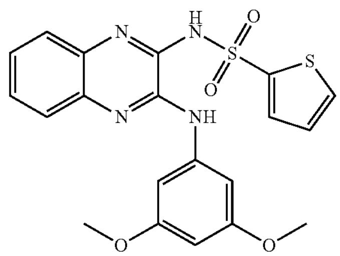 [SMILES: COc1cc(Nc2nc3ccccc3nc2NS(=O)(=O)c2cccs2)cc(OC)c1] | N-(3-{[3,5-bis(methoxy)phenyl]amino}quinoxalin-2-yl)thiophene-2-sulfonamide |
| 713 | 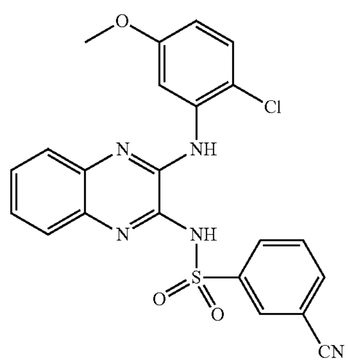 [SMILES: COc1ccc(Cl)c(Nc2nc3ccccc3nc2NS(=O)(=O)c2cccc(C#N)c2)c1] | N-(3-{[2-chloro-5-(methoxy)phenyl]amino}quinoxalin-2-yl)-3-cyanobenzenesulfonamide |
| 714 | 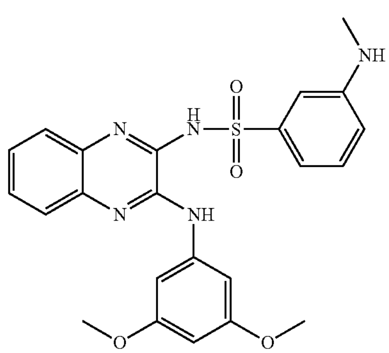 [SMILES: CNc1cccc(S(=O)(=O)Nc2nc3ccccc3nc2Nc2cc(OC)cc(OC)c2)c1] | N-(3-{[3,5-bis(methoxy)phenyl]amino}quinoxalin-2-yl)-3-(methylamino)benzenesulfonamide |
| 715 | 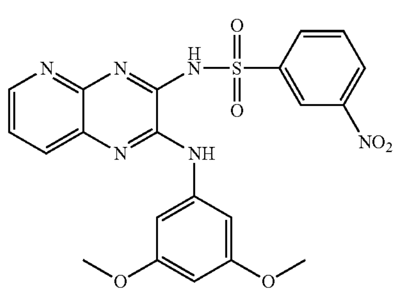 | N-(2-{[3,5-bis(methoxy)phenyl]amino}pyrido[2,3-b]pyrazin-3-yl)-3-nitrobenzenesulfonamide |

TABLE 1-continued

| Cpd. No. | Structure | Name |
|---|---|---|
| 716 | 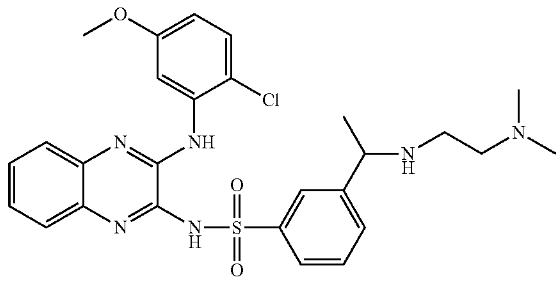 [SMILES: COc1ccc(Cl)c(Nc2nc3ccccc3nc2NS(=O)(=O)c2cccc(C(C)NCCN(C)C)c2)c1] | N-(3-{[2-chloro-5-(methoxy)phenyl]amino}quinoxalin-2-yl)-3-(1-{[2-(dimethylamino)ethyl]amino}ethyl)ben-zenesulfonamide |
| 717 | 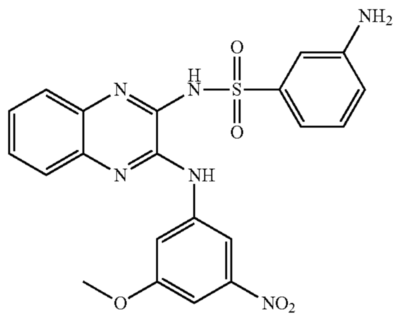 | 3-amino-N-(3-{[3-(methoxy)-5-nitrophenyl]amino}quinoxalin-2-yl)benzenesulfonamide |
| 718 | 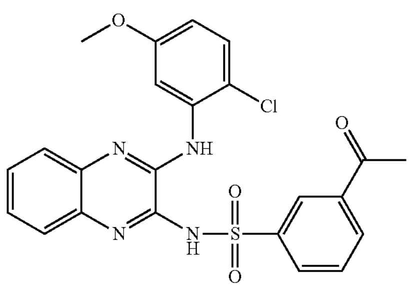 [SMILES: COc1ccc(Cl)c(Nc2nc3ccccc3nc2NS(=O)(=O)c2cccc(C(C)=O)c2)c1] | 3-acetyl-N-(3-{[2-chloro-5-(methoxy)phenyl]amino}quinoxalin-2-yl)benzenesulfonamide |
| 719 | 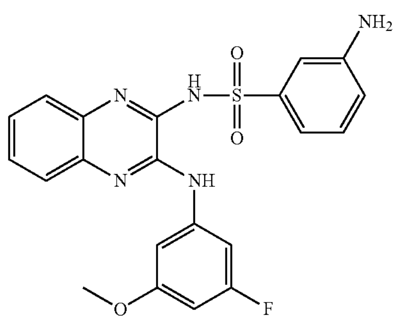 | 3-amino-N-(3-{[3-fluoro-5-(methoxy)phenyl]amino}quinoxalin-2-yl)benzenesulfonamide |
| 720 | 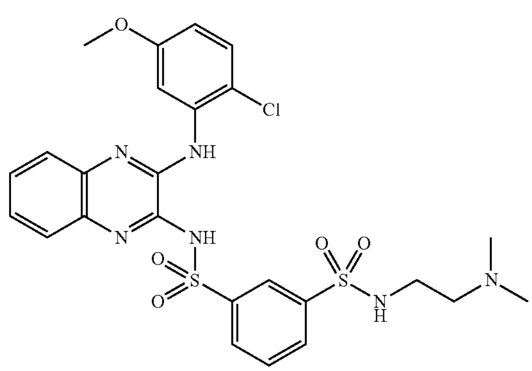 [SMILES: COc1ccc(Cl)c(Nc2nc3ccccc3nc2NS(=O)(=O)c2cccc(S(=O)(=O)NCCN(C)C)c2)c1] | N-(3-{[2-chloro-5-(methoxy)phenyl]amino}quinoxalin-2-yl)-N'-[2-(dimethylamino)ethyl]benzene-1,3-disulfonamide |

TABLE 1-continued

| Cpd. No. | Structure | Name |
|---|---|---|
| 721 | 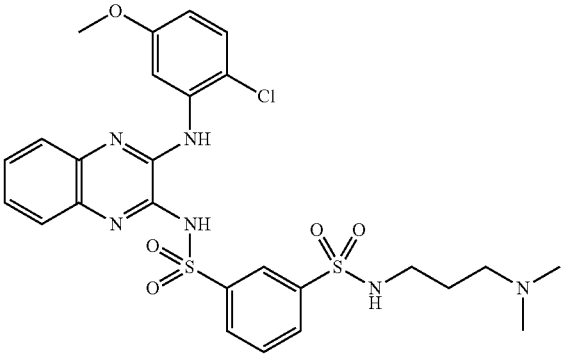 [SMILES: COc1ccc(Cl)c(Nc2nc3ccccc3nc2NS(=O)(=O)c2cccc(S(=O)(=O)NCCCN(C)C)c2)c1] | N-(3-{[2-chloro-5-(methoxy)phenyl]amino}quinoxalin-2-yl)-N'-[3-(dimethylamino)propyl]benzene-1,3-disulfonamide |
| 722 | 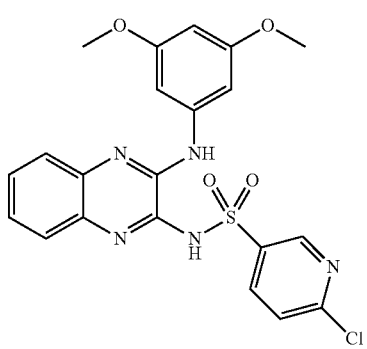 [SMILES: COc1cc(Nc2nc3ccccc3nc2NS(=O)(=O)c2ccc(Cl)nc2)cc(OC)c1] | N-(3-{[3,5-bis(methoxy)phenyl]amino}quinoxalin-2-yl)-6-chloropyridine-3-sulfonamide |
| 723 | 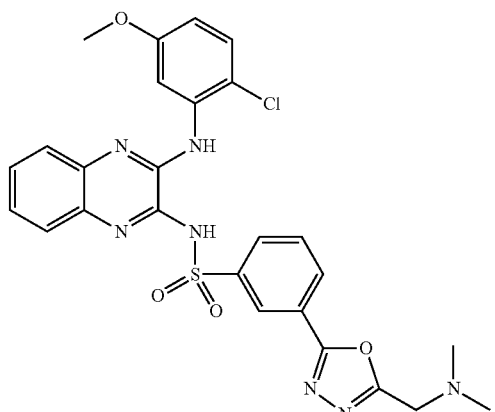 | N-(3-{[2-chloro-5-(methoxy)phenyl]amino}quinoxalin-2-yl)-3-{5-[(dimethylamino)methyl]-1,3,4-oxadiazol-2-yl}benzenesulfonamide |
| 724 | 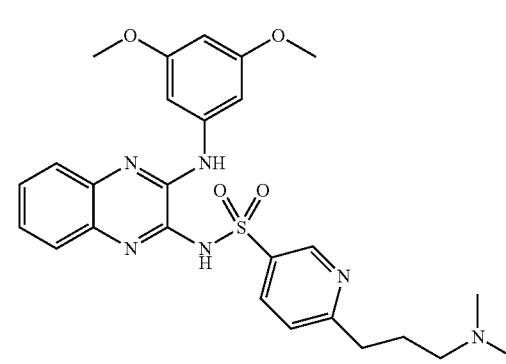 | N-(3-{[3,5-bis(methoxy)phenyl]amino}quinoxalin-2-yl)-6-{[2-(dimethylamino)ethyl]amino}pyridine-3-sulfonamide |

TABLE 1-continued
| Cpd. No. | Structure | Name |
|---|---|---|
| 725 | 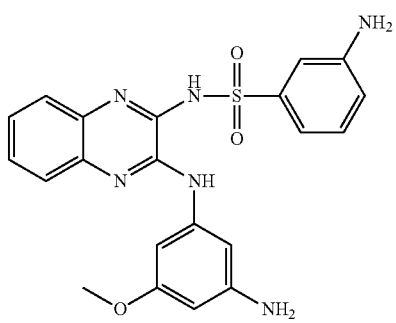 | 3-amino-N-(3-{[3-amino-5-(methoxy)phenyl]amino}quinoxalin-2-yl)benzenesulfonamide |
| 726 | 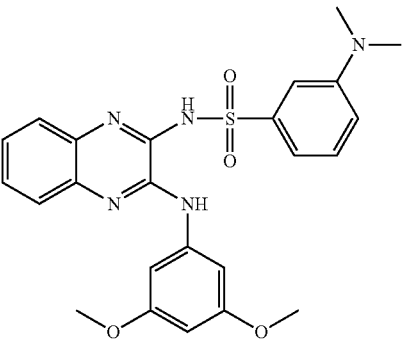 [SMILES: COc1cc(Nc2nc3ccccc3nc2NS(=O)(=O)c2cccc(N(C)C)c2)cc(OC)c1] | N-(3-{[3,5-bis(methoxy)phenyl]amino}quinoxalin-2-yl)-3-(dimethylamino)benzenesulfonamide |
| 727 | 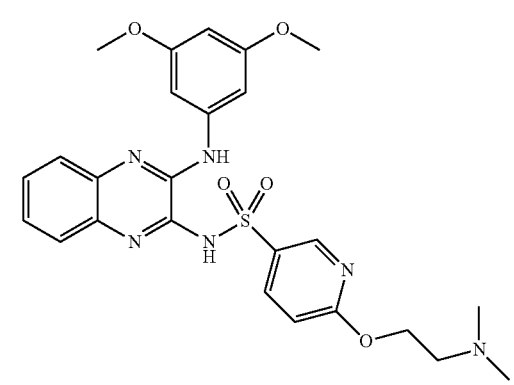 [SMILES: COc1cc(Nc2nc3ccccc3nc2NS(=O)(=O)c2ccc(OCCN(C)C)nc2)cc(OC)c1] | N-(3-{[3,5-bis(methoxy)phenyl]amino}quinoxalin-2-yl)-6-{[2-(dimethylamino)ethyl]oxy}pyridine-3-sulfonamide |
| 728 | 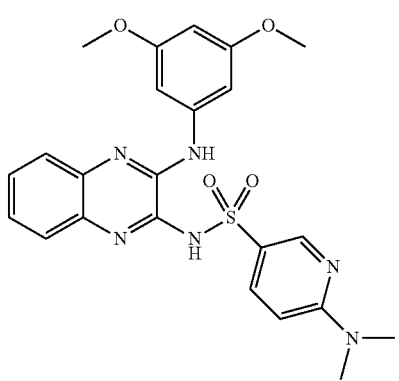 [SMILES: COc1cc(Nc2nc3ccccc3nc2NS(=O)(=O)c2ccc(N(C)C)nc2)cc(OC)c1] | N-(3-{[3,5-bis(methoxy)phenyl]amino}quinoxalin-2-yl)-6-(dimethylamino)pyridine-3-sulfonamide |

TABLE 1-continued
| Cpd. No. | Structure | Name |
|---|---|---|
| 729 | 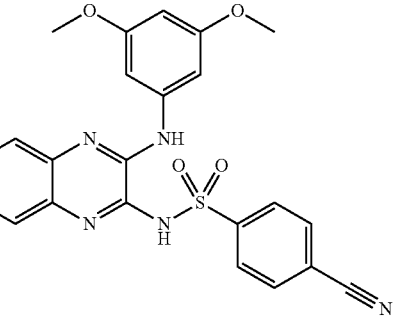 | N-(3-{[3,5-bis(methoxy)phenyl]amino}quinoxalin-2-yl)-4-cyanobenzenesulfonamide |
| 730 | 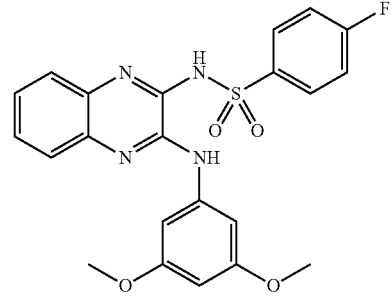 [SMILES: COc1cc(Nc2nc3ccccc3nc2NS(=O)(=O)c2ccc(F)cc2)cc(OC)c1] | N-(3-{[3,5-bis(methoxy)phenyl]amino}quinoxalin-2-yl)-4-fluorobenzenesulfonamide |
| 731 | 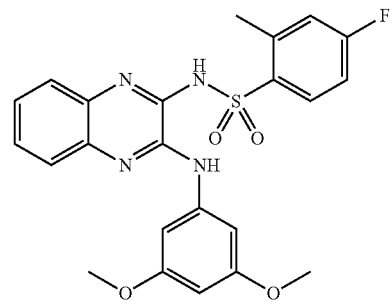 [SMILES: COc1cc(Nc2nc3ccccc3nc2NS(=O)(=O)c2ccc(F)cc2C)cc(OC)c1] | N-(3-{[3,5-bis(methoxy)phenyl]amino}quinoxalin-2-yl)-4-fluoro-2-methylbenzenesulfonamide |
| 732 | 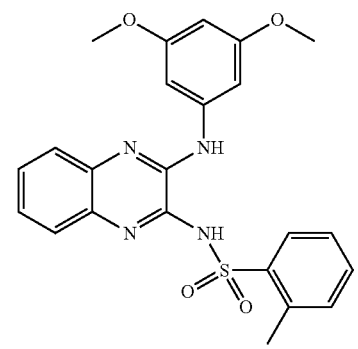 [SMILES: COc1cc(Nc2nc3ccccc3nc2NS(=O)(=O)c2ccccc2C)cc(OC)c1] | N-(3-{[3,5-bis(methoxy)phenyl]amino}quinoxalin-2-yl)-2-methylbenzenesulfonamide |

TABLE 1-continued

| Cpd. No. | Structure | Name |
|---|---|---|
| 733 | 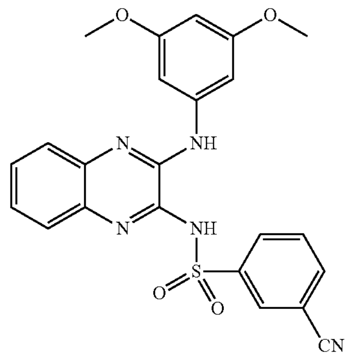 [SMILES: COc1cc(Nc2nc3ccccc3nc2NS(=O)(=O)c2cccc(C#N)c2)cc(OC)c1] | N-(3-{[3,5-bis(methoxy)phenyl]amino}quinoxalin-2-yl)-3-cyanobenzenesulfonamide |
| 734 | 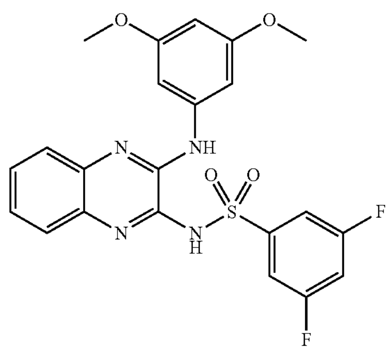 [SMILES: COc1cc(Nc2nc3ccccc3nc2NS(=O)(=O)c2cc(F)cc(F)c2)cc(OC)c1] | N-(3-{[3,5-bis(methoxy)phenyl]amino}quinoxalin-2-yl)-3,5-difluorobenzenesulfonamide |
| 735 | 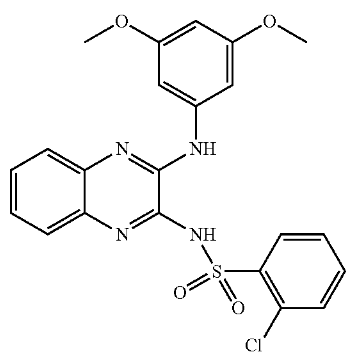 [SMILES: COc1cc(Nc2nc3ccccc3nc2NS(=O)(=O)c2ccccc2Cl)cc(OC)c1] | N-(3-{[3,5-bis(methoxy)phenyl]amino}quinoxalin-2-yl)-2-chlorobenzenesulfonamide |
| 736 | 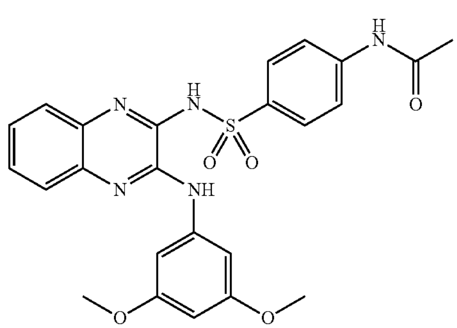 [SMILES: COc1cc(Nc2nc3ccccc3nc2NS(=O)(=O)c2ccc(NC(C)=O)cc2)cc(OC)c1] | N-(4-{[(3-{[3,5-bis(methoxy)phenyl]amino}quinoxalin-2-yl)amino)sulfonyl}phenyl)acetamide |

| Cpd. No. | Structure | Name |
|---|---|---|
| 737 | 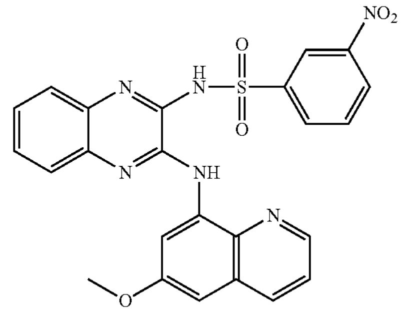 [SMILES: COc1cc(Nc2nc3ccccc3nc2NS(=O)(=O)c2cccc([N+](=O)[O-])c2)c2ncccc2c1] | N-(3-{[6-(methoxy)quinolin-8-yl]amino}quinoxalin-2-yl)-3-nitrobenzenesulfonamide |
| 738 | 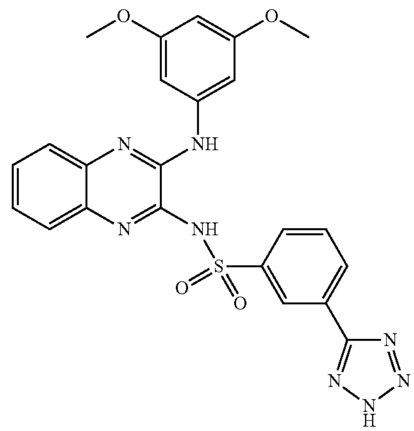 [SMILES: COc1cc(Nc2nc3ccccc3nc2NS(=O)(=O)c2cccc(-c3nn[nH]n3)c2)cc(OC)c1] | N-(3-{[3,5-bis(methoxy)phenyl]amino}quinoxalin-2-yl)-3-(2H-tetrazol-5-yl)benzenesulfonamide |
| 739 | 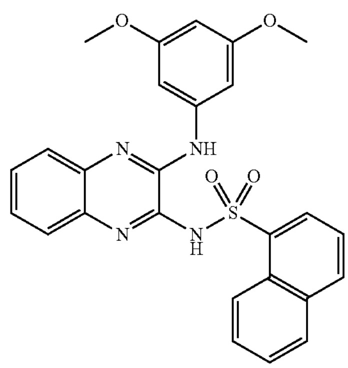 [SMILES: COc1cc(Nc2nc3ccccc3nc2NS(=O)(=O)c2cccc3ccccc23)cc(OC)c1] | N-(3-{[3,5-bis(methoxy)phenyl]amino}quinoxalin-2-yl)naphthalene-1-sulfonamide |
| 740 | 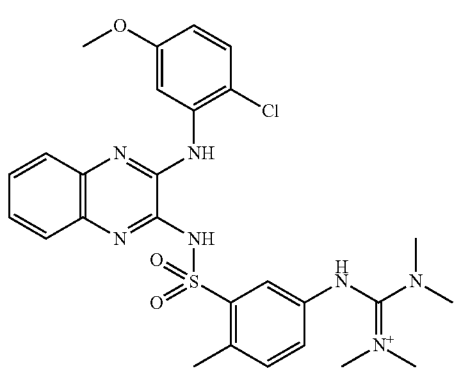 [SMILES: COc1ccc(Cl)c(Nc2nc3ccccc3nc2NS(=O)(=O)c2cc(NC(N(C)C)=[N+](C)C)ccc2C)c1] | N-{[(3-{[(3-{[2-chloro-5-(methoxy)phenyl]amino}quinoxalin-2-yl)amino]sulfonyl}-4-methylphenyl)amino](dimethylamino)methylidene}-N-methylmethanaminium |

TABLE 1-continued

| Cpd. No. | Structure | Name |
|---|---|---|
| 741 | 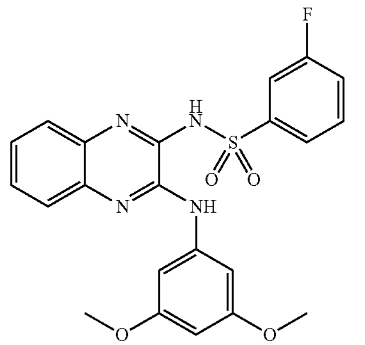 [SMILES: COc1cc(Nc2nc3ccccc3nc2NS(=O)(=O)c2cccc(F)c2)cc(OC)c1] | N-(3-{[3,5-bis(methoxy)phenyl]amino}quinoxalin-2-yl)-3-fluorobenzenesulfonamide |
| 742 | 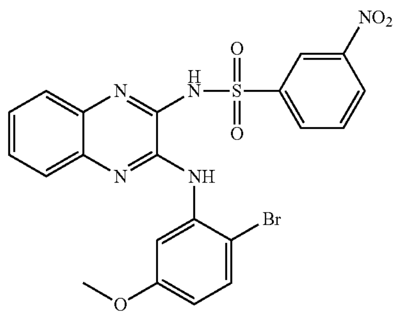 [SMILES: COc1ccc(Br)c(Nc2nc3ccccc3nc2NS(=O)(=O)c2cccc([N+](=O)[O-])c2)c1] | N-(3-{[2-bromo-5-(methoxy)phenyl]amino}quinoxalin-2-yl)-3-nitrobenzenesulfonamide |
| 743 | 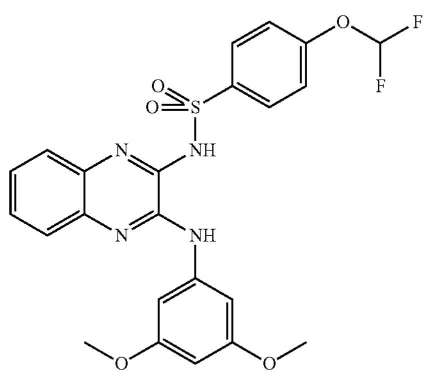 [SMILES: COc1cc(Nc2nc3ccccc3nc2NS(=O)(=O)c2ccc(OC(F)F)cc2)cc(OC)c1] | N-(3-{[3,5-bis(methoxy)phenyl]amino}quinoxalin-2-yl)-4-[(difluoromethyl)oxy]benzenesulfonamide |
| 744 | 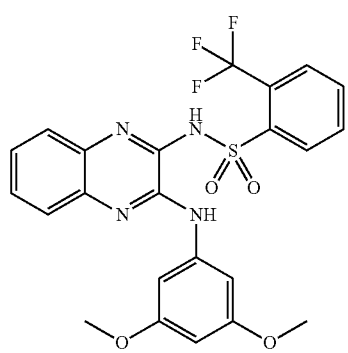 [SMILES: COc1cc(Nc2nc3ccccc3nc2NS(=O)(=O)c2ccccc2C(F)(F)F)cc(OC)c1] | N-(3-{[3,5-bis(methoxy)phenyl]amino}quinoxalin-2-yl)-2-(trifluoromethyl)benzenesulfonamide |

TABLE 1-continued

| Cpd. No. | Structure | Name |
|---|---|---|
| 745 | 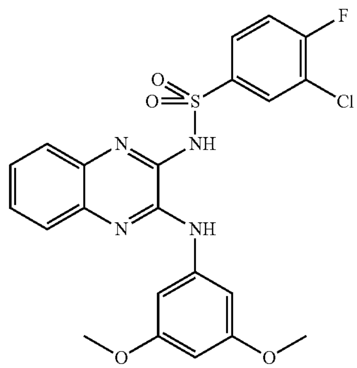 [SMILES: COc1cc(Nc2nc3ccccc3nc2NS(=O)(=O)c2ccc(F)c(Cl)c2)cc(OC)c1] | N-(3-{[3,5-bis(methoxy)phenyl]amino}quinoxalin-2-yl)-3-chloro-4-fluorobenzenesulfonamide |
| 746 | 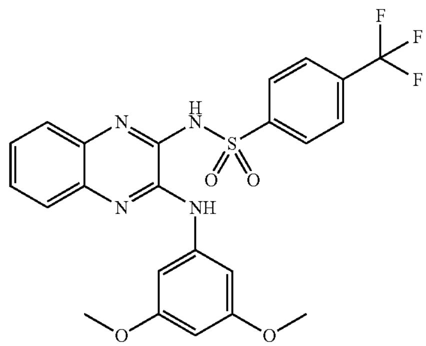 [SMILES: COc1cc(Nc2nc3ccccc3nc2NS(=O)(=O)c2ccc(C(F)(F)F)cc2)cc(OC)c1] | N-(3-{[3,5-bis(methoxy)phenyl]amino}quinoxalin-2-yl)-4-(trifluoromethyl)benzenesulfonamide |
| 747 | 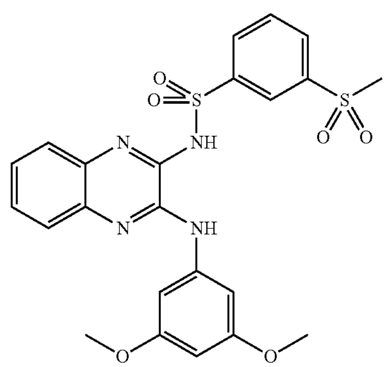 [SMILES: COc1cc(Nc2nc3ccccc3nc2NS(=O)(=O)c2cccc(S(C)(=O)=O)c2)cc(OC)c1] | N-(3-{[3,5-bis(methoxy)phenyl]amino}quinoxalin-2-yl)-3-(methylsulfonyl)benzenesulfonamide |
| 748 | 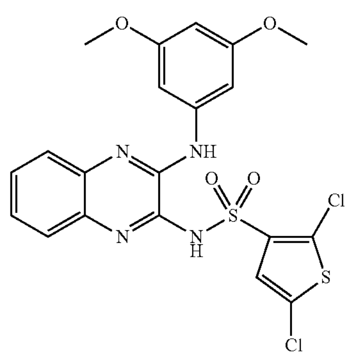 [SMILES: COc1cc(Nc2nc3ccccc3nc2NS(=O)(=O)c2cc(Cl)sc2Cl)cc(OC)c1] | N-(3-{[3,5-bis(methoxy)phenyl]amino}quinoxalin-2-yl)-2,5-dichlorothiophene-3-sulfonamide |

| Cpd. No. | Structure | Name |
|---|---|---|
| 749 | 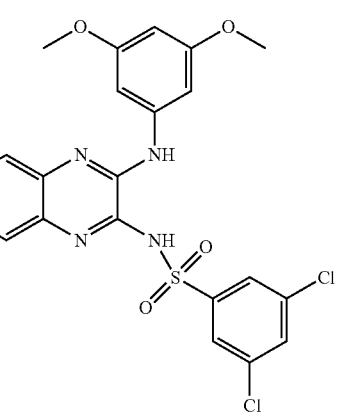 | N-(3-{[3,5-bis(methoxy)phenyl]amino}quinoxalin-2-yl)-3,5-dichlorobenzenesulfonamide |
| 750 | 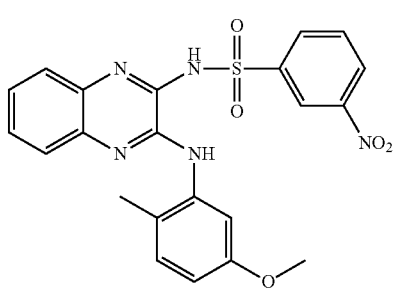 | N-(3-{[2-methyl-5-(methoxy)phenyl]amino}quinoxalin-2-yl)-3-nitrobenzenesulfonamide |
| 751 | 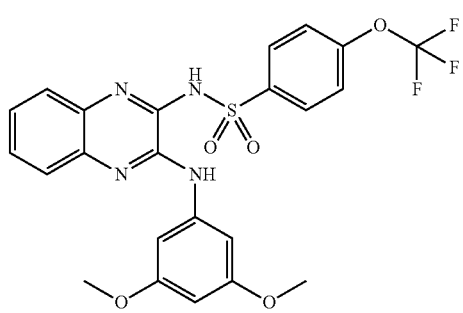 [SMILES: COc1cc(Nc2nc3ccccc3nc2NS(=O)(=O)c2ccc(OC(F)(F)F)cc2)cc(OC)c1] | N-(3-{[3,5-bis(methoxy)phenyl]amino}quinoxalin-2-yl)-4-[(trifluoromethyl)oxy]benzenesulfonamide |
| 752 | 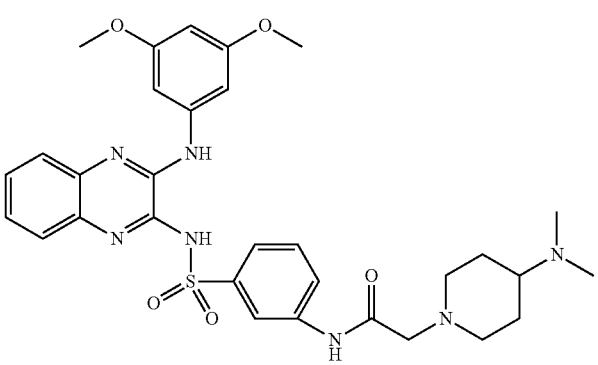 [SMILES: COc1cc(Nc2nc3ccccc3nc2NS(=O)(=O)c2cccc(NC(=O)CN3CCC(N(C)C)CC3)c2)cc(OC)c1] | N-(3-{[(3-{[3,5-bis(methoxy)phenyl]amino}quinoxalin-2-yl)amino]sulfonyl}phenyl)-2-[4-(dimethylamino)piperidin-1-yl]acetamide |

TABLE 1-continued

| Cpd. No. | Structure | Name |
|---|---|---|
| 753 | 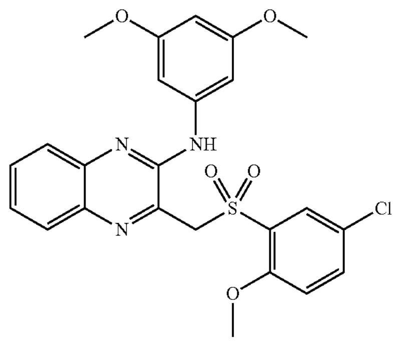 [SMILES: COc1cc(Nc2nc3ccccc3nc2CS(=O)(=O)c2cc(Cl)ccc2OC)cc(OC)c1] | N-(3-{[3,5-bis(methoxy)phenyl]amino}quinoxalin-2-yl)-5-chloro-2-(methoxy)benzenesulfonamide |
| 754 | 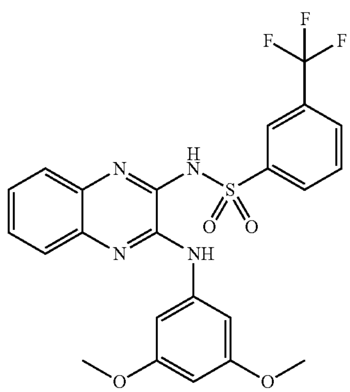 [SMILES: COc1cc(Nc2nc3ccccc3nc2NS(=O)(=O)c2cccc(C(F)(F)F)c2)cc(OC)c1] | N-(3-{[3,5-bis(methoxy)phenyl]amino}quinoxalin-2-yl)-3-(trifluoromethyl)benzenesulfonamide |
| 755 | 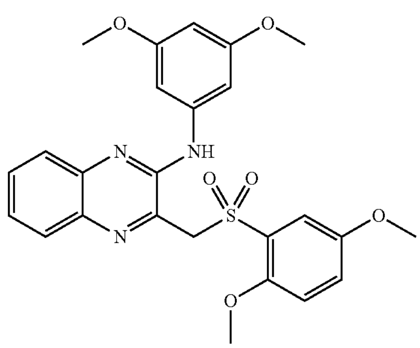 [SMILES: COc1cc(Nc2nc3ccccc3nc2CS(=O)(=O)c2cc(OC)ccc2OC)cc(OC)c1] | N-(3-{[3,5-bis(methoxy)phenyl]amino}quinoxalin-2-yl)-2,5-bis(methoxy)benzenesulfonamide |
| 756 | 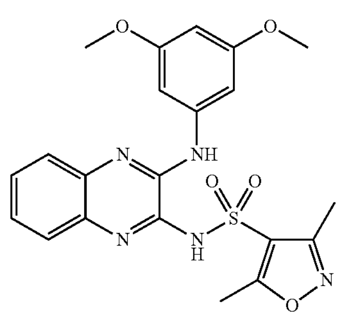 [SMILES: COc1cc(Nc2nc3ccccc3nc2NS(=O)(=O)c2c(C)noc2C)cc(OC)c1] | N-(3-{[3,5-bis(methoxy)phenyl]amino}quinoxalin-2-yl)-3,5-dimethylisoxazole-4-sulfonamide |

TABLE 1-continued

| Cpd. No. | Structure | Name |
| --- | --- | --- |
| 757 | 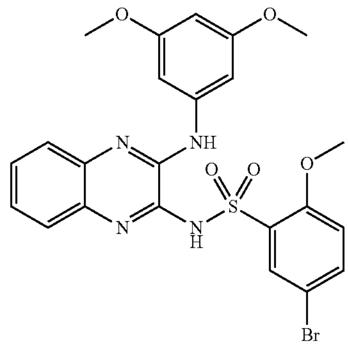 [SMILES: COc1cc(Nc2nc3ccccc3nc2NS(=O)(=O)c2cc(Br)ccc2OC)cc(OC)c1] | N-(3-{[3,5-bis(methoxy)phenyl]amino}quinoxalin-2-yl)-5-bromo-2-(methoxy)benzenesulfonamide |
| 758 | 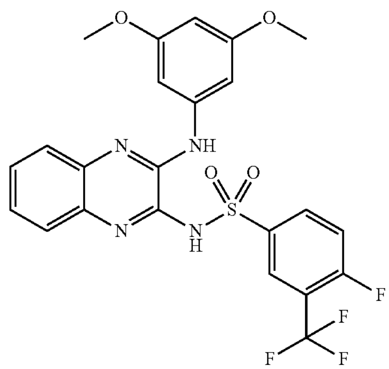 [SMILES: COc1cc(Nc2nc3ccccc3nc2NS(=O)(=O)c2ccc(F)c(C(F)(F)F)c2)cc(OC)c1] | N-(3-{[3,5-bis(methoxy)phenyl]amino}quinoxalin-2-yl)-4-fluoro-3-(trifluoromethyl)benzenesulfonamide |
| 759 | 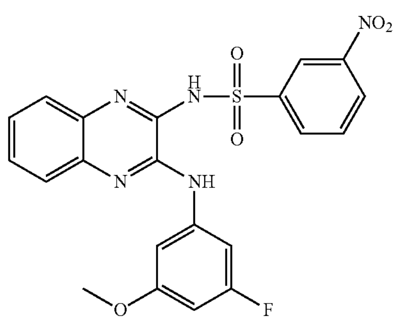 [SMILES: COc1cc(F)cc(Nc2nc3ccccc3nc2NS(=O)(=O)c2cccc([N+](=O)[O-])c2)c1] | N-(3-{[3-fluoro-5-(methoxy)phenyl]amino}quinoxalin-2-yl)-3-nitrobenzenesulfonamide |
| 760 | 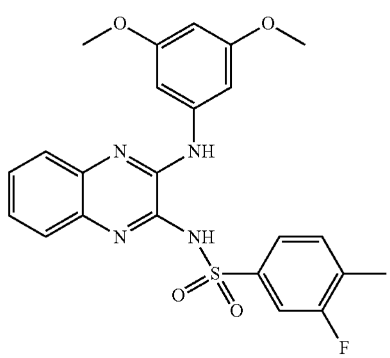 [SMILES: COc1cc(Nc2nc3ccccc3nc2NS(=O)(=O)c2ccc(C)c(F)c2)cc(OC)c1] | N-(3-{[3,5-bis(methoxy)phenyl]amino}quinoxalin-2-yl)-3-fluoro-4-methylbenzenesulfonamide |

| Cpd. No. | Structure | Name |
|---|---|---|
| 761 | 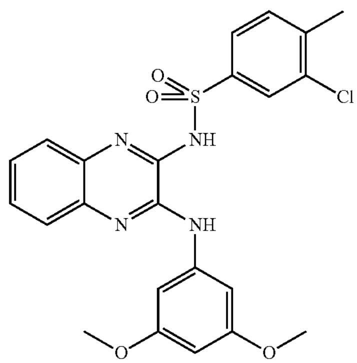 [SMILES: COc1cc(Nc2nc3ccccc3nc2NS(=O)(=O)c2ccc(C)c(Cl)c2)cc(OC)c1] | N-(3-{[3,5-bis(methoxy)phenyl]amino}quinoxalin-2-yl)-3-chloro-4-methylbenzenesulfonamide |
| 762 | 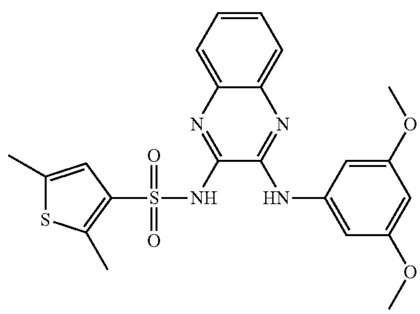 [SMILES: COc1cc(Nc2nc3ccccc3nc2NS(=O)(=O)c2cc(C)sc2C)cc(OC)c1] | N-(3-{[3,5-bis(methoxy)phenyl]amino}quinoxalin-2-yl)-2,5-dimethylthiophene-3-sulfonamide |
| 763 | 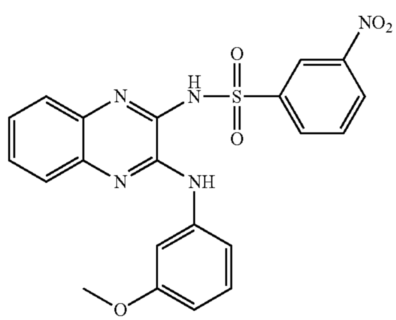 [SMILES: COc1cccc(Nc2nc3ccccc3nc2NS(=O)(=O)c2cccc([N+](=O)[O-])c2)c1] | N-(3-{[3-(methoxy)phenyl]amino}quinoxalin-2-yl)-3-nitrobenzenesulfonamide |
| 764 | 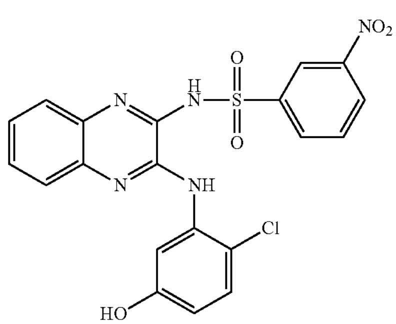 [SMILES: O=[N+]([O-])c1cccc(S(=O)(=O)Nc2nc3ccccc3nc2Nc2cc(O)ccc2Cl)c1] | N-{3-[(2-chloro-5-hydroxyphenyl)amino]quinoxalin-2-yl}-3-nitrobenzenesulfonamide |

TABLE 1-continued

| Cpd. No. | Structure | Name |
|---|---|---|
| 765 | 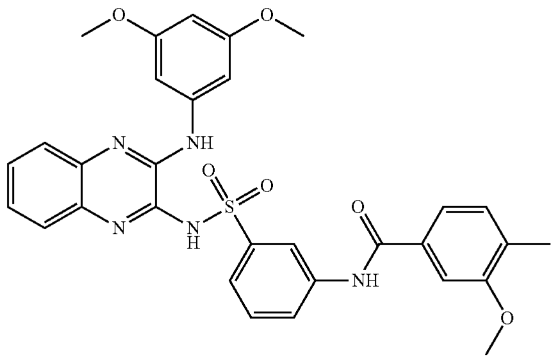 [SMILES: COc1cc(Nc2nc3ccccc3nc2NS(=O)(=O)c2cccc(NC(=O)c3ccc(C)c(OC)c3)c2)cc(OC)c1] | N-(3-{[(3-{[3,5-bis(methoxy)phenyl]amino}quinoxalin-2-yl)amino]sulfonyl}phenyl)-4-methyl-3-(methoxy)benzamide |
| 766 | 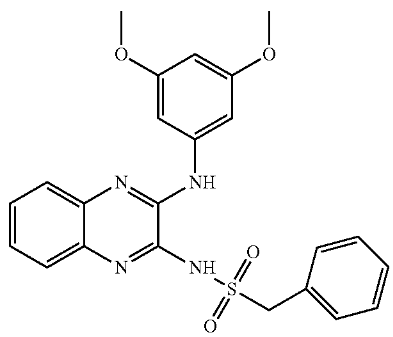 [SMILES: COc1cc(Nc2nc3ccccc3nc2NS(=O)(=O)Cc2ccccc2)cc(OC)c1] | N-(3-{[3,5-bis(methoxy)phenyl]amino}quinoxalin-2-yl)-1-phenylmethanesulfonamide |
| 767 | 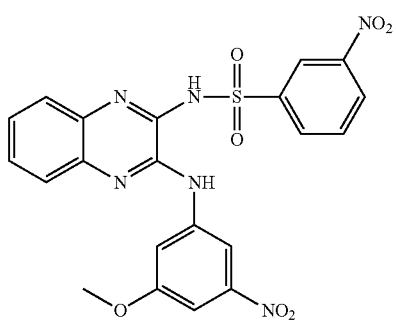 [SMILES: COc1cc(Nc2nc3ccccc3nc2NS(=O)(=O)c2cccc([N+](=O)[O-])c2)cc([N+](=O)[O-])c1] | N-(3-{[3-(methoxy)-5-nitrophenyl]amino}quinoxalin-2-yl)-3-nitrobenzenesulfonamide |
| 768 | 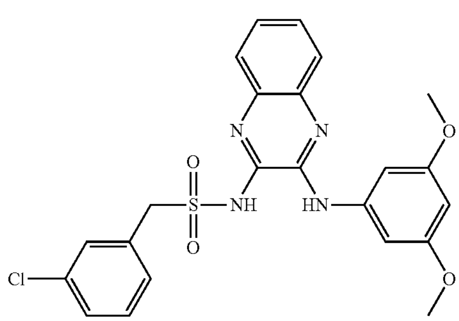 [SMILES: COc1cc(Nc2nc3ccccc3nc2NS(=O)(=O)Cc2cccc(Cl)c2)cc(OC)c1] | N-(3-{[3,5-bis(methoxy)phenyl]amino}quinoxalin-2-yl)-1-(3-chlorophenyl)methanesulfonamide |

TABLE 1-continued

| Cpd. No. | Structure | Name |
| --- | --- | --- |
| 769 | 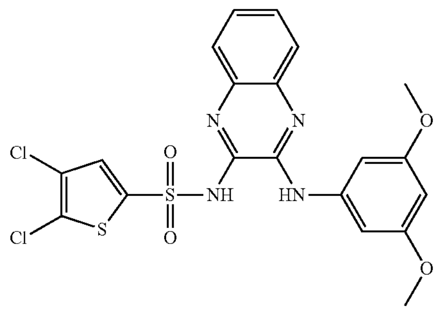 [SMILES: COc1cc(Nc2nc3ccccc3nc2NS(=O)(=O)c2cc(Cl)c(Cl)s2)cc(OC)c1] | N-(3-{[3,5-bis(methoxy)phenyl]amino}quinoxalin-2-yl)-4,5-dichlorothiophene-2-sulfonamide |
| 770 | 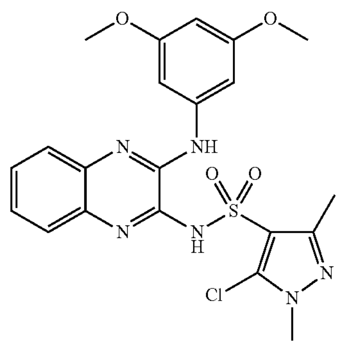 [SMILES: COc1cc(Nc2nc3ccccc3nc2NS(=O)(=O)c2c(C)nn(C)c2Cl)cc(OC)c1] | N-(3-{[3,5-bis(methoxy)phenyl]amino}quinoxalin-2-yl)-5-chloro-1,3-dimethyl-1H-pyrazole-4-sulfonamide |
| 771 | 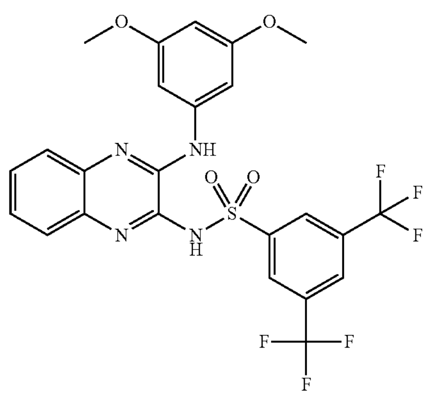 [SMILES: COc1cc(Nc2nc3ccccc3nc2NS(=O)(=O)c2cc(C(F)(F)F)cc(C(F)(F)F)c2)cc(OC)c1] | N-(3-{[3,5-bis(methoxy)phenyl]amino}quinoxalin-2-yl)-3,5-bis(trifluoromethyl)benzenesulfonamide |

Inhibitors

The compound of formula I of the present invention can be co-administered with an inhibitor of a kinase/kinase receptor which is upregulated by administration of the formula I compound. In this regard, it has been discovered that cancer cells exposed to formula I compounds display a subsequent upregulation of a number of kinase pathways in an apparent attempt to compensate for the PI3K inhibition caused by the compound. Inhibiting these upregulated kinases when employing a therapy regime of a formula I compound will synergistically inhibit tumor cell viability and, therefore, improve the effectiveness of the administered compound. Accordingly, in one aspect of the invention, inhibitors of HER3, HER2, MSPR, Axl, MAP3K (ERK, JNK, and p38 MAPK), MEKK kinases/kinase receptors, INSR, IGF-IR, and FGFR2 kinases/kinase receptors can be co-administered with a formula I compound to a patient undergoing treatment for cancer. In one aspect of the invention, inhibitors of HER2 and/or HER3 can be co-administered with a formula I compound to a patient undergoing treatment for cancer. In some embodiments, an inhibitor of HER2 and/or HER3 can be co-administered with a formula I compound to a patient undergoing treatment for cancer. In some embodiments, an inhibitor of HER2 and/or HER3 can be co-administered with a formula I compound to a patient undergoing treatment for cancer, wherein the cancer is a cancer overexpressing HER2, for example, a HER2 overexpressing breast cancer.

In some embodiments, the HER2 inhibitor is lapatinib (N-[3-chloro-4-[(3-fluorophenyl)methoxy]phenyl]-6-[5-[(2-methylsulfonylethylamino)methyl]-2-furyl]quinazolin-4-amine, for example, in the form of lapatinib ditosylate, commercially available under the tradename TYKERB®. Lapatinib has the chemical structure:

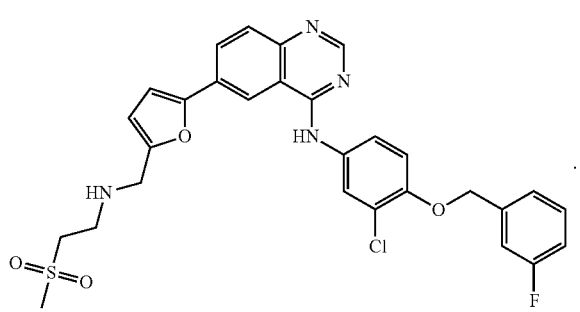 [SMILES: CS(=O)(=O)CCNCc1ccc(-c2ccc3ncnc(Nc4ccc(OCc5cccc(F)c5)c(Cl)c4)c3c2)o1]

The lapatinib dosage used can be directly determined by a prescribing physician using routine skill in the art. In some embodiments, the dosage of lapatinib administered in combination with a compound of formula I can range from about 0.1 mg/kg to about 100 mg/kg per day, for example a daily dose ranging from about 100, or 200, or 300, or 500, or 600, or 700, or 800, or 900, or 1,000, to about 1,500, or about 1,600, or about 2,000 mg per day.

In one embodiment, the inhibitor can be a functional nucleic acid. As used herein, the category of "functional nucleic acids" encompasses siRNA molecules, shRNA molecules, miRNA molecules, and antisense nucleic acid molecules. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

In one example, the functional nucleic acid targets the gene or transcript of a kinase receptor, such as the extracellular domain at which ligand binding occurs. In another example, the functional nucleic acid targets the intracellular protein kinase domain. In another example, the functional nucleic acid targets the heterodimer binding site (i.e. the amino-acid sequence that is involved in binding with other EGF receptor family members which form heterodimers with HER2 operable to stabilize ligand binding and enhance kinase-mediated activation of downstream signaling pathways. Numerous suitable functional nucleic acids are commercially available. See e.g. Qiagen, Valencia, Calif. Alternatively, functional nucleic acids can be identified and/or synthesized through experimentation or though rational design based on nucleotide sequence information on the target kinase/receptor using well-known methods in the field. The sequences can be determined by reference to bioinformatic databases (for example GENBANK, NCBI, PKR, and the like) that disclose the coding regions of genes known to express the particular kinase of interest, (target) i.e. HER3, HER2, MSPR, Axl, MAP3K (ERK, JNK, and p38 MAPK), MEKK kinases/kinase receptors, INSR, IGF-IR, and FGFR2. For purely illustrative purposes, the bioinformatic sequences for HER2 are provided below. Other kinases and kinase receptor mRNA and amino acid sequences for which inhibition is contemplated herein for example, HER3, MSPR, Axl, MAP3K (ERK, JNK, and p38 MAPK), MEKK kinases/kinase receptors, INSR, IGF-IR, and FGFR2 can also be identified using the above referenced databases.

In some embodiments, the generation of functional nucleic acids that can hybridize to an mRNA encoding one of several functional HER2 polypeptides is provided in SEQ ID NO: 1. It is noted that the below mRNA sequence is an exemplary HER2 mRNA sequence, other variant sequences (including splicing variants) which encode other isoforms of human HER2 and/or HER3 are known to those of ordinary skill in the art and are also contemplated herein, for example NM_004448.1, GI: 4758297. A cDNA clone operable to express the HER2 mRNA is commercially available from GeneCopoeia™ as product ID No. B0017. As provided below, SEQ ID NO: 1 is the mRNA transcript variant NM 004448 Version NM 004448.2; GI 54792095.

siRNA Inhibitors of HER2 and/or HER3

The rational design process can involve the use of a computer program to evaluate the criteria for every sequence of 18-30 base pairs or only sequences of a fixed length, e.g., 19 base pairs. Preferably, the computer program is designed such that it provides a report ranking of all of the potential siRNAs 18-30 base pairs, ranked according to which sequences generate the highest value. A higher value refers to a more efficient siRNA for a particular target gene. The computer program that may be used may be developed in any computer language that is known to be useful for scoring nucleotide sequences, or it may be developed with the assistance of commercially available product, such as Microsoft's product.net. Additionally, rather than run every sequence through one and/or another formula, one may compare a subset of the sequences, which may be desirable if for example only a subset are available. For instance, it may be desirable to first perform a BLAST (Basic Local Alignment Search Tool) search and to identify sequences that have no homology to other targets. Alternatively, it may be desirable to scan the sequence and to identify regions of moderate GC context, then perform relevant calculations using one of the above-described formulas on these regions. These calculations can be done manually or with the aid of a computer.

In some embodiments, the targeted kinase is HER2 and/or HER3, HER2 and/or HER3 mutant, or alternative splice variants thereof, particularly of human HER2 and/or HER3.

The term "target" is used in a variety of different forms throughout this disclosure and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of homology and the antisense strand exhibits varying degrees of complementarity. The phrase "siRNA target" can refer to the gene, mRNA, or protein against which an siRNA is directed. Similarly, "target silencing" can refer to the state of a gene, or the corresponding mRNA or protein.

The siRNA can comprise partially purified RNA, substantially pure RNA, synthetic RNA, or recombinantly produced RNA, as well as altered RNA that differs from naturally-occurring RNA by the addition, deletion, substitution, and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion. The siRNA can be targeted to any stretch of approximately 18-30 contiguous nucleotides in any of the target mRNA sequences, for example, 18, 19, 20, 21, 22, 23, 24, 25, 26, 27, 28, 29, or 30 nucleotides in each strand, wherein one of the strands is substantially complementary to, e.g., at least 80% (or more, e.g., 85%, 90%, 95%, or 100%) complementary to, e.g., having for example 3, 2, 1, or 0 mismatched nucleotide(s), a target mRNA sequence. Techniques for selecting target sequences for siRNA are provided, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Gottingen, Germany; and can be found by accessing the website of the Max Planck Institute and searching with the keyword "siRNA." Thus, the sense strand of the present siRNA comprises a nucleotide sequence identical to any contiguous stretch of about 18 to about 30 nucleotides in the target mRNA.

In some embodiments, one or both strands of the siRNA can also comprise a 3' overhang. As used herein, a "3' overhang" refers to at least one unpaired nucleotide extending from the 3'-end of a duplexed RNA strand. In some embodiments, the siRNA comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length. In the embodiment in which both strands of the siRNA molecule comprise a 3' overhang, the length of the overhangs can be the same or different for each strand. In some embodiments, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be obtained using a number of techniques known to those of skill in the art. For example, the siRNA can be chemically synthesized or recombinantly produced using methods known in the art, such as the *Drosophila* in vitro system described in U.S. published application 2002/0086356 of Tuschl et al., the entire disclosure of which is herein incorporated by reference.

Preferably, the siRNA are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo. USA), Pierce Chemical (part of Perbio Science, Rockford, Ill. USA), Glen Research (Sterling, Va. USA), ChemGenes (Ashland, Mass. USA), and Cruachem (Glasgow, UK).

Alternatively, siRNA can also be expressed from recombinant circular or linear DNA plasmids using any suitable promoter. Suitable promoters for expressing siRNA from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the area of neovascularization in vivo. The use of recombinant plasmids to deliver siRNA to cells in vivo is discussed in more detail below.

siRNA can be expressed from a recombinant plasmid either as two separate, complementary RNA molecules, or as a single RNA molecule with two complementary regions.

Methods of selecting plasmids suitable for expressing siRNA, methods for inserting nucleic acid sequences for expressing the siRNA into the plasmid, and methods for delivering the recombinant plasmid to the cells of interest are within the skill in the art. See, e.g., Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference. A plasmid comprising nucleic acid sequences for expressing an siRNA is described in Example 7 below. That plasmid, called pAAVsiRNA, comprises a sense RNA strand coding sequence in operable connection with a polyT termination sequence under the control of a human U6 RNA promoter and an antisense RNA strand coding sequence in operable connection with a polyT termination sequence under the control of a human U6 RNA promoter. The plasmid pAAVsiRNA is ultimately intended for use in producing an recombinant adeno-associated viral vector comprising the same nucleic acid sequences for expressing an siRNA.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "under the control" of a promoter means that the nucleic acid sequences encoding the sense or antisense strands are located 3' of the promoter, so that the promoter can initiate transcription of the sense or antisense coding sequences.

The siRNA can also be expressed from recombinant viral vectors intracellularly at or near the area of the HER2 and/or HER3 gene expressed tumor in vivo. The recombinant viral vectors of the invention comprise sequences encoding the siRNA and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment.

In some embodiments, the siRNA can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV), adeno-associated virus (AAV), retroviruses (e.g., lentiviruses (LV), Rhabdoviruses, murine leukemia virus), herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Methods for selecting of recombinant viral vectors suitable for use in the invention, methods for inserting nucleic acid sequences for expressing the siRNA into the vector, and methods for delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; and Anderson W F (1998), Nature 392: 25-30, the entire disclosures of which are herein incorporated by reference. In some cases, a commercially available viral delivery system can be used (e.g., vectors for siRNA delivery that are available from Ambion, Austin, Tex.). Other methods for delivery are known to those in the art (e.g., siRNA Delivery Centre, sirna.dk/index.html).

Preferred viral vectors are those derived from AV and AAV. In a particularly preferred embodiment, the siRNA is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA, a method for constructing the recombinant AV vector, and a method for delivering the vector into target cells, are described in Xia H et al. (2002), Nat. Biotech. 20: 1006-1010, the entire disclosures of which are herein incorporated by reference.

Suitable AAV vectors for expressing the siRNA, methods for constructing the recombinant AAV vector, and methods for delivering the vectors into target cells are described in Samulski R et al. (1987), J. Virol. 61: 3096-3101; Fisher K J et al. (1996), J. Virol., 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

The ability of an siRNA containing a given target sequence to cause RNAi-mediated degradation of the target mRNA can be evaluated using standard techniques for measuring the levels of RNA or protein in cells. For example, siRNA can be delivered to cultured cells, and the levels of target mRNA can be measured by Northern blot or dot blotting techniques or by quantitative RT-PCR. Alternatively, the levels of HER3, HER2, MSPR, Axl, MAP3K (ERK, JNK, and p38 MAPK), MEKK kinases/kinase receptors, INSR, IGF-IR, and FGFR2 kinases/kinase receptor protein in the infected cells can be measured by ELISA or Western blot. A suitable cell culture system for measuring the effect of the present siRNA on target mRNA or protein levels is described in the Examples below.

In some embodiments, specific siRNAs for downregulating the activity and/or expression of HER2 and/or HER3 in vitro and/or in vivo can be synthesized. Illustrative siRNA pairs for HER2 inhibition can include the sequence pairs: SEQ ID NO: 3-:CCUGGAACUCACCUACCUGdTdT/SEQ ID NO: 4-CAGGUAGGUGAGUUCCAGGdTdT; SEQ ID NO: 5-CUACCUUUCUACGGACGUGdTdT/SEQ ID NO: 6-CACGUCCGUAGAAAGGUAGdTdT; and SEQ ID NO: 7-GAUCCGGAAGUACACGAUGdTdT/SEQ ID NO: 8-CAUCGUGUACUUCCGGAUCdTdT) can be chemically synthesized and annealed. These rationally designed siRNAs can be synthesized and commercially available from Dharmacon. In still other embodiments, siRNAs shRNAs, and lentiviral vectors capable of expressing shRNA sequences useful in inhibiting HER2 and/or HER3 expression and/or activity are commercially available under Catalog Nos.: sc-156048, and sc-29405 from Santa Cruz Biotechnology (Santa Cruz, Calif., USA).

In some embodiments, the efficacy of the functional nucleic acids useful herein can be increased when the functional nucleic acids, for example, siRNAs are tumor targeted, delivered systemically, repeatedly, and safely. Low transfection efficiency, nuclease degeneration, poor tissue penetration, and non-specific immune degradation can be overcome when the functional nucleic acids are incorporated into protective and functional vehicles, for example, viral vectors, liposomes complexed with polyethyleneimine (PEI), linked with vascular endothelial growth factor (VEGF) receptor-2, and PEI that was PEGylated with an RGD peptide ligand at the distal end, protamine-antibody fusion protein, and tumor-targeting immunoliposome complexes. Any combination of these strategies can ameliorate and abrogate the above described problems previously seen with first generation delivery methods. In some embodiments, the functional nucleic acid is administered to the subject either as naked siRNA, in conjunction with a delivery reagent, or as a recombinant plasmid or viral vector which expresses the siRNA.

Suitable delivery reagents for administration in conjunction with the present siRNA include the Mirus Transit TKO lipophilic reagent, lipofectin, lipofectamine, cellfectin, or polycations (e.g., polylysine), bacterial minicells, or liposomes. A preferred delivery reagent is a liposome.

Liposomes can aid in the delivery of the siRNA to a particular tissue, such as a tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

In some embodiments, the liposomes encapsulating the present siRNA comprises a ligand molecule that can target the liposome to a particular cell or tissue at or near the site of angiogenesis. Ligands which bind to receptors prevalent in HER2 and/or HER3 overexpressing tumors, such as monoclonal antibodies that bind to tumor antigens, are preferred. For example, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand. As used herein, opsonization-inhibition moieties for use in preparing the liposomes of the invention are illustratively large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. These liposomes are sometimes called "concealed" liposomes.

Concealed liposomes are known to accumulate in tissues fed by porous or "leaky" microvasculature. Thus, target tissue characterized by such microvasculature defects, for example solid tumors, will efficiently accumulate these liposomes. In addition, the reduced uptake by the reticuloendothelial system lowers the toxicity of concealed liposomes by preventing significant accumulation in the liver and spleen. Thus, liposomes of the invention that are modified with opsonization-inhibition moieties can deliver the present siRNA to tumor cells as exemplified herein.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, and gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan, aminated polysaccharides or oligosaccharides (linear or branched), or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Illustrative recombinant plasmids which can express siRNA are discussed above. Such recombinant plasmids can also be administered directly or in conjunction with a suitable delivery reagent, including the Mirus Transit LT1 lipophilic reagent, lipofectin, lipofectamine, cellfectin, polycations (e.g., polylysine), bacterial minicells, or liposomes. Recombinant viral vectors which express siRNA are also discussed above, and methods for delivering such vectors to a solid tumor in a patient are within the skill in the art. In some embodiments, the delivery method can include sterotactic injection of the vector into the tumor, or the surrounding tissue.

The siRNA can be administered to the subject by any means suitable for delivering the siRNA to the cells of the tumor tissue at or near the tumor. For example, the siRNA can be administered by gene gun, electroporation, stereotactic injection, or by other suitable parenteral or enteral administration routes. Suitable enteral administration routes include oral, rectal, transdermal, or intranasal delivery.

Suitable parenteral administration routes include intravascular administration (e.g. intravenous bolus injection, intravenous infusion, intra-arterial bolus injection, intra-arterial infusion and catheter instillation into the vasculature), peri- and intra-tissue administration (e.g., peri-tumoral and intra-tumoral injection), subcutaneous injection or deposition including subcutaneous infusion (such as by osmotic pumps), direct (e.g., injection) application to the area at or near the site of the tumor, for example by a catheter, syringe, or other placement device (e.g., an implant comprising a porous, non-porous, or gelatinous material), inhalation, or stereotactic injection.

In some embodiments, injections or infusions of the siRNA are given at or near the site of the HER2 overexpressing tumor. More preferably, the siRNA is administered directly by injection to the tumor or into the vascualture supplying nutrients to the tumor.

The siRNA can be administered in a single dose or in multiple doses. Where the administration of the siRNA is by infusion, the infusion can be a single sustained dose or can be delivered by multiple infusions. Injection of the agent directly into the tumor tissue is at or near the site of the HER2 overexpressing tumor/cancer, for example, breast cancer. Multiple injections of the agent into the tumor tissue or at or near the site of the tumor are particularly preferred.

One skilled in the art can also readily determine an appropriate dosage regimen for administering the siRNA to a given subject. For example, the siRNA can be administered to the subject once, such as by a single injection or deposition at, into, or near the tumor. Alternatively, the siRNA can be administered to a subject multiple times daily or weekly. For example, the siRNA can be administered to a subject once weekly for a period of from about three to about twenty-eight weeks, more preferably from about seven to about ten weeks. In a preferred dosage regimen, the siRNA is injected into or at or near the tumor site (e.g., stereotactic injection) once a week for seven weeks. In other embodiments, the siRNA is administered intravenously, using a single or multiple daily, or weekly, or monthly doses. It is understood that periodic administrations of the siRNA for an indefinite length of time may be necessary for subjects suffering from a chronic HER2 overexpressing cancer disease, such as HER2 overexpressing breast cancer, that is naïve or is refractory or non-responsive to another cancer treatment.

Where a dosage regimen comprises multiple administrations, it is understood that the effective amount of siRNA administered to the subject can comprise the total amount of siRNA administered over the entire dosage regimen.

The siRNA are preferably formulated as pharmaceutical compositions prior to administering to a subject, according to techniques known in the art. Pharmaceutical compositions of the present invention are characterized as being at least, therapeutically effective, sterile, pyrogen-free, and that are pharmaceutically effective, meaning that there is a reasonable salt solutions, 0.4% saline, 0.3% glycine, hyaluronic acid, and the like.

Pharmaceutical compositions can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), and optionally, additions of calcium or sodium salts (for example, calcium chloride, calcium ascorbate, calcium gluconate, or calcium lactate). Pharmaceutical compositions of the invention can be packaged for use in liquid form or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA. A pharmaceutical composition for aerosol (inhalational) administration can comprise 0.01-20% by weight, preferably 1%-10% by weight, of one or more siRNA encapsulated in a liposome as described above, and a propellant. A carrier can also be included as desired; e.g., lecithin for intranasal delivery.

shRNA Inhibitory Molecules

In some embodiments, a shRNA nucleic acid molecule refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. One portion or segment of a duplex stem of the shRNA structure is anti-sense strand or complementary, e.g., fully complementary, to a section of about 18 to about 40 or more nucleotides of the mRNA of the target gene, for example, HER2 and/or HER3. In contrast to siRNAs, shRNAs mimic the natural precursors of micro RNAs (miRNAs). miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNAi agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

In some embodiments, the shRNA molecules of the invention are designed to produce any of the siRNAs described above when processed in a cell e.g., by Dicer present within the cell. The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two-, or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

One strand of the stem portion of the shRNA is further sufficiently complementary (e.g., antisense) to a target RNA of HER2 and/or HER3 (e.g., mRNA of HER2, for example, as provided in SEQ ID NO: 1) sequence to mediate degradation or cleavage of said target RNA via RNA interference (RNAi). The antisense portion can be on the 5' or 3' end of the stem. The stem portions of a shRNA are preferably about 15 to about 50 nucleotides in length. Preferably the two stem portions are about 18 or 19 to about 25, 30, 35, 37, 38, 39, or 40 or more nucleotides in length. When used in mammalian cells, the length of the stem portions should be less than about 30 nucleotides to avoid provoking non-specific responses, such as the interferon pathway. In non-mammalian cells, the stem can be longer than 30 nucleotides. In fact, a stem portion can include much larger sections complementary to the target mRNA (up to, and including the entire mRNA). The two portions of the duplex stem must be sufficiently complementary to hybridize to form the duplex stem. Thus, the two portions can be, but need not be, fully or perfectly complementary.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In some embodiments, shRNAs of the invention include the sequences of a desired siRNA molecule described above. In other embodiments, the sequence of the antisense portion of a shRNA can be designed essentially as described above or generally by selecting an 18, 19, 20, or 21 nucleotide, or longer, sequence from within the target RNA (e.g., HER2 and/or HER3 mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR, provided said portion is distant from the site of the gain-of-function mutation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Specific functional nucleic acids (e.g. shRNA clones) which target mRNA of HER2 and/or HER3, for example, HER2 NM_004448.1 (based on Product ID B0017), are also commercially available from GeneCopoeia™ (GeneCopoeia, Rockville, Md., USA) as Product ID No. HSH004969, which are shRNA expression constructs. The hairpin consists of a 7 base loop and 19-29 base stem optimized for the specific gene sequence of target mRNA Accession No. NM_004448.2 (shown as SEQ ID NO: 1)

Antisense Inhibitors of HER2 and/or HER3

Isolated functional nucleic acid molecules that are antisense to a HER2 and/or HER3 nucleotide sequence are useful for reducing activity or expression of the HER2 and/or HER3 mRNA or polypeptide. An "antisense" functional nucleic acid (antisense oligonucleotide) can include a nucleotide sequence that is complementary to a "sense" nucleic acid encoding a protein, e.g., complementary to the coding strand of a double-stranded cDNA molecule, or complementary to an mRNA sequence, for example, as provided in SEQ ID NO: 1. The antisense nucleic acid can be complementary to an entire HER2 and/or HER3 coding strand, or to only a portion thereof (e.g., coding region of a human HER2 and/or HER3 nucleotide sequence). In another embodiment, the antisense nucleic acid molecule is antisense to a "noncoding region" of the coding strand of a nucleotide sequence encoding a HER2 and/or HER3 polypeptide (e.g., the 5' or 3' untranslated regions).

An antisense nucleic acid can be designed such that it is complementary to the entire coding region of HER2 and/or HER3 mRNA, but in general, is an oligonucleotide that is antisense to only a portion of the coding or noncoding region of HER2 and/or HER3 mRNA. For example, the antisense oligonucleotide can be complementary to the region surrounding the translation start site of HER2 and/or HER3 mRNA, e.g., between the −10 and +10 regions of the target gene nucleotide sequence of interest. An antisense oligonucleotide can be, e.g., about 5-100, or from about 7, 10, 15, 20, 25, 30, 35, 40, 45, 50, 55, 60, 65, 70, 75, or 80 or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used (see, e.g., Protocols for Oligonucleotide Conjugates. Totowa, N.J.: Humana Press, 1994, and commercially available services from, for example, Dharmacon, Lafayette, Colo., USA. and Ambion, Austin, Tex., USA.). The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest). Antisense nucleic acids can also be produced from synthetic methods such as phosphoramidite methods, H-phosphonate methodology, and phosphite trimester methods. Antisense nucleic acids can also be produced by PCR methods. Such methods produce cDNA and cRNA sequences complementary to the mRNA.

In some embodiments, antisense molecules can be modified or unmodified RNA, DNA, or mixed polymer oligonucleotides and primarily function by specifically binding to matching sequences resulting in inhibition of peptide synthesis, for example, inhibition in the expression of one or more of HER3, HER2, MSPR, Axl, MAP3K (ERK, JNK, and p38 MAPK), MEKK kinases/kinase receptors, INSR, IGF-IR, and FGFR2. antisense molecules can be modified or unmodified RNA, DNA, or mixed polymer oligonucleotides and primarily function by specifically binding to matching sequences resulting in inhibition of peptide synthesis, for example, inhibition in the expression of HER2 and/or HER3. The antisense oligonucleotide binds to target RNA by Watson Crick base-pairing and blocks gene expression by preventing ribosomal translation of the bound sequences either by steric blocking or by activating RNase H enzyme. Antisense molecules can also alter protein synthesis by interfering with RNA processing or transport from the nucleus into the cytoplasm.

An antisense nucleic acid can be an α-anomeric nucleic acid molecule. An α-anomeric nucleic acid molecule forms specific double-stranded hybrids with complementary RNA in which, contrary to the usual β-units, the strands run parallel to each other. The antisense nucleic acid molecule can also comprise a 2'-O-methylribonucleotide or a chimeric RNA-DNA analog and can have mixed internucleoside linkages (see, e.g., Protocols for Oligonucleotide Conjugates. Totowa N.J.: Humana Press, 1994).

In some embodiments, methods for treating a cancer comprise administering to a patient a combination of compound 1 and antisense nucleic acids. In some embodiments, antisense nucleic acid molecules are typically administered to a subject (e.g., by direct injection at a tissue site) or are generated in situ such that they hybridize with or bind to cellular RNA (e.g., mRNA) and/or genomic DNA encoding a HER2 and/or HER3 protein, for example, as provided in SEQ ID NO: 2 or splice variants thereof, to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens present on tumor cells, for example, HER2 over-expressing tumor cells. The antisense nucleic acid molecules can also be delivered to tumor cells using the vectors described herein. To achieve sufficient intracellular concentrations of the antisense molecules, vector constructs in which the antisense nucleic acid molecule is placed under the control of a strong pol II or pol III promoter. Methods of administering antisense nucleic molecules are also known in the art (e.g., Wacheck et al. *Chemosensitisation of malignant melanoma by BCL2 antisense therapy* (2000) Lancet 356:1728-1733; Webb et al. *BCL-2 antisense therapy in patients with non-Hodgkin lymphoma* (1997) Lancet 349:1137-1141).

In some embodiments, HER2 and/or HER3 gene expression can be inhibited by targeting nucleotide sequences complementary to the regulatory region of the HER2 and/or HER3 (e.g., the HER2 and/or HER3 promoter and/or enhancers) to form triple helical structures that prevent transcription of the HER2 and/or HER3 gene in target cells. See generally, Hurst, H. C., Breast Cancer Res 2001, 3:395-398; Helene (1991) Anticancer Drug Des. 6(6):569-84; Helene et al. (1992) Ann. N.Y. Acad. Sci. 660:27-36; and Maher (1992) Bioassays 14:807-15), which are incorporated herein by reference in their entireties. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

A HER2 and/or HER3 functional nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) Bioorgan. Med. Chem. 4:5-23). As used herein, the terms "peptide nucleic acid" or "PNA" refer to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996, supra) and Perry-O'Keefe et al. (1996) Proc. Natl. Acad. Sci. U.S.A. 93:14670-14675).

PNAs of HER2 and/or HER3 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of HER2 and/or HER3 nucleic acid molecules can also be used in the analysis of single base pair mutations in a gene, (e.g., by PNA-directed PCR clamping), as "artificial restriction enzymes" when used in combination with other enzymes, (e.g., S nucleases (Hyrup (1996, supra)), or as probes or primers for DNA sequencing or hybridization (Hyrup et al. (1996, supra); Perry-O'Keefe et al. (1996, supra)).

Antibody Inhibitors of HER2 and/or HER3

In another embodiment, the inhibitor can be an antibody or fragments thereof. The antibody can inhibit the upregulated kinase activity by, for example, binding to the extracellular domain of the kinase receptor. A variety of suitable antibodies are known in the field and commercially available. For example, antibodies to each of the HER2, HER3, MSPR, Axl, MAP3K (ERK, JNK, and p38 MAPK) and MEKK kinases can be obtained from R&D Systems (Minneapolis, Minn.). See, e.g. R&D Systems Catalog: for MSPR (catalog Nos. AF691, FAB691A, BAF691, FAB691F, MAB691, FAB691P, DYC1947E, DYC1947-2, DYC1947-5, DYC691-2, DYC691-5, AF431, BAF431, 1947-MS-050 and 431-MS-100); for Axl (catalog Nos. AF154 BAF154, DY154, MAB154 and FAB1541); for MAP3k (catalog Nos: 4540-KS-010, MAB4540, MAB6095); for MEKK (catalog No. MAB6095); for HER2 (catalog Nos. AF1768, MAB1129, AF1129, MAB11291, AF4438, MAB4360); for HER3 (catalog Nos. MAB3482, MAB3483, FAB3481P and MAB348); for INSR (catalog Nos. AF1544, MAB1544, MAB15441 and AF2507); for IGF-IR (catalog Nos. MAB391, AF-305-NA and FAB391C); and for FGFR2 (catalog Nos. MAB6842, MAB684, MAB665 and MAB6841). U3-1287 (U3 Pharma, Martinsried, Germany), and MM-121, which is antibody Ab#6 in WO 08/100,624, (Merrimack Pharmaceuticals, Cambridge, Mass.) are additional examples of well-known anti-HER3 antibodies. Further anti-HER3 antibodies are disclosed in WO 97/35885, EP 1414494, WO 08/100,624, U.S. Pat. No. 7,705,130, US2010/0047829, and Chen et al., J. Biol. Chem., 271:7620-7629 (1996), all of which are hereby incorporated by reference.

In one aspect, the HER3 inhibitor is an anti-ErbB3 antibody that binds to ErbB3 with a $K_D$ of at least 4 nM as measured using a surface plasmon resonance assay or a cell binding assay. In one embodiment, such an antibody comprises the following CDRs:

```
VH CDR1-SEQ ID NO: 9:
HYVMA

VH CDR2-SEQ ID NO: 10:
SISSSGGWTLYADSVKG

VH CDR3-SEQ ID NO: 11:
GLKMATIFDY

VL CDR1-SEQ ID NO: 12:
TGTSSDVGSYNVVS

VL CDR2-SEQ ID NO: 13:
EVSQRPS

VL CDR3-SEQ ID NO: 14:
CSYAGSSIFVI
```

In another embodiment, such an antibody comprises a heavy chain variable region having an amino acid sequence of

```
SEQ ID NO: 15:
EVQLLESGGGLVQPGGSLRLSCAASGFTFSAYNMRWVRQAPGKGLEWVS

VIYPSGGATRYADSVKGRFTISRDNSKNTLYLQMNSLRAEDTAVYYCAR

GYYYYGMDVWGQGTLVTVSS
``` and a light chain variable region having a sequence of

```
SEQ ID NO: 16:
QSVLTQPPSASGTPGQRVTISCSGSDSNIGRNYIYWYQQFPGTAPKLLI

YRNNQRPSGVPDRISGSKSGTSASLAISGLRSEDEAEYHCGTWDDSLSG

PVFGGGTKLTVL
```

In another embodiment, such an antibody is MM-121, which comprises a heavy chain with the following amino acid sequence

```
SEQ ID NO: 17:
  1 EVQLLESGGG LVQPGGSLRL SCAASGFTFS HYVMAWVRQA PGKGLEWVSS

51 ISSSGGWTLY ADSVKGRFTI SRDNSKNTLY LQMNSLRAED TAVYYCTRGL

101 KMATIFDYWG QGTLVTVSSA STKGPSVFPL APCSRSTSES TAALGCLVKD

151 YFPEPVTVSW NSGALTSGVH TFPAVLQSSG LYSLSSVVTV PSSNFGTQTY

201 TCNVDHKPSN TKVDKTVERK CCVECPPCPA PPVAGPSVFL FPPKPKDTLM

251 ISRTPEVTCV VVDVSHEDPE VQFNWYVDGV EVHNAKTKPR EEQFNSTFRV

301 VSVLTVVHQD WLNGKEYKCK VSNKGLPAPI EKTISKTKGQ PREPQVYTLP
```

```
                            -continued
351  PSREEMTKNQ  VSLTCLVKGF  YPSDIAVEWE  SNGQPENNYK  TTPPMLDSDG

401  SFFLYSKLTV  DKSRWQQGNV  FSCSVMHEAL  HNHYTQKSLS  LSPGK
``` and light chain with the following amino acid sequence

```
SEQ ID NO: 18:
  1  QSALTQPASV  SGSPGQSITI  SCTGTSSDVG  SYNVVSWYQQ  HPGKAPKLII

51  YEVSQRPSGV  SNRFSGSKSG  NTASLTISGL  QTEDEADYYC  CSYAGSSIFV

101  IFGGGTKVTV  LGQPKAAPSV  TLFPPSSEEL  QANKATLVCL  VSDFYPGAVT

151  VAWKADGSPV  KVGVETTKPS  KQSNNKYAAS  SYLSLTPEQW  KSHRSYSCRV

201  THEGSTVEKT  VAPAECS.
```

In some embodiments, the antibody inhibitor of HER2 can include trastuzumab, commercially available as HERCEPTIN® ((huMAb4D5-8, rhuMAb HER2, U.S. Pat. No. 5,821,337) Genentech, Inc., San Francisco, Calif.). In some embodiments, trastuzumab is administered to the subject in combination with a compound of formula I. The dosage of trastuzumab for such administration can be readily determined by a prescribing physician without undue experimentation. For example, the weekly dosage of trastuzumab to be administered with the combination of a compound of formula I, can range from about 0.01 mg/kg to about 100 mg/kg, or from about 0.1 mg/kg to about 100 mg/kg, or from about 1 mg/kg to about 100 mg/kg, or from about 0.1 mg/kg to about 50 mg/kg, or from about 0.1 mg/kg to about 10 mg/kg per week, preferably administered intravenously.

In some embodiments, the HER2 antibody inhibitor includes the antibody pertuzumab (disclosed in U.S. Pat. No. 7,449,184 and incorporated herein in its entirety) administered in one or more doses, in an amount ranging from about 100 mg per dose to about 1500 mg per dose, administered approximately every week, approximately every 2 weeks, approximately every 3 weeks, or approximately every 4 weeks.

Anti-HER2 antibodies of murine origin and their humanized and chimeric versions are suitable for use in the methods of the present invention. Examples of such HER2 antibodies include, but are not limited to, the 4D5 antibody (described in U.S. Pat. Nos. 5,677,171 and 5,772,997) and the 520C9 antibody and its functional equivalents (WO93/21319), designated 452F2, 736G9, 741F8, 758G5, and 761B10 (described in U.S. Pat. No. 6,054,561); all of these patents and patent applications herein incorporated by reference. In some embodiments, HER2 antibody inhibitors can include one or more antibodies selected from humanized anti-HER2 antibodies, for example, huMAb4D5-1, huMAb4D5-2, huMAb4D5-3, huMAb4D5-4, huMAb4D5-5, huMAb4D5-6, huMAb4D5-7, and 4D5-8 as described in Table 3 of U.S. Pat. No. 5,821,337, which is incorporated herein by reference in its entirety, and humanized 2C4 antibodies. Alternatively, suitable antibodies can be prepared readily using well-known techniques, as described below.

Preparation of Antibodies

Polyclonal Antibodies

Polyclonal antibodies are preferably raised in animals by multiple subcutaneous (sc) or intraperitoneal (ip) injections of the relevant antigen and an adjuvant. Alternatively, antigen may be injected directly into the animal's lymph node (see Kilpatrick et al., Hybridoma, 16:381-389, 1997). An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, or other agents known in the art.

Animals are immunized against the antigen, immunogenic conjugates, or derivatives by combining, e.g., 100 μg of the protein or conjugate (for mice) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated through a different cross-linking reagent. Conjugates also can be made in recombinant cell culture as protein fusions. Also, aggregating agents such as alum are suitably used to enhance the immune response.

Monoclonal Antibodies

Monoclonal antibodies can be made using the hybridoma method first described by Kohler et al., Nature, 256:495 (1975), or by recombinant DNA methods. In the hybridoma method, a mouse or other appropriate host animal, such as rats, hamster, or macaque monkey, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M. C.-11 mouse tumors available from the Salk Institute Cell Distribution Center, San Diego, Calif. USA, and SP-2 or X63-Ag8-653 cells available from the American Type Culture Collection, Rockville, Md. USA. Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can be determined, for example, by BIAcore or Scatchard analysis (Munson et al., Anal. Biochem., 107:220 (1980)).

After hybridoma cells are identified that produce antibodies of the desired specificity, affinity, and/or activity, the clones can be subcloned by limiting dilution procedures and grown by standard methods (Goding, Monoclonal Antibodies: Principles and Practice, pp. 59-103 (Academic Press, 1986)). Suitable culture media for this purpose include, for example, D-MEMO or RPMI 1640 medium. In addition, the hybridoma cells can be grown in vivo as ascites tumors in an animal. The monoclonal antibodies secreted by the subclones are suitably separated from the culture medium, ascites fluid, or serum by conventional immunoglobulin purification procedures, such as protein A-Sepharose, hydroxylapatite chromatography, gel electrophoresis, dialysis, or affinity chromatography.

Recombinant Production of Antibodies

The amino acid sequence of an immunoglobulin of interest can be determined by direct protein sequencing, and suitable encoding nucleotide sequences can be designed according to a universal codon table.

Alternatively, DNA encoding the monoclonal antibodies can be isolated and sequenced from the hybridoma cells using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or mRNA encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library can be constructed by reverse transcription of polyA+ mRNA, preferably membrane-associated mRNA, and the library screened using probes specific for human immunoglobulin polypeptide gene sequences. In a preferred embodiment, the polymerase chain reaction (PCR) is used to amplify cDNAs (or portions of full-length cDNAs) encoding an immunoglobulin gene segment of interest (e.g., a light chain variable segment). The amplified sequences can be cloned readily into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, PCR is used to amplify cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning. The sequence of the amplified or cloned nucleic acid is then determined. Typically the sequence encoding an entire variable region of the immunoglobulin polypeptide is determined, however, sometimes only a portion of a variable region need be sequenced, for example, the CDR-encoding portion. Typically the sequenced portion will be at least 30 bases in length, and more often bases coding for at least about one-third or at least about one-half of the length of the variable region will be sequenced. Sequencing can be carried out on clones isolated from a cDNA library or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, a skilled artisan can determine readily, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be operably linked to expression control sequences or placed into expression vectors, which are then transfected into host cells such as *E. coli* cells, simian COS cells, Chinese hamster ovary (CHO) cells, or myeloma cells that do not otherwise produce immunoglobulin protein, to direct the synthesis of monoclonal antibodies in the recombinant host cells.

Expression control sequences denote DNA sequences necessary for the expression of an operably linked coding sequence in a particular host organism. The control sequences that are suitable for prokaryotes, for example, include a promoter, optionally an operator sequence, and a ribosome-binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking can be accomplished by ligation at convenient restriction sites. If such sites do not exist, synthetic oligonucleotide adaptors or linkers can be used in accordance with conventional practice.

Cell, cell line, and cell culture are often used interchangeably, and all such designations include progeny. Transformants and transformed cells include the primary subject cell and cultures derived therefrom without regard for the number of transfers. It also is understood that all progeny may not be precisely identical in DNA content, due to deliberate or inadvertent mutations. Mutant progeny that have the same function or biological activity as screened for in the originally transformed cell are included.

Isolated nucleic acids also are provided that encode specific antibodies, optionally operably linked to control sequences recognized by a host cell, vectors, and host cells comprising the nucleic acids, and recombinant techniques for the production of the antibodies, which may comprise culturing the host cell so that the nucleic acid is expressed and, optionally, recovering the antibody from the host cell culture or culture medium.

A variety of vectors are known in the art. Vector components can include one or more of the following: a signal sequence (that, for example, can direct secretion of the antibody), an origin of replication, one or more selective marker genes (that, for example, can confer antibiotic or other drug resistance, complement auxotrophic deficiencies, or supply critical nutrients not available in the media), an enhancer element, a promoter, and a transcription termination sequence, all of which are well known in the art.

Suitable host cells include prokaryote, yeast, or higher eukaryote cells. Suitable prokaryotes include eubacteria, such as Gram-negative or Gram-positive organisms, for example, Enterohacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas*, and *Streptomyces*. In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available, such as *Pichia*, e.g. *P. pastoris*, *Schizosaccharomyces pombe*; *Kluyveromyces*, *Yarrowia*; *Candida*; *Trichoderma reesia*; *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-I variant of *Autographa californica* NPV and the Bm-5 strain of *Bombyx mori* NPV.

However, interest has been greatest in vertebrate cells, and propagation of vertebrate cells in culture (tissue culture) has become routine. Examples of useful mammalian host cell-lines are Chinese hamster ovary cells, including CHOKI cells (ATCC CCL61) and Chinese hamster ovary cells/-DHFR (DXB-11, DG-44; Urlaub et al, Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., J. Gen Virol. 36: 59 (1977)]; baby hamster kidney cells (BHK, ATCC CCL 10); mouse Sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells; and FS4 cells.

The host cells can be cultured in a variety of media. Commercially available media, such as Ham's F10 (Sigma), Minimal Essential Medium ((MEM), (Sigma), RPMI-1640 (Sigma), and Dulbecco's Modified Eagle's Medium ((DMEM), Sigma), are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 can be used as culture media for the host cells. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™. drug), trace elements (defined as inorganic compounds usually present at final concentrations in the micromolar range), and glucose or an equivalent energy source. Any other necessary supplements also can be included at appropriate concentrations that would be known to those skilled in the art. The culture conditions, such as temperature, pH, and the like, are those previously used with the host cell selected for expression, and will be apparent to the artisan.

The antibody composition can be purified using, for example, hydroxylapatite chromatography, cation or anion exchange chromatography, or preferably affinity chromatography, using the antigen of interest or protein A or protein G as an affinity ligand. Protein A can be used to purify antibodies that are based on human .gamma. 1, .gamma.2, or .gamma.4 heavy chains (Lindmark et al., J. Immunol. Meth. 62: 1-13 (1983)). Protein G is recommended for all mouse isotypes and for human .gamma.3 (Guss et al., 20 EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, 25 NJ.) is useful for purification. Other techniques for protein purification such as ethanol precipitation, Reverse Phase HPLC, chromatofocusing, SDS-PAGE, and ammonium sulfate precipitation are also possible depending on the specific binding agent or antibody to be recovered.

Fragments of the anti-HER2 and/or HER3 antibodies are suitable for use in the methods of the invention so long as they retain the desired affinity of the full-length antibody. Thus, a fragment of an anti-HER2 and/or HER3 antibody will retain the ability to bind to the HER2 and/or HER3 receptor protein. Fragments of an antibody comprise a portion of a full-length antibody, generally the antigen binding or variable region thereof. Examples of antibody fragments include, but are not limited to, Fab, Fab'F(ab')$_2$, and Fv fragments and single-chain antibody molecules. By "single-chain Fv" or "sFv" antibody fragments is intended fragments comprising the V$_H$ and V$_L$ domains of an antibody, wherein these domains are present in a single polypeptide chain. See, for example, U.S. Pat. Nos. 4,946,778, 5,260,203, 5,455,030, and 5,856,456, each of which is herein incorporated by reference. Generally, the Fv polypeptide further comprises a polypeptide linker between the V$_H$ and V$_L$ domains that enables the sFv to form the desired structure for antigen binding. For a review of sFv see Pluckthun (1994) in The Pharmacology of Monoclonal Antibodies, Vol. 113, ed. Rosenburg and Moore (Springer-Verlag, N.Y.), pp. 269-315.

Antibodies or antibody fragments can be isolated from antibody phage libraries generated using the techniques described in McCafferty et al. (1990) Nature 348:552-554 (1990). Clackson et al. (1991) Nature 352:624-628 and Marks et al. (1991) J. Mol. Biol. 222:581-597 describe the isolation of murine and human antibodies, respectively, using phage libraries. Subsequent publications describe the production of high affinity (nM range) human antibodies by chain shuffling (Marks et al. (1992) Bio/Technology 10:779-783), as well as combinatorial infection and in vivo recombination as a strategy for constructing very large phage libraries (Waterhouse et al. (1993) Nucleic. Acids Res. 21:2265-2266). Thus, these techniques are viable alternatives to traditional monoclonal antibody hybridoma techniques for isolation of monoclonal antibodies.

A humanized antibody has one or more amino acid residues introduced into it from a source that is non-human. These non-human amino acid residues are often referred to as "donor" residues, which are typically taken from a "donor" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting rodent CDRs or CDR sequences for the corresponding sequences of a human antibody. See, for example, U.S. Pat. Nos. 5,225,539; 5,585,089; 5,693,761; 5,693,762; 5,859,205; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205.

Various techniques have been developed for the production of antibody fragments. Traditionally, these fragments were derived via proteolytic digestion of intact antibodies (see, e.g., Morimoto et al. (1992) Journal of Biochemical and Biophysical Methods 24:107-117 (1992) and Brennan et al. (1985) Science 229:81). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al. (1992) Bio/Technology 10:163-167). According to another approach, F(ab')$_2$ fragments can be isolated directly from recombinant host cell culture. Other techniques for the production of antibody fragments will be apparent to the skilled practitioner.

Alternatively, methods for producing proteins that have reduced immunogenic response may be used to generate anti-HER2 and/or HER3 antibodies suitable for use in the methods of the present invention. See, for example, the methods disclosed in WO 98/52976, which is herein incorporated by reference. Anti-HER2 and/or HER3 antibodies generated using such a method are encompassed by the term "Anti-HER2 and/or HER3 antibody" as used herein.

Further, any of the previously described anti-HER2 and/or HER3 antibodies may be conjugated prior to use in the methods of the present invention. Such conjugated antibodies are available in the art. Thus, the anti-HER2 and/or HER3 antibody may be labeled using an indirect labeling or indirect labeling approach. By "indirect labeling" or "indirect labeling approach" is intended that a chelating agent is covalently attached to an antibody and at least one radionuclide is inserted into the chelating agent. See, for example, the chelating agents and radionuclides described in Srivagtava and Mease (1991) Nucl. Med. Bio. 18: 589-603, which is herein incorporated by reference. Alternatively, the anti-HER2 and/or HER3 antibody may be labeled using "direct labeling" or a "direct labeling approach," where a radionuclide is covalently attached directly to an antibody (typically via an amino acid residue). Preferred radionuclides are provided in Srivagtava and Mease (1991) supra. The indirect labeling approach is particularly preferred.

General Administration

In one aspect, the invention provides pharmaceutical compositions comprising an inhibitor of PI3K according to the invention and a pharmaceutically acceptable carrier, excipient, or diluent in combination with an antibody, administered in the same or separate vehicles. In certain other specific embodiments, administration may specifically be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages. When treating brain cancers, including glioblastomas, the administration may specifically be by placing a gliadel, a dissolvable material that contains the chemotherapy drug (in particular BCNU), directly into brain tumors during an operation.

The compositions will include a compound of formula I or Ia as the/an active agent and can include a conventional pharmaceutical carrier or excipient and in addition may include other medicinal agents and pharmaceutical agents that are generally administered to a patient being treated for cancer.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances, such as wetting or emulsifying agents, pH buffering agents, antioxidants, and the like, such as citric acid, sorbitan monolaurate, triethanolamine oleate, butylalted hydroxytoluene, etc.

The choice of formulation depends on various factors, such as the mode of drug administration (e.g., for oral administration, formulations in the form of tablets, pills, or capsules) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm, in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters (such as ethyl oleate). Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate, and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt or solvate thereof, and optional pharmaceutical adjuvants in a carrier, such as water, saline, aqueous dextrose, glycerol, ethanol, and the like; solubilizing agents and emulsifiers, such as ethyl alcohol, isopropyl alcohol, ethyl carbonate, ethyl acetate, benzyl alcohol, benzyl benzoate, propyleneglycol, 1,3-butyleneglycol, dimethylformamide, and the like; oils, such as cottonseed oil, groundnut oil, corn germ oil, olive oil, castor oil, sesame oil, and the like; glycerol; tetrahydrofurfuryl alcohol; polyethyleneglycols; and fatty acid esters of sorbitan; or mixtures of these substances, and the like, to thereby form a solution or suspension.

In addition to the active compounds, suspensions may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt or solvate thereof, and 99% to 1% by weight of a suitable pharmaceutical excipient. In one example, the composition will be between about 5% and about 75% by weight of a compound(s) of the invention, or a pharmaceutically acceptable salt or solvate thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt or solvate thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Representative pharmaceutical formulations containing a compound of formula I or Ia are described below in the Pharmaceutical Composition Examples.

The inhibitors of HER3, HER2, MSPR, Axl, MAP3K (ERK, JNK, and p38 MAPK), MEKK kinases/kinase receptors, INSR, IGF-IR, and FGFR-2 kinases/kinase receptors can be formulated into solid or liquid forms using pharmaceutically acceptable excipients for oral or parenteral administration, as described above. Methods and dosage forms for administering functional nucleic acids are readily known, for example, they may be formulated in sterile aqueous reagents specifically designed for the mode of administering the functional nucleic acid in question. In one embodiment of the invention, the functional nucleic acid may be in the form of a prodrug. Oligonucleotides are, by virtue, negatively charged ions. Due to the lipophilic nature of cell membranes the cellular uptake of oligonucleotides are reduced compared to neutral or lipophilic equivalents. This polarity "hindrance" can be avoided by using the pro-drug approach. In this approach the oligonucleotides are prepared in a protected manner so that the oligo is neutral when it is administered. These protecting groups are designed in such a way that so they can be removed, and then the oligo is taken up be the cells. Examples of such protecting groups are S-acetylthioethyl (SATE) or S-pivaloylthioethyl (t-butyl-SATE). These protecting groups are nuclease resistant and are selectively removed intracellulary.

Functional nucleic acids can be linked to ligands/conjugates to facilitate delivery to the intended target site and enhance activity of the functional nucleic acid, i.e. to increase the cellular uptake of functional nucleic acid. This conjugation can take place at the terminal positions 5'/3'-OH, but the ligands may also take place at the sugars and/or the bases. Other examples of conjugates/ligands are cholesterol moieties, liposomes, neutral lipids, duplex intercalators, such as acridine, poly-L-lysine, "end-capping" with one or more nuclease-resistant linkage groups.

In some embodiments, the functional nucleic acids can comprise two or more different functional nucleic acids. Pharmaceutically acceptable binding agents and adjuvants may comprise part of the formulated drug. Capsules, tablets, pills, etc. may contain, for example, the following compounds: microcrystalline cellulose, gum or gelatin as binders; starch or lactose as excipients; stearates as lubricants; and various sweetening or flavoring agents. For capsules, the dosage unit may contain a liquid carrier, such as fatty oils. Likewise coatings of sugar or enteric agents may be part of the dosage unit. The oligonucleotide formulations may also be emulsions of the active pharmaceutical ingredients and a lipid forming a micellular emulsion. An oligonucleotide of the invention may be mixed with any material that do not impair the desired action, or with material that supplement the desired action. These could include other drugs including other nucleotide compounds.

For parenteral, subcutaneous, intradermal, or topical administration, the formulation may include a sterile diluent, buffers, regulators of tonicity, and antibacterials. Functional nucleic acids may be prepared with carriers that protect against degradation or immediate elimination from the body, for example antinuclease activity, including implants or microcapsules with controlled release properties. For intravenous administration, the preferred carriers are physiological saline or phosphate buffered saline. Preferably, a functional nucleic acid is included in a unit formulation, such as in a pharmaceutically acceptable carrier or diluent in an amount sufficient to deliver to a patient a therapeutically effective amount without causing serious side effects in the treated patient.

The functional nucleic acid co-administered with a compound of formula I of the present invention can be administered in a number of ways depending upon whether local or systemic treatment is desired and upon the area to be treated. Administration may be: (a) oral; (b) pulmonary, e.g., by inhalation or insufflation of powders or aerosols, including by nebulizer; intratracheal, or intranasal; (c) topical including epidermal, transdermal, ophthalmic, and to mucous membranes including vaginal and rectal delivery; (d) parenteral including intravenous, intraarterial, subcutaneous, intraperitoneal, or intramuscular injection or infusion; or (e) intracranial, e.g., intrathecal or intraventricular, administration. In one embodiment, the active oligo is administered IV, IP, orally, topically, as a bolus injection, or administered directly in to the target organ. In some embodiments, the functional nucleic acid is administered via stereaotactic injection directly into the affected tissue or intratumoral injection with or without the aid of scanning devices such as CT scans, PET scanning devices, and MRI scanning devices. Compositions and formulations for parenteral, intrathecal, or intratumoral administration may include sterile aqueous solutions which may also contain buffers, diluents, and other suitable additives such as, but not limited to, penetration enhancers, carrier compounds, and other pharmaceutically acceptable carriers or excipients.

Antibodies of the present invention can be administered to a cancer patient in any standard medically accepted way. Such compositions may be conveniently administered in unit dose and may be prepared in accordance with methods known in the pharmaceutical art. See Remington's Pharmaceutical Sciences, (Mack Publishing Co., Easton Pa., (1980)). By the term "unit dose" is meant a therapeutic composition of the present invention employed in a physically discrete unit suitable as unitary dosages for a primate such as a human, each unit containing a pre-determined quantity of active material calculated to produce the desired therapeutic effect in association with the required diluent or carrier. The unit dose will depend on a variety of factors, including the type and severity of the cancer to be treated, capacity of the subject's blood to deliver the antibody, and the ability of the patient to tolerate sufficiently high doses without intolerable side effects. Precise amounts of the antibody to be administered typically will be guided by judgment of the practitioner, typically titrating from a high dose to a tolerable lower dose having comparable tumoricidal activity however, the unit dose will generally depend on the route of administration and be in the range of 10 ng/kg body weight to 100 mg/kg body weight per day, more typically in the range of 100 ng/kg body weight to about 40 mg/kg body weight per day. Suitable regimens for booster administration are also variable but are typified by an initial administration followed by repeated doses at one or more hour intervals by a subsequent injection or other administration. Alternatively, continuous or intermittent intravenous infusions may be made sufficient to maintain concentrations of at least from about 10 nanomolar to 10 micromolar of the antibody in the blood.

Kits

In some embodiments, the present invention provides kits for preparing an cancer treatment composition comprising a first container comprising: (a) a therapeutically effective amount of a compound of formula I; (b) a second container comprising a therapeutically effective amount of a solution of antibodies, such as anti-HER2 and/or HER3 antibodies (alternatively in lyophilized form); (c) optionally, one or more medicament delivery devices, for example syringes and the like; (d) optionally, a diluent for resuspending the anti-HER2 and/or HER3 antibody; and (e) a set of instructions for preparing the composition for treatment of cancer in the patient.

Utility

Compounds of formula I have been tested using the assay described in Biological Example 1 of WO2007044729 and have been determined to be PI3K inhibitors. As such, compounds of formula I are useful for treating diseases, particularly cancer in which PI3K activity contributes to the pathology and/or symptomatology of the disease. For example, cancer in which PI3K activity contributes to its pathology and/or symptomatology include breast cancer, colon cancer, rectal cancer, endometrial cancer, gastric carcinoma, glioblastoma, hepatocellular carcinoma, small cell lung cancer, non-small cell lung cancer, melanoma, ovarian cancer, pancreatic cancer, prostate carcinoma, acute myelogenous leukemia (AML), chronic myelogenous leukemia (CML), and thyroid carcinoma, and the like.

In some embodiments, methods for identifying a compensatory kinase pathway can be used to design novel cancer therapeutics. For example, in one embodiment, the present invention provides a method for identifying a compensatory kinase pathway in a cancer cell which attenuates the effect of a PI3K inhibitor. The method includes the steps: (a) contacting the cancer cell with a composition comprising a compound of formula I; (b) incubating the mixture of cancer cells in the presence and absence of the composition; (c) measuring the expression of a plurality of kinase enzymes in the presence and absence of the composition after the period of incubation; and (d) determining whether a kinase enzyme within the group of tested kinase enzymes displays an increase in either kinase expression or kinase activity when compared to the kinase enzyme in the cancer cell incubated in the absence of the composition containing the compound of formula I. If an increase in the kinase enzyme activity or expression is found, then the identified kinase enzyme is an indication of the identified kinase enzyme being involved in a compensatory kinase pathway which attenuates the effect of the PI3K inhibitor.

Suitable in vitro assays for measuring PI3K activity and the inhibition thereof by compounds are known. Typically, the assay will measure PI3K-induced ATP consumption. For further details of an in vitro assay for measuring PI3K activity see Biological Examples, Example 1 infra. Cellular activity can be determined using assays as described in Biological Examples 2, 3, and 4 of WO2007044729. Suitable in vivo models of cancer are known to those of ordinary skill in the art. For further details of in vivo assays see Biological Examples 5-10, of WO2007044729. Examples describing the administration of a compound of formula I in combination with anticancer agents are described in Biological Examples 11-14, of WO2007044729. Following the examples disclosed herein, as well as that disclosed in the art, a person of ordinary skill in the art can determine what combinations of a compound of formula I and anti-cancer agents would be effective for treating cancer.

Preparations of the Intermediates and Compounds of Formula I

Compounds of this invention can be made by the synthetic procedures described in WO 2007/044729 and WO 2008/127594, the disclosures of which are incorporated by reference herein.

The starting materials and reagents used in preparing these compounds are either available from commercial suppliers such as Aldrich Chemical Co. (Milwaukee, Wis.), or Bache (Torrance, Calif.), or are prepared by methods known to those skilled in the art following procedures set forth in references such as Fisher and Fisher's Reagents for Organic Synthesis, Volumes 1-17 (John Wiley and Sons, 1991); Rod's Chemistry of Carbon Compounds, Volumes 1-5 and Supplemental (Elsevier Science Publishers, 1989); Organic Reactions, Volumes 1-40 (John Wiley and Sons, 1991), March's Advanced Organic Chemistry, (John Wiley and Sons, $4^{th}$ Edition), and Larch's Comprehensive Organic Transformations (VICHY Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure and over a temperature range from about −78° C. to about 150° C., in another embodiment from about 0° C. to about 125° C., and more specifically at about room (or ambient) temperature, e.g., about 20° C. Unless otherwise stated (as in the case of a hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of formula I that may be prepared through the syntheses described herein may exist as single stereoisomers, racemates, and as mixtures of enantiomers and diastereomers. The compounds may also exist as geometric isomers. All such single stereoisomers, racemates, and mixtures thereof, and geometric isomers are intended to be within the scope of this invention. Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

In particular, in this application B can be 2-hydroxy-pyridinyl, also described as its structure:

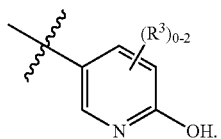

14

Both 2-hydroxy-pyridinyl and the above structure 14 include, and are equivalent to, pyridin-2(1H)-one and its structure 15:

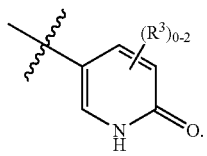

15

Regardless of which structure or which terminology is used, each tautomer is included within the scope of the Invention.

The present invention also includes N-oxide derivatives and protected derivatives of compounds of formula I. For example, when compounds of formula I contain an oxidizable nitrogen atom, the nitrogen atom can be converted to an N-oxide by methods well known in the art. When compounds of formula I contain groups such as hydroxy, carboxy, thiol, or any group containing a nitrogen atom(s), these groups can be protected with a suitable "protecting group" or "protective group." A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts, or solvents, or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In compounds of formula I:

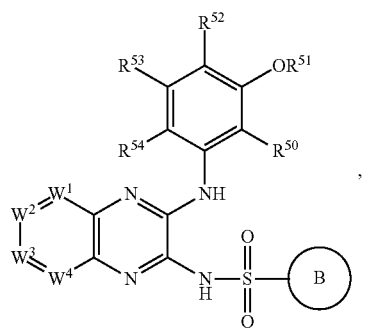

the hydrogen on the —NHS(O)$_2$— group is highly acidic. Thus, intermediates leading to compounds of formula I, as well as compounds of formula I themselves, can be recovered as uncharged or zwitterionic molecules, or cationic salts such a sodium or potassium, depending on the substitutions on the B ring and on reaction conditions. In the examples that follow, unless otherwise specified, the final form of the compound was assumed to be the uncharged molecule in the absence of analytical techniques that would have determined otherwise.

Compounds of formula I can be prepared using methods known to one of ordinary skill in the art. In another embodiment, fusion of appropriate reagents at 180° C. in the presence of a base such as K$_2$CO$_3$ and metallic copper is known to provide intermediates of formula 1 (see S. H. Dandegaonker and C. K. Mesta, *J. Med. Chem.* 1965, 8, 884).

Alternatively, the intermediate of formula 3 can be prepared according to the scheme below, where each LG$^1$ is a leaving group (in one embodiment halo, in another embodiment chloro), and all other groups are as defined in the Detailed Description.

Scheme 1

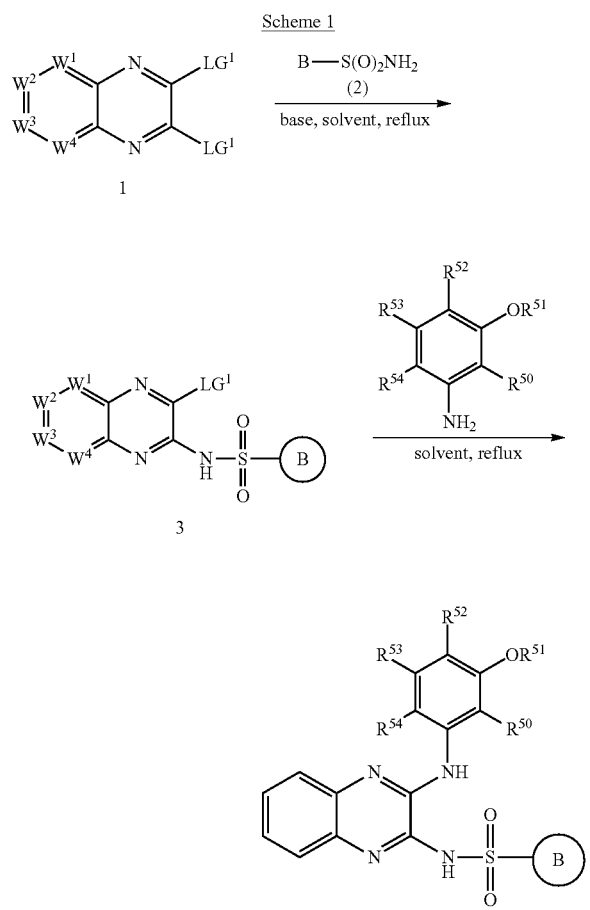

In scheme 1, an intermediate of formula 3 can be prepared by briefly heating commercially available 2,3-dichloroquinoxaline and an intermediate of formula 2 (which are commercially available or can be prepared by one of ordinary skill in the art), a base, such as $K_2CO_3$, in a solvent, such as DMF or DMSO. Upon completion (about 2 hours), the reaction mixture is then poured into water and followed by 2 N HCl. The product is then extracted into a solvent, such as ethyl acetate, and washed with water and brine. The organic layers are combined and dried over a drying agent such as sodium sulfate, filtered, and concentrated under vacuum.

The intermediate of formula 3 is then treated with an intermediate of formula 4 in a solvent, such as DMF or p-xylene, at reflux temperature. Upon completion of the reaction (about 16 hours or less), the reaction is allowed to cool, extracted into DCM, washed with 2 N HCl and brine, dried over a drying agent such as sodium sulfate or magnesium sulfate, filtered, and concentrated to give a compound of formula I.

Alternatively, other methods to prepare quinoxaline derivatives are known to one skilled in the art and include, but are not limited to S. V. Litvinenko, V. I. Savich, D. D. Bobrovnik, *Chem. Heterocycl. Compd*. (Engl. Transl), 1994, 30, 340 and W. C. Lumma, R. D. Hartman, *J. Med. Chem.* 1981, 24, 93.

Compounds of formula I where B is phenyl substituted with $R^{3a}$ where $R^{3a}$ is alkylamino or dialkylamino or B is heteroaryl substituted with $R^3$ where $R^3$ is amino, alkylamino, or dialkylamino, and all other groups are as defined in the Summary can be prepared according to Scheme 2.

Scheme 2

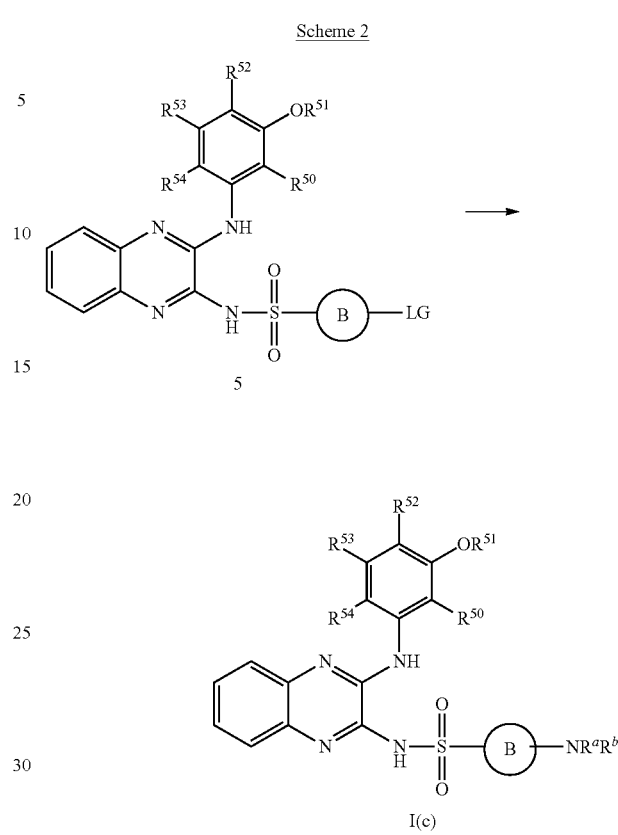

LG is a leaving group such as chloro. 5 is reacted with $NHR^aR^b$ or $HO-C_1-C_6$-alkylene-$NHR^aR^b$, where $R^a$ and $R^b$ are independently hydrogen or alkyl. The reaction is carried out in the presence of a base, such as $KHCO_3$, in a solvent, such as DMF.

Compounds of formula I where B is phenyl substituted with $R^{3a}$ where $R^{3a}$ is aminoalkyloxy, alkylaminoalkyloxy, or dialkylaminoalkyloxy or B is heteroaryl substituted with $R^3$ where $R^3$ is aminoalkyloxy, alkylaminoalkyloxy, or dialkylaminoalkyloxy, and all other groups are as defined in the Summary can be prepared according to Scheme 3.

Scheme 3

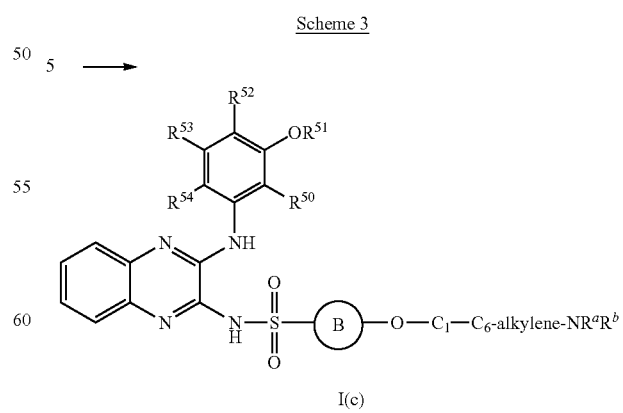

The reaction is carried out in the presence of a base such as NaH in a solvent such as DMF.

Compounds of formula I, where B is phenyl substituted with $R^{3a}$; or B is heteroaryl substituted with $R^3$; where $R^{3a}$ and $R^3$ are:

i. —N($R^7$)C(O)—$C_1$-$C_6$-alkylene-N($R^{7a}$)($R^{7b}$), where $R^7$, $R^{7a}$, and $R^{7b}$ are as defined in the Summary;

ii. —N$R^9$C(O)$R^{9a}$, where $R^9$ is as defined in the Summary;

iii. —N$R^{11}$C(O)N$R^{11a}R^{11b}$, where $R^{11}$, $R^{11a}$, and $R^{11b}$ are as defined in the Summary;

iv. —N$R^{13}$C(O)O$R^{13a}$, where $R^{13}$ and $R^{13a}$ are as defined in the Summary;

v. —N($R^{18}$)C(O)—$C_1$-$C_6$-alkylene-N($R^{18b}$)C(O)$R^{18a}$, where $R^{18}$, $R^{18a}$, and $R^{18b}$ are as defined in the Summary;

vi. —N($R^{20}$)C(O)—$C_1$-$C_6$-alkylene-C(O)$R^{20a}$, where $R^{20}$ and $R^{20a}$ as defined in the Summary;

vii. —N$R^{21}$S(O)$_2$—$C_1$-$C_6$-alkylene-N($R^{21b}$)$R^{21a}$, where $R^{21}$, $R^{21a}$, and $R^{21b}$ are as defined in the Summary;

viii. —N($R^{22}$)C(O)—$C_0$-$C_6$-alkylene-N($R^{22b}$)—N($R^{22c}$)($R^{22a}$), where $R^{22}$, $R^{22a}$ and $R^{22b}$ are as defined in the Summary;

ix. —N$R^{24}$C(O)—$C_1$-$C_6$-alkylene-O$R^{24a}$, where $R^{24}$ and $R^{24a}$ are as defined in the Summary;

and where the alkylene in $R^3$ and $R^{3a}$ are independently optionally substituted as described in the Summary can be prepared according to Scheme 4 by reacting with an intermediate of formula 9(a), 9(b), 9(c), 9(d), 9(e), 9(f), or 9(g):

9(a) HOC(O)—$C_1$-$C_6$-alkylene-N($R^{7a}$)($R^{7b}$), where $R^a$ is $R^{7a}$ or a N-protecting group, such as Boc or Fmoc;

9(b) HOC(O)$R^{9a}$;

9(c) HOC(O)N$R^{11a}R^{11b}$;

9(d) HOC(O)O$R^{13a}$;

9(e) HOC(O)—$C_1$-$C_6$-alkylene-N($R^{18b}$)C(O)$R^{18a}$;

9(f) HOC(O)—$C_1$-$C_6$-alkylene-C(O)$R^{20a}$;

9(g) LG-S(O)$_2$—$C_1$-$C_6$-alkylene-N($R^{21b}$)$R^a$ where $R^a$ is $R^{21a}$ or a N-protecting group, such as Boc or Fmoc.

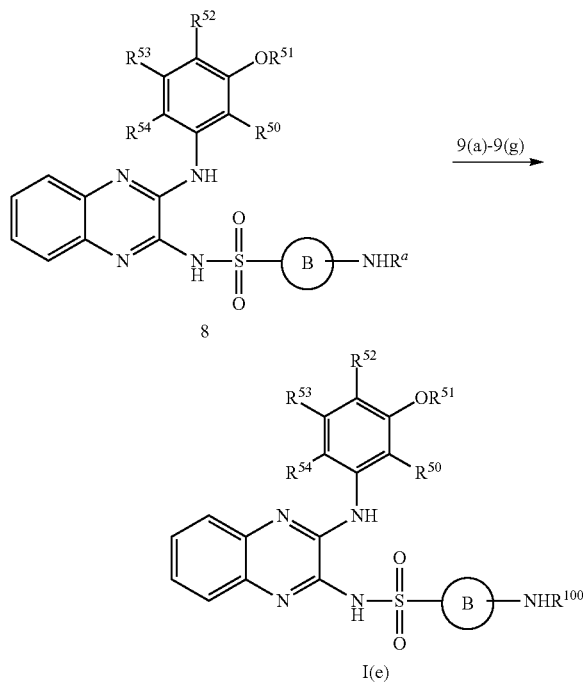

Scheme 4

$R^{100}$ in Scheme 4 is —C(O)$R^{9a}$, —C(O)N$R^{11a}R^{11b}$, —C(O)O$R^{13a}$, —C(O)—$C_1$-$C_6$-alkylene-N($R^{18b}$)C(O)$R^{18a}$, —C(O)—$C_1$-$C_6$-alkylene-C(O)$R^{20a}$, or —S(O)$_2$—$C_1$-$C_6$-alkylene-N($R^{21b}$)$R^a$. The reaction is carried out under standard amide coupling conditions known to one of ordinary skill in the art. In particular, the reaction is carried out in the presence of a coupling agent, such as HATU, a base, such as DIEA, and in a solvent, such as DMF. Where applicable, the N-protecting group is then removed using procedures known to one of ordinary skill in the art, such as treating with acid where PG is Boc.

Proceeding as described for Scheme 4, compounds of the invention, where B is phenyl substituted with $R^{3a}$; or B is heteroaryl substituted with $R^3$; where $R^{3a}$ and $R^3$ are a) —C(O)N$R^8R^{8a}$;

b) —C(O)N($R^{10}$)—$C_1$-$C_6$-alkylene-N($R^{10a}$)$R^{10b}$;

c) —C(O)$R^{12}$ where $R^{12}$ is an N-substituted heterocycloalkyl;

d) —C(O)N($R^{14}$)N($R^{14a}$)($R^{14b}$);

e) —C(O)N($R^{16}$)—$C_1$-$C_6$-alkylene-C(O)O$R^{16a}$; or f) —C(O)N($R^{19}$)—$C_1$-$C_6$-alkylene-C(O)$R^{19a}$; or can be prepared by exchanging the starting materials as necessary. In particular, the intermediate of formula 11:

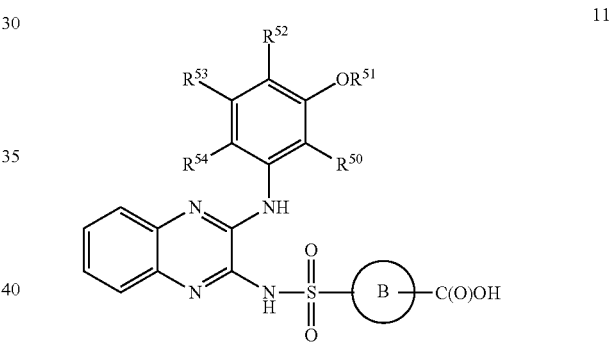

is used instead of 8.

Compounds of formula I, where B is phenyl substituted with $R^{3a}$; or B is heteroaryl substituted with $R^3$, where $R^{3a}$ and $R^3$ are —NHC(O)CH$_2$N$R^{7a}R^{7b}$, where $R^{7a}$ and $R^{7b}$ are as defined in the Summary, can be prepared according to Scheme 5.

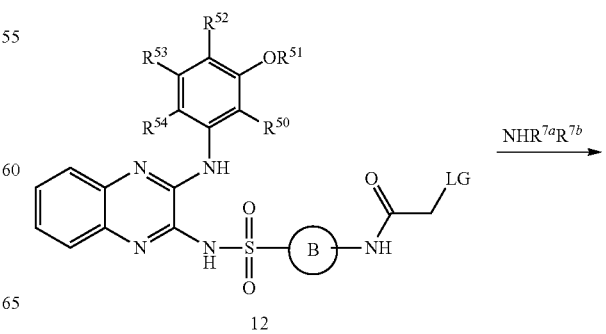

Scheme 5

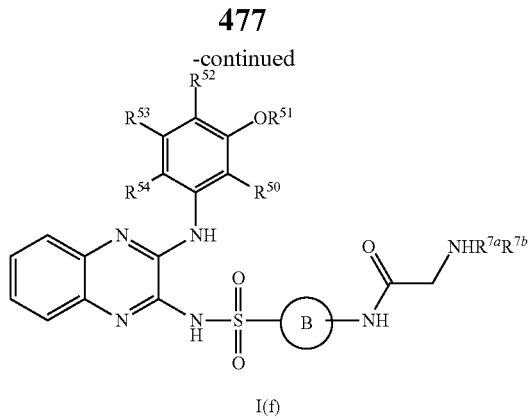

I(f)

LG is a leaving group such as bromo or chloro. 12 is reacted with NH(R$^{7b}$)R$^{7a}$ in the presence of a base, such as DIEA, in a solvent, such as ACN.

Compounds of formula I can be prepared according to Scheme 6.

Scheme 6

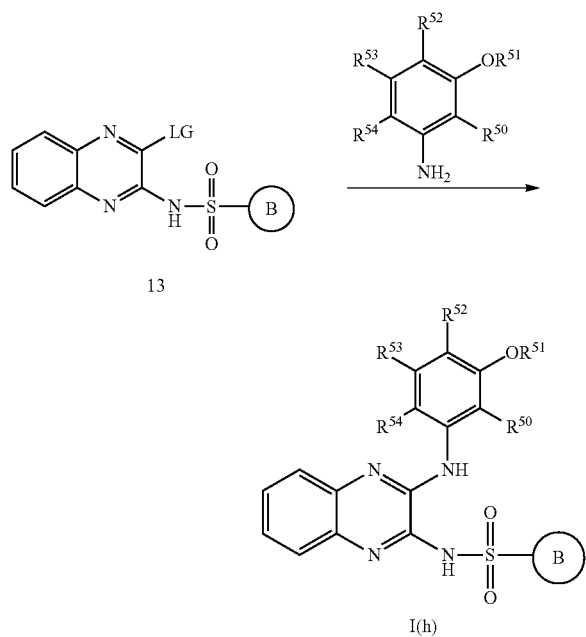

I(h)

LG in Scheme 6 is a leaving group, such as chloro. The reaction can be carried out by irradiating in a solvent, such as DMA. Alternatively, the reaction can be carried out in the presence of acetic acid in a solvent, such as DMA and by heating.

General Alkylation Procedure 1

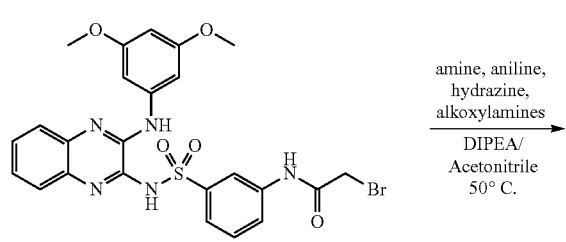

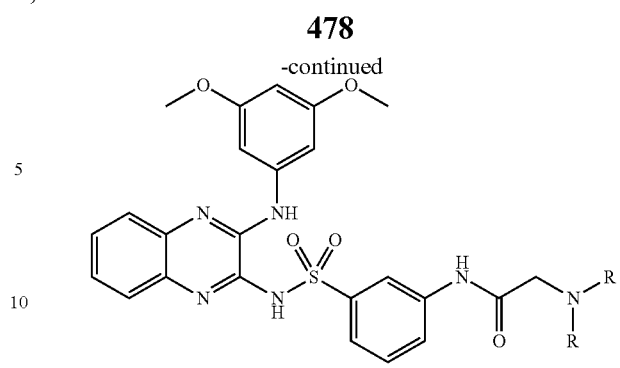

Into a 2-dram vial was placed 2-bromo-N-(3-(N-(3-(3,5-dimethoxy-phenylamino)quinoxalin-2-yl)sulfamoyl)phenyl)acetamide (86 mg, 0.15 mmol), prepared using standard procedures, along with 2 mL of acetonitrile. Eight equivalents (1.2 mmol) of the desired amine, aniline, hydrazine, or alkoxyamine were added followed by the addition of Hunig's Base (41 µL, 0.25 mmol). The reaction then was stirred at 50° C. for one hour (overnight for aniline reagents). Preparative reverse-phase HPLC was used to isolate the desired product directly from the crude reaction mixture. A Waters Fractionlynx preparative reverse-phase HPLC (equipped with a Waters SunFire Prep C18, OCD 5 µM, 30×70 mm column and running a 5-100% gradient with a binary solvent system of 25 mM ammonium acetate in water/acetonitrile) was used to carry out the purification.

General Library Acylation Procedure 1

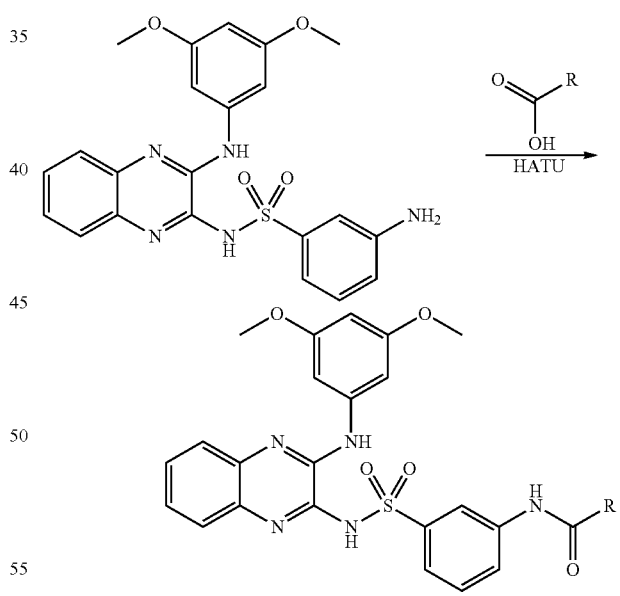

Into a 2-dram vial were added 3-amino-N-(3-(3,5-dimethoxy-phenylamino)quinoxalin-2-yl)benzenesulfonamide (54 mg, 0.12 mmol), prepared using standard procedures, DMA (2 mL), and the desired carboxylic acid (0.17 mmol). DIEA (70 µL, 0.4 mmol), followed by HATU (53 mg, 0.14 mmol), was added to the vial, and the reaction mixture was stirred at 50° C. overnight. Preparative reverse-phase HPLC was used to isolate the desired product directly from the crude reaction mixture. A Waters Fractionlynx preparative reverse-phase HPLC (equipped with a Waters SunFire Prep C18, OCD 5 μM, 30×70 mm column and running a 5-100% gradient with a binary solvent system of 25 mM ammonium acetate in water/acetonitrile) was used to carry out the purification.

General Amination Procedure 1a

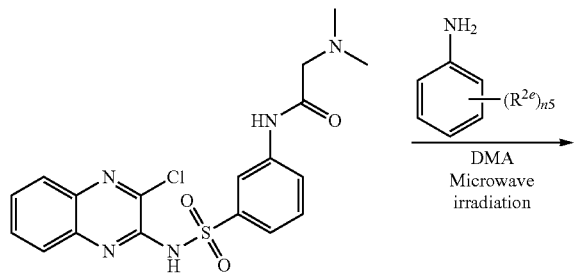

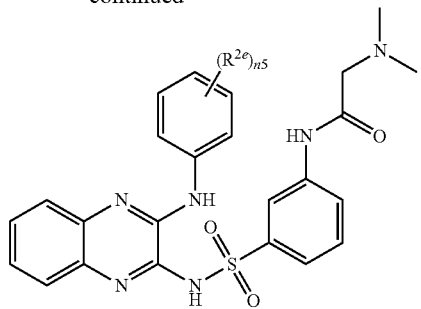

A CEM microwave reaction vessel was charged with N-(3-(N-(3-chloroquinoxalin-2-yl)sulfamoyl)phenyl)-2-(dimethylamino)acetamide (62 mg, 0.147 mmol), prepared using standard procedures, the desired aniline (0.567 mmol, 4 eq), and 1.0 mL of toluene. The vessel was sealed, and the reaction mixture was heated under microwave radiation for 60 minutes at 180° C. in a CEM Discover microwave instrument. The solvent was removed on a rotary-evaporator. Purification of the final product was done by preparatory HPLC with NH$_4$OAc/ACN as eluent to yield the desired product.

General Acylation Procedure 2

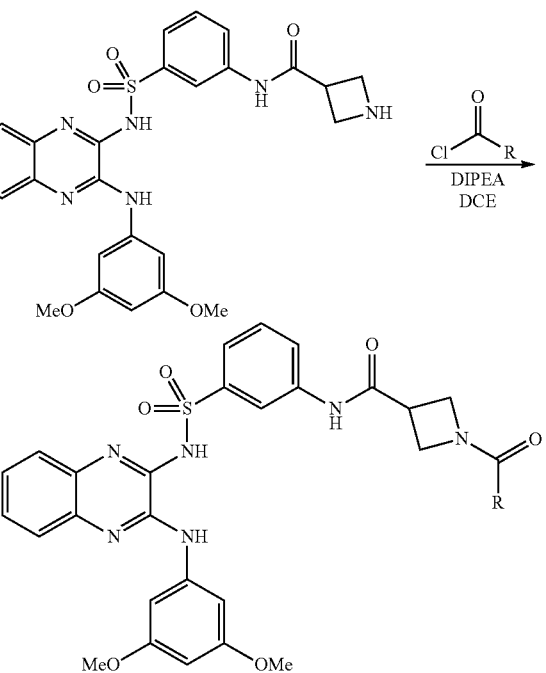

A CEM microwave reaction vessel was charged with N-(3-(N-(3-chloroquinoxalin-2-yl)sulfamoyl)phenyl)-2-(dimethylamino)acetamide (30 mg, 0.071 mmol), prepared using standard procedures, the desired aniline (16 mg, 0.14 mmol, 2 eq), and 0.5 mL of dimethylacetamide. The vessel was sealed, and the reaction mixture was heated under microwave radiation for 70 minutes at 140° C. in a CEM Discover microwave instrument. The solvent was then removed by rotary-evaporation. Purification of the final product was accomplished by preparatory reverse-phase HPLC with the eluents 25 mM aqueous NH$_4$OAc/ACN to the desired product.

General Amination Procedure 1b

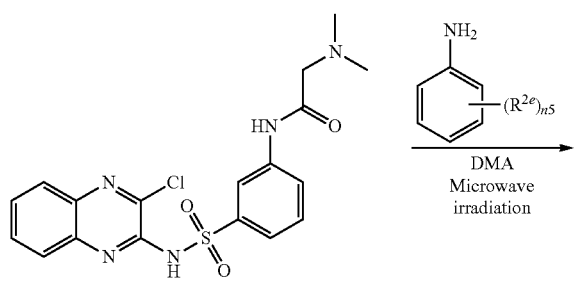

N-(3-(N-(3-(3,5-dimethoxy-phenylamino)quinoxalin-2-yl)-sulfamoyl)phenyl)azetidine-3-carboxamide (125 mg, 0.23 mmol), prepared using standard procedures, was dissolved into 5 mL DCE in a 10 mL round-bottom flask. DIEA (1.17 mmol, 5.0 equiv.) was then added with stirring, followed by acid chloride (0.47 mmol, 2.0 equiv.). The reaction was then stirred at room temperature for 1 hour or until complete as indicated by LCMS. The solvent was subsequently removed under reduced pressure on a rotary evaporator. The crude material was then redissolved in methanol. Purification of the final product was accomplished by preparatory reverse-phase HPLC with the eluents 25 mM aqueous NH$_4$OAc/CAN. A Waters Fractionlynx preparative reverse-phase HPLC (equipped with a Waters SunFire Prep C18, OCD 5 μM, 30×70 mm column and running a 5-100% gradient with a binary solvent system of 25 mM ammonium acetate in water/acetonitrile) was used to carry out the purification.

General Reductive Amination Procedure 1

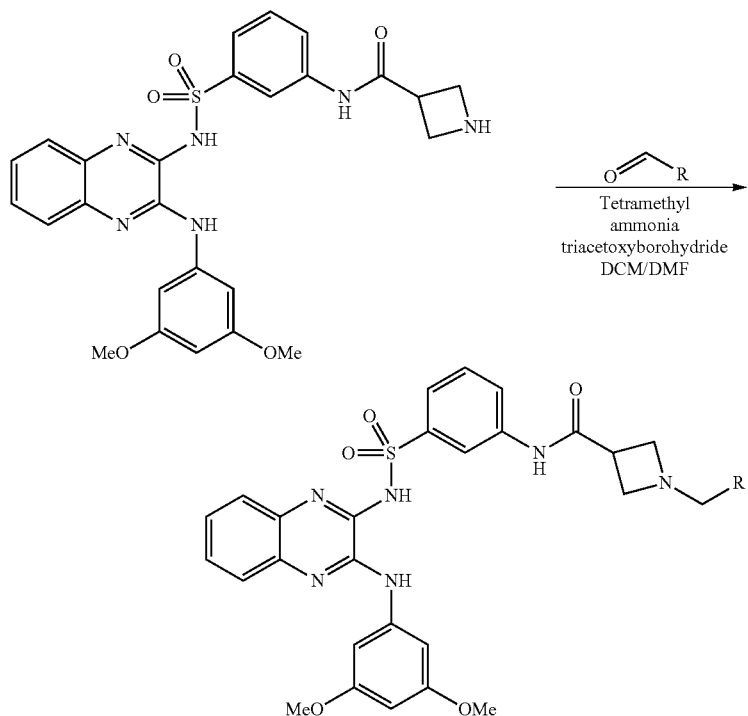

To a solution of N-(3-(N-(3-(3,5-dimethoxy-phenylamino)quinoxalin-2-yl)sulfamoyl)phenyl)azetidine-3-carboxamide (110 mg, 0.19 mmol), prepared using standard procedures, in 3 mL of DCE and 200 μL of DMF, aldehyde (0.77 mmol, 4.0 eq.) was added slowly, followed by tetramethylammonium triacetoxyborohydride (1.16 mmol, 6.0 eq). The reaction was stirred at room temperature overnight. LC/MS indicated the reaction was completed. The solvent was subsequently removed under reduced pressure on a rotary evaporator. The crude material was then redissolved in methanol. Purification of the final product was accomplished by preparatory reverse-phase HPLC with the eluents 25 mM aqueous NH$_4$OAc/CAN. A Waters Fractionlynx preparative reverse-phase HPLC (equipped with a Waters SunFire Prep C18, OCD 5 μM, 30×70 mm column and running a 5-100% gradient with a binary solvent system of 25 mM ammonium acetate in water/acetonitrile) was used to carry out the purification.

General Amide Formation Procedure 1a

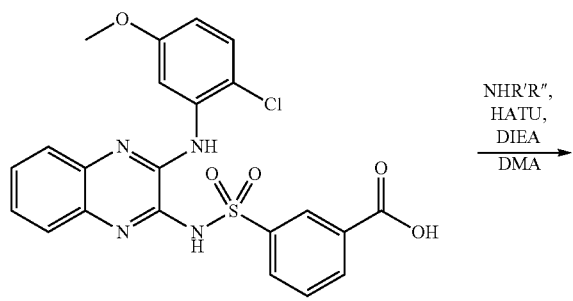

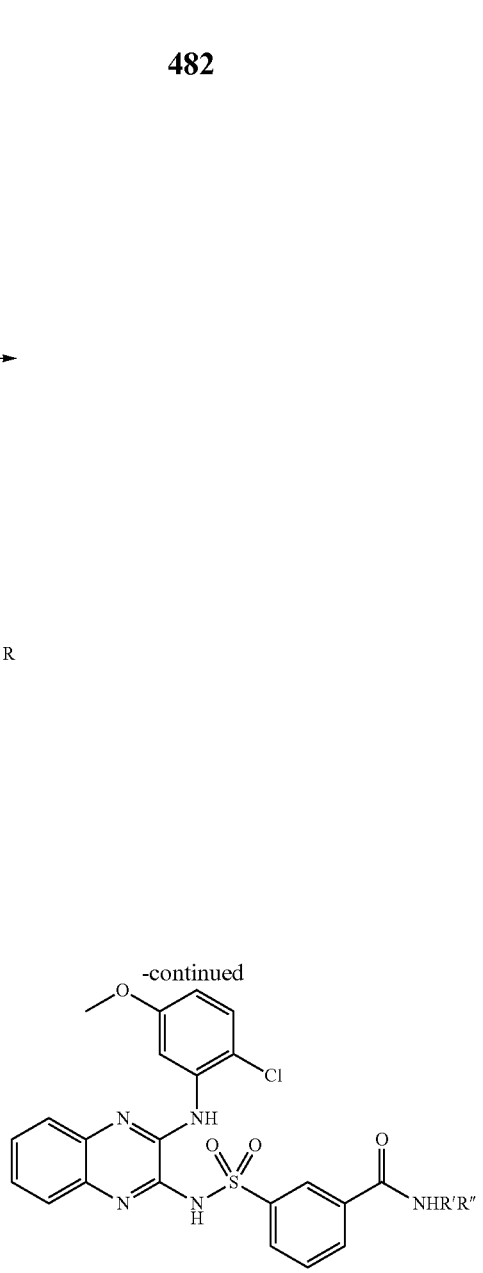

Into a small 1 dram vial was added 3-(N-(3-(2-chloro-5-methoxy-phenylamino)-quinoxalin-2-yl)sulfamoyl)benzoic acid (61 mg, 0.13 mmol, 1.1 equiv), prepared using standard procedures. The acid was dissolved in DMA (1 mL), and DIEA (42 μL, 0.24 mmol, 2 equiv) was added then added to the solution. The amine reagent (1 mL of 0.12 M solution in DMA) was added to solution with stirring, followed by HATU (64 mg, 0.17 mMol, 1.4 equiv). The reaction was stirred overnight at room temperature. Upon completion as indicated by LCMS analysis, 2 mL of methanol was added to the solution. Preparative reverse-phase HPLC was used to isolate the desired product. A Waters Fractionlynx preparative reverse-phase HPLC (equipped with a Waters SunFire Prep C18, OCD 5 μM, 30×70 mm column and running a 5-100% gradient with a binary solvent system of 25 mM ammonium acetate in water/acetonitrile) was used to carry out the purification.

General Amide Formation Procedure 1b

The procedure outlined in General Amide Formation Procedure 1a was used to incorporate a number of amines that contained a second amine group protected as the tert-butyl-carbamate (i.e., where R', within NHR'R," contained a Boc-protected amine group). The deprotection was carried out after HPLC purification of the Boc-protected precursor.

Into a small 1 dram vial was added 3-(N-(3-(2-chloro-5-methoxy-phenylamino)quinoxalin-2-yl)sulfamoyl)benzoic acid (61 mg, 0.13 mmol, 1.1 equiv). The acid was dissolved in 1 mL of DMA, and DIEA (42 µL, 0.24 mmol, 2 equiv) was then added to the solution. The mono-Boc-protected diamine reagent (1 mL of 0.12 M solution in DMA, 1 equiv) was added to solution with stirring, followed by HATU (64 mg, 0.17 mmol, 1.4 equiv). The reaction was stirred overnight at room temperature. Upon completion as indicated by LCMS analysis, 2 mL of methanol was added to the solution. Preparative reverse-phase HPLC was used to isolate the desired product directly from this crude reaction solution. A Waters Fractionlynx preparative reverse-phase HPLC (equipped with a Waters SunFire Prep C18, OCD 5 µM, 30×70 mm column and running a 5-100% gradient with a binary solvent system of 25 mM ammonium acetate in water/acetonitrile) was used to carry out the purification. The product fractions were combined and concentrated to dryness under reduced pressure by rotary evaporation. A solution of 4 N HCl in dioxane (2 mL) was added. The solution was then stirred at room temperature until no starting material was detected. The deprotected product precipitated out of solution as an HCL salt and was collected by filtration, washed with ether and dried under vacuum.

Biological Examples

Example 1

Figure 1A:
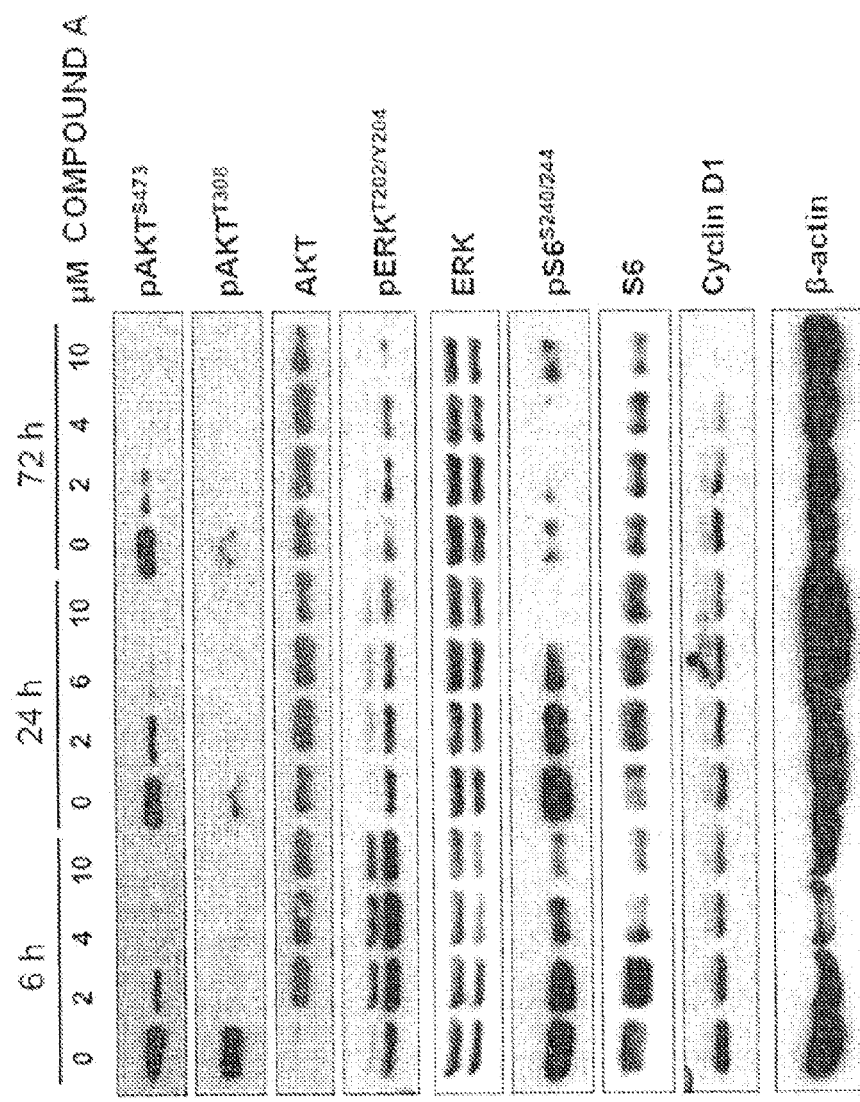
Figures 4A, 4B:
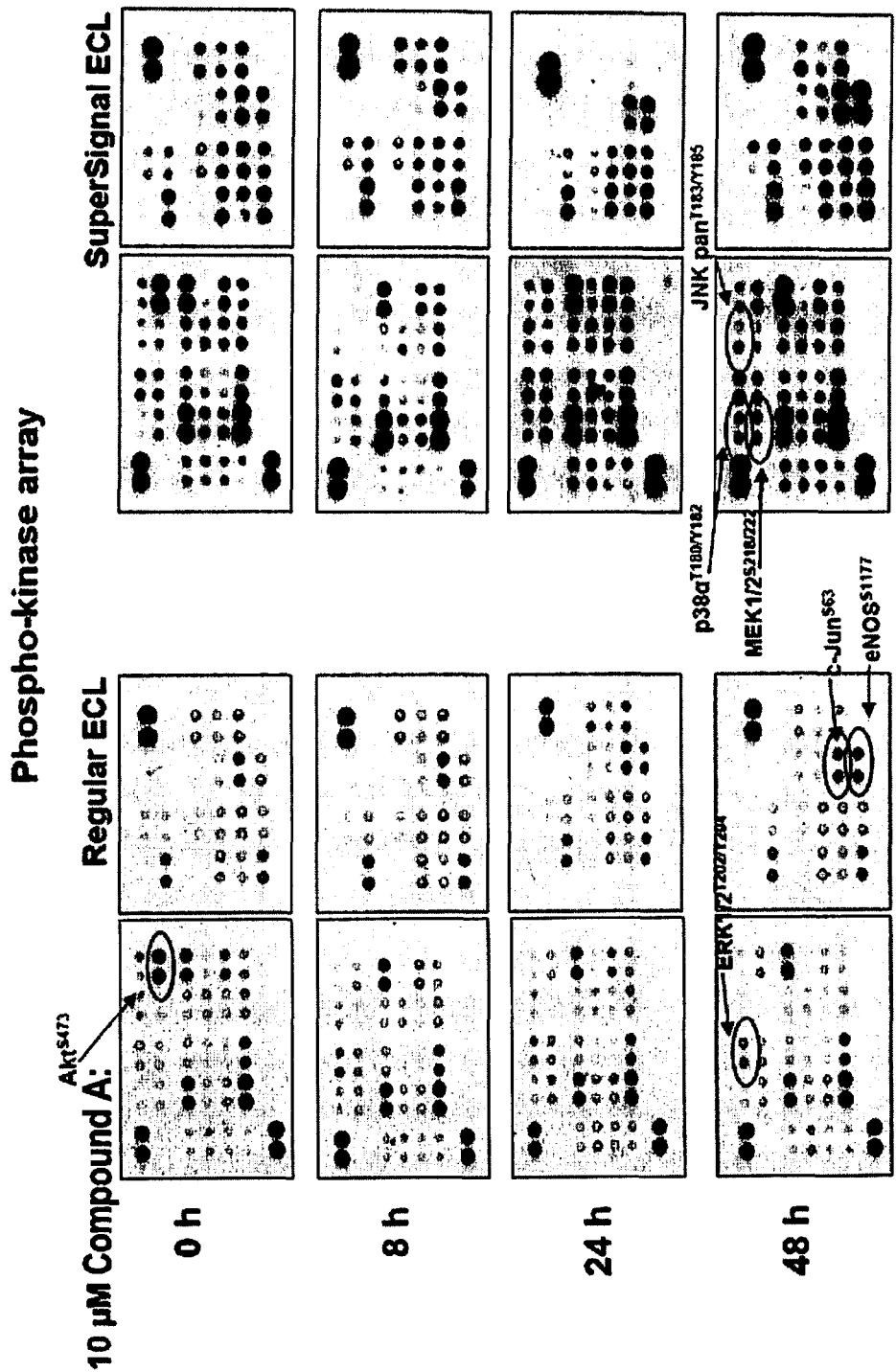
Figure 5:
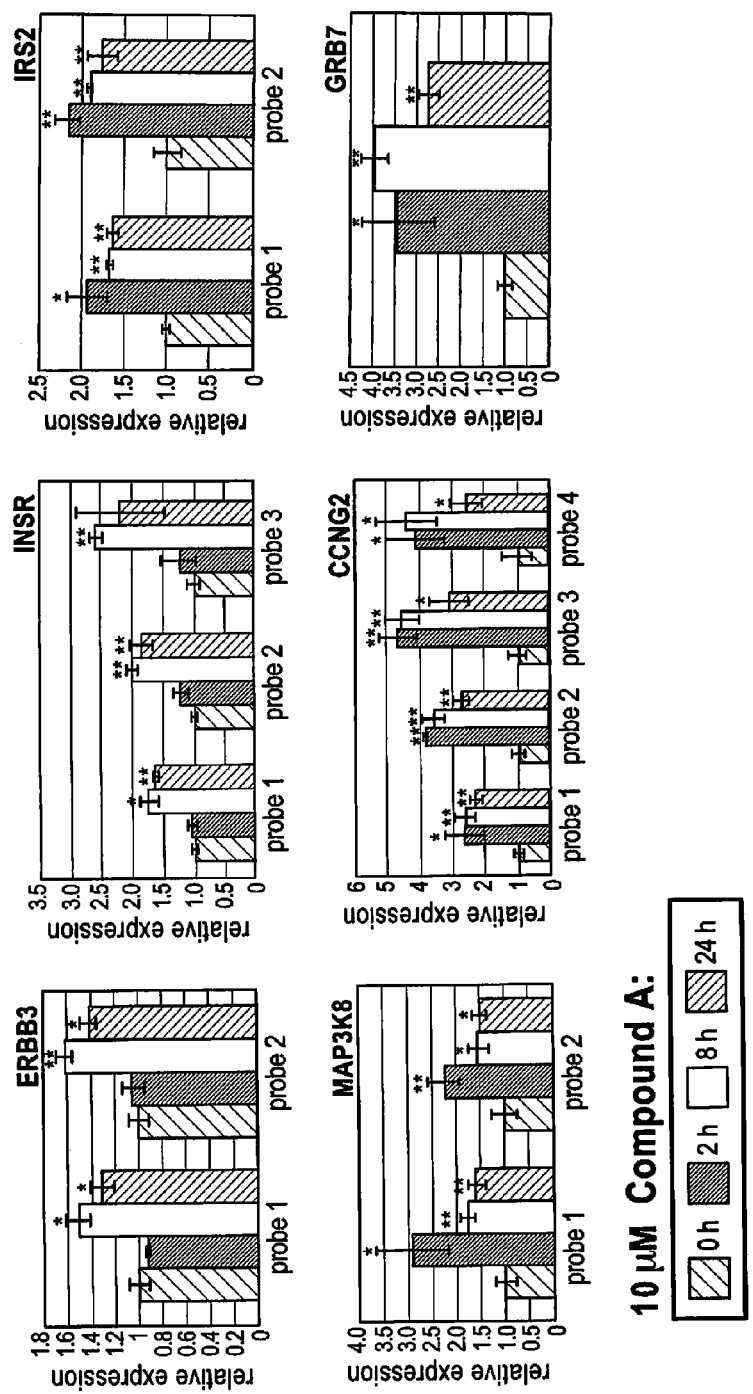

Identification of Kinases that Compensate for PI3K Inhibition in Breast Cancer Cells The purpose of the present study is to identify kinases and kinase-regulated signaling pathways that compensate for PI3K inhibition in human breast cancer cells. To this end, siRNA screen is employed targeting 779 human kinases in order to determine if downregulation of specific kinases increases the sensitivity of HCC1937 human breast cancer cells to the PI3K inhibitor compound A, which a compound of formula I and of Table 1. Compound A is an ATP-mimetic that inhibits the p110α catalytic subunit of PI3K with an in vitro $IC_{50}$ of 39 nM. HCC1937 cells lack PTEN, the negative regulator of the PI3K pathway, and are growth inhibited by compound A with an $IC_{50}$ of 10 µM. Following reverse transfection with the siRNA library, cells are treated with either DMSO or 10 µM compound A for 72 hours in a medium containing 2.5% fetal bovine serum (FIGS. 1A and 2) and the alamar blue assay is used to measure cell viability FIG. 1B. In parallel, gene expression is performed using microarrays, phospho-receptor tyrosine kinase (RTK) arrays, and phospho-intracellular kinase arrays (FIGS. 3 and 4) using RNA or lysates from HCC1937 cells±compound A in order to determine which kinases and pathways are upregulated upon inhibition of PI3K. Compound A treatment results in increased expression and/or phosphorylation of many RTKs and intracellular kinases within 8-48 hours. Eight and 24 hour treatments with compound A suppressed phospho-Akt at both S473 and T308, but at 48 hours, phosphorylation at S473 is partially restored. From these approaches, several kinases and pathways that are upregulated by compound A are identified and that, when downregulated by siRNA, increased sensitivity to compound A. These include several RTKs, such as HER3, MSPR, and Axl, and members of the MAP kinase signaling pathway, such as several MAP3Ks/MEKKs. Western blotting confirms that compound A treatment decreases phospho-Akt at S473 and T308 and increases phospho- and total HER3. Compound A also increases phosphorylation of the MAP kinases ERK, JNK, and p38 MAPK. HCC1937 cells were treated with 10 µM compound A in medium containing 2.5% FBS for 0, 2, 8, or 24 hours. RNA was isolated with Trizol and purified using the RNeasy column (Qiagen). Gene expression from three independent experiments was measured using the Gene titan 3' microarray. *, $p<0.05$; **, $p<0.01$ versus 0 hours, as shown in FIG. 5. Combined treatment with compound A and HER3 siRNA inhibits HCC1937 cell growth to a larger degree than each intervention alone (FIG. 5), suggesting that the upregulation of phospho-HER3 compensates for growth inhibition as a result of pharmacological inhibition of PI3K. These results suggest that combining compounds that inhibit these kinases or pathways along with PI3K inhibitors may improve the anti-tumor activity of PI3K inhibitors.

The results are further summarized in Tables 2 and 3.

TABLE 2

Kinases essential for HCC1937 cell viability

| siRNA | % Growth (round 1) | % Growth (round 2) |
|---|---|---|
| WEE1 | 7.2 | 14.2 |
| AURKA | 10.4 | 19.0 |
| PLK1 | 22.0 | 17.8 |
| PKN3 | 26.6 | 23.2 |
| CHEK1 | 27.9 | 20.4 |

TABLE 3

Candidate kinases upregulated or phosphorylated upon treatment with Compound A

| siRNA | Survival fraction (round 1) | Survival fraction (round 2) | Average |
|---|---|---|---|
| MAP3K8 | 23.3% | 28.9% | 26.1% |
| MST1R | 28.3% | 30.0% | 29.2% |
| MAPK8 | 33.2% | 28.3% | 30.7% |
| ERBB3 | 31.2% | 31.0% | 31.1% |
| AXL | 43.0% | 25.7% | 34.4% |

MAP3K8 = Cot/Tpl-2
MST1-R = Macrophage stimulating 1 receptor; MSPR
MAPK8 = JNK1
ERBB3 = HER3

Figure 6A:
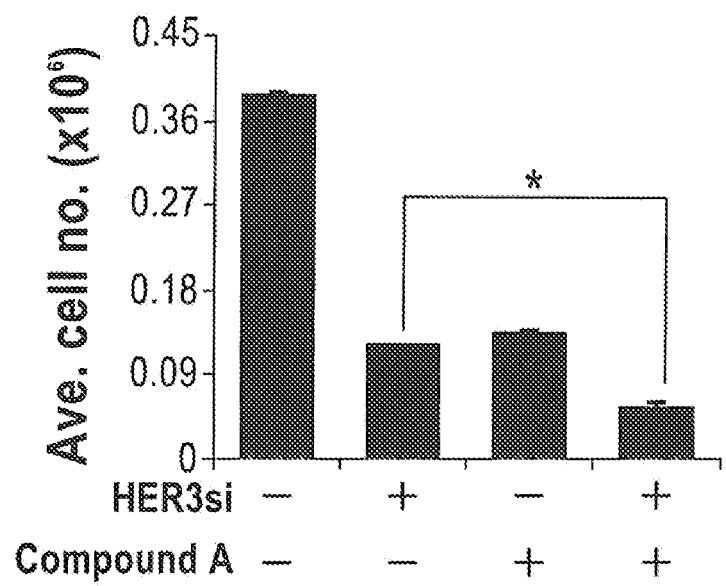
Figure 6B:
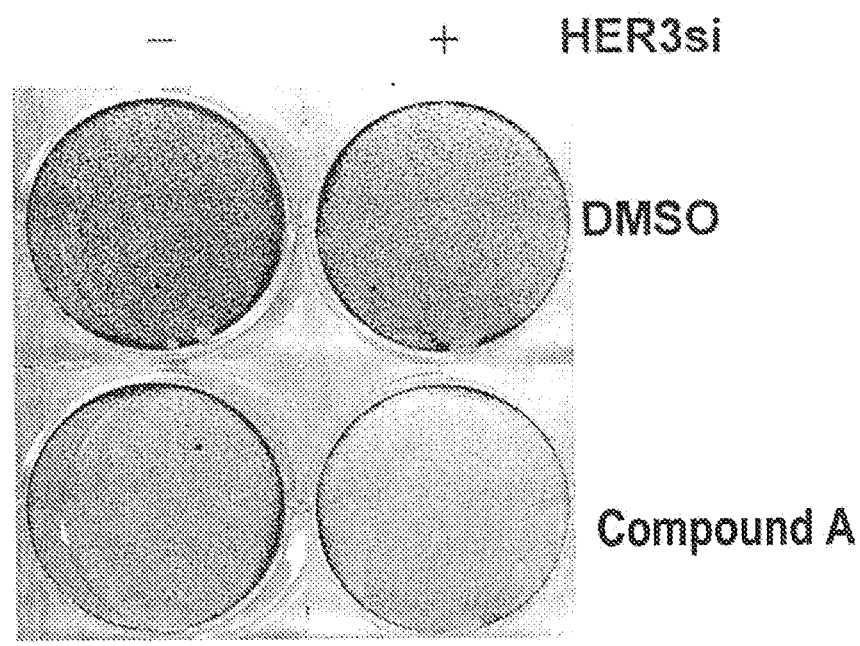
Figure 7:
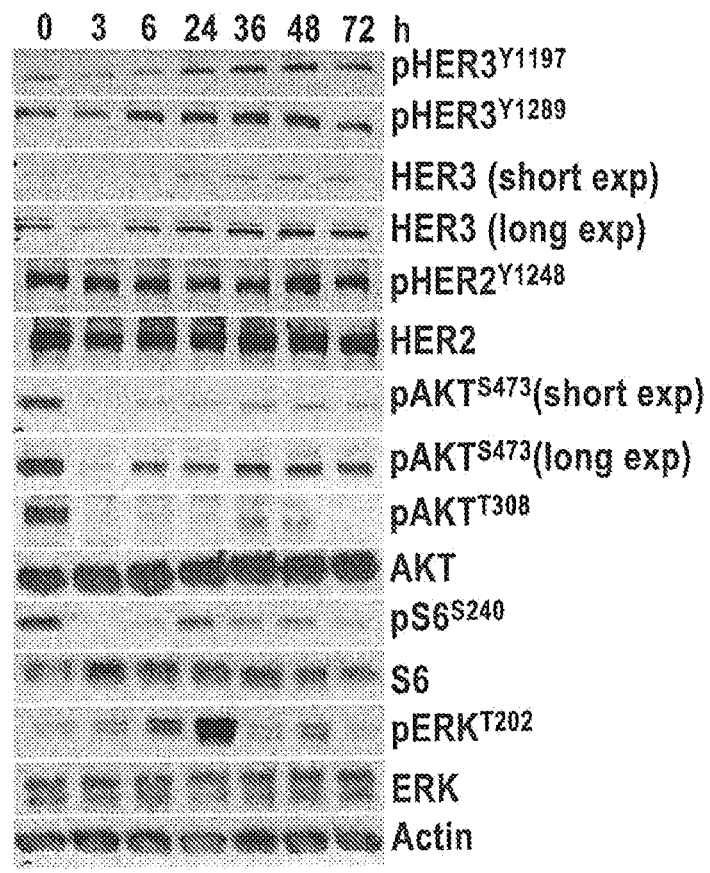

Example 2 siRNA Inhibition of HER3 (ErbB3)-Mediated Compensation in Cells Treated with PI3K Inhibitors The antitumor effect of the PI3K inhibitor compound A is examined in a panel of human breast cancer cells with mutational activation of the PI3K/Akt pathway (as a result of PIK3CA mutations, PTEN loss, and/or HER2 gene amplification). A time course with Compound A-treated BT-474 cells where the inhibitor is added every 24 hours, shows a time-dependent upregulation of HER3 RNA and protein, beginning at 6 hours and increasing through 72 hours (FIG. 7). Site-specific antibodies reveals HER3 phosphorylation at Y1197 and Y1289, two of the six p85 binding sites in HER3. Recovery of P-HER3 correlates temporally with recovery of T308 and S473 P-Akt (FIG. 7), suggesting that cells upregulate mechanisms upstream PI3K when PI3K is blocked by exogenous inhibitors. The upregulation of HER3 RNA and protein and partial maintenance of P-HER3 and P-Akt suggests that combined inhibition of HER3 and PI3K might synergistically inhibit tumor cell viability. Transfection with HER3 siRNA sensitized BT-474 cells to Compound A (FIG. 6A and FIG. 6B).

Similar results are obtained with SKBR-3 and MDA-453 cells. Both cell lines exhibit HER2 gene amplification. The MDA-453 cells also harbor a H1047R (exon 20) mutation in PIK3CA and a PTEN mutant allele. In both cell lines, the inhibition of P-Akt, P-S6, and growth is enhanced in cells when treated with compound A and also transfected with HER3 siRNA compared to each intervention alone. Like in BT-474 cells (FIG. 7), P-Erk is upregulated in cells treated with compound A and this upregulation is dampened upon transfection of HER3 siRNA in SKBR-3 but not in MDA-453 cells (FIG. 8).

Figure 8A:
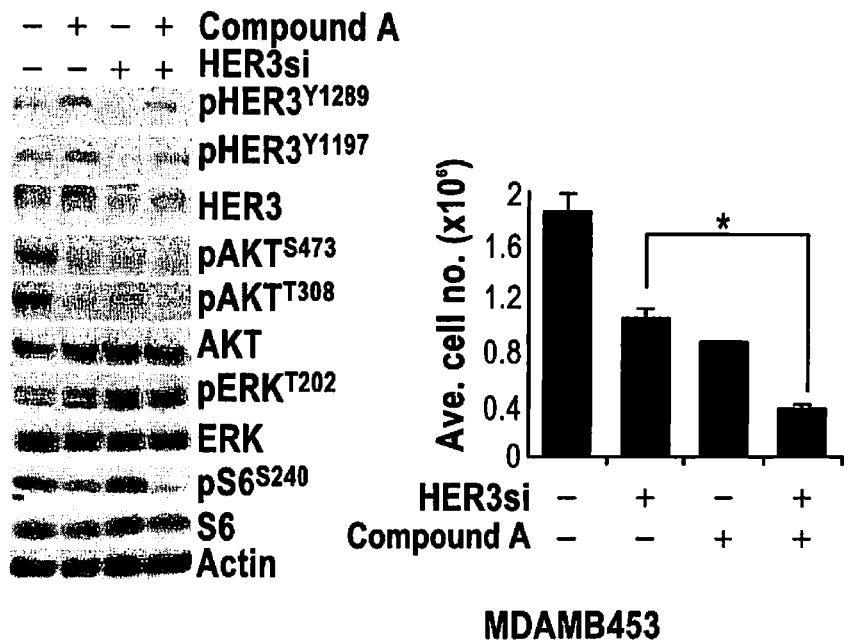
Figure 8B:
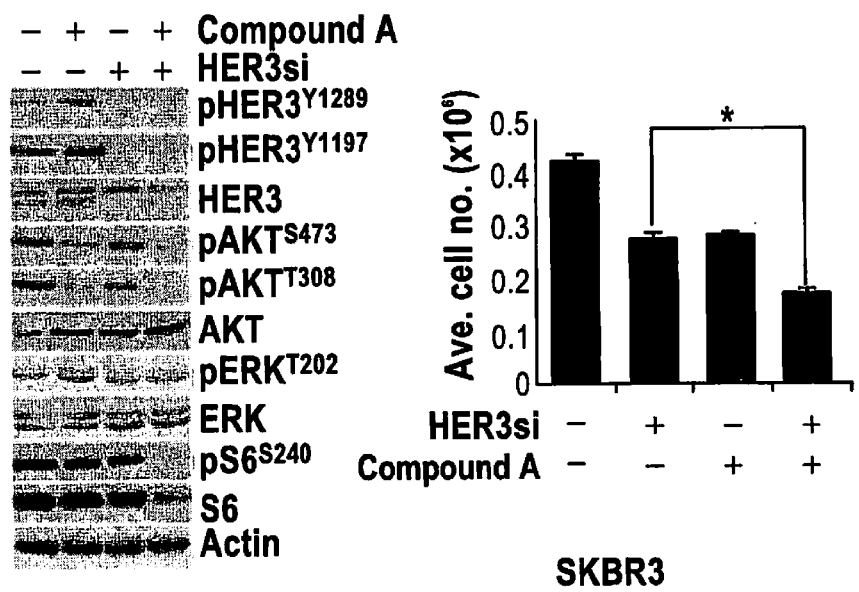

The results shown in FIGS. 7 and 8 suggest that inhibition of active PI3K/Akt depresses transcription of HER3. In addition to these transcriptional mechanisms, the recovery of P-HER3 upon compound A-mediated inhibition of PI3K suggests the engagement of an upstream tyrosine kinase transactivating HER3 which, in turn, partially maintains PIP3 levels. This compensatory phosphorylation of HER3 partially maintains PI3K/Akt and counteracts the full action of PI3K antagonists.

Example 3

In Vitro Evaluation of Antibody Inhibition of HER3 (ErbB3)-Mediated Compensation in Cells Treated with PI3K Inhibitors To establish that an anti-HER3 Ab can delay or abrogate feedback upregulation of HER3 in human breast cancer cells treated with a PI3K inhibitor, human breast cancer cells with or without overexpression of HER2 are treated with compound A±a saturating concentration of an anti-HER3 Ab, such as MM-121. Experimental endpoints are: (1) association of p85 with HER3, (2) growth in 3D-Matrigel, (3) colony formation in soft agar, (4) apoptosis assays in both serum-free conditions and in suspension (to induce anoikis), (5) motility in wound closure and transwell assays, (6) PI3K activity in HA pull downs subjected to an in vitro PI3K reaction, and (7) total HER3 and P-HER3, P-Akt, P-Erk, P-S6, P-4EBP-1 by immunoblot.

Example 4

In Vivo Evaluation of Antibody Inhibition of HER3 (ErbB3)-Mediated Compensation in Cells Treated with PI3K Inhibitors Xenografts in athymic mice are established according to known methods. Once tumors reach a volume ≥250 mm3, they are randomized to four treatment arms: (1) control IgG1 (30 mg/kg×2/week i.p.), (2) compound A (100 mg/kg/day via orogastric gavage), (3) MM-121 (30 mg/kg×2/week i.p.), and (4) compound A plus an anti-HER3 Ab, such as MM-121 (Merrimack Pharmaceuticals, Cambridge, Mass., USA). Treatment is delivered for up to five weeks, and tumor growth is monitored thereafter. Study endpoints are assessed after one and five weeks of treatment and following discontinuation of therapy. After one week of treatment, some tumors are harvested, fixed in formalin, or snap-frozen in liquid N2. This time point can be used to identify early molecular predictors of tumor response. Tumor volume in mm$^3$ is calculated by the formula: volume=width$^2$×length/2. Mice whose tumors are completely eliminated will be followed for up to one year and evaluated serially for tumor recurrences. Recurrent tumors measuring ≥3 mm$^3$ will be scored as positive and collected.

Biochemical and Molecular Analysis.

Formalin-fixed, paraffin-embedded tumor sections are stained with H&E for assessment of tumor grade. Tumor sections are subjected to IHC to detect total HER3, Y1289, Y1197, and Y1222 P-HER3, T308 P-Akt, S473 P-Akt, and P-Erk antibodies using established methods. In addition, immunoblots of tumor lysates can be performed with the same antibodies. Using immunoprecipitation followed by immunoblot analysis, the impact of the anti-HER3 Ab upon the association of p85 with HER3 in the xenografts can be determined. HER3 transcript levels are measured using RNA from flash frozen tumor aliquots to confirm any increases in HER3 mRNA levels.

Example 5

Cell Lines and Inhibitors

All cell lines were purchased from the American Type Culture Collection. Media and fetal bovine serum (FBS) were purchased from Invitrogen (Carlsbad, Calif., USA). The following growth media were used: HCC1937, HCC1954: RPMI-1640/10% FBS; for BT474: IMEM/10% FBS; SKBR3: McCoy's 5A/15% FBS; UACC893: DMEM/10% FBS; MDA453: DMEM/F12 (1:1)/20% FBS; and SUM190: DMEM/F12 (1:1)/5% FBS. All cells were grown in a humidified 5% CO$_2$ incubator at 37° C. The following reagents were used: lapatinib (GW-572016, LC Laboratories), trastuzumab (Genentech, San Francisco, Calif., USA), LY294002 (Calbiochem), the allosteric AKT1/2 inhibitor 5J8, rapamycin (LC Laboratories), and compound A, a compound of formula I (Exelixis, Inc.).

Example 6

Cell Proliferation and Crystal Violet Assays

Cells were seeded in 12-well plates at a density of 2.5-3.5× 10$^4$ cells/well in medium containing 2.5% FBS±inhibitors. Media and inhibitors were replaced every 3 days. On the days indicated in figures, cells were trypsinized and counted in a Beckman Coulter counter. For crystal violet assay, 5×10$^4$ cells/well were seeded in 6-well plates and grown in absence or presence of compound A for 6 days, fixed in methanol, stained with crystal violet, and photographed using an Olympus DP10 camera.

Example 7

Cell Cycle Analysis

Cells were plated in 100-mm dishes in media containing 2.5% FBS±compound A. After 3 days, both detached and adherent cells were pooled, fixed and labeled with propidium iodide using the APO-BrdU kit (Phoenix Flow Systems). Labeled cells were analyzed using the Becton Dickinson FACScalibur system.

Example 8

Cytoplasmic and Nuclear Fractionation

Cytoplasmic and nuclear extracts were prepared using the Nuclear Extract Kit from Active Motif. Briefly, cells were plated in 100-mm dishes, treated with inhibitors at the indicated concentrations for 3-4 hours, washed with ice-cold PBS/phosphatase inhibitors, lysed in hypotonic buffer and centrifuged for 30 seconds at 14,000 rpm at 4° C. to collect the supernatant (cytoplasmic extract). The pellet (nuclear fraction) was resuspended in complete lysis buffer and centrifuged for 10 minutes at 14,000 rpm at 4° C. to collect the supernatant (nuclear fraction).

Example 9

Phosphatidylinositol-3 Kinase (PI3K) Signalling in Cancer Cells

The phosphatidylinositol-3 kinase (PI3K) transmits signals from ligand-activated receptor tyrosine kinases (RTKs) to intracellular molecules that regulate cell growth, metabolism, size, motility, and survival. Multiple PI3K families exist in higher eukaryotes. To date, mainly class $I_A$ PI3K has been implicated in cancer. Class $I_A$ PI3K is a heterodimer consisting of a regulatory (p85) and a p110 catalytic subunit. PI3K is activated by phosphorylated adaptors or receptors containing YXXM motifs that engage the N-SH2 domain of p85. This binding relieves the inhibition of p110 by p85 and recruits the p85-p110 dimer to phosphatidylinositol-4,5-bisphosphate (PIP2) at the plasma membrane. PI3K phosphorylates PIP2 to produce the second messenger phosphatidylinositol-3,4,5-trisphosphate (PIP3). Negative regulation of this pathway is mediated by the PIP3 lipid phosphatase PTEN (phosphatase and tensin homologue at chromosome ten). A subset of pleckstrin homology (PH) domain-containing proteins, including AKT and PDK1, bind to PIP3 at the plasma membrane. The phosphorylation of AKT at T308 by PDK1 and at S473 by a complex involving mTOR/Rictor (TORC2) results in full activation of this enzyme. AKT phosphorylates a host of cellular proteins, including GSK3α, GSK3β, FoxO transcription factors, MDM2, BAD, and p27$^{KIP1}$ to facilitate survival and cell cycle entry. In addition, AKT phosphorylates and inactivates Tuberin, a GTPase-activating protein (GAP) for the Ras homologue Rheb. Inactivation of Tuberin allows GTP bound-Rheb to accumulate and activate the mTOR/Raptor (TORC1) complex, which ultimately regulates protein synthesis and cell growth.

Abundant evidence indicates that the PI3K/AKT is arguably the most commonly altered signaling pathway in human cancers. First, gain of function mutations in PIK3CA, the gene encoding p110α, are present in high frequency in multiple human tumors. Second, the phosphatase PTEN is a tumor suppressor gene frequently inactivated by mutation, gene deletion, targeting by microRNA, and promoter methylation. Furthermore, PI3K is potently activated by oncogenes like mutant Ras and many tyrosine kinases such as Bcr-Abl, HER2 (ErbB2), MET, KIT, etc., which themselves are the targets of mutational activation and/or gene amplification. In ovarian, pancreatic, breast, and gastric cancers, PI3K pathway is also activated by the Akt1 or Akt2 gene amplification. A transforming mutation in the PH domain of AKT1 (E17K), resulting in its constitutive localization at the plasma membrane and activation, has been detected in a small percentage of breast, colorectal, and ovarian cancers. Together, these indicate that a large repertoire of tumors with molecular alterations in the PI3K/AKT pathway is therapeutically targetable with specific inhibitors.

Several PI3K pathway antagonists have been developed and are the subject of recent reviews. Some of these compounds are ATP-mimetics that bind competitively and reversibly in the ATP-binding pocket of the kinase domain in p110 and are also active against oncogenic mutant forms of this enzyme. The present Examples have examined the effect of compound A (from Exelixis, Inc.) against a panel of human breast cancer cell lines harboring a molecular alteration indicative of PI3K dependence, such as HER2 gene amplification, a PIK3CA (p110α) activating mutation, and/or loss of PTEN. Compound A is an ATP-competitive reversible PI3K inhibitor with an $IC_{50}$ against p110α of 39 nM which has just completed phase I clinical development.

In a panel of HER2-overexpressing human breast cancer cell lines, treatment with compound A abrogated the phosphorylation of AKT and S6, two major effectors of the PI3K/AKT pathway. This inhibition was also associated with induction of both expression and phosphorylation of HER3 and other RTKs. The increase in mRNA expression of these RTKs depended on transcription by the Forkhead transcription factors FoxO3a and FoxO1, which are negatively regulated by AKT. In HER2+ cells, phosphorylation of the upregulated HER3 co-receptor was maintained by the HER2 tyrosine kinase resulting, in turn, in partial recovery of pAKT and, thus, limiting the antitumor action of PI3K inhibitors. Knockdown of HER3 with siRNA or simultaneous treatment with the HER2 inhibitors trastuzumab or lapatinib sensitized HER2+ breast cancer cells to compound A both in vitro and in vivo. Further, therapies targeted against HER2/HER3 should be added to PI3K inhibitors in HER2-dependent cells in order to maximally disable PI3K/AKT signaling.

Example 10

Synergistic Effects in Cancer Cells

The present Examples have provided insight into the cellular and molecular effects of an inhibitor of phosphatidilinositol-3 kinase (PI3K), compound A, against human breast cancer cell lines with constitutive PI3K activation. Treatment with compound A resulted in dose-dependent inhibition of cell growth and levels of pAKT and pS6, signal transducers in the PI3K/AKT/TOR pathway. In HER2-overexpressing cells, simultaneous with inhibition of PI3K, there was upregulation of expression and phosphorylation of multiple RTKs, including HER3. Knockdown of FoxO1 and FoxO3a proteins suppressed the induction of HER3, InsR, IGF-IR, and FGFR-2 mRNAs upon inhibition of PI3K. In HER2+ cells, knockdown of HER3 with siRNA or cotreatment with the HER2 inhibitors trastuzumab or lapatinib enhanced compound A-induced cell death and compound A-mediated inhibition of pAKT and pS6. Trastuzumab and lapatinib each synergized with compound A for inhibition of pAKT and growth of established BT474 xenografts. These data suggest PI3K antagonists will inhibit AKT and relieve suppression of RTK expression and their activity. Relief of this feedback limits the sustained inhibition of the pathway and attenuates the response to these agents. In patients with HER2+ breast cancer, PI3K inhibitors should be used in combination with HER2-HER3 antagonists.

Example 11

Three-Dimensional (3D) Growth

Cells were seeded in 8-well chamber slides in growth-factor reduced Matrigel (BD Biosciences, San Jose Calif., USA)±compound A according to published methods. Fresh medium and drugs were replenished every third day. Colonies were photographed with an inverted light microscope with an ocular magnification of 10 times on the days recited in figures herein.

Example 12

Immunoprecipitation, Immunoblotting and Receptor Tyrosine Kinase (RTK) Arrays Immunoprecipitation, immunoblotting, and RTK assays were performed according to published methods. Primary antibodies included AKT, pAKT$^{S473}$, pAKT$^{T308}$, ERK, pERK$^{T202/Y204}$, pHER2$^{Y1248}$, pHER3$^{Y1197}$, pHER3$^{Y1222}$, pHER3$^{Y1289}$, S6, pS6$^{S240/244}$, p27, pRb$^{S780}$, FoxO1, FoxO3a, MEK1/2 (Cell Signaling Technology, Danvers, Mass., USA), p85, 4G10 pTyr (Millipore, Billerica, Mass., USA), HER3, CyclinD1, RhoA, HDAC3 (Santa Cruz Biotechnology, Santa Cruz, Calif., USA), PARP (BD Transduction Laboratories), β-actin (Sigma, St. Louis, Mo., USA), and HER2 (Neomarkers, division of Thermo Scientific, Freemenot, Calif., USA). Species-specific horseradish peroxidase-conjugated secondary antibodies were from Promega (Madison Wis., USA). Immunoreactive signals were detected by enhanced chemilluminsecence (Pierce, Rockford, Ill., USA). Phospho-RTK arrays were from R&D Systems (Minneapolis, Minn., USA) total cell lysates were used to hybridize with the arrays according to the manufacturer's instructions.

Example 13

RNA Interference siRNA duplexes for mismatch control and human HER3 were described previously (Wang, S. E., et al. (2008) *Mol. Cell. Biol.* 28:5605-5620, incorporated by reference herein in its entirety); Human FoxO1 and FoxO3a-specific Silencer® Select siRNA duplexes were purchased from Ambion (Applied Biosystems, Austin, Tex., USA) (FoxO1 sense strand, SEQ ID NO: 19: CCAUGGACAACAACAGUAAtt; FoxO3a sense strand, SEQ ID NO:20: GCCUUGUCGAAUUCUGU-CAtt). Human IGF-IR and InsR siRNA duplexes were obtained from Qiagen (Valencia, Calif., USA) (IGF-IR sense strand, SEQ ID NO:21: GGAGAAUAAUCCAGUCCUAtt; InsR sense strand, SEQ ID NO:22: GAACGAUGUUG-GACUCAUAtt). Transfections were performed with Lipofectamine RNAiMAX (Invitrogen, Carlsbad, Calif., USA).

Example 14

Xenograft Experiments

Animal experiments were approved by the Institutional Animal Care Committee of Vanderbilt University Medical Center (VUMC). Mice were housed in the accredited Animal Care Facility of the VUMC. A 17β-estradiol pellet (Innovative Research of America) was injected subcutaneously (s.c.) into each 6- to 7-week-old athymic female mice (Harlan Sprague Dawley, Inc.) the day before tumor cell injection. BT474 cells (3×10$^6$) mixed 1:1 with Matrigel (BD Biosciences) were injected s.c. into the right flank of each mouse. Tumor diameters were measured with calipers twice-a-week and volume in mm$^3$ calculated with the formula: volume=width$^2$×length/2. Once tumors reached ≥200 mm$^3$, treatment was initiated with the following, either alone or in combination: trastuzumab 30 mg/kg twice-a-week i.p., lapatinib 100 mg/kg daily via orogastric gavage, compound A 100 mg/kg daily via orogastric gavage. Mice were euthanized after 28 days of treatment.

Example 15

Immunohistochemistry

All tumor samples (collected within 1 hour of last treatment) were fixed in 10% neutral buffered formalin for 24 hours at room temperature, followed by dehydration and paraffin embedding. Immunostaining was done on 5-μm tissue sections. After deparaffinization in xylene and graded alcohols heat-induced antigen retrieval was performed in a pH 6.0 citrate buffer followed by incubation with 3% hydrogen peroxide for 20 minutes, with protein block (Dako) for 10 minutes, and finally with primary antibody overnight at 4° C. The Envision Visualization System (Dako, Carpinteria, Calif., USA) was used, followed by DAB as chromagen and counterstained with hematoxylin. Tumor sections were studied on a light microscope with an ocular magnification of 400 times. Average percentage and intensity of tumor cell staining was calculated as a histoscore (H-score) (as described in Goulding, H., et al. (1995), *Hum. Pathol.* 26:291-294, which is incorporated herein by reference in its entirety). An expert pathologist (MGK) scoring the sections was blinded to the type of treatment.

Example 16

Inhibition of PI3K is Associated with Induction of HER3 and pHER3

Figure 9A:
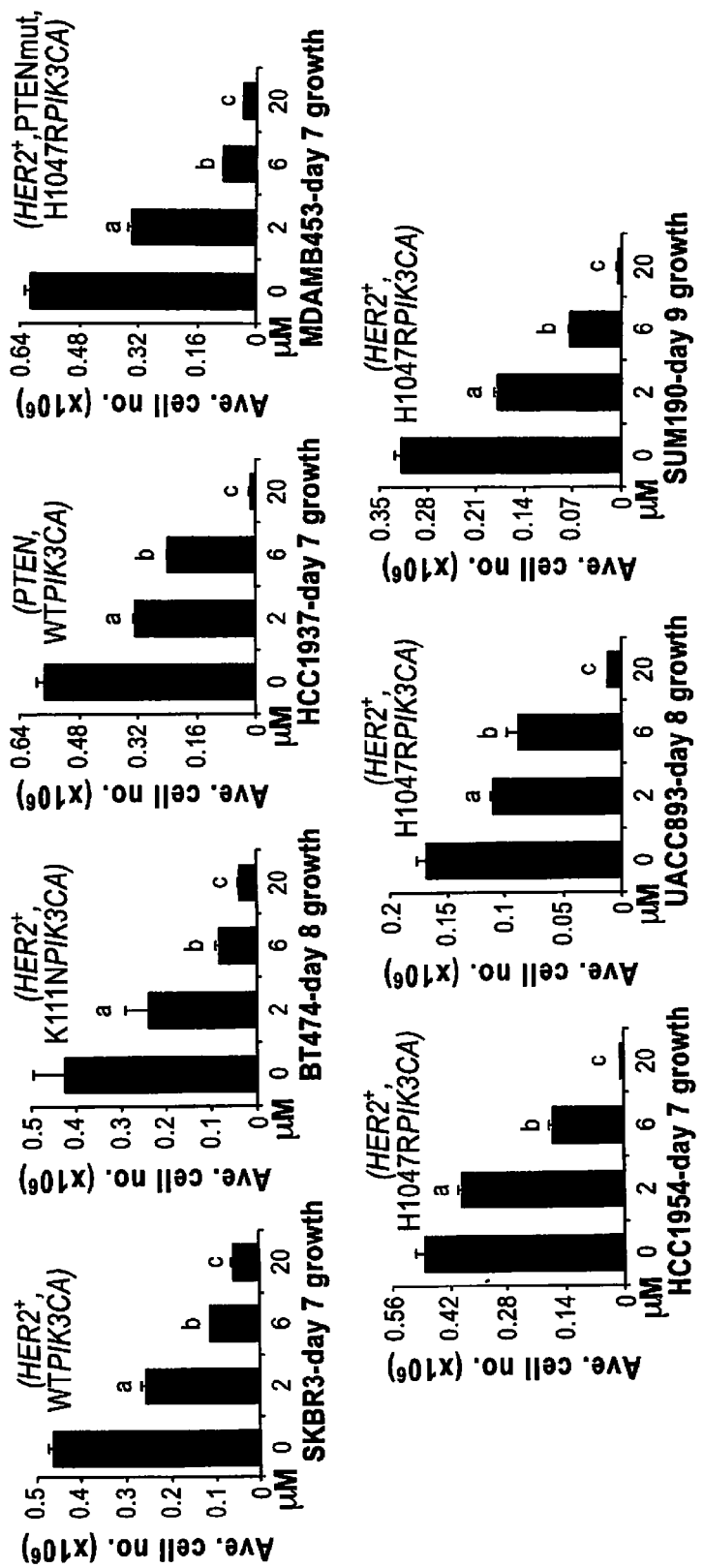
FIG. 9A depicts a bar chart representing the growth of SKBR3, BT474, HCC1937, MDAMMB453, HCC1954, UACC893, and SUM190 cells in the presence of compound A.
Figure 9B:
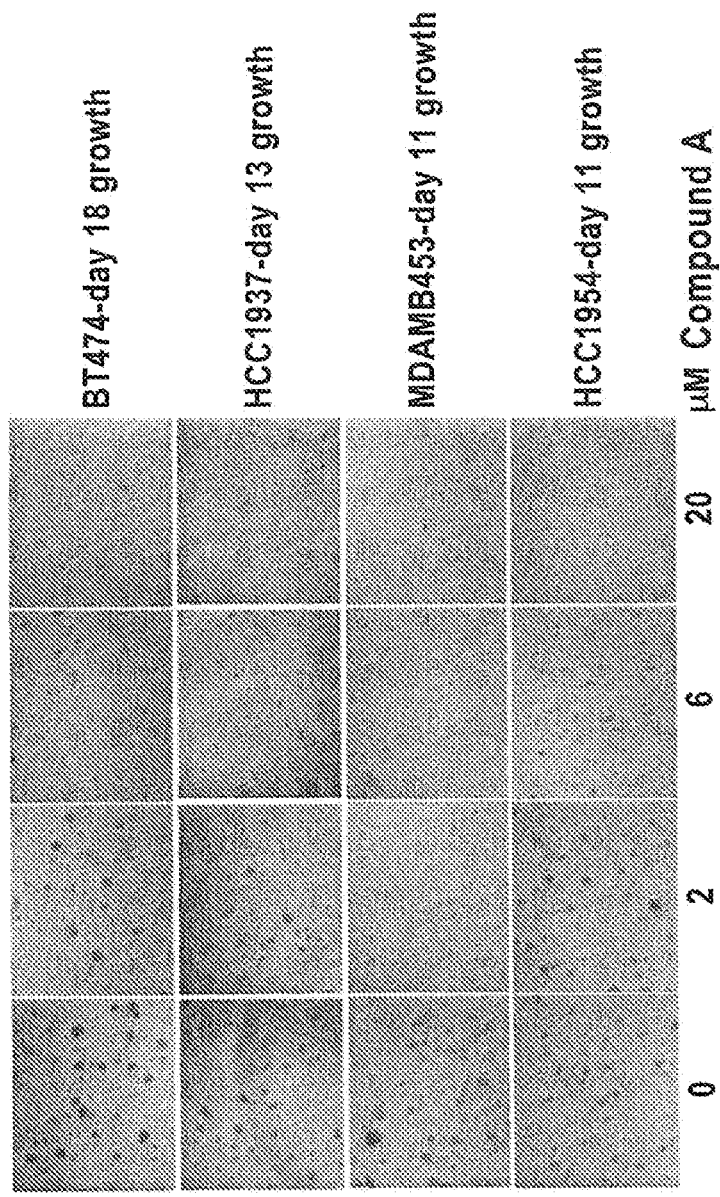
FIG. 9B depicts photomicrographs of BT474, HCC1937, MDA453, and HCC1954 cells cultured in Matrigel in the absence and presence of 0-20 μM compound A.

A panel of breast cancer cell lines with dysregulated PI3K activity was treated with increasing doses of compound A under two- and three-dimensional (2D and 3D) growth conditions. All experiments were conducted in 2.5% FBS-containing media, unless otherwise stated. Treatment with compound A inhibited the 2D growth of all cell lines in a dose-dependent manner as shown in FIG. 9A. A similar IC$_{50}$ of ≤6 M was observed in cells tested in 3D as shown in FIG. 9B, consistent with the fact that all of the selected cell lines in the present experiments harbor a molecular alteration in the PI3K pathway. Analysis of the growth curves using the initial amount of cells at the start of treatment as baseline indicated that at the IC$_{50}$ of approximately 6 μM, the main effect of compound A was inhibition of cell proliferation. At 20 μM, however, compound A induced cell death as revealed by the reduction in cell number below the baseline as shown in FIG. 10A. This was further confirmed by immunoblot analysis of biomarkers of cell death and G$_1$-S cell cycle transition in lysates from cells treated for 24 hours with compound A as shown in FIG. 10B. In all cell lines, treatment with compound A resulted in dose-dependent inhibition of PI3K signaling as measured by pAKT$^{S473}$. Consistent with the inhibition of cell proliferation at concentrations below 20 μM, compound A induced a reduction in cyclin D1 and pRB and an increase in levels of the CDK inhibitor p27$^{KIP1}$ but no change in levels of total or cleaved PARP, a biomarker of cell death (see FIG. 10B).

Experiments were performed to examine the effect of compound A on a more comprehensive panel of molecules in the PI3K and TOR signaling pathways. In all cell lines, treatment with compound A resulted in a dose-dependent reduction in pAKT$^{S473/T308}$ and pS6$^{S240/244}$. Surprisingly, in 6/7 cell lines, compound A also caused upregulation of total HER3 and/or pHER3$^{Y1289}$ levels at 24 hours. In 5/6 HER2-overexpressing cell lines, total HER2 and/or pHER2$^{Y1248}$ were also modestly upregulated upon inhibition of PI3K, the results of which are illustrated in FIG. 11.

Example 17

Compound A-Induced Upregulation of HER3 is Dependent on FoxO-Mediated Transcription The half-life of the HER3 protein in absence and presence of compound A was determined using cycloheximide, an inhibitor of protein synthesis. The rate of decay of the HER3 was not significantly altered upon treatment of BT474 cells with compound A (data not shown). Next the levels of HER3 mRNA was examined by qPCR upon inhibition of PI3K over a time course using the approximate IC$_{50}$ of compound A (6 μM). BT474, SKBR3, and MDA453 cells showed an increase in HER3 mRNA that appeared maximal at 6 hours and was maintained up to 48 hours after the addition of the p110α inhibitor as shown in FIGS. 12A and 12C. Other PI3K pathway inhibitors induced a similar effect: 5J8, an allosteric inhibitor of AKT1/2 and the PI3K inhibitor LY294002 but not the mTOR inhibitor rapamycin also upregulated HER3 mRNA levels, as shown in FIG. 12B.

To delineate the mechanisms of upregulation of HER3 transcription, the FoxO family of Forkhead transcription factors were examined, as AKT regulates the subcellular localization of these molecules by phosphorylation thereby preventing them from translocating to the nucleus and regulating transcription. The FoxO family consists of three members, FoxO1, FoxO3a, and FoxO4 (also known as FKHR, FKHR-L1, and AFX, respectively) which bind as monomers through the consensus sequence TTGTTTAC at the promoter of target genes. In absence of AKT activity, FoxO is believed to be predominantly nuclear and therefore can activate transcription. Further, using the PROMO database (Farre, D., et al., (2003), *Nucleic Acids Res.* 31:3651-3653, & Messeguer, X., et al., (2002), *Bioinformatics* 18:333-334) multiple putative FoxO-binding sites in the HER3 (ERBB3) promoter (up to 5000 bp upstream of the transcription start site) were identified.

First, the subcellular distribution of FoxO proteins following inhibition of PI3K and AKT with compound A and 5J8, respectively was determined. FoxO4 was almost undetectable; thus FoxO1 and FoxO3a was focused on. Treatment with compound A and 5J8 resulted in accumulation of both FoxO factors in the nucleus of BT474 and MDA453 cells, sometimes accompanied by a reduction in the baseline levels in the cytosol as demonstrated in FIG. 12D. To determine if FoxO is involved in the increase of HER3 transcription subsequent to inhibition of PI3K/AKT, cells were transfected with siRNA duplexes specific for FoxO1 and FoxO3a or control siRNAs and levels of HER3 mRNA were examined by qPCR. The siRNAs reduced 70-80% the levels of both FoxO mRNAs in all three cell lines as shown in FIG. 12F. Finally, simultaneous knockdown of FoxO1 and FoxO3a abrogated the compound A-induced increase in HER3 mRNA in BT474, SKBR3, and MDA453 cells (see FIG. 12E).

Example 18

Knockdown of Compensatory Feedback to HER3 Sensitizes to PI3K Inhibitor

A detailed time-course analysis of BT474 cells treated with 6 μM compound A for 0-72 hours revealed time-dependent upregulation of total HER3, HER3 phosphorylated at Y1197 and Y1289, two PI3K binding sites, and AKT phosphorylated at its PDK1 site T308 and its TORC2 site S473. In line with the increase in total and pHER3, pAKT, and pS6 levels also recovered within 6 hours of drug treatment as shown in FIG. 13A, implying partial resurgence of the PI3K/AKT/mTOR signaling. Although pHER3 is known to activate the extracellular signal regulated kinase (ERK/MAPK) via its interaction through the adaptor protein Shc, recovery of pERK upon feedback reactivation of HER3 was not detected consistently as shown in FIG. 13A. Even though recovery of pAKT was less, feedback upregulation of total HER3 and pHER3 was more noticeable with a supra-pharmacological dose of 20 μM, further suggesting inhibition of PI3K causes feedback activation of HER3, illustrated in FIG. 13B. These data suggest that upon inhibition of PI3K with an ATP-mimetic of p110α, cells partially restore HER3 phosphorylation in order to maintain some levels of PIP3 which, in turn, counteract or limit a total inhibitory effect of compound A on the PI3K/AKT pathway.

In HER2 overexpressing cells, although not bound by any particular theory, it is believed that the main mechanism of activation of PI3K is the coupling of pHER3 to an SH2 domain in the N-terminus of p85, the regulatory subunit of PI3K. In these cells, the main tyrosine phosphorylated protein precipitated with p85 antibodies is pHER3; this association between HER3 and p85 (PI3K) depends on the catalytic activity of HER2 as it is disrupted by HER2 tyrosine kinase inhibitors (TKI). Given the above association, it was examined whether upon inhibition of PI3K and consistent with the recovery of pHER3, there was maintenance or recovery of the association between HER3 and p85. BT474 cells were treated with increasing concentrations of compound A followed by pulldown with p85 antibodies and subsequent pTyr and HER3 immunoblot analyses. Following treatment with compound A, there was a dose-dependent increase of approximately 200-kDa main pTyr band as well as other smaller and less abundant pTyr proteins as shown in FIG. 13C, marked with arrows. Consistent with previous studies, the p85-associated approximately 200-kDa band was also detected with HER3 and pHER3$^{Y1197}$ antibodies as shown in FIGS. 13D and 13F. Knockdown of HER3 with siRNA eliminated the HER3 and pHER3$^{Y1197}$ band in the p85 pulldowns of lysates from compound A-treated cells, further confirming HER3 as the p85-associated approximately 200-kDa pTyr band as shown in FIGS. 13E and 13F.

The compensatory upregulation of total HER3 and partial maintenance of pHER3 and pAKT upon inhibition of PI3K suggested that combined inhibition of PI3K and HER3 would synergistically inhibit tumor cell proliferation and/or viability. Therefore, we transfected BT474 cells with either control or HER3 siRNA duplexes, treated them with compound A, and measured cell proliferation and apoptosis. Cell proliferation in monolayer was significantly reduced by a combination of HER3 knockdown and compound A compared to either intervention alone as shown in FIGS. 13G and 13H. Consistent with a synergistic pro-apoptotic effect, only the combination induced a greater proportion of cells in the sub-G$_1$ phase DNA fraction (degraded DNA) as well as PARP cleavage as shown in FIGS. 14A and 14B, both biomarkers of cell death. Similar results were obtained with MDA453 and SKBR3 cells plated in monolayer shown in FIGS. 15B and 15D. In both of these cell lines, the combination of HER3 knockdown and compound A inhibited T308 and S473 pAKT and pS6 more effectively than each treatment alone (see FIGS. 15A and 15C).

Example 19

Recovery of HER3 Phosphorylation Depends on HER2 and is Limited by HER2 Inhibitors In breast cancer cells with HER2 gene amplification (overexpressing HER2 breast cancer), the HER2 receptor is the main tyrosine kinase that phosphorylates HER3 which, in turn, directly couples to and activates PI3K. Since compound A does not affect the catalytic activity or autophosphorylation of HER2 (see for example, FIG. 11), it is logical to speculate that in HER2-overexpressing cells, HER2 remains as the tyrosine kinase maintaining and/or increasing the phosphorylation of HER3 upon inhibition of PI3K. Therefore, the effect of compound A in combination with the HER2 antibody trastuzumab or the HER2 reversible tyrosine kinase inhibitor lapatinib was examined with respect to cell proliferation and HER3 phosphorylation. In BT474 cells, either of these combinations was significantly more effective at inhibiting cell proliferation than compound A or the HER2 inhibitor alone as shown in FIGS. 16A and 16B. (As shown in FIG. 16, Lap is lapatinib, and Tras is trastuzumab). Consistent with this result, PARP cleavage was only observed in cells treated with the combination but not in cells treated with a single inhibitor shown in FIG. 16C. Similar results were observed with MDA453 and SKBR3 cells, two other HER2-overexpressing lines shown in FIGS. 17A-17D.

Without wishing to be bound to any particular theory, it was believed that the synergistic action of compound A in combination with lapatinib or trastuzumab on cell growth was due to a reduction in the recovery of pHER3 but not to inhibition of HER3 mRNA transcription. Experiments were performed using quantitative PCR (qPCR) for HER3 in RNA isolated from BT474 cells treated with compound A plus lapatinib or compound A plus trastuzumab or each inhibitor alone. Treatment with trastuzumab alone did not increase in HER3 mRNA levels but in combination with compound A, it enhanced the upregulation of HER3 mRNA induced by the PI3K inhibitor as shown in FIG. 16D. Lapatinib alone markedly induced HER3 mRNA, this action, as in compound A, is the result of PI3K inhibition followed by derepression of FoxO-mediated transcription. The effect of lapatinib was more prominent when used in combination with compound A as shown in FIG. 16D, probably as the result of a more pronounced inhibition of PI3K/AKT compared to either agent alone. In contrast to the mRNA data, treatment with the combination of compound A plus lapatinib or compound A plus trastuzumab for 24 h attenuated the recovery of pHER3 compared to cells treated with compound A alone as shown in FIG. 16E, suggesting that inhibition of the HER2 kinase with lapatinib or of ligand-independent HER2/HER3 dimers with trastuzumab limits the activating input of HER2 to HER3.

Example 20

Combined Inhibition of HER2 and PI3K is Synergistic Against HER2-Dependent Xenografts Experiments were further performed to determine whether combined inhibition of PI3K and the feedback recovery of pHER3 will be synergistic against HER2-dependent xenografts. Thus, experiments were performed to test if the addition of trastuzumab or lapatinib would enhance the anti-tumor effect of compound A against BT474 xenografts in vivo. Athymic mice bearing established BT474 xenografts were randomized to therapy with compound A, lapatinib, trastuzumab or compound A plus each HER2 antagonist/inhibitor for 4 weeks. Each monotherapy significantly delayed tumor growth with trastuzumab being the only agent that induced a complete tumor response in 1/8 mice. Both combinations were superior to the respective drugs given alone. The combination of lapatinib plus compound A significantly reduced tumor volume, while the combination of compound A and trastuzumab induced complete tumor regressions (FIG. 18A). There was no significant drug-related toxicity in any of the treatment arms.

Using immunohistochemistry (IHC), experiments were performed to examine pharmacodynamic biomarkers of target inactivation in xenografts after 28 days of treatment. Levels of HER3 by IHC did not change in any of the treatment arms. However, consistent with data shown in FIG. 16E, compound A did not reduce membrane pHER3, lapatinib was more effective than trastuzumab in reducing pHER3 in tumor content, and the combination of compound A plus trastuzumab was clearly more inhibitory for pHER3 levels than each drug given alone as shown in FIGS. 18B and 18C. The oncogenic action of AKT has been shown to correlate with the levels of both cytoplasmic and nuclear $pAKT^{S473}$. Therefore, experiments were performed to quantify differences in $pAKT^{S473}$ expression in both cytoplasmic and nuclear compartments in xenograft sections. In line with differences in tumor growth among the treatment arms, nuclear pAKT was lower in xenografts treated with compound A plus lapatinib or compound A plus trastuzumab compared each to tumors treated with single agent inhibitor. Of all three drugs, compound A was the only one that statistically inhibited nuclear pAKT levels. There were no detectable changes in the cytoplasmic content of pAKT as shown in FIGS. 18B and 18C. Overall, these results suggest that combined inhibition of HER2 and PI3K in HER2-overexpressing xenografts is required to maximally inhibit signaling output of the PI3K/AKT pathway. The levels of total HER3 observed after 28 days of treatment as shown in FIG. 18B, top row, did not reproduce the upregulation of HER3 mRNA and protein shown in cells in culture after shorter term assays. While not wishing to be bound to any particular theory, it is believed that this could be the result of the late timing (28 days) of the analysis of the xenografts.

Example 21

Inhibition of PI3K Induces RTKs Other than HER3

FIG. 13C shows an increase in detectable levels of p85-associated pTyr proteins upon compound A-mediated inhibition of PI3K in BT474 cells. Results provided herein also demonstrate a prominent approximately 200-kDa pTyr band that coprecipitates with p85 (PI3K) is recognized by HER3 and pHER3 antibodies as shown in FIGS. 13D-13F, and is eliminated upon knockdown of HER3 with siRNAs as shown in FIGS. 13E and 13F. However, the dose-dependent increase in the lower-MW pTyr bands when PI3K is inhibited (shown in FIG. 13C) suggests an increase in p85-associated proteins other than HER3. In addition, results provided in FIG. 19A show that upon knockdown of HER3 with siRNA, there is still an increase in the p85-associated approximately 200-kDa band, leading further to speculation of the presence of other compensatory p85-associated tyrosine kinases and/or adaptors aimed at partially maintaining PI3K active. In order to test this hypothesis, two different concentrations (high and low) of lysates from BT474 cells treated over a 24-h time course with compound A were hybridized to arrays containing probes for 42 different receptors of tyrosine kinase (RTKs). Treatment with compound A resulted in an increase in not only HER3, but also multiple other RTKs including EGFR, ERBB4/HER4, fibroblast growth factor receptor (FGFR)-1, -2, -3, and -4, insulin receptor (InsR), insulin-like growth factor-I receptor (IGF-IR), ephrin receptor A1 (EphA1), endothelium-specific receptor tyrosine kinase 2 (Tie2), neurotrophic tyrosine kinase receptor type 1 (TrkA), Fms like tyrosine kinase 3 receptor (Flt3), tyrosine-protein kinase Mer (MER) and macrophage-stimulating protein receptor (MSPR), as shown in FIGS. 19B and 19C. Several of these RTKs migrate at approximately 200 kDa, such as EGFR, ERBB4, and InsR, and may explain the persistent high-MW pTyr band associated with p85 in cells where HER3 has been knocked down as shown in FIG. 19A. qPCR was performed and analyzed to determine whether upregulation of these RTKs occurred at the transcriptional level. In BT474 cells following treatment with compound A, there was an increase in ERBB4, IGF-IR, InsR, EphA1, FGFR2, and FGFR3 mRNAs, with IGF-IR and InsR being the most prominent, as shown in FIG. 19D.

Using the PROMO database, multiple putative FoxO-binding sites in the InsR, IGF-IR, and FGFR2 gene promoters (up to 5000 bp upstream of the transcription start site) were identified. Consistent with FoxO-mediated regulation, knockdown of FoxO1 and FoxO3a with siRNA limited the induction of IGF-IR, InsR, and FGFR2 mRNAs in BT474 cells treated with compound A as shown in FIG. 19E. To determine the potential therapeutic relevance of this feedback, experiments were performed to examine whether depletion of these RTKs sensitized cells to the PI3K inhibitor. For this purpose, HER2-overexpressing BT474 and MDA453 cells and PI3K-mutant MCF7 cells were transfected with siRNA duplexes against IGF-IR and InsR followed by treatment with compound A. Knockdown of both RTKs was effective in all three cell lines as shown in FIGS. 20A and 20B. Depletion of either RTK sensitized all three cells to compound A-mediated growth inhibition as shown in FIGS. 20C-20E. Taken together, these data suggest that cancer cells limit the inhibition of PI3K by feedback mechanisms that upregulate multiple RTKs or adaptors capable of engaging p85 and thus activating PI3K. In turn, these molecules partially maintain PI3K/AKT signaling and over time and limit the antitumor effect of therapeutic inhibitors of the PI3K/AKT pathway given alone.

Example 22

Cancer Treatments Employing a Compound of Formula I and an Inhibitor of HER2 and/or HER3

The present invention is not limited to a particular mechanism. Indeed, an understanding of the mechanism is not necessary to practice the present invention. Cellular effects of PI3K inhibition with the small molecule compound A in a panel of cancer cell lines suggest PI3K dependence. The illustrative experiments provided herein have examined PI3K inhibition and its cellular effects in breast cancer cells with HER2 gene amplification. At doses that abrogated pAKT, pS6 and cell growth, inhibition of PI3K with compound A resulted in time-dependent, feedback upregulation of HER3 expression and phosphorylation. In turn, pHER3 engaged p85, activated PI3K, and induced partial recovery of pAKT and pS6 as shown in FIGS. 11, 13, and 15. AKT has been shown to phosphorylate the FoxO family of transcription factors and thereby prevent their nuclear translocation. Therefore, the initial inhibition of AKT resulted in accumulation of FoxO3a and FoxO I proteins in the nucleus as shown in FIG. 12D. Knockdown of both FoxO proteins suppressed the induction of HER3 mRNA upon inhibition of PI3K/AKT with compound A (FIG. 12E). While not wishing to be bound to any particular theory, it is believed that the results provided herein suggest that HER3 is downregulated by PI3K/AKT and are consistent with a recent observation in ovarian cancer cells where the PI3K inhibitor GDC-0941 blocked downregulation of the HER3 mRNA upon treatment with the HER3 activating ligand heregulin.

Upregulation of HER3 expression and phosphorylation limited the antitumor effect of the PI3K inhibitor. This is supported by the fact that siRNA-mediated knockdown of HER3 sensitized to compound A-induced cell death, as shown in FIG. 14, and enhanced compound A-mediated inhibition of pAKT and pS6, as shown in FIGS. 15A and 15C. This result has particular relevance for HER2-overexpressing cells where the kinase-deficient HER3 co-receptor, once dimerized with and activated by the HER2 kinase, is the key mechanism engaging p85 and activating PI3K. Indeed, breast cancer cells with HER2 amplification, are particularly sensitive to apoptosis induced by PI3K inhibitors. Further, this association of HER2/HER3 dimer with p85 has been found by others to be essential for the viability of HER2-dependent cells and, therefore, sustained inhibition of the output of HER2/HER3 to PI3K is required for the antitumor effect of HER2 inhibitors.

As inhibition of PI3K did not affect the HER2 kinase, HER3 phosphorylation was maintained and further increased, remaining associated with p85 in compound A-treated cells as shown in FIGS. 13D-13F. Addition of the HER2 antibody trastuzumab or the HER2TKI lapatinib attenuated the rebound of pHER3 upon treatment with compound A as shown in FIG. 16E, even though HER3 transcription was further increased by the combinations of inhibitors compared to each inhibitor alone (see for example, FIG. 16D). Further, both combinations of compound A with each HER2 antagonist were more effective than each inhibitor alone at reducing pHER3 and pAKT levels in HER2-overexpressing xenografts and inhibiting their growth as shown in FIG. 18. These data strongly suggest that, in HER2-overexpressing cells, inhibition of the HER2 kinase with lapatinib or disruption of ligand-independent HER2/HER3 dimers with trastuzumab limits the activating input of HER2 to the upregulated HER3 co-receptor when PI3K is inhibited.

Figure 1B:
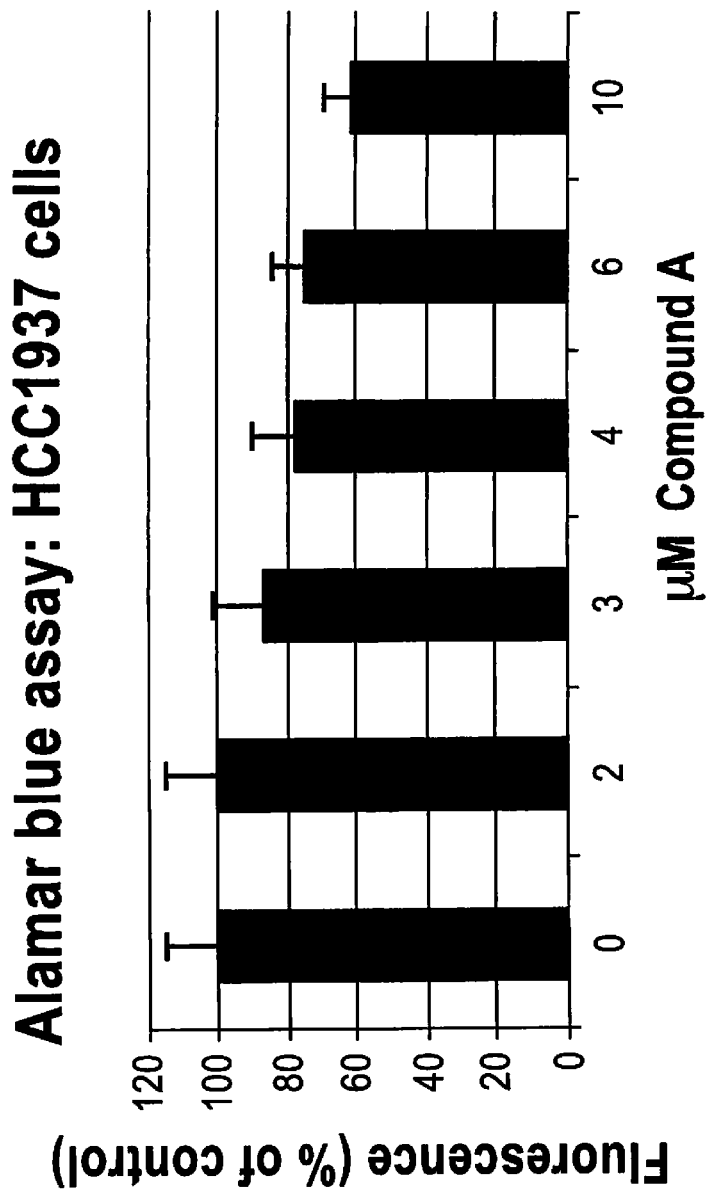
Figure 2:
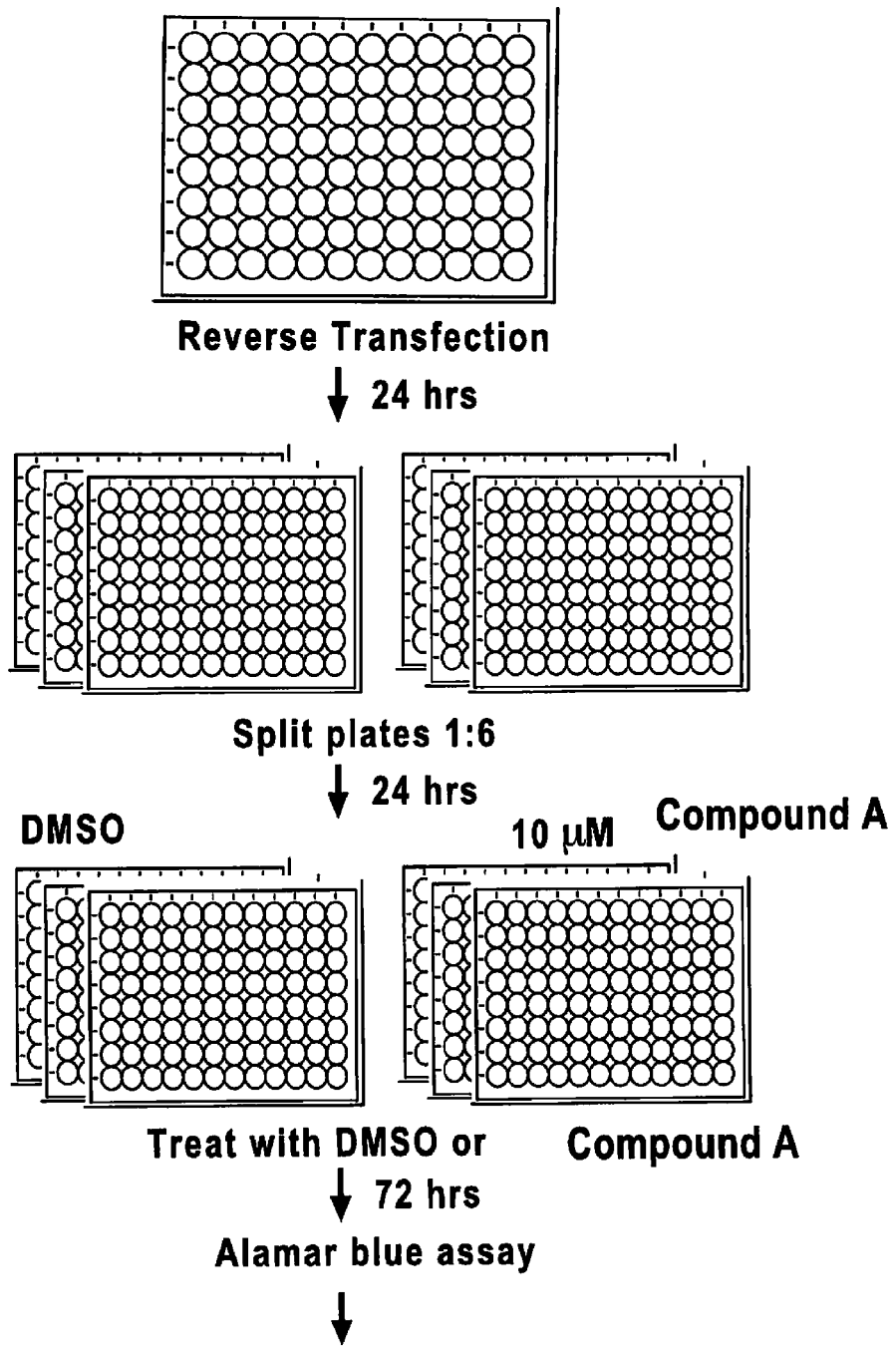

The data presented herein are reminiscent of reports where inhibition of mTOR with rapamycin or rapalogs relieves suppression of insulin and IGF-I signaling via upregulation of IRS-1, thereby activating PI3K/AKT and ERK. Furthermore, dual inhibitors of TORC1 and PI3K have also been shown to induce HER3 expression. However, the TORC1 inhibitor rapamycin did not mirror the effect of compound A or the AKT inhibitor 5J8 on HER3 mRNA (FIG. 1B). Similarly, treatment with the TORC1 inhibitor RAD001 (everolimus) and the MEK inhibitor CI-1040 did not upregulate HER3 mRNA/protein or pHER3 (data not shown). This suggests that the effects of AKT inhibition on FoxO-mediated feedback upregulation of HER3 are not mediated by TORC1.

The experimental data provided herein have implications that apply to therapeutic inhibitors of RTKs that rely on PI3K/AKT signaling such as HER2. For example, trastuzumab when given alone is a weak inhibitor of AKT as shown in FIGS. 18B and 18C, thus not relieving AKT-mediated suppression of FoxO-induced HER3 transcription. On the other hand, the prompt and stronger inhibition of pAKT with the TKI lapatinib results in strong upregulation of HER3 expression in BT474 as shown in FIG. 16D, SKBR3, and SUM225 cells (data not shown). The combination of lapatinib and compound A was synergistic in vitro as shown in FIG. 16A and FIGS. 16A and 16C and in vivo as shown in FIG. 18A, but was also the most potent at inducing HER3 mRNA as shown in FIG. 16D. Despite the weaker inhibition of pAKT by trastuzumab, the combination of compound A and trastuzumab appeared to be superior to the combination of compound A and lapatinib at inhibiting pAKT and growth of BT474 xenografts. While not wishing to be bound by any particular theory, it is believed that these differences may be explained by (1) the ability of trastuzumab to engage immune effectors of antibody-dependent, cell-mediated cytotoxicity (ADCC) and (2) the relative inability of trastuzumab to derepress compensatory HER3 expression.

Experimental evidence provided herein suggests that an increase in tyrosine phosphorylated proteins associated with p85 upon inhibition of PI3K with compound A. Indeed, a p85-associated approximately 200-kDa P-Tyr band that comigrates with HER3 was still detectable in compound A-treated BT474 cells after HER3 had been knockdown with siRNA as shown in FIG. 19A. This result suggests the presence of other compensatory p85-associated RTKs and/or adaptors aimed at partially maintaining PI3K active. Using RTK arrays and siRNA knockdown experiments, data provided the finding of FoxO-dependent upregulation of InsR, IGF-IR, and FGFR2 upon inhibition of PI3K/AKT with compound A as shown in FIGS. 19C-19E. In several cell lines, knockdown of InsR and IGF-IR sensitized to the PI3K inhibitor as shown in FIGS. 20C-20E. One of these, the MCF-7 cell line, harbors an activating mutation in PIK3CA but not HER2 gene amplification. Interestingly, the gene promoters of these three RTKs contain putative FoxO-binding sites (PROMO analysis). These data imply that PI3K inhibition could be associated with the induction of expression and phosphorylation of a group of RTKs over a range of tumor cells.

These findings have several clinical implications. In cancer cells, therapeutic antagonists of the PI3K pathway will inhibit AKT and relieve suppression of RTK expression and their activity. Relief of this feedback limits the sustained inhibition of the pathway and attenuates the therapeutic response to these agents. Relief of this feedback is commensurate with the magnitude and intensity of inhibition of AKT and cannot be applied to all types of PI3K pathway antagonists (i.e., trastuzumab vs. lapatinib vs. compound A). Whether relief of this feedback also occurs in normal tissues and/or ameliorates drug-related toxicities requires further research. While not bound by any specific theory, it is believed that in HER2-overexpressing cells, upregulated expression of HER3 and HER2-induced phosphorylation of HER3 are the main mechanisms that counteract inhibition of PI3K/AKT. Therefore, PI3K inhibitors should be used in combination with HER2 antagonists in breast cancers of this subtype. The most appropriate anti-cancer agents to combine with PI3K/AKT inhibitors in other PI3K-dependent cancers without HER2 gene amplification will depend on the main compensatory feedback mechanisms that are activated upon inhibition of this pathway.

Example 23

Evaluation of Combination of Compound A and MM-121 in Non-HER2 Amplified Tumors

The present study was designed to evaluate the efficacy of a combination of compound A and MM-121 in treating non-HER2 amplified tumors. The lung cancer cell line A549 was selected for this study. In this regard, A549 cells do not express high HER2 levels, as shown in Bunn et al., Clinical Cancer Research, 7:3239-3250 (2001). Lung A549 cells were implanted s.c. in female Swiss nude mice using standard techniques. The A549 xenografts were treated when the tumors reached a mean volume of 152.9±94.7 mm3, with four combination conditions, employing two doses of MM-121 and compound A, using seven mice per group. Control groups were left untreated. Compound A was administered at 100 or 30 mg/kg/adm, by PO daily administrations, for 32 consecutive days (from D37 to D68: Q1Dx32). MM-121 was administered at 5 or 30 mg/kg/inj by IP route once every 3 days (D37, D40, D43, D46, D49, D52, D55, D58, D61, D64 and D67; Q3Dx11). The four combination conditions were as follows: compound A at 100 mg/kg/adm, daily administered with MM-121 at 30 mg/kg once a day every three days; compound A at 100 mg/kg/adm, daily administered with MM-121 at 5 mg/kg once a day every three days; compound A at 30 mg/kg/adm, daily administered with MM-121 at 30 mg/kg once a day every three days; and compound A at 30 mg/kg/adm, daily administered with MM-121 at 5 mg/kg once a day every three days.

For the evaluation of anti-tumor activity of conjugates, animals were weighed daily and tumors were measured twice weekly by caliper. A dosage producing a 20% weight loss at nadir (mean of group) or a 15% weight loss (mean of group) three successive times or drug deaths, was considered an excessively toxic dosage. Animal body weights included the tumor weights. Tumor weights were calculated using the formula mass (mg)=[length (mm)×width (mm)2]/2. The primary efficacy end points are $\Delta T/\Delta T$, percent median regression, partial and complete regressions (PR and CR), and Tumor free survivors (TFS). Changes in tumor volume for each treated (T) and control (C) were calculated for each tumor by subtracting the tumor volume on the day of first treatment (staging day) from the tumor volume on the specified observation day. The median $\Delta T$ was calculated for the treated group, and the median $\Delta T$ was calculated for the control group. Then the ratio $\Delta T/\Delta T$ was calculated and expressed as a percentage: $\Delta T/\Delta T$=(delta T/delta C)×100. A dose is considered therapeutically active when $\Delta T/\Delta T$ is lower than 40% and very active when $\Delta T/\Delta T$ is lower than 10%. If $\Delta T/\Delta T$ is lower than 0, the dose is considered as highly active, and the percentage of regression is dated. Percent tumor regression is defined as the percent of tumor volume decrease in the treated group at a specified observation day compared to its volume on the first day of first treatment. At a specific time point and for each animal, percent regression is calculated. The median percent regression is then calculated for the group. % regression (at t)=[volume$_{t0}$−volume$_t$/volumen$_{t0}$]×100. Partial regression (PR): Regressions are defined as partial if the tumor volume decreases to 50% of the tumor volume at the start of treatment. Complete regression (CR): Complete regression is achieved when tumor volume=0 mm$^3$ (CR is considered when tumor volume cannot be recorded). TFS: Tumor free is defined as the animals with undetectable tumors at the end of the study (>100 days post last treatment).

Results are presented in Table 4. Based on the mean body weight change calculated between D37 and D68, a dose dependant body weight loss was observed for mice treated with compound A at 30 and 100 mg/kg (−7.3 and −10.3% at nadir, respectively). In the same manner a dose dependant body weight loss was observed for mice treated with MM-121 at 5 and 30 mg/kg (−3.9 and −6.2% at nadir, respectively) followed by a complete recovery. A dose dependant body weight loss was observed for mice treated with compound A at 30 and 100 mg/kg in combination with MM-121 at 5 or 30 mg/kg when compared to mice treated with compound A or MM-121 administered alone at the same respective doses (−8.4, −11.4, −12.4 and −12.9% at nadir, respectively). No significant difference on body weight loss was observed for compound A at 100 mg/kg in combination with MM-121 at 5 or 30 mg/kg compared to compound A at the same dose alone. Compound A and MM-121 combination did not induce added toxicity.

MM-121 was marginally active at 30 mg/kg with a ΔT/ΔT of 31% and inactive at 5 mg/kg with a ΔT/ΔT of 66%. Compound A was very active at 30 mg/kg with a ΔT/ΔT of 5% ($p<0.05$ vs control) and highly active at 100 mg/kg with a ΔT/ΔT of −4% ($p<0.001$) and tumor regression of 15%. Compound A at 100 mg/kg in combination with MM-121 at 30 mg/kg was highly active with a ΔT/ΔT of −20% ($p<0.001$ vs control) and tumor regression of 39%. This combination was more active than the best single agent (compound A at 100 mg/kg, $p<0.01$) indicating a therapeutic synergy in these combination conditions. The combination of compound A at 100 mg/kg with MM-121 at 5 mg/kg was highly active with a ΔT/ΔT of −17% ($p<0.001$ vs control) and tumor regression of 41%. The combination of compound A at 30 mg/kg with MM-121 at 30 mg/kg was highly active with a ΔT/ΔT of −7% ($p<0.001$ vs control) and tumor regression of 15%. This combination was more active than the best single agent (compound A at 30 mg/kg, $p<0.01$) indicating a therapeutic synergy in these combination conditions. The combination of compound A at 30 mg/kg with MM-121 at 5 mg/kg was active with a ΔT/ΔT of 16% ($p<0.01$ vs control).

In conclusion, the combination of the two agents co-administered at therapeutic doses in mouse bearing A549 tumor xenografts which do not have amplified or overexpressed HER2, did not show added toxicity as assessed by mortality and body weight changes. MM-121 single agent exhibited a marginal activity at 30 mg/kg, and compound A single agent exhibited high activity at 30 and 100 mg/kg. A therapeutic synergy was observed with the combination between compound A at 100 mg/kg and MM-121 at 30 mg/kg and with the combination between compound A at 30 mg/kg and MM-121 at 30 mg/kg compared to best single agent for both conditions (compound A at 100 mg/kg, $p<0.01$ and compound A at 30 mg/kg, $p<0.01$, respectively).

In addition, HER3 modulation by compound A and MM-121 was evaluated for each compound at two doses and for one combination condition, on measurable lung A549 tumors implanted SC in female Swiss nude mice. Briefly, mice bearing measurable lung A549 tumors implanted SC have been left untreated or treated either by MM121 as a single agent (at dose of 5 mg/kg or 30 mg/kg, one administration) or by compound A as a single agent (at dose of 30 mg/kg or 100 mg/kg, daily administrations) or by a combination of both (at 30 mg/kg for MM121 and 100 mg/kg for compound A). The HER3 expression level in xenografted tumors has been followed for up to 96 hours.

The results in Table 5 show that PI3K inhibition by compound A induces a slight increase of HER3 expression in A549 lung model, while MM-121 treatment decreases significantly HER3 expression. The combined treatment with compound A and MM-121 resulted in a significant decrease of HER3. By downregulating HER3 levels, MM-121 enhances the inhibition of PI3K-AKT pathway and thus the anti-tumor activity of compound A.

TABLE 4

Antitumor activity of combination of Compound A and MM-121 in nude mice bearing subcutaneous A-549 human lung xenografts

| Agent (batch) | Route/ Dosage in mL/kg per injection | Dosage in mg/kg per injection (total dose) | Schedule | Drug death (Day of death) | Average body weight change in % per mouse at nadir (day of nadir) | Median ΔT/ΔC in % day 68 | Median % of regression on day 68 | Biostatistic p value [a] | Biological response at day 68 |
|---|---|---|---|---|---|---|---|---|---|
| MM121 | IP | 30 (330) | Q3Dx11 | 0/7 | −6.15 (43) | 31 | — | 0.3701 | Active |
| MM121 | IP | 5 (55) | Q3Dx11 | 0/7 | −3.87 (43) | 66 | — | 1 | Inactive |
| Compound A | PO | 100 (3200) | Q1Dx32 | 0/7 | −10.25 (65) | −4 | 15 | <.0001 | Highly active |
| Compound A | PO | 5 (160) | Q1Dx32 | 0/7 | −7.34 (65) | 5 | — | 0.0184 | Very active |
| MM121 | IP | 30 (330) | Q3Dx11 | 0/7 | −12.90 (43) | −20 | 39 | <.0001 | Highly active |
| Compound A | PO | 100 (3200) | Q1Dx32 | | | | | | |
| MM121 | IP | 30 (330) | Q3Dx11 | 0/7 | −11.43 (65) | −7 | 15 | <.0001 | Highly active |
| Compound A | PO | 30 (960) | Q1DX32 | | | | | | |
| MM121 | IP | 5 (55) | Q3Dx11 | 0/7 | −12.38 (65) | −17 | 41 | <.0001 | Highly active |
| Compound A | PO | 100 (3200) | Q1Dx32 | | | | | | |
| MM121 | IP | 5 (55)5 | Q3Dx11 | 0/7 | −8.42 (65) | 16 | — | 0.0047 | Active |
| Compound A | PO | 30 (960) | Q1Dx32 | | | | | | |
| Control | — | — | — | 0/7 | −5.04 (43) | — | — | — | — |

[a] p-value: Dunnett's test versus control after 2-way Anova with repealed measures on rank transformed changes of tumour volume from baseline followed by Winer Analysis at each day

TABLE 5

Modulation of HER3 expression by Compound A and MM-121 or a combination of both compounds in A549 human lung xenografts.

| Dose of compound | Schedule of administration | Time of sampling after the last administration (h) | Change vs Control (%) |
|---|---|---|---|
| Control | | 4 | 0 |
| MM121 5 mg/kg | IP: Q1Dx1 | 4 | −48 |
| | | 24 | −63 |
| | | 48 | −27 |
| | | 72 | −9 |
| | | 96 | −25 |
| MM121 30 mg/kg | IP: Q1Dx1 | 4 | −74 |
| | | 24 | −41 |
| | | 48 | −71 |
| | | 72 | −75 |
| | | 96 | −76 |

TABLE 5-continued

Modulation of HER3 expression by Compound A and MM-121 or a combination of both compounds in A549 human lung xenografts.

| Dose of compound | Schedule of administration | Time of sampling after the last administration (h) | Change vs Control (%) |
|---|---|---|---|
| Compound A 30 mg/kg | PO: Q1Dx1 | 4 | −3 |
|  |  | 24 | 12 |
|  | PO: Q1Dx2 | 24 | 23 |
|  | PO: Q1Dx3 | 24 | 27 |
| Compound A 100 mg/kg | PO: Q1Dx1 | 4 | 10 |
|  |  | 24 | 19 |
|  | PO: Q1Dx2 | 24 | 45 |
|  | PO: Q1Dx3 | 24 | 37 |
| MM121 30 mg/kg + Compound A 100 mg/kg | IP: Q1Dx1 + | 4 | −81 |
|  | PO: Q1Dx1 | 24 | −70 |
|  | IP: Q1Dx1 + PO: Q1Dx2 | 24 | −60 |
|  | IP: Q1Dx1 + PO: Q1Dx3 | 24 | −68 |
|  | IP: Q1Dx1 + PO: Q1Dx3 | 48 | −75 |

Embodiments

1. A method for treating cancer in a patient comprising co-administering a therapeutically effective amount of a compound of formula I and a therapeutically effective amount of a HER2 and/or HER3 inhibitor to said patient.

2. The method according to embodiment 1, wherein the compound of formula I is a compound of:

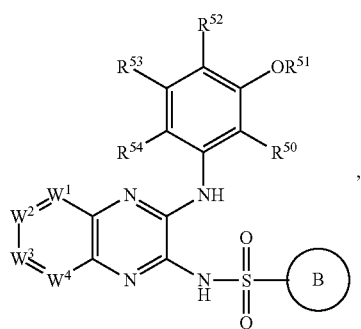

I or a single isomer thereof, where the compound is optionally as a pharmaceutically acceptable salt, additionally optionally as a hydrate, and additionally optionally as a solvate thereof; or administering a pharmaceutical composition comprising a therapeutically effective amount of a compound of formula I and a pharmaceutically acceptable carrier, excipient, or diluent in combination with one or more inhibitors of HER3, HER2, MSPR, Axl, MAP3K (ERK, JNK, and p38 MAPK), MEKK kinases/kinase receptors, INSR, IGF-IR, and FGFR2, where the compound of formula I is that wherein:

$W^1$, $W^2$, $W^3$, and $W^4$ are —C($R^1$)═; or one or two of $W^1$, $W^2$, $W^3$, and $W^4$ are independently —N═ and the remaining are —C($R^1$)═; and where each $R^1$ is independently hydrogen, alkyl, haloalkyl, nitro, alkoxy, haloalkoxy, halo, hydroxy, cyano, amino, alkylamino, or dialkylamino;

$R^{51}$ is hydrogen or alkyl;

$R^{52}$ is hydrogen or halo;

$R^{50}$, $R^{53}$, and $R^{54}$ are independently hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$N$R^{55}R^{55a}$, or alkylcarbonylamino, and $R^{55}$ and $R^{55b}$ are independently hydrogen, alkyl, or alkenyl, and $R^{55a}$ is hydrogen, alkyl, alkenyl, hydroxy, or alkoxy; or $R^{53}$ and $R^{54}$ together with the carbons to which they are attached form a 5- or 6-membered heteroaryl or 5- or 6-membered heterocycloalkyl;

B is phenyl substituted with $R^{3a}$ and optionally further substituted with one, two, or three $R^3$; or B is heteroaryl optionally substituted with one, two, or three $R^3$;

$R^{3a}$ is cyano, hydroxyamino, carboxy, alkoxycarbonyl, alkylamino, dialkylamino, alkylcarbonyl, haloalkoxy, alkylsulfonyl, aminoalkyloxy, alkylaminoalkyloxy, or dialkylaminoalkyloxy; or a) —N($R^7$)C(O)—$C_1$-$C_6$-alkylene-N($R^{7a}$)($R^{7b}$), where $R^7$ is hydrogen, alkyl, or alkenyl, and $R^{7a}$ and $R^{7b}$ are independently hydrogen, alkyl, alkenyl, hydroxyalkyl, haloalkyl, alkoxy, alkoxyalkyl, aminoalkyl, alkylaminoalkyl, dialkylaminoalkyl, cycloalkyl, cycloalkylalkyl, heterocycloalkyl, heterocycloalkylalkyl, heteroaryl, heteroarylalkyl, aryl, arylalkyl, or arylalkyloxy, and where the aryl, cycloalkyl, heterocycloalkyl and heteroaryl rings in $R^{7a}$ and $R^{7b}$ (either alone or as part of arylalkyl, cycloalkylalkyl, heterocycloalkylalkyl, and heteroarylalkyl) are independently optionally substituted with 1, 2, or 3 groups independently selected from alkyl, amino, alkylamino, dialkylamino, hydroxy, halo, alkoxy, alkylthio, and oxo;

b) —C(O)N$R^8R^{8a}$, where $R^8$ is hydrogen, hydroxy, alkoxy, alkyl, alkenyl, haloalkyl, or haloalkoxy, and $R^{8a}$ is hydrogen, alkyl, alkenyl, hydroxyalkyl, cyanoalkyl, alkoxyalkyl, alkylthioalkyl, heterocycloalkyl, heterocycloalkylalkyl, cycloalkyl, cycloalkylalkyl, heteroaryl, heteroarylalkyl, aryl, or arylalkyl, and where the aryl, cycloalkyl, heteroaryl, and heterocycloalkyl rings in $R^{8a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, halo, haloalkyl, haloalkoxy, hydroxy, hydroxyalkyl, oxo, amino, alkylamino, dialkylamino, alkylcarbonyl, aminoalkyl, alkylaminoalkyl, dialkylaminoalkyl, alkoxycarbonyl, and —C(O)H;

c) —N$R^9$C(O)$R^{9a}$, where $R^9$ is hydrogen, hydroxy, alkoxy, alkyl, alkenyl, haloalkyl, or haloalkoxy, and $R^9$ is hydrogen, $C_2$-$C_6$-alkyl, alkenyl, hydroxyalkyl, alkoxyalkyl, cycloalkyl, cycloalkylalkyl, heterocycloalkyl, heterocycloalkylalkyl, heteroaryl, heteroarylalkyl, aryl, or arylalkyl, and where the aryl, cycloalkyl, heteroaryl, and heterocycloalkyl rings in $R^{9a}$ (either alone or as part of arylalkyl, cycloalkylalkyl, heterocycloalkylalkyl, and heteroarylalkyl) are independently optionally substituted with 1, 2, or 3 groups independently selected from alkyl, alkenyl, alkoxy, hydroxy, hydroxyalkyl, halo, haloalkyl, haloalkoxy, oxo, amino, alkylamino, dialkylamino, alkylcarbonyl, alkoxycarbonyl, —C(O)H, aryl (optionally substituted with one or two halo), arylalkyl, heteroaryl, heteroarylalkyl, heterocycloalkyl, heterocycloalkylalkyl, cyloalkyl, cyloalkylalkyl, and cycloalkylcarbonyl;

d) —C(O)N($R^{10}$)—$C_1$-$C_6$-alkylene-N($R^{10a}$)$R^{10b}$, where $R^{10a}$ is hydrogen, hydroxy, alkoxy, alkyl, alkenyl, haloalkyl, aminoalkyl, alkylaminoalkyl, dialkylaminoalkyl, or hydroxyalkyl, and $R^{10}$ and $R^{10b}$ are indepen-

503 dently hydrogen, alkyl, alkenyl, haloalkyl, aminoalkyl, alkylaminoalkyl, dialkylaminoalkyl, or hydroxyalkyl;

e) —NR$^{11}$C(O)NR$^{11a}$R$^{11b}$, where R$^{11a}$ is hydrogen, alkyl, alkenyl, hydroxy, or alkoxy, and R$^{11}$ and R$^{11b}$ are independently hydrogen, alkyl, alkenyl, aminoalkyl, alkylaminoalkyl, or dialkylaminoalkyl;

f) —C(O)R$^{12}$, where R$^{12}$ is heterocycloalkyl optionally substituted with 1, 2, or 3 groups selected from alkyl, oxo, amino, alkylamino, and heterocycloalkylalkyl;

g) —NR$^{13}$C(O)OR$^{13a}$, where R$^{13}$ is hydrogen, alkyl, or alkenyl, and R$^{13a}$ is aminoalkyl, alkylaminoalkyl, dialkylaminoalkyl, aryl, or arylalkyl;

h) —C(O)N(R$^{14}$)N(R$^{14a}$)(R$^{14b}$), where R$^{14}$, R$^{14a}$, and R$^{14b}$ are independently hydrogen, alkyl, or alkenyl;

i) —S(O)$_2$N(R$^{15}$)—C$_1$-C$_6$-alkylene-N(R$^{15a}$)R$^{15b}$, where R$^{15}$, R$^{15a}$, and R$^{15b}$ are independently hydrogen, alkyl, or alkenyl;

j) —C(O)N(R$^{16}$)—C$_1$-C$_6$-alkylene-C(O)OR$^{16a}$, where R$^{16}$ is hydrogen, alkyl, or alkenyl, and R$^{16a}$ is alkyl or alkenyl;

k) heteroaryl optionally substituted with one or two aminoalkyl, alkylaminoalkyl, or dialkylaminoalkyl;

l) —N(R$^{17}$)—C(=N((R$^{17b}$)(R$^{17a}$))(NR$^{17c}$R$^{17d}$) where R$^{17}$, R$^{17a}$, R$^{17b}$, R$^{17c}$, and R$^{17d}$ are independently hydrogen, alkyl, or alkenyl;

m) —N(R$^{18}$)C(O)—C$_1$-C$_6$-alkylene-N(R$^{18b}$)C(O)R$^{18a}$, where R$^{18a}$ is hydrogen, alkyl, alkenyl, or alkoxy, and R$^{18}$ and R$^{18b}$ are independently hydrogen, alkyl, or alkenyl;

n) —C(O)N(R$^{19}$)—C$_1$-C$_6$-alkylene-C(O)R$^{19a}$, where R$^{19}$ is hydrogen, alkyl, or alkenyl, and R$^{19a}$ is amino, alkylamino, dialkylamino, or heterocycloalkyl;

o) —N(R$^{20}$)C(O)—C$_1$-C$_6$-alkylene-C(O)R$^{20a}$, where R$^{20}$ is hydrogen, alkyl, or alkenyl, and R$^{20a}$ is cycloalkyl or heterocycloalkyl;

p) —NR$^{21}$S(O)$_2$—C$_1$-C$_6$-alkylene-N(R$^{21b}$)R$^{21a}$, where R$^{21}$ is hydrogen, alkyl, or alkenyl, and R$^{21a}$ and R$^{21b}$ are independently hydrogen, alkyl, or alkenyl;

q) —N(R$^{22}$)C(O)—C$_1$-C$_6$-alkylene-N(R$^{22b}$)—N(R$^{22c}$)(R$^{22a}$), where R$^{22}$, R$^{22a}$ and R$^{22b}$ are independently hydrogen, alkyl, or alkenyl;

r) —C$_0$-C$_6$-alkylene-N(R$^{23}$)—C$_1$-C$_6$-alkylene-N(R$^{23b}$)R$^{23a}$, where R$^{23}$, R$^{23a}$ and R$^{23b}$ are independently hydrogen, alkyl, or alkenyl; or s) —NR$^{24}$C(O)—C$_1$-C$_6$-alkylene-OR$^{24a}$, where R$^{24}$ is hydrogen, alkyl, or alkenyl, and R$^{24a}$ is alkoxyalkyl or aryl optionally substituted with one or two halo or alkyl; and wherein each of the alkylene in R$^{3a}$ is independently optionally further substituted with 1, 2, 3, 4, or 5 groups selected from halo, hydroxy, amino, alkylamino, and dialkylamino; and each R$^3$ (when R$^3$ is present) is independently alkyl, alkenyl, alkynyl, halo, hydroxy, oxo, alkoxy, cyano, hydroxyamino, carboxy, alkoxycarbonyl, amino, alkylamino, dialkylamino, alkylcarbonyl, haloalkoxy, alkylsulfonyl, aminoalkyloxy, alkylaminoalkyloxy, or dialkylaminoalkyloxy; or a) —N(R$^7$)C(O)—C$_1$-C$_6$-alkylene-N(R$^{7a}$)(R$^{7b}$), where R$^7$ is hydrogen, alkyl, or alkenyl, and R$^{7a}$ and R$^{7b}$ are independently hydrogen, alkyl, alkenyl, hydroxyalkyl, haloalkyl, alkoxy, alkoxyalkyl, aminoalkyl, alkylaminoalkyl, dialkylaminoalkyl, cycloalkyl, cycloalkylalkyl, heterocycloalkyl, heterocycloalkylalkyl, heteroaryl, heteroarylalkyl, aryl, arylalkyl, or arylalkyloxy, and where the aryl, cycloalkyl, heterocycloalkyl and heteroaryl rings in R$^{7a}$ and R$^{7b}$ (either alone or as part of arylalkyl, cycloalkylalkyl, heterocycloalkylalkyl, and heteroarylalkyl) are independently optionally substituted with 1, 2, or 3 groups independently selected from alkyl, amino, alkylamino, dialkylamino, hydroxy, halo, alkoxy, alkylthio, and oxo;

504 b) —C(O)NR$^8$R$^{8a}$, where R$^8$ is hydrogen, hydroxy, alkoxy, alkyl, alkenyl, haloalkyl, or haloalkoxy, and R$^{8a}$ is hydrogen, alkyl, alkenyl, hydroxyalkyl, cyanoalkyl, alkoxyalkyl, alkylthioalkyl, heterocycloalkyl, heterocloalkylalkyl, cycloalkyl, cycloalkylalkyl, heteroaryl, heteroarylalkyl, aryl, or arylalkyl, and where the aryl, cycloalkyl, heteroaryl, and heterocycloalkyl rings in R$^{8a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, halo, haloalkyl, haloalkoxy, hydroxy, hydroxyalkyl, oxo, amino, alkylamino, dialkylamino, alkylcarbonyl, aminoalkyl, alkylaminoalkyl, dialkylaminoalkyl, alkoxycarbonyl, and —C(O)H;

c) —NR$^9$C(O)R$^{9a}$, where R$^9$ is hydrogen, hydroxy, alkoxy, alkyl, alkenyl, haloalkyl, or haloalkoxy, and R$^{9a}$ is hydrogen, C$_2$-C$_6$-alkyl, alkenyl, hydroxyalkyl, alkoxyalkyl, cycloalkyl, cycloalkylalkyl, heterocycloalkyl, heterocycloalkylalkyl, heteroaryl, heteroarylalkyl, aryl, or arylalkyl, and where the aryl, cycloalkyl, heteroaryl, and heterocycloalkyl rings in R$^{9a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, hydroxy, hydroxyalkyl, halo, haloalkyl, haloalkoxy, oxo, amino, alkylamino, dialkylamino, alkylcarbonyl, alkoxycarbonyl, —C(O)H, aryl (optionally substituted with one or two halo), arylalkyl, heteroaryl, heteroarylalkyl, heterocycloalkyl, heterocycloalkylalkyl, cyloalkyl, cyloalkylalkyl, and cycloalkylcarbonyl;

d) —C(O)N(R$^{10}$)—C$_1$-C$_6$alkylene-N(R$^{10a}$)R$^{10b}$, where R$^{10a}$ is hydrogen, hydroxy, alkoxy, alkyl, alkenyl, haloalkyl, or hydroxyalkyl, and R$^{10}$ and R$^{10b}$ are independently hydrogen, alkyl, alkenyl, haloalkyl, or hydroxyalkyl;

e) —NR$^{11}$C(O)NR$^{11a}$R$^{11b}$, where R$^{11a}$ is hydrogen, alkyl, alkenyl, hydroxy, or alkoxy, and R$^{11}$ and R$^{11b}$ are independently hydrogen, alkyl, alkenyl, aminoalkyl, alkylaminooalkyl, or dialkylaminoalkyl;

f) —C(O)R$^{12}$, where R$^{12}$ is heterocycloalkyl optionally substituted with 1, 2, or 3 groups selected from alkyl, oxo, amino, alkylamino, and heterocycloalkylalkyl;

g) —NR$^{13}$C(O)OR$^{13a}$, where R$^{13}$ is hydrogen, alkyl, or alkenyl and R$^{13a}$ is aminoalkyl, alkylaminoalkyl, dialkylaminoalkyl, aryl, or arylalkyl);

h) —C(O)N(R$^{14}$)N(R$^{14a}$)(R$^{14b}$), where R$^{14}$, R$^{14a}$, and R$^{14b}$ are independently hydrogen, alkyl, or alkenyl;

i) —S(O)$_2$N(R$^{15}$)—C$_1$-C$_6$-alkylene-N(R$^{15a}$)R$^{15b}$, where R$^{15}$, R$^{15a}$, and R$^{15b}$ are independently hydrogen, alkyl, or alkenyl;

j) —C(O)N(R$^6$)—C$_1$-C$_6$-alkylene-C(O)OR$^{16a}$, where R$^{16}$ is hydrogen, alkyl, or alkenyl, and R$^{16a}$ is alkyl or alkenyl;

k) heteroaryl optionally substituted with one or two aminoalkyl, alkylaminoalkyl, or dialkylaminoalkyl;

l) —N(R$^{17}$)—C(=N(R$^{17b}$)(R$^{17a}$))(NR$^{17c}$R$^{17d}$), where R$^{17}$, R$^{17a}$, R$^{17b}$, R$^{17c}$, and R$^{17d}$ are independently hydrogen, alkyl, or alkenyl;

m) —N(R$^{18}$)C(O)—C$_1$-C$_6$-alkylene-N(R$^{18b}$)C(O)R$^{18a}$, where R$^{18a}$ is hydrogen, alkyl, alkenyl, or alkoxy, and R$^{18}$ and R$^{18b}$ are independently hydrogen, alkyl, or alkenyl;

n) —C(O)N(R$^{19}$)—C$_1$-C$_6$-alkylene-C(O)R$^{19a}$, where R$^{19}$ is hydrogen, alkyl, or alkenyl, and R$^{19a}$ is amino, alkylamino, dialkylamino, or heterocycloalkyl;

o) —N(R$^{20}$)C(O)—C$_1$-C$_6$-alkylene-C(O)R$^{20a}$, where R$^{20}$ is hydrogen, alkyl, or alkenyl, and R$^{20a}$ is cycloalkyl or heterocycloalkyl;

p) —NR²S(O)₂—C₁-C₆-alkylene-N(R²¹ᵇ)R²¹ᵃ, where R²¹ is hydrogen, alkyl, or alkenyl, and R²¹ᵃ and R²¹ᵇ are independently hydrogen, alkyl, or alkenyl;

q) —N(R²²)C(O)—C₁-C₆-alkylene-N(R²²ᵇ)—N(R²²ᶜ)(R²²ᵃ), where R²², R²²ᵃ and R²²ᵇ are independently hydrogen, alkyl, or alkenyl;

r) —C₀-C₆-alkylene-N(R³)—C₁-C₆-alkylene-N(R²³ᵇ)R²³ᵃ, where R²³, R²³ᵃ and R²³ᵇ are independently hydrogen, alkyl, or alkenyl; or s) —NR²⁴C(O)—C₁-C₆-alkylene-OR²⁴ᵃ, where R²⁴ is hydrogen, alkyl, or alkenyl, and R²⁴ᵃ is alkoxyalkyl or aryl optionally substituted with one or two halo or alkyl;

wherein each of the alkylene in R³ is independently optionally further substituted with 1, 2, 3, 4, or 5 groups selected from halo, hydroxy, amino, alkylamino, and dialkylamino; and provided that when R⁵⁰ and R⁵² are hydrogen, R⁵¹ is hydrogen or methyl, R⁵³ is hydrogen or methoxy, and R⁵⁴ is hydrogen or methoxy, then B is not 2,3-dihydro-1,4-benzodioxinyl, thien-2-yl, or thien-2-yl, substituted with one R³, where R³ is halo.

3. The method according to any one of embodiments 1 and 2, wherein the compound of formula I is a compound specifically recited in Table 1.

4. The method according to any one of embodiments 1, 2, and 3, wherein the HER2 and/or HER3 inhibitor is lapatinib, a functional nucleic acid, an anti-HER2, or an anti-HER3 antibody.

5. The method according to any one of embodiments 1, 2 and 3, wherein the HER3 inhibitor is an anti-HER3 antibody.

6. The method according to any one of embodiments 1, 2 and 3, wherein the cancer comprises a HER2 non-overexpressing cancer.

7. The method according to any one of embodiments 1, 2 and 3, wherein the cancer comprises a non-HER2 amplified tumor.

8. The method according to any one of embodiments 1, 2 and 3, wherein a therapeutically effective amount of Compound A is co-administered with a therapeutically effective amount of MM-121.

9. The method according to any one of embodiments 1, 2 and 3, wherein the combination exhibits therapeutic synergy in the treatment of cancer.

10. The method according to embodiment 9, wherein the combination effects a log₁₀ cell kill of at least 2.8, at least 2.9 or at least 3.0.

11. The method according to any to any one of embodiments 1, 2 and 3, wherein the cancer is lung cancer.

12. The method according to any one of embodiments 1, 2, 3 and 4, wherein the functional nucleic acid is a siRNA molecule, a shRNA molecule, a miRNA molecule, or an antisense nucleic acid molecule.

13. The method according to any one of embodiments 1, 2, 3, 4 and 5, wherein the siRNA comprises a polynucleotide having 18 to 30 nucleotides and is operable to bind to HER2 and/or HER3 mRNA.

14. The method according to embodiment 12, wherein the mRNA comprises a nucleotide sequence provided in SEQ ID NO: 1.

15. The method according to embodiment 12, wherein the siRNA comprises the polynucleotide sequence of SEQ ID NO:3, 4, 6, 7, or 8.

16. The method according to embodiment 12, wherein the siRNA is naked, linked, or encapsulated.

17. The method according to embodiment 5, wherein the antisense nucleic acid is complementary to a double stranded cDNA molecule or complementary to an mRNA sequence which encodes a HER2 and/or HER3 polypeptide.

18. The method according to embodiment 17, wherein the double stranded cDNA molecule is operable to encode a HER2 polypeptide having an amino acid sequence of SEQ ID NO:2, a fragment thereof, or a variant thereof.

19. The method according to embodiment 17, wherein the mRNA sequence which encodes a HER2 polypeptide has a polynucleotide sequence of SEQ ID NO: 1, a fragment thereof, or a variant thereof.

20. The method according to any one of embodiments 5-19, wherein the functional nucleic acid is administered to the subject in a recombinant vector, the vector being operable to express the functional nucleic acid in the tumor or near the site of the tumor and inhibit the expression and/or activity of HER2 and/or HER3 in the tumor.

21. The method according to embodiment 4, wherein the anti-HER2 antibody comprises trastuzumab, pertuzumab, 4D5, 520C9, 452F2, 736G9, 741F8, 758G5, 761B 10, huMAb4D5-1, huMAb4D5-2, huMAb4D5-3, huMAb4D5-4, huMAb4D5-5, huMAb4D5-6, huMAb4D5-7, 4D5-8, or combinations thereof.

22. The method according to embodiment 21, wherein the anti-HER2 antibody is trastuzumab.

23. The method according to embodiment 1, wherein co-administering a therapeutically effective amount of a compound of formula I and a therapeutically effective amount of a HER2 and/or HER3 inhibitor to said patient comprises administering the compound of formula I simultaneously with the HER2 and/or HER3 inhibitor, or before or after administering to the HER2 and/or HER3 inhibitor.

24. The method according to embodiment 23, wherein the amount of compound of formula I administered to the patient comprises administering about 0.01 to about 1,000 mg per day of compound of formula I.

25. The method according to embodiment 24, wherein the amount of compound of formula I administered comprises administering an amount of compound of formula I ranging from about 0.01 to about 100 mg per kilogram of body weight per day.

26. The method according to embodiment 25, wherein administering the HER2 and/or HER3 inhibitor comprises administering from about 0.001 to about 100 mg per kilogram of body weight per day of the HER2 and/or HER3 inhibitor.

27. The method according to any one of embodiments 1-26, wherein the cancer comprises: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Breast: ductal carcinoma in situ, infiltrating ductal carcinoma, medullary carcinoma, infiltrating lobular carcinoma, tubular carcinoma, mucinous carcinoma, inflammatory breast cancer; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma.

27. The method according to embodiment 26, wherein the cancer is breast cancer, colon cancer, rectal cancer, endometrial cancer, gastric carcinoma (including gastrointestinal carcinoid tumors and gastrointestinal stromal tumors), glioblastoma, hepatocellular carcinoma, small cell lung cancer, non-small cell lung cancer (NSCLC), melanoma, ovarian cancer, cervical cancer, pancreatic cancer, prostate carcinoma, acute myelogenous leukemia (AML), chronic myelogenous leukemia (CML), non-Hodgkin's lymphoma, and thyroid carcinoma.

28. The method according to embodiment 26, wherein the cancer is a $HER^2$ overexpressing cancer.

29. The method according to embodiment 28, wherein the HER2 overexpressing cancer is a HER2 overexpressing breast cancer.

30. The method of embodiment 1, wherein the compound is a compound according to Formula I(a):

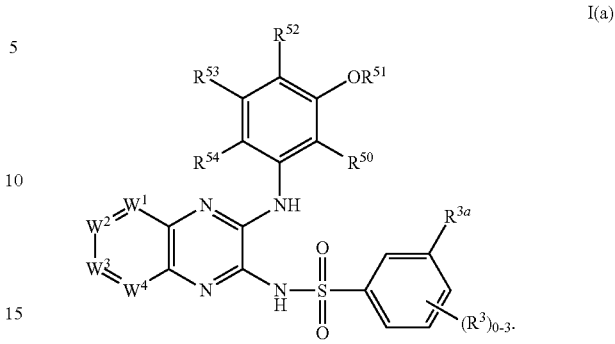

I(a)

or a single stereoisomer or mixture of stereoisomers thereof and optionally as a pharmaceutically acceptable salt thereof, wherein:

$W^1$, $W^2$, $W^3$, and $W^4$ are —C(H)—;

$R^{50}$ is hydrogen;

$R^{51}$ is methyl;

$R^{52}$ is hydrogen;

$R^{53}$ is hydrogen or alkoxy; and $R^{54}$ is hydrogen, alkyl, alkoxy, or halo; or $R^{53}$ and $R^{54}$ together with the carbons to which they are attached form a 6-membered heteroaryl; and $R^3$ is halo or methyl; and $R^{3a}$ is —N(R)C(O)—$C_1$-$C^6$-alkylene-N($R^{7a}$)($R^{7b}$) where $R^7$ is hydrogen and $R^{7a}$ and $R^{7b}$ are independently hydrogen, alkyl, aminoalkyl, alkylaminoalkyl, or dialkylaminoalkyl.

The Compound of embodiment 30, where $R^{51}$ is methyl; and $R^{50}$, $R^{52}$, and $R^{53}$ are hydrogen and $R^{54}$ is halo or alkoxy or $R^{50}$, $R^{52}$, and $R^{54}$ are hydrogen and $R^{53}$ is alkoxy; or a single stereoisomer or mixture of stereoisomers thereof and optionally as a pharmaceutically acceptable salt thereof.

The Compound of embodiment 31, wherein $R^{3a}$ is —NHC(O)$CH_2$NH($CH_3$), —NHC(O)CH($CH_3$)$NH_2$, —NHC(O)C($CH_3$)$_2$$NH_2$, —NHC(O)—$CH_2$N($CH_3$)$_2$, —NHC(O)$CH_2$N($CH_3$)$CH_2$$CH_2$N($CH_3$)$_2$, —NHC(O)CH($NH_2$)$CH_2$$CH_3$, —NHC(O)$CH_2$N($CH_3$)$CH_2$$CH_2$N($CH_3$)$_2$, or —NHC(O)CH($CH_3$)NH($CH_3$), or geometric isomer thereof and optionally as a pharmaceutically acceptable salt thereof.

The Compound of embodiment 31 which is:

| Structure | Name |
|---|---|
| 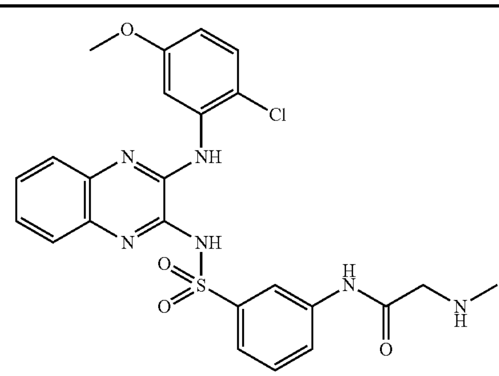 | N-(3-{[(3-{[2-chloro-5-(methoxy)phenyl]amino}quinoxalin-2-yl)amino]sulfonyl}-phenyl)-N-2-methylglycinamide |

-continued

| Structure | Name |
|---|---|
| 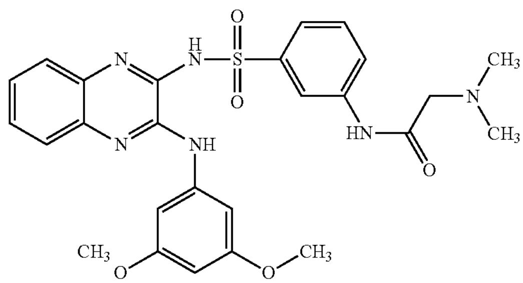 | N-(3-{[(3-{[3,5-bis(methoxy)phenyl]amino}quinoxalin-2-yl)amino]sulfonyl}phenyl)-N-2-,N-2-dimethylglycinamide |
| 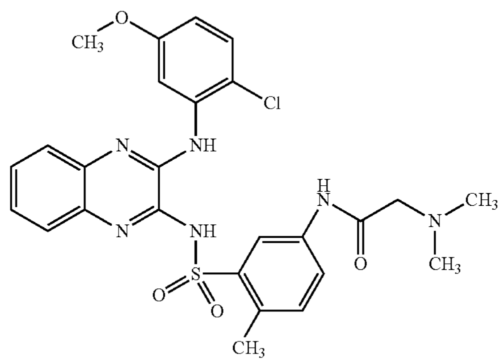 [SMILES: COc1ccc(Cl)c(Nc2nc3ccccc3nc2NS(=O)(=O)c2cc(NC(=O)CN(C)C)ccc2C)c1] | N-(3-{[(3-{[2-chloro-5-(methoxy)phenyl]amino}quinoxalin-2-yl)amino]sulfonyl}-4-methylphenyl)-N-2-,N-2-dimethylglycinamide |
| 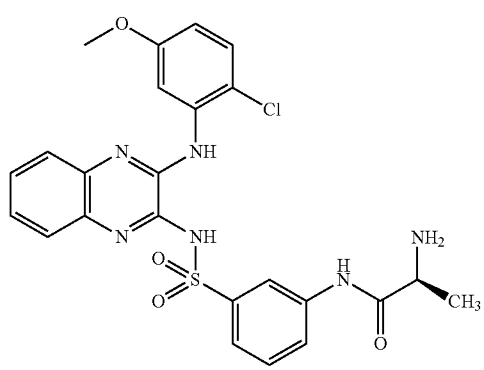 [SMILES: COc1ccc(Cl)c(Nc2nc3ccccc3nc2NS(=O)(=O)c2cccc(NC(=O)[C@H](C)N)c2)c1] | N-(3-{[(3-{[2-chloro-5-(methoxy)phenyl]amino}quinoxalin-2-yl)amino]sulfonyl}phenyl)-L-alaninamide |
| 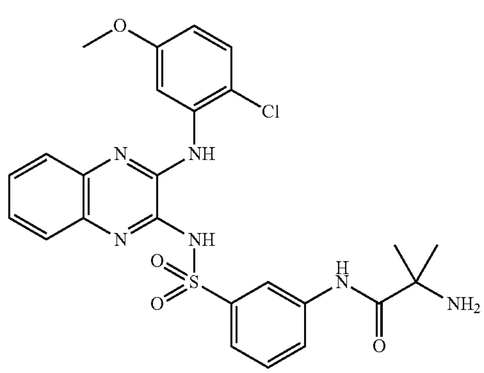 [SMILES: COc1ccc(Cl)c(Nc2nc3ccccc3nc2NS(=O)(=O)c2cccc(NC(=O)C(C)(C)N)c2)c1] | N-(3-{[(3-{[2-chloro-5-(methoxy)phenyl]amino}quinoxalin-2-yl)amino]sulfonyl}phenyl)-2-methylalaninamide |

| Structure | Name |
|---|---|
| 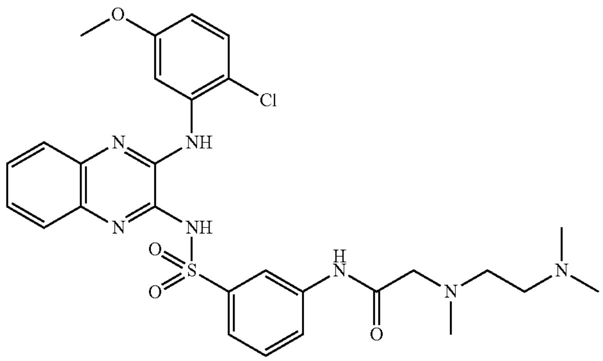 [SMILES: COc1ccc(Cl)c(Nc2nc3ccccc3nc2NS(=O)(=O)c2cccc(NC(=O)CN(C)CCN(C)C)c2)c1] | N-(3-{[(3-{[2-chloro-5-(methoxy)phenyl]amino}quinoxalin-2-yl)amino]sulfonyl}phenyl)-N-2-[2-(dimethylamino)ethyl]-N-2-methylglycinamide |
| 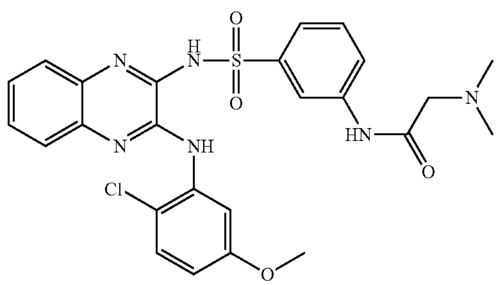 [SMILES: COc1ccc(Cl)c(Nc2nc3ccccc3nc2NS(=O)(=O)c2cccc(NC(=O)CN(C)C)c2)c1] | N-(3-{[(3-{[2-chloro-5-(methoxy)phenyl]amino}quinoxalin-2-yl)amino]sulfonyl}phenyl)-N-2-,N-2-dimethylglycinamide |
| 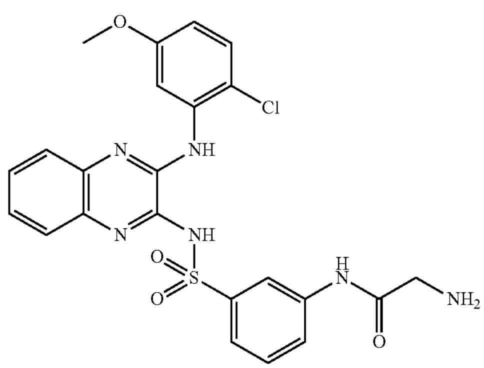 [SMILES: COc1ccc(Cl)c(Nc2nc3ccccc3nc2NS(=O)(=O)c2cccc(NC(=O)CN)c2)c1] | N-(3-{[(3-{[2-chloro-5-(methoxy)phenyl]amino}quinoxalin-2-yl)amino]sulfonyl}phenyl)glycinamide |
| 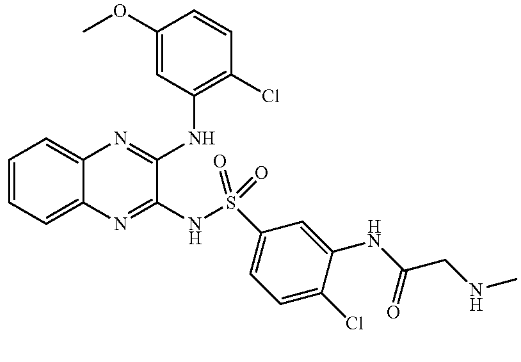 [SMILES: CNCC(=O)Nc1cc(S(=O)(=O)Nc2nc3ccccc3nc2Nc2cc(OC)ccc2Cl)ccc1Cl] | N-(2-chloro-5-{[(3-{[2-chloro-5-(methoxy)phenyl]amino}quinoxalin-2-yl)amino]sulfonyl}phenyl)-N-2-methylglycinamide |

-continued

| Structure | Name |
|---|---|
| 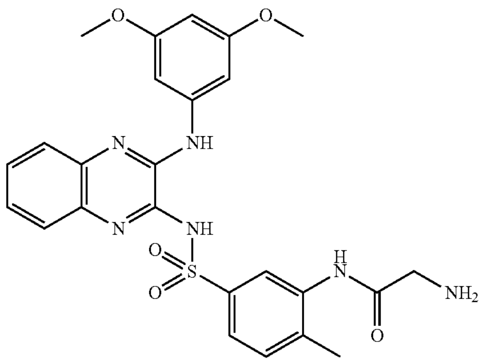 [SMILES: COc1cc(Nc2nc3ccccc3nc2NS(=O)(=O)c2ccc(C)c(NC(=O)CN)c2)cc(OC)c1] | N-(5-{[(3-{[3,5-bis(methoxy)phenyl]amino}quinoxalin-2-yl)amino]sulfonyl}-2-methylphenyl)glycinamide |
| 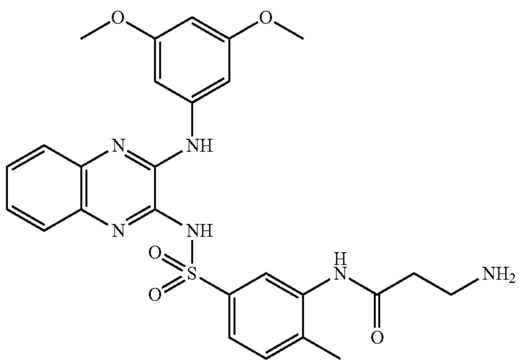 [SMILES: COc1cc(Nc2nc3ccccc3nc2NS(=O)(=O)c2ccc(C)c(NC(=O)CCN)c2)cc(OC)c1] | N-(5-{[(3-{[3,5-bis(methoxy)phenyl]amino}quinoxalin-2-yl)amino]sulfonyl}-2-methylphenyl)-beta-alaninamide |
| | N-(5-{[(3-{[2-chloro-5-(methoxy)phenyl]amino}quinoxalin-2-yl)amino]sulfonyl}-2-methylphenyl)-N-2-,N-2-dimethylglycinamide | or a pharmaceutically acceptable salt thereof.

The Compound of embodiment 31 which is:

or a pharmaceutically acceptable salt thereof.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for treating cancer in a patient comprising co-administering a therapeutically effective amount of Compound A

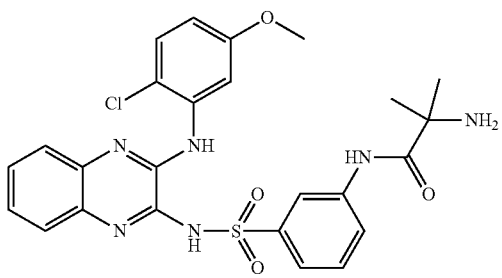 [SMILES: COc1ccc(Cl)c(Nc2nc3ccccc3nc2NS(=O)(=O)c2cccc(NC(=O)C(C)(C)N)c2)c1]

and a therapeutically effective amount of an anti-HERS antibody,
wherein the anti-HERS antibody comprises a heavy chain comprising SEQ ID. NO:17; and a light chain comprising SEQ ID NO:18:
and wherein the cancer is breast cancer, colon cancer, rectal cancer, endometrial cancer, gastric carcinoma (including gastrointestinal carcinoid tumors and gastrointestinal stromal tumors), glioblastoma, hepatocellular carcinoma, small cell lung cancer, non-small cell lung cancer (NSCLC), melanoma, ovarian cancer, cervical cancer, pancreatic cancer, prostate carcinoma, acute myelogenous leukemia (AML), chronic myelogenous leukemia (CML), non-Hodgkin's lymphoma, and thyroid carcinoma.

2. The method according to claim 1 wherein the cancer is a HER2-overexpressing cancer.

3. The method according to claim 2, wherein the HER2-overexpressing cancer is a HER2-overexpressing breast cancer.

4. The method according to claim 1, wherein the cancer comprises a non-HER2-overexpressing cancer.

5. The method according to claim 1, wherein the cancer comprises a non-HER2 amplified tumor.

6. The method according to claim 4, wherein the combination effects a $\log_{10}$ cell kill of at least 2.8, at least 2.9 or at least 3.0.

7. The method according to claim 4, wherein the cancer is lung cancer.

8. The method according to claim 5, wherein the combination effects a $\log_{10}$ cell kill of at least 2.8, at least 2.9 or at least 3.0.

9. The method according to claim 5, wherein the cancer is lung cancer.

* * * * *